United States Patent
Kudirka et al.

(10) Patent No.: US 11,654,199 B2
(45) Date of Patent: May 23, 2023

(54) THIENOAZEPINE IMMUNOCONJUGATES, AND USES THEREOF

(71) Applicant: BOLT BIOTHERAPEUTICS, INC., Redwood City, CA (US)

(72) Inventors: Romas Kudirka, Redwood City, CA (US); Brian Safina, Redwood City, CA (US)

(73) Assignee: BOLT BIOTHERAPEUTICS, INC., Redwood City, CA (US)

( * ) Notice: Subject to any disclaimer, the term of this patent is extended or adjusted under 35 U.S.C. 154(b) by 363 days.

(21) Appl. No.: 17/078,467

(22) Filed: Oct. 23, 2020

(65) Prior Publication Data
US 2021/0128744 A1 May 6, 2021

Related U.S. Application Data

(60) Provisional application No. 62/984,184, filed on Mar. 2, 2020, provisional application No. 62/926,333, filed on Oct. 25, 2019.

(51) Int. Cl.
A61K 47/68 (2017.01)
C07K 16/28 (2006.01)

(52) U.S. Cl.
CPC ...... *A61K 47/6889* (2017.08); *A61K 47/6803* (2017.08); *A61K 47/6849* (2017.08); *C07K 16/2827* (2013.01)

(58) Field of Classification Search
None
See application file for complete search history.

(56) References Cited

FOREIGN PATENT DOCUMENTS

| WO | 2011022508 A2 | 2/2011 |
| WO | 2018140831 A2 | 8/2018 |
| WO | 2019222676 A1 | 11/2019 |
| WO | 2020252254 A1 | 12/2020 |
| WO | 2020252294 A1 | 12/2020 |
| WO | 2021081402 A1 | 4/2021 |

OTHER PUBLICATIONS

Migianu, E., et al., "Synthesis of New Thieno[b]azepinediones from alpha-Methylene Ketones", Synthesis 2002(8), 1096-1100 (2002).
Patent Cooperation Treaty, International Searching Authority, Search Report and Written Opinion for PCT/US2020/057162, 17 pages, dated Feb. 1, 2021.
Patent Cooperation Treaty, International Searching Authority, Search Report and Written Opinion for PCT/US2020/057167, 17 pages, dated Feb. 1, 2021.

*Primary Examiner* — Karl J Puttlitz
(74) *Attorney, Agent, or Firm* — Vikanins Harris Padys Malen LLP

(57) ABSTRACT

The invention provides immunoconjugates of Formula I comprising an antibody linked by conjugation to one or more thienoazepine derivatives. The invention also provides thienoazepine derivative intermediate compositions comprising a reactive functional group. Such intermediate compositions are suitable substrates for formation of the immunoconjugates through a linker or linking moiety. The invention further provides methods of treating cancer with the immunoconjugates.

26 Claims, 29 Drawing Sheets

Specification includes a Sequence Listing.

| Binding agent | SEQ ID NO: | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|---|
| 1 | 1 | SYAIS | 24 | VINPSAGSTDYAQKFQG | 58 | DLYPYVVVAAGSYGMDV | 96 | RASQGIDSYLA | 129 | AASSLQS | 152 | QQSYSTPIT |
| 2 | 2 | SYYMH | 25 | WMNPNSDIAGYAQKFQG | 59 | PSIVGAYDAFDI | 97 | RASQSISSWLA | 129 | AASSLQS | 153 | QQSYTTPIT |
| 3 | 3 | RHLLH | 26 | WISPQHGVRNYAQKFQG | 60 | ESVEGYFDL | 98 | RASQSISSYLN | 129 | AASSLQS | 154 | QQIFSTPLT |
| 4 | 4 | SHHMH | 27 | WVSPSHGLTGYAQKFQG | 61 | DNWNVHDAFDI | 99 | RASQGISSYLA | 130 | GASNLQS | 155 | QQSYSTPLT |
| 5 | 5 | RFMH | 28 | WMSLNSGLTGYAQKFQG | 62 | GTYNDAFDI | 100 | RASQTISNYLN | 129 | AASSLQS | 153 | QQSYTTPIT |
| 6 | 6 | SYYIH | 29 | WMKPSSGTTGYAQKFQG | 63 | EQWLVNDAFDI | 101 | RASQSVDRNYVT | 131 | GASTRAT | 156 | QQSYTTPYT |
| 7 | 7 | NYYIH | 30 | WMNPNGDVAGYAQKFQG | 64 | DSSGWMRNDAFDI | 102 | RASQGISQYLA | 132 | GASNLHS | 157 | QQTFTPLT |
| 8 | 2 | SYYMH | 31 | GIDPNSGTNYAQKFQG | 65 | SMFPTIFGDNAFDI | 103 | QASQDIGNYLN | 133 | AASSLES | 155 | QQSYSTPLT |
| 9 | 8 | HYYMH | 32 | WMNPDSGSTGYAQKFQG | 66 | ALFPYPFYYYMDV | 104 | RASQGIRNDLG | 134 | SASNLQS | 158 | QQANSFPFT |
| 10 | 9 | GYYMH | 33 | WMSLNSGLTGYAQKFQG | 67 | DRGWFDP | 97 | RASQSISSWLA | 135 | AASTLES | 159 | QQSYTTPYS |

*Fig. 1A*

| | | | | | | | | | | | | |
|---|---|---|---|---|---|---|---|---|---|---|---|---|
| 11 | 7 | NYYIH | 34 | WMNPNGDVAGYADSFQG | 64 | DSSGWMRNDAFDI | 102 | RASQGISQYLA | 132 | GASNLHS | 160 | QQTFITPLT |
| 12 | 10 | NYMYH | 35 | WISTYHGSTNYAQKFQG | 68 | DARGYSGYDL | 105 | RASQIIGNYLA | 136 | HASILET | 161 | QQSYSTPT |
| 13 | 2 | SYYMH | 25 | WMNPNSDIAGYAQKFQG | 69 | EGRHGEYLY | 106 | RASQIISSYLN | 129 | AASSLQS | 162 | QQGFSTPFT |
| 14 | 11 | TYYVH | 36 | WMNPNTVYTGSAQKFQG | 70 | EGWGSSGYFDY | 107 | QASQDISNYLN | 129 | AASSLQS | 163 | QQSFTNPVT |
| 15 | 12 | SYALS | 37 | RIIPAVGSVTYAQKFQG | 71 | HLFPTVFDDYYGMDV | 108 | RASQGISNYLA | 137 | AASTLQS | 164 | QQSYSAPYT |
| 16 | 1 | SYAIS | 38 | GIIPIFGTANYAQKFQG | 72 | GGYSYGSFQH | 109 | RASQGISNNLN | 138 | AATTLQS | 165 | QQSYSTPYT |
| 17 | 13 | RHYVH | 39 | WMSPSSGITGYAQKFQG | 73 | VRWSSDAFDI | 98 | RASQSISSYLN | 129 | AASSLQS | 165 | QQSYSTPLT |
| 18 | 2 | SYYMH | 40 | WMTPSTGNAGYAQKFQG | 74 | EEWLGHFQH | 110 | RASQGISNGLS | 137 | AASTLQS | 166 | QQSHSTPLT |
| 19 | 14 | SHYMH | 41 | WMNPNSGNTGYAQKFQG | 75 | ERFLGGMDV | 111 | RASQSITGWLA | 129 | AASSLQS | 165 | QQSYSTPYT |
| 20 | 15 | DYYMH | 42 | WMHPNSGHTGYAQKFQG | 74 | EEWLGHFQH | 97 | RASQSISSWLA | 139 | DATHLET | 152 | QQSYSTPIT |
| 21 | 14 | SHYMH | 43 | WMNPNSGHTGNAQKFQG | 76 | GNWVDAFDI | 112 | RASQGIRNDLA | 137 | AASTLQS | 155 | QQSYSTPLT |
| 22 | 16 | GYTLH | 44 | WIDPNSGVTSSAQKFQG | 77 | ESEVMMAYFQH | 113 | QASQDISSYLN | 140 | AASSLQT | 165 | QQSYSTPYT |
| 23 | 9 | GYYMH | 45 | WISPNSGVTDFTQKFQG | 78 | ESWSGEFDY | 114 | RASQSITTYLN | 141 | AASSLQG | 165 | QQSYSTPYT |

*Fig. 1B*

| # | HCDR1 | SEQ ID NO: | HCDR2 | SEQ ID NO: | HCDR3 | SEQ ID NO: | LCDR1 | SEQ ID NO: | LCDR2 | SEQ ID NO: | LCDR3 |
|---|---|---|---|---|---|---|---|---|---|---|---|
| 24 | NHYMH | 17 | WMNPNSGHTGYAQRFQG | 46 | EAVAGPMDV | 79 | RASQSISSYLN | 98 | AASSLQS | 129 | QQSYSTPLT |
| 25 | GYYMH | 9 | WMNPNSDIAGYAQKFQG | 25 | DAWELLAFDI | 80 | RASQSVSTWLA | 115 | AASNLES | 142 | QQSYSTPYT |
| 26 | NHYMH | 17 | WMNPNSGNTGYAQKFQG | 41 | DRWDGDYYSA | 81 | RASQSISNWLA | 116 | DVSHLES | 143 | QQSYSTPFT |
| 27 | NYYIH | 7 | WMSPNGGNTGYAQKFQG | 47 | ESWELTGFDY | 82 | QASQGISNYLA | 117 | DASSLQS | 144 | QQSYSTPLT |
| 28 | SYYMH | 2 | WMNPNSGNTGYAQKFQG | 41 | ERFAGGMDA | 83 | RASQSLSSSSLA | 118 | GASTRAT | 131 | QQYGSSPFT |
| 29 | NSYMH | 18 | WMDPSSGYTGSAHKFQG | 48 | DSGGAFDI | 84 | RASEHIANWLA | 119 | GVSSLES | 145 | QQSYSTPYT |
| 30 | TYYMH | 19 | WMNPHSADTGYAEKFQG | 49 | EVFEGGMDV | 85 | RASQSVGSWVA | 120 | PASTLQS | 146 | QQSYSTPLT |
| 31 | SYYMH | 2 | WLTPSTGHAGYAQKFQG | 50 | EGYGGNYGN | 86 | RASQSISPWLA | 121 | DASNLET | 147 | QQTYSTPIT |
| 32 | SYYMH | 2 | WMNPNSGHTGYAQKFQG | 51 | EDFYGDFDY | 87 | RASQGISRYLA | 122 | AASTLQS | 137 | QQSYSTPLT |
| 33 | RHFIH | 20 | WIDPNSGVTSSAQKFQG | 44 | ELSRWGFDY | 88 | RASQTVSSNYLA | 123 | GASTRAS | 148 | QQYYTTPLT |
| 34 | RHLLH | 3 | WISPQHGVRNYAHKFQG | 52 | ESVEGYFDL | 60 | | | | | |

Fig. 1C

| | | | | | | | | | | |
|---|---|---|---|---|---|---|---|---|---|---|
| 35 | SYYMH | 2 | MINPSGGSTSYAQKFQG | 53 | DIFPTMIAGGGFDL | 89 | RASQSISSYLN | 98 | AASSLQS | 129 | QQSFSTPLT | 171 |
| 36 | TFGIS | 21 | GIIPIFGTANYAQKFQG | 38 | GGYSYGSFDY | 90 | RASQSISSWLA | 97 | DASNLET | 147 | QQSYSTPPT | 172 |
| 37 | SYGIN | 22 | WMNPNSGNTGYAQKFQG | 41 | GSFPLVFTIFGVGDV | 91 | RASQGISNNLN | 109 | ATSTLQS | 150 | QQSYSTPYT | 165 |
| 38 | SYYMH | 2 | WISPRSGVTSYAQKFQG | 54 | DLDYVRAFDI | 92 | RSSQGIRNDLS | 124 | LASNSHS | 151 | LQHNSYPLT | 173 |
| 39 | SYYMH | 2 | WMDPNSGNTGYAQKFQG | 55 | ESWGGYFDL | 93 | RASQSISRWLA | 126 | AASSLQS | 129 | QQSYSTPYT | 165 |
| 40 | NHYVH | 23 | WMNPTGGITGYAQKFQG | 56 | DRTTYAFDI | 94 | RASQSISSWLA | 97 | DSSSLQT | 149 | QQSYSTPVT | 174 |
| 41 | SHYMH | 14 | WMNPNSGHTGNAQKFQG | 43 | GNWVDAFDI | 76 | RDSHSITTWLA | 125 | AASNLES | 142 | QHFYNTQYT | 175 |
| 42 | RHLLH | 3 | WVSPIHGLTGYAPRFQG | 57 | VHGSGSDGMDV | 95 | RASQVIRNDLA | 127 | AASTLQS | 137 | QQSLQYPSHF | 176 |

*Fig. 1D*

| Binding Agent | SEQ ID NO: | HFW1 | SEQ ID NO: | HFW2 | SEQ ID NO: | HFW3 | SEQ ID NO: | HFW4 |
|---|---|---|---|---|---|---|---|---|
| 1 | 177 | QVQLVQSGAEVKKPGASVKVSCKASGGTFS | 192 | WVRQAPGQGLEWMG | 196 | RVTMTRDTSTSTVYMELSSLRSEDTAVYYCAR | 202 | WGQGTLVTVSS |
| 2 | 178 | QVQLVQSGAEVKKPGASVKVSCKASGYTFT | 192 | WVRQAPGQGLEWMG | 197 | RVTMTRDTSTSTVYMELSSLRSEDTAVYYCAI | 202 | WGQGTLVTVSS |
| 3 | 178 | QVQLVQSGAEVKKPGASVKVSCKASGYTFT | 192 | WVRQAPGQGLEWMG | 196 | RVTMTRDTSTSTVYMELSSLRSEDTAVYYCAR | 202 | WGQGTLVTVSS |
| 4 | 178 | QVQLVQSGAEVKKPGASVKVSCKASGYTFT | 192 | WVRQAPGQGLEWMG | 196 | RVTMTRDTSTSTVYMELSSLRSEDTAVYYCAR | 202 | WGQGTLVTVSS |
| 5 | 179 | QVQLVQSGAEVKKPGASVKVSCKASGYTFN | 192 | WVRQAPGQGLEWLG | 198 | RVTMTRDTSTSTVYMELSSLRSEDTAVYYCTR | 202 | WGQGTLVTVSS |
| 6 | 178 | QVQLVQSGAEVKKPGASVKVSCKASGYTFT | 192 | WVRQAPGQGLEWMG | 196 | RVTMTRDTSTSTVYMELSSLRSEDTAVYYCAR | 202 | WGQGTLVTVSS |
| 7 | 178 | QVQLVQSGAEVKKPGASVKVSCKASGYTFT | 193 | WVRQAPGQGLEWMG | 197 | RVTMTRDTSTSTVYMELSSLRSEDTAVYYCAI | 202 | WGQGTLVTVSS |
| 8 | 180 | QVQLVQSGAEVKKPGASVKVSCKASGNTFT | 192 | WVRQAPGQGLEWMG | 196 | RVTMTRDTSTSTVYMELSSLRSEDTAVYYCAR | 202 | WGQGTLVTVSS |
| 9 | 181 | QVQLVQSGAEVKKPGASVKVSCKASGHSFT | 192 | WVRQAPGQGLEWMG | 196 | RVTMTRDTSTSTVYMELSSLRSEDTAVYYCAR | 202 | WGQGTLVTVSS |
| 10 | 178 | QVQLVQSGAEVKKPGASVKVSCKASGYTFT | 194 | WVRQAPGQGLEWIG | 196 | RVTMTRDTSTSTVYMELSSLRSEDTAVYYCAR | 202 | WGQGTLVTVSS |

*Fig. 2A*

| | | | | | | | | |
|---|---|---|---|---|---|---|---|---|
| 11 | QVQLVQSGAEVKKPGASVKVSCKASGYTFT | 178 | 193 | WVRQAPGQGLEWLG | 197 | RVTMTRDTSTSTVYMELSSLRSEDTAVYYCAI | 202 | WGQGTLVTVSS |
| 12 | QVQLVQSGAEVKKPGASVKVSCKASGGTFS | 177 | 192 | WVRQAPGQGLEWMG | 196 | RVTMTRDTSTSTVYMELSSLRSEDTAVYYCAR | 202 | WGQGTLVTVSS |
| 13 | QVQLVQSGAEVKKPGASVKVSCKASGYPFT | 182 | 192 | WVRQAPGQGLEWMG | 196 | RVTMTRDTSTSTVYMELSSLRSEDTAVYYCAR | 202 | WGQGTLVTVSS |
| 14 | QVQLVQSGAEVKKPGASVKVSCKASGYRFT | 183 | 192 | WVRQAPGQGLEWMG | 196 | RVTMTRDTSTSTVYMELSSLRSEDTAVYYCAR | 202 | WGQGTLVTVSS |
| 15 | QVQLVQSGAEVKKPGSSVKVSCKASGGTFS | 184 | 192 | WVRQAPGQGLEWMG | 199 | RVTITADESTSTAYMELSSLRSEDTAVYYCAR | 202 | WGQGTLVTVSS |
| 16 | QVQLVQSGAEVKKPGSSVKVSCKASGGTFS | 184 | 192 | WVRQAPGQGLEWMG | 199 | RVTITADESTSTAYMELSSLRSEDTAVYYCAR | 202 | WGQGTLVTVSS |
| 17 | QVQLVQSGAEVKKPGASVKVSCKASGDTFT | 185 | 192 | WVRQAPGQGLEWMG | 196 | RVTMTRDTSTSTVYMELSSLRSEDTAVYYCAR | 202 | WGQGTLVTVSS |
| 18 | QVQLVQSGAEVKKPGASVKVSCKASGYTFT | 178 | 195 | WVRQAPGQGLEWVG | 196 | RVTMTRDTSTSTVYMELSSLRSEDTAVYYCAR | 202 | WGQGTLVTVSS |
| 19 | QVQLVQSGAEVKKPGASVKVSCKASGYTFT | 178 | 192 | WVRQAPGQGLEWMG | 196 | RVTMTRDTSTSTVYMELSSLRSEDTAVYYCAR | 203 | WGQGTTVTVSS |
| 20 | QVQLVQSGAEVKKPGASVKVSCKASGYTFT | 178 | 192 | WVRQAPGQGLEWMG | 200 | RVTMTRDTSTSTVNMELSSLRSEDTAVYYCAR | 202 | WGQGTLVTVSS |
| 21 | QVQLVQSGAEVKKPGASVKVSCKASGYTFT | 178 | 192 | WVRQAPGQGLEWMG | 196 | RVTMTRDTSTSTVYMELSSLRSEDTAVYYCAR | 204 | WGQGTMVTVSS |
| 22 | QVQLVQSGAEVKKPGASVKVSCKASGYTFT | 178 | 192 | WVRQAPGQGLEWMG | 196 | RVTMTRDTSTSTVYMELSSLRSEDTAVYYCAR | 202 | WGQGTLVTVSS |

*Fig. 2B*

| | | | | | | | | | |
|---|---|---|---|---|---|---|---|---|---|
| 23 | QVQLVQSGAEVKKPGASVK VSCKASGYTFT | 178 | 192 | WVRQAPGQG LEWMG | 196 | RVTMTRDTSTSTVYMELSSLR SEDTAVYYCAR | 202 | WGQGTLVT VSS |
| 24 | QVQLVQSGAEVKKPGASVK VSCKASGDTFT | 185 | 192 | WVRQAPGQG LEWMG | 196 | RVTMTRDTSTSTVYMELSSLR SEDTAVYYCAR | 203 | WGQGTTVT VSS |
| 25 | QVQLVQSGAEVKKPGASVK VSCKASGYTFT | 178 | 192 | WVRQAPGQG LEWMG | 196 | RVTMTRDTSTSTVYMELSSLR SEDTAVYYCAR | 202 | WGQGTLVT VSS |
| 26 | QVQLAQSGAEVKKPGASVK VSCKASGYTFT | 186 | 192 | WVRQAPGQG LEWMG | 196 | RVTMTRDTSTSTVYMELSSLR SEDTAVYYCAR | 202 | WGQGTLVT VSS |
| 27 | QVQLVQSGAEVKKPGASVK VSCKASGYTFT | 178 | 192 | WVRQAPGQG LEWMG | 196 | RVTMTRDTSTSTVYMELSSLR SEDTAVYYCAR | 202 | WGQGTLVT VSS |
| 28 | QVQLVQSGAEVKKPGASVK VSCKASGYTFT | 178 | 192 | WVRQAPGQG LEWMG | 196 | RVTMTRDTSTSTVYMELSSLR SEDTAVYYCAR | 203 | WGQGTTVT VSS |
| 29 | QVQLVQSGAEVKKPGASVK VSCKASGYTFS | 187 | 192 | WVRQAPGQG LEWMG | 201 | RVTMTRDTSTSTVYMELSSLR SEDTAVYYCAE | 204 | WGQGTMVT VSS |
| 30 | QVQLVQSGAEVKKPGASVK VSCKASGYPFS | 188 | 192 | WVRQAPGQG LEWMG | 196 | RVTMTRDTSTSTVYMELSSLR SEDTAVYYCAR | 203 | WGQGTTVT VSS |
| 31 | QVQLVQSGAEVKKPGASVK VSCKASGYTFT | 178 | 192 | WVRQAPGQG LEWMG | 196 | RVTMTRDTSTSTVYMELSSLR SEDTAVYYCAR | 202 | WGQGTLVT VSS |
| 32 | QVQLVQSGAEVKKPGASVK VSCKASGYTFT | 178 | 192 | WVRQAPGQG LEWMG | 196 | RVTMTRDTSTSTVYMELSSLR SEDTAVYYCAR | 202 | WGQGTLVT VSS |
| 33 | QVQLVQSGAEVKKPGASVK VSCKASGYTFT | 178 | 192 | WVRQAPGQG LEWMG | 196 | RVTMTRDTSTSTVYMELSSLR SEDTAVYYCAR | 205 | WGPGTMVT VSS |
| 34 | QVQLVQSGAEVKKPGASVK VSCKASGYTFT | 178 | 192 | WVRQAPGQG LEWMG | 196 | RVTMTRDTSTSTVYMELSSLR SEDTAVYYCAR | 206 | WGRGTLVT VSS |

*Fig. 2C*

| | | | | | | | |
|---|---|---|---|---|---|---|---|
| 35 | QVQLVQSGAEVKKPGASVK VSCKASGYPFS | 188 | WVRQAPGQG LEWMG | 196 | RVTMTRDTSTSTVYMELSSLR SEDTAVYYCAR | 206 | WGRGTLVT VSS |
| 36 | QVQLVQSGAEVKKPGSSVK VSCKASGGTFS | 184 | WVRQAPGQG LEWMG | 199 | RVTITADESTSTAYMELSSLRS EDTAVYYCAR | 202 | WGQGTLVT VSS |
| 37 | QVQLVQSGAEVKKPGASVK VSCKASGYTFT | 178 | WVRQAPGQG LEWMG | 196 | RVTMTRDTSTSTVYMELSSLR SEDTAVYYCAR | 204 | WGQGTMVT VSS |
| 38 | QVQLVQSGAEVKKPGASVK VSCKASGYTFT | 178 | WVRQAPGQG LEWMG | 196 | RVTMTRDTSTSTVYMELSSLR SEDTAVYYCAR | 203 | WGQGTTVT VSS |
| 39 | QVQLVQSGAEVKKPGASVK VSCKASGYSFT | 189 | WVRQAPGQG LEWMG | 196 | RVTMTRDTSTSTVYMELSSLR SEDTAVYYCAR | 206 | WGRGTLVT VSS |
| 40 | QVQLVQSGAEVKKPGASVK VSCKASGYTFI | 190 | WVRQAPGQG LEWMG | 196 | RVTMTRDTSTSTVYMELSSLR SEDTAVYYCAR | 204 | WGQGTMVT VSS |
| 41 | QVQLVQSGAEVKKPGASVK VSCKASGYTFT | 178 | WVRQAPGQG LEWMG | 196 | RVTMTRDTSTSTVYMELSSLR SEDTAVYYCAR | 204 | WGQGTMVT VSS |
| 42 | QVQLVQSGAEVKKPGSSVK VSCKASGYTFT | 191 | WVRQAPGQG LEWMG | 199 | RVTITADESTSTAYMELSSLRS EDTAVYYCAR | 203 | WGQGTTVT VSS |

*Fig. 2D*

| Binding agent | SEQ ID NO. | LFW1 | SEQ ID NO. | LFW2 | SEQ ID NO. | LFW3 | SEQ ID NO. | LFW4 |
|---|---|---|---|---|---|---|---|---|
| 1 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 2 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 3 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 4 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 5 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 6 | 208 | EIVMTQSPATLSVSPGERATLSC | 211 | WYQQKPGQAPRLLIY | 214 | GIPARFSGSGSGTEFTLTISSLQSEDFAVYYC | 218 | FGQGTKVEIK |
| 7 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 8 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 9 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 10 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |

*Fig. 3A*

| | | | | | | | | |
|---|---|---|---|---|---|---|---|---|
| 11 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 12 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 13 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 14 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 15 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 16 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 17 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 18 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 19 | 207 | DIQMTQSPSSLSASVGDRVTITC | 210 | WYQQKPGKAPKLLIY | 213 | GVPSRFSGSGSGTDFTLTISSLQPEDFATYYC | 218 | FGGGTKVEIK |
| 20 | 207 | DIQMTQSPSSLSASVGDRVTITC | 210 | WYQQKPGKAPKLLIY | 213 | GVPSRFSGSGSGTDFTLTISSLQPEDFATYYC | 219 | FGQGTRLEIK |
| 21 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 22 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |

Fig. 3B

| | | | | | | | |
|---|---|---|---|---|---|---|---|
| 23 | 207 | DIQMTQSPSSLSASVGDRVTIT C | 210 | WYQQKPGKAPKLLI Y | 213 | GVPSRFSGSGSGTDFTLTISSLQPEDFATYY C | 218 | FGQGTKVEI K |
| 24 | 207 | DIQMTQSPSSLSASVGDRVTIT C | 210 | WYQQKPGKAPKLLI Y | 213 | GVPSRFSGSGSGTDFTLTISSLQPEDFATYY C | 220 | FGGGTKLEIK |
| 25 | 207 | DIQMTQSPSSLSASVGDRVTIT C | 210 | WYQQKPGKAPKLLI Y | 213 | GVPSRFSGSGSGTDFTLTISSLQPEDFATYY C | 221 | FGQGTKLEIK |
| 26 | 207 | DIQMTQSPSSLSASVGDRVTIT C | 210 | WYQQKPGKAPKLLI Y | 213 | GVPSRFSGSGSGTDFTLTISSLQPEDFATYY C | 222 | FGPGTKVDI K |
| 27 | 207 | DIQMTQSPSSLSASVGDRVTIT C | 210 | WYQQKPGKAPKLLI Y | 213 | GVPSRFSGSGSGTDFTLTISSLQPEDFATYY C | 217 | FGGGTKVEI K |
| 28 | 208 | EIVMTQSPATLSVSPGERATLS C | 211 | WYQQKPGQAPRLLI Y | 214 | GIPARFSGSGSGTEFTLTISSLQSEDFAVYY C | 222 | FGPGTKVDI K |
| 29 | 207 | DIQMTQSPSSLSASVGDRVTIT C | 210 | WYQQKPGKAPKLLI Y | 213 | GVPSRFSGSGSGTDFTLTISSLQPEDFATYY C | 221 | FGQGTKLEIK |
| 30 | 207 | DIQMTQSPSSLSASVGDRVTIT C | 210 | WYQQKPGKAPKLLI Y | 213 | GVPSRFSGSGSGTDFTLTISSLQPEDFATYY C | 217 | FGGGTKVEI K |
| 31 | 207 | DIQMTQSPSSLSASVGDRVTIT C | 210 | WYQQKPGKAPKLLI Y | 213 | GVPSRFSGSGSGTDFTLTISSLQPEDFATYY C | 219 | FGQGTRLEIK |
| 32 | 207 | DIQMTQSPSSLSASVGDRVTIT C | 210 | WYQQKPGKAPKLLI Y | 213 | GVPSRFSGSGSGTDFTLTISSLQPEDFATYY C | 218 | FGQGTKVEI K |
| 33 | 208 | EIVMTQSPATLSVSPGERATLS C | 211 | WYQQKPGQAPRLLI Y | 214 | GIPARFSGSGSGTEFTLTISSLQSEDFAVYY C | 217 | FGGGTKVEI K |
| 34 | 207 | DIQMTQSPSSLSASVGDRVTIT C | 210 | WYQQKPGKAPKLLI Y | 213 | GVPSRFSGSGSGTDFTLTISSLQPEDFATYY C | 219 | FGQGTRLEIK |

*Fig. 3C*

| | | | | | | | | |
|---|---|---|---|---|---|---|---|---|
| 35 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 36 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 37 | 207 | DIQMTQSPSSLSASVGDRVTITC | 210 | WYQQKPGKAPKLLIY | 213 | GVPSRFSGSGSGTDFTLTISSLQPEDFATYYC | 217 | FGGGTKVEIK |
| 38 | 207 | DIQMTQSPSSLSASVGDRVTITC | 210 | WYQQKPGKAPKLLIY | 213 | GVPSRFSGSGSGTDFTLTISSLQPEDFATYYC | 221 | FGQGTKLEIK |
| 39 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 40 | 209 | DIQMTQSPSSLSASVGYRLTITC | 212 | WYHQKPWNAPKLMIY | 215 | GVPSRFSGSGSGTYFTLTISSLQPEDFATYYC | 218 | FGQGTKVEIK |
| 41 | 207 | DIQMTQSPSSLSASVGDRVTITC | 210 | WYQQKPGKAPKLLIY | 213 | GVPSRFSGSGSGTDFTLTISSLQPEDFATYYC | 218 | FGQGTKVEIK |
| 42 | 207 | DIQMTQSPSSLSASVGDRVTITC | 210 | WYQQKPGKAPKLLIY | 216 | GVPSRFSGSGSGTDFTLTISSLQPEDFAPYYC | 222 | FGPGTKVDIK |

*Fig. 3D*

| Binding agent | SEQ ID NO: | VH |
|---|---|---|
| 1 | 223 | QVQLVQSGAEVKKPGASVKVSCKASGGTFSSYAISWVRQAPGQGLEWMGVINPSAGSTDYAQKFQGRVTMTRDTSTSTV YMELSSLRSEDTAVYYCARDLYPYVVVVAAGSYGMDVWGQGTLVTVSS |
| 2 | 224 | QVQLVQSGAEVKKPGASVKVSCKASGYTFTSYYMHWVRQAPGQGLEWMGWMNPNSDIAGYAQKFQGRVTMTRDTSTS TVYMELSSLRSEDTAVYYCAIPSIVGAYDAFDIWGQGTLVTVSS |
| 3 | 225 | QVQLVQSGAEVKKPGASVKVSCKASGYTFTRHLLHWVRQAPGQGLEWMGWISPQHGVRNYAQKFQGRVTMTRDTSTST VYMELSSLRSEDTAVYYCARESVEGYFDLWGQGTLVTVSS |
| 4 | 226 | QVQLVQSGAEVKKPGASVKVSCKASGYTFTSHHMHWVRQAPGQGLEWMGWVSPSHGLTGYAQKFQGRVTMTRDTSTST VYMELSSLRSEDTAVYYCARDNWNVHDAFDIWGQGTLVTVSS |
| 5 | 227 | QVQLVQSGAEVKKPGASVKVSCKASGYTFNRFMHWVRQAPGQGLEWMGWMSLNSGLTGYAQKFQGRVTMTRDTSTST VYMELSSLRSEDTAVYYCTRGTYNDAFDIWGQGTLVTVSS |
| 6 | 228 | QVQLVQSGAEVKKPGASVKVSCKASGYTFTSYYIHWVRQAPGQGLEWMGWMKPSSGTTGYAQKFQGRVTMTRDTSTST VYMELSSLRSEDTAVYYCAREQWLVNDAFDIWGQGTLVTVSS |
| 7 | 229 | QVQLVQSGAEVKKPGASVKVSCKASGYTFTSYYIHWVRQAPGQGLEWMGWMKPSSGTTGYAQKFQGRVTMTRDTSTST VYMELSSLRSEDTAVYYCAREQWLVNDAFDIWGQGTLVTVSS |
| 8 | 230 | QVQLVQSGAEVKKPGASVKVSCKASGNTFTSYYMHWVRQAPGQGLEWMGGIDPNSGGTNYAQKFQGRVTMTRDTSTST VYMELSSLRSEDTAVYYCARSMFPTIFGDNAFDIWGQGTLVTVSS |
| 9 | 231 | QVQLVQSGAEVKKPGASVKVSCKASGHSFTHYYMHWVRQAPGQGLEWMGWMNPDSGSTGYAQKFQGRVTMTRDTSTS TVYMELSSLRSEDTAVYYCARALFYPFYYYMDVWGQGTLVTVSS |
| 10 | 232 | QVQLVQSGAEVKKPGASVKVSCKASGYTFTGYYMHWVRQAPGQGLEWIGWMSLNSGLTGYAQKFQGRVTMTRDTSTST VYMELSSLRSEDTAVYYCARDRGWFDPWGQGTLVTVSS |
| 11 | 233 | QVQLVQSGAEVKKPGASVKVSCKASGYTFTNYYIHWVRQAPGQGLEWLGWMNPNGDVAGYADSFQGRVTMTRDTSTST VYMELSSLRSEDTAVYYCAIDSSGWMRNDAFDIWGQGTLVTVSS |

*Fig. 4A*

| | | |
|---|---|---|
| 12 | 234 | QVQLVQSGAEVKKPGASVKVSCKASGGTFSNYMYHWVRQAPGQGLEWMGWISTYHGSTNYAQKFQGRVTMTRDTSTST VYMELSSLRSEDTAVYYCARDARGYSGYDLWGQGTLVTVSS |
| 13 | 235 | QVQLVQSGAEVKKPGASVKVSCKASGYPFTSYYMHWVRQAPGQGLEWMGWMNPNSDIAGYAQKFQGRVTMTRDTSTS TVYMELSSLRSEDTAVYYCAREGRHGEYLYWGQGTLVTVSS |
| 14 | 236 | QVQLVQSGAEVKKPGASVKVSCKASGYRFTTYYVHWVRQAPGQGLEWMGWMNPNTVYTGSAQKFQGRVTMTRDTSTS TVYMELSSLRSEDTAVYYCAREGWGSSGYFDYWGQGTLVTVSS |
| 15 | 237 | QVQLVQSGAEVKKPGSSVKVSCKASGGTFSSYALSWVRQAPGQGLEWMGRIIPAVGSVTYAQKFQGRVTITADESTSTAY MELSSLRSEDTAVYYCARHLFPTVFDDYYGMDVWGQGTLVTVSS |
| 16 | 238 | QVQLVQSGAEVKKPGSSVKVSCKASGGTFSSYAISWVRQAPGQGLEWMGGIIPIFGTANYAQKFQGRVTITADESTSTAYM ELSSLRSEDTAVYYCARGGYSYGSFQHWGQGTLVTVSS |
| 17 | 239 | QVQLVQSGAEVKKPGASVKVSCKASGDTFTRHYVHWVRQAPGQGLEWMGWMSPSSGITGYAQKFQGRVTMTRDTSTST VYMELSSLRSEDTAVYYCARVRWSSDAFDIWGQGTLVTVSS |
| 18 | 240 | QVQLVQSGAEVKKPGASVKVSCKASGYTFTSYYMHWVRQAPGQGLEWVGWMTPSTGNAGYAQKFQGRVTMTRDTSTS TVYMELSSLRSEDTAVYYCAREEWLGHFQHWGQGTLVTVSS |
| 19 | 241 | QVQLVQSGAEVKKPGASVKVSCKASGYTFTSHYMHWVRQAPGQGLEWMGWMNPNSGNTGYAQKFQGRVTMTRDTSTS TVYMELSSLRSEDTAVYYCARERFLGGMDVWGQGTTVTVSS |
| 20 | 242 | QVQLVQSGAEVKKPGASVKVSCKASGYTFTDYYMHWVRQAPGQGLEWMGWMHPNSGHTGYAQKFQGRVTMTRDTSTS TVNMELSSLRSEDTAVYYCAREEWLGHFQHWGQGTMVTVSS |
| 21 | 243 | QVQLVQSGAEVKKPGASVKVSCKASGYTFTSHYMHWVRQAPGQGLEWMGWMNPNSGHTGNAQKFQGRVTMTRDTSTS TVYMELSSLRSEDTAVYYCARGNWVDAFDIWGQGTMVTVSS |
| 22 | 244 | QVQLVQSGAEVKKPGASVKVSCKASGYTFTGYTLHWVRQAPGQGLEWMGWIDPNSGVTSSAQKFQGRVTMTRDTSTSTV YMELSSLRSEDTAVYYCARESEVMMAYFQHWGQGTLVTVSS |
| 23 | 245 | QVQLVQSGAEVKKPGASVKVSCKASGYTFTGYYMHWVRQAPGQGLEWMGWISPNSGVTDFTQKFQGRVTMTRDTSTST VYMELSSLRSEDTAVYYCARESWSGEFDYWGQGTLVTVSS |

*Fig. 4B*

| | | |
|---|---|---|
| 24 | 246 | QVQLVQSGAEVKKPGASVKVSCKASGDTFTNHYMHWVRQAPGQGLEWMGWMNPNSGHTGYAQRFQGRVTMTRDTSTS TVYMELSSLRSEDTAVYYCAREAVAGPMDVWGQGTTVTVSS |
| 25 | 247 | QVQLVQSGAEVKKPGASVKVSCKASGYTFTGYYMHWVRQAPGQGLEWMGWMNPNSDIAGYAQKFQGRVTMTRDTSTS TVYMELSSLRSEDTAVYYCARDAWELLAFDIWGQGTLVTVSS |
| 26 | 248 | QVQLAQSGAEVKKPGASVKVSCKASGYTFTNHYMHWVRQAPGQGLEWMGWMNPNSGNTGYAQKFQGRVTMTRDTSTS TVYMELSSLRSEDTAVYYCARDRWDGDYYSAWGQGTLVTVSS |
| 27 | 249 | QVQLVQSGAEVKKPGASVKVSCKASGYTFTNYYIHWVRQAPGQGLEWMGWMSPNGGNTGYAQKFQGRVTMTRDTSTST VYMELSSLRSEDTAVYYCARESWELTGFDYWGQGTLVTVSS |
| 28 | 250 | QVQLVQSGAEVKKPGASVKVSCKASGYTFTSYYMHWVRQAPGQGLEWMGWMNPNSGNTGYAQKFQGRVTMTRDTSTS TVYMELSSLRSEDTAVYYCARERFAGGMDAWGQGTTVTVSS |
| 29 | 251 | QVQLVQSGAEVKKPGASVKVSCKASGYTFSNSYMHWVRQAPGQGLEWMGWMDPSSGYTGSAHKFQGRVTMTRDTSTST VYMELSSLRSEDTAVYYCAEDSGGAFDIWGQGTMVTVSS |
| 30 | 252 | QVQLVQSGAEVKKPGASVKVSCKASGYPFSTYYMHWVRQAPGQGLEWMGWMNPHSADTGYAEKFQGRVTMTRDTSTS TVYMELSSLRSEDTAVYYCAREVFEGGMDVWGQGTMVTVSS |
| 31 | 253 | QVQLVQSGAEVKKPGASVKVSCKASGYTFTSYYMHWVRQAPGQGLEWMGWLTPSTGHAGYAQKFQGRVTMTRDTSTST VYMELSSLRSEDTAVYYCAREGYGGNYGNWGQGTLVTVSS |
| 32 | 254 | QVQLVQSGAEVKKPGASVKVSCKASGYTFTSYYMHWVRQAPGQGLEWMGWMNPNSGHTGYAQKFQGRVTMTRDTSTS TVYMELSSLRSEDTAVYYCAREDFYGDFDYWGQGTLVTVSS |
| 33 | 255 | QVQLVQSGAEVKKPGASVKVSCKASGYTFTRHFIHWVRQAPGQGLEWMGWIDPNSGVTSSAQKFQGRVTMTRDTSTSTV YMELSSLRSEDTAVYYCARELSRWGFDYWGPGTMVTVSS |
| 34 | 256 | QVQLVQSGAEVKKPGASVKVSCKASGYTFTRHLLHWVRQAPGQGLEWMGWISPQHGVRNYAHKFQGRVTMTRDTSTST VYMELSSLRSEDTAVYYCARESVEGYFDLWGRGTLVTVSS |
| 35 | 257 | QVQLVQSGAEVKKPGASVKVSCKASGYPFSSYYMHWVRQAPGQGLEWMGMINPSGGSTSYAQKFQGRVTMTRDTSTST VYMELSSLRSEDTAVYYCARDIFPTMIAGGGFDLWGRGTLVTVSS |

*Fig. 4C*

| | | |
|---|---|---|
| 36 | 258 | QVQLVQSGAEVKKPGSSVKVSCKASGGTFSTFGISWVRQAPGQGLEWMGGIIPIFGTANYAQKFQGRVTITADESTSTAYMELSSLRSEDTAVYYCARGGYSYGSFDYWGQGTLVTVSS |
| 37 | 259 | QVQLVQSGAEVKKPGASVKVSCKASGYTFTSYGINWVRQAPGQGLEWMGWMNPNSGNTGYAQKFQGRVTMTRDTSTSTVYMELSSLRSEDTAVYYCARGSFPLVFTIFGVDVWGQGTMVTVSS |
| 38 | 260 | QVQLVQSGAEVKKPGASVKVSCKASGYTFTSYYMHWVRQAPGQGLEWMGWISPRSGVTSYAQKFQGRVTMTRDTSTSTVYMELSSLRSEDTAVYYCARDLDYVRAFDIWGQGTTVTVSS |
| 39 | 261 | QVQLVQSGAEVKKPGASVKVSCKASGYSFTSYYMHWVRQAPGQGLEWMGWMDPNSGNTGYAQKFQGRVTMTRDTSTSTVYMELSSLRSEDTAVYYCARESWGGYFDLWGRGTLVTVSS |
| 40 | 262 | QVQLVQSGAEVKKPGASVKVSCKASGYTFINHYVHWVRQAPGQGLEWMGWMNPTGGITGYAQKFQGRVTMTRDTSTSTVYMELSSLRSEDTAVYYCARDRTTYAFDIWGQGTMVTVSS |
| 41 | 263 | QVQLVQSGAEVKKPGASVKVSCKASGYTFTSHYMHWVRQAPGQGLEWMGWMNPNSGHTGNAQKFQGRVTMTRDTSTSTVYMELSSLRSEDTAVYYCARGNWVDAFDIWGQGTMVTVSS |
| 42 | 264 | QVQLVQSGAEVKKPGSSVKVSCKASGYTFTRHLLHWVRQAPGQGLEWMGWVSPIHGLTGYAPRFQGRVTITADESTSTAYMELSSLRSEDTAVYYCARVHGSGSDGMDVWGQGTTVTVSS |

*Fig. 4D*

| Binding agent | SEQ ID NO: | VL |
|---|---|---|
| 1 | 265 | DIQMTQSPSSLSASVGDRVTITCRASQGIDSYLAWYQQKPGKAPKLLIYAASSLQSGVPSRFSGSGSGTDFTLTISSLQPEDFATYYCQQSYSTPITFGGGTKVEIK |
| 2 | 266 | DIQMTQSPSSLSASVGDRVTITCRASQSISSWLAWYQQKPGKAPKLLIYAASSLQSGVPSRFSGSGSGTDFTLTISSLQPEDFATYYCQQSYTTPITFGGGTKVEIK |
| 3 | 267 | DIQMTQSPSSLSASVGDRVTITCRASQSISSYLNWYQQKPGKAPKLLIYAASSLQSGVPSRFSGSGSGTDFTLTISSLQPEDFATYYCQQIFSTPLTFGGGTKVEIK |
| 4 | 268 | DIQMTQSPSSLSASVGDRVTITCRASQGISSYLAWYQQKPGKAPKLLIYGASNLQSGVPSRFSGSGSGTDFTLTISSLQPEDFATYYCQQSYSTPLTFGGGTKVEIK |
| 5 | 269 | DIQMTQSPSSLSASVGDRVTITCRASQTISNYLNWYQQKPGKAPKLLIYAASSLQSGVPSRFSGSGSGTDFTLTISSLQPEDFATYYCQQSYTTPITFGGGTKVEIK |
| 6 | 270 | EIVMTQSPATLSVSPGERATLSCRASQSVDRNYVTWYQQKPGQAPRLLIYGASTRATGIPARFSGSGSGTEFTLTISSLQSEDFAVYYCQQSYTTPYTFGQGTKVEIK |
| 7 | 271 | DIQMTQSPSSLSASVGDRVTITCRASQGISQYLAWYQQKPGKAPKLLIYGASNLHSGVPSRFSGSGSGTDFTLTISSLQPEDFATYYCQQTFTTPLTFGGGTKVEIK |
| 8 | 272 | DIQMTQSPSSLSASVGDRVTITCQASQDIGNYLNWYQQKPGKAPKLLIYAASSLESGVPSRFSGSGSGTDFTLTISSLQPEDFATYYCQQSYSTPLTFGGGTKVEIK |
| 9 | 273 | DIQMTQSPSSLSASVGDRVTITCRASQGIRNDLGWYQQKPGKAPKLLIYSASNLQSGVPSRFSGSGSGTDFTLTISSLQPEDFATYYCQQANSFPFTFGGGTKVEIK |
| 10 | 274 | DIQMTQSPSSLSASVGDRVTITCRASQSISSWLAWYQQKPGKAPKLLIYAASTLESGVPSRFSGSGSGTDFTLTISSLQPEDFATYYCQQSYTTPYSFGGGTKVEIK |
| 11 | 275 | DIQMTQSPSSLSASVGDRVTITCRASQGISQYLAWYQQKPGKAPKLLIYGASNLHSGVPSRFSGSGSGTDFTLTISSLQPEDFATYYCQQTFITPLTFGGGTKVEIK |
| 12 | 276 | DIQMTQSPSSLSASVGDRVTITCRASQIIGNYLAWYQQKPGKAPKLLIYHASILETGVPSRFSGSGSGTDFTLTISSLQPEDFATYYCQQSYSTPTFGGGTKVEIK |
| 13 | 277 | DIQMTQSPSSLSASVGDRVTITCRASQIISSYLNWYQQKPGKAPKLLIYAASSLQSGVPSRFSGSGSGTDFTLTISSLQPEDFATYYCQQGFSTPFTFGGGTKVEIK |
| 14 | 278 | DIQMTQSPSSLSASVGDRVTITCQASQDISNYLNWYQQKPGKAPKLLIYAASSLQSGVPSRFSGSGSGTDFTLTISSLQPEDFATYYCQQSFTNPVTFGGGTKVEIK |
| 15 | 279 | DIQMTQSPSSLSASVGDRVTITCRASQGISNYLAWYQQKPGKAPKLLIYAASTLQSGVPSRFSGSGSGTDFTLTISSLQPEDFATYYCQQSYSAPYTFGGGTKVEIK |
| 16 | 280 | DIQMTQSPSSLSASVGDRVTITCRASQGISNNLNWYQQKPGKAPKLLIYAATTLQSGVPSRFSGSGSGTDFTLTISSLQPEDFATYYCQQSYSTPYTFGGGTKVEIK |

*Fig. 4E*

| | | |
|---|---|---|
| 17 | 281 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPL TFGGGTKVEIK |
| 18 | 282 | DIQMTQSPSSLSASVGDRVTITCRASQGISNGLSWYQQKPGKAPKLLIYAASTLQSGVPSRFSGSGSGTDFTLTISSLQPEDFATYYCQQSHSTPL TFGGGTKVEIK |
| 19 | 283 | DIQMTQSPSSLSASVGDRVTITCRASQSITGWLAWYQQKPGKAPKLLIYAASSLQSGVPSRFSGSGSGTDFTLTISSLQPEDFATYYCQQSYSTP YTFGQGTKVEIK |
| 20 | 284 | DIQMTQSPSSLSASVGDRVTITCRASQSISSWLAWYQQKPGKAPKLLIYDATHLETGVPSRFSGSGSGTDFTLTISSLQPEDFATYYCQQSYSTPI TFGQGTRLEIK |
| 21 | 285 | DIQMTQSPSSLSASVGDRVTITCRASQGIRNDLAWYQQKPGKAPKLLIYAASTLQSGVPSRFSGSGSGTDFTLTISSLQPEDFATYYCQQSYSTP LTFGGGTKVEIK |
| 22 | 286 | DIQMTQSPSSLSASVGDRVTITCQASQDISSYLNWYQQKPGKAPKLLIYAASSLQTGVPSRFSGSGSGTDFTLTISSLQPEDFATYYCQQSYSTPY TFGQGTKLEIK |
| 23 | 287 | DIQMTQSPSSLSASVGDRVTITCRASQSITTYLNWYQQKPGKAPKLLIYAASSLQGGVPSRFSGSGSGTDFTLTISSLQPEDFATYYCQQSYSTPY TFGQGTKVEIK |
| 24 | 288 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPL TFGGGTKLEIK |
| 25 | 289 | DIQMTQSPSSLSASVGDRVTITCRASQSVSTWLAWYQQKPGKAPKLLIYAASNLESGVPSRFSGSGSGTDFTLTISSLQPEDFATYYCQQSYSTP YTFGQGTKLEIK |
| 26 | 290 | DIQMTQSPSSLSASVGDRVTITCRASQSISNWLAWYQQKPGKAPKLLIYDVSHLESGVPSRFSGSGSGTDFTLTISSLQPEDFATYYCQQSYSTPF TFGPGTKVDIK |
| 27 | 291 | DIQMTQSPSSLSASVGDRVTITCQASQGISNYLAWYQQKPGKAPKLLIYDASSLQSGVPSRFSGSGSGTDFTLTISSLQPEDFATYYCQQSYSTPL TFGGGTKVEIK |
| 28 | 292 | EIVMTQSPATLSVSPGERATLSCRASQSLSSSSLAWYQQKPGQAPRLLIYGASTRATGIPARFSGSGSGTEFTLTISSLQSEDFAVYYCQQYGSSP FTFGPGTKVDIK |
| 29 | 293 | DIQMTQSPSSLSASVGDRVTITCRASEHIANWLAWYQQKPGKAPKLLIYGVSSLESGVPSRFSGSGSGTDFTLTISSLQPEDFATYYCQQSYSTP YTFGQGTKLEIK |
| 30 | 294 | DIQMTQSPSSLSASVGDRVTITCRASQSVGSWVAWYQQKPGKAPKLLIYPASTLQSGVPSRFSGSGSGTDFTLTISSLQPEDFATYYCQQSYSTP LTFGGGTKVEIK |
| 31 | 295 | DIQMTQSPSSLSASVGDRVTITCRASQSISPWLAWYQQKPGKAPKLLIYDASNLETGVPSRFSGSGSGTDFTLTISSLQPEDFATYYCQQTYSTPI TFGQGTKVEIK |
| 32 | 296 | DIQMTQSPSSLSASVGDRVTITCRASQGISRYLAWYQQKPGKAPKLLIYAASTLQSGVPSRFSGSGSGTDFTLTISSLQPEDFATYYCQQSYSTPL TFGQGTKVEIK |
| 33 | 297 | EIVMTQSPATLSVSPGERATLSCRASQTVSSNYLAWYQQKPGQAPRLLIYGASTRASGIPARFSGSGSGTEFTLTISSLQSEDFAVYYCQQYYTT PLTFGGGTKVEIK |
| 34 | 298 | DIQMTQSPSSLSASVGDRVTITCRASQSISSYLNWYQQKPGKAPKLLIYAASSLQSGVPSRFSGSGSGTDFTLTISSLQPEDFATYYCQQSFSTPLT FGQGTRLEIK |

*Fig. 4F*

| | | |
|---|---|---|
| 35 | 299 | DIQMTQSPSSLSASVGDRVTITCRASQSISSWLAWYQQKPGKAPKLLIYDASNLETGVPSRFSGSGSGTDFTLTISSLQPEDFATYYCQQSYSTPPTFGQGTKVEIK |
| 36 | 300 | DIQMTQSPSSLSASVGDRVTITCRASQGISNNLNWYQQKPGKAPKLLIYATSTLQSGVPSRFSGSGSGTDFTLTISSLQPEDFATYYCQQSYSTPYTFGQGTKVEIK |
| 37 | 301 | DIQMTQSPSSLSASVGDRVTITCRSSQGIRNDLSWYQQKPGKAPKLLIYLASNSHSGVPSRFSGSGSGTDFTLTISSLQPEDFATYYCLQHNSYPLTFGGGTKVEIK |
| 38 | 302 | DIQMTQSPSSLSASVGDRVTITCRASQSISRWLAWYQQKPGKAPKLLIYAASSLQSGVPSRFSGSGSGTDFTLTISSLQPEDFATYYCQQSYSTPYTFGQGTKLEIK |
| 39 | 303 | DIQMTQSPSSLSASVGDRVTITCRASQSISSWLAWYQQKPGKAPKLLIYDSSSLQTGVPSRFSGSGSGTDFTLTISSLQPEDFATYYCQQSYSTPVTFGQGTKVEIK |
| 40 | 304 | DIQITHSPSSLSASVGYRLTITCRDSHSITTWLAWYHQKPWNAPKLMIYAASNLESGVPSRFSGSGSGTYFTLTISSLQPEDFATYYCQHFYNTQYTFGQGTKVEIK |
| 41 | 305 | DIQMTQSPSSLSASVGDRVTITCRASQVIRNDLAWYQQKPGKAPKLLIYAASTLQSGVPSRFSGSGSGTDFTLTISSLQPEDFATYYCQQSLQYPSHFFGQGTKVEIK |
| 42 | 306 | DIQMTQSPSSLSASVGDRVTITCRASQSISRYLNWYQQKPGKAPKLLIYAASTLQSGVPSRFSGSGSGTDFTLTISSLQPEDFAPYYCQQSYSTPLTFGPGTKVDIK |

*Fig. 4G*

| Binding agent | SEQ ID NO. | HCDR1 | SEQ ID NO. | HCDR2 | SEQ ID NO. | HCDR3 | SEQ ID NO. | LCDR1 | SEQ ID NO. | LCDR2 | SEQ ID NO. | LCDR3 |
|---|---|---|---|---|---|---|---|---|---|---|---|---|
| 1 | 308 | SDYMH | 322 | WMSPYNGITGYAQKFQG | 339 | DRFSGSYDY | 360 | RASQSISSWLA | 375 | AASSLQS | 387 | QQSYSTPYT |
| 2 | 309 | GYYMH | 323 | WMSPSSGITGYAQKFQG | 340 | DRGWFDP | 361 | RASQSVGTWLA | 376 | AASTLEN | 388 | QQSFSTPYT |
| 3 | 310 | SYYMH | 324 | WMTTNSGITGYAQKFQG | 341 | EGYSSGLDY | 360 | RASQSISSWLA | 375 | AASSLQS | 387 | QQSYSTPYT |
| 4 | 311 | GYYIH | 325 | GIIPIFGTASYAQKFQG | 342 | DGRFWSGYPDY | 362 | RASQGISNYLA | 377 | RASNLES | 389 | QQSYSTPLT |
| 5 | 312 | THYMH | 326 | WMNPNSGHAGSAQKFQG | 343 | ESIAVAGYDY | 360 | RASQSISSWLA | 378 | AASTLQR | 387 | QQSYSTPYT |
| 6 | 313 | SHDIN | 327 | WMNPNSGNTGYAQKFQG | 344 | DRWYMGSADY | 363 | RASQSISTWLA | 379 | AASTLQS | 390 | QQSYSTPFT |
| 7 | 310 | SYYMH | 327 | WMNPNSGNTGYAQKFQG | 345 | DDWGGDWFDP | 364 | QASQDISNHLN | 380 | GASNLQR | 391 | QQSYSTPIT |
| 8 | 312 | THYMH | 328 | WMNPNSGNTGYSQKFQG | 346 | ERLSVAGFDY | 365 | RASQGISSWLA | 375 | AASSLQS | 387 | QQSYSTPYT |
| 9 | 314 | DHYLH | 329 | WMNPNIGNTGYAQKFQG | 347 | EPLQLGGFDY | 366 | RASESISSWLA | 375 | AASSLQS | 389 | QQSYSTPLT |
| 10 | 309 | GYYMH | 330 | WMNPNGGTTGYAQNFQG | 348 | EGFGPNAFDI | 360 | RASQSISSWLA | 381 | AASNLQS | 392 | QQYYSTPYT |
| 11 | 309 | GYYMH | 327 | WMNPNSGNTGYAQKFQG | 349 | DSWYGDWFDP | 367 | RASQSVGSWLA | 382 | GASSLQS | 389 | QQSYSTPLT |
| 12 | 309 | GYYMH | 322 | WMSPYNGITGYAQKFQG | 350 | EVIEVGMDV | 360 | RASQSISSWLA | 383 | AASHLQS | 387 | QQSYSTPYT |
| 13 | 315 | NYYMH | 323 | WMSPSSGITGYAQKFQG | 351 | EAWFGELST | 368 | RASQNISNFLN | 375 | AASSLQS | 393 | QQSYSLPYT |
| 14 | 316 | AYYVH | 331 | WMNPNRGITDSAQKFQG | 352 | EAYVAAFDI | 365 | RASQGISSWLA | 375 | AASSLQS | 389 | QQSYSTPLT |
| 15 | 317 | RHYVH | 332 | WMNPNSGSAGYAQKFQG | 353 | ERGYNAFDY | 369 | RASQSLSSSYLA | 131 | GASTRAT | 394 | HQYFTTPLT |
| 16 | 318 | NYIH | 333 | WIHPRSGATGYAPKFQG | 354 | DSVFGLDY | 370 | RASQSISSYLN | 379 | AASTLQS | 395 | QQSYSMPYT |
| 17 | 310 | SYYMH | 334 | WISPRSGVTSYAQKFQG | 355 | DLDYVRAFDI | 371 | RASQSISRWLA | 375 | AASSLQS | 387 | QQSYSTPYT |

*Fig. 5A*

|    |       |     |                       |     |             |     |                 |     |         |     |             |
|----|-------|-----|-----------------------|-----|-------------|-----|-----------------|-----|---------|-----|-------------|
| 18 | SYYMH | 310 | WMDPNSGNTGYAQKFQG     | 335 | ESWGGYFDL   | 356 | RASQSISSWLA     | 360 | DSSSLQT | 385 | QQSYSTPVT   |
| 19 | NHYVH | 319 | WMNPTGGITGYAQKFQG     | 336 | DRTTYAFDI   | 357 | RDSHSITTWLA     | 372 | AASNLES | 386 | QHFYNTQYT   |
| 20 | SHYMH | 320 | WMNPNSGHTGNAQKFQG     | 337 | GNWVDAFDI   | 358 | RASQVIRNDLA     | 373 | AASTLQS | 379 | QQSLQYPSHF  |
| 21 | RHLLH | 321 | WVSPHGLTGYAPRFQG      | 338 | VHGSGSDGMDV | 359 | RASQSISRYLN     | 374 | AASTLQS | 379 | QQSYSTPLT   |

*Fig. 5B*

| Binding agent | HFW1 | SEQ ID NO: | HFW2 | SEQ ID NO: | HFW3 | SEQ ID NO: | HFW4 | SEQ ID NO: |
|---|---|---|---|---|---|---|---|---|
| 1 | QVQLVQSGAEVKKPGASVKVSCKASGYTFS | 399 | WVRQAPGQGLEWMG | 407 | RVTMTRDTSTSTVYMELSSLRSEDTAVYYCAR | 409 | WGQGTLVTVSS | 411 |
| 2 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTLVTVSS | 411 |
| 3 | QVQLVQSGAEVKKPGASVKVSCKASGYTFS | 399 | WVRQAPGQGLEWMG | 407 | RVTMTRDTSTSTVYMELSSLRSEDTAVYYCAR | 409 | WGQGTLVTVSS | 411 |
| 4 | QVQLVQSGAEVKKPGSSVKVSCKASGYTFT | 401 | WVRQAPGQGLEWMG | 407 | RVTITADESTSTAYMELSSLRSEDTAVYYCAR | 410 | WGQGTLVTVSS | 411 |
| 5 | QVQLVQSGAEVKKPGASVKVSCKASGYTFS | 399 | WVRQAPGQGLEWMG | 407 | RVTMTRDTSTSTVYMELSSLRSEDTAVYYCAR | 409 | WGQGTLVTVSS | 411 |
| 6 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTLVTVSS | 411 |
| 7 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTLVTVSS | 411 |
| 8 | QVQLVQSGAEVKKPGASVKVSCKASGYTFS | 399 | WMRQAPGQGLEWIG | 408 | RVTMTRDTSTSTVYMELSSLRSEDTAVYYCAR | 409 | WGQGTLVTVSS | 411 |
| 9 | QVQLVQSGAEVKEPGASVKVSCKASGYTFT | 402 | WVRQAPGQGLEWMG | 407 | RVTMTRDTSTSTVYMELSSLRSEDTAVYYCAR | 409 | WGQGTLVTVSS | 411 |
| 10 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTTVTVSS | 412 |
| 11 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTLVTVSS | 411 |
| 12 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTTVTVSS | 412 |
| 13 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTLVTVSS | 411 |
| 14 | QVQLVQSGAEVKKPGASVKVSCKASGYNFS | 403 | WVRQAPGQGLEWMG | 407 | RVTMTRDTSTSTVYMELSSLRSEDTAVYYCAR | 409 | WGQGTTVTVSS | 412 |
| 15 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTLVTVSS | 411 |
| 16 | QVQLVQSGAEVKKPGASVKVSCKASGYTLP | 607 | WVRQAPGQGLEWMG | 407 | RVTMTRDTSTSTVYMELSSLRSEDTAVYYCAR | 409 | WGQGTLVTVSS | 411 |
| 17 | QVQLVQSGAEVKKPGASVKVSCKASGYTFT | 400 | WVRQAPGQGLEWMG | 407 | RVTMTRDTSTSTVYMELSSLRSEDTAVYYCAR | 409 | WGQGTTVTVSS | 412 |

*Fig. 6A*

| 18 | QVQLVQSGAEVKKPGASVKV SCKASGYSFT | 405 | WVRQAPGQGLEW MG | 407 | RVTMTRDTSTSTVYMELSSLRSED TAVYYCAR | 409 | WGRGTLVTV SS | 413 |
|---|---|---|---|---|---|---|---|---|
| 19 | QVQLVQSGAEVKKPGASVKV SCKASGYTFI | 406 | WVRQAPGQGLEW MG | 407 | RVTMTRDTSTSTVYMELSSLRSED TAVYYCAR | 409 | WGQGTMVTV SS | 414 |
| 20 | QVQLVQSGAEVKKPGASVKV SCKASGYTFT | 400 | WVRQAPGQGLEW MG | 407 | RVTMTRDTSTSTVYMELSSLRSED TAVYYCAR | 409 | WGQGTMVTV SS | 414 |
| 21 | QVQLVQSGAEVKKPGSSVKV SCKASGYTFT | 401 | WVRQAPGQGLEW MG | 407 | RVTITADESTSTAYMELSSLRSEDT AVYYCAR | 410 | WGQGTTVTV SS | 412 |

*Fig. 6B*

| Binding agent | SEQ ID NO. | LFW1 | SEQ ID NO. | LFW2 | SEQ ID NO. | LFW3 | SEQ ID NO. | LFW4 |
|---|---|---|---|---|---|---|---|---|
| 1 | 415 | DIQMTQSPSSLSASVGDRVTITC | 418 | WYQQKPGKAPKLLIY | 421 | GVPSRFSGSGSGTDFTLTISSLQPEDFATYYC | 425 | FGGGTKVEIK |
| 2 | 415 | DIQMTQSPSSLSASVGDRVTITC | 418 | WYQQKPGKAPKLLIY | 421 | GVPSRFSGSGSGTDFTLTISSLQPEDFATYYC | 425 | FGGGTKVEIK |
| 3 | 415 | DIQMTQSPSSLSASVGDRVTITC | 418 | WYQQKPGKAPKLLIY | 421 | GVPSRFSGSGSGTDFTLTISSLQPEDFATYYC | 425 | FGGGTKVEIK |
| 4 | 415 | DIQMTQSPSSLSASVGDRVTITC | 418 | WYQQKPGKAPKLLIY | 421 | GVPSRFSGSGSGTDFTLTISSLQPEDFATYYC | 425 | FGGGTKVEIK |
| 5 | 415 | DIQMTQSPSSLSASVGDRVTITC | 418 | WYQQKPGKAPKLLIY | 421 | GVPSRFSGSGSGTDFTLTISSLQPEDFATYYC | 426 | FGQGTKLEIK |
| 6 | 415 | DIQMTQSPSSLSASVGDRVTITC | 418 | WYQQKPGKAPKLLIY | 421 | GVPSRFSGSGSGTDFTLTISSLQPEDFATYYC | 427 | FGQGTKVEIK |
| 7 | 415 | DIQMTQSPSSLSASVGDRVTITC | 418 | WYQQKPGKAPKLLIY | 421 | GVPSRFSGSGSGTDFTLTISSLQPEDFATYYC | 428 | FGQGTRLEIK |
| 8 | 415 | DIQMTQSPSSLSASVGDRVTITC | 418 | WYQQKPGKAPKLLIY | 421 | GVPSRFSGSGSGTDFTLTISSLQPEDFATYYC | 427 | FGQGTKVEIK |
| 9 | 415 | DIQMTQSPSSLSASVGDRVTITC | 418 | WYQQKPGKAPKLLIY | 421 | GVPSRFSGSGSGTDFTLTISSLQPEDFATYYC | 426 | FGQGTKLEIK |
| 10 | 415 | DIQMTQSPSSLSASVGDRVTITC | 418 | WYQQKPGKAPKLLIY | 421 | GVPSRFSGSGSGTDFTLTISSLQPEDFATYYC | 427 | FGQGTKVEIK |
| 11 | 415 | DIQMTQSPSSLSASVGDRVTITC | 418 | WYQQKPGKAPKLLIY | 421 | GVPSRFSGSGSGTDFTLTISSLQPEDFATYYC | 425 | FGGGTKVEIK |
| 12 | 415 | DIQMTQSPSSLSASVGDRVTITC | 418 | WYQQKPGKAPKLLIY | 421 | GVPSRFSGSGSGTDFTLTISSLQPEDFATYYC | 428 | FGQGTRLEIK |

*Fig. 7A*

| | | | | | | | | |
|---|---|---|---|---|---|---|---|---|
| 13 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 14 | 415 | DIQMTQSPSSLSASVGDR VTITC | 418 | WYQQKPGKAPKLLIY | 421 | GVPSRFSGSGSGTDFTLTISSLQPE DFATYYC | 425 | FGGGTKVEIK |
| 15 | 416 | EIVMTQSPATLSVSPGER ATLSC | 419 | WYQQKPGQAPRLLIY | 422 | GIPARFSGSGSGTEFTLTISSLQSED FAVYYC | 428 | FGQGTRLEIK |
| 16 | 415 | DIQMTQSPSSLSASVGDR VTITC | 418 | WYQQKPGKAPKLLIY | 421 | GVPSRFSGSGSGTDFTLTISSLQPE DFATYYC | 426 | FGQGTKLEIK |
| 17 | 415 | DIQMTQSPSSLSASVGDR VTITC | 418 | WYQQKPGKAPKLLIY | 421 | GVPSRFSGSGSGTDFTLTISSLQPE DFATYYC | 426 | FGQGTKLEIK |
| 18 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 19 | 417 | DIQITHSPSSLSASVGYRL TITC | 420 | WYHQKPWNAPKLMIY | 423 | GVPSRFSGSGSGTYFTLTISSLQPE DFATYYC | 427 | FGQGTKVEIK |
| 20 | 415 | DIQMTQSPSSLSASVGDR VTITC | 418 | WYQQKPGKAPKLLIY | 421 | GVPSRFSGSGSGTDFTLTISSLQPE DFATYYC | 427 | FGQGTKVEIK |
| 21 | 415 | DIQMTQSPSSLSASVGDR VTITC | 418 | WYQQKPGKAPKLLIY | 424 | GVPSRFSGSGSGTDFTLTISSLQPE DFAPYYC | 429 | FGPGTKVDIK |

*Fig. 7B*

| Binding agent | SEQ ID NO: | VH |
|---|---|---|
| 1 | 430 | QVQLVQSGAEVKKPGASVKVSCKASGYTFSSDYMHWVRQAPGQGLEWMGWMSPYNGITGYAQKFQGRVTMTRDTSTSTVYMELSSLRSEDTAVYYCARDRFSGSYDYWGQGTLVTVSS |
| 2 | 431 | QVQLVQSGAEVKKPGASVKVSCKASGYTFTGYYMHWVRQAPGQGLEWMGWMSPSSGITGYAQKFQGRVTMTRDTSTSTVYMELSSLRSEDTAVYYCARDRGWFDPWGQGTLVTVSS |
| 3 | 432 | QVQLVQSGAEVKKPGASVKVSCKASGYTFSSYYMHWVRQAPGQGLEWMGWMTTNSGITGYAQKFQGRVTMTRDTSTSTVYMELSSLRSEDTAVYYCAREGYSSGLDYWGQGTLVTVSS |
| 4 | 433 | QVQLVQSGAEVKKPGSSVKVSCKASGYTFTGYYIHWVRQAPGQGLEWMGGIIPIFGTASYAQKFQGRVTITADESTSTAYMELSSLRSEDTAVYYCARDGRFWSGYPDYWGQGTLVTVSS |
| 5 | 434 | QVQLVQSGAEVKKPGASVKVSCKASGYTFSTHYMHWVRQAPGQGLEWMGWMNPNSGHAGSAQKFQGRVTMTRDTSTSTVYMELSSLRSEDTAVYYCARESIAVAGYDYWGQGTLVTVSS |
| 6 | 435 | QVQLVQSGAEVKKPGASVKVSCKASGYTFTSHDINWVRQAPGQGLEWMGWMNPNSGNTGYAQKFQGRVTMTRDTSTSTVYMELSSLRSEDTAVYYCARDRWYMGSADYWGQGTLVTVSS |
| 7 | 436 | QVQLVQSGAEVKKPGASVKVSCKASGYTFTSYYMHWVRQAPGQGLEWMGWMNPNSGNTGYAQKFQGRVTMTRDTSTSTVYMELSSLRSEDTAVYYCARDDWGGDWFDPWGQGTLVTVSS |
| 8 | 437 | QVQLVQSGAEVKKPGASVKVSCKASGYTFSTHYMHWVRQAPGQGLEWMGWMNPNSGNTGYSQKFQGRVTMTRDTSTSTVYMELSSLRSEDTAVYYCARERLSVAGFDYWGQGTLVTVSS |
| 9 | 438 | QVQLVQSGAEVKKPEPGASVKVSCKASGYTFTDHYLHWVRQAPGQGLEWMGWMNPNIGNTGYAQKFQGRVTMTRDTSTSTVYMELSSLRSEDTAVYYCAREPLQLGGFDYWGQGTLVTVSS |
| 10 | 439 | QVQLVQSGAEVKKPGASVKVSCKASGYTFTGYYMHWVRQAPGQGLEWMGWMNPNGGTTGYAQNFQGRVTMTRDTSTSTVYMELSSLRSEDTAVYYCAREGFGPNAFDIWGQGTTVTVSS |
| 11 | 440 | QVQLVQSGAEVKKPGASVKVSCKASGYTFTGYYMHWVRQAPGQGLEWMGWMNPNSGNTGYAQKFQGRVTMTRDTSTSTVYMELSSLRSEDTAVYYCARDSWYGDWFDPWGQGTLVTVSS |

*Fig. 8A*

| | | |
|---|---|---|
| 12 | 441 | QVQLVQSGAEVKKPGASVKVSCKASGYTFTGYYMHWMRQAPGQGLEWIGWMSPYNGITGYAQKFQGRVTMTRDTSTSTVYMELSSLRSEDTAVYYCAREVIEVGMDVWGQGTTVTVSS |
| 13 | 442 | QVQLVQSGAEVKKPGASVKVSCKASGYTFTNYYMHWVRQAPGQGLEWMGWMSPSSGITGYAQKFQGRVTMTRDTSTSTVYMELSSLRSEDTAVYYCAREAWFGELSTWGQGTLVTVSS |
| 14 | 443 | QVQLVQSGAEVKKPGASVKVSCKASGYNFSAYYVHWVRQAPGQGLEWMGWMNPNRGITDSAQKFQGRVTMTRDTSTSTVYMELSSLRSEDTAVYYCAREAYVAAFDIWGQGTTVTVSS |
| 15 | 444 | QVQLVQSGAEVKKPGASVKVSCKASGYTFTRHYVHWVRQAPGQGLEWMGWMNPNSGSAGYAQKFQGRVTMTRDTSTSTVYMELSSLRSEDTAVYYCARERGYNAFDYWGQGTLVTVSS |
| 16 | 445 | QVQLVQSGAEVKKPGASVKVSCKASGYTLPNYIHWVRQAPGQGLEWMGWIHPRSGATGYAPKFQGRVTMTRDTSTSTVYMELSSLRSEDTAVYYCARDSVFGLDYWGQGTLVTVSS |
| 17 | 446 | QVQLVQSGAEVKKPGASVKVSCKASGYTFTSYYMHWVRQAPGQGLEWMGWISPRSGVTSYAQKFQGRVTMTRDTSTSTVYMELSSLRSEDTAVYYCARDLDYVRAFDIWGQGTTVTVSS |
| 18 | 447 | QVQLVQSGAEVKKPGASVKVSCKASGYSFTSYYMHWVRQAPGQGLEWMGWMDPNSGNTGYAQKFQGRVTMTRDTSTSTVYMELSSLRSEDTAVYYCARESWGGYFDLWGRGTLVTVSS |
| 19 | 448 | QVQLVQSGAEVKKPGASVKVSCKASGYTFINHYVHWVRQAPGQGLEWMGWMNPTGGITGYAQKFQGRVTMTRDTSTSTVYMELSSLRSEDTAVYYCARDRTTYAFDIWGQGTMVTVSS |
| 20 | 449 | QVQLVQSGAEVKKPGASVKVSCKASGYTFTSHYMHWVRQAPGQGLEWMGWMNPNSGHTGNAQKFQGRVTMTRDTSTSTVYMELSSLRSEDTAVYYCARGNWDAFDIWGQGTMVTVSS |
| 21 | 450 | QVQLVQSGAEVKKPGSSVKVSCKASGYTFTRHLLHWVRQAPGQGLEWMGWVSPIHGLTGYAPRFQGRVTITADESTSTAYMELSSLRSEDTAVYYCARVHGSGSDGMDVWGQGTTVTVSS |

*Fig. 8B*

| Binding agent | SEQ ID NO: | VL |
|---|---|---|
| 1 | 451 | DIQMTQSPSSLSASVGDRVTITCRASQSISSWLAWYQQKPGKAPKLLIYAASSLQSGVPSRFSGSGSGTDFTLTISSLQPEDFATYYCQQSYSTPYTFGGGTKVEIK |
| 2 | 452 | DIQMTQSPSSLSASVGDRVTITCRASQSVGTWLAWYQQKPGKAPKLLIYAASTLENGVPSRFSGSGSGTDFTLTISSLQPEDFATYYCQQSFSTPYTFGQGTKVEIK |
| 3 | 453 | DIQMTQSPSSLSASVGDRVTITCRASQSISSWLAWYQQKPGKAPKLLIYAASSLQSGVPSRFSGSGSGTDFTLTISSLQPEDFATYYCQQSYSTPYTFGGGTKVEIK |
| 4 | 454 | DIQMTQSPSSLSASVGDRVTITCRASQGISNYLAWYQQKPGKAPKLLIYRASNLESGVPSRFSGSGSGTDFTLTISSLQPEDFATYYCQQSYSTPLTFGGGTKVEIK |
| 5 | 455 | DIQMTQSPSSLSASVGDRVTITCRASQSISSWLAWYQQKPGKAPKLLIYAASTLQRGVPSRFSGSGSGTDFTLTISSLQPEDFATYYCQQSYSTPYTFGQGTKLEIK |
| 6 | 456 | DIQMTQSPSSLSASVGDRVTITCRASQSISTWLAWYQQKPGKAPKLLIYAASTLQSGVPSRFSGSGSGTDFTLTISSLQPEDFATYYCQQSYSTPFTFGQGTKVEIK |
| 7 | 457 | DIQMTQSPSSLSASVGDRVTITCQASQDISNHLNWYQQKPGKAPKLLIYGASNLQRGVPSRFSGSGSGTDFTLTISSLQPEDFATYYCQQSYSTPITFGQGTRLEIK |
| 8 | 458 | DIQMTQSPSSLSASVGDRVTITCRASQGISSWLAWYQQKPGKAPKLLIYAASSLQSGVPSRFSGSGSGTDFTLTISSLQPEDFATYYCQQSYSTPYTFGQGTKVEIK |
| 9 | 459 | DIQMTQSPSSLSASVGDRVTITCRASESISSWLAWYQQKPGKAPKLLIYAASSLQSGVPSRFSGSGSGTDFTLTISSLQPEDFATYYCQQSYSTPLTFGQGTKLEIK |
| 10 | 460 | DIQMTQSPSSLSASVGDRVTITCRASQSISSWLAWYQQKPGKAPKLLIYAASNLQSGVPSRFSGSGSGTDFTLTISSLQPEDFATYYCQQYYSTPYTFGQGTKVEIK |
| 11 | 461 | DIQMTQSPSSLSASVGDRVTITCRASQSVGSWLAWYQQKPGKAPKLLIYGASSLQSGVPSRFSGSGSGTDFTLTISSLQPEDFATYYCQQSYSTPLTFGGGTKVEIK |
| 12 | 462 | DIQMTQSPSSLSASVGDRVTITCRASQSISSWLAWYQQKPGKAPKLLIYAASHLQSGVPSRFSGSGSGTDFTLTISSLQPEDFATYYCQQSYSTPYTFGQGTRLEIK |

*Fig. 8C*

| | | |
|---|---|---|
| 13 | 463 | DIQMTQSPSSLSASVGDRVTITCRASQNISNFLNWYQQKPGKAPKLLIYAASSLQSGVPSRFSGSGSGTDFTLTISSLQPEDFATYYCQQSYSLPYTFGQGTKVEIK |
| 14 | 464 | DIQMTQSPSSLSASVGDRVTITCRASQGISSWLAWYQQKPGKAPKLLIYAASSLQSGVPSRFSGSGSGTDFTLTISSLQPEDFATYYCQQSYSTPLTFGGGTKVEIK |
| 15 | 465 | EIVMTQSPATLSVSPGERATLSCRASQSLSSSYLAWYQQKPGQAPRLLIYGASTRATGIPARFSGSGSGTEFTLTISSLQSEDFAVYYCHQYFTTPLTFGQGTRLEIK |
| 16 | 466 | DIQMTQSPSSLSASVGDRVTITCRASQSISSYLNWYQQKPGKAPKLLIYAASTLQSGVPSRFSGSGSGTDFTLTISSLQPEDFATYYCQQSYSMPYTFGQGTKLEIK |
| 17 | 467 | DIQMTQSPSSLSASVGDRVTITCRASQSISRWLAWYQQKPGKAPKLLIYAASSLQSGVPSRFSGSGSGTDFTLTISSLQPEDFATYYCQQSYSTPYTFGQGTKLEIK |
| 18 | 468 | DIQMTQSPSSLSASVGDRVTITCRASQSISSWLAWYQQKPGKAPKLLIYDSSSLQTGVPSRFSGSGSGTDFTLTISSLQPEDFATYYCQQSYSTPVTFGQGTKVEIK |
| 19 | 469 | DIQITHSPSSLSASVGYRLTITCRDSHSITTWLAWYHQKPWNAPKLMIYAASNLESGVPSRFSGSGSGTYFTLTISSLQPEDFATYYCQHFYNTQYTFGQGTKVEIK |
| 20 | 470 | DIQMTQSPSSLSASVGDRVTITCRASQVIRNDLAWYQQKPGKAPKLLIYAASTLQSGVPSRFSGSGSGTDFTLTISSLQPEDFATYYCQQSLQYPSHFFGGGTKVEIK |
| 21 | 471 | DIQMTQSPSSLSASVGDRVTITCRASQSISRYLNWYQQKPGKAPKLLIYAASTLQSGVPSRFSGSGSGTDFTLTISSLQPEDFAPYYCQQSYSTPLTFGPGTKVDIK |

*Fig. 8D*

THIENOAZEPINE IMMUNOCONJUGATES, AND USES THEREOF

CROSS REFERENCE TO RELATED APPLICATIONS

This non-provisional application claims the benefit of priority to U.S. Provisional Application No. 62/926,333, filed 25 Oct. 2019, and to U.S. Provisional Application No. 62/984,184, filed 2 Mar. 2020, each of which is incorporated by reference in its entirety.

SEQUENCE LISTING

The instant application contains a Sequence Listing which has been submitted electronically in ASCII format and is hereby incorporated by reference in its entirety. Said ASCII copy, created on Oct. 5, 2020, is named 17019_006US1_SL.txt and is 286,001 bytes in size.

FIELD OF THE INVENTION

The invention relates generally to an immunoconjugate comprising an antibody conjugated to one or more thienoazepine molecules.

BACKGROUND OF THE INVENTION

New compositions and methods for the delivery of antibodies and immune adjuvants are needed in order to reach inaccessible tumors and/or to expand treatment options for cancer patients and other subjects. The invention provides such compositions and methods.

SUMMARY OF THE INVENTION

The invention is generally directed to immunoconjugates comprising an antibody linked by conjugation to one or more thienoazepine derivatives. The invention is further directed to thienoazepine derivative intermediate compositions comprising a reactive functional group. Such intermediate compositions are suitable substrates for formation of immunoconjugates wherein an antibody may be covalently bound by a linker L to a thienoazepine (TAZ) moiety having the formula:

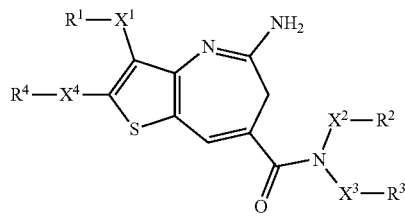

where one of $R^1$, $R^2$, $R^3$ and $R^4$ is attached to L. The $R^1$, $R^2$, $R^3$ and $R^4$ substituents are defined herein.

The invention is further directed to use of such an immunoconjugates in the treatment of an illness, in particular cancer.

An aspect of the invention is an immunoconjugate comprising an antibody covalently attached to a linker which is covalently attached to one or more thienoazepine moieties.

Another aspect of the invention is a thienoazepine-linker compound.

Another aspect of the invention is a method for treating cancer comprising administering a therapeutically effective amount of an immunoconjugate comprising an antibody linked by conjugation to one or more thienoazepine moieties.

Another aspect of the invention is a use of an immunoconjugate comprising an antibody linked by conjugation to one or more thienoazepine moieties for treating cancer.

Another aspect of the invention is a method of preparing an immunoconjugate by conjugation of one or more thienoazepine moieties with an antibody.

BRIEF DESCRIPTION OF THE DRAWINGS

FIGS. 1A-D show heavy chain and light chain CDRs of PD-L1 Type A binding agents 1-42.

FIGS. 2A-D show first (HFW1), second (HFW2), third (HFW3), and fourth (HFW4) heavy chain framework region polypeptides of PD-L1 Type A binding agents 1-42.

FIGS. 3A-D show first (LFW1), second (LFW2), third (LFW3), and fourth (LFW4) light chain framework region polypeptides of PD-L1 Type A binding agents 1-42.

FIGS. 4 A-D show heavy chain variable region (VH) of PD-L1 Type A binding agents 1-42.

FIGS. 4 E-G show light chain variable region (VL) of PD-L1 Type A binding agents 1-42.

FIGS. 5A-B show heavy chain and light chain CDRs of PD-L1 Type B binding agents 1-21.

FIGS. 6A-B show first (HFW1), second (HFW2), third (HFW3), and fourth (HFW4) heavy chain framework region polypeptides of PD-L1 Type B binding agents 1-21.

FIGS. 7A-B show first (LFW1), second (LFW2), third (LFW3), and fourth (LFW4) light chain framework region polypeptides of PD-L1 Type B binding agents 1-21.

FIGS. 8A-B show heavy chain variable region (VH) of PD-L1 Type B binding agents 1-21.

FIGS. 8C-D show light chain variable region (VL) of PD-L1 Type B binding agents 1-21.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the invention as defined by the claims.

One skilled in the art will recognize many methods and materials similar or equivalent to those described herein, which could be used in the practice of the present invention. The invention is in no way limited to the methods and materials described.

Definitions

The term "immunoconjugate" refers to an antibody construct that is covalently bonded to an adjuvant moiety via a linker, the term "adjuvant" refers to a substance capable of eliciting an immune response in a subject exposed to the adjuvant. The phrase "adjuvant moiety" refers to an adjuvant that is covalently bonded to an antibody construct, e.g., through a linker, as described herein. The adjuvant moiety can elicit the immune response while bonded to the antibody construct or after cleavage (e.g., enzymatic cleavage) from the antibody construct following administration of an immunoconjugate to the subject.

"Adjuvant" refers to a substance capable of eliciting an immune response in a subject exposed to the adjuvant. The phrase "adjuvant moiety" refers to an adjuvant that is covalently bonded to an antibody construct, e.g., through a linker, as described herein. The adjuvant moiety can elicit the immune response while bonded to the antibody construct or after cleavage (e.g., enzymatic cleavage) from the antibody construct following administration of an immunoconjugate to the subject.

The terms "Toll-like receptor" and "TLR" refer to any member of a family of highly-conserved mammalian proteins which recognizes pathogen-associated molecular patterns and acts as key signaling elements in innate immunity. TLR polypeptides share a characteristic structure that includes an extracellular domain that has leucine-rich repeats, a transmembrane domain, and an intracellular domain that is involved in TLR signaling.

The terms "Toll-like receptor 7" and "TLR7" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ99026 for human TLR7 polypeptide, or GenBank accession number AAK62676 for murine TLR7 polypeptide.

The terms "Toll-like receptor 8" and "TLR8" refer to nucleic acids or polypeptides sharing at least about 70%, about 80%, about 90%, about 95%, about 96%, about 97%, about 98%, about 99%, or more sequence identity to a publicly-available TLR7 sequence, e.g., GenBank accession number AAZ95441 for human TLR8 polypeptide, or GenBank accession number AAK62677 for murine TLR8 polypeptide.

A "TLR agonist" is a substance that binds, directly or indirectly, to a TLR (e.g., TLR7 and/or TLR8) to induce TLR signaling. Any detectable difference in TLR signaling can indicate that an agonist stimulates or activates a TLR. Signaling differences can be manifested, for example, as changes in the expression of target genes, in the phosphorylation of signal transduction components, in the intracellular localization of downstream elements such as nuclear factor-κB (NF-κB), in the association of certain components (such as IL-1 receptor associated kinase (IRAK)) with other proteins or intracellular structures, or in the biochemical activity of components such as kinases (such as mitogen-activated protein kinase (MAPK)).

"Antibody" refers to a polypeptide comprising an antigen binding region (including the complementarity determining region (CDRs)) from an immunoglobulin gene or fragments thereof. The term "antibody" specifically encompasses monoclonal antibodies (including full length monoclonal antibodies), polyclonal antibodies, multispecific antibodies (e.g., bispecific antibodies), and antibody fragments that exhibit the desired biological activity. An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa) connected by disulfide bonds. Each chain is composed of structural domains, which are referred to as immunoglobulin domains. These domains are classified into different categories by size and function, e.g., variable domains or regions on the light and heavy chains ($V_L$ and $V_H$, respectively) and constant domains or regions on the light and heavy chains ($C_L$ and $C_H$, respectively). The N-terminus of each chain defines a variable region of about 100 to 110 or more amino acids, referred to as the paratope, primarily responsible for antigen recognition, i.e., the antigen binding domain. Light chains are classified as either kappa or lambda. Heavy chains are classified as gamma, mu, alpha, delta, or epsilon, which in turn define the immunoglobulin classes, IgG, IgM, IgA, IgD and IgE, respectively. IgG antibodies are large molecules of about 150 kDa composed of four peptide chains. IgG antibodies contain two identical class γ heavy chains of about 50 kDa and two identical light chains of about 25 kDa, thus a tetrameric quaternary structure. The two heavy chains are linked to each other and to a light chain each by disulfide bonds. The resulting tetramer has two identical halves, which together form the Y-like shape. Each end of the fork contains an identical antigen binding domain. There are four IgG subclasses (IgG1, IgG2, IgG3, and IgG4) in humans, named in order of their abundance in serum (i.e., IgG1 is the most abundant). Typically, the antigen binding domain of an antibody will be most critical in specificity and affinity of binding to cancer cells.

"Antibody construct" refers to an antibody or a fusion protein comprising (i) an antigen binding domain and (ii) an Fc domain.

In some embodiments, the binding agent is an antigen-binding antibody "fragment," which is a construct that comprises at least an antigen-binding region of an antibody, alone or with other components that together constitute the antigen-binding construct. Many different types of antibody "fragments" are known in the art, including, for instance, (i) a Fab fragment, which is a monovalent fragment consisting of the $V_L$, $V_H$, $C_L$, and $CH_1$ domains, (ii) a F(ab')$_2$ fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an F(ab')$_2$ fragment using mild reducing conditions, (v) a disulfide-stabilized Fv fragment (dsFv), and (vi) a single chain Fv (scFv), which is a monovalent molecule consisting of the two domains of the Fv fragment (i.e., $V_L$ and $V_H$) joined by a synthetic linker which enables the two domains to be synthesized as a single polypeptide chain.

The antibody or antibody fragments can be part of a larger construct, for example, a conjugate or fusion construct of the antibody fragment to additional regions. For instance, in some embodiments, the antibody fragment can be fused to an Fc region as described herein. In other embodiments, the antibody fragment (e.g., a Fab or scFv) can be part of a chimeric antigen receptor or chimeric T-cell receptor, for instance, by fusing to a transmembrane domain (optionally with an intervening linker or "stalk" (e.g., hinge region)) and optional intercellular signaling domain. For instance, the antibody fragment can be fused to the gamma and/or delta chains of a t-cell receptor, so as to provide a T-cell receptor like construct that binds PD-L1. In yet another embodiment, the antibody fragment is part of a bispecific T-cell engager (BiTEs) comprising a CD1 or CD3 binding domain and linker.

"Epitope" means any antigenic determinant or epitopic determinant of an antigen to which an antigen binding domain binds (i.e., at the paratope of the antigen binding domain). Antigenic determinants usually consist of chemically active surface groupings of molecules, such as amino acids or sugar side chains, and usually have specific three dimensional structural characteristics, as well as specific charge characteristics.

The terms "Fc receptor" or "FcR" refer to a receptor that binds to the Fc region of an antibody. There are three main classes of Fc receptors: (1) FcγR which bind to IgG, (2) FcαR which binds to IgA, and (3) FcεR which binds to IgE. The FcγR family includes several members, such as FcγI (CD64), FcγRIIA (CD32A), FcγRIIB (CD32B), FcγRIIIA (CD16A), and FcγRIIIB (CD16B). The Fcγ receptors differ in their affinity for IgG and also have different affinities for the IgG subclasses (e.g., IgG1, IgG2, IgG3, and IgG4).

Nucleic acid or amino acid sequence "identity," as referenced herein, can be determined by comparing a nucleic acid or amino acid sequence of interest to a reference nucleic acid or amino acid sequence. The percent identity is the number of nucleotides or amino acid residues that are the same (i.e., that are identical) as between the optimally aligned sequence of interest and the reference sequence divided by the length of the longest sequence (i.e., the length of either the sequence of interest or the reference sequence, whichever is longer). Alignment of sequences and calculation of percent identity can be performed using available software programs. Examples of such programs include CLUSTAL-W, T-Coffee, and ALIGN (for alignment of nucleic acid and amino acid sequences), BLAST programs (e.g., BLAST 2.1, BL2SEQ, BLASTp, BLASTn, and the like) and FASTA programs (e.g., FASTA3x, FASTM, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 706(10): 3770-3775 (2009), Durbin et al., eds., *Biological Sequence Analysis; Probalistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)). Percent (%) identity of sequences can be also calculated, for example, as $100 \times [(\text{identical positions})/\min(TG_A, TG_B)]$, where $TG_A$ and $TG_B$ are the sum of the number of residues and internal gap positions in peptide sequences A and B in the alignment that minimizes $TG_A$ and $TG_B$. See, e.g., Russell et al., *J. Mol Biol.*, 244: 332-350 (1994).

The binding agent comprises Ig heavy and light chain variable region polypeptides that together form the antigen binding site. Each of the heavy and light chain variable regions are polypeptides comprising three complementarity determining regions (CDR1, CDR2, and CDR3) connected by framework regions. The binding agent can be any of a variety of types of binding agents known in the art that comprise Ig heavy and light chains. For instance, the binding agent can be an antibody, an antigen-binding antibody "fragment," or a T-cell receptor.

"Biosimilar" refers to an approved antibody construct that has active properties similar to, for example, a PD-L1-targeting antibody construct previously approved such as atezolizumab (TECENTRIQ™, Genentech, Inc.), durvalumab (IMFINZI™, AstraZeneca), and avelumab (BAVENCIO™, EMD Serono, Pfizer); a HER2-targeting antibody construct previously approved such as trastuzumab (HERCEPTIN™, Genentech, Inc.), and pertuzumab (PERJETA™, Genentech, Inc.); or a CEA-targeting antibody such as labetuzumab (CEA-CIDE™, MN-14, hMN14, Immunomedics) CAS Reg. No. 219649-07-7).

"Biobetter" refers to an approved antibody construct that is an improvement of a previously approved antibody construct, such as atezolizumab, durvalumab, avelumab, trastuzumab, pertuzumab, and labetuzumab. The biobetter can have one or more modifications (e.g., an altered glycan profile, or a unique epitope) over the previously approved antibody construct.

"Amino acid" refers to any monomeric unit that can be incorporated into a peptide, polypeptide, or protein. Amino acids include naturally-occurring α-amino acids and their stereoisomers, as well as unnatural (non-naturally occurring) amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid). The amino acids can be glycosylated (e.g., A-linked glycans, O-linked glycans, phosphoglycans, C-linked glycans, or glypication) or deglycosylated. Amino acids may be referred to herein by either the commonly known three letter symbols or by the one-letter symbols recommended by the IUPAC-IUB Biochemical Nomenclature Commission.

Naturally-occurring amino acids are those encoded by the genetic code, as well as those amino acids that are later modified, e.g., hydroxyproline, γ-carboxyglutamate, and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Naturally-occurring amino acids include those formed in proteins by post-translational modification, such as citrulline (Cit).

Unnatural (non-naturally occurring) amino acids include, without limitation, amino acid analogs, amino acid mimetics, synthetic amino acids, TV-substituted glycines, and A-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, and methionine methyl sulfonium. "Amino acid mimetics" refer to chemical compounds that have a structure that is different from the general chemical structure of an amino acid, but that functions in a manner similar to a naturally-occurring amino acid.

"Linker" refers to a functional group that covalently bonds two or more moieties in a compound or material. For example, the linking moiety can serve to covalently bond an adjuvant moiety to an antibody construct in an immunoconjugate.

"Linking moiety" refers to a functional group that covalently bonds two or more moieties in a compound or material. For example, the linking moiety can serve to covalently bond an adjuvant moiety to an antibody in an immunoconjugate. Useful bonds for connecting linking moieties to proteins and other materials include, but are not limited to, amides, amines, esters, carbamates, ureas, thioethers, thiocarbamates, thiocarbonates, and thioureas.

"Divalent" refers to a chemical moiety that contains two points of attachment for linking two functional groups; polyvalent linking moieties can have additional points of attachment for linking further functional groups. Divalent radicals may be denoted with the suffix "diyl". For example, divalent linking moieties include divalent polymer moieties such as divalent poly(ethylene glycol), divalent cycloalkyl, divalent heterocycloalkyl, divalent aryl, and divalent heteroaryl group. A "divalent cycloalkyl, heterocycloalkyl, aryl, or heteroaryl group" refers to a cycloalkyl, heterocycloalkyl, aryl, or heteroaryl group having two points of attachment for covalently linking two moieties in a molecule or material. Cycloalkyl, heterocycloalkyl, aryl, or heteroaryl groups can be substituted or unsubstituted. Cycloalkyl, heterocycloalkyl, aryl, or heteroaryl groups can be substituted with one or more groups selected from halo, hydroxy, amino, alkylamino, amido, acyl, nitro, cyano, and alkoxy.

A wavy line ("∼") represents a point of attachment of the specified chemical moiety. If the specified chemical moiety has two wavy lines ("∼") present, it will be understood that the chemical moiety can be used bilaterally, i.e., as read from left to right or from right to left. In some embodiments, a specified moiety having two wavy lines ("∼") present is considered to be used as read from left to right.

"Alkyl" refers to a straight (linear) or branched, saturated, aliphatic radical having the number of carbon atoms indicated. Alkyl can include any number of carbons, for example from one to twelve. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, and the like. Alkyl groups can be substituted or unsubstituted. "Substituted alkyl" groups can be substituted with one or more groups selected from halo, hydroxy, amino, oxo (=O), alkylamino, amido, acyl, nitro, cyano, and alkoxy.

The term "alkyldiyl" refers to a divalent alkyl radical. Examples of alkyldiyl groups include, but are not limited to, methylene (—CH$_2$—), ethylene (—CH$_2$CH$_2$—), propylene (—CH$_2$CH$_2$CH$_2$—), and the like. An alkyldiyl group may also be referred to as an "alkylene" group.

"Alkenyl" refers to a straight (linear) or branched, unsaturated, aliphatic radical having the number of carbon atoms indicated and at least one carbon-carbon double bond, sp2. Alkenyl can include from two to about 12 or more carbons atoms. Alkenyl groups are radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$). butenyl, pentenyl, and isomers thereof. Alkenyl groups can be substituted or unsubstituted. "Substituted alkenyl" groups can be substituted with one or more groups selected from halo, hydroxy, amino, oxo (=O), alkylamino, amido, acyl, nitro, cyano, and alkoxy.

The terms "alkenylene" or "alkenyldiyl" refer to a linear or branched-chain divalent hydrocarbon radical. Examples include, but are not limited to, ethylenylene or vinylene (—CH=CH—), allyl (—CH$_2$CH=CH—), and the like.

"Alkynyl" refers to a straight (linear) or branched, unsaturated, aliphatic radical having the number of carbon atoms indicated and at least one carbon-carbon triple bond, sp. Alkynyl can include from two to about 12 or more carbons atoms. For example, C$_2$-C$_6$ alkynyl includes, but is not limited to ethynyl (—C≡CH), propynyl (propargyl, —CH$_2$C≡CH), butynyl, pentynyl, hexynyl, and isomers thereof Alkynyl groups can be substituted or unsubstituted. "Substituted alkynyl" groups can be substituted with one or more groups selected from halo, hydroxy, amino, oxo (=O), alkylamino, amido, acyl, nitro, cyano, and alkoxy.

The term "alkynylene" or "alkynyldiyl" refer to a divalent alkynyl radical.

The terms "carbocycle", "carbocyclyl", "carbocyclic ring" and "cycloalkyl" refer to a saturated or partially unsaturated, monocyclic, fused bicyclic, or bridged polycyclic ring assembly containing from 3 to 12 ring atoms, or the number of atoms indicated. Saturated monocyclic carbocyclic rings include, for example, cyclopropyl, cyclobutyl, cyclopentyl, cyclohexyl, and cyclooctyl. Saturated bicyclic and polycyclic carbocyclic rings include, for example, norbornane, [2.2.2] bicyclooctane, decahydronaphthalene and adamantane. Carbocyclic groups can also be partially unsaturated, having one or more double or triple bonds in the ring. Representative carbocyclic groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene.

The term "cycloalkyldiyl" refers to a divalent cycloalkyl radical.

"Aryl" refers to a monovalent aromatic hydrocarbon radical of 6-20 carbon atoms (C$_6$-C$_{20}$) derived by the removal of one hydrogen atom from a single carbon atom of a parent aromatic ring system. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl.

The terms "arylene" or "aryldiyl" mean a divalent aromatic hydrocarbon radical of 6-20 carbon atoms (C$_6$-C$_{20}$) derived by the removal of two hydrogen atom from a two carbon atoms of a parent aromatic ring system. Some aryldiyl groups are represented in the exemplary structures as "Ar". Aryldiyl includes bicyclic radicals comprising an aromatic ring fused to a saturated, partially unsaturated ring, or aromatic carbocyclic ring. Typical aryldiyl groups include, but are not limited to, radicals derived from benzene (phenyldiyl), substituted benzenes, naphthalene, anthracene, biphenylene, indenylene, indanylene, 1,2-dihydronaphthalene, 1,2,3,4-tetrahydronaphthyl, and the like. Aryldiyl groups are also referred to as "arylene", and are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heterocyclyldiyl" refers to a divalent, saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents as described. Examples of 5-membered and 6-membered heterocyclyldiyls include morpholinyldiyl, piperidinyldiyl, piperazinyldiyl, pyrrolidinyldiyl, dioxanyldiyl, thiomorpholinyldiyl, and S-dioxothiomorpholinyldiyl.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The term "heteroaryldiyl" refers to a divalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of 5-membered and 6-membered heteroaryldiyls include pyridyldiyl, imidazolyldiyl, pyrimidinyldiyl, pyrazolyldiyl, triazolyldiyl, pyrazinyldiyl, tetrazolyldiyl, furyldiyl, thienyldiyl, isoxazolyldiyl, thiazolyldiyl, oxadiazolyldiyl, oxazolyldiyl, isothiazolyldiyl, and pyrrolyldiyl.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "halo" and "halogen," by themselves or as part of another substituent, refer to a fluorine, chlorine, bromine, or iodine atom.

The term "carbonyl," by itself or as part of another substituent, refers to C(=O) or —C(=O)—, i.e., a carbon atom double-bonded to oxygen and bound to two other groups in the moiety having the carbonyl.

As used herein, the phrase "quaternary ammonium salt" refers to a tertiary amine that has been quaternized with an alkyl substituent (e.g., a $C_1$-$C_4$ alkyl such as methyl, ethyl, propyl, or butyl).

The terms "treat," "treatment," and "treating" refer to any indicia of success in the treatment or amelioration of an injury, pathology, condition (e.g., cancer), or symptom (e.g., cognitive impairment), including any objective or subjective parameter such as abatement; remission; diminishing of symptoms or making the symptom, injury, pathology, or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, for example, the result of a physical examination.

The terms "cancer," "neoplasm," and "tumor" are used herein to refer to cells which exhibit autonomous, unregulated growth, such that the cells exhibit an aberrant growth phenotype characterized by a significant loss of control over cell proliferation. Cells of interest for detection, analysis, and/or treatment in the context of the invention include cancer cells (e.g., cancer cells from an individual with cancer), malignant cancer cells, pre-metastatic cancer cells, metastatic cancer cells, and non-metastatic cancer cells. Cancers of virtually every tissue are known. The phrase "cancer burden" refers to the quantum of cancer cells or cancer volume in a subject. Reducing cancer burden accordingly refers to reducing the number of cancer cells or the cancer cell volume in a subject. The term "cancer cell" as used herein refers to any cell that is a cancer cell (e.g., from any of the cancers for which an individual can be treated, e.g., isolated from an individual having cancer) or is derived from a cancer cell, e.g., clone of a cancer cell. For example, a cancer cell can be from an established cancer cell line, can be a primary cell isolated from an individual with cancer, can be a progeny cell from a primary cell isolated from an individual with cancer, and the like. In some embodiments, the term can also refer to a portion of a cancer cell, such as a sub-cellular portion, a cell membrane portion, or a cell lysate of a cancer cell. Many types of cancers are known to those of skill in the art, including solid tumors such as carcinomas, sarcomas, glioblastomas, melanomas, lymphomas, and myelomas, and circulating cancers such as leukemias.

As used herein, the term "cancer" includes any form of cancer, including but not limited to, solid tumor cancers (e.g., skin, lung, prostate, breast, gastric, bladder, colon, ovarian, pancreas, kidney, liver, glioblastoma, medulloblastoma, leiomyosarcoma, head & neck squamous cell carcinomas, melanomas, and neuroendocrine) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors.

"PD-L1 expression" refers to a cell that has a PD-L1 receptor on the cell's surface. As used herein "PD-L1 overexpression" refers to a cell that has more PD-L1 receptors as compared to corresponding non-cancer cell.

"HER2" refers to the protein human epidermal growth factor receptor 2.

"HER2 expression" refers to a cell that has a HER2 receptor on the cell's surface. For example, a cell may have from about 20,000 to about 50,000 HER2 receptors on the cell's surface. As used herein "HER2 overexpression" refers to a cell that has more than about 50,000 HER2 receptors. For example, a cell 2, 5, 10, 100, 1,000, 10,000, 100,000, or 1,000,000 times the number of HER2 receptors as compared to corresponding non-cancer cell (e.g., about 1 or 2 million HER2 receptors). It is estimated that HER2 is overexpressed in about 25% to about 30% of breast cancers.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, and invasion of surrounding or distant tissues or organs, such as lymph nodes.

As used herein, the phrases "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs, therefore, tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part that is not directly connected to the organ of the original cancerous tumor. Metastasis can also be defined as several steps of a process, such as the departure of cancer cells from an original tumor site, and migration and/or invasion of cancer cells to other parts of the body.

The phrases "effective amount" and "therapeutically effective amount" refer to a dose or amount of a substance such as an immunoconjugate that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); *Goodman & Gilman's The Pharmacological Basis of Therapeutics*, $11^{th}$ Edition (McGraw-Hill, 2006); and *Remington; The Science and Practice of Pharmacy*, $22^{nd}$ Edition, (Pharmaceutical Press, London, 2012)). In the case of cancer, the therapeutically effective amount of the immunoconjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the immunoconjugate may prevent growth and/or kill existing cancer cells, it may be cytostatic and/or cytotoxic. For cancer therapy, efficacy can, for example, be measured by assessing the time to disease progression (TTP) and/or determining the response rate (RR)

"Recipient," "individual," "subject," "host," and "patient" are used interchangeably and refer to any mammalian subject for whom diagnosis, treatment, or therapy is desired (e.g., humans). "Mammal" for purposes of treatment refers to any animal classified as a mammal, including humans, domestic and farm animals, and zoo, sports, or pet animals, such as dogs, horses, cats, cows, sheep, goats, pigs, camels, etc. In certain embodiments, the mammal is human.

The phrase "synergistic adjuvant" or "synergistic combination" in the context of this invention includes the combination of two immune modulators such as a receptor agonist, cytokine, and adjuvant polypeptide, that in combination elicit a synergistic effect on immunity relative to either administered alone. Particularly, the immunoconjugates disclosed herein comprise synergistic combinations of the claimed adjuvant and antibody construct. These synergistic combinations upon administration elicit a greater effect on immunity, e.g., relative to when the antibody construct or adjuvant is administered in the absence of the other moiety.

Further, a decreased amount of the immunoconjugate may be administered (as measured by the total number of antibody constructs or the total number of adjuvants administered as part of the immunoconjugate) compared to when either the antibody construct or adjuvant is administered alone.

As used herein, the term "administering" refers to parenteral, intravenous, intraperitoneal, intramuscular, intratumoral, intralesional, intranasal, or subcutaneous administration, oral administration, administration as a suppository, topical contact, intrathecal administration, or the implantation of a slow-release device, e.g., a mini-osmotic pump, to the subject.

The terms "about" and "around," as used herein to modify a numerical value, indicate a close range surrounding the numerical value. Thus, if "X" is the value, "about X" or "around X" indicates a value of from 0.9X to 1.1X, e.g., from 0.95X to 1.05X or from 0.99X to 1.01X. A reference to "about X" or "around X" specifically indicates at least the values X, 0.95X, 0.96X, 0.97X, 0.98X, 0.99X, 1.01X, 1.02X, 1.03X, 1.04X, and 1.05X. Accordingly, "about X" and "around X" are intended to teach and provide written description support for a claim limitation of, e.g., "0.98X."

Antibodies

The immunoconjugate of the invention comprises an antibody. Included in the scope of the embodiments of the invention are functional variants of the antibody constructs or antigen binding domain described herein. The term "functional variant" as used herein refers to an antibody construct having an antigen binding domain with substantial or significant sequence identity or similarity to a parent antibody construct or antigen binding domain, which functional variant retains the biological activity of the antibody construct or antigen binding domain of which it is a variant. Functional variants encompass, for example, those variants of the antibody constructs or antigen binding domain described herein (the parent antibody construct or antigen binding domain) that retain the ability to recognize target cells expressing PD-L1, HER2 or CEA to a similar extent, the same extent, or to a higher extent, as the parent antibody construct or antigen binding domain.

In reference to the antibody construct or antigen binding domain, the functional variant can, for instance, be at least about 30%, about 50%, about 75%, about 80%, about 85%, about 90%, about 91%, about 92%, about 93%, about 94%, about 95%, about 96%, about 97%, about 98%, about 99% or more identical in amino acid sequence to the antibody construct or antigen binding domain.

A functional variant can, for example, comprise the amino acid sequence of the parent antibody construct or antigen binding domain with at least one conservative amino acid substitution. Alternatively, or additionally, the functional variants can comprise the amino acid sequence of the parent antibody construct or antigen binding domain with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent antibody construct or antigen binding domain.

The antibodies comprising the immunoconjugates of the invention include Fc engineered variants. In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/I332E/A330L), GA (G236A), ALIE (A330L/I332E), GASDALIE (G236A/S239D/A330L/I332E), V9 (G237D/P238D/P271G/A330R), and V11 (G237D/P238D/H268D/P271G/A330R), and/or one or more mutations at the following amino acids: E345R, E233, G237, P238, H268, P271, L328 and A330. Additional Fc region modifications for modulating Fc receptor binding are described in, for example, U.S. Patent Application Publication 2016/0145350 and U.S. Pat. Nos. 7,416,726 and 5,624,821, which are hereby incorporated by reference in their entireties herein.

The antibodies comprising the immunoconjugates of the invention include glycan variants, such as afucosylation. In some embodiments, the Fc region of the binding agents are modified to have an altered glycosylation pattern of the Fc region compared to the native non-modified Fc region.

Amino acid substitutions of the inventive antibody constructs or antigen binding domains are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g., Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The antibody construct or antigen binding domain can consist essentially of the specified amino acid sequence or sequences described herein, such that other components, e.g., other amino acids, do not materially change the biological activity of the antibody construct or antigen binding domain functional variant.

In some embodiments, the antibodies in the immunoconjugates contain a modified Fc region, wherein the modification modulates the binding of the Fc region to one or more Fc receptors.

In some embodiments, the antibodies in the immunoconjugates (e.g., antibodies conjugated to at least two adjuvant moieties) contain one or more modifications (e.g., amino acid insertion, deletion, and/or substitution) in the Fc region that results in modulated binding (e.g., increased binding or decreased binding) to one or more Fc receptors (e.g., FcγRI (CD64), FcγRIIA (CD32A), FcγRIIB (CD32B), FcγRIIIA (CD16a), and/or FcγRIIIB (CD16b)) as compared to the native antibody lacking the mutation in the Fc region. In some embodiments, the antibodies in the immunoconjugates contain one or more modifications (e.g., amino acid insertion, deletion, and/or substitution) in the Fc region that reduce the binding of the Fc region of the antibody to FcγRIIB. In some embodiments, the antibodies in the immunoconjugates contain one or more modifications (e.g., amino acid insertion, deletion, and/or substitution) in the Fc region of the antibody that reduce the binding of the antibody to FcγRIIB while maintaining the same binding or having increased binding to FcγRI (CD64), FcγRIIA (CD32A), and/or FcRγIIIA (CD16a) as compared to the native antibody lacking the mutation in the Fc region. In some embodiments, the antibodies in the immunoconjugates contain one of more modifications in the Fc region that increase the binding of the Fc region of the antibody to FcγRIIB.

In some embodiments, the modulated binding is provided by mutations in the Fc region of the antibody relative to the native Fc region of the antibody. The mutations can be in a CH2 domain, a CH3 domain, or a combination thereof. A "native Fc region" is synonymous with a "wild-type Fc region" and comprises an amino acid sequence that is identical to the amino acid sequence of an Fc region found in nature or identical to the amino acid sequence of the Fc region found in the native antibody (e.g., cetuximab). Native sequence human Fc regions include a native sequence human IgG1 Fc region, native sequence human IgG2 Fc region, native sequence human IgG3 Fc region, and native sequence human IgG4 Fc region, as well as naturally occurring variants thereof. Native sequence Fc includes the various allotypes of Fcs (Jefferis et al., (2009) *mAbs,* 1(4):332-338).

In some embodiments, the mutations in the Fc region that result in modulated binding to one or more Fc receptors can include one or more of the following mutations: SD (S239D), SDIE (S239D/I332E), SE (S267E), SELF (S267E/L328F), SDIE (S239D/I332E), SDIEAL (S239D/I332E/A330L), GA (G236A), ALIE (A330L/I332E), GASDALIE (G236A/S239D/A330L/I332E), V9 (G237D/P238D/P271G/A330R), and V11 (G237D/P238D/H268D/P271G/A330R), and/or one or more mutations at the following amino acids: E233, G237, P238, H268, P271, L328 and A330. Additional Fc region modifications for modulating Fc receptor binding are described in, for example, US 2016/0145350 and U.S. Pat. Nos. 7,416,726 and 5,624,821, which are hereby incorporated by reference in their entireties.

In some embodiments, the Fc region of the antibodies of the immunoconjugates are modified to have an altered glycosylation pattern of the Fc region compared to the native non-modified Fc region.

Human immunoglobulin is glycosylated at the Asn297 residue in the Cγ2 domain of each heavy chain. This N-linked oligosaccharide is composed of a core heptasaccharide, N-acetylglucosamine4Mannose3 (GlcNAc4Man3). Removal of the heptasaccharide with endoglycosidase or PNGase F is known to lead to conformational changes in the antibody Fc region, which can significantly reduce antibody-binding affinity to activating FcγR and lead to decreased effector function. The core heptasaccharide is often decorated with galactose, bisecting GlcNAc, fucose, or sialic acid, which differentially impacts Fc binding to activating and inhibitory FcγR. Additionally, it has been demonstrated that α2,6-sialyation enhances anti-inflammatory activity in vivo, while defucosylation leads to improved FcγRIIIa binding and a 10-fold increase in antibody-dependent cellular cytotoxicity and antibody-dependent phagocytosis. Specific glycosylation patterns, therefore, can be used to control inflammatory effector functions.

In some embodiments, the modification to alter the glycosylation pattern is a mutation. For example, a substitution at Asn297. In some embodiments, Asn297 is mutated to glutamine (N297Q). Methods for controlling immune response with antibodies that modulate FcγR-regulated signaling are described, for example, in U.S. Pat. No. 7,416,726 and U.S. Patent Application Publications 2007/0014795 and 2008/0286819, which are hereby incorporated by reference in their entireties.

In some embodiments, the antibodies of the immunoconjugates are modified to contain an engineered Fab region with a non-naturally occurring glycosylation pattern. For example, hybridomas can be genetically engineered to secrete afucosylated mAb, desialylated mAb or deglycosylated Fc with specific mutations that enable increased FcRγIIIa binding and effector function. In some embodiments, the antibodies of the immunoconjugates are engineered to be afucosylated.

In some embodiments, the entire Fc region of an antibody in the immunoconjugates is exchanged with a different Fc region, so that the Fab region of the antibody is conjugated to a non-native Fc region. For example, the Fab region of cetuximab, which normally comprises an IgG1 Fc region, can be conjugated to IgG2, IgG3, IgG4, or IgA, or the Fab region of nivolumab, which normally comprises an IgG4 Fc region, can be conjugated to IgG1, IgG2, IgG3, IgA1, or IgG2. In some embodiments, the Fc modified antibody with a non-native Fc domain also comprises one or more amino acid modification, such as the S228P mutation within the IgG4 Fc, that modulate the stability of the Fc domain described. In some embodiments, the Fc modified antibody with a non-native Fc domain also comprises one or more amino acid modifications described herein that modulate Fc binding to FcR.

In some embodiments, the modifications that modulate the binding of the Fc region to FcR do not alter the binding of the Fab region of the antibody to its antigen when compared to the native non-modified antibody. In other embodiments, the modifications that modulate the binding of the Fc region to FcR also increase the binding of the Fab region of the antibody to its antigen when compared to the native non-modified antibody.

In an exemplary embodiment, the immunoconjugates of the invention comprise an antibody construct that comprises an antigen binding domain that specifically recognizes and binds PD-L1.

Programmed Death-Ligand 1 (PD-L1, cluster of differentiation 274, CD274, B7-homolog 1, or B7-H1) belongs to the B7 protein superfamily, and is a ligand of programmed cell death protein 1 (PD-1, PDCD1, cluster of differentiation 279, or CD279). PD-L1 can also interact with B7.1 (CD80) and such interaction is believed to inhibit T cell priming. The PD-L1/PD-1 axis plays a large role in suppressing the adaptive immune response. More specifically, it is believed that engagement of PD-L1 with its receptor, PD-1, delivers a signal that inhibits activation and proliferation of T-cells. Agents that bind to PD-L1 and prevent the ligand from binding to the PD-1 receptor prevent this immunosuppression, and can, therefore, enhance an immune response when desired, such as for the treatment of cancers, or infections. PD-L1/PD-1 pathway also contributes to preventing autoimmunity and therefore agonistic agents against PD-L1 or agents that deliver immune inhibitory payloads may help treatment of autoimmune disorders.

Several antibodies targeting PD-L1 have been developed for the treatment of cancer, including atezolizumab (TECENTRIQ™), durvalumab (IMFINZI™), and avelumab (BAVENCIO™). Nevertheless, there continues to be a need for new PD-L1-binding agents, including agents that bind PD-L1 with high affinity and effectively prevent PD-L1/PD-1 signaling and agents that can deliver therapeutic payloads to PD-L1 expressing cells. In addition, there is a need for new PD-L1-binding agents to treat autoimmune disorders and infections.

A method is provided of delivering a thienoazepine derivative payload to a cell expressing PD-L1 comprising administering to the cell, or mammal comprising the cell, an immunoconjugate comprising an anti-PD-L1 antibody covalently attached to a linker which is covalently attached to one or more thienoazepine moieties.

Also provided is a method for enhancing or reducing or inhibiting an immune response in a mammal, and a method for treating a disease, disorder, or condition in a mammal that is responsive to PD-L1 inhibition, which methods comprise administering a PD-L1 immunoconjugate thereof, to the mammal.

The invention provides a PD-L1 binding agent comprising an immunoglobulin heavy chain variable region polypeptide and an immunoglobulin light chain variable region polypeptide.

The PD-L1 binding agent specifically binds PD-L1. The binding specificity of the agent allows for targeting PD-L1 expressing cells, for instance, to deliver therapeutic payloads to such cells.

In some embodiments, the PD-L1 binding agent (Type A or Type B) binds to human PD-L1, for example, a protein comprising SEQ ID NO: 307. However, binding agents that bind to any PD-L1 homolog or paralog also are encompassed. In some embodiments, the PD-L1 protein comprises at least about 70%, about 75%, about 80%, about 85%, about 90%, about 91%, about 92%, about 93%, about 94%, about 95%, about 96%, about 97%, about 98%, about 99%, or more sequence identity to SEQ ID NO: 307. In some embodiments, the binding agent binds human PD-L1 and cynomolgus PD-L1; or human, cynomolgus and mouse PD-L1.

SEQ ID NO: 307
MRIFAVFIFMTYWHLLNAFTVTVPKDLYVVEYGSNMTIECKFPVEKQLDL

AALIVYWEMEDKNITQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET

In some embodiments, the PD-L1 binding agent binds PD-L1 without substantially inhibiting or preventing PD-L1 from binding to its receptor, PD-1. However, in other embodiments, the PD-L1 binding agent can completely or partially block (inhibit or prevent) binding of PD-L1 to its receptor, PD-1, such that the antibody can be used to inhibit PD-L1/PD-1 signaling (e.g., for therapeutic purposes).

The antibody or antigen-binding antibody fragment can be monospecific for PD-L1, or can be bispecific or multispecific. For instance, in bivalent or multivalent antibodies or antibody fragments, the binding domains can be different targeting different epitopes of the same antigen or targeting different antigens. Methods of constructing multivalent binding constructs are known in the art. Bispecific and multispecific antibodies are known in the art. Furthermore, a diabody, triabody, or tetrabody can be provided, which is a dimer, trimer, or tetramer of polypeptide chains each comprising a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a multimeric molecule having two, three, or four functional antigen binding sites. Also, bis-scFv fragments, which are small scFv fragments with two different variable domains can be generated to produce bispecific bis-scFv fragments capable of binding two different epitopes. Fab dimers (Fab2) and Fab trimers (Fab3) can be produced using genetic engineering methods to create multispecific constructs based on Fab fragments.

The PD-L1-binding agent also can be an antibody conjugate. In this respect, the PD-L1-binding agent can be a conjugate of (1) an antibody, an alternative scaffold, or fragments thereof, and (2) a protein or non-protein moiety. For example, the PD-L1 binding agent can be conjugated to a peptide, a fluorescent molecule, chemotherapeutic or other cytotoxic payload, immune-activating or immune-suppressive agent.

The PD-L1-binding agent can be, or can be obtained from, a human antibody, a non-human antibody, a humanized antibody, or a chimeric antibody, or corresponding antibody fragments. A "chimeric" antibody is an antibody or fragment thereof typically comprising human constant regions and non-human variable regions. A "humanized" antibody is a monoclonal antibody typically comprising a human antibody scaffold but with non-human origin amino acids or sequences in at least one CDR (e.g., 1, 2, 3, 4, 5, or all six CDRs).

PD-L1-Binding Agents—Type A

Provided herein are PD-L1 binding agents comprising an immunoglobulin heavy chain variable region polypeptide and an immunoglobulin light chain variable region polypeptide. In some embodiments, the PD-L1 binding agents (Type A) comprise an immunoglobulin heavy chain variable region of any one of SEQ ID NOs: 223-264, or at least the CDRs thereof; and an immunoglobulin light chain variable region of any one of SEQ ID NOs: 265-306 or at least the CDRs thereof. In other embodiments, the PD-L1 binding agents (Type A) comprise an immunoglobulin heavy chain variable region polypeptide with an amino acid sequence that is at least 90% identical to any one of SEQ ID NOs: 223-264, and an immunoglobulin light chain variable region polypeptide with an amino acid sequence that is at least 90% identical to any one of SEQ ID NOs: 265-306. In yet other embodiments, the PD-L1 binding agent (Type A), the immunoglobulin heavy chain variable region polypeptide comprises a complementarity determining region 1 (HCDR1) comprising any one of SEQ ID NOs: 1-23, a complementarity determining region 2 (HCDR2) comprising any one of SEQ ID NOs: 24-57, and a complementarity determining region 3 (HCDR3) comprising any one of SEQ ID NOs: 58-95; and/or the immunoglobulin light chain variable region polypeptide comprises a complementarity determining region 1 (LCDR1) comprising any one of SEQ ID NOs: 96-128, a complementarity determining region 2 (LCDR2) comprising any one of SEQ ID NOs: 129-151, and a complementarity determining region 3 (LCDR3) comprising any one of SEQ ID NOs: 152-155. Also provided are nucleic acids encoding the PD-L1 binding agents, or the individual heavy and light chains thereof; vectors and cells comprising the nucleic acids; and compositions comprising the binding agents or nucleic acids.

Furthermore, in some embodiments, the PD-L1 binding agents (Type A) provided herein cause cellular internalization of PD-L1 or the PD-L1/PD-L1 binding agent complex upon binding to PD-L1 on the cell surface. Without wishing to be bound by any particular theory or mechanism of action, it is believed that the PD-L1 binding agents according to this embodiment cause PD-L1 internalization upon binding, and remain bound to PD-L1 during internalization resulting in internalization of the binding agent along with PD-L1. Cellular internalization of PD-L1 and bound PD-L1 binding agent can be determined by any suitable method, such as assaying for persistence on the cell surface and/or detection of internalized antibodies. In some embodiments, the PD-L1 binding agent internalizes strongly enough that at least about 25% (e.g., at least about 35%, at least about 50%, at least about 75%, or at least about 90%) of the PD-L1 binding agent that binds PD-L1 on the cell surface is internalized (e.g., using a surface persistence assay, about 75% or less, about 65% or less, about 50% or less, about 25% or less or about 10% or less of PD-L1 binding agent molecules bound to PD-L1 on the cell surface at the beginning of the assay remain bound at the end of the assay).

In an embodiment, the PD-L1 binding agent (Type A) comprises an immunoglobulin heavy chain variable region of any one of SEQ ID NOs: 223-264, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 223-264, or at least the CDRs thereof; and/or an immunoglobulin light chain variable region of any one of SEQ ID NOs: 265-306, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 265-306, or at least the CDRs thereof.

By way of further illustration, the PD-L1 binding agent (Type A) can comprise:

(1) an immunoglobulin heavy chain variable region of SEQ ID NO: 223, or at least the CDRs thereof, and/or an immunoglobulin light chain variable region of SEQ ID NO: 265, or at least the CDRs thereof;

(2) an immunoglobulin heavy chain variable region of SEQ ID NO: 224, or at least the CDRs thereof, and/or an immunoglobulin light chain variable region of SEQ ID NO: 266, or at least the CDRs thereof;

(3) an immunoglobulin heavy chain variable region of SEQ ID NO: 225, or at least the CDRs thereof, and/or an immunoglobulin light chain variable region of SEQ ID NO: 267, or at least the CDRs thereof;

(4) an immunoglobulin heavy chain variable region of SEQ ID NO: 226, or at least the CDRs thereof, and/or an immunoglobulin light chain variable region of SEQ ID NO: 268, or at least the CDRs thereof;

(5) an immunoglobulin heavy chain variable region of SEQ ID NO: 227, or at least the CDRs thereof, and/or an immunoglobulin light chain variable region of SEQ ID NO: 269, or at least the CDRs thereof;

(6) an immunoglobulin heavy chain variable region of SEQ ID NO: 228, or at least the CDRs thereof, and/or an immunoglobulin light chain variable region of SEQ ID NO: 270, or at least the CDRs thereof;

(7) an immunoglobulin heavy chain variable region of SEQ ID NO: 229, or at least the CDRs thereof, and/or an immunoglobulin light chain variable region of SEQ ID NO: 271, or at least the CDRs thereof;

(8) an immunoglobulin heavy chain variable region of SEQ ID NO: 230, or at least the CDRs thereof, and/or an immunoglobulin light chain variable region of SEQ ID NO: 272, or at least the CDRs thereof;

(9) an immunoglobulin heavy chain variable region of SEQ ID NO: 231, or at least the CDRs thereof, and/or an immunoglobulin light chain variable region of SEQ ID NO: 273, or at least the CDRs thereof;

(10) an immunoglobulin heavy chain variable region of SEQ ID NO: 232, or at least the CDRs thereof, and/or an immunoglobulin light chain variable region of SEQ ID NO: 274, or at least the CDRs thereof;

(11) an immunoglobulin heavy chain variable region of SEQ ID NO: 233, or at least the CDRs thereof, and/or an immunoglobulin light chain variable region of SEQ ID NO: 275, or at least the CDRs thereof;

(12) an immunoglobulin heavy chain variable region of SEQ ID NO: 234, or at least the CDRs thereof, and/or an immunoglobulin light chain variable region of SEQ ID NO: 276, or at least the CDRs thereof;

(13) an immunoglobulin heavy chain variable region of SEQ ID NO: 235, or at least the CDRs thereof, and/or an immunoglobulin light chain variable region of SEQ ID NO: 277, or at least the CDRs thereof;

(14) an immunoglobulin heavy chain variable region of SEQ ID NO: 236, or at least the CDRs thereof, and/or an immunoglobulin light chain variable region of SEQ ID NO: 278, or at least the CDRs thereof;

(15) an immunoglobulin heavy chain variable region of SEQ ID NO: 237, or at least the CDRs thereof, and/or an immunoglobulin light chain variable region of SEQ ID NO: 279, or at least the CDRs thereof;

(16) an immunoglobulin heavy chain variable region of SEQ ID NO: 238, or at least the CDRs thereof, and/or an immunoglobulin light chain variable region of SEQ ID NO: 280, or at least the CDRs thereof;

(17) an immunoglobulin heavy chain variable region of SEQ ID NO: 239, or at least the CDRs thereof, and/or an immunoglobulin light chain variable region of SEQ ID NO: 281, or at least the CDRs thereof;

(18) an immunoglobulin heavy chain variable region of SEQ ID NO: 240, or at least the CDRs thereof, and/or an immunoglobulin light chain variable region of SEQ ID NO: 282, or at least the CDRs thereof;

(19) an immunoglobulin heavy chain variable region of SEQ ID NO: 241, or at least the CDRs thereof, and/or an immunoglobulin light chain variable region of SEQ ID NO: 283, or at least the CDRs thereof;

(20) an immunoglobulin heavy chain variable region of SEQ ID NO: 242, or at least the CDRs thereof, and/or an immunoglobulin light chain variable region of SEQ ID NO: 284, or at least the CDRs thereof;

(21) an immunoglobulin heavy chain variable region of SEQ ID NO: 243, or at least the CDRs thereof, and/or an immunoglobulin light chain variable region of SEQ ID NO: 285, or at least the CDRs thereof;

(22) an immunoglobulin heavy chain variable region of SEQ ID NO: 244, or at least the CDRs thereof, and/or an immunoglobulin light chain variable region of SEQ ID NO: 286, or at least the CDRs thereof;

(23) an immunoglobulin heavy chain variable region of SEQ ID NO: 245, or at least the CDRs thereof, and/or an immunoglobulin light chain variable region of SEQ ID NO: 287, or at least the CDRs thereof;

(24) an immunoglobulin heavy chain variable region of SEQ ID NO: 246, or at least the CDRs thereof, and/or an immunoglobulin light chain variable region of SEQ ID NO: 288, or at least the CDRs thereof;

(25) an immunoglobulin heavy chain variable region of SEQ ID NO: 247, or at least the CDRs thereof, and/or an immunoglobulin light chain variable region of SEQ ID NO: 289, or at least the CDRs thereof;

(26) an immunoglobulin heavy chain variable region of SEQ ID NO: 248, or at least the CDRs thereof, and/or an immunoglobulin light chain variable region of SEQ ID NO: 290, or at least the CDRs thereof;

(27) an immunoglobulin heavy chain variable region of SEQ ID NO: 249, or at least the CDRs thereof, and/or an immunoglobulin light chain variable region of SEQ ID NO: 291, or at least the CDRs thereof;

(28) an immunoglobulin heavy chain variable region of SEQ ID NO: 250, or at least the CDRs thereof, and/or an immunoglobulin light chain variable region of SEQ ID NO: 292, or at least the CDRs thereof;

(29) an immunoglobulin heavy chain variable region of SEQ ID NO: 251, or at least the CDRs thereof, and/or an immunoglobulin light chain variable region of SEQ ID NO: 293, or at least the CDRs thereof;

(30) an immunoglobulin heavy chain variable region of SEQ ID NO: 252, or at least the CDRs thereof, and/or an immunoglobulin light chain variable region of SEQ ID NO: 294, or at least the CDRs thereof;

(31) an immunoglobulin heavy chain variable region of SEQ ID NO: 253, or at least the CDRs thereof, and/or an immunoglobulin light chain variable region of SEQ ID NO: 295, or at least the CDRs thereof;

(32) an immunoglobulin heavy chain variable region of SEQ ID NO: 254, or at least the CDRs thereof, and/or an immunoglobulin light chain variable region of SEQ ID NO: 296, or at least the CDRs thereof;

(33) an immunoglobulin heavy chain variable region of SEQ ID NO: 255, or at least the CDRs thereof, and/or an immunoglobulin light chain variable region of SEQ ID NO: 297, or at least the CDRs thereof;

(34) an immunoglobulin heavy chain variable region of SEQ ID NO: 256, or at least the CDRs thereof, and/or an immunoglobulin light chain variable region of SEQ ID NO: 298, or at least the CDRs thereof;

(35) an immunoglobulin heavy chain variable region of SEQ ID NO: 257, or at least the CDRs thereof, and/or an immunoglobulin light chain variable region of SEQ ID NO: 299, or at least the CDRs thereof;

(36) an immunoglobulin heavy chain variable region of SEQ ID NO: 258, or at least the CDRs thereof, and/or an immunoglobulin light chain variable region of SEQ ID NO: 300, or at least the CDRs thereof;

(37) an immunoglobulin heavy chain variable region of SEQ ID NO: 259, or at least the CDRs thereof, and/or an immunoglobulin light chain variable region of SEQ ID NO: 301, or at least the CDRs thereof;

(38) an immunoglobulin heavy chain variable region of SEQ ID NO: 260, or at least the CDRs thereof, and/or an immunoglobulin light chain variable region of SEQ ID NO: 302, or at least the CDRs thereof;

(39) an immunoglobulin heavy chain variable region of SEQ ID NO: 261, or at least the CDRs thereof, and/or an immunoglobulin light chain variable region of SEQ ID NO: 303, or at least the CDRs thereof;

(40) an immunoglobulin heavy chain variable region of SEQ ID NO: 262, or at least the CDRs thereof, and/or an immunoglobulin light chain variable region of SEQ ID NO: 304, or at least the CDRs thereof;

(41) an immunoglobulin heavy chain variable region of SEQ ID NO: 263, or at least the CDRs thereof, and/or an immunoglobulin light chain variable region of SEQ ID NO: 305, or at least the CDRs thereof;

(42) an immunoglobulin heavy chain variable region of SEQ ID NO: 164, or at least the CDRs thereof, and/or an immunoglobulin light chain variable region of SEQ ID NO: 306, or at least the CDRs thereof; and/or

(43) an immunoglobulin heavy chain variable region of FIGS. 4A-D and/or an immunoglobulin light chain variable region of FIGS. 4E-G, or at least the CDRs thereof.

The CDRs of a given heavy or light chain Ig sequence can be determined in accordance with any of the various known Ig numbering schemes (e.g., Rabat, Chothia, Martin (Enhanced Chothia), IGMT, AbM). In certain embodiments, the PD-L1 binding agent (Type A) comprises one or more of the following CDRs:

a HCDR1 comprising or consisting of any one of SEQ ID NOs: 1-23 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 1-23;

a HCDR2 comprising or consisting of any one of SEQ ID NOs: 24-57 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 24-57; and a HCDR3 comprising or consisting of any one of SEQ ID NOs: 58-95 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 58-95; and/or the immunoglobulin light chain polypeptide comprises a LCDR1 comprising or consisting of any one of SEQ ID NOs: 96-128 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 96-128;

a LCDR2 comprising or consisting of any one of SEQ ID NOs: 129-151 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 129-151; and a LCDR3 comprising or consisting of any one of SEQ ID NOs: 152-155 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 152-155.

In particular embodiments, the binding agent (Type A) comprises an immunoglobulin heavy chain polypeptide and an immunoglobulin light chain polypeptide, wherein:

(1) the immunoglobulin heavy chain polypeptide comprises a HCDR1 comprising or consisting of SEQ ID NO: 1, a HCDR2 comprising or consisting of SEQ ID NO: 24, and a HCDR3 comprising or consisting of SEQ ID NO: 58; and/or the immunoglobulin light chain polypeptide comprises a LCDR1 comprising or consisting of SEQ ID NO: 96, a LCDR2 comprising or consisting of SEQ ID NO: 129, and a LCDR3 comprising or consisting of SEQ ID NO: 152;

(2) the immunoglobulin heavy chain polypeptide comprises a HCDR1 comprising or consisting of SEQ ID NO: 2, a HCDR2 comprising or consisting of SEQ ID NO: 25, and a HCDR3 comprising or consisting of SEQ ID NO: 59; and/or the immunoglobulin light chain polypeptide comprises a LCDR1 comprising or consisting of SEQ ID NO: 97, a LCDR2 comprising or consisting of SEQ ID NO: 129, and a LCDR3 comprising or consisting of SEQ ID NO: 153;

(3) the immunoglobulin heavy chain polypeptide comprises a HCDR1 comprising or consisting of SEQ ID NO: 3, a HCDR2 comprising or consisting of SEQ ID NO: 26, and a HCDR3 comprising or consisting of SEQ ID NO: 60; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 154;

(4) the immunoglobulin heavy chain polypeptide comprises a HCDR1 comprising or consisting of SEQ ID NO: 4, a HCDR2 comprising or consisting of SEQ ID NO: 27, and a HCDR3 comprising or consisting of SEQ ID NO: 61; and/or the immunoglobulin light chain polypeptide comprises a LCDR1 comprising or consisting of SEQ ID NO: 99, a LCDR2 comprising or consisting of SEQ ID NO: 130, and a LCDR3 comprising or consisting of SEQ ID NO: 155;

(5) the immunoglobulin heavy chain polypeptide comprises a HCDR1 comprising or consisting of SEQ ID NO: 5, a HCDR2 comprising or consisting of SEQ ID NO: 28, and a HCDR3 comprising or consisting of SEQ ID NO: 62; and/or the immunoglobulin light chain polypeptide comprises a LCDR1 comprising or consisting of SEQ ID NO: 100, a LCDR2 comprising or consisting of SEQ ID NO: 129, and a LCDR3 comprising or consisting of SEQ ID NO: 153;

(6) the immunoglobulin heavy chain polypeptide comprises a HCDR1 comprising or consisting of SEQ ID NO: 6, a HCDR2 comprising or consisting of SEQ ID NO: 29, and a HCDR3 comprising or consisting of SEQ ID NO: 63; and/or the immunoglobulin light chain polypeptide comprises a LCDR1 comprising or consisting of SEQ ID NO: 101, a LCDR2 comprising or consisting of SEQ ID NO: 131, and a LCDR3 comprising or consisting of SEQ ID NO: 156;

(7) the immunoglobulin heavy chain polypeptide comprises a HCDR1 comprising or consisting of SEQ ID NO: 7, a HCDR2 comprising or consisting of SEQ ID NO: 30, and a HCDR3 comprising or consisting of SEQ ID NO: 64; and/or the immunoglobulin light chain polypeptide comprises a LCDR1 comprising or consisting of SEQ ID NO: 102, a LCDR2 comprising or consisting of SEQ ID NO: 132, and a LCDR3 comprising or consisting of SEQ ID NO: 157;

(8) the immunoglobulin heavy chain polypeptide comprises a HCDR1 comprising or consisting of SEQ ID NO: 2, a HCDR2 comprising or consisting of SEQ ID NO: 31, and a HCDR3 comprising or consisting of SEQ ID NO: 65; and/or the immunoglobulin light chain polypeptide comprises a LCDR1 comprising or consisting of SEQ ID NO: 103, a LCDR2 comprising or consisting of SEQ ID NO: 133, and a LCDR3 comprising or consisting of SEQ ID NO: 155;

(9) the immunoglobulin heavy chain polypeptide comprises a HCDR1 comprising or consisting of SEQ ID NO: 8, a HCDR2 comprising or consisting of SEQ ID NO: 32, and a HCDR3 comprising or consisting of SEQ ID NO: 66; and/or the immunoglobulin light chain polypeptide comprises a LCDR1 comprising or consisting of SEQ ID NO: 104, a LCDR2 comprising or consisting of SEQ ID NO: 134, and a LCDR3 comprising or consisting of SEQ ID NO: 158;

(10) the immunoglobulin heavy chain polypeptide comprises a HCDR1 comprising or consisting of SEQ ID NO: 9, a HCDR2 comprising or consisting of SEQ ID NO: 33, and a HCDR3 comprising or consisting of SEQ ID NO: 67; and/or the immunoglobulin light chain polypeptide comprises a LCDR1 comprising or consisting of SEQ ID NO: 97, a LCDR2 comprising or consisting of SEQ ID NO: 135, and a LCDR3 comprising or consisting of SEQ ID NO: 159;

(11) the immunoglobulin heavy chain polypeptide comprises a HCDR1 comprising or consisting of SEQ ID NO: 7, a HCDR2 comprising or consisting of SEQ ID NO: 34, and a HCDR3 comprising or consisting of SEQ ID NO: 64; and/or the immunoglobulin light chain polypeptide comprises a LCDR1 comprising or consisting of SEQ ID NO: 102, a LCDR2 comprising or consisting of SEQ ID NO: 132, and a LCDR3 comprising or consisting of SEQ ID NO: 160;

(12) the immunoglobulin heavy chain polypeptide comprises a HCDR1 comprising or consisting of SEQ ID NO: 10, a HCDR2 comprising or consisting of SEQ ID NO: 35, and a HCDR3 comprising or consisting of SEQ ID NO: 68; and/or the immunoglobulin light chain polypeptide comprises a LCDR1 comprising or consisting of SEQ ID NO: 105, a LCDR2 comprising or consisting of SEQ ID NO: 136, and a LCDR3 comprising or consisting of SEQ ID NO: 161;

(13) the immunoglobulin heavy chain polypeptide comprises a HCDR1 comprising or consisting of SEQ ID NO: 2, a HCDR2 comprising or consisting of SEQ ID NO: 25, and a HCDR3 comprising or consisting of SEQ ID NO: 69; and/or the immunoglobulin light chain polypeptide comprises a LCDR1 comprising or consisting of SEQ ID NO: 106, a LCDR2 comprising or consisting of SEQ ID NO: 129, and a LCDR3 comprising or consisting of SEQ ID NO: 162;

(14) the immunoglobulin heavy chain polypeptide comprises a HCDR1 comprising or consisting of SEQ ID NO: 11, a HCDR2 comprising or consisting of SEQ ID NO: 36, and a HCDR3 comprising or consisting of SEQ ID NO: 70; and/or the immunoglobulin light chain polypeptide comprises a LCDR1 comprising or consisting of SEQ ID NO: 107, a LCDR2 comprising or consisting of SEQ ID NO: 129, and a LCDR3 comprising or consisting of SEQ ID NO: 163;

(15) the immunoglobulin heavy chain polypeptide comprises a HCDR1 comprising or consisting of SEQ ID NO: 12, a HCDR2 comprising or consisting of SEQ ID NO: 37, and a HCDR3 comprising or consisting of SEQ ID NO: 71; and/or the immunoglobulin light chain polypeptide comprises a LCDR1 comprising or consisting of SEQ ID NO: 108, a LCDR2 comprising or consisting of SEQ ID NO: 137, and a LCDR3 comprising or consisting of SEQ ID NO: 164;

(16) the immunoglobulin heavy chain polypeptide comprises a HCDR1 comprising or consisting of SEQ ID NO: 1, a HCDR2 comprising or consisting of SEQ ID NO: 38, and a HCDR3 comprising or consisting of SEQ ID NO: 72; and/or the immunoglobulin light chain polypeptide comprises a LCDR1 comprising or consisting of SEQ ID NO: 109, a LCDR2 comprising or consisting of SEQ ID NO: 138, and a LCDR3 comprising or consisting of SEQ ID NO: 165;

(17) the immunoglobulin heavy chain polypeptide comprises a HCDR1 comprising or consisting of SEQ ID NO: 13, a HCDR2 comprising or consisting of SEQ ID NO: 39, and a HCDR3 comprising or consisting of SEQ ID NO: 73; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(18) the immunoglobulin heavy chain polypeptide comprises a HCDR1 comprising or consisting of SEQ ID NO: 2, a HCDR2 comprising or consisting of SEQ ID NO: 40, and a HCDR3 comprising or consisting of SEQ ID NO: 74; and/or the immunoglobulin light chain polypeptide comprises a LCDR1 comprising or consisting of SEQ ID NO: 110, a LCDR2 comprising or consisting of SEQ ID NO: 137, and a LCDR3 comprising or consisting of SEQ ID NO: 166;

(19) the immunoglobulin heavy chain polypeptide comprises a HCDR1 comprising or consisting of SEQ ID NO: 14, a HCDR2 comprising or consisting of SEQ ID NO: 41, and a HCDR3 comprising or consisting of SEQ ID NO: 75; and/or the immunoglobulin light chain polypeptide comprises a LCDR1 comprising or consisting of SEQ ID NO:

111, a LCDR2 comprising or consisting of SEQ ID NO: 129, and a LCDR3 comprising or consisting of SEQ ID NO: 165;

(20) the immunoglobulin heavy chain polypeptide comprises a HCDR1 comprising or consisting of SEQ ID NO: 15, a HCDR2 comprising or consisting of SEQ ID NO: 42, and a HCDR3 comprising or consisting of SEQ ID NO: 74; and/or the immunoglobulin light chain polypeptide comprises a LCDR1 comprising or consisting of SEQ ID NO: 97, a LCDR2 comprising or consisting of SEQ ID NO: 139, and a LCDR3 comprising or consisting of SEQ ID NO: 152;

(21) the immunoglobulin heavy chain polypeptide comprises a HCDR1 comprising or consisting of SEQ ID NO: 14, a HCDR2 comprising or consisting of SEQ ID NO: 43, and a HCDR3 comprising or consisting of SEQ ID NO: 76; and/or the immunoglobulin light chain polypeptide comprises a LCDR1 comprising or consisting of SEQ ID NO: 112, a LCDR2 comprising or consisting of SEQ ID NO: 137, and a LCDR3 comprising or consisting of SEQ ID NO: 155;

(22) the immunoglobulin heavy chain polypeptide comprises a HCDR1 comprising or consisting of SEQ ID NO: 16, a HCDR2 comprising or consisting of SEQ ID NO: 44, and a HCDR3 comprising or consisting of SEQ ID NO: 77; and/or the immunoglobulin light chain polypeptide comprises a LCDR1 comprising or consisting of SEQ ID NO: 113, a LCDR2 comprising or consisting of SEQ ID NO: 140, and a LCDR3 comprising or consisting of SEQ ID NO: 165;

(23) the immunoglobulin heavy chain polypeptide comprises a HCDR1 comprising or consisting of SEQ ID NO: 9, a HCDR2 comprising or consisting of SEQ ID NO: 45, and a HCDR3 comprising or consisting of SEQ ID NO: 78; and/or the immunoglobulin light chain polypeptide comprises a LCDR1 comprising or consisting of SEQ ID NO: 114, a LCDR2 comprising or consisting of SEQ ID NO: 141, and a LCDR3 comprising or consisting of SEQ ID NO: 165;

(24) the immunoglobulin heavy chain polypeptide comprises a HCDR1 comprising or consisting of SEQ ID NO: 17, a HCDR2 comprising or consisting of SEQ ID NO: 46, and a HCDR3 comprising or consisting of SEQ ID NO: 79; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 155;

(25) the immunoglobulin heavy chain polypeptide comprises a HCDR1 comprising or consisting of SEQ ID NO: 9, a HCDR2 comprising or consisting of SEQ ID NO: 25, and a HCDR3 comprising or consisting of SEQ ID NO: 80; and/or the immunoglobulin light chain polypeptide comprises a LCDR1 comprising or consisting of SEQ ID NO: 115, a LCDR2 comprising or consisting of SEQ ID NO: 142, and a LCDR3 comprising or consisting of SEQ ID NO: 165;

(26) the immunoglobulin heavy chain polypeptide comprises a HCDR1 comprising or consisting of SEQ ID NO: 17, a HCDR2 comprising or consisting of SEQ ID NO: 41, and a HCDR3 comprising or consisting of SEQ ID NO: 81; and/or the immunoglobulin light chain polypeptide comprises a LCDR1 comprising or consisting of SEQ ID NO: 116, a LCDR2 comprising or consisting of SEQ ID NO: 143, and a LCDR3 comprising or consisting of SEQ ID NO: 167;

(27) the immunoglobulin heavy chain polypeptide comprises a HCDR1 comprising or consisting of SEQ ID NO: 7, a HCDR2 comprising or consisting of SEQ ID NO: 47, and a HCDR3 comprising or consisting of SEQ ID NO: 82; and/or the immunoglobulin light chain polypeptide comprises a LCDR1 comprising or consisting of SEQ ID NO: 117, a LCDR2 comprising or consisting of SEQ ID NO: 144, and a LCDR3 comprising or consisting of SEQ ID NO: 155;

(28) the immunoglobulin heavy chain polypeptide comprises a HCDR1 comprising or consisting of SEQ ID NO: 2, a HCDR2 comprising or consisting of SEQ ID NO: 41, and a HCDR3 comprising or consisting of SEQ ID NO: 83; and/or the immunoglobulin light chain polypeptide comprises a LCDR1 comprising or consisting of SEQ ID NO: 118, a LCDR2 comprising or consisting of SEQ ID NO: 131, and a LCDR3 comprising or consisting of SEQ ID NO: 168;

(29) the immunoglobulin heavy chain polypeptide comprises a HCDR1 comprising or consisting of SEQ ID NO: 18, a HCDR2 comprising or consisting of SEQ ID NO: 48, and a HCDR3 comprising or consisting of SEQ ID NO: 84; and/or the immunoglobulin light chain polypeptide comprises a LCDR1 comprising or consisting of SEQ ID NO: 119, a LCDR2 comprising or consisting of SEQ ID NO: 145, and a LCDR3 comprising or consisting of SEQ ID NO: 165;

(30) the immunoglobulin heavy chain polypeptide comprises a HCDR1 comprising or consisting of SEQ ID NO: 19, a HCDR2 comprising or consisting of SEQ ID NO: 49, and a HCDR3 comprising or consisting of SEQ ID NO: 85; and/or the immunoglobulin light chain polypeptide comprises a LCDR1 comprising or consisting of SEQ ID NO: 120, a LCDR2 comprising or consisting of SEQ ID NO: 146, and a LCDR3 comprising or consisting of SEQ ID NO: 155;

(31) the immunoglobulin heavy chain polypeptide comprises a HCDR1 comprising or consisting of SEQ ID NO: 2, a HCDR2 comprising or consisting of SEQ ID NO: 50, and a HCDR3 comprising or consisting of SEQ ID NO: 86; and/or the immunoglobulin light chain polypeptide comprises a LCDR1 comprising or consisting of SEQ ID NO: 121, a LCDR2 comprising or consisting of SEQ ID NO: 147, and a LCDR3 comprising or consisting of SEQ ID NO: 169;

(32) the immunoglobulin heavy chain polypeptide comprises a HCDR1 comprising or consisting of SEQ ID NO: 2, a HCDR2 comprising or consisting of SEQ ID NO: 51, and a HCDR3 comprising or consisting of SEQ ID NO: 87; and/or the immunoglobulin light chain polypeptide comprises a LCDR1 comprising or consisting of SEQ ID NO: 122, a LCDR2 comprising or consisting of SEQ ID NO: 137, and a LCDR3 comprising or consisting of SEQ ID NO: 155;

(33) the immunoglobulin heavy chain polypeptide comprises a HCDR1 comprising or consisting of SEQ ID NO: 20, a HCDR2 comprising or consisting of SEQ ID NO: 44, and a HCDR3 comprising or consisting of SEQ ID NO: 88; and/or the immunoglobulin light chain polypeptide comprises a LCDR1 comprising or consisting of SEQ ID NO: 123, a LCDR2 comprising or consisting of SEQ ID NO: 148, and a LCDR3 comprising or consisting of SEQ ID NO: 170;

(34) the immunoglobulin heavy chain polypeptide comprises a HCDR1 comprising or consisting of SEQ ID NO: 3, a HCDR2 comprising or consisting of SEQ ID NO: 52, and a HCDR3 comprising or consisting of SEQ ID NO: 60; and/or the immunoglobulin light chain polypeptide comprises a LCDR1 comprising or consisting of SEQ ID NO: 98, a LCDR2 comprising or consisting of SEQ ID NO: 129, and a LCDR3 comprising or consisting of SEQ ID NO: 171;

(35) the immunoglobulin heavy chain polypeptide comprises a HCDR1 comprising or consisting of SEQ ID NO: 2, a HCDR2 comprising or consisting of SEQ ID NO: 53, and a HCDR3 comprising or consisting of SEQ ID NO: 89; and/or the immunoglobulin light chain polypeptide comprises a LCDR1 comprising or consisting of SEQ ID NO: 97, a LCDR2 comprising or consisting of SEQ ID NO: 147, and a LCDR3 comprising or consisting of SEQ ID NO: 172;

(36) the immunoglobulin heavy chain polypeptide comprises a HCDR1 comprising or consisting of SEQ ID NO: 21, a HCDR2 comprising or consisting of SEQ ID NO: 38, and a HCDR3 comprising or consisting of SEQ ID NO: 90; and/or the immunoglobulin light chain polypeptide comprises a LCDR1 comprising or consisting of SEQ ID NO: 109, a LCDR2 comprising or consisting of SEQ ID NO: 150, and a LCDR3 comprising or consisting of SEQ ID NO: 165;

(37) the immunoglobulin heavy chain polypeptide comprises a HCDR1 comprising or consisting of SEQ ID NO: 22, a HCDR2 comprising or consisting of SEQ ID NO: 41, and a HCDR3 comprising or consisting of SEQ ID NO: 91; and/or the immunoglobulin light chain polypeptide comprises a LCDR1 comprising or consisting of SEQ ID NO: 124, a LCDR2 comprising or consisting of SEQ ID NO: 151, and a LCDR3 comprising or consisting of SEQ ID NO: 173;

(38) the immunoglobulin heavy chain polypeptide comprises a HCDR1 comprising or consisting of SEQ ID NO: 2, a HCDR2 comprising or consisting of SEQ ID NO: 54, and a HCDR3 comprising or consisting of SEQ ID NO: 92; and/or the immunoglobulin light chain polypeptide comprises a LCDR1 comprising or consisting of SEQ ID NO: 126, a LCDR2 comprising or consisting of SEQ ID NO: 129, and a LCDR3 comprising or consisting of SEQ ID NO: 165;

(39) the immunoglobulin heavy chain polypeptide comprises a HCDR1 comprising or consisting of SEQ ID NO: 2, a HCDR2 comprising or consisting of SEQ ID NO: 55, and a HCDR3 comprising or consisting of SEQ ID NO: 93; and/or the immunoglobulin light chain polypeptide comprises a LCDR1 comprising or consisting of SEQ ID NO: 97, a LCDR2 comprising or consisting of SEQ ID NO: 149, and a LCDR3 comprising or consisting of SEQ ID NO: 174;

(40) the immunoglobulin heavy chain polypeptide comprises a HCDR1 comprising or consisting of SEQ ID NO: 23, a HCDR2 comprising or consisting of SEQ ID NO: 56, and a HCDR3 comprising or consisting of SEQ ID NO: 94; and/or the immunoglobulin light chain polypeptide comprises a LCDR1 comprising or consisting of SEQ ID NO: 125, a LCDR2 comprising or consisting of SEQ ID NO: 142, and a LCDR3 comprising or consisting of SEQ ID NO: 175;

(41) the immunoglobulin heavy chain polypeptide comprises a HCDR1 comprising or consisting of SEQ ID NO: 14, a HCDR2 comprising or consisting of SEQ ID NO: 43, and a HCDR3 comprising or consisting of SEQ ID NO: 76; and/or the immunoglobulin light chain polypeptide comprises a LCDR1 comprising or consisting of SEQ ID NO: 127, a LCDR2 comprising or consisting of SEQ ID NO: 137, and a LCDR3 comprising or consisting of SEQ ID NO: 176;

(42) the immunoglobulin heavy chain polypeptide comprises a HCDR1 comprising or consisting of SEQ ID NO: 3, a HCDR2 comprising or consisting of SEQ ID NO: 57, and a HCDR3 comprising or consisting of SEQ ID NO: 95; and/or the immunoglobulin light chain polypeptide comprises a LCDR1 comprising or consisting of SEQ ID NO: 128, a LCDR2 comprising or consisting of SEQ ID NO: 137, and a LCDR3 comprising or consisting of SEQ ID NO: 155; and/or

(43) the immunoglobulin heavy chain polypeptide and light chain polypeptide comprises any combination of the CDRs listed in FIGS. 1A-D of PD-L1 Type A binding agents 1-42

In particular embodiments, the binding agent comprises an immunoglobulin heavy chain polypeptide and an immunoglobulin light chain polypeptide, wherein the immunoglobulin heavy chain polypeptide comprises a first framework region, a second framework region, a third framework region, and/or a fourth framework region; and/or the immunoglobulin light chain polypeptide comprises a first framework region, a second framework region, a third framework region, and/or a fourth framework region; and/or the immunoglobulin heavy chain polypeptide and light chain polypeptide comprises any combination of the framework regions listed in FIGS. 2A-D and FIGS. 3A-D, respectively.

PD-L1-Binding Agents—Type B

Provided herein are PD-L1 binding agents (Type B) comprising an immunoglobulin heavy chain variable region polypeptide and an immunoglobulin light chain variable region polypeptide. In some embodiments, the PD-L1 binding agents (Type B) comprise an immunoglobulin heavy chain variable region of any one of SEQ ID NOs: 430-450, or at least the CDRs thereof; and an immunoglobulin light chain variable region of any one of SEQ ID NOs: 451-471, or at least the CDRs thereof. In other embodiments, the PD-L1 binding agents comprise an immunoglobulin heavy chain variable region polypeptide with an amino acid sequence that is at least 90% identical to any one of SEQ ID NOs: 430-450, and an immunoglobulin light chain variable region polypeptide with an amino acid sequence that is at least 90% identical to any one of SEQ ID NOs: 451-471. In yet other embodiments, the PD-L1 binding agent, the immunoglobulin heavy chain variable region polypeptide comprises a complementarity determining region 1 (HCDR1) comprising any one of SEQ ID NOs: 308-321, a complementarity determining region 2 (HCDR2) comprising any one of SEQ ID NOs: 322-338, and a complementarity determining region 3 (HCDR3) comprising any one of SEQ ID NOs: 339-359; and/or the immunoglobulin light chain variable region polypeptide comprises a complementarity determining region 1 (LCDR1) comprising any one of SEQ ID NOs: 360-374, a complementarity determining region 2 (LCDR2) comprising any one of SEQ ID NOs: 131 and 375-386, and a complementarity determining region 3 (LCDR3) comprising any one of SEQ ID NOs: 387-398. Also provided are nucleic acids encoding the PD-L1 binding agents, or the individual heavy and light chains thereof; vectors and cells comprising the nucleic acids; and compositions comprising the binding agents or nucleic acids.

In an embodiment, the PD-L1 binding agent (Type B) comprises an immunoglobulin heavy chain variable region of any one of SEQ ID NOs: 430-450, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 430-450, or at least the CDRs thereof; and/or an immunoglobulin light chain variable region of any one of SEQ ID NOs: 451-471, a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 451-471, or at least the CDRs thereof.

By way of further illustration, the PD-L1 binding agent (Type B) can comprise:

(1) an immunoglobulin heavy chain variable region of SEQ ID NO: 429, or at least the CDRs thereof, and/or an immunoglobulin light chain variable region of SEQ ID NO: 450, or at least the CDRs thereof;

(2) an immunoglobulin heavy chain variable region of SEQ ID NO: 430, or at least the CDRs thereof, and/or an immunoglobulin light chain variable region of SEQ ID NO: 451, or at least the CDRs thereof;

(3) an immunoglobulin heavy chain variable region of SEQ ID NO: 431, or at least the CDRs thereof, and/or an immunoglobulin light chain variable region of SEQ ID NO: 452, or at least the CDRs thereof;

(4) an immunoglobulin heavy chain variable region of SEQ ID NO: 432, or at least the CDRs thereof, and/or an immunoglobulin light chain variable region of SEQ ID NO: 453, or at least the CDRs thereof;

(5) an immunoglobulin heavy chain variable region of SEQ ID NO: 433, or at least the CDRs thereof, and/or an immunoglobulin light chain variable region of SEQ ID NO: 454, or at least the CDRs thereof;

(6) an immunoglobulin heavy chain variable region of SEQ ID NO: 434, or at least the CDRs thereof, and/or an immunoglobulin light chain variable region of SEQ ID NO: 455, or at least the CDRs thereof;

(7) an immunoglobulin heavy chain variable region of SEQ ID NO: 435, or at least the CDRs thereof, and/or an immunoglobulin light chain variable region of SEQ ID NO: 456, or at least the CDRs thereof;

(8) an immunoglobulin heavy chain variable region of SEQ ID NO: 436, or at least the CDRs thereof, and/or an immunoglobulin light chain variable region of SEQ ID NO: 457, or at least the CDRs thereof;

(9) an immunoglobulin heavy chain variable region of SEQ ID NO: 437, or at least the CDRs thereof, and/or an immunoglobulin light chain variable region of SEQ ID NO: 458, or at least the CDRs thereof;

(10) an immunoglobulin heavy chain variable region of SEQ ID NO: 438, or at least the CDRs thereof, and/or an immunoglobulin light chain variable region of SEQ ID NO: 459, or at least the CDRs thereof;

(11) an immunoglobulin heavy chain variable region of SEQ ID NO: 439, or at least the CDRs thereof, and/or an immunoglobulin light chain variable region of SEQ ID NO: 460, or at least the CDRs thereof;

(12) an immunoglobulin heavy chain variable region of SEQ ID NO: 440, or at least the CDRs thereof, and/or an immunoglobulin light chain variable region of SEQ ID NO: 461, or at least the CDRs thereof;

(13) an immunoglobulin heavy chain variable region of SEQ ID NO: 441, or at least the CDRs thereof, and/or an immunoglobulin light chain variable region of SEQ ID NO: 462, or at least the CDRs thereof;

(14) an immunoglobulin heavy chain variable region of SEQ ID NO: 442, or at least the CDRs thereof, and/or an immunoglobulin light chain variable region of SEQ ID NO: 463, or at least the CDRs thereof;

(15) an immunoglobulin heavy chain variable region of SEQ ID NO: 443, or at least the CDRs thereof, and/or an immunoglobulin light chain variable region of SEQ ID NO: 464, or at least the CDRs thereof;

(16) an immunoglobulin heavy chain variable region of SEQ ID NO: 444, or at least the CDRs thereof, and/or an immunoglobulin light chain variable region of SEQ ID NO: 465, or at least the CDRs thereof;

(17) an immunoglobulin heavy chain variable region of SEQ ID NO: 445, or at least the CDRs thereof, and/or an immunoglobulin light chain variable region of SEQ ID NO: 466, or at least the CDRs thereof;

(18) an immunoglobulin heavy chain variable region of SEQ ID NO: 446, or at least the CDRs thereof, and/or an immunoglobulin light chain variable region of SEQ ID NO: 467, or at least the CDRs thereof;

(19) an immunoglobulin heavy chain variable region of SEQ ID NO: 447, or at least the CDRs thereof, and/or an immunoglobulin light chain variable region of SEQ ID NO: 468, or at least the CDRs thereof;

(20) an immunoglobulin heavy chain variable region of SEQ ID NO: 448, or at least the CDRs thereof, and/or an immunoglobulin light chain variable region of SEQ ID NO: 469, or at least the CDRs thereof; and/or

(21) an immunoglobulin heavy chain variable region of SEQ ID NO: 449, or at least the CDRs thereof, and/or an immunoglobulin light chain variable region of SEQ ID NO: 470, or at least the CDRs thereof; and/or

(22) an immunoglobulin heavy chain variable region of FIGS. 8A-B and/or an immunoglobulin light chain variable region of FIGS. 8C-D, or at least the CDRs thereof.

The CDRs of a given heavy or light chain Ig sequence can be determined in accordance with any of the various known Ig numbering schemes (e.g., Rabat, Chothia, Martin (Enhanced Chothia), IGMT, AbM). In certain embodiments, the PD-L1 binding agent comprises one or more of the following CDRs:

a HCDR1 comprising or consisting of any one of SEQ ID NOs: 308-321 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 308-321;

a HCDR2 comprising or consisting of any one of SEQ ID NOs: 322-338 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 322-338; and a HCDR3 comprising or consisting of any one of SEQ ID NOs: 339-359 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 339-359; and/or the immunoglobulin light chain polypeptide comprises a LCDR1 comprising or consisting of any one of SEQ ID NOs: 360-374 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 360-374;

a LCDR2 comprising or consisting of any one of SEQ ID NOs: 375-386 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 375-386; and a LCDR3 comprising or consisting of any one of SEQ ID NOs: 387-398 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 387-398.

In particular embodiments, the binding agent comprises an immunoglobulin heavy chain polypeptide and an immunoglobulin light chain polypeptide, wherein:

(1) the immunoglobulin heavy chain polypeptide comprises a HCDR1 comprising or consisting of SEQ ID NO: 308, a HCDR2 comprising or consisting of SEQ ID NO: 322, and a HCDR3 comprising or consisting of SEQ ID NO: 339; and/or the immunoglobulin light chain polypeptide comprises a LCDR1 comprising or consisting of SEQ ID NO: 360, a LCDR2 comprising or consisting of SEQ ID NO: 375, and a LCDR3 comprising or consisting of SEQ ID NO: 387;

(2) the immunoglobulin heavy chain polypeptide comprises a HCDR1 comprising or consisting of SEQ ID NO: 309, a HCDR2 comprising or consisting of SEQ ID NO: 323, and a HCDR3 comprising or consisting of SEQ ID NO: 340; and/or the immunoglobulin light chain polypeptide comprises a LCDR1 comprising or consisting of SEQ ID NO: 361, a LCDR2 comprising or consisting of SEQ ID NO: 376, and a LCDR3 comprising or consisting of SEQ ID NO: 388;

(3) the immunoglobulin heavy chain polypeptide comprises a HCDR1 comprising or consisting of SEQ ID NO: 310, a HCDR2 comprising or consisting of SEQ ID NO: 324, and a HCDR3 comprising or consisting of SEQ ID NO: 341; and/or the immunoglobulin light chain polypeptide comprises a LCDR1 comprising or consisting of SEQ ID NO: 360, a LCDR2 comprising or consisting of SEQ ID NO: 375, and a LCDR3 comprising or consisting of SEQ ID NO: 387;

(4) the immunoglobulin heavy chain polypeptide comprises a HCDR1 comprising or consisting of SEQ ID NO: 311, a HCDR2 comprising or consisting of SEQ ID NO: 325, and a HCDR3 comprising or consisting of SEQ ID NO: 342; and/or the immunoglobulin light chain polypeptide comprises a LCDR1 comprising or consisting of SEQ ID NO: 362, a LCDR2 comprising or consisting of SEQ ID NO: 377, and a LCDR3 comprising or consisting of SEQ ID NO: 389;

(5) the immunoglobulin heavy chain polypeptide comprises a HCDR1 comprising or consisting of SEQ ID NO: 312, a HCDR2 comprising or consisting of SEQ ID NO: 326, and a HCDR3 comprising or consisting of SEQ ID NO: 343; and/or the immunoglobulin light chain polypeptide comprises a LCDR1 comprising or consisting of SEQ ID NO: 360, a LCDR2 comprising or consisting of SEQ ID NO: 378, and a LCDR3 comprising or consisting of SEQ ID NO: 387;

(6) the immunoglobulin heavy chain polypeptide comprises a HCDR1 comprising or consisting of SEQ ID NO: 313, a HCDR2 comprising or consisting of SEQ ID NO: 327, and a HCDR3 comprising or consisting of SEQ ID NO: 344; and/or the immunoglobulin light chain polypeptide comprises a LCDR1 comprising or consisting of SEQ ID NO: 363, a LCDR2 comprising or consisting of SEQ ID NO: 379, and a LCDR3 comprising or consisting of SEQ ID NO: 390;

(7) the immunoglobulin heavy chain polypeptide comprises a HCDR1 comprising or consisting of SEQ ID NO: 314, a HCDR2 comprising or consisting of SEQ ID NO: 327, and a HCDR3 comprising or consisting of SEQ ID NO: 345; and/or the immunoglobulin light chain polypeptide comprises a LCDR1 comprising or consisting of SEQ ID NO: 364, a LCDR2 comprising or consisting of SEQ ID NO: 380, and a LCDR3 comprising or consisting of SEQ ID NO: 391;

(8) the immunoglobulin heavy chain polypeptide comprises a HCDR1 comprising or consisting of SEQ ID NO: 312, a HCDR2 comprising or consisting of SEQ ID NO: 328, and a HCDR3 comprising or consisting of SEQ ID NO: 346; and/or the immunoglobulin light chain polypeptide comprises a LCDR1 comprising or consisting of SEQ ID NO: 365, a LCDR2 comprising or consisting of SEQ ID NO: 375, and a LCDR3 comprising or consisting of SEQ ID NO: 387;

(9) the immunoglobulin heavy chain polypeptide comprises a HCDR1 comprising or consisting of SEQ ID NO: 314, a HCDR2 comprising or consisting of SEQ ID NO: 329, and a HCDR3 comprising or consisting of SEQ ID NO: 347; and/or the immunoglobulin light chain polypeptide comprises a LCDR1 comprising or consisting of SEQ ID NO: 366, a LCDR2 comprising or consisting of SEQ ID NO: 375, and a LCDR3 comprising or consisting of SEQ ID NO: 389;

(10) the immunoglobulin heavy chain polypeptide comprises a HCDR1 comprising or consisting of SEQ ID NO: 309, a HCDR2 comprising or consisting of SEQ ID NO: 330, and a HCDR3 comprising or consisting of SEQ ID NO: 348; and/or the immunoglobulin light chain polypeptide comprises a LCDR1 comprising or consisting of SEQ ID NO: 360, a LCDR2 comprising or consisting of SEQ ID NO: 381, and a LCDR3 comprising or consisting of SEQ ID NO: 392;

(11) the immunoglobulin heavy chain polypeptide comprises a HCDR1 comprising or consisting of SEQ ID NO: 309, a HCDR2 comprising or consisting of SEQ ID NO: 327, and a HCDR3 comprising or consisting of SEQ ID NO: 349; and/or the immunoglobulin light chain polypeptide comprises a LCDR1 comprising or consisting of SEQ ID NO: 367, a LCDR2 comprising or consisting of SEQ ID NO: 382, and a LCDR3 comprising or consisting of SEQ ID NO: 389;

(12) the immunoglobulin heavy chain polypeptide comprises a HCDR1 comprising or consisting of SEQ ID NO: 309, a HCDR2 comprising or consisting of SEQ ID NO: 322, and a HCDR3 comprising or consisting of SEQ ID NO: 350; and/or the immunoglobulin light chain polypeptide comprises a LCDR1 comprising or consisting of SEQ ID NO: 360, a LCDR2 comprising or consisting of SEQ ID NO: 383, and a LCDR3 comprising or consisting of SEQ ID NO: 387;

(13) the immunoglobulin heavy chain polypeptide comprises a HCDR1 comprising or consisting of SEQ ID NO: 315, a HCDR2 comprising or consisting of SEQ ID NO: 323, and a HCDR3 comprising or consisting of SEQ ID NO: 351; and/or the immunoglobulin light chain polypeptide comprises a LCDR1 comprising or consisting of SEQ ID NO: 368, a LCDR2 comprising or consisting of SEQ ID NO: 375, and a LCDR3 comprising or consisting of SEQ ID NO: 393;

(14) the immunoglobulin heavy chain polypeptide comprises a HCDR1 comprising or consisting of SEQ ID NO:316, a HCDR2 comprising or consisting of SEQ ID NO: 331, and a HCDR3 comprising or consisting of SEQ ID NO: 352; and/or the immunoglobulin light chain polypeptide comprises a LCDR1 comprising or consisting of SEQ ID NO: 365, a LCDR2 comprising or consisting of SEQ ID NO: 375, and a LCDR3 comprising or consisting of SEQ ID NO: 389;

(15) the immunoglobulin heavy chain polypeptide comprises a HCDR1 comprising or consisting of SEQ ID NO: 317, a HCDR2 comprising or consisting of SEQ ID NO: 332, and a HCDR3 comprising or consisting of SEQ ID NO: 353; and/or the immunoglobulin light chain polypeptide comprises a LCDR1 comprising or consisting of SEQ ID NO: 369, a LCDR2 comprising or consisting of SEQ ID NO: 384, and a LCDR3 comprising or consisting of SEQ ID NO: 394;

(16) the immunoglobulin heavy chain polypeptide comprises a HCDR1 comprising or consisting of SEQ ID NO: 318, a HCDR2 comprising or consisting of SEQ ID NO: 333, and a HCDR3 comprising or consisting of SEQ ID NO: 354; and/or the immunoglobulin light chain polypeptide comprises a LCDR1 comprising or consisting of SEQ ID NO: 370, a LCDR2 comprising or consisting of SEQ ID NO: 379, and a LCDR3 comprising or consisting of SEQ ID NO: 395;

(17) the immunoglobulin heavy chain polypeptide comprises a HCDR1 comprising or consisting of SEQ ID NO:310, a HCDR2 comprising or consisting of SEQ ID NO: 334, and a HCDR3 comprising or consisting of SEQ ID NO:

355; and/or the immunoglobulin light chain polypeptide comprises a LCDR1 comprising or consisting of SEQ ID NO: 371, a LCDR2 comprising or consisting of SEQ ID NO: 375, and a LCDR3 comprising or consisting of SEQ ID NO: 387;

(18) the immunoglobulin heavy chain polypeptide comprises a HCDR1 comprising or consisting of SEQ ID NO:310, a HCDR2 comprising or consisting of SEQ ID NO: 335, and a HCDR3 comprising or consisting of SEQ ID NO: 356; and/or the immunoglobulin light chain polypeptide comprises a LCDR1 comprising or consisting of SEQ ID NO: 360, a LCDR2 comprising or consisting of SEQ ID NO: 385, and a LCDR3 comprising or consisting of SEQ ID NO: 396;

(19) the immunoglobulin heavy chain polypeptide comprises a HCDR1 comprising or consisting of SEQ ID NO: 319, a HCDR2 comprising or consisting of SEQ ID NO: 336, and a HCDR3 comprising or consisting of SEQ ID NO: 357; and/or the immunoglobulin light chain polypeptide comprises a LCDR1 comprising or consisting of SEQ ID NO: 372, a LCDR2 comprising or consisting of SEQ ID NO: 386, and a LCDR3 comprising or consisting of SEQ ID NO: 397;

(20) the immunoglobulin heavy chain polypeptide comprises a HCDR1 comprising or consisting of SEQ ID NO: 320, a HCDR2 comprising or consisting of SEQ ID NO: 337, and a HCDR3 comprising or consisting of SEQ ID NO: 358; and/or the immunoglobulin light chain polypeptide comprises a LCDR1 comprising or consisting of SEQ ID NO: 373, a LCDR2 comprising or consisting of SEQ ID NO: 379, and a LCDR3 comprising or consisting of SEQ ID NO: 398;

(21) the immunoglobulin heavy chain polypeptide comprises a HCDR1 comprising or consisting of SEQ ID NO: 321, a HCDR2 comprising or consisting of SEQ ID NO: 338, and a HCDR3 comprising or consisting of SEQ ID NO: 359; and/or the immunoglobulin light chain polypeptide comprises a LCDR1 comprising or consisting of SEQ ID NO: 374, a LCDR2 comprising or consisting of SEQ ID NO: 379, and a LCDR3 comprising or consisting of SEQ ID NO: 389; and/or

(22) the immunoglobulin heavy chain polypeptide and light chain polypeptide comprises any combination of the CDRs listed in FIGS. 5A-B (Type B).

In particular embodiments, the binding agent comprises an immunoglobulin heavy chain polypeptide and an immunoglobulin light chain polypeptide, wherein the immunoglobulin heavy chain polypeptide comprises a first framework region, a second framework region, a third framework region, and/or a fourth framework region; and/or the immunoglobulin light chain polypeptide comprises a first framework region, a second framework region, a third framework region, and/or a fourth framework region; and/or the immunoglobulin heavy chain polypeptide and light chain polypeptide comprises any combination of the framework regions listed in FIGS. 6A-B and/or FIGS. 7A-B (Type B), respectively.

In an exemplary embodiment, the immunoconjugates of the invention comprise an antibody construct that comprises an antigen binding domain that specifically recognizes and binds HER2.

In certain embodiments, immunoconjugates of the invention comprise anti-HER2 antibodies. In one embodiment of the invention, an anti-HER2 antibody of an immunoconjugate of the invention comprises a humanized anti-HER2 antibody, e.g., huMAb4D5-1, huMAb4D5-2, huMAb4D5-3, huMAb4D5-4, huMAb4D5-5, huMAb4D5-6, huMAb4D5-7 and huMAb4D5-8, as described in Table 3 of U.S. Pat. No. 5,821,337, which is specifically incorporated by reference herein. Those antibodies contain human framework regions with the complementarity-determining regions of a murine antibody (4D5) that binds to HER2. The humanized antibody huMAb4D5-8 is also referred to as trastuzumab, commercially available under the tradename HERCEPTIN™ (Genentech, Inc.).

Trastuzumab (CAS 180288-69-1, HERCEPTIN®, huMAb4D5-8, rhuMAb HER2, Genentech) is a recombinant DNA-derived, IgG1 kappa, monoclonal antibody that is a humanized version of a murine anti-HER2 antibody (4D5) that selectively binds with high affinity in a cell-based assay (Kd=5 nM) to the extracellular domain of HER2 (U.S. Pat. Nos. 5,677,171; 5,821,337; 6,054,297; 6,165,464; 6,339,142; 6,407,213; 6,639,055; 6,719,971; 6,800,738; 7,074,404; Coussens et al (1985) *Science* 230:1132-9; Slamon et al (1989) *Science* 244:707-12; Slamon et al (2001) *New Engl. J. Med.* 344:783-792).

In an embodiment of the invention, the antibody construct or antigen binding domain comprises the CDR regions of trastuzumab. In an embodiment of the invention, the anti-HER2 antibody further comprises the framework regions of the trastuzumab. In an embodiment of the invention, the anti-HER2 antibody further comprises one or both variable regions of trastuzumab.

In another embodiment of the invention, an anti-HER2 antibody of an immunoconjugate of the invention comprises a humanized anti-HER2 antibody, e.g., humanized 2C4, as described in U.S. Pat. No. 7,862,817. An exemplary humanized 2C4 antibody is pertuzumab (CAS Reg. No. 380610-27-5), PERJETA™ (Genentech, Inc.). Pertuzumab is a HER dimerization inhibitor (HDI) and functions to inhibit the ability of HER2 to form active heterodimers or homodimers with other HER receptors (such as EGFR/HER1, HER2, HER3 and HER4). See, for example, Harari and Yarden, *Oncogene* 19:6102-14 (2000); Yarden and Sliwkowski. *Nat Rev Mol Cell Biol* 2:127-37 (2001); Sliwkowski *Nat Struct Biol* 10:158-9 (2003); Cho et al. *Nature* 421:756-60 (2003); and Malik et al. *Pro Am Soc Cancer Res* 44:176-7 (2003). PERJETA™ is approved for the treatment of breast cancer.

In an embodiment of the invention, the antibody construct or antigen binding domain comprises the CDR regions of pertuzumab. In an embodiment of the invention, the anti-HER2 antibody further comprises the framework regions of the pertuzumab. In an embodiment of the invention, the anti-HER2 antibody further comprises one or both variable regions of pertuzumab.

In an exemplary embodiment, the immunoconjugates of the invention comprise an antibody construct that comprises an antigen binding domain that specifically recognizes and binds CEA. Carcinoembryonic antigen-related cell adhesion molecule 5 (CEACAM5) also known as CD66e (Cluster of Differentiation 66e), is a member of the carcinoembryonic antigen (CEA) gene family.

In an exemplary embodiment, the immunoconjugates of the invention comprise an antibody construct that comprises an antigen binding domain that specifically recognizes and binds Caprin-1 (Ellis J A, Luzio J P (1995) *J Biol Chem.* 270(35):20717-23; Wang B, et al (2005) *J Immunol.* 175 (7):4274-82; Solomon S, et al (2007) *Mol Cell Biol.* 27(6): 2324-42). Caprin-1 is also known as GPIAP1, GPIP137, GRIP137, M11S1, RNG105, p137GPI, and cell cycle associated protein 1.

Cytoplasmic activation/proliferation-associated protein-1 (caprin-1) is an RNA-binding protein that participates in the regulation of cell cycle control-associated genes. Caprin-1 selectively binds to c-Myc and cyclin D2 mRNAs, which accelerates cell progression through the $G_1$ phase into the S phase, enhances cell viability and promotes cell growth, indicating that it may serve an important role in tumorigenesis (Wang B, et al (2005) *J Immunol.* 175:4274-4282). Caprin-1 acts alone or in combination with other RNA-binding proteins, such as RasGAP SH3-domain-binding protein 1 and fragile X mental retardation protein. In the tumorigenesis process, caprin-1 primarily functions by activating cell proliferation and upregulating the expression of immune checkpoint proteins. Through the formation of stress granules, caprin-1 is also involved in the process by which tumor cells adapt to adverse conditions, which contributes to radiation and chemotherapy resistance. Given its role in various clinical malignancies, caprin-1 holds the potential to be used as a biomarker and a target for the development of novel therapeutics (Yang, Z-S, et al (2019) Oncology Letters 18:15-21).

Antibodies that target caprin-1 for treatment and detection have been described (WO 2011/096519; WO 2013/125654; WO 2013/125636; WO 2013/125640; WO 2013/125630; WO 2013/018889; WO 2013/018891; WO 2013/018883; WO 2013/018892; WO 2014/014082; WO 2014/014086; WO 2015/020212; WO 2018/079740).

In an exemplary embodiment, the immunoconjugates of the invention comprise an antibody construct that comprises an antigen binding domain that specifically recognizes and binds CEA.

Elevated expression of carcinoembryonic antigen (CEA, CD66e, CEACAM5) has been implicated in various biological aspects of neoplasia, especially tumor cell adhesion, metastasis, the blocking of cellular immune mechanisms, and having antiapoptosis functions. CEA is also used as a blood marker for many carcinomas. Labetuzumab (CEA-CIDE™, Immunomedics, CAS Reg. No. 219649-07-7), also known as MN-14 and hMN14, is a humanized IgG1 monoclonal antibody and has been studied for the treatment of colorectal cancer (Blumenthal, R. et al (2005) Cancer Immunology Immunotherapy 54(4):315-327). Labetuzumab conjugated to a camptothecin analog (labetuzumab govitecan, IMMU-130) targets carcinoembryonic antigen-related cell adhesion mol. 5 (CEACAM5) and is being studied in patients with relapsed or refractory metastatic colorectal cancer (Sharkey, R. et al, (2018), Molecular Cancer Therapeutics 17(1): 196-203; Cardillo, T. et al (2018) Molecular Cancer Therapeutics 17(1): 150-160).

In an embodiment of the invention, the CEA-targeting antibody construct or antigen binding domain comprises the Variable light chain (VL kappa) of hMN-14/labetuzumab SEQ ID NO. 472 (U.S. Pat. No. 6,676,924).

```
                                             SEQ ID NO. 472
DIQLTQSPSSLSASVGDRVTITCKASQDVGTSVAWYQQKPGKAPKLLIYW
TSTRHTGVPSRFSGSGSGTDFTFTISSLQPEDIATYYCQQYSLYRSFGQG
TKVEIK
```

In an embodiment of the invention, the CEA-targeting antibody construct or antigen binding domain comprises the light chain CDR (complementarity determining region) or light chain framework (LFR) sequences of hMN-14/labetuzumab SEQ ID NO. 473-479 (U.S. Pat. No. 6,676,924).

| Region  | Sequence Fragment                  | Residues | Length | SEQ ID NO. |
|---------|------------------------------------|----------|--------|------------|
| LFR1    | DIQLTQSPSSLSASVGDRVTITC            | 1-23     | 23     | 473        |
| CDR-L1  | KASQDVGTSVA                        | 24-34    | 11     | 474        |
| LFR2    | WYQQKPGKAPKLLIY                    | 35-49    | 15     | 475        |
| CDR-L2  | WTSTRHT                            | 50-56    | 7      | 476        |
| LFR3    | GVPSRFSGSGSGTDFTFTISSLQPEDIATYYC   | 57-88    | 32     | 477        |
| CDR-L3  | QQYSLYRS                           | 89-96    | 8      | 478        |
| LFR4    | FGQGTKVEIK                         | 97-106   | 10     | 479        |

In an embodiment of the invention, the CEA-targeting antibody construct or antigen binding domain comprises the Variable heavy chain (VH) of hMN-14/labetuzumab SEQ ID NO. 480 (U.S. Pat. No. 6,676,924).

```
                                             SEQ ID NO. 480
EVQLVESGGGVVQPGRSLRLSCSSSGFDFTTYWMSWVRQAPGKGLEWVA
EIHPDSSTINYAPSLKDRFTISRDNSKNTLFLQMDSLRPEDTGVYFCAS
LYFGFPWFAYWGQGTPVTVSS
```

In an embodiment of the invention, the CEA-targeting antibody construct or antigen binding domain comprises the heavy chain CDR (complementarity determining region) or heavy chain framework (HFR) sequences of hMN-14/labetuzumab SEQ ID NO. 481-487 (U.S. Pat. No. 6,676,924).

| Region  | Sequence Fragment                  | Residues | Length | SEQ ID NO. |
|---------|------------------------------------|----------|--------|------------|
| HFR1    | EVQLVESGGGVVQPGRSLRLSCSSSGFDFT     | 1-30     | 30     | 481        |
| CDR-H1  | TYWMS                              | 31-35    | 5      | 482        |
| HFR2    | WVRQAPGKGLEWVA                     | 36-49    | 14     | 483        |
| CDR-H2  | EIHPDSSTINYAPSLKD                  | 50-66    | 17     | 484        |
| HFR3    | RFTISRDNSKNTLFLQMDSLRPEDTGVYFCAS   | 67-98    | 32     | 485        |
| CDR-H3  | LYFGFPWFAY                         | 99-108   | 10     | 486        |
| HFR4    | WGQGTPVTVSS                        | 109-119  | 11     | 487        |

In an embodiment of the invention, the CEA-targeting antibody construct or antigen binding domain comprises the Variable light chain (VL kappa) of hPR1A3 SEQ ID NO. 488 (U.S. Pat. No. 8,642,742).

SEQ ID NO. 488
DIQMTQSPSSLSASVGDRVTITCKASAAVGTYVAWYQQKPGKAPKLLIY
SASYRKRGVPSRFSGSGSGTDFTLTISSLQPEDFATYYCHQYYTYPLFT
FGQGTKLEIK

In an embodiment of the invention, the CEA-targeting antibody construct or antigen binding domain comprises the light chain CDR (complementarity determining region) or light chain framework (LFR) sequences of hPR1A3 SEQ ID NO. 489-495 (U.S. Pat. No. 8,642,742).

| Region | Sequence Fragment | Residues | Length | SEQ ID NO. |
|---|---|---|---|---|
| LFR1 | DIQMTQSPSSLSASVGDRVTITC | 1-23 | 23 | 489 |
| CDR-L1 | KASAAVGTYVA | 24-34 | 11 | 490 |
| LFR2 | WYQQKPGKAPKLLIY | 35-49 | 15 | 491 |
| CDR-L2 | SASYRKR | 50-56 | 7 | 492 |
| LFR3 | GVPSRFSGSGSGTDFTLTISSLQPEDFATYYC | 57-88 | 32 | 493 |
| CDR-L3 | HQYYTYPLFT | 89-98 | 10 | 494 |
| LFR4 | FGQGTKLEIK | 99-108 | 10 | 495 |

In an embodiment of the invention, the CEA-targeting antibody construct or antigen binding domain comprises the heavy chain CDR (complementarity determining region) or heavy chain framework (HFR) sequences of hPR1A3 SEQ ID NO. 496-502 (U.S. Pat. No. 8,642,742).

| Region | Sequence Fragment | Residues | Length | SEQ ID NO. |
|---|---|---|---|---|
| HFR1 | QVQLVQSGAEVKKPGASVKVSCKASGYTFT | 1-30 | 30 | 496 |
| CDR-H1 | EFGMN | 31-35 | 5 | 497 |
| HFR2 | WVRQAPGQGLEWMG | 36-49 | 14 | 498 |
| CDR-H2 | WINTKTGEATYVEEFKG | 50-66 | 17 | 499 |
| HFR3 | RVTFTTDTSTSTAYMELRSLRSDDTAVYYCAR | 67-98 | 32 | 500 |
| CDR-H3 | WDFAYYVEAMDY | 99-110 | 12 | 501 |
| HFR4 | WGQGTTVTVSS | 111-121 | 11 | 502 |

In an embodiment of the invention, the CEA-targeting antibody construct or antigen binding domain comprises the Variable light chain (VL kappa) of hMFE-23 SEQ ID NO. 503 (U.S. Pat. No. 723,288).

SEQ ID NO. 503
ENVLTQSPSSMSASVGDRVNIACSASSSVSYMHWFQQKPGKSPKLWIYST
SNLASGVPSRFSGSGSGTDYSLTISSMQPEDAATYYCQQRSSYPLTFGGG
TKLEIK

In an embodiment of the invention, the CEA-targeting antibody construct or antigen binding domain comprises the light chain CDR (complementarity determining region) or light chain framework (LFR) sequences of hMFE-23 SEQ ID NO. 504-510 (U.S. Pat. No. 723,288).

| Region | Sequence Fragment | Residues | Length | SEQ ID NO. |
|---|---|---|---|---|
| LFR1 | ENVLTQSPSSMSASVGDRVNIAC | 1-23 | 23 | 504 |
| CDR-L1 | SASSSVSYMH | 24-33 | 10 | 505 |
| LFR2 | WFQQKPGKSPKLWIY | 34-48 | 15 | 506 |
| CDR-L2 | STSNLAS | 49-55 | 7 | 507 |
| LFR3 | GVPSRFSGSGSGTDYSLTISSMQPEDAATYYC | 56-87 | 32 | 508 |
| CDR-L3 | QQRSSYPLT | 88-96 | 9 | 509 |
| LFR4 | FGGGTKLEIK | 97-106 | 10 | 510 |

In an embodiment of the invention, the CEA-targeting antibody construct or antigen binding domain comprises the Variable heavy chain (VH) of hMFE-23 SEQ ID NO. 511 (U.S. Pat. No. 723,288).

SEQ ID NO. 511
QVKLEQSGAEVVKPGASVKLSCKASGFNIKDSYMHWLRQGPGQRLEWIGW
IDPENGDTEYAPKFQGKATFTTDTSANTAYLGLSSLRPEDTAVYYCNEGT
PTGPYYFDYWGQGTLVTVSS

In an embodiment of the invention, the CEA-targeting antibody construct or antigen binding domain comprises the heavy chain CDR (complementarity determining region) or heavy chain framework (HFR) sequences of hMFE-23 SEQ ID NO. 512-518 (U.S. Pat. No. 723,288).

| Region | Sequence Fragment | Residues | Length | SEQ ID NO. |
|---|---|---|---|---|
| HFR1 | QVKLEQSGAEVVKPGASVKLSCKASGFNIK | 1-30 | 30 | 512 |
| CDR-H1 | DSYMH | 31-35 | 5 | 513 |
| HFR2 | WLRQGPGQRLEWIG | 36-49 | 14 | 514 |
| CDR-H2 | WIDPENGDTEYAPKFQG | 50-66 | 17 | 515 |
| HFR3 | KATFTTDTSANTAYLGLSSLRPEDTAVYYCNE | 67-98 | 32 | 516 |
| CDR-H3 | GTPTGPYYFDY | 99-109 | 11 | 517 |
| HFR4 | WGQGTLVTVSS | 110-120 | 11 | 518 |

In an embodiment of the invention, the CEA-targeting antibody construct or antigen binding domain comprises the Variable light chain (VL kappa) of SM3E SEQ ID NO. 519 (U.S. Pat. No. 723,288).

SEQ ID NO. 519
ENVLTQSPSSMSVSVGDRVTIACSASSSVPYMHWLQQKPGKSPKLLIYLT
SNLASGVPSRFSGSGSGTDYSLTISSVQPEDAATYYCQQRSSYPLTFGGG
TKLEIK

In an embodiment of the invention, the CEA-targeting antibody construct or antigen binding domain comprises the light chain CDR (complementarity determining region) or light chain framework (LFR) sequences of SM3E SEQ ID NO. 520-526 (U.S. Pat. No. 723,288).

| Region | Sequence Fragment | Residues | Length | SEQ ID NO. |
|---|---|---|---|---|
| LFR1 | ENVLTQSPSSMSVSVGDRVTIAC | 1-23 | 23 | 520 |
| CDR-L1 | SASSSVPYMH | 24-33 | 10 | 521 |
| LFR2 | WLQQKPGKSPKLLIY | 34-48 | 15 | 522 |
| CDR-L2 | LTSNLAS | 49-55 | 7 | 523 |
| LFR3 | GVPSRFSGSGSGTDYSLTISSVQPEDAATYYC | 56-87 | 32 | 524 |
| CDR-L3 | QQRSSYPLT | 88-96 | 9 | 525 |
| LFR4 | FGGGTKLEIK | 97-106 | 10 | 526 |

In an embodiment of the invention, the CEA-targeting antibody construct or antigen binding domain comprises the Variable heavy chain (VH) of SM3E SEQ ID NO. 527 (U.S. Pat. No. 723,288).

```
                                        SEQ ID NO. 527
QVKLEQSGAEVVKPGASVKLSCKASGFNIKDSYMHWLRQGPGQRLEWIGW
IDPENGDTEYAPKFQGKATFTTDTSANTAYLGLSSLRPEDTAVYYCNEGT
PTGPYYFDYWGQGTLVTVSS
```

In an embodiment of the invention, the CEA-targeting antibody construct or antigen binding domain comprises the heavy chain CDR (complementarity determining region) or heavy chain framework (HFR) sequences of SM3E SEQ ID NO. 528-534 (U.S. Pat. No. 723,288).

| Region | Sequence Fragment | Residues | Length | SEQ ID NO. |
|---|---|---|---|---|
| HFR1 | QVKLEQSGAEVVKPGASVKLSCKASGFNIK | 1-30 | 30 | 528 |
| CDR-H1 | DSYMH | 31-35 | 5 | 529 |
| HFR2 | WLRQGPGQRLEWIG | 36-49 | 14 | 530 |
| CDR-H2 | WIDPENGDTEYAPKFQG | 50-66 | 17 | 531 |
| HFR3 | KATFTTDTSANTAYLGLSSLRPEDTAVYYCNE | 67-98 | 32 | 532 |
| CDR-H3 | GTPTGPYYFDY | 99-109 | 11 | 533 |
| HFR4 | WGQGTLVTVSS | 110-120 | 11 | 534 |

In an embodiment of the invention, the CEA-targeting antibody construct or antigen binding domain comprises the light chain CDR (complementarity determining region) or light chain framework (LFR) sequences of NP-4/arcitumomab SEQ ID NO. 535-541.

| Region | Sequence Fragment | Residues | Length | SEQ ID NO. |
|---|---|---|---|---|
| LFR1 | QTVLSQSPAILSASPGEKVTMTC | 1-23 | 23 | 535 |
| CDR-L1 | RASSSVTYIH | 24-33 | 10 | 536 |
| LFR2 | WYQQKPGSSPKSWIY | 34-48 | 15 | 537 |
| CDR-L2 | ATSNLAS | 49-55 | 7 | 538 |
| LFR3 | GVPARFSGSGSGTSYSLTISRVEAEDAATYYC | 56-87 | 32 | 539 |
| CDR-L3 | QHWSSKPPT | 88-96 | 9 | 540 |
| LFR4 | FGGGTKLEIK | 97-106 | 10 | 541 |

In an embodiment of the invention, the CEA-targeting antibody construct or antigen binding domain comprises the Variable heavy chain (VH) of NP-4/arcitumomab SEQ ID NO. 542.

```
                                   SEQ ID NO. 542
EVKLVESGGGLVQPGGSLRLSCATSGFTFTDYYMNWVRQPPGKALEWLGFI
GNKANGYTTEYSASVKGRFTISRDKSQSILYLQMNTLRAEDSATYYCTRDR
GLRFYFDYWGQGTTLTVSS.
```

In an embodiment of the invention, the CEA-targeting antibody construct or antigen binding domain comprises the heavy chain CDR (complementarity determining region) or heavy chain framework (HFR) sequences of NP-4 SEQ ID NO. 543-549.

| Region | Sequence Fragment | Residues | Length | SEQ ID NO. |
|---|---|---|---|---|
| HFR1 | EVKLVESGGGLVQPGGSLRLSCATSGFTFT | 1-30 | 30 | 543 |
| CDR-H1 | DYYMN | 31-35 | 5 | 544 |
| HFR2 | WVRQPPGKALEWLG | 36-49 | 14 | 545 |
| CDR-H2 | FIGNKANGYTTEYSASVKG | 50-68 | 19 | 546 |
| HFR3 | RFTISRDKSQSILYLQMNTLRAEDSATYYCTR | 69-100 | 32 | 547 |
| CDR-H3 | DRGLRFYFDY | 101-110 | 10 | 548 |
| HFR4 | WGQGTTLTVSS | 111-121 | 11 | 549 |

In an embodiment of the invention, the CEA-targeting antibody construct or antigen binding domain comprises the Variable light chain (VL kappa) of M5A/hT84.66 SEQ ID NO. 550 (U.S. Pat. No. 7,776,330).

```
                                   SEQ ID NO. 550
DIQLTQSPSSLSASVGDRVTITCRAGESVDIFGVGFLHWYQQKPGKAPKL
LIYRASNLESGVPSRFSGSGSRTDFTLTISSLQPEDFATYYCQQTNEDPY
TFGQGTKVEIK
```

In an embodiment of the invention, the CEA-targeting antibody construct or antigen binding domain comprises the light chain CDR (complementarity determining region) or light chain framework (LFR) sequences of M5A/hT84.66 SEQ ID NO. 551-557 (U.S. Pat. No. 7,776,330).

| Region | Sequence Fragment | Residues | Length | SEQ ID NO. |
|---|---|---|---|---|
| LFR1 | DIQLTQSPSSLSASVGDRVTITC | 1-23 | 23 | 551 |
| CDR-L1 | RAGESVDIFGVGFLH | 24-38 | 15 | 552 |
| LFR2 | WYQQKPGKAPKLLIY | 39-53 | 15 | 553 |
| CDR-L2 | RASNLES | 54-60 | 7 | 554 |
| LFR3 | GVPSRFSGSGSRTDFTLTISSLQPEDFATYYC | 61-92 | 32 | 555 |
| CDR-L3 | QQTNEDPYT | 93-101 | 9 | 556 |
| LFR4 | FGQGTKVEIK | 102-111 | 10 | 557 |

In an embodiment of the invention, the CEA-targeting antibody construct or antigen binding domain comprises the Variable heavy chain (VH) of M5A/hT84.66 SEQ ID NO. 558 (U.S. Pat. No. 7,776,330).

```
                                     SEQ ID NO. 558
EVQLVESGGGLVQPGGSLRLSCAASGFNIKDTYMHWVRQAPGKGLEWVAR
IDPANGNSKYADSVKGRFTISADTSKNTAYLQMNSLRAEDTAVYYCAPFG
YYVSDYAMAYWGQGTLVTVSS
```

In an embodiment of the invention, the CEA-targeting antibody construct or antigen binding domain comprises the heavy chain CDR (complementarity determining region) or heavy chain framework (HFR) sequences of M5A/hT84.66 SEQ ID NO. 559-565 (U.S. Pat. No. 7,776,330).

| Region | Sequence Fmgment | Residues | Length | SEQ ID NO. |
|---|---|---|---|---|
| HFR1 | EVQLVESGGGLVQPGGSLRLSCAASGFNIK | 1-30 | 30 | 559 |
| CDR-H1 | DTYMH | 31-35 | 5 | 560 |
| HFR2 | WVRQAPGKGLEWVA | 36-49 | 14 | 561 |
| CDR-H2 | RIDPANGNSKYADSVKG | 50-66 | 17 | 562 |
| HFR3 | RFTISADTSKNTAYLQMNSLRAEDTAVYYCAP | 67-98 | 32 | 563 |
| CDR-H3 | FGYYVSDYAMAY | 99-110 | 12 | 564 |
| HFR4 | WGQGTLVTVSS | 111-121 | 11 | 565 |

In an embodiment of the invention, the CEA-targeting antibody construct or antigen binding domain comprises the Variable light chain (VL kappa) of hAb2-3 SEQ ID NO. 566 (U.S. Pat. No. 9,617,345).

```
                                     SEQ ID NO. 566
DIQMTQSPASLSASVGDRVTITCRASENIFSYLAWYQQKPGKSPKLLVYN
TRTLAEGVPSRFSGSGSGTDFSLTISSLQPEDFATYYCQHHYGTPFTFGS
GTKLEIK
```

In an embodiment of the invention, the CEA-targeting antibody construct or antigen binding domain comprises the light chain CDR (complementarity determining region) or light chain framework (LFR) sequences of hAb2-3 SEQ ID NO. 567-573 (U.S. Pat. No. 9,617,345).

| Region | Sequence Fmgment | Residues | Length | SEQ ID NO. |
|---|---|---|---|---|
| LFR1 | DIQMTQSPASLSASVGDRVTITC | 1-23 | 23 | 567 |
| CDR-L1 | RASENIFSYLA | 24-34 | 11 | 568 |
| LFR2 | WYQQKPGKSPKLLVY | 35-49 | 15 | 569 |
| CDR-L2 | NTRTLAE | 50-56 | 7 | 570 |
| LFR3 | GVPSRFSGSGSGTDFSLTISSLQPEDFATYYC | 57-88 | 32 | 571 |
| CDR-L3 | QHHYGTPFT | 89-97 | 9 | 572 |
| LFR4 | FGSGTKLEIK | 98-107 | 10 | 573 |

In an embodiment of the invention, the CEA-targeting antibody construct or antigen binding domain comprises the Variable heavy chain (VH) of SEQ ID NO. 574 (U.S. Pat. No. 9,617,345).

```
                                     SEQ ID NO. 574
EVQLQESGPGLVKPGGSLSLSCAASGFVFSSYDMSWVRQTPERGLEWVAY
ISSGGGITYAPSTVKGRFTVSRDNAKNTLYLQMNSLTSEDTAVYYCAAHY
FGSSGPFAYWGQGTLVTVSS
```

In an embodiment of the invention, the CEA-targeting antibody construct or antigen binding domain comprises the heavy chain CDR (complementarity determining region) or heavy chain framework (HFR) sequences of hAb2-3 SEQ ID NO. 575-581.

| Region | Sequence Fragment | Residues | Length | SEQ ID NO. |
| --- | --- | --- | --- | --- |
| HFR1 | EVQLQESGPGLVKPGGSLSLSCAASGFVFS | 1-30 | 30 | 575 |
| CDR-H1 | SYDMS | 31-35 | 5 | 576 |
| HFR2 | WVRQTPERGLEWVA | 36-49 | 14 | 577 |
| CDR-H2 | YISSGGGITYAPSTVKG | 50-66 | 17 | 578 |
| HFR3 | RFTVSRDNAKNTLYLQMNSLTSEDTAVYYCAA | 67-98 | 32 | 579 |
| CDR-H3 | HYFGSSGPFAY | 99-109 | 11 | 580 |
| HFR4 | WGQGTLVTVSS | 110-120 | 11 | 581 |

In an embodiment of the invention, the CEA-targeting antibody construct or antigen binding domain comprises the Variable light chain (VL kappa) of A240VL-B9VH/AMG-211 SEQ ID NO. 582 (U.S. Pat. No. 9,982,063).

```
                                    SEQ ID NO. 582
QAVLTQPASLSASPGASASLTCTLRRGINVGAYSIYWYQQKPGSPPQYL
LRYKSDSDKQQGSGVSSRFSASKDASANAGILLISGLQSEDEADYYCMI
WHSGASAVFGGGTKLTVL
```

In an embodiment of the invention, the CEA-targeting antibody construct or antigen binding domain comprises the light chain CDR (complementarity determining region) or light chain framework (LFR) sequences of A240VL-B9VH/AMG-211 SEQ ID NO. 583-589 (U.S. Pat. No. 9,982,063).

| Region | Sequence Fragment | Residues | Length | SEQ ID NO. |
| --- | --- | --- | --- | --- |
| LFR1 | QAVLTQPASLSASPGASASLTC | 1-22 | 22 | 583 |
| CDR-L1 | TLRRGINVGAYSIY | 23-36 | 14 | 584 |
| LFR2 | WYQQKPGSPPQYLLR | 37-51 | 15 | 585 |
| CDR-L2 | YKSDSDKQQGS | 52-62 | 11 | 586 |
| LFR3 | GVSSRFSASKDASANAGILLISGLQSEDEADYYC | 63-96 | 34 | 587 |
| CDR-L3 | MIWHSGASAV | 97-106 | 10 | 588 |
| LFR4 | FGGGTKLTVL | 107-116 | 10 | 589 |

In an embodiment of the invention, the CEA-targeting antibody construct or antigen binding domain comprises the Variable heavy chain (VH) of B9VH SEQ ID NO. 590 (U.S. Pat. No. 9,982,063),

```
                                    SEQ ID NO. 590
EVQLVESGGGLVQPGRSLRLSCAASGFTVSSYWMHWVRQAPGKGLEWVG
FIRNKANGGTTEYAASVKGRFTISRDDSKNTLYLQMNSLRAEDTAVYYC
ARDRGLRFYFDYWGQGTTVTSS
```

In an embodiment of the invention, the CEA-targeting antibody construct or antigen binding domain comprises the heavy chain CDR (complementarity determining region) or heavy chain framework (HFR) sequences of SEQ ID NO. 591-598 (U.S. Pat. No. 9,982,063). The embodiment includes two variants of CDR-H2, SEQ ID NO.:594 and SEQ ID NO.:595.

| Region | Sequence Fragment | Residues | Length | SEQ ID NO. |
|---|---|---|---|---|
| HFR1 | EVQLVESGGGLVQPGRSLRLSCAASGFTVS | 1-30 | 30 | 591 |
| CDR-H1 | SYWMH | 31-35 | 5 | 592 |
| HFR2 | WVRQAPGKGLEWVG | 36-49 | 14 | 593 |
| CDR-H2 | FIRNKANGGTTEYAASVKG | 50-68 | 19 | 594 |
| CDR-H2 | FIRNKANSGTTEYAASVKG | 50-68 | 19 | 595 |
| HFR3 | RFTISRDDSKNTLYLQMNSLRAEDTAVYYCAR | 69-100 | 32 | 596 |
| CDR-H3 | DRGLRFYFDY | 101-110 | 10 | 597 |
| HFR4 | WGQGTTVTVSS | 111-121 | 11 | 598 |

In an embodiment of the invention, the CEA-targeting antibody construct or antigen binding domain comprises the Variable heavy chain (VH) of E12VH SEQ ID NO. 599 (U.S. Pat. No. 9,982,063).

SEQ ID NO. 599
EVQLVESGGGLVQPGRSLRLSCAASGFTVSSYWMHWVRQAPGKGLEWVG
FILNKANGGTTEYAASVKGRFTISRDDSKNTLYLQMNSLRAEDTAVYYC
ARDRGLRFYFDYWGQGTTVTVSS

In an embodiment of the invention, the CEA-targeting antibody construct or antigen binding domain comprises the heavy chain CDR (complementarity determining region) or heavy chain framework (HFR) sequences of SEQ ID NO. 600-606 (U.S. Pat. No. 9,982,063).

| Region | Sequence Fragment | Residues | Length | SEQ ID NO. |
|---|---|---|---|---|
| HFR1 | EVQLVESGGGLVQPGRSLRLSCAASGFTVS | 1-30 | 30 | 600 |
| CDR-H1 | SYWMH | 31-35 | 5 | 601 |
| HFR2 | WVRQAPGKGLEWVG | 36-49 | 14 | 602 |
| CDR-H2 | FILNKANGGTTEYAASVKG | 50-68 | 19 | 603 |
| HFR3 | RFTISRDDSKNTLYLQMNSLRAEDTAVYYCAR | 69-100 | 32 | 604 |
| CDR-H3 | DRGLRFYFDY | 101-110 | 10 | 605 |
| HFR4 | WGQGTTVTVSS | 111-121 | 11 | 606 |

In some embodiments, the antibody construct further comprises an Fc domain. In certain embodiments, the antibody construct is an antibody. In certain embodiments, the antibody construct is a fusion protein. The antigen binding domain can be a single-chain variable region fragment (scFv). A single-chain variable region fragment (scFv), which is a truncated Fab fragment including the variable (V) domain of an antibody heavy chain linked to a V domain of a light antibody chain via a synthetic peptide, can be generated using routine recombinant DNA technology techniques. Similarly, disulfide-stabilized variable region fragments (dsFv) can be prepared by recombinant DNA technology. The antibody construct or antigen binding domain may comprise one or more variable regions (e.g., two variable regions) of an antigen binding domain of an anti-PD-L1 antibody, an anti-HER2 antibody, or an anti-CEA antibody, each variable region comprising a CDR1, a CDR2, and a CDR3.

In some embodiments, the antibodies in the immunoconjugates contain a modified Fc region, wherein the modification modulates the binding of the Fc region to one or more Fc receptors.

In some embodiments, the Fc region is modified by inclusion of a transforming growth factor beta 1 (TGFβ1) receptor, or a fragment thereof, that is capable of binding TGFβ1. For example, the receptor can be TGFβ receptor II (TGFβRII). In some embodiments, the TGFβ receptor is a human TGFβ receptor. In some embodiments, the IgG has a C-terminal fusion to a TGFβRII extracellular domain (ECD) as described in U.S. Pat. No. 9,676,863, incorporated herein. An "Fc linker" may be used to attach the IgG to the TGFβRII extracellular domain. The Fc linker may be a short, flexible peptide that allows for the proper three-dimensional folding of the molecule while maintaining the binding-specificity to the targets. In some embodiments, the N-terminus of the TGFβ receptor is fused to the Fc of the antibody construct (with or without an Fc linker). In some embodiments, the C-terminus of the antibody construct heavy chain is fused to the TGFβ receptor (with or without an Fc linker). In some embodiments, the C-terminal lysine residue of the antibody construct heavy chain is mutated to alanine.

In some embodiments, the antibodies in the immunoconjugates are glycosylated.

In some embodiments, the antibodies in the immunoconjugates is a cysteine-engineered antibody which provides for site-specific conjugation of an adjuvant, label, or drug moiety to the antibody through cysteine substitutions at sites where the engineered cysteines are available for conjugation but do not perturb immunoglobulin folding and assembly or alter antigen binding and effector functions (Junutula, et al., 2008b Nature Biotech., 26(8):925-932; Dornan et al. (2009)

Blood 114(13):2721-2729; U.S. Pat. Nos. 7,521,541; 7,723,485; US 2012/0121615; WO 2009/052249). A "cysteine engineered antibody" or "cysteine engineered antibody variant" is an antibody in which one or more residues of an antibody are substituted with cysteine residues. Cysteine-engineered antibodies can be conjugated to the thienoazepine adjuvant moiety as a thienoazepine-linker compound with uniform stoichiometry (e.g., up to two thienoazepine moieties per antibody in an antibody that has a single engineered cysteine site).

In some embodiments, cysteine-engineered antibodies used to prepare the immunoconjugates of Table 3 have a cysteine residue introduced at the 149-lysine site of the light chain (LC K149C). In other embodiments, the cysteine-engineered antibodies have a cysteine residue introduced at the 118-alanine site (EU numbering) of the heavy chain (HC A118C). This site is alternatively numbered 121 by Sequential numbering or 114 by Kabat numbering. In other embodiments, the cysteine-engineered antibodies have a cysteine residue introduced in the light chain at G64C or R142C according to Kabat numbering, or in the heavy chain at D101C, V184C or T205C according to Kabat numbering.

Thienoazepine Adjuvant Compounds

The immunoconjugate of the invention comprises a thienoazepine adjuvant moiety. The adjuvant moiety described herein is a compound that elicits an immune response (i.e., an immunostimulatory agent). Generally, the adjuvant moiety described herein is a TLR agonist. TLRs are type-I transmembrane proteins that are responsible for the initiation of innate immune responses in vertebrates. TLRs recognize a variety of pathogen-associated molecular patterns from bacteria, viruses, and fungi and act as a first line of defense against invading pathogens. TLRs elicit overlapping yet distinct biological responses due to differences in cellular expression and in the signaling pathways that they initiate. Once engaged (e.g., by a natural stimulus or a synthetic TLR agonist), TLRs initiate a signal transduction cascade leading to activation of nuclear factor-κB (NF-κB) via the adapter protein myeloid differentiation primary response gene 88 (MyD88) and recruitment of the IL-1 receptor associated kinase (IRAK). Phosphorylation of IRAK then leads to recruitment of TNF-receptor associated factor 6 (TRAF6), which results in the phosphorylation of the NF-κB inhibitor I-κB. AS a result, NF-κB enters the cell nucleus and initiates transcription of genes whose promoters contain NF-κB binding sites, such as cytokines. Additional modes of regulation for TLR signaling include TIR-domain containing adapter-inducing interferon-β (TRIF)-dependent induction of TNF-receptor associated factor 6 (TRAF6) and activation of MyD88 independent pathways via TRIF and TRAF3, leading to the phosphorylation of interferon response factor three (IRF3). Similarly, the MyD88 dependent pathway also activates several IRF family members, including IRF5 and IRF7 whereas the TRIF dependent pathway also activates the NF-κB pathway.

Typically, the adjuvant moiety described herein is a TLR7 and/or TLR8 agonist. TLR7 and TLR8 are both expressed in monocytes and dendritic cells. In humans, TLR7 is also expressed in plasmacytoid dendritic cells (pDCs) and B cells. TLR8 is expressed mostly in cells of myeloid origin, i.e., monocytes, granulocytes, and myeloid dendritic cells. TLR7 and TLR8 are capable of detecting the presence of "foreign" single-stranded RNA within a cell, as a means to respond to viral invasion. Treatment of TLR8-expressing cells, with TLR8 agonists can result in production of high levels of IL-12, IFN-γ, IL-1, TNF-α, IL-6, and other inflammatory cytokines. Similarly, stimulation of TLR7-expressing cells, such as pDCs, with TLR7 agonists can result in production of high levels of IFN-α and other inflammatory cytokines. TLR7/TLR8 engagement and resulting cytokine production can activate dendritic cells and other antigen-presenting cells, driving diverse innate and acquired immune response mechanisms leading to tumor destruction.

Exemplary thienoazepine compounds (TAZ) of the invention are shown in Tables 1a-c. Each compound was synthesized, purified, and characterized by mass spectrometry and shown to have the mass indicated. Additional experimental procedures are found in the Examples. Activity against HEK293 NFKB reporter cells expressing human TLR7 or human TLR8 was measured according to Example 202. The thienoazepine compounds of Tables 1a-c demonstrate the surprising and unexpected property of TLR8 agonist selectivity which may predict useful therapeutic activity to treat cancer and other disorders.

TABLE 1a

| | Thienoazepine compounds (TAZ) | | | |
|---|---|---|---|---|
| TAZ No. | Structure | MW | HEK293 hTLR7 EC50 (nM) | HEK293 hTLR8 EC50 (nM) |
| TAZ-1 | 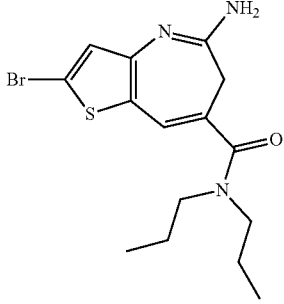 [SMILES: CCCN(CCC)C(=O)C1=Cc2sc(Br)cc2N=C(N)C1] | 370.3 | >9000 | >9000 |

TABLE 1a-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-2 | 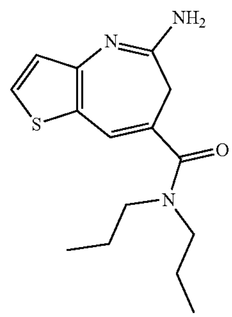 [SMILES: CCCN(CCC)C(=O)C1=Cc2sccc2N=C(N)C1] | 291.4 | >9000 | 2390 |
| TAZ-3 | 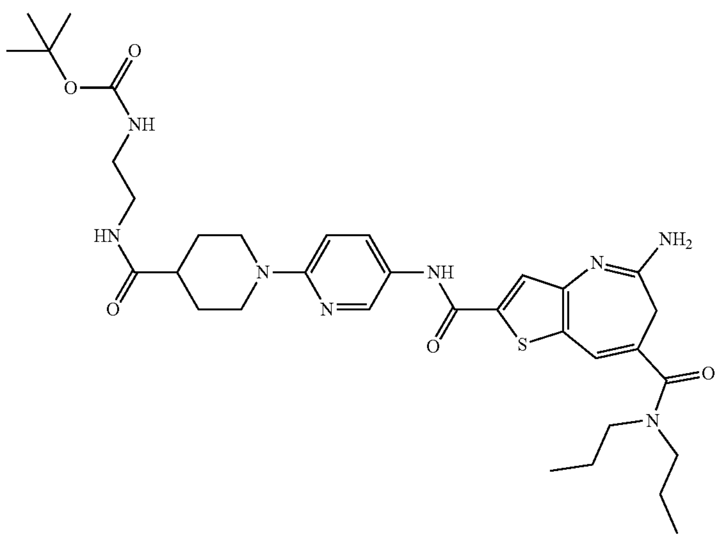 [SMILES: CCCN(CCC)C(=O)C1=Cc2sc(C(=O)Nc3ccc(N4CCC(C(=O)NCCNC(=O)OC(C)(C)C)CC4)nc3)cc2N=C(N)C1] | 680.9 | >9000 | >9000 |
| TAZ-4 | 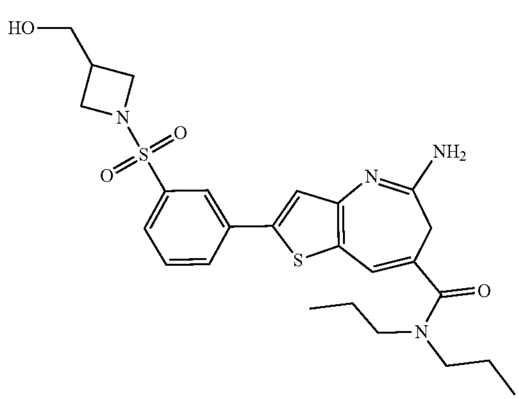 [SMILES: CCCN(CCC)C(=O)C1=Cc2sc(-c3cccc(S(=O)(=O)N4CC(CO)C4)c3)cc2N=C(N)C1] | 516.7 | >9000 | >9000 |

TABLE 1a-continued
| | Thienoazepine compounds (TAZ) | | | |
|---|---|---|---|---|
| TAZ No. | Structure | MW | HEK293 hTLR7 EC50 (nM) | HEK293 hTLR8 EC50 (nM) |
| TAZ-5 | 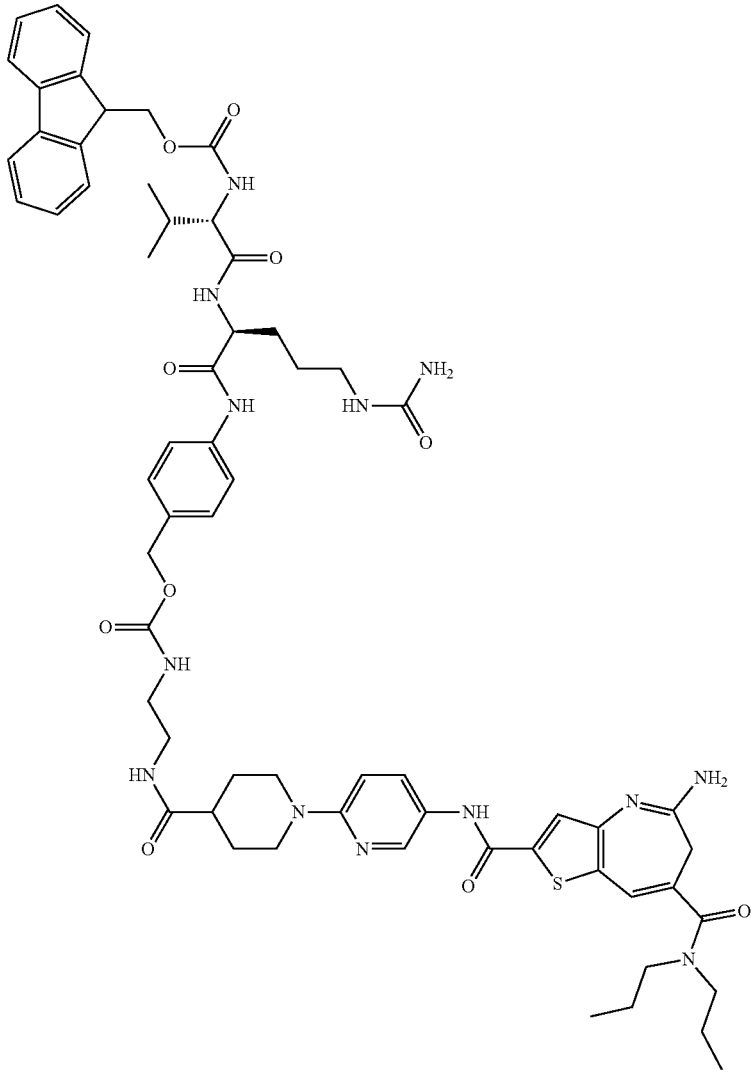 [SMILES: CCCN(CCC)C(=O)C1=Cc2sc(C(=O)Nc3ccc(N4CCC(C(=O)NCCNC(=O)OCc5ccc(NC(=O)[C@H](CCCNC(N)=O)NC(=O)[C@@H](NC(=O)OCC6c7ccccc7-c7ccccc76)C(C)C)cc5)CC4)nc3)cc2N=C(N)C1] | 1208.4 | Not Determined | Not Determined |
| TAZ-6 | 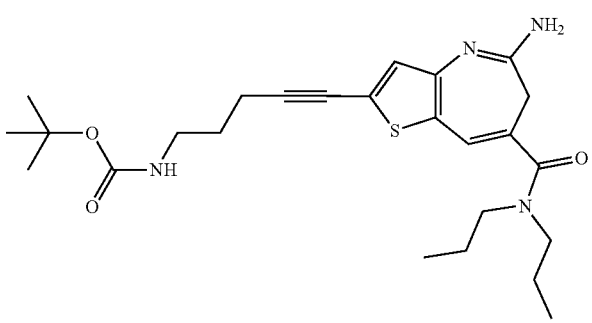 [SMILES: CCCN(CCC)C(=O)C1=Cc2sc(C#CCCCNC(=O)OC(C)(C)C)cc2N=C(N)C1] | 472.7 | >9000 | >9000 |

TABLE 1a-continued

| | Thienoazepine compounds (TAZ) | | | |
|---|---|---|---|---|
| TAZ No. | Structure | MW | HEK293 hTLR7 EC50 (nM) | HEK293 hTLR8 EC50 (nM) |
| TAZ-7 | | 305.4 | >9000 | >9000 |
| TAZ-8 | | 406.5 | 589 | 1533 |
| TAZ-9 | | 485.4 | >9000 | >9000 |

TABLE 1a-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-10 | 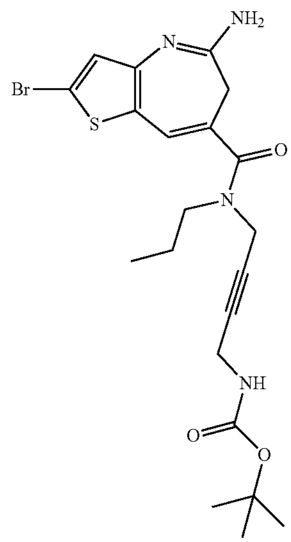 [SMILES: CCCN(CC#CCNC(=O)OC(C)(C)C)C(=O)C1=Cc2sc(Br)cc2N=C(N)C1] | 495.4 | 7767 | >9000 |
| TAZ-11 | 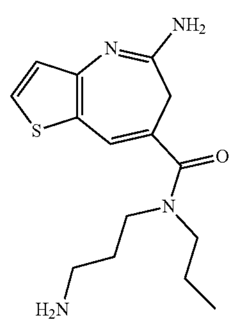 [SMILES: CCCN(CCCN)C(=O)C1=Cc2sccc2N=C(N)C1] | 306.4 | >9000 | >9000 |
| TAZ-12 | 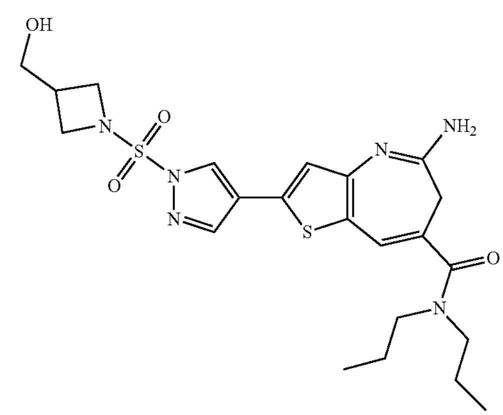 [SMILES: CCCN(CCC)C(=O)C1=Cc2sc(-c3cnn(S(=O)(=O)N4CC(CO)C4)c3)cc2N=C(N)C1] | 506.6 | >9000 | >9000 |

TABLE 1a-continued

| | Thienoazepine compounds (TAZ) | | | |
|---|---|---|---|---|
| TAZ No. | Structure | MW | HEK293 hTLR7 EC50 (nM) | HEK293 hTLR8 EC50 (nM) |
| TAZ-13 | | 476.7 | >9000 | >9000 |
| TAZ-14 | | 376.6 | >9000 | 4940 |
| TAZ-15 | | 287.1 | Not Determined | Not Determined |
| TAZ-16 | | 416.5 | >9000 | 6111 |

TABLE 1a-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-17 | 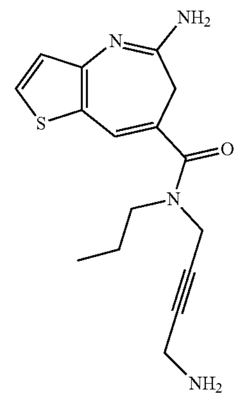 [SMILES: CCCN(CC#CCN)C(=O)C1=Cc2sccc2N=C(N)C1] | 316.4 | >9000 | 4101 |
| TAZ-18 | 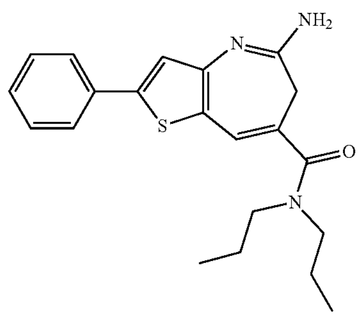 [SMILES: CCCN(CCC)C(=O)C1=Cc2sc(-c3ccccc3)cc2N=C(N)C1] | 367.5 | >9000 | >9000 |
| TAZ-19 | 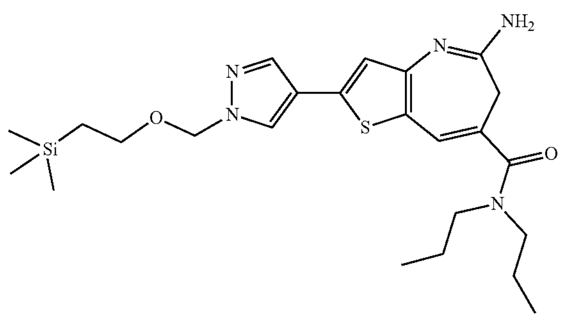 [SMILES: CCCN(CCC)C(=O)C1=Cc2sc(-c3cnn(COCC[Si](C)(C)C)c3)cc2N=C(N)C1] | 487.7 | >9000 | >9000 |
| TAZ-20 | 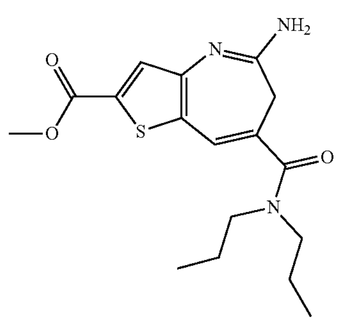 [SMILES: CCCN(CCC)C(=O)C1=Cc2sc(C(=O)OC)cc2N=C(N)C1] | 349.4 | >9000 | >9000 |

TABLE 1a-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-21 | 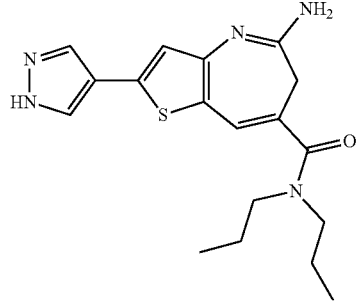 [SMILES: CCCN(CCC)C(=O)C1=Cc2sc(-c3cn[nH]c3)cc2N=C(N)C1] | 357.5 | >9000 | >9000 |
| TAZ-22 | 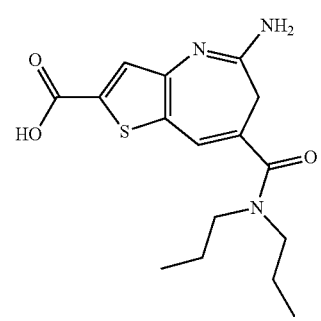 [SMILES: CCCN(CCC)C(=O)C1=Cc2sc(C(=O)O)cc2N=C(N)C1] | 335.4 | >9000 | >9000 |
| TAZ-23 | 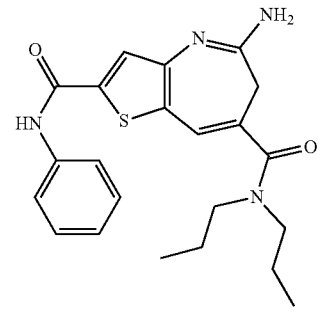 [SMILES: CCCN(CCC)C(=O)C1=Cc2sc(C(=O)Nc3ccccc3)cc2N=C(N)C1] | 410.5 | >9000 | >9000 |
| TAZ-24 | 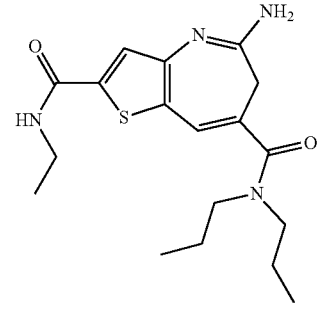 [SMILES: CCCN(CCC)C(=O)C1=Cc2sc(C(=O)NCC)cc2N=C(N)C1] | 362.5 | >9000 | >9000 |

TABLE 1a-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-25 | 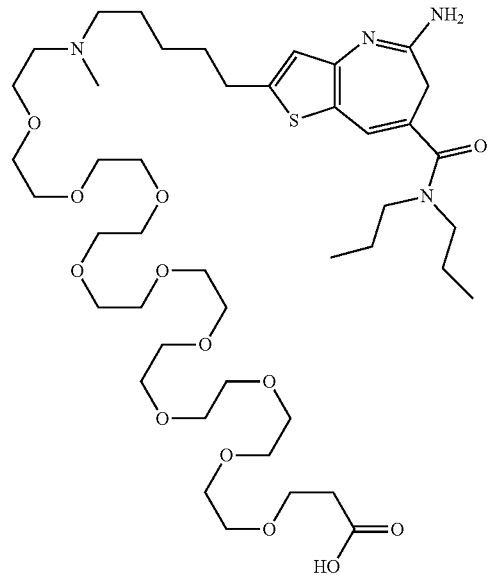 [SMILES: CCCN(CCC)C(=O)C1=Cc2sc(CCCCCN(C)CCOCCOCCOCCOCCOCCOCCOCCOCCOCCOCCC(=O)O)cc2N=C(N)C1] | 903.2 | Not Determined | Not Determined |
| TAZ-26 | 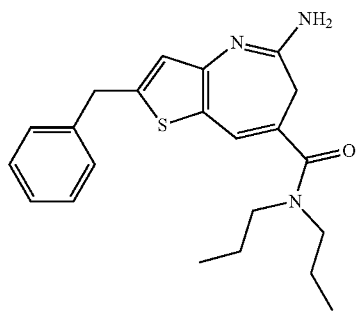 [SMILES: CCCN(CCC)C(=O)C1=Cc2sc(Cc3ccccc3)cc2N=C(N)C1] | 381.5 | >9000 | >9000 |
| TAZ-27 | 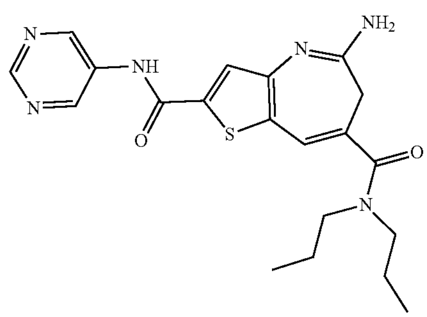 [SMILES: CCCN(CCC)C(=O)C1=Cc2sc(C(=O)Nc3cncnc3)cc2N=C(N)C1] | 412.5 | >9000 | >9000 |
| TAZ-28 | 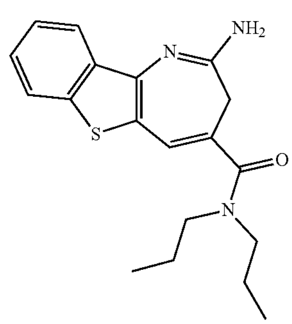 [SMILES: CCCN(CCC)C(=O)C1=Cc2sc3ccccc3c2N=C(N)C1] | 341.5 | >9000 | >9000 |

TABLE 1a-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-29 | 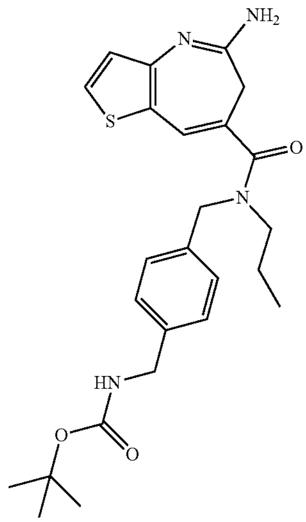 [SMILES: CCCN(Cc1ccc(CNC(=O)OC(C)(C)C)cc1)C(=O)C1=Cc2sccc2N=C(N)C1] | 468.6 | >9000 | >9000 |
| TAZ-30 | 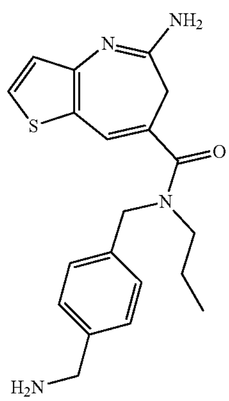 [SMILES: CCCN(Cc1ccc(CN)cc1)C(=O)C1=Cc2sccc2N=C(N)C1] | 368.5 | >9000 | 641 |

TABLE 1b

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-31 | 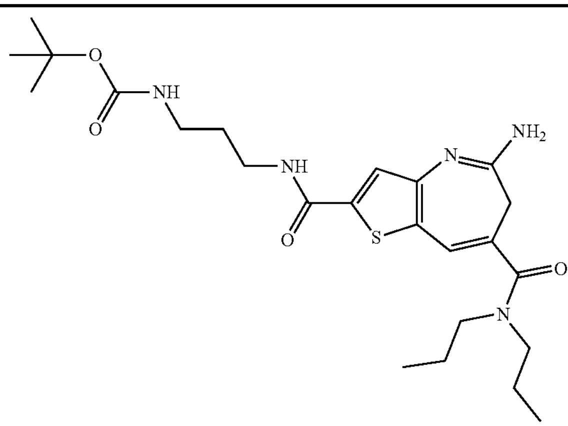 | 491.65 | >9000 | >9000 |

TABLE 1b-continued

Thienoazepine compounds (TAZ)

| TAZ No. | Structure | MW | HEK293 hTLR7 EC50 (nM) | HEK293 hTLR8 EC50 (nM) |
| --- | --- | --- | --- | --- |
| TAZ-32 | 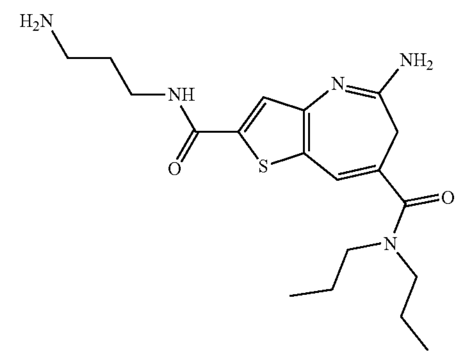 [SMILES: CCCN(CCC)C(=O)C1=Cc2sc(C(=O)NCCCN)cc2N=C(N)C1] | 391.53 | >9000 | >9000 |
| TAZ-33 | 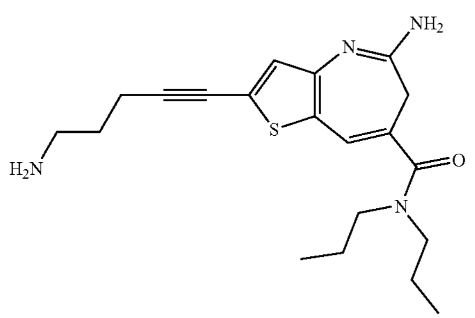 [SMILES: CCCN(CCC)C(=O)C1=Cc2sc(C#CCCCN)cc2N=C(N)C1] | 372.53 | >9000 | >9000 |
| TAZ-34 | 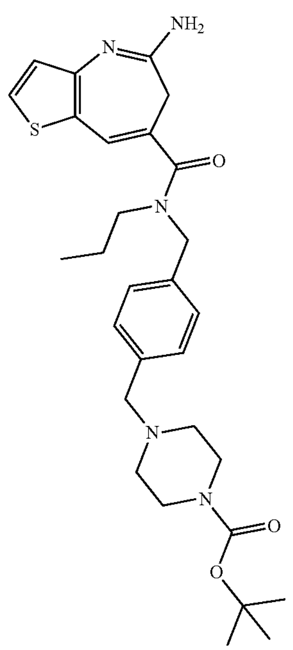 [SMILES: CCCN(Cc1ccc(CN2CCN(C(=O)OC(C)(C)C)CC2)cc1)C(=O)C1=Cc2sccc2N=C(N)C1] | 537.72 | >9000 | 339 |

TABLE 1b-continued

Thienoazepine compounds (TAZ)

| TAZ No. | Structure | MW | HEK293 hTLR7 EC50 (nM) | HEK293 hTLR8 EC50 (nM) |
| --- | --- | --- | --- | --- |
| TAZ-35 | 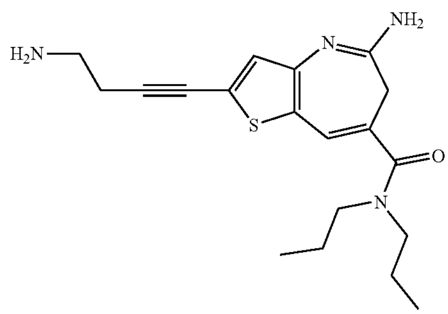 [SMILES: CCCN(CCC)C(=O)C1=Cc2sc(C#CCCN)cc2N=C(N)C1] | 358.5 | >9000 | 2870 |
| TAZ-36 | 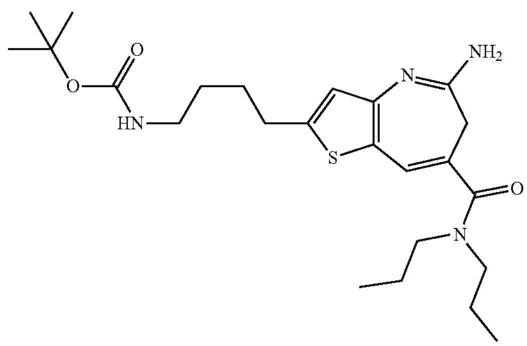 [SMILES: CCCN(CCC)C(=O)C1=Cc2sc(CCCCNC(=O)OC(C)(C)C)cc2N=C(N)C1] | 462.65 | 8524 | >9000 |
| TAZ-37 | 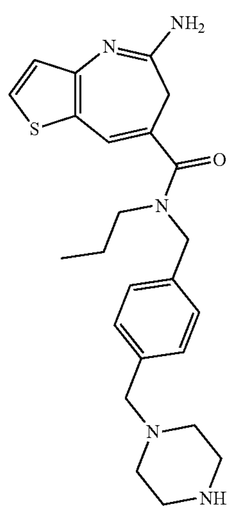 [SMILES: CCCN(Cc1ccc(CN2CCNCC2)cc1)C(=O)C1=Cc2sccc2N=C(N)C1] | 437.6 | >9000 | 2938 |
| TAZ-38 | 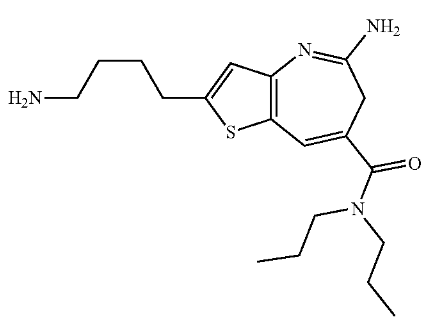 [SMILES: CCCN(CCC)C(=O)C1=Cc2sc(CCCCN)cc2N=C(N)C1] | 362.53 | 4148 | 3752 |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-39 | 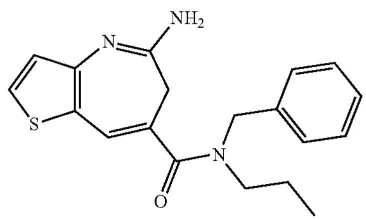 [SMILES: CCCN(Cc1ccccc1)C(=O)C1=Cc2sccc2N=C(N)C1] | 339.46 | >9000 | >9000 |
| TAZ-40 | 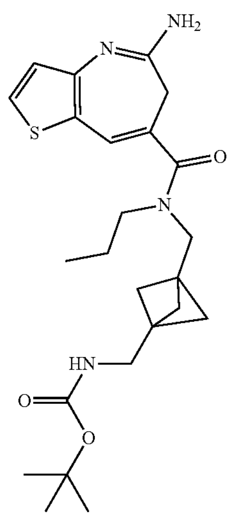 [SMILES: CCCN(CC12CC(CNC(=O)OC(C)(C)C)(C1)C2)C(=O)C1=Cc2sccc2N=C(N)C1] | 458.62 | >9000 | >9000 |
| TAZ-41 | 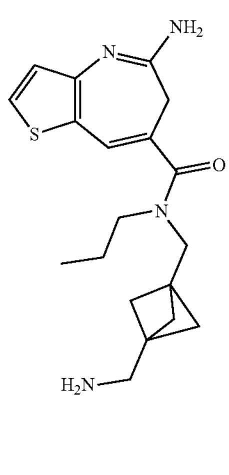 [SMILES: CCCN(CC12CC(CN)(C1)C2)C(=O)C1=Cc2sccc2N=C(N)C1] | 358.5 | >9000 | >9000 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-42 | 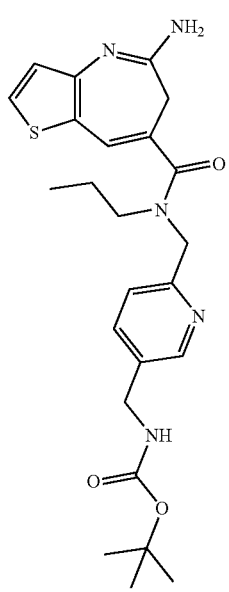 [SMILES: CCCN(Cc1ccc(CNC(=O)OC(C)(C)C)cn1)C(=O)C1=Cc2sccc2N=C(N)C1] | 469.6 | >9000 | >9000 |
| TAZ-43 | 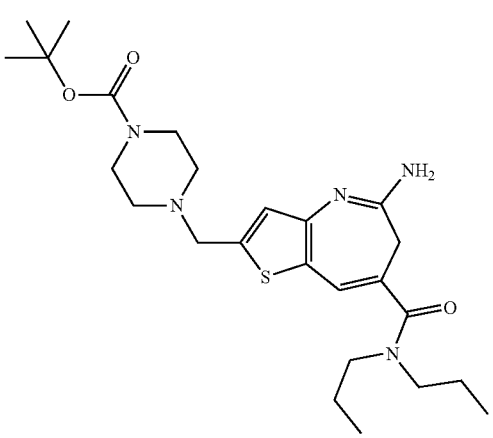 [SMILES: CCCN(CCC)C(=O)C1=Cc2sc(CN3CCN(C(=O)OC(C)(C)C)CC3)cc2N=C(N)C1] | 489.68 | >9000 | >9000 |
| TAZ-44 | 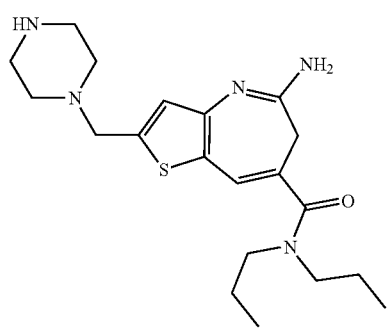 [SMILES: CCCN(CCC)C(=O)C1=Cc2sc(CN3CCNCC3)cc2N=C(N)C1] | 389.56 | 4526 | 593 |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-45 | 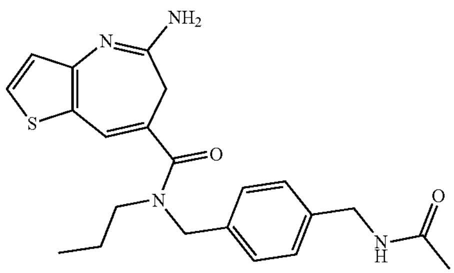 [SMILES: CCCN(Cc1ccc(CNC(C)=O)cc1)C(=O)C1=Cc2sccc2N=C(N)C1] | 410.53 | >9000 | 1779 |
| TAZ-46 | 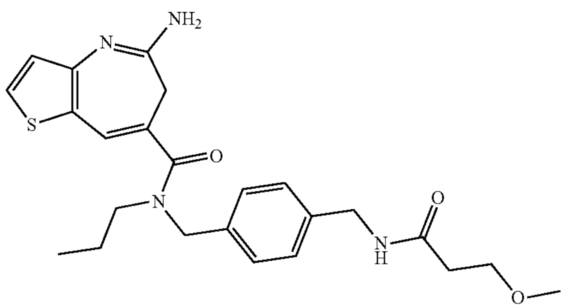 [SMILES: CCCN(Cc1ccc(CNC(=O)CCOC)cc1)C(=O)C1=Cc2sccc2N=C(N)C1] | 454.59 | >9000 | 1576 |
| TAZ-47 | 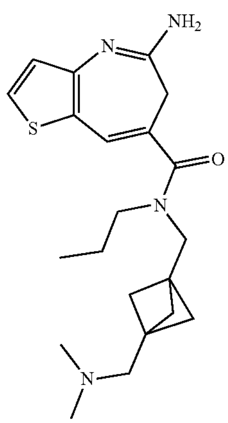 [SMILES: CCCN(CC12CC(CN(C)C)(C1)C2)C(=O)C1=Cc2sccc2N=C(N)C1] | 386.56 | >9000 | >9000 |
| TAZ-48 | 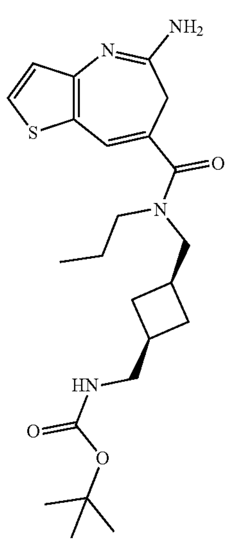 [SMILES: CCCN(C[C@H]1C[C@@H](CNC(=O)OC(C)(C)C)C1)C(=O)C1=Cc2sccc2N=C(N)C1] | 446.61 | >9000 | >9000 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-49 | 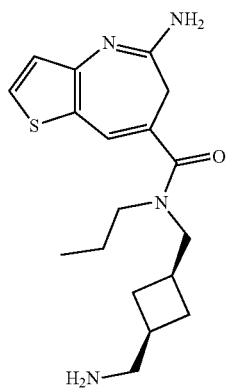 [SMILES: CCCN(C[C@H]1C[C@@H](CN)C1)C(=O)C1=Cc2sccc2N=C(N)C1] | 346.49 | >9000 | >9000 |
| TAZ-50 | 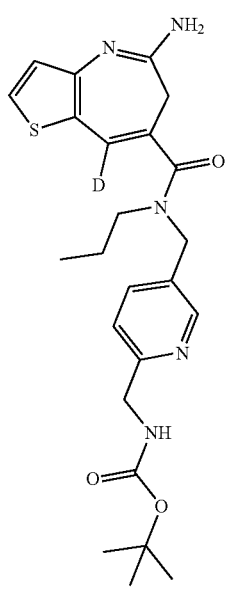 [SMILES: [2H]C1=C(C(=O)N(CCC)Cc2ccc(CNC(=O)OC(C)(C)C)nc2)CC(N)=Nc2ccsc21] | 469.6 | 7125 | 7938 |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-51 | 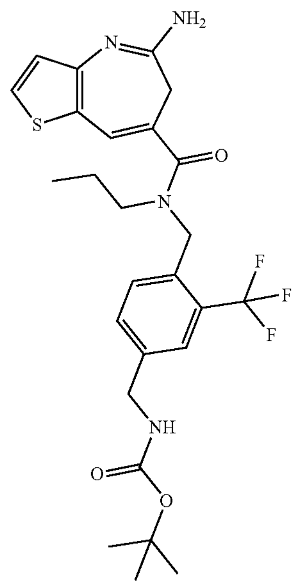 [SMILES: CCCN(Cc1ccc(CNC(=O)OC(C)(C)C)cc1C(F)(F)F)C(=O)C1=Cc2sccc2N=C(N)C1] | 536.61 | >9000 | 5635 |
| TAZ-52 | 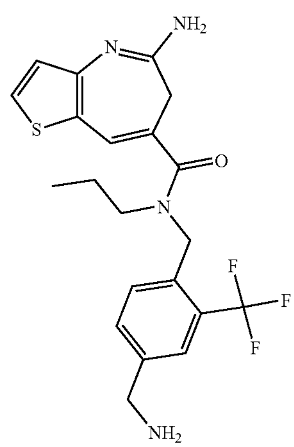 [SMILES: CCCN(Cc1ccc(CN)cc1C(F)(F)F)C(=O)C1=Cc2sccc2N=C(N)C1] | 436.5 | 2705 | 151 |
| TAZ-53 | 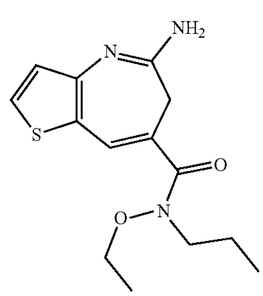 [SMILES: CCCN(OCC)C(=O)C1=Cc2sccc2N=C(N)C1] | 293.39 | 3621 | 181 |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-54 | 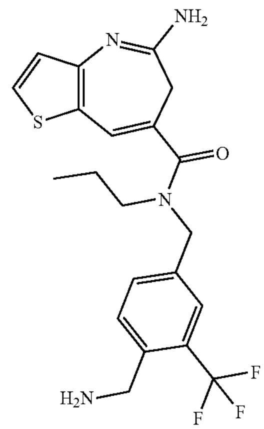 [SMILES: CCCN(Cc1ccc(CN)c(C(F)(F)F)c1)C(=O)C1=Cc2sccc2N=C(N)C1] | 436.5 | 905 | 35 |
| TAZ-55 | 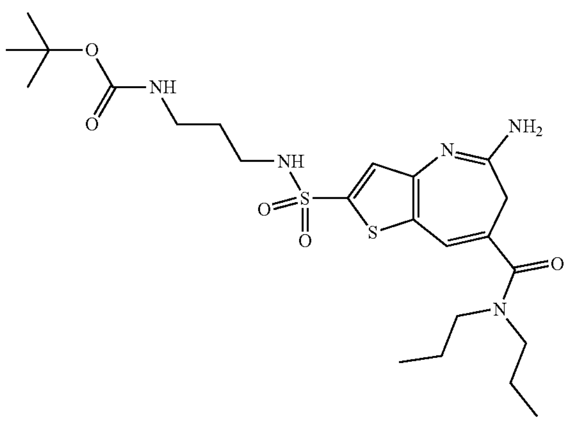 [SMILES: CCCN(CCC)C(=O)C1=Cc2sc(S(=O)(=O)NCCCNC(=O)OC(C)(C)C)cc2N=C(N)C1] | 527.7 | >9000 | >9000 |
| TAZ-56 | 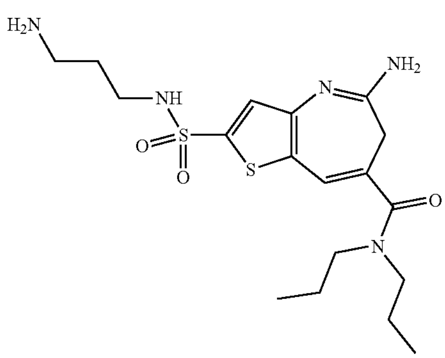 [SMILES: CCCN(CCC)C(=O)C1=Cc2sc(S(=O)(=O)NCCCN)cc2N=C(N)C1] | 427.58 | >9000 | >9000 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-57 | 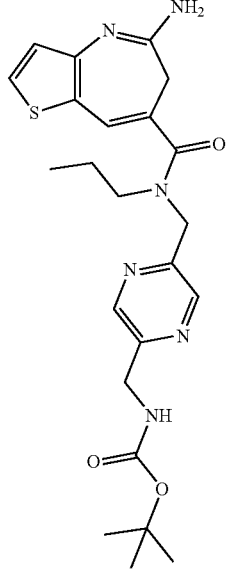 [SMILES: CCCN(Cc1cnc(CNC(=O)OC(C)(C)C)cn1)C(=O)C1=Cc2sccc2N=C(N)C1] | 470.59 | 1053 | 3850 |
| TAZ-58 | 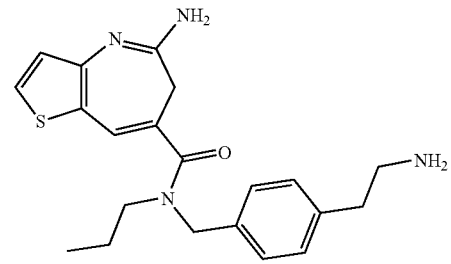 [SMILES: CCCN(Cc1ccc(CCN)cc1)C(=O)C1=Cc2sccc2N=C(N)C1] | 382.52 | >9000 | 1296 |
| TAZ-59 | 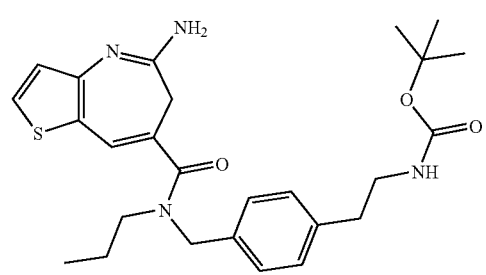 [SMILES: CCCN(Cc1ccc(CCNC(=O)OC(C)(C)C)cc1)C(=O)C1=Cc2sccc2N=C(N)C1] | 482.64 | >9000 | >9000 |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-60 | 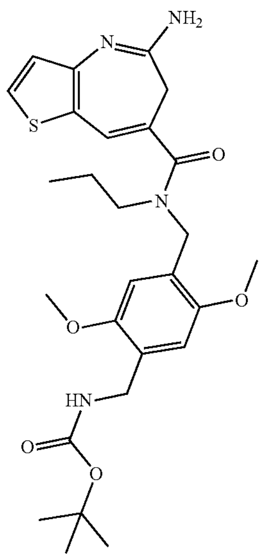 [SMILES: CCCN(Cc1cc(OC)c(CNC(=O)OC(C)(C)C)cc1OC)C(=O)C1=Cc2sccc2N=C(N)C1] | 528.67 | Not available | Not available |
| TAZ-61 | 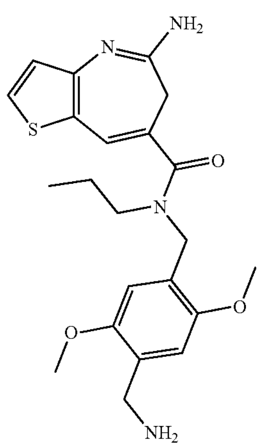 [SMILES: CCCN(Cc1cc(OC)c(CN)cc1OC)C(=O)C1=Cc2sccc2N=C(N)C1] | 428.55 | Not available | Not available |
| TAZ-62 | 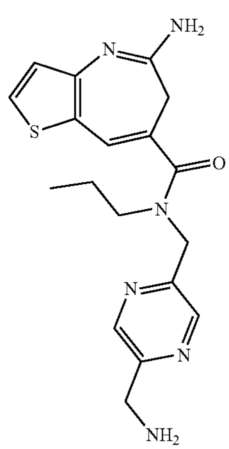 [SMILES: CCCN(Cc1cnc(CN)cn1)C(=O)C1=Cc2sccc2N=C(N)C1] | 370.47 | 8317 | 178 |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-63 | 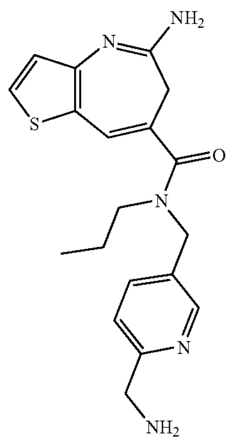 [SMILES: CCCN(Cc1ccc(CN)nc1)C(=O)C1=Cc2sccc2N=C(N)C1] | 369.48 | 4209 | 517 |
| TAZ-64 | 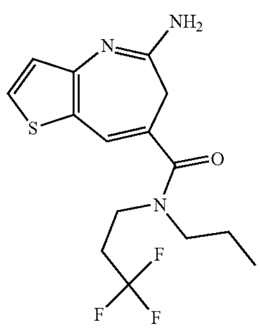 [SMILES: CCCN(CCC(F)(F)F)C(=O)C1=Cc2sccc2N=C(N)C1] | 345.38 | 5057 | 2742 |
| TAZ-65 | 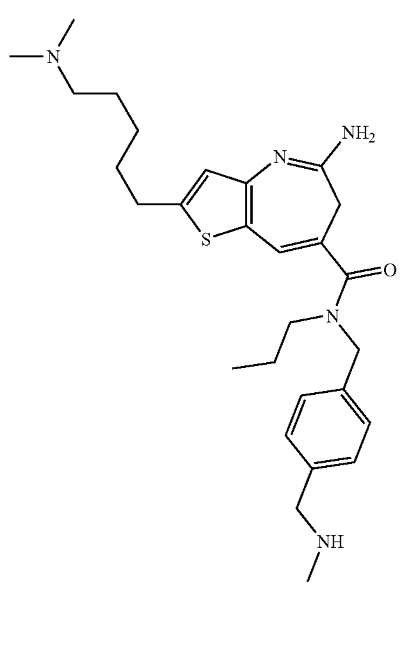 [SMILES: CCCN(Cc1ccc(CNC)cc1)C(=O)C1=Cc2sc(CCCCCN(C)C)cc2N=C(N)C1] | 495.73 | >9000 | 311 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-66 | 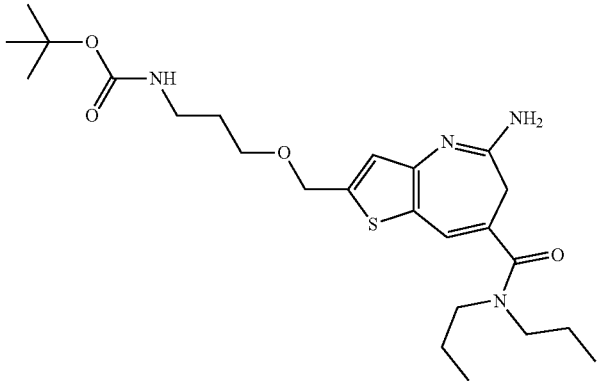 [SMILES: CCCN(CCC)C(=O)C1=Cc2sc(COCCCNC(=O)OC(C)(C)C)cc2N=C(N)C1] | 478.65 | 4423 | 4236 |
| TAZ-67 | 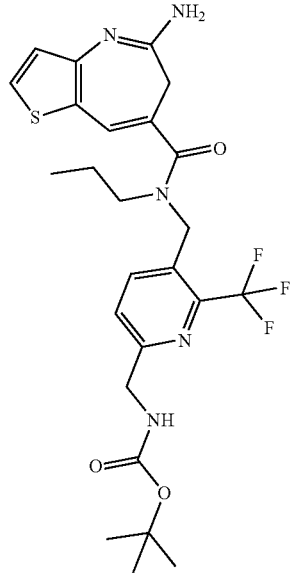 [SMILES: CCCN(Cc1ccc(CNC(=O)OC(C)(C)C)nc1C(F)(F)F)C(=O)C1=Cc2sccc2N=C(N)C1] | 537.6 | Not available | Not available |
| TAZ-68 | 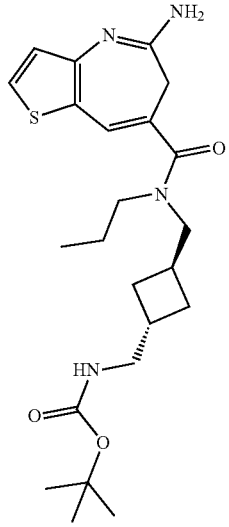 [SMILES: CCCN(C[C@H]1C[C@H](CNC(=O)OC(C)(C)C)C1)C(=O)C1=Cc2sccc2N=C(N)C1] | 446.61 | Not available | Not available |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-69 | 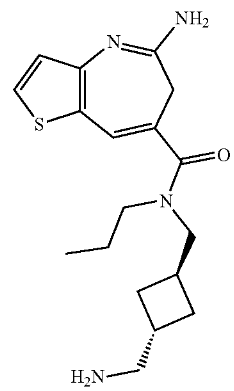 [SMILES: CCCN(C[C@H]1C[C@H](CN)C1)C(=O)C1=Cc2sccc2N=C(N)C1] | 346.49 | >9000 | 4297 |
| TAZ-70 | 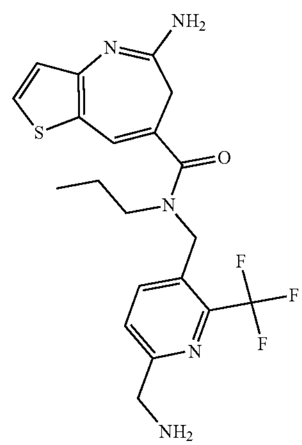 [SMILES: CCCN(Cc1ccc(CN)nc1C(F)(F)F)C(=O)C1=Cc2sccc2N=C(N)C1] | 437.48 | 6613 | 75 |
| TAZ-71 | 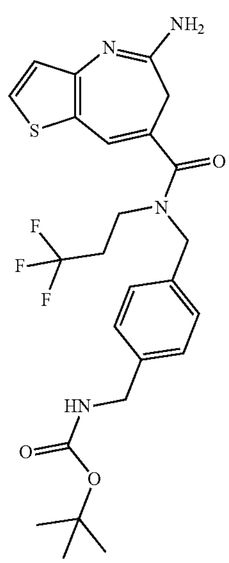 [SMILES: CC(C)(C)OC(=O)NCc1ccc(CN(CCC(F)(F)F)C(=O)C2=Cc3sccc3N=C(N)C2)cc1] | 522.58 | | |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-72 | 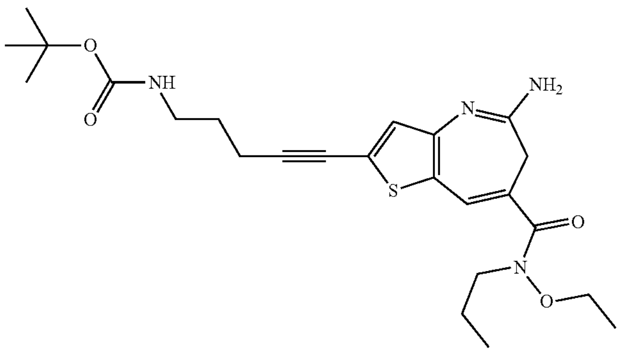 [SMILES: CCCN(OCC)C(=O)C1=Cc2sc(C#CCCCNC(=O)OC(C)(C)C)cc2N=C(N)C1] | 474.62 | 3146 | 2834 |
| TAZ-73 | 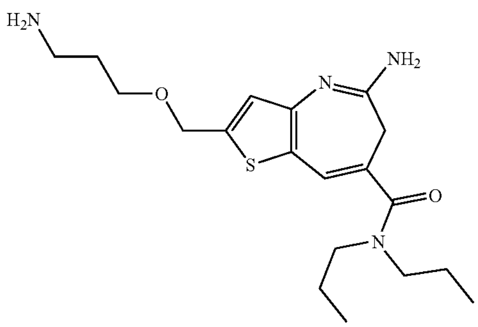 [SMILES: CCCN(CCC)C(=O)C1=Cc2sc(COCCCN)cc2N=C(N)C1] | 378.53 | >9000 | 2985 |
| TAZ-74 | 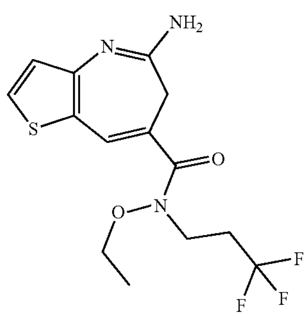 [SMILES: CCON(CCC(F)(F)F)C(=O)C1=Cc2sccc2N=C(N)C1] | 347.36 | 4108 | 301 |
| TAZ-75 | 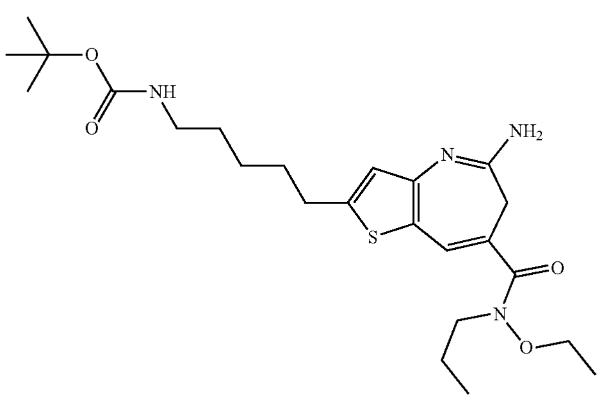 [SMILES: CCCN(OCC)C(=O)C1=Cc2sc(CCCCCNC(=O)OC(C)(C)C)cc2N=C(N)C1] | 478.65 | 5079 | 2025 |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-76 | 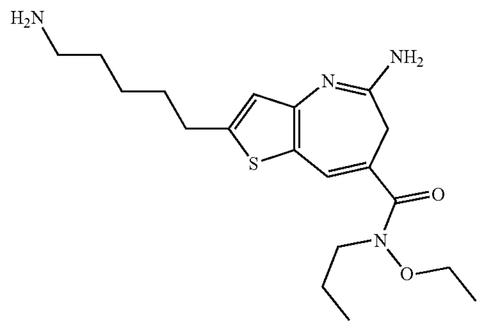 [SMILES: CCCN(OCC)C(=O)C1=Cc2sc(CCCCCN)cc2N=C(N)C1] | 378.53 | 3436 | 1418 |
| TAZ-77 | 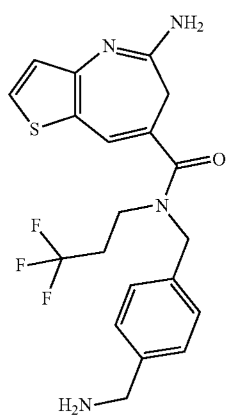 [SMILES: NCc1ccc(CN(CCC(F)(F)F)C(=O)C2=Cc3sccc3N=C(N)C2)cc1] | 422.47 | 3896 | 59 |
| TAZ-78 | 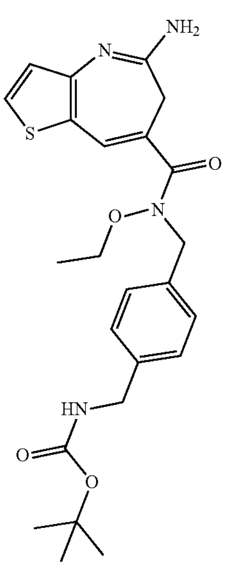 [SMILES: CCON(Cc1ccc(CNC(=O)OC(C)(C)C)cc1)C(=O)C1=Cc2sccc2N=C(N)C1] | 470.59 | Not available | Not available |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-79 | 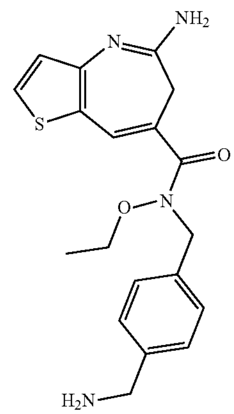 [SMILES: CCON(Cc1ccc(CN)cc1)C(=O)C1=Cc2sccc2N=C(N)C1] | 370.47 | >9000 | 4126 |
| TAZ-80 | 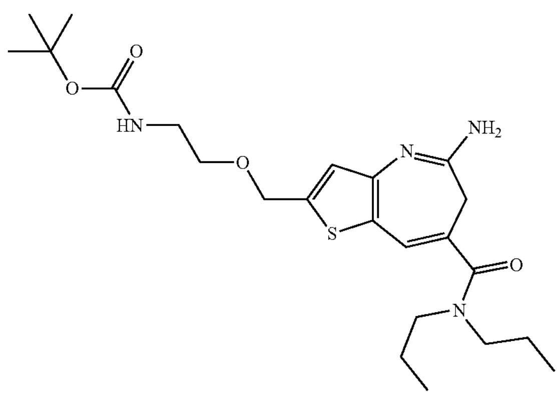 [SMILES: CCCN(CCC)C(=O)C1=Cc2sc(COCCNC(=O)OC(C)(C)C)cc2N=C(N)C1] | 464.62 | 4002 | 3793 |
| TAZ-81 | 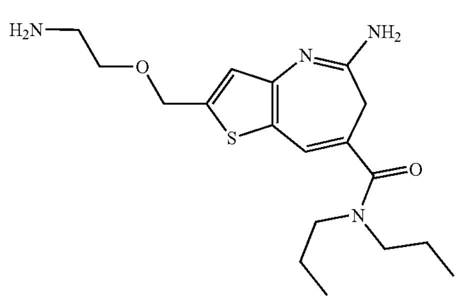 [SMILES: CCCN(CCC)C(=O)C1=Cc2sc(COCCN)cc2N=C(N)C1] | 364.51 | >9000 | 7951 |

TABLE 1b-continued
| Thienoazepine compounds (TAZ) | | | | |
|---|---|---|---|---|
| TAZ No. | Structure | MW | HEK293 hTLR7 EC50 (nM) | HEK293 hTLR8 EC50 (nM) |
| TAZ-82 | 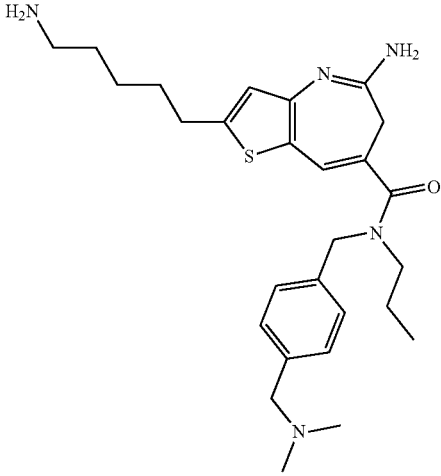 | 481.7 | 4998 | 2870 |
| TAZ-83 | 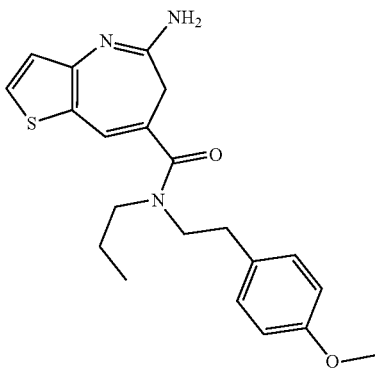 [SMILES: CCCN(CCc1ccc(OC)cc1)C(=O)C1=Cc2sccc2N=C(N)C1] | 383.51 | 3519 | 3369 |
| TAZ-84 | 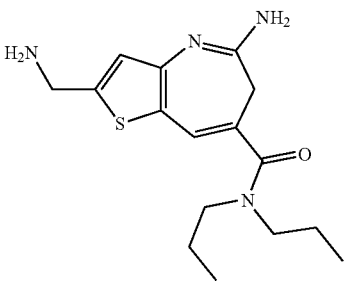 [SMILES: CCCN(CCC)C(=O)C1=Cc2sc(CN)cc2N=C(N)C1] | 320.45 | 4950 | 1373 |
| TAZ-85 | 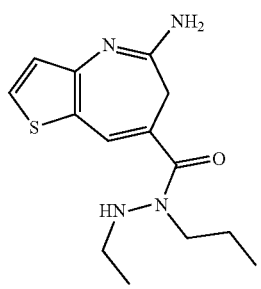 [SMILES: CCCN(NCC)C(=O)C1=Cc2sccc2N=C(N)C1] | 292.4 | >9000 | 4026 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-86 | 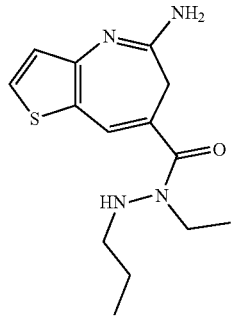 [SMILES: CCCNN(CC)C(=O)C1=Cc2sccc2N=C(N)C1] | 292.4 | >9000 | 4919 |
| TAZ-87 | 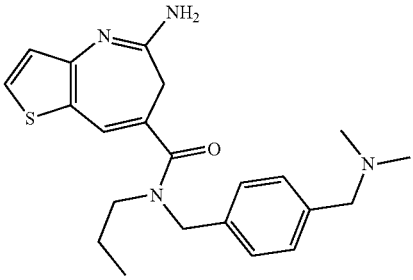 [SMILES: CCCN(Cc1ccc(CN(C)C)cc1)C(=O)C1=Cc2sccc2N=C(N)C1] | 396.55 | 1939 | 214 |
| TAZ-88 | 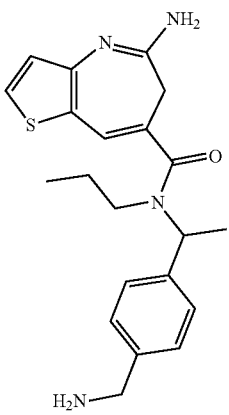 [SMILES: CCCN(C(=O)C1=Cc2sccc2N=C(N)C1)C(C)c1ccc(CN)cc1] | 382.52 | >9000 | 2270 |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-89 | 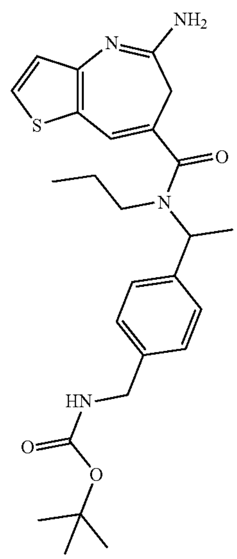 [SMILES: CCCN(C(=O)C1=Cc2sccc2N=C(N)C1)C(C)c1ccc(CNC(=O)OC(C)(C)C)cc1] | 482.64 | Not available | Not available |
| TAZ-90 | 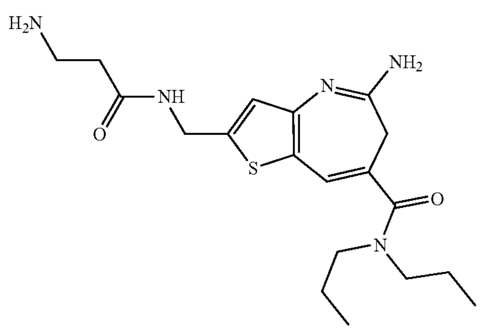 [SMILES: CCCN(CCC)C(=O)C1=Cc2sc(CNC(=O)CCN)cc2N=C(N)C1] | 391.53 | 909 | 3190 |
| TAZ-91 | 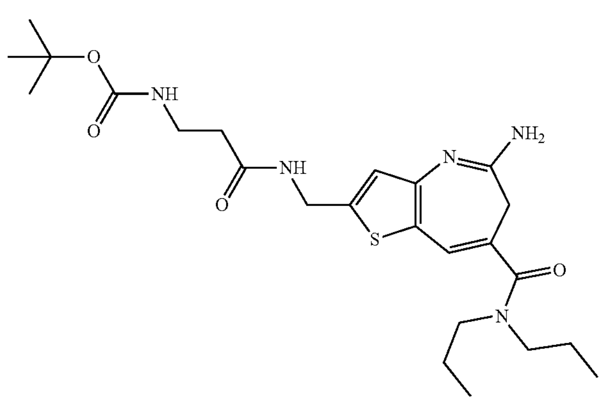 [SMILES: CCCN(CCC)C(=O)C1=Cc2sc(CNC(=O)CCNC(=O)OC(C)(C)C)cc2N=C(N)C1] | 491.65 | 4276 | 4151 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-92 | 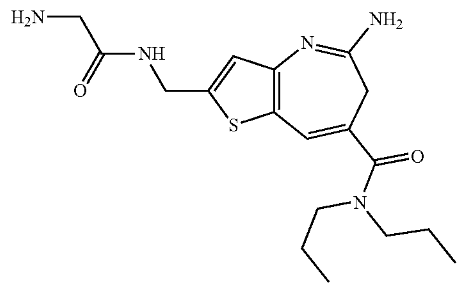 [SMILES: CCCN(CCC)C(=O)C1=Cc2sc(CNC(=O)CN)cc2N=C(N)C1] | 377.51 | >9000 | 2835 |
| TAZ-93 | 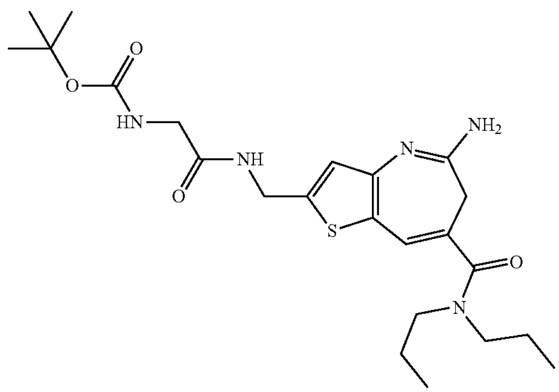 [SMILES: CCCN(CCC)C(=O)C1=Cc2sc(CNC(=O)CNC(=O)OC(C)(C)C)cc2N=C(N)C1] | 477.62 | 4494 | 3134 |
| TAZ-94 | 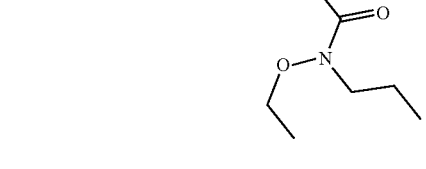 | 391.53 | 6202 | 101 |
| TAZ-95 | 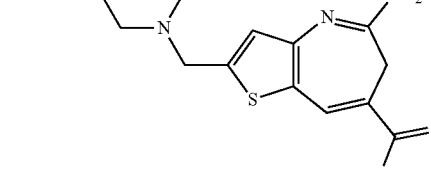 | 491.65 | Not available | Not available |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-96 | 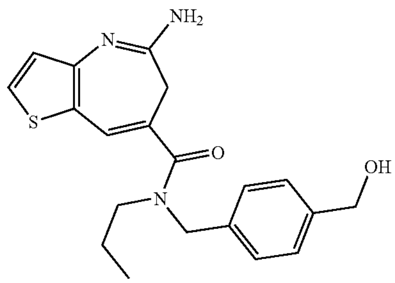 [SMILES: CCCN(Cc1ccc(CO)cc1)C(=O)C1=Cc2sccc2N=C(N)C1] | 369.48 | 2964 | 326 |
| TAZ-97 | 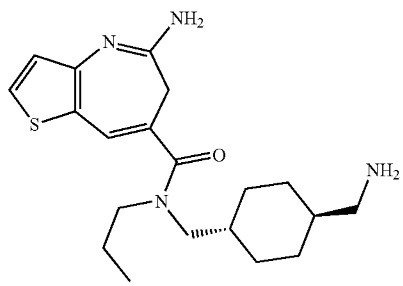 [SMILES: CCCN(C[C@H]1CC[C@H](CN)CC1)C(=O)C1=Cc2sccc2N=C(N)C1] | 374.54 | Not available | >9000 |
| TAZ-98 | 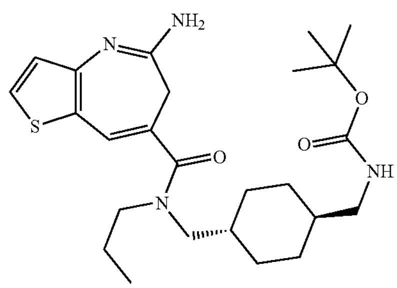 [SMILES: CCCN(C[C@H]1CC[C@H](CNC(=O)OC(C)(C)C)CC1)C(=O)C1=Cc2sccc2N=C(N)C1] | 474.66 | Not available | 631 |
| TAZ-99 | 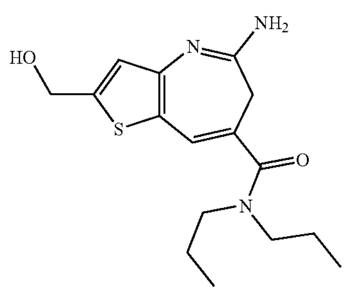 [SMILES: CCCN(CCC)C(=O)C1=Cc2sc(CO)cc2N=C(N)C1] | 321.44 | >9000 | 3622 |
| TAZ-100 | 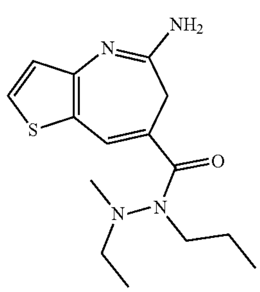 [SMILES: CCCN(C(=O)C1=Cc2sccc2N=C(N)C1)N(C)CC] | 306.43 | Not available | >9000 |

TABLE 1b-continued

Thienoazepine compounds (TAZ)

| TAZ No. | Structure | MW | HEK293 hTLR7 EC50 (nM) | HEK293 hTLR8 EC50 (nM) |
| --- | --- | --- | --- | --- |
| TAZ-101 | 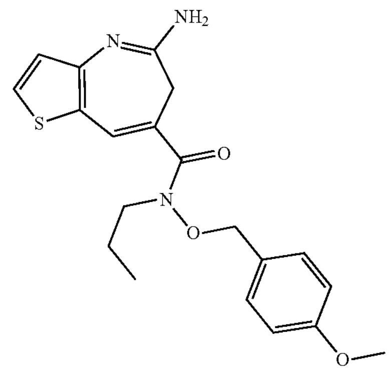 [SMILES: CCCN(OCc1ccc(OC)cc1)C(=O)C1=Cc2sccc2N=C(N)C1] | 385.48 | Not available | 203 |
| TAZ-102 | 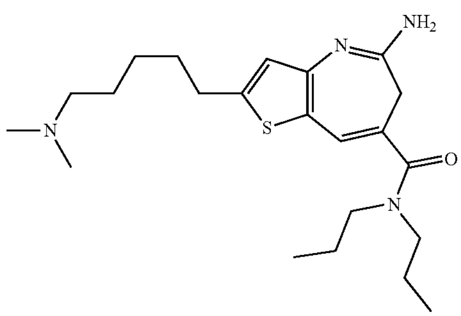 [SMILES: CCCN(CCC)C(=O)C1=Cc2sc(CCCCCN(C)C)cc2N=C(N)C1] | 404.61 | 793 | 384 |
| TAZ-103 | 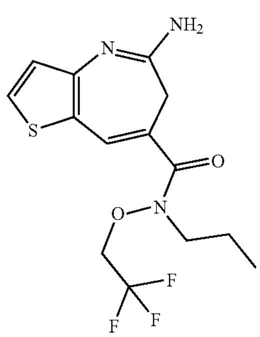 [SMILES: CCCN(OCC(F)(F)F)C(=O)C1=Cc2sccc2N=C(N)C1] | 347.36 | 3824 | 1377 |
| TAZ-104 | 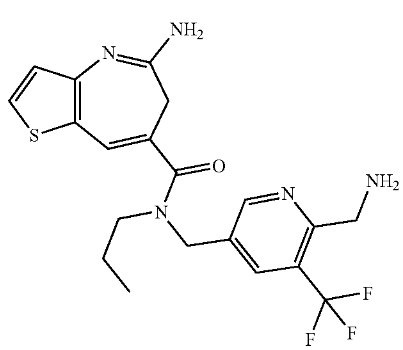 [SMILES: CCCN(Cc1cnc(CN)c(C(F)(F)F)c1)C(=O)C1=Cc2sccc2N=C(N)C1] | 437.48 | 3173 | 1444 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-105 | 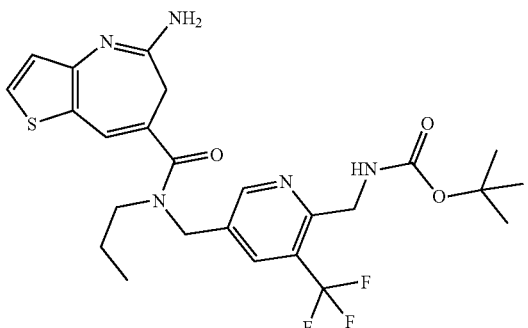 | 537.6 | Not available | Not available |
| TAZ-106 | 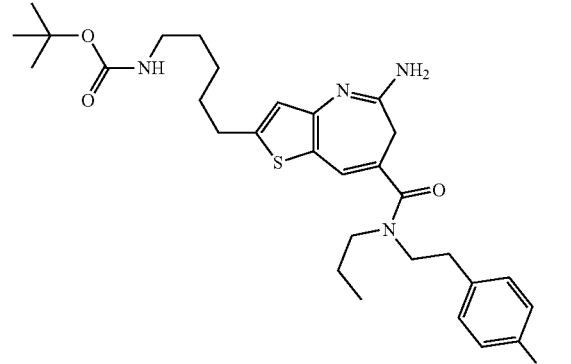 | 568.77 | 4732 | >9000 |
| TAZ-107 | 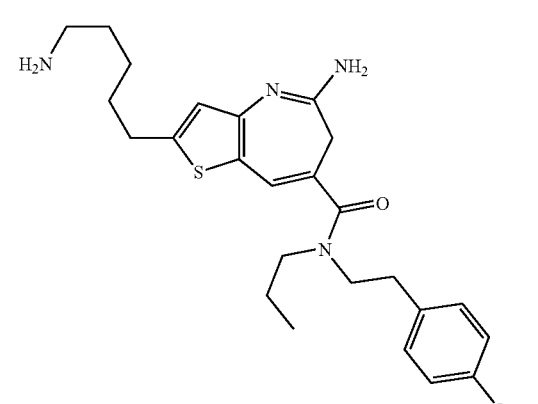 | 468.66 | 3579 | 6984 |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-108 | 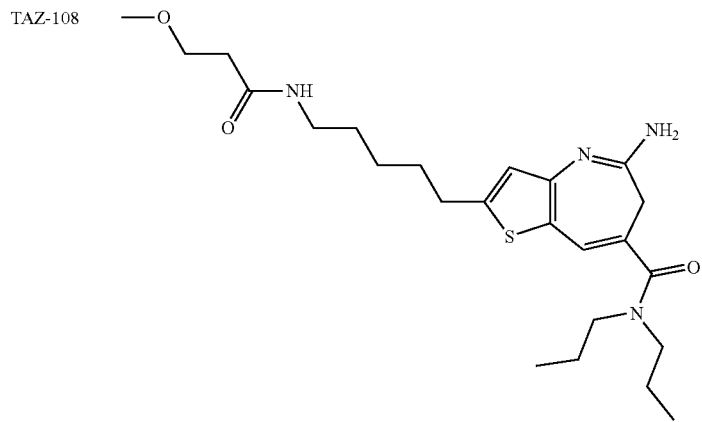 | 462.65 | 3852 | 3472 |
| TAZ-109 | 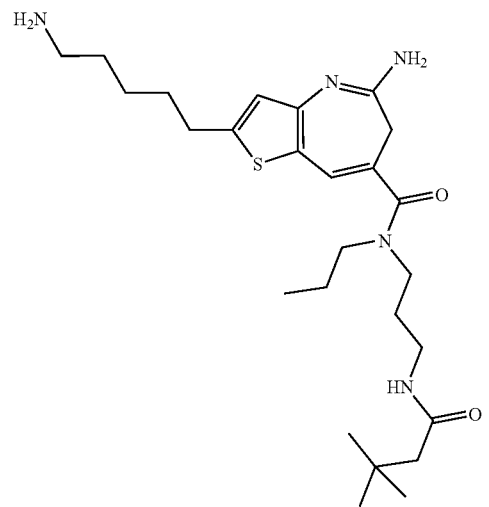 [SMILES: CCCN(CCCNC(=O)CC(C)(C)C)C(=O)C1=Cc2sc(CCCCCN)cc2N=C(N)C1] | 489.72 | | |
| TAZ-110 | 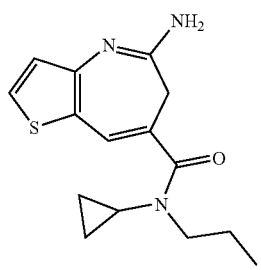 [SMILES: CCCN(C(=O)C1=Cc2sccc2N=C(N)C1)C1CC1] | 289.4 | | |
| TAZ-111 | 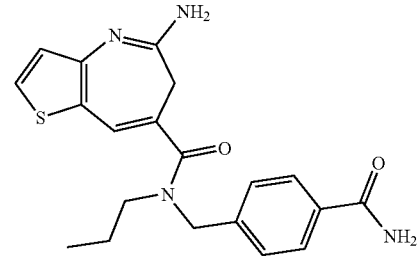 [SMILES: CCCN(Cc1ccc(C(N)=O)cc1)C(=O)C1=Cc2sccc2N=C(N)C1] | 382.48 | | |

TABLE 1b-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-112 | 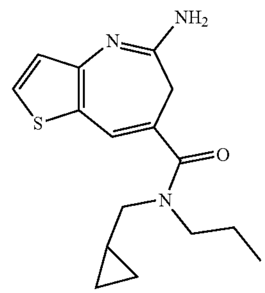 [SMILES: CCCN(CC1CC1)C(=O)C1=Cc2sccc2N=C(N)C1] | 303.42 | | |
| TAZ-113 | 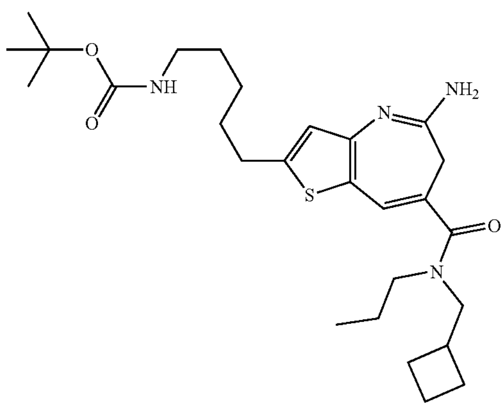 [SMILES: CCCN(CC1CCC1)C(=O)C1=Cc2sc(CCCCCNC(=O)OC(C)(C)C)cc2N=C(N)C1] | 502.71 | | |
| TAZ-114 | 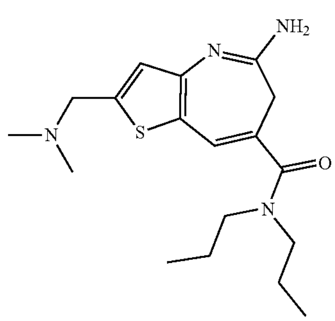 [SMILES: CCCN(CCC)C(=O)C1=Cc2sc(CN(C)C)cc2N=C(N)C1] | 348.51 | | |

TABLE 1b-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-115 | 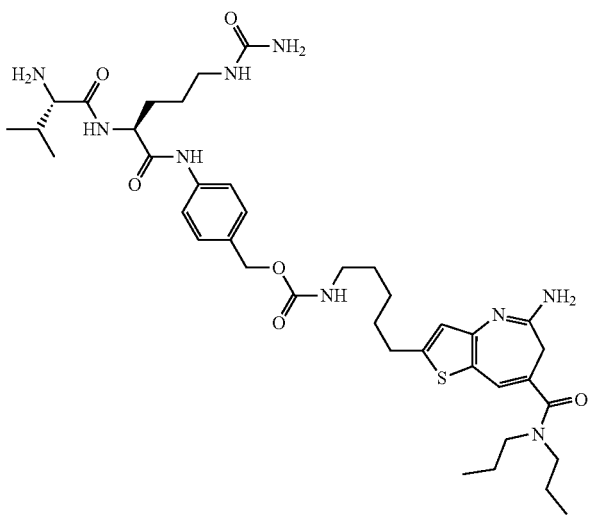 [SMILES: CCCN(CCC)C(=O)C1=Cc2sc(CCCCCNC(=O)OCc3ccc(NC(=O)[C@H](CCCNC(N)=O)NC(=O)[C@@H](N)C(C)C)cc3)cc2N=C(N)C1] | 782.01 | | |
TABLE 1c
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-116 | 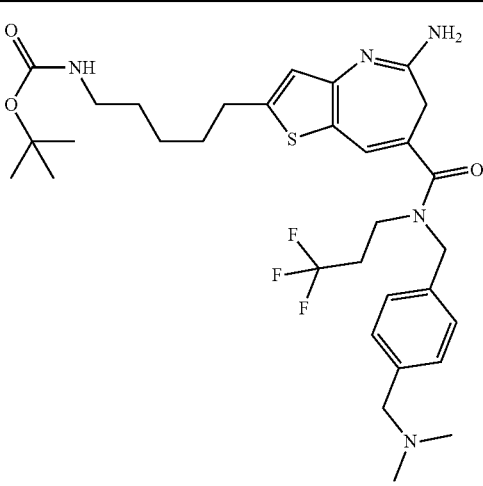 | 635.8 | 1617 | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-117 | 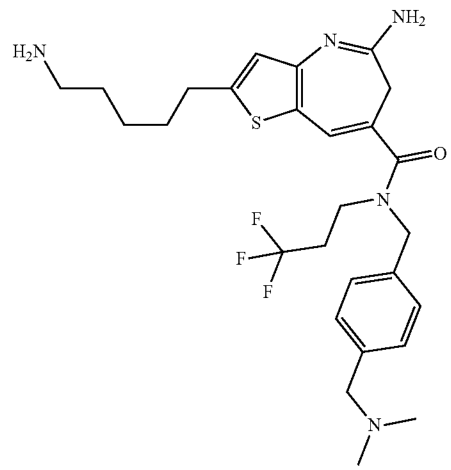 [SMILES: CN(C)Cc1ccc(CN(CCC(F)(F)F)C(=O)C2=Cc3sc(CCCCCN)cc3N=C(N)C2)cc1] | 535.7 | 9000 | 9000 |
| TAZ-118 | 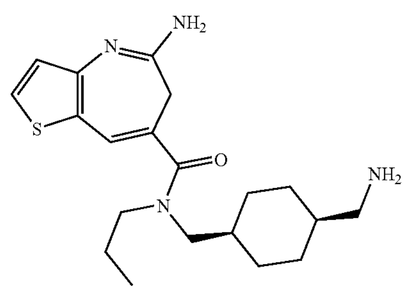 [SMILES: CCCN(C[C@H]1CC[C@@H](CN)CC1)C(=O)C1=Cc2sccc2N=C(N)C1] | 374.5 | 9000 | 4438 |
| TAZ-119 | 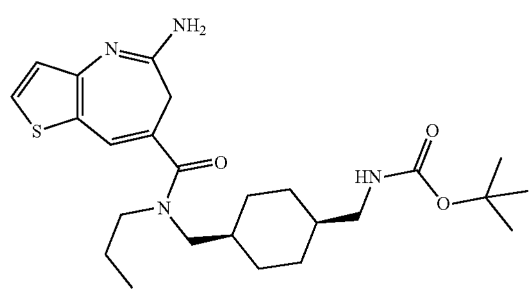 [SMILES: CCCN(C[C@H]1CC[C@@H](CNC(=O)OC(C)(C)C)CC1)C(=O)C1=Cc2sccc2N=C(N)C1] | 474.7 | 2875 | 9000 |
| TAZ-120 | 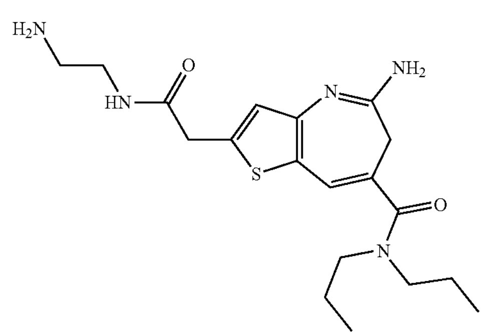 [SMILES: CCCN(CCC)C(=O)C1=Cc2sc(CC(=O)NCCN)cc2N=C(N)C1] | 391.5 | 9000 | 9000 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-121 | 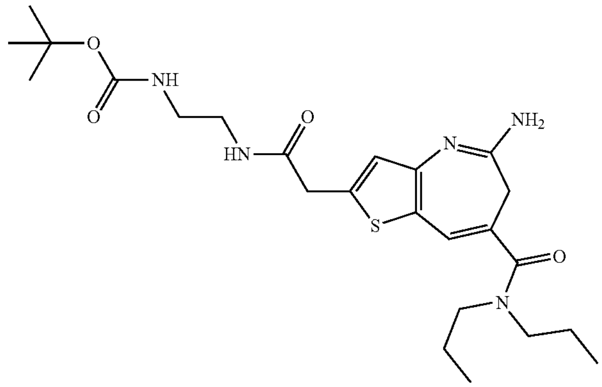 [SMILES: CCCN(CCC)C(=O)C1=Cc2sc(CC(=O)NCCNC(=O)OC(C)(C)C)cc2N=C(N)C1] | 491.7 | | |
| TAZ-122 | 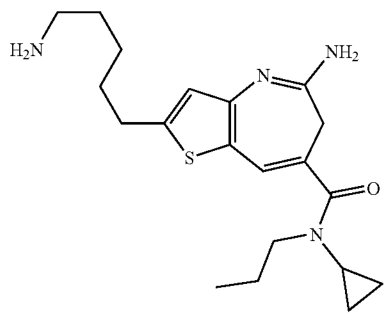 [SMILES: CCCN(C(=O)C1=Cc2sc(CCCCCN)cc2N=C(N)C1)C1CC1] | 374.5 | 3349 | 3244 |
| TAZ-123 | 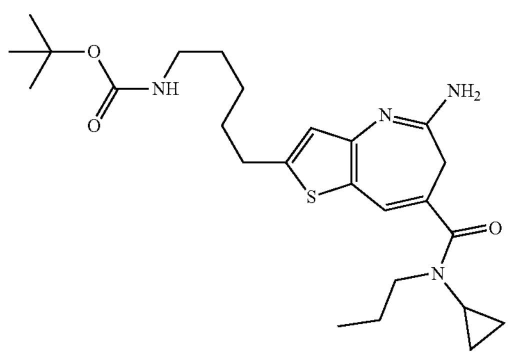 [SMILES: CCCN(C(=O)C1=Cc2sc(CCCCCNC(=O)OC(C)(C)C)cc2N=C(N)C1)C1CC1] | 474.7 | 4629 | 9000 |
| TAZ-124 | 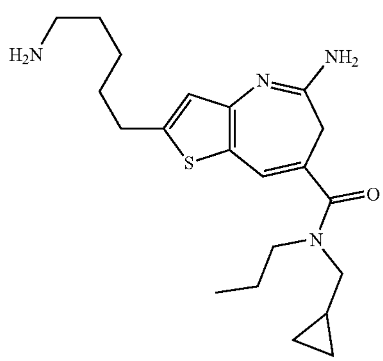 [SMILES: CCCN(CC1CC1)C(=O)C1=Cc2sc(CCCCCN)cc2N=C(N)C1] | 388.6 | 1727 | 1942 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-125 | 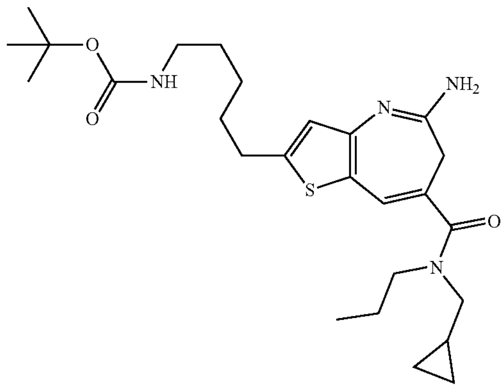 [SMILES: CCCN(CC1CC1)C(=O)C1=Cc2sc(CCCCCNC(=O)OC(C)(C)C)cc2N=C(N)C1] | 488.7 | 2705 | 9000 |
| TAZ-126 | 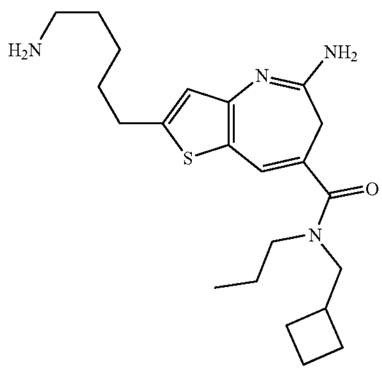 [SMILES: CCCN(CC1CCC1)C(=O)C1=Cc2sc(CCCCCN)cc2N=C(N)C1] | 402.6 | 950 | 633 |
| TAZ-127 | 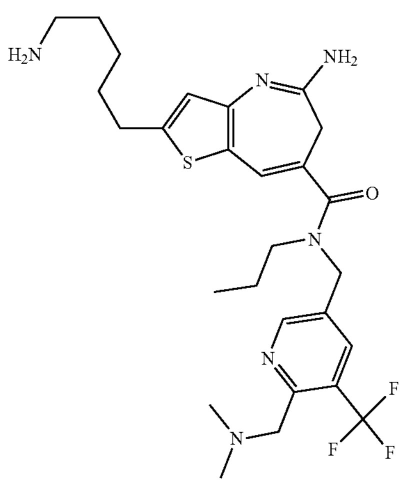 [SMILES: CCCN(Cc1cnc(CN(C)C)c(C(F)(F)F)c1)C(=O)C1=Cc2sc(CCCCCN)cc2N=C(N)C1] | 550.7 | 9000 | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-128 | 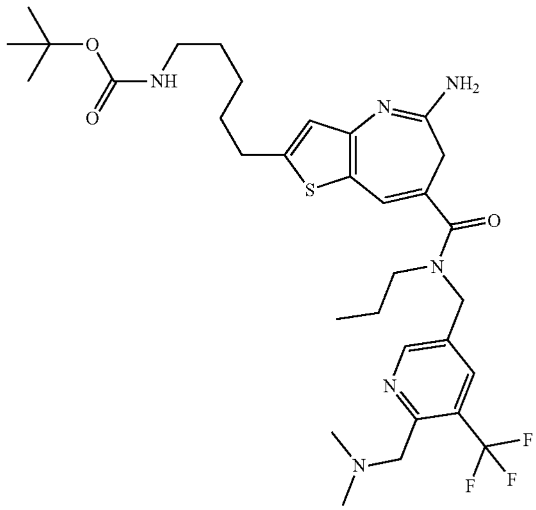 [SMILES: CCCN(Cc1cnc(CN(C)C)c(C(F)(F)F)c1)C(=O)C1=Cc2sc(CCCCCNC(=O)OC(C)(C)C)cc2N=C(N)C1] | 650.8 | 9000 | 9000 |
| TAZ-129 | 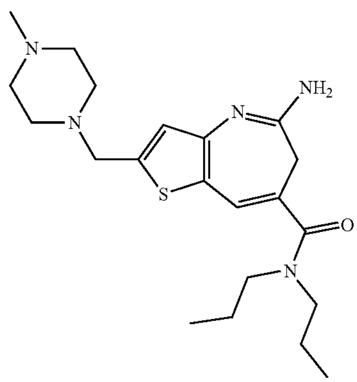 [SMILES: CCCN(CCC)C(=O)C1=Cc2sc(CN3CCN(C)CC3)cc2N=C(N)C1] | 403.6 | 5571 | 848 |
| TAZ-130 | 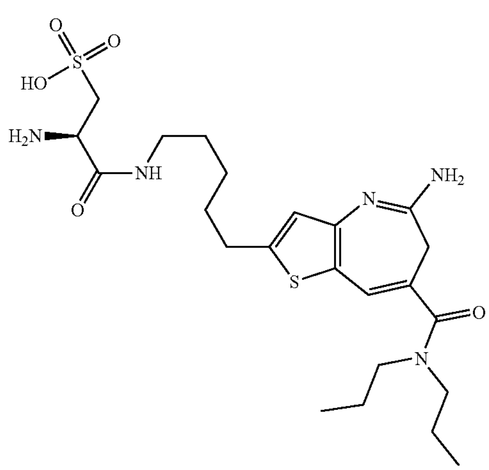 [SMILES: CCCN(CCC)C(=O)C1=Cc2sc(CCCCCNC(=O)[C@@H](N)CS(=O)(=O)O)cc2N=C(N)C1] | 527.7 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-131 | 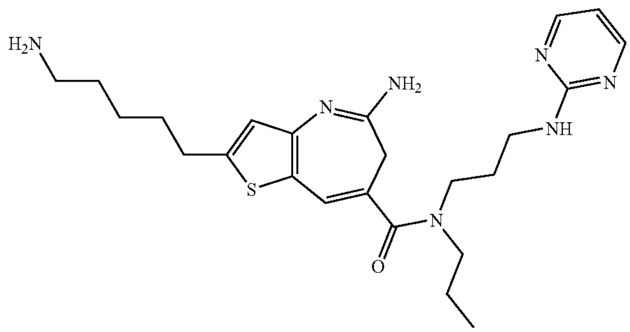 [SMILES: CCCN(CCCNc1ncccn1)C(=O)C1=Cc2sc(CCCCCN)cc2N=C(N)C1] | 469.7 | | |
| TAZ-132 | 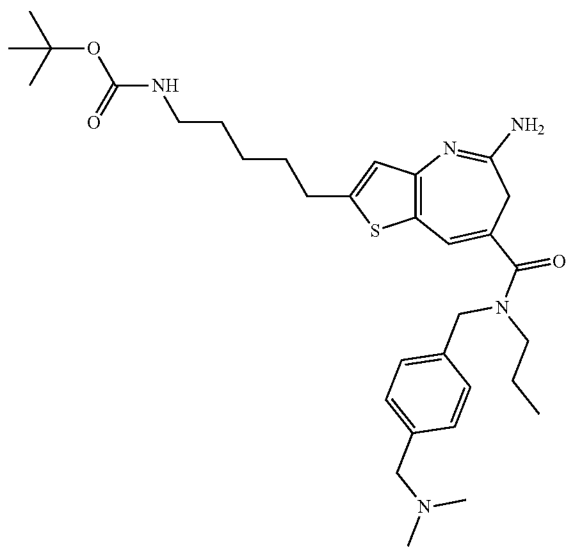 [SMILES: CCCN(Cc1ccc(CN(C)C)cc1)C(=O)C1=Cc2sc(CCCCCNC(=O)OC(C)(C)C)cc2N=C(N)C1] | 581.8 | | |
| TAZ-133 | 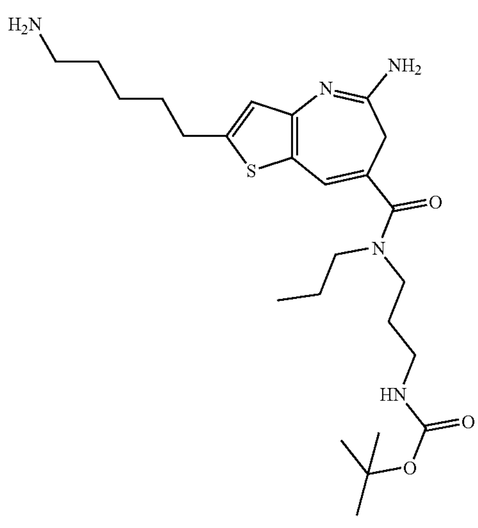 [SMILES: CCCN(CCCNC(=O)OC(C)(C)C)C(=O)C1=Cc2sc(CCCCCN)cc2N=C(N)C1] | 491.7 | 586 | 3008 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-134 | 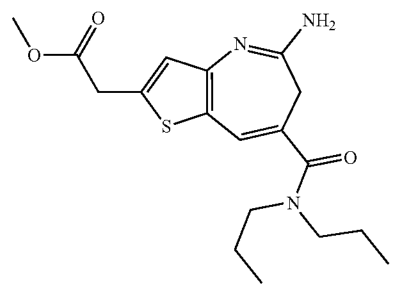 [SMILES: CCCN(CCC)C(=O)C1=Cc2sc(CC(=O)OC)cc2N=C(N)C1] | 363.5 | 4697 | 3420 |
| TAZ-135 | 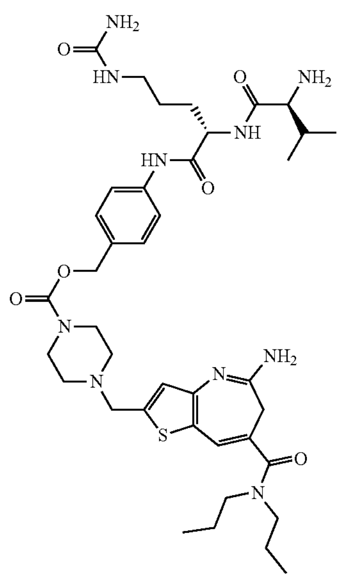 [SMILES: CCCN(CCC)C(=O)C1=Cc2sc(CN3CCN(C(=O)OCc4ccc(NC(=O)[C@H](CCCNC(N)=O)NC(=O)[C@@H](N)C(C)C)cc4)CC3)cc2N=C(N)C1] | 795.0 | | |
| TAZ-136 | 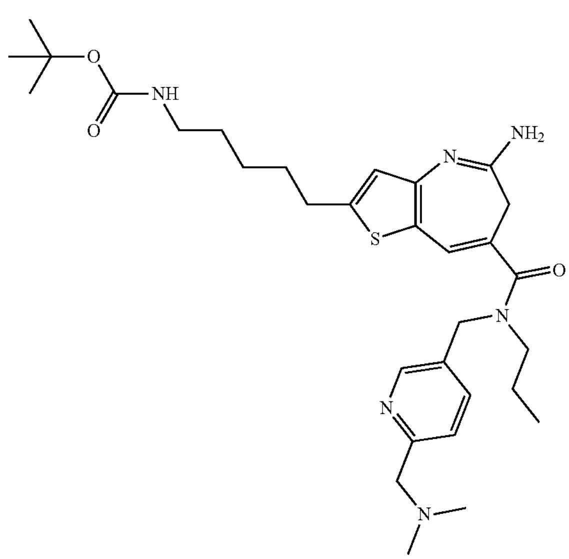 [SMILES: CCCN(Cc1ccc(CN(C)C)nc1)C(=O)C1=Cc2sc(CCCCCNC(=O)OC(C)(C)C)cc2N=C(N)C1] | 582.8 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-137 | 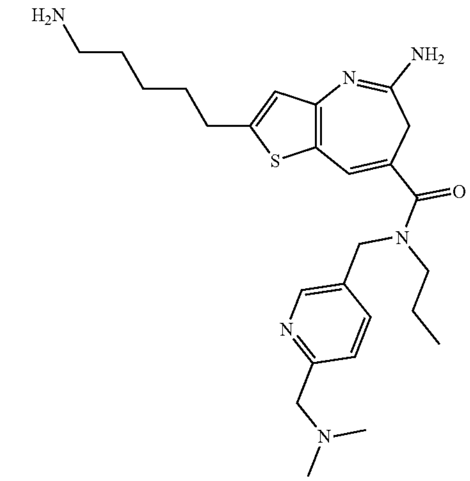 [SMILES: CCCN(Cc1ccc(CN(C)C)nc1)C(=O)C1=Cc2sc(CCCCCN)cc2N=C(N)C1] | 482.7 | | |
| TAZ-138 | 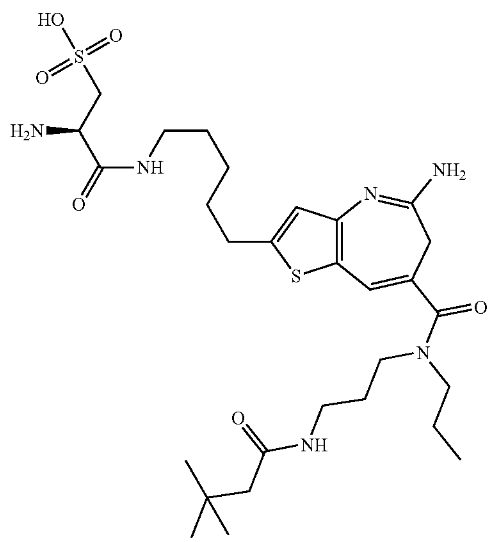 [SMILES: CCCN(CCCNC(=O)CC(C)(C)C)C(=O)C1=Cc2sc(CCCCCNC(=O)[C@@H](N)CS(=O)(=O)O)cc2N=C(N)C1] | 640.9 | | |
| TAZ-139 | 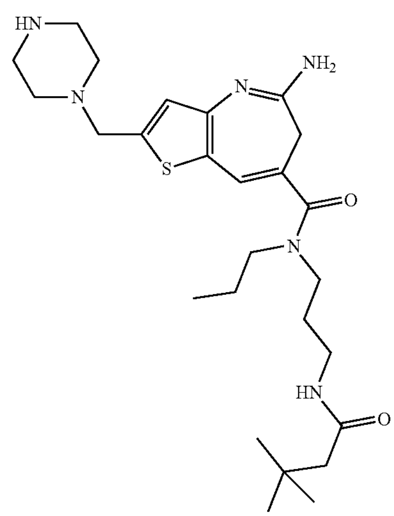 [SMILES: CCCN(CCCNC(=O)CC(C)(C)C)C(=O)C1=Cc2sc(CN3CCNCC3)cc2N=C(N)C1] | 502.7 | 4206 | 9000 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-140 | 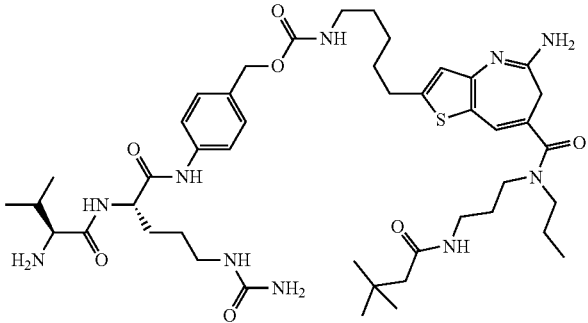 [SMILES: CCCN(CCCNC(=O)CC(C)(C)C)C(=O)C1=Cc2sc(CCCCCNC(=O)OCc3ccc(NC(=O)[C@H](CCCNC(N)=O)NC(=O)[C@@H](N)C(C)C)cc3)cc2N=C(N)C1] | 895.2 | | |
| TAZ-141 | 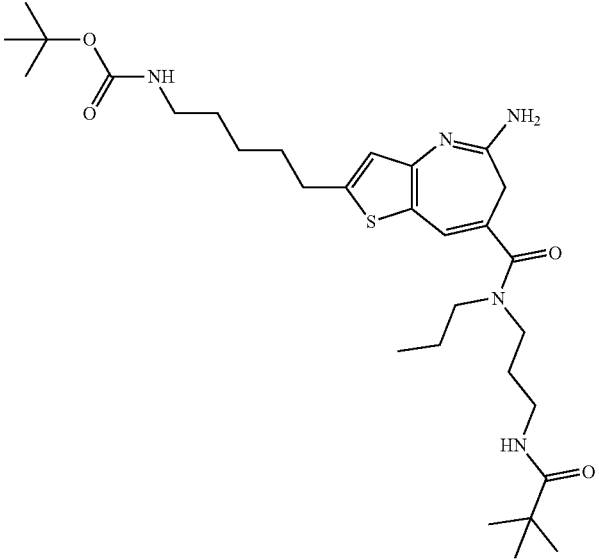 [SMILES: CCCN(CCCNC(=O)C(C)(C)C)C(=O)C1=Cc2sc(CCCCCNC(=O)OC(C)(C)C)cc2N=C(N)C1] | 575.8 | 380 | 3583 |
| TAZ-142 | 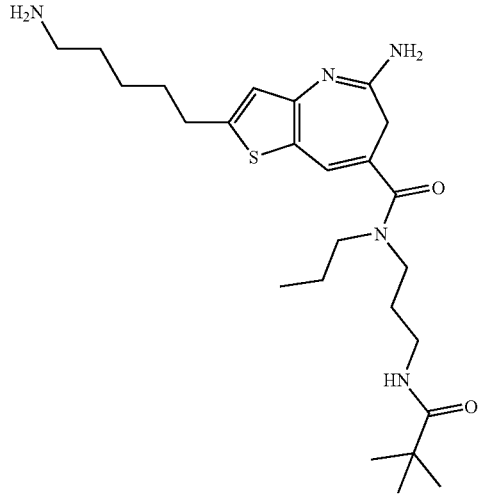 [SMILES: CCCN(CCCNC(=O)C(C)(C)C)C(=O)C1=Cc2sc(CCCCCN)cc2N=C(N)C1] | 475.7 | 827 | 9000 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-143 | 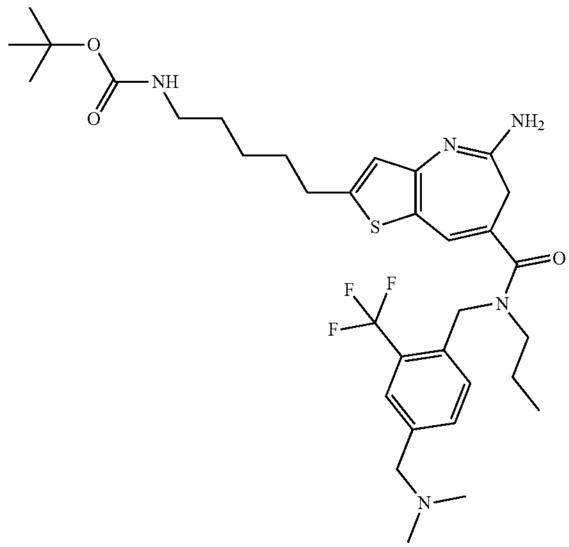 [SMILES: CCCN(Cc1ccc(CN(C)C)cc1C(F)(F)F)C(=O)C1=Cc2sc(CCCCCNC(=O)OC(C)(C)C)cc2N=C(N)C1] | 649.8 | 1884 | 9000 |
| TAZ-144 | 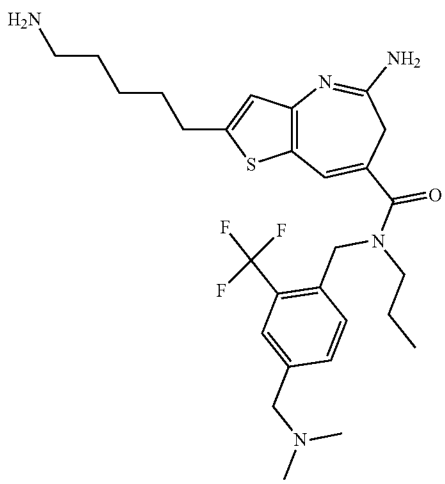 [SMILES: CCCN(Cc1ccc(CN(C)C)cc1C(F)(F)F)C(=O)C1=Cc2sc(CCCCCN)cc2N=C(N)C1] | 549.7 | 1282 | 2855 |
| TAZ-145 | 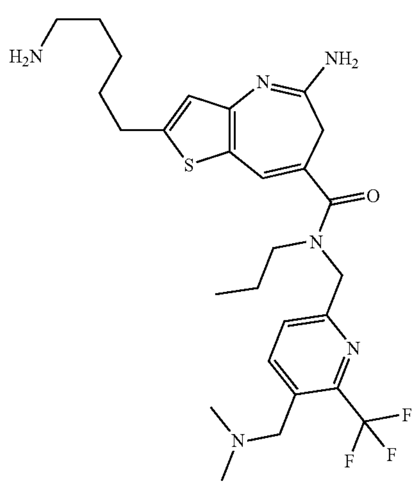 [SMILES: CCCN(Cc1ccc(CN(C)C)c(C(F)(F)F)n1)C(=O)C1=Cc2sc(CCCCCN)cc2N=C(N)C1] | 550.7 | 5940 | 4009 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-146 | 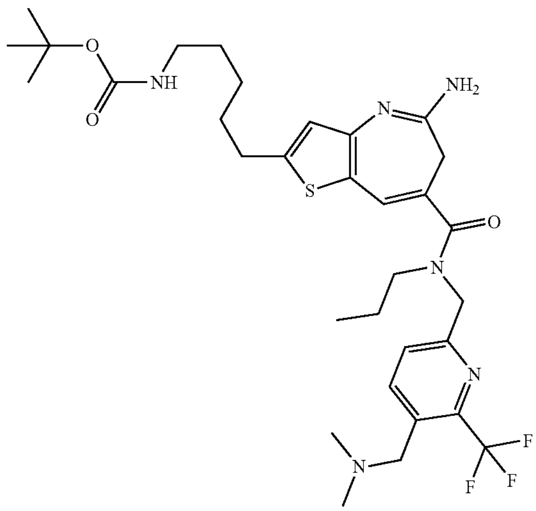 [SMILES: CCCN(Cc1ccc(CN(C)C)c(C(F)(F)F)n1)C(=O)C1=Cc2sc(CCCCCNC(=O)OC(C)(C)C)cc2N=C(N)C1] | 650.8 | 9000 | 9000 |
| TAZ-147 | 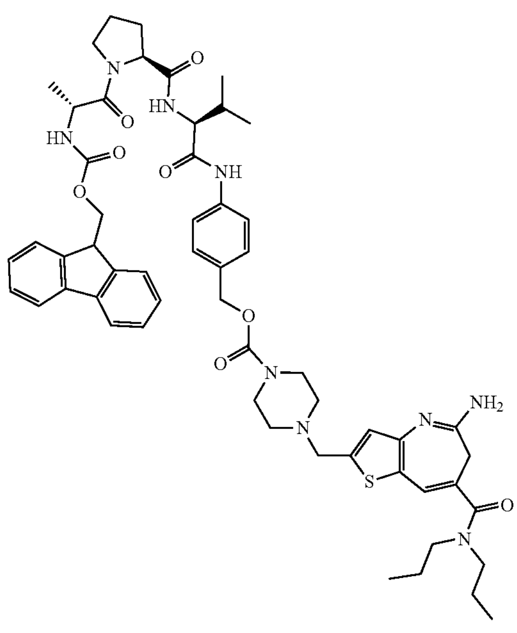 [SMILES: CCCN(CCC)C(=O)C1=Cc2sc(CN3CCN(C(=O)OCc4ccc(NC(=O)[C@@H](NC(=O)[C@@H]5CCCN5C(=O)[C@@H](C)NC(=O)OCC5c6ccccc6-c6ccccc65)C(C)C)cc4)CC3)cc2N=C(N)C1] | 1028.3 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-148 | 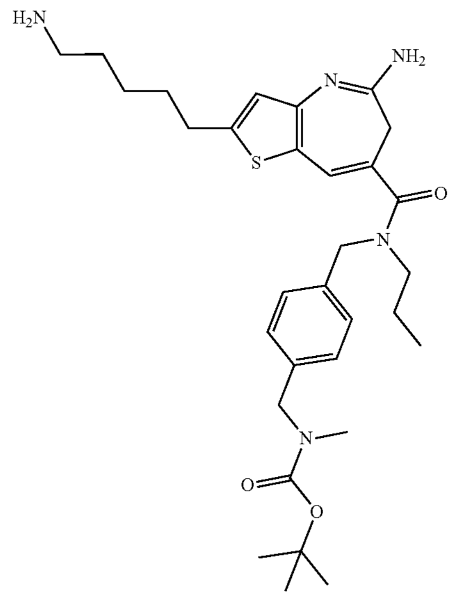 [SMILES: CCCN(Cc1ccc(CN(C)C(=O)OC(C)(C)C)cc1)C(=O)C1=Cc2sc(CCCCCN)cc2N=C(N)C1] | 567.8 | | |
| TAZ-149 | 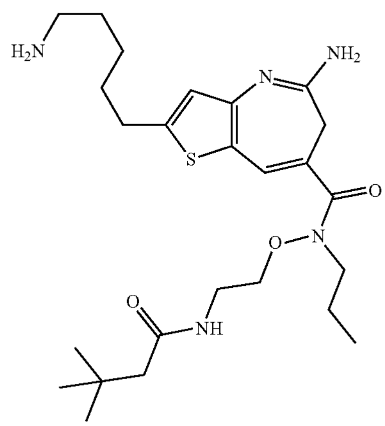 [SMILES: CCCN(OCCNC(=O)CC(C)(C)C)C(=O)C1=Cc2sc(CCCCCN)cc2N=C(N)C1] | 491.7 | 534 | 2237 |
| TAZ-150 | 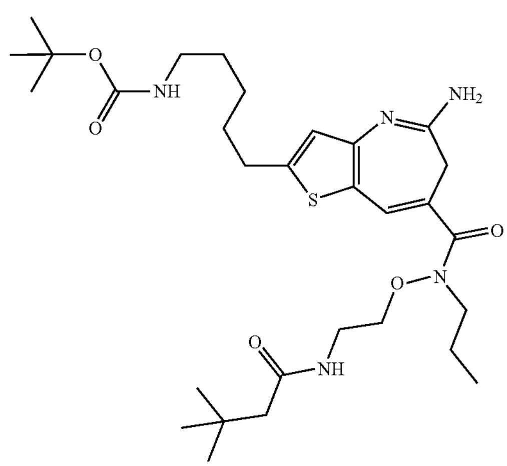 [SMILES: CCCN(OCCNC(=O)CC(C)(C)C)C(=O)C1=Cc2sc(CCCCCNC(=O)OC(C)(C)C)cc2N=C(N)C1] | 591.8 | 1990 | 1668 |

TABLE 1c-continued

| | Thienoazepine compounds (TAZ) | | | |
|---|---|---|---|---|
| TAZ No. | Structure | MW | HEK293 hTLR7 EC50 (nM) | HEK293 hTLR8 EC50 (nM) |
| TAZ-151 | | 491.7 | | |
| TAZ-152 | | 650.8 | | |
| TAZ-153 | | 550.7 | | |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-154 | 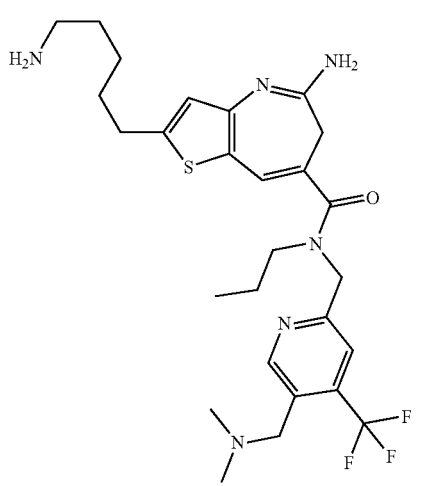 [SMILES: CCCN(Cc1cc(C(F)(F)F)c(CN(C)C)cn1)C(=O)C1=Cc2sc(CCCCCN)cc2N=C(N)C1] | 550.7 | | |
| TAZ-155 | 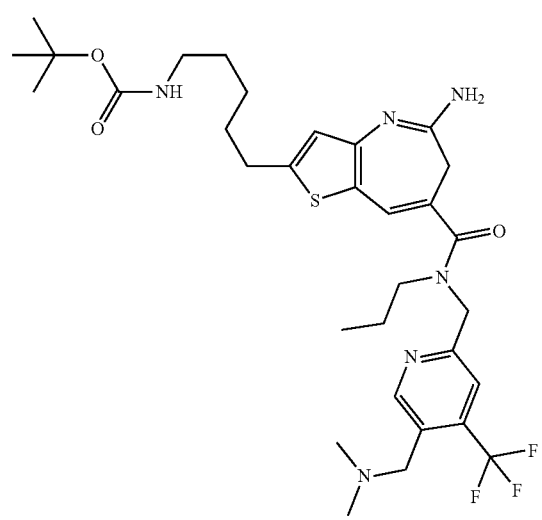 [SMILES: CCCN(Cc1cc(C(F)(F)F)c(CN(C)C)cn1)C(=O)C1=Cc2sc(CCCCCNC(=O)OC(C)(C)C)cc2N=C(N)C1] | 650.8 | | |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-156 | 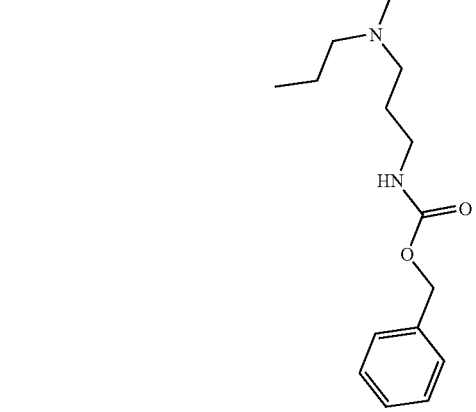 | 525.7 | | |
| TAZ-157 | 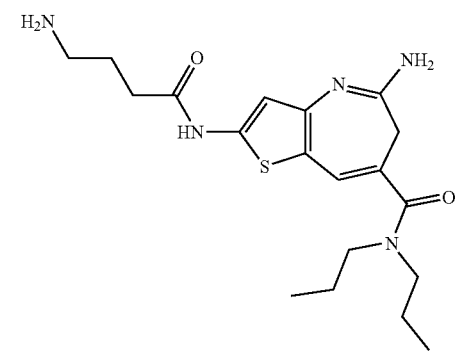 [SMILES: CCCN(CCC)C(=O)C1=Cc2sc(NC(=O)CCCN)cc2N=C(N)C1] | 391.5 | | |
| TAZ-158 | 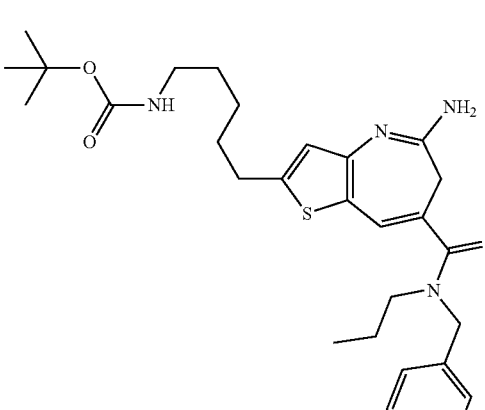 | 578.8 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-159 | 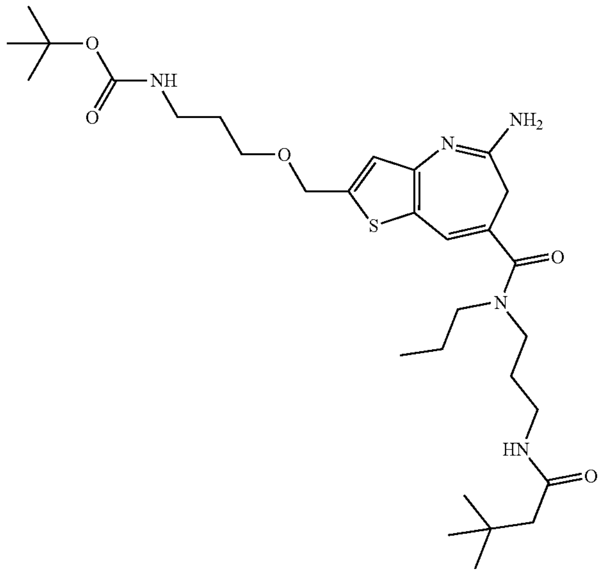 [SMILES: CCCN(CCCNC(=O)CC(C)(C)C)C(=O)C1=Cc2sc(COCCCNC(=O)OC(C)(C)C)cc2N=C(N)C1] | 591.8 | | |
| TAZ-160 | 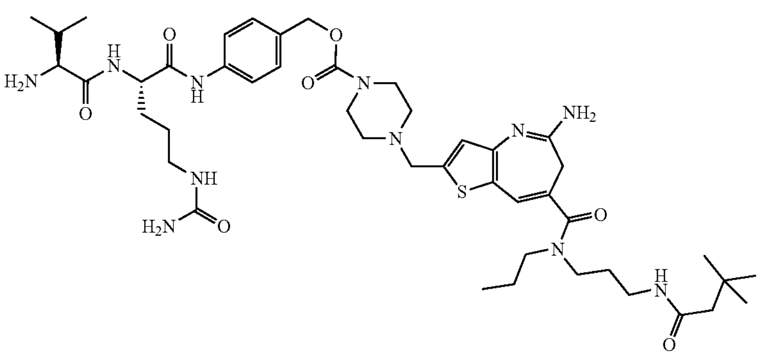 [SMILES: CCCN(CCCNC(=O)CC(C)(C)C)C(=O)C1=Cc2sc(CN3CCN(C(=O)OCc4ccc(NC(=O)[C@H](CCCNC(N)=O)NC(=O)[C@@H](N)C(C)C)cc4)CC3)cc2N=C(N)C1] | 908.2 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-161 | 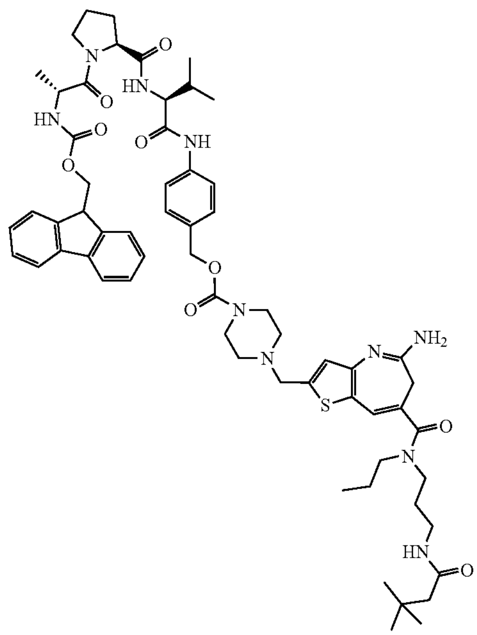 [SMILES: CCCN(CCCNC(=O)CC(C)(C)C)C(=O)C1=Cc2sc(CN3CCN(C(=O)OCc4ccc(NC(=O)[C@@H](NC(=O)[C@@H]5CCCN5C(=O)[C@@H](C)NC(=O)OCC5c6ccccc6-c6ccccc65)C(C)C)cc4)CC3)cc2N=C(N)C1] | 1141.4 | | |
| TAZ-162 | 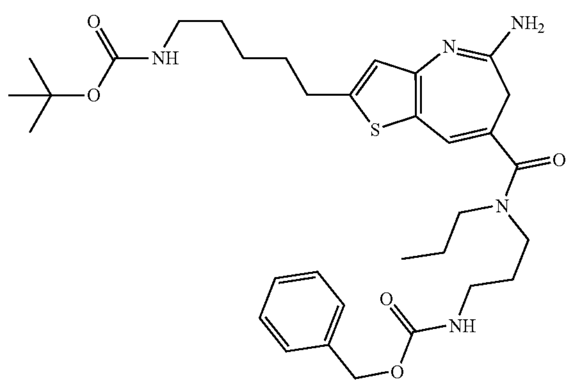 [SMILES: CCCN(CCCNC(=O)OCc1ccccc1)C(=O)C1=Cc2sc(CCCCCNC(=O)OC(C)(C)C)cc2N=C(N)C1] | 625.8 | 1238 | 1247 |
| TAZ-163 | 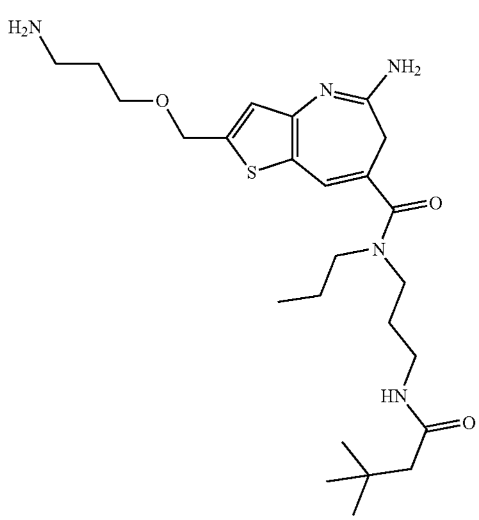 [SMILES: CCCN(CCCNC(=O)CC(C)(C)C)C(=O)C1=Cc2sc(COCCCN)cc2N=C(N)C1] | 491.7 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-164 | 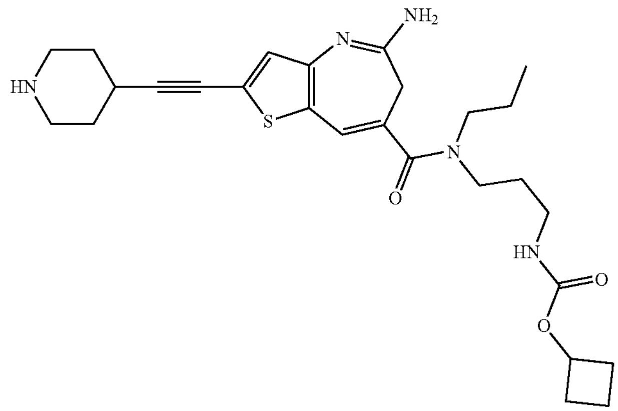 [SMILES: CCCN(CCCNC(=O)OC1CCC1)C(=O)C1=Cc2sc(C#CC3CCNCC3)cc2N=C(N)C1] | 511.7 | 476 | 3889 |
| TAZ-165 | 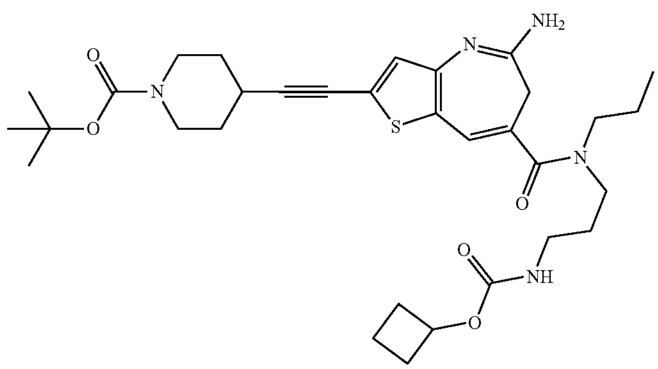 [SMILES: CCCN(CCCNC(=O)OC1CCC1)C(=O)C1=Cc2sc(C#CC3CCN(C(=O)OC(C)(C)C)CC3)cc2N=C(N)C1] | 611.8 | 9000 | |
| TAZ-166 | 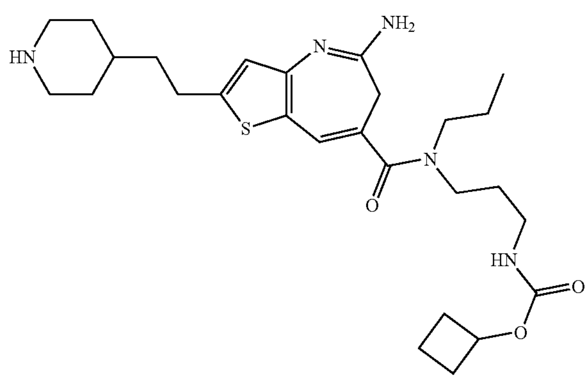 [SMILES: CCCN(CCCNC(=O)OC1CCC1)C(=O)C1=Cc2sc(CCC3CCNCC3)cc2N=C(N)C1] | 515.7 | 802 | 3697 |
| TAZ-167 | 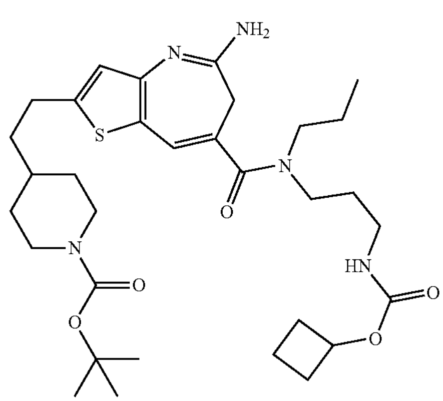 [SMILES: CCCN(CCCNC(=O)OC1CCC1)C(=O)C1=Cc2sc(CCC3CCN(C(=O)OC(C)(C)C)CC3)cc2N=C(N)C1] | 615.8 | 3129 | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-168 | 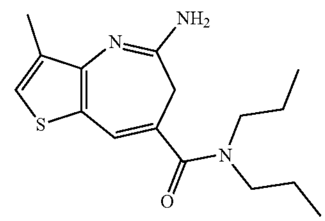 [SMILES: CCCN(CCC)C(=O)C1=Cc2scc(C)c2N=C(N)C1] | 305.4 | 9000 | 3875 |
| TAZ-169 | 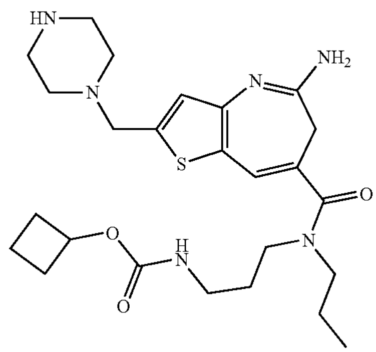 [SMILES: CCCN(CCCNC(=O)OC1CCC1)C(=O)C1=Cc2sc(CN3CCNCC3)cc2N=C(N)C1] | 502.7 | 3174 | 9000 |
| TAZ-170 | 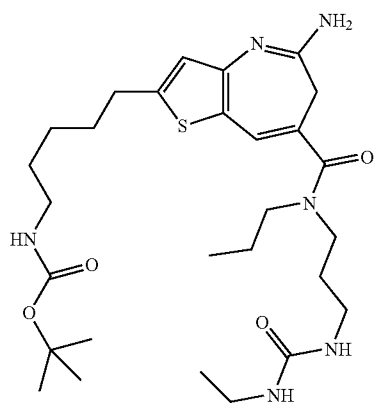 [SMILES: CCCN(CCCNC(=O)NCC)C(=O)C1=Cc2sc(CCCCCNC(=O)OC(C)(C)C)cc2N=C(N)C1] | 562.8 | 282 | 3371 |
| TAZ-171 | 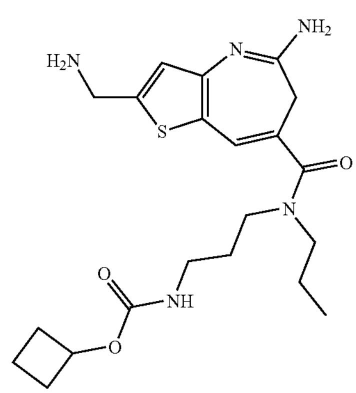 [SMILES: CCCN(CCCNC(=O)OC1CCC1)C(=O)C1=Cc2sc(CN)cc2N=C(N)C1] | 433.6 | 5288 | 3128 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-172 | 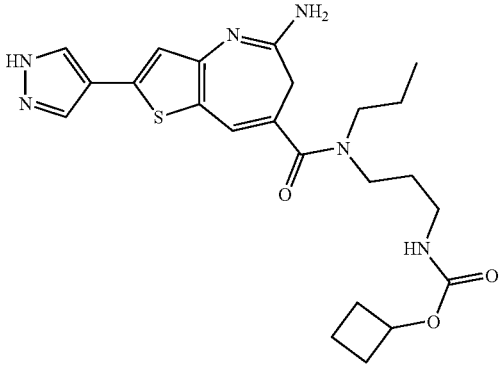 [SMILES: CCCN(CCCNC(=O)OC1CCC1)C(=O)C1=Cc2sc(-c3cn[nH]c3)cc2N=C(N)C1] | 470.6 | 153 | 3695 |
| TAZ-173 | 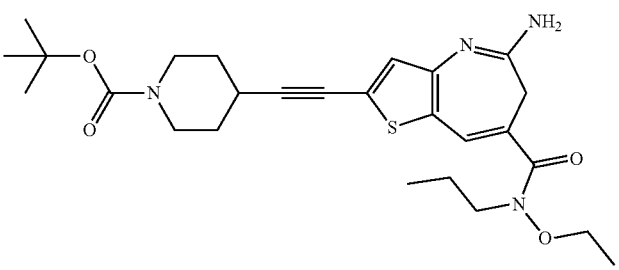 [SMILES: CCCN(OCC)C(=O)C1=Cc2sc(C#CC3CCN(C(=O)OC(C)(C)C)CC3)cc2N=C(N)C1] | 500.7 | 7689 | 9000 |
| TAZ-174 | 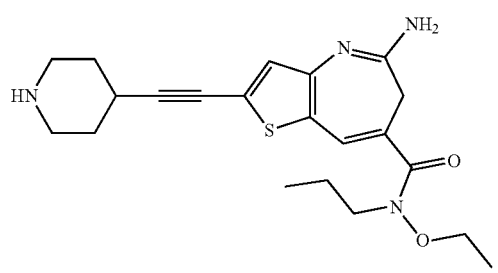 [SMILES: CCCN(OCC)C(=O)C1=Cc2sc(C#CC3CCNCC3)cc2N=C(N)C1] | 400.5 | 5809 | 1641 |
| TAZ-175 | 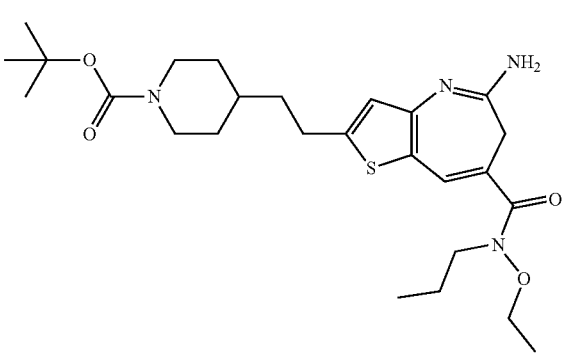 [SMILES: CCCN(OCC)C(=O)C1=Cc2sc(CCC3CCN(C(=O)OC(C)(C)C)CC3)cc2N=C(N)C1] | 504.7 | 4178 | 474 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-176 | 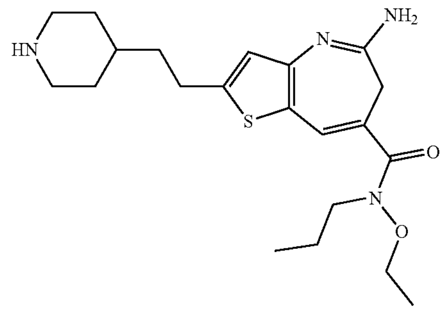 [SMILES: CCCN(OCC)C(=O)C1=Cc2sc(CCC3CCNCC3)cc2N=C(N)C1] | 404.6 | 915 | 249 |
| TAZ-177 | 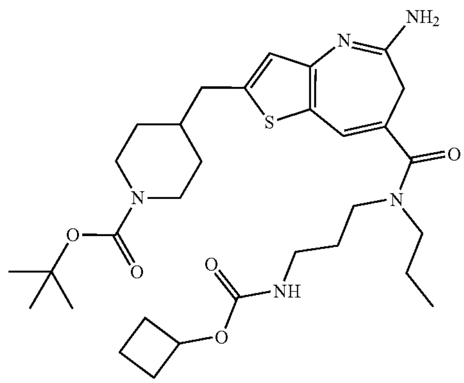 [SMILES: CCCN(CCCNC(=O)OC1CCC1)C(=O)C1=Cc2sc(CC3CCN(C(=O)OC(C)(C)C)CC3)cc2N=C(N)C1] | 601.8 | 882 | 3402 |
| TAZ-178 | 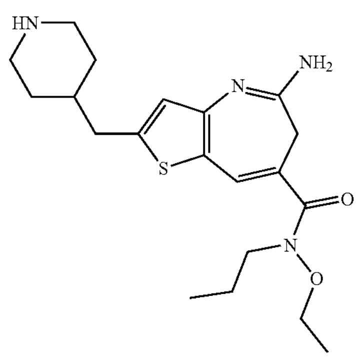 [SMILES: CCCN(OCC)C(=O)C1=Cc2sc(CC3CCNCC3)cc2N=C(N)C1] | 390.5 | 714 | 124 |
| TAZ-179 | 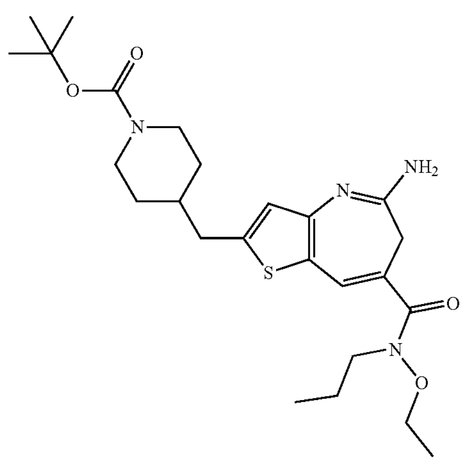 [SMILES: CCCN(OCC)C(=O)C1=Cc2sc(CC3CCN(C(=O)OC(C)(C)C)CC3)cc2N=C(N)C1] | 490.7 | 9000 | 2543 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-180 | 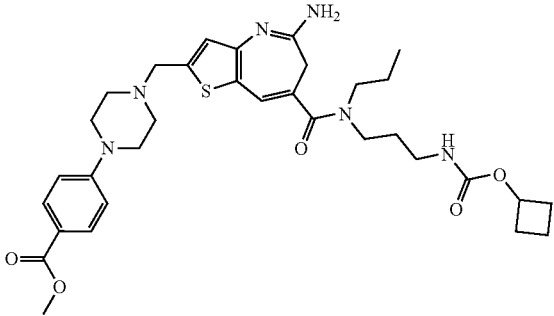 [SMILES: CCCN(CCCNC(=O)OC1CCC1)C(=O)C1=Cc2sc(CN3CCN(c4ccc(C(=O)OC)cc4)CC3)cc2N=C(N)C1] | 636.8 | 3648 | 9000 |
| TAZ-181 | 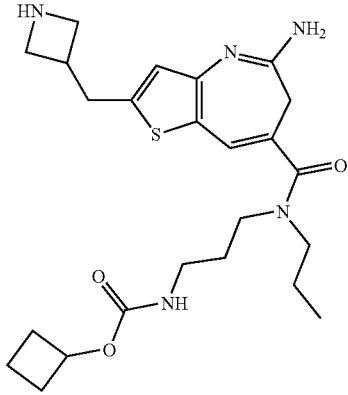 [SMILES: CCCN(CCCNC(=O)OC1CCC1)C(=O)C1=Cc2sc(CC3CNC3)cc2N=C(N)C1] | 473.6 | 2032 | 9000 |
| TAZ-182 | 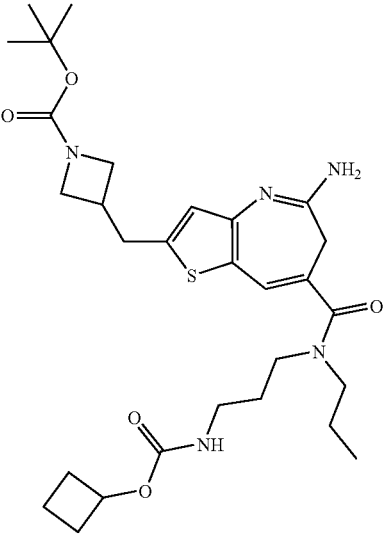 [SMILES: CCCN(CCCNC(=O)OC1CCC1)C(=O)C1=Cc2sc(CC3CN(C(=O)OC(C)(C)C)C3)cc2N=C(N)C1] | 573.8 | 101 | 840 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-183 | 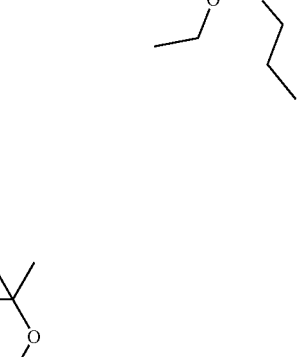 | 362.5 | 3560 | 485 |
| TAZ-184 | 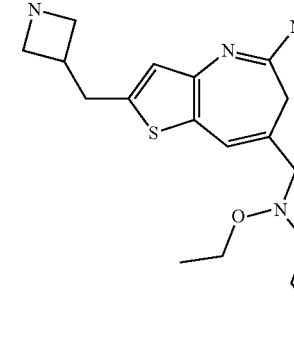 | 462.6 | 922 | 930 |
| TAZ-185 | 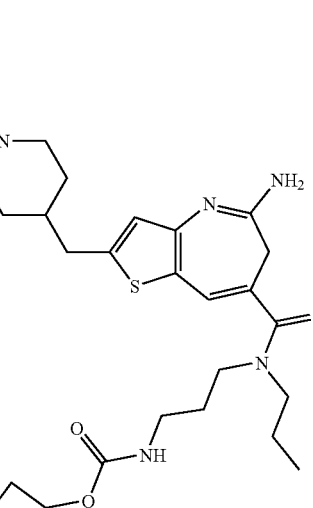 | 501.7 | 3704 | 9000 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-186 | 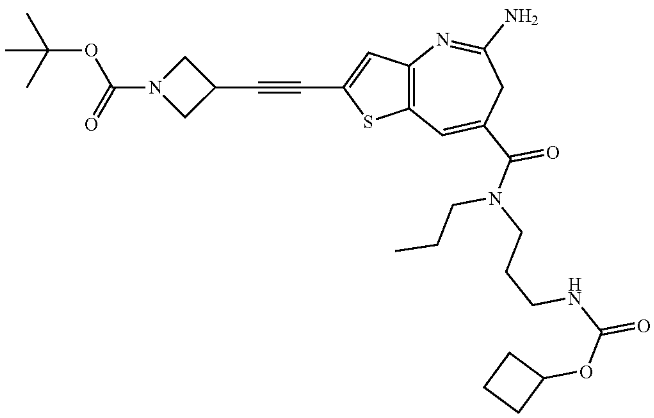 [SMILES: CCCN(CCCNC(=O)OC1CCC1)C(=O)C1=Cc2sc(C#CC3CN(C(=O)OC(C)(C)C)C3)cc2N=C(N)C1] | 583.7 | | |
| TAZ-187 | 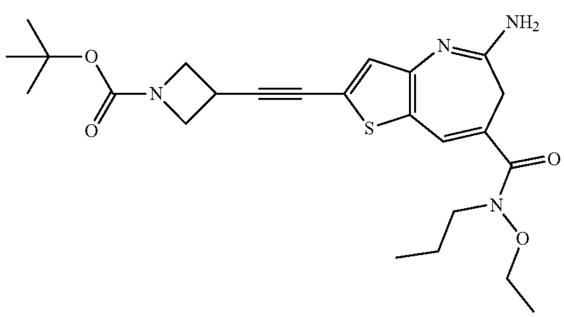 [SMILES: CCCN(OCC)C(=O)C1=Cc2sc(C#CC3CN(C(=O)OC(C)(C)C)C3)cc2N=C(N)C1] | 472.6 | 9000 | 964 |
| TAZ-188 | 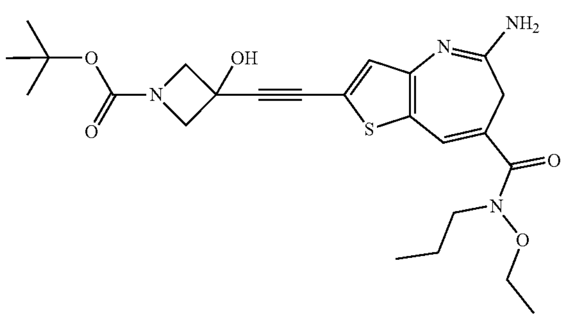 [SMILES: CCCN(OCC)C(=O)C1=Cc2sc(C#CC3(O)CN(C(=O)OC(C)(C)C)C3)cc2N=C(N)C1] | 488.6 | 9000 | 7798 |
| TAZ-189 | 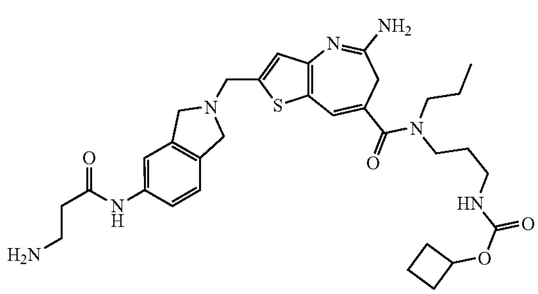 [SMILES: CCCN(CCCNC(=O)OC1CCC1)C(=O)C1=Cc2sc(CN3Cc4ccc(NC(=O)CCN)cc4C3)cc2N=C(N)C1] | 621.8 | 5721 | 3391 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-190 | 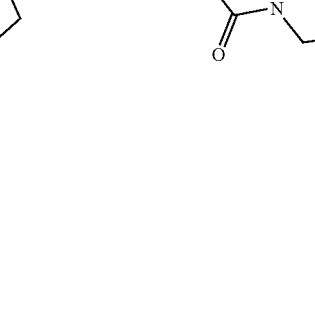 | 607.8 | 2988 | 4803 |
| TAZ-191 | 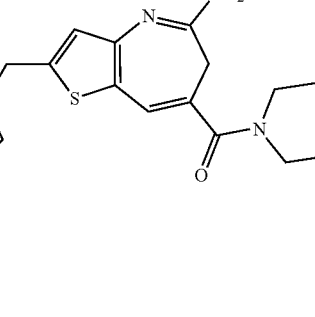 | 707.9 | | |
| TAZ-192 | 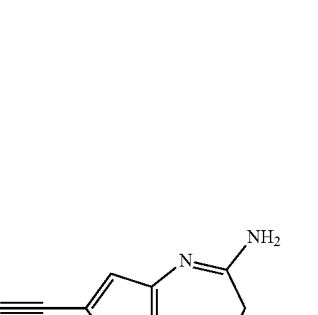 | 483.6 | 824 | 3484 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-193 | 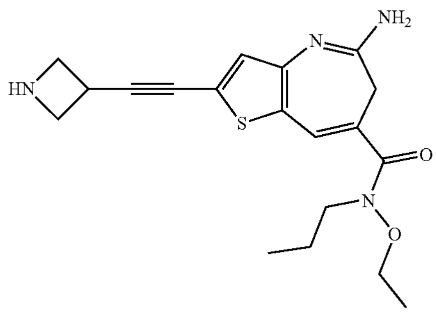 [SMILES: CCCN(OCC)C(=O)C1=Cc2sc(C#CC3CNC3)cc2N=C(N)C1] | 372.5 | 3362 | 1517 |
| TAZ-194 | 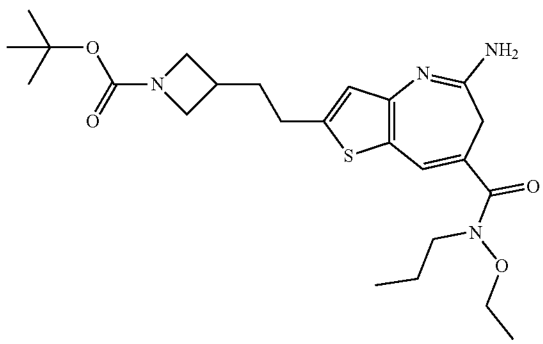 [SMILES: CCCN(OCC)C(=O)C1=Cc2sc(CCC3CN(C(=O)OC(C)(C)C)C3)cc2N=C(N)C1] | 476.6 | 467 | 631 |
| TAZ-195 | 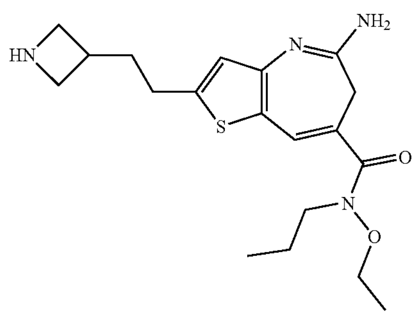 [SMILES: CCCN(OCC)C(=O)C1=Cc2sc(CCC3CNC3)cc2N=C(N)C1] | 376.5 | 6603 | 953 |
| TAZ-196 | 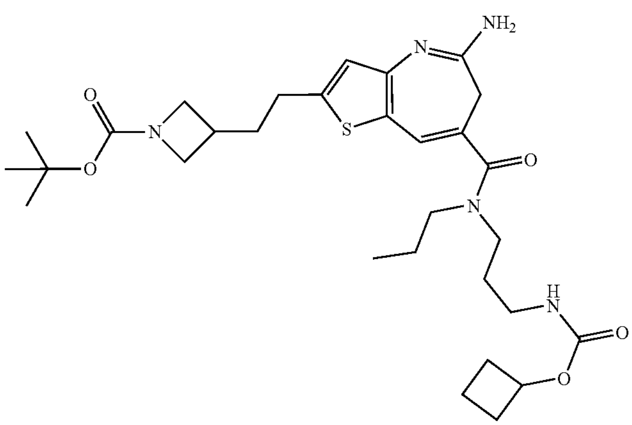 [SMILES: CCCN(CCCNC(=O)OC1CCC1)C(=O)C1=Cc2sc(CCC3CN(C(=O)OC(C)(C)C)C3)cc2N=C(N)C1] | 587.8 | | |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-197 | 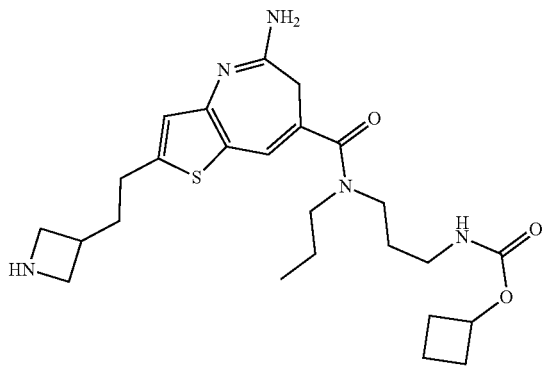 [SMILES: CCCN(CCCNC(=O)OC1CCC1)C(=O)C1=Cc2sc(CCC3CNC3)cc2N=C(N)C1] | 487.7 | 1808 | 9000 |
| TAZ-198 | 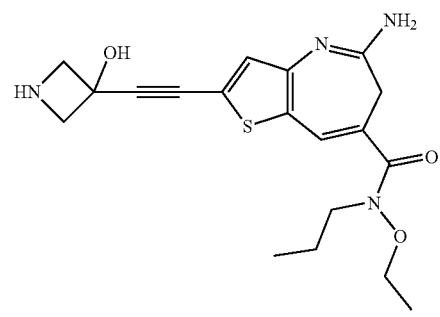 [SMILES: CCCN(OCC)C(=O)C1=Cc2sc(C#CC3(O)CNC3)cc2N=C(N)C1] | 388.5 | 9000 | 4275 |
| TAZ-199 | 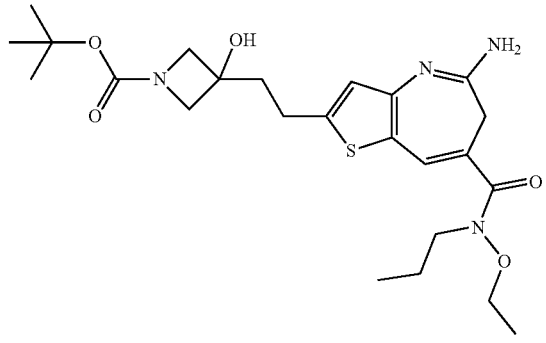 [SMILES: CCCN(OCC)C(=O)C1=Cc2sc(CCC3(O)CN(C(=O)OC(C)(C)C)C3)cc2N=C(N)C1] | 492.6 | 31 | 1614 |
| TAZ-200 | 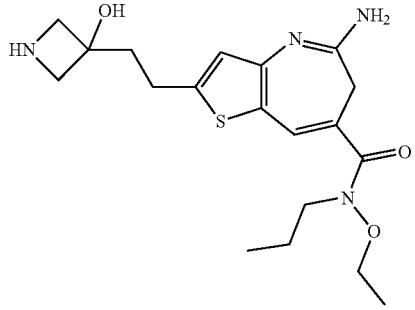 [SMILES: CCCN(OCC)C(=O)C1=Cc2sc(CCC3(O)CNC3)cc2N=C(N)C1] | 392.5 | 2916 | 4071 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-201 | 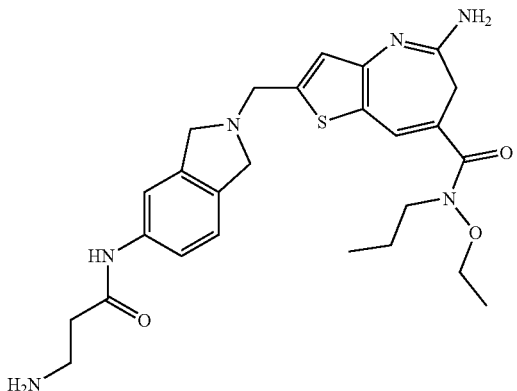 | 510.7 | 9000 | 2957 |
| TAZ-202 | 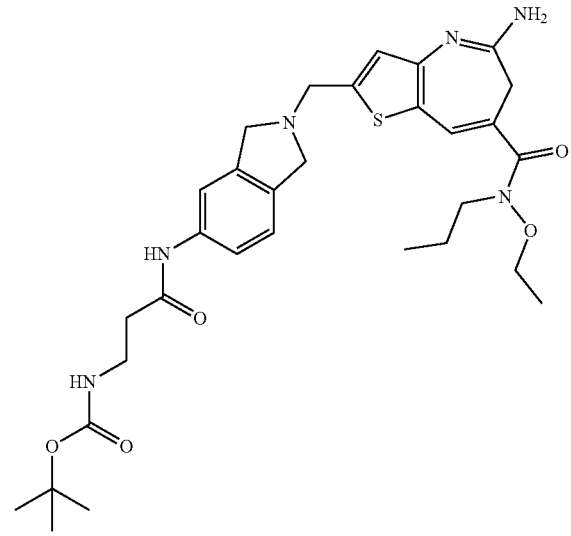 [SMILES: CCCN(OCC)C(=O)C1=Cc2sc(CN3Cc4ccc(NC(=O)CCNC(=O)OC(C)(C)C)cc4C3)cc2N=C(N)C1] | 610.8 | 3680 | 1373 |
| TAZ-203 | 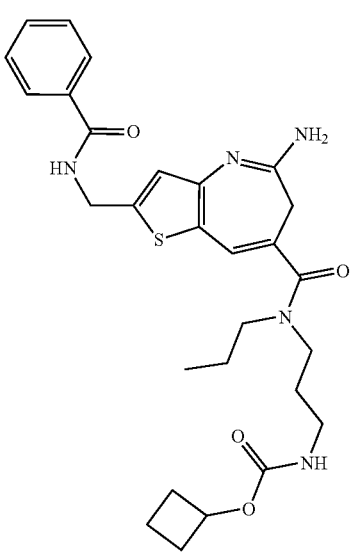 [SMILES: CCCN(CCCNC(=O)OC1CCC1)C(=O)C1=Cc2sc(CNC(=O)c3ccccc3)cc2N=C(N)C1] | 537.7 | 3261 | 3251 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-204 | 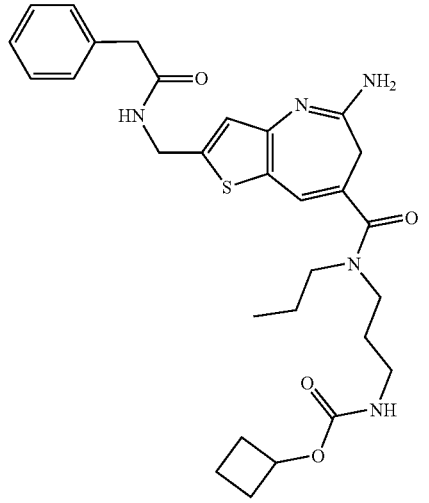 [SMILES: CCCN(CCCNC(=O)OC1CCC1)C(=O)C1=Cc2sc(CNC(=O)Cc3ccccc3)cc2N=C(N)C1] | 551.7 | 2665 | 2550 |
| TAZ-205 | 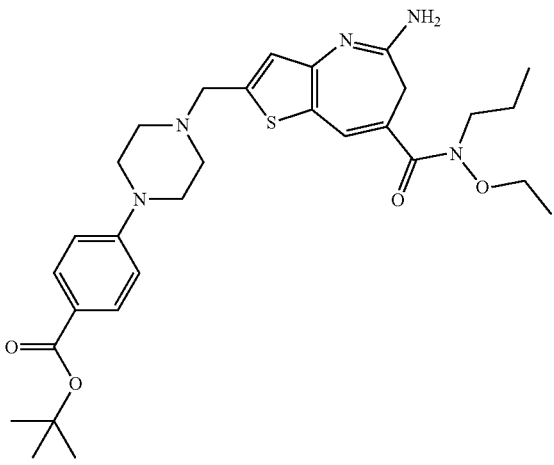 | 567.8 | 9000 | 9000 |
| TAZ-206 | 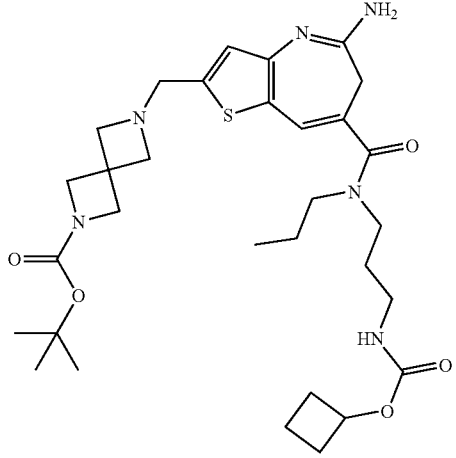 [SMILES: CCCN(CCCNC(=O)OC1CCC1)C(=O)C1=Cc2sc(CN3CC4(C3)CN(C(=O)OC(C)(C)C)C4)cc2N=C(N)C1] | 614.8 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-207 | 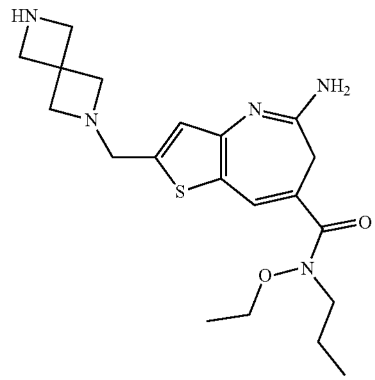 [SMILES: CCCN(OCC)C(=O)C1=Cc2sc(CN3CC4(CNC4)C3)cc2N=C(N)C1] | 403.5 | 9000 | 9000 |
| TAZ-208 | 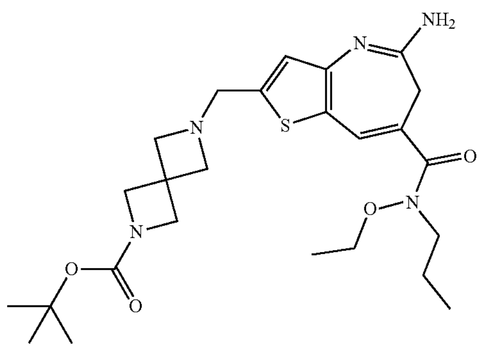 [SMILES: CCCN(OCC)C(=O)C1=Cc2sc(CN3CC4(C3)CN(C(=O)OC(C)(C)C)C4)cc2N=C(N)C1] | 503.7 | 3614 | 8507 |
| TAZ-209 | 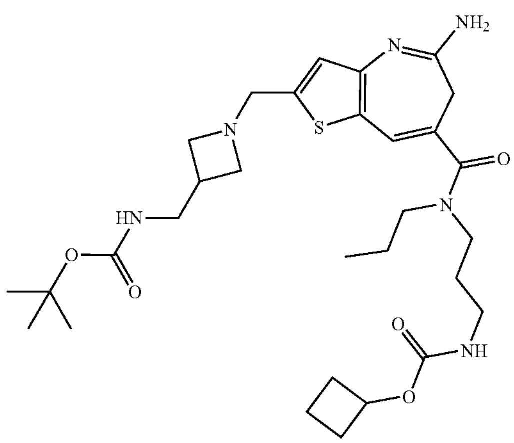 [SMILES: CCCN(CCCNC(=O)OC1CCC1)C(=O)C1=Cc2sc(CN3CC(CNC(=O)OC(C)(C)C)C3)cc2N=C(N)C1] | 602.8 | | |
| TAZ-210 | 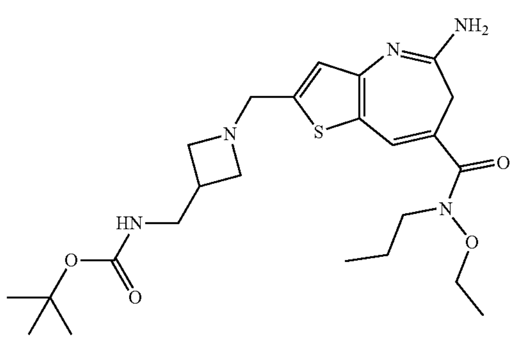 [SMILES: CCCN(OCC)C(=O)C1=Cc2sc(CN3CC(CNC(=O)OC(C)(C)C)C3)cc2N=C(N)C1] | 491.7 | 1546 | 2939 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-211 | 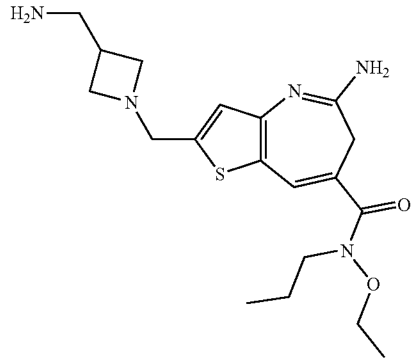 [SMILES: CCCN(OCC)C(=O)C1=Cc2sc(CN3CC(CN)C3)cc2N=C(N)C1] | 391.5 | 9000 | 4316 |
| TAZ-212 | 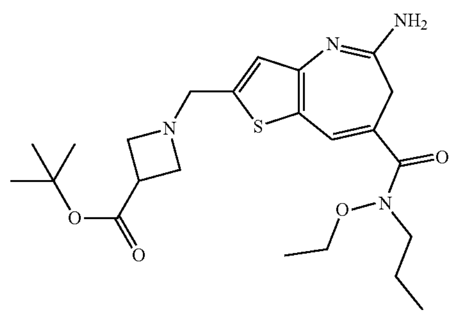 [SMILES: CCCN(OCC)C(=O)C1=Cc2sc(CN3CC(C(=O)OC(C)(C)C)C3)cc2N=C(N)C1] | 462.6 | 1265 | 2542 |
| TAZ-213 | 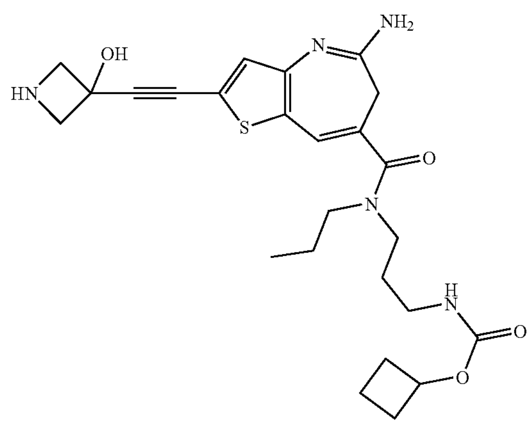 [SMILES: CCCN(CCCNC(=O)OC1CCC1)C(=O)C1=Cc2sc(C#CC3(O)CNC3)cc2N=C(N)C1] | 499.6 | | |
| TAZ-214 | 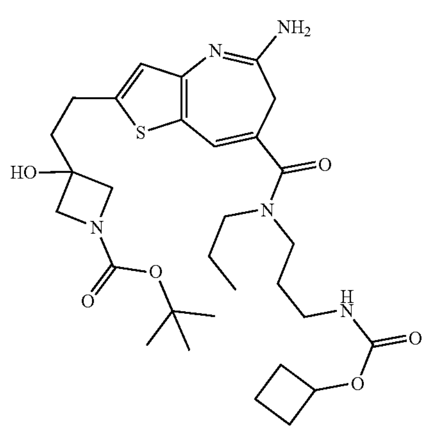 [SMILES: CCCN(CCCNC(=O)OC1CCC1)C(=O)C1=Cc2sc(CCC3(O)CN(C(=O)OC(C)(C)C)C3)cc2N=C(N)C1] | 603.8 | | |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-215 | 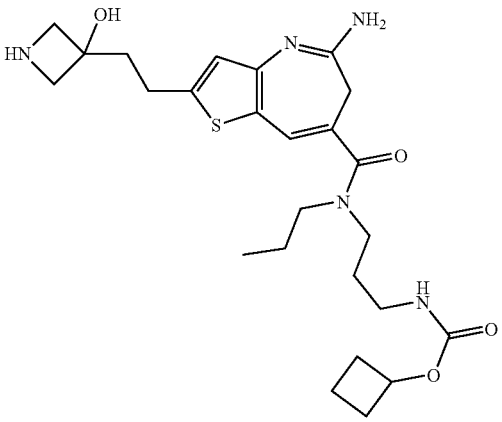 [SMILES: CCCN(CCCNC(=O)OC1CCC1)C(=O)C1=Cc2sc(CCC3(O)CNC3)cc2N=C(N)C1] | 503.7 | | |
| TAZ-216 | 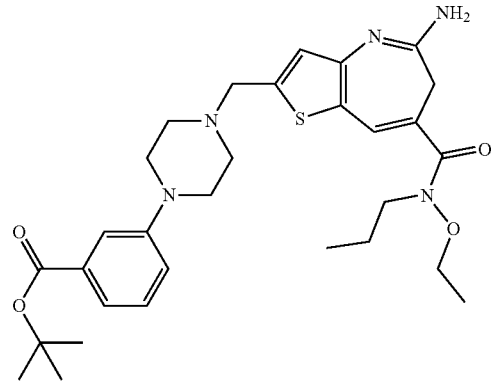 [SMILES: CCCN(OCC)C(=O)C1=Cc2sc(CN3CCN(c4cccc(C(=O)OC(C)(C)C)c4)CC3)cc2N=C(N)C1] | 567.8 | 9000 | |
| TAZ-217 | 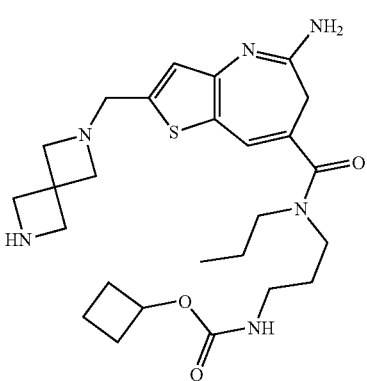 [SMILES: CCCN(CCCNC(=O)OC1CCC1)C(=O)C1=Cc2sc(CN3CC4(CNC4)C3)cc2N=C(N)C1] | 514.7 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-218 | 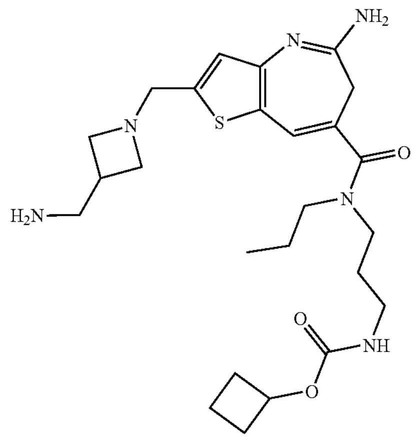 [SMILES: CCCN(CCCNC(=O)OC1CCC1)C(=O)C1=Cc2sc(CN3CC(CN)C3)cc2N=C(N)C1] | 502.7 | | |
| TAZ-219 | 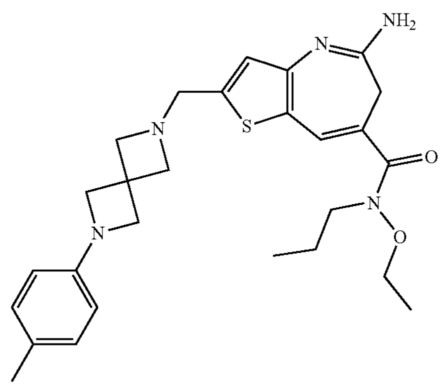 [SMILES: CCCN(OCC)C(=O)C1=Cc2sc(CN3CC4(C3)CN(c3ccc(C)cc3)C4)cc2N=C(N)C1] | 493.7 | 3197 | 847 |
| TAZ-220 | 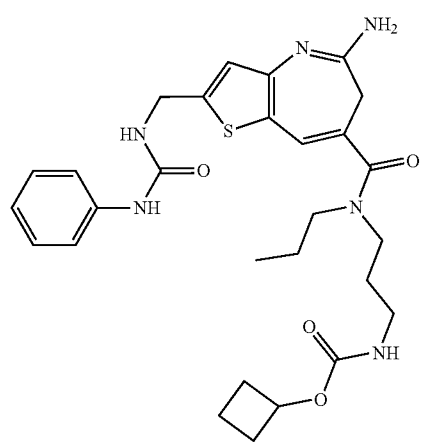 [SMILES: CCCN(CCCNC(=O)OC1CCC1)C(=O)C1=Cc2sc(CNC(=O)Nc3ccccc3)cc2N=C(N)C1] | 552.7 | | |
| TAZ-221 | 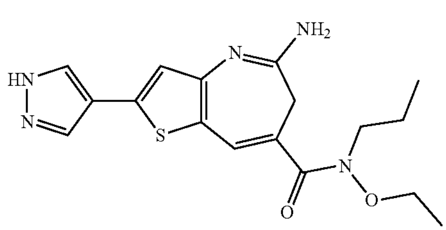 | 359.5 | 6118 | 6698 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-222 | 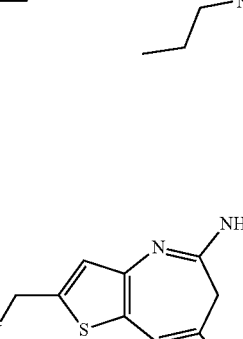 | 448.6 | 4892 | 2826 |
| TAZ-223 | 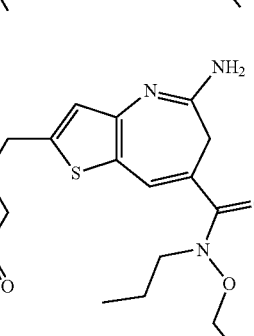 | 448.6 | 3803 | 3138 |
| TAZ-224 | 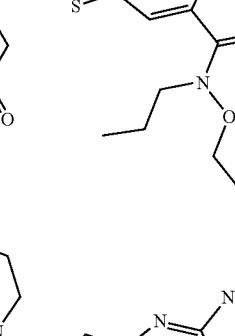 | 405.5 | 3410 | 2723 |
| TAZ-225 | 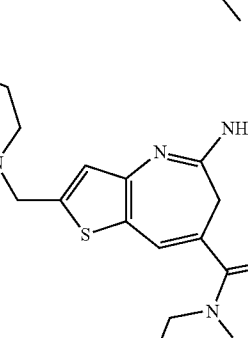 | 405.6 | 2560 | 1212 |

TABLE 1c-continued

| | Thienoazepine compounds (TAZ) | | | |
|---|---|---|---|---|
| TAZ No. | Structure | MW | HEK293 hTLR7 EC50 (nM) | HEK293 hTLR8 EC50 (nM) |
| TAZ-226 | | 505.7 | 436 | 4434 |
| TAZ-227 | | 417.6 | 4393 | 2289 |
| TAZ-228 | | 517.7 | 3759 | 3237 |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-229 | 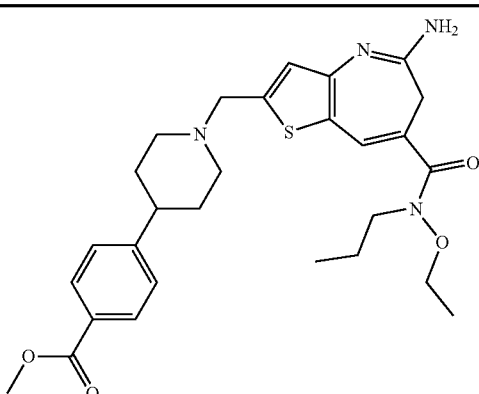 | 524.7 | 9000 | 9000 |
| TAZ-230 | 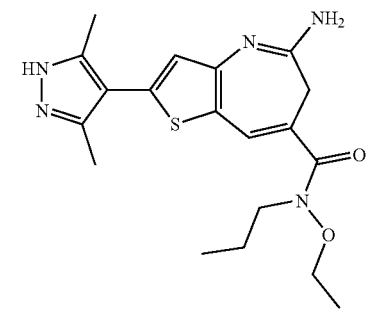 [SMILES: CCCN(OCC)C(=O)C1=Cc2sc(-c3c(C)n[nH]c3C)cc2N=C(N)C1] | 387.5 | | |
| TAZ-231 | 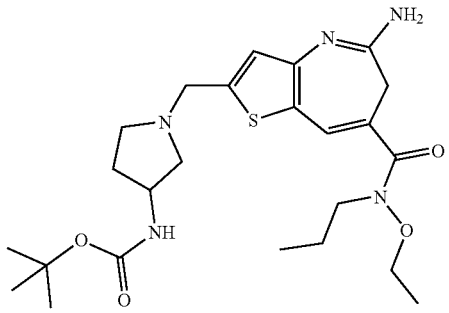 [SMILES: CCCN(OCC)C(=O)C1=Cc2sc(CN3CCC(NC(=O)OC(C)(C)C)C3)cc2N=C(N)C1] | 491.7 | | |
| TAZ-232 | 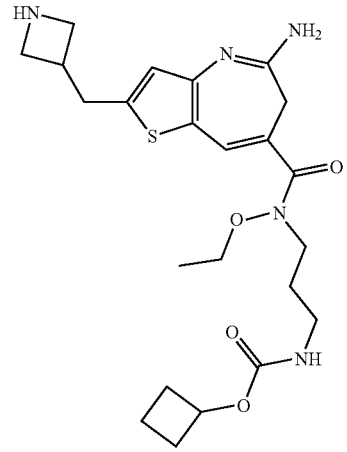 | 475.6 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-233 | 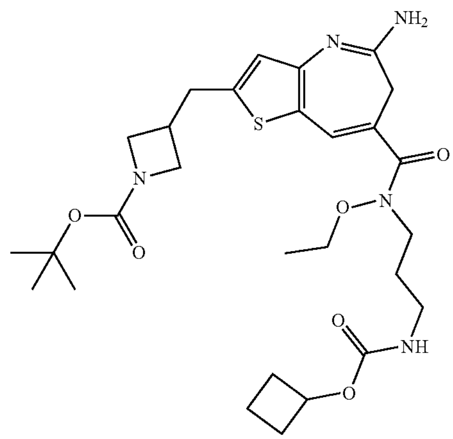 [SMILES: CCON(CCCNC(=O)OC1CCC1)C(=O)C1=Cc2sc(CC3CN(C(=O)OC(C)(C)C)C3)cc2N=C(N)C1] | 575.7 | | |
| TAZ-234 | 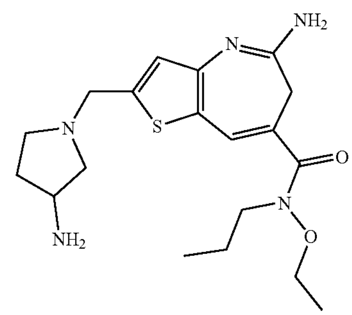 [SMILES: CCCN(OCC)C(=O)C1=Cc2sc(CN3CCC(N)C3)cc2N=C(N)C1] | 391.5 | 3326 | 361 |
| TAZ-235 | 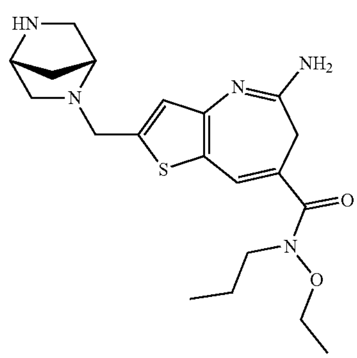 | 403.5 | 4570 | 3052 |
| TAZ-236 | 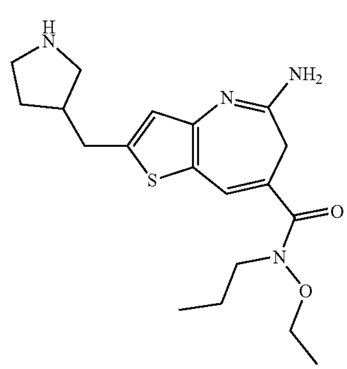 | 376.5 | 2216 | 423 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-237 | 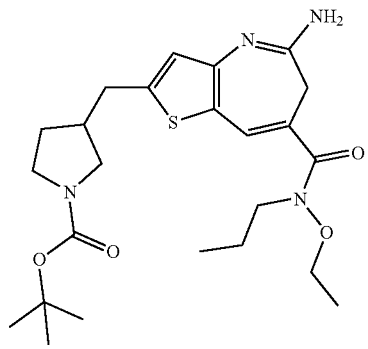 [SMILES: CCCN(OCC)C(=O)C1=Cc2sc(CC3CCN(C(=O)OC(C)(C)C)C3)cc2N=C(N)C1] | 476.6 | | |
| TAZ-238 | 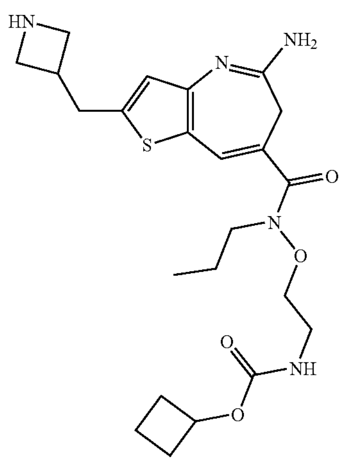 [SMILES: CCCN(OCCNC(=O)OC1CCC1)C(=O)C1=Cc2sc(CC3CNC3)cc2N=C(N)C1] | 475.6 | 112 | 286 |
| TAZ-239 | 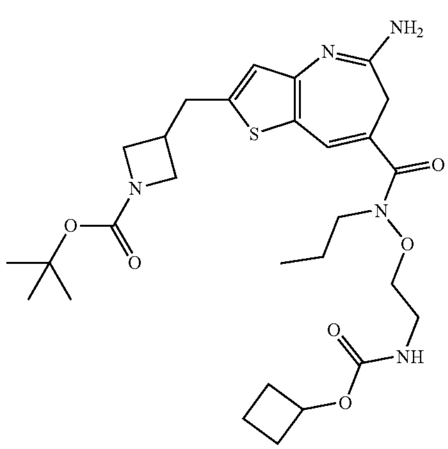 [SMILES: CCCN(OCCNC(=O)OC1CCC1)C(=O)C1=Cc2sc(CC3CN(C(=O)OC(C)(C)C)C3)cc2N=C(N)C1] | 575.7 | | |

TABLE 1c-continued

Thienoazepine compounds (TAZ)

| TAZ No. | Structure | MW | HEK293 hTLR7 EC50 (nM) | HEK293 hTLR8 EC50 (nM) |
| --- | --- | --- | --- | --- |
| TAZ-240 | 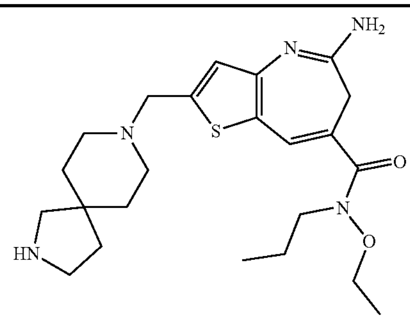 | 445.6 | 4245 | 5461 |
| TAZ-241 | 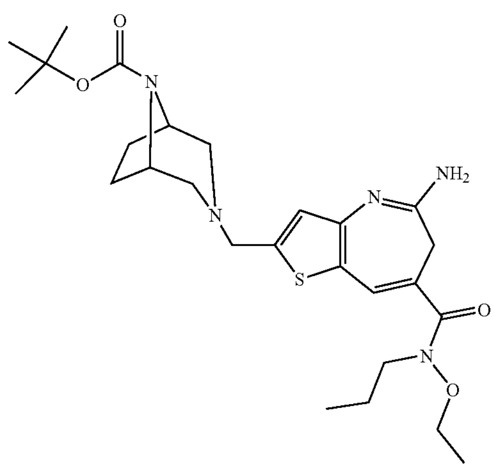 [SMILES: CCCN(OCC)C(=O)C1=Cc2sc(CN3CC4CCC(C3)N4C(=O)OC(C)(C)C)cc2N=C(N)C1] | 517.7 | 2815 | 3061 |
| TAZ-242 | 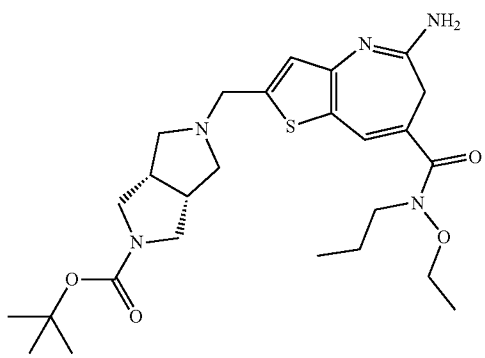 [SMILES: CCCN(OCC)C(=O)C1=Cc2sc(CN3C[C@@H]4CN(C(=O)OC(C)(C)C)C[C@@H]4C3)cc2N=C(N)C1] | 517.7 | 9000 | 3777 |
| TAZ-243 | 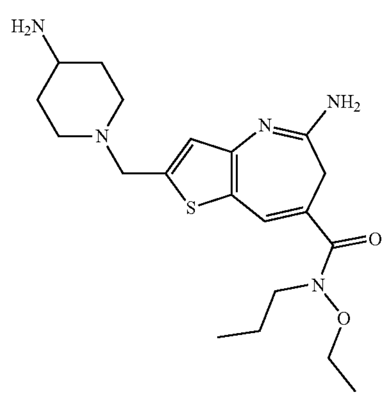 [SMILES: CCCN(OCC)C(=O)C1=Cc2sc(CN3CCC(N)CC3)cc2N=C(N)C1] | 405.6 | 9000 | 164 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-244 | 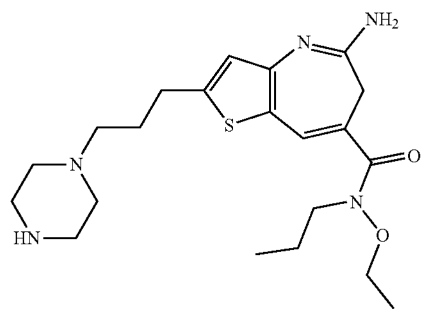 [SMILES: CCCN(OCC)C(=O)C1=Cc2sc(CCCN3CCNCC3)cc2N=C(N)C1] | 419.6 | 2460 | 146 |
| TAZ-245 | 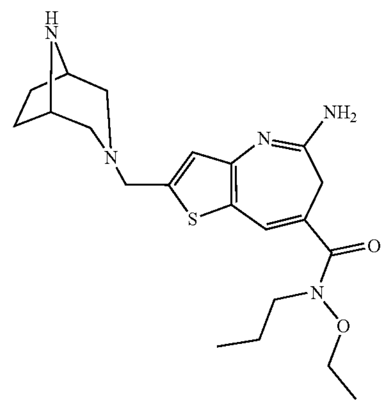 [SMILES: CCCN(OCC)C(=O)C1=Cc2sc(CN3CC4CCC(C3)N4)cc2N=C(N)C1] | 417.6 | 5023 | 145 |
| TAZ-246 | 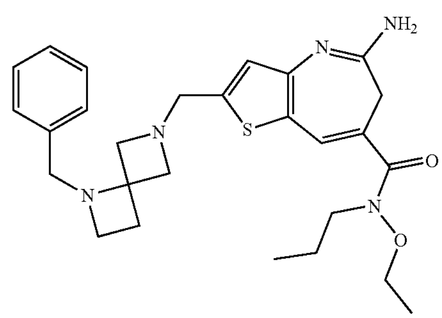 [SMILES: CCCN(OCC)C(=O)C1=Cc2sc(CN3CC4(CCN4Cc4ccccc4)C3)cc2N=C(N)C1] | 493.7 | 9000 | 1107 |
| TAZ-247 | 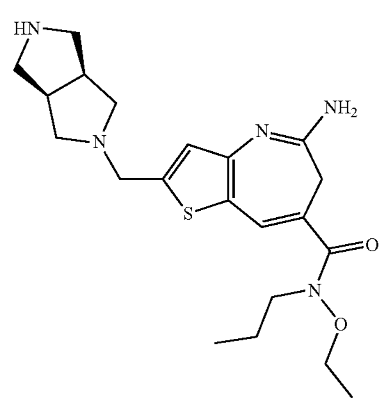 [SMILES: CCCN(OCC)C(=O)C1=Cc2sc(CN3C[C@H]4CNC[C@H]4C3)cc2N=C(N)C1] | 417.6 | 9000 | 418 |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-248 | 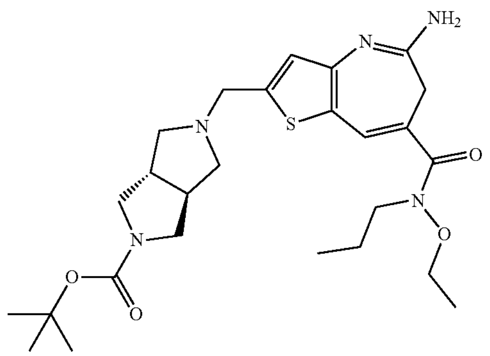 [SMILES: CCCN(OCC)C(=O)C1=Cc2sc(CN3C[C@H]4CN(C(=O)OC(C)(C)C)C[C@@H]4C3)cc2N=C(N)C1] | 517.7 | 9000 | 1114 |
| TAZ-249 | 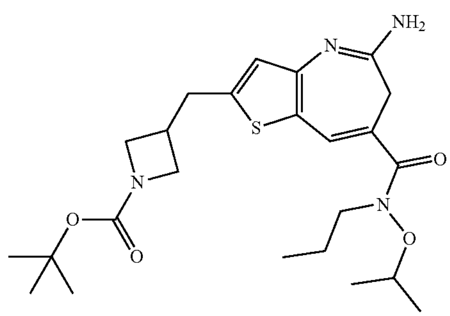 [SMILES: CCCN(OC(C)C)C(=O)C1=Cc2sc(CC3CN(C(=O)OC(C)(C)C)C3)cc2N=C(N)C1] | 476.6 | 362 | 640 |
| TAZ-250 | 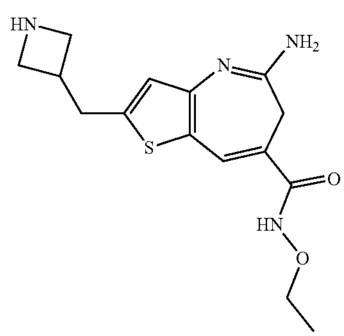 [SMILES: CCONC(=O)C1=Cc2sc(CC3CNC3)cc2N=C(N)C1] | 320.4 | 9000 | 9000 |
| TAZ-251 | 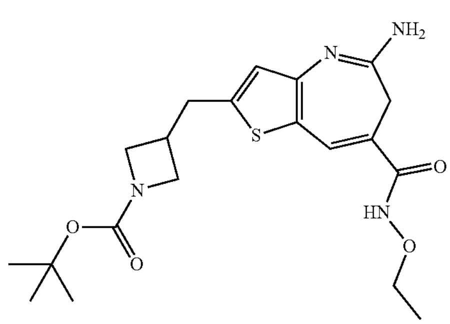 [SMILES: CCONC(=O)C1=Cc2sc(CC3CN(C(=O)OC(C)(C)C)C3)cc2N=C(N)C1] | 420.5 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-252 | 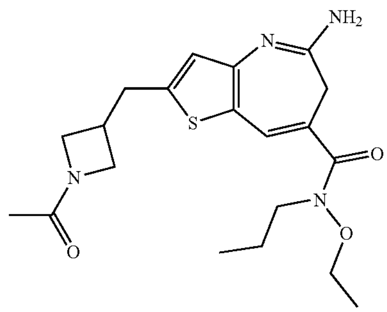 [SMILES: CCCN(OCC)C(=O)C1=Cc2sc(CC3CN(C(C)=O)C3)cc2N=C(N)C1] | 404.5 | 4453 | 868 |
| TAZ-253 | 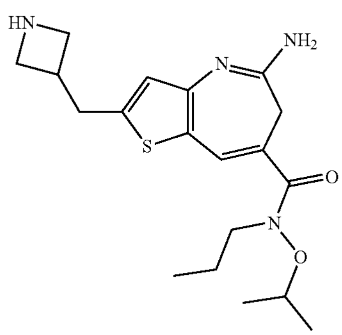 [SMILES: CCCN(OC(C)C)C(=O)C1=Cc2sc(CC3CNC3)cc2N=C(N)C1] | 376.5 | 7166 | 192 |
| TAZ-254 | 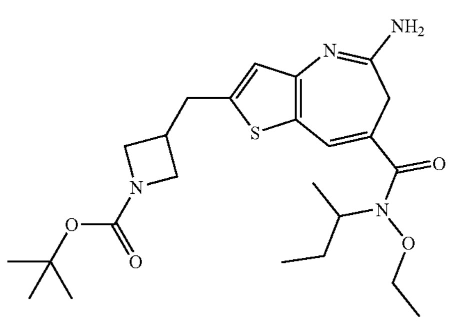 [SMILES: CCON(C(=O)C1=Cc2sc(CC3CN(C(=O)OC(C)(C)C)C3)cc2N=C(N)C1)C(C)CC] | 476.6 | 8133 | 8267 |
| TAZ-255 | 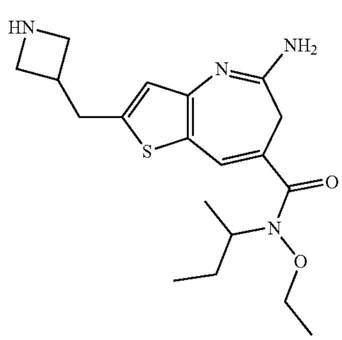 [SMILES: CCON(C(=O)C1=Cc2sc(CC3CNC3)cc2N=C(N)C1)C(C)CC] | 376.5 | | |

TABLE 1c-continued
Thienoazepine compounds (TAZ)
| TAZ No. | Structure | MW | HEK293 hTLR7 EC50 (nM) | HEK293 hTLR8 EC50 (nM) |
|---|---|---|---|---|
| TAZ-256 | 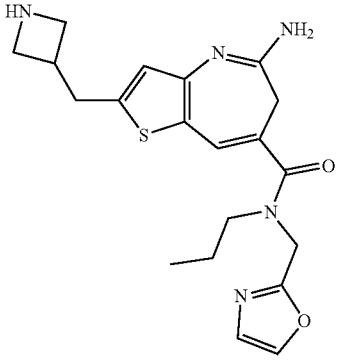 [SMILES: CCCN(Cc1ncco1)C(=O)C1=Cc2sc(CC3CNC3)cc2N=C(N)C1] | 399.5 | 9000 | 3409 |
| TAZ-257 | 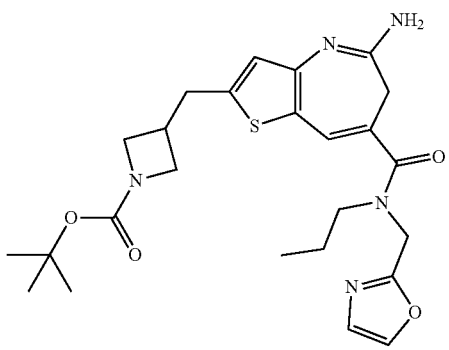 [SMILES: CCCN(Cc1ncco1)C(=O)C1=Cc2sc(CC3CN(C(=O)OC(C)(C)C)C3)cc2N=C(N)C1] | 499.6 | | |
| TAZ-258 | 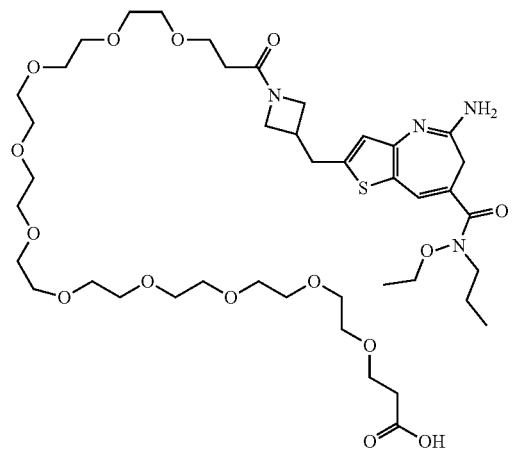 [SMILES: CCCN(OCC)C(=O)C1=Cc2sc(CC3CN(C(=O)CCOCCOCCOCCOCCOCCOCCOCCOCCOCCOCCC(=O)O)C3)cc2N=C(N)C1] | 903.1 | | |
| TAZ-259 | 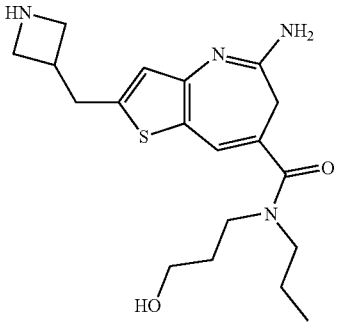 [SMILES: CCCN(CCCO)C(=O)C1=Cc2sc(CC3CNC3)cc2N=C(N)C1] | 376.5 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-260 | 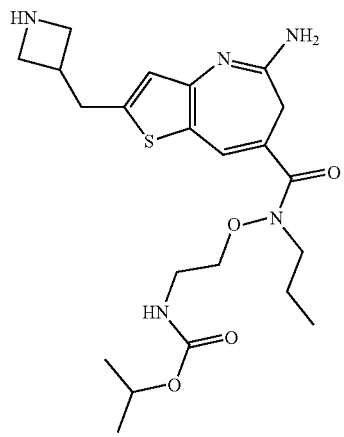 [SMILES: CCCN(OCCNC(=O)OC(C)C)C(=O)C1=Cc2sc(CC3CNC3)cc2N=C(N)C1] | 463.6 | | |
| TAZ-261 | 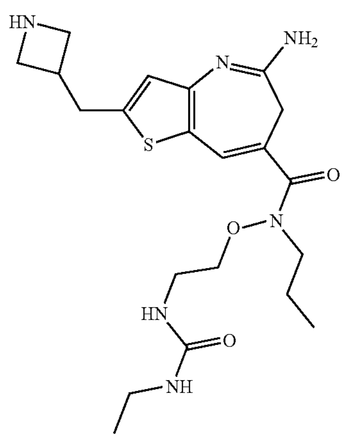 [SMILES: CCCN(OCCNC(=O)NCC)C(=O)C1=Cc2sc(CC3CNC3)cc2N=C(N)C1] | 448.6 | | |
| TAZ-262 | 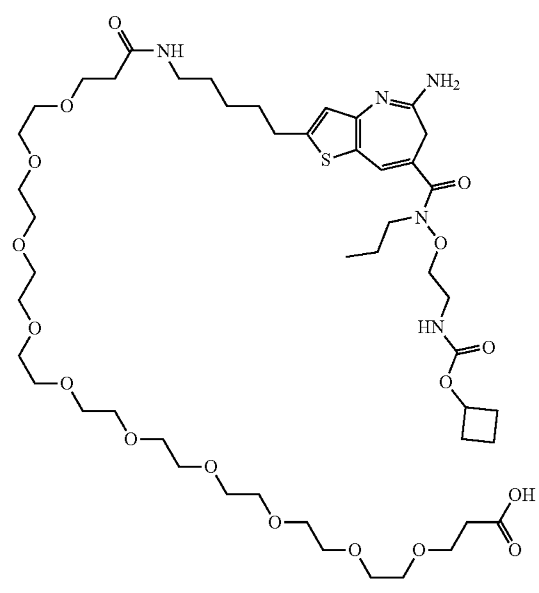 [SMILES: CCCN(OCCNC(=O)OC1CCC1)C(=O)C1=Cc2sc(CCCCCNC(=O)CCOCCOCCOCCOCCOCCOCCOCCOCCOCCOCCC(=O)O)cc2N=C(N)C1] | 1032.2 | | |

TABLE 1c-continued

Thienoazepine compounds (TAZ)

| TAZ No. | Structure | MW | HEK293 hTLR7 EC50 (nM) | HEK293 hTLR8 EC50 (nM) |
|---|---|---|---|---|
| TAZ-263 | 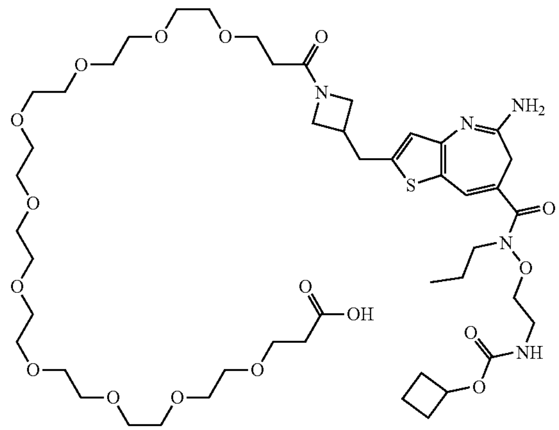 [SMILES: CCCN(OCCNC(=O)OC1CCC1)C(=O)C1=Cc2sc(CC3CN(C(=O)CCOCCOCCOCCOCCOCCOCCOCCOCCOCCOCCC(=O)O)C3)cc2N=C(N)C1] | 1016.2 | | |

Thienoazepine-Linker Compounds

The immunoconjugates of the invention are prepared by conjugation of an antibody with a thienoazepine-linker compound. The thienoazepine-linker compounds comprise a thienoazepine (TAZ) moiety covalently attached to a linker unit. The linker units comprise functional groups and sub-units which affect stability, permeability, solubility, and other pharmacokinetic, safety, and efficacy properties of the immunoconjugates. The linker unit includes a reactive functional group which reacts, i.e. conjugates, with a reactive functional group of the antibody. For example, a nucleophilic group such as a lysine side chain amino of the antibody reacts with an electrophilic reactive functional group of the TAZ-linker compound to form the immunoconjugate. Also, for example, a cysteine thiol of the antibody reacts with a maleimide or bromoacetamide group of the TAZ-linker compound to form the immunoconjugate.

Electrophilic reactive functional groups suitable for the TAZ-linker compounds include, but are not limited to, N-hydroxysuccinimidyl (NHS) esters and N-hydroxysulfo-succinimidyl (sulfo-NHS) esters (amine reactive); carbodiimides (amine and carboxyl reactive); hydroxymethyl phosphines (amine reactive); maleimides (thiol reactive); halogenated acetamides such as A-iodoacetamides (thiol reactive); aryl azides (primary amine reactive); fluorinated aryl azides (reactive via carbon-hydrogen (C—H) insertion); pentafluorophenyl (PFP) esters (amine reactive); tetrafluorophenyl (TFP) esters (amine reactive); imidoesters (amine reactive); isocyanates (hydroxyl reactive); vinyl sulfones (thiol, amine, and hydroxyl reactive); pyridyl disulfides (thiol reactive); and benzophenone derivatives (reactive via C—H bond insertion). Further reagents include, but are not limited, to those described in Hermanson, *Bioconjugate Techniques* 2$^{nd}$ Edition, Academic Press, 2008.

The invention provides solutions to the limitations and challenges to the design, preparation and use of immunoconjugates. Some linkers may be labile in the blood stream, thereby releasing unacceptable amounts of the adjuvant/drug prior to internalization in a target cell (Khot, A. et al (2015) *Bioanalysis* 7(13): 1633-1648). Other linkers may provide stability in the bloodstream, but intracellular release effectiveness may be negatively impacted. Linkers that provide for desired intracellular release typically have poor stability in the bloodstream. Alternatively stated, bloodstream stability and intracellular release are typically inversely related. In addition, in standard conjugation processes, the amount of adjuvant/drug moiety loaded on the antibody, i.e. drug loading, the amount of aggregate that is formed in the conjugation reaction, and the yield of final purified conjugate that can be obtained are interrelated. For example, aggregate formation is generally positively correlated to the number of equivalents of adjuvant/drug moiety and derivatives thereof conjugated to the antibody. Under high drug loading, formed aggregates must be removed for therapeutic applications. As a result, drug loading-mediated aggregate formation decreases immunoconjugate yield and can render process scale-up difficult.

Exemplary embodiments include a 5-aminothienoazepine-linker compound of Formula II:

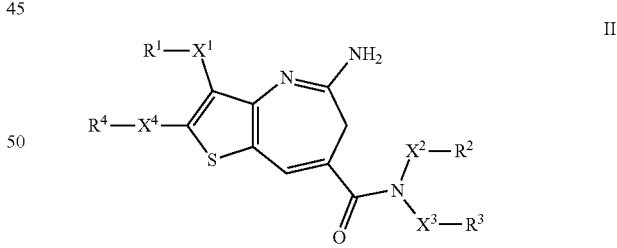

II where one of $R^1$, $R^2$, $R^3$, and $R^4$ is attached to L;

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:

—($C_1$-$C_{12}$ alkyldiyl)-N($R^5$)—*;
—($C_1$-$C_{12}$ alkyldiyl)-N($R^5$)$_2$;
—($C_1$-$C_{12}$ alkyldiyl)-O$R^5$;
—($C_3$-$C_{12}$ carbocyclyl);

—($C_3$-$C_{12}$ carbocyclyl)-*;
—($C_3$-$C_{12}$ carbocyclyl)-($C_1$-$C_{12}$ alkyldiyl)-$NR^5$—*;
—($C_3$-$C_{12}$ carbocyclyl)-($C_1$-$C_{12}$ alkyldiyl)-$N(R^5)_2$;
—($C_3$-$C_{12}$ carbocyclyl)-$NR^5$—C(=$NR^5$)$NR^5$—*;
—($C_6$-$C_{20}$ aryl);
—($C_6$-$C_{20}$ aryl)-*;
—($C_6$-$C_{20}$ aryldiyl)-$N(R^5)$—*;
—($C_6$-$C_{20}$ aryldiyl)-($C_1$-$C_{12}$ alkyldiyl)-$N(R^5)$—*;
—($C_6$-$C_{20}$ aryldiyl)-($C_1$-$C_{12}$ alkyldiyl)-($C_2$-$C_{20}$ heterocyclyldiyl)-*;
—($C_6$-$C_{20}$ aryldiyl)-($C_1$-$C_{12}$ alkyldiyl)-$N(R^5)_2$;
—($C_6$-$C_{20}$ aryldiyl)-($C_1$-$C_{12}$ alkyldiyl)-$NR^5$—C(=$NR^{5a}$)$N(R^5)$—*;
—($C_2$-$C_{20}$ heterocyclyl);
—($C_2$-$C_{20}$ heterocyclyl)-*;
—($C_2$-$C_9$ heterocyclyl)-($C_1$-$C_{12}$ alkyldiyl)-$NR^5$—*;
—($C_2$-$C_9$ heterocyclyl)-($C_1$-$C_{12}$ alkyldiyl)-$N(R^5)_2$;
—($C_2$-$C_9$ heterocyclyl)-C(=O)—($C_1$-$C_{12}$ alkyldiyl)-$N(R^5)$—*;
—($C_2$-$C_9$ heterocyclyl)-$NR^5$—C(=$NR^{5a}$)$NR^5$—*;
—($C_2$-$C_9$ heterocyclyl)-$NR^5$—($C_6$-$C_{20}$ aryldiyl)-($C_1$-$C_{12}$ alkyldiyl)-$N(R^5)$—*;
—($C_2$-$C_9$ heterocyclyl)-($C_6$-$C_{20}$ aryldiyl)-*;
—($C_1$-$C_{20}$ heteroaryl);
—($C_1$-$C_{20}$ heteroaryl)-*;
—($C_1$-$C_{20}$ heteroaryl)-($C_1$-$C_{12}$ alkyldiyl)-$N(R^5)$—*;
—($C_1$-$C_{20}$ heteroaryl)-($C_1$-$C_{12}$ alkyldiyl)-$N(R^5)_2$;
—($C_1$-$C_{20}$ heteroaryl)-$NR^5$—C(=$NR^{5a}$)$N(R^5)$—*;
—($C_1$-$C_{20}$ heteroaryl)-$N(R^5)$C(=O)—($C_1$-$C_{12}$ alkyldiyl)-$N(R^5)$—*;
—C(=O)—*;
—C(=O)—($C_1$-$C_{12}$ alkyldiyl)-$N(R^5)$—*;
—C(=O)—($C_2$-$C_{20}$ heterocyclyldiyl)-*;
—C(=O)$N(R^5)_2$;
—C(=O)$N(R^5)$—*;
—C(=O)$N(R^5)$—($C_1$-$C_{12}$ alkyldiyl)-$N(R^5)$C(=O)$R^5$;
—C(=O)$N(R^5)$—($C_1$-$C_{12}$ alkyldiyl)-$N(R^5)$C(=O)$N(R^5)_2$;
—C(=O)$NR^5$—($C_1$-$C_{12}$ alkyldiyl)-$N(R^5)$$CO_2R^5$;
—C(=O)$NR^5$—($C_1$-$C_{12}$ alkyldiyl)-$N(R^5)$C(=$NR^{5a}$)$N(R^5)_2$;
—C(=O)$NR^5$—($C_1$-$C_{12}$ alkyldiyl)-$NR^5$C(=$NR^{5a}$)$R^5$;
—C(=O)$NR^5$—($C_1$-$C_8$ alkyldiyl)-$NR^5$($C_2$-$C_5$ heteroaryl);
—C(=O)$NR^5$—($C_1$-$C_{20}$ heteroaryldiyl)-$N(R^5)$—*;
—C(=O)$NR^5$—($C_1$-$C_{20}$ heteroaryldiyl)-*;
—C(=O)$NR^5$—($C_1$-$C_{20}$ heteroaryldiyl)-($C_1$-$C_{12}$ alkyldiyl)-$N(R^5)_2$;
—C(=O)$NR^5$—($C_1$-$C_{20}$ heteroaryldiyl)-($C_2$-$C_{20}$ heterocyclyldiyl)-C(=O)$NR^5$—($C_1$-$C_{12}$ alkyldiyl)-$NR^5$—*;
—$N(R^5)_2$;
—$N(R^5)$—*;
—$N(R^5)$C(=O)$R^5$;
—$N(R^5)$C(=O)—*;
—$N(R^5)$C(=O)$N(R^5)_2$;
—$N(R^5)$C(=O)$N(R^5)$—*;
—$N(R^5)$$CO_2R^5$;
—$NR^5$C(=$NR^{5a}$)$N(R^5)_2$;
—$NR^5$C(=$NR^{5a}$)$N(R^5)$—*;
—$NR^5$C(=$NR^{5a}$)$R^5$;
—$N(R^5)$C(=O)—($C_1$-$C_{12}$ alkyldiyl)-$N(R^5)$—*;
—$N(R^5)$—($C_2$-$C_5$ heteroaryl);
—$N(R^5)$—S(=O)$_2$—($C_1$-$C_{12}$ alkyl);
—O—($C_1$-$C_{12}$ alkyl);
—O—($C_1$-$C_{12}$ alkyldiyl)-$N(R^5)_2$;
—O—($C_1$-$C_{12}$ alkyldiyl)-$N(R^5)$—*;
—S(=O)$_2$—($C_2$-$C_{20}$ heterocyclyldiyl)-*;
—S(=O)$_2$—($C_2$-$C_{20}$ heterocyclyldiyl)-($C_1$-$C_{12}$ alkyldiyl)-$N(R^5)_2$;
—S(=O)$_2$—($C_2$-$C_{20}$ heterocyclyldiyl)-($C_1$-$C_{12}$ alkyldiyl)-$NR^5$—*; and
—S(=O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(=O), C(=O)$N(R^5)$, O, $N(R^5)$, S, S(O)$_2$, and S(O)$_2N(R^5)$;

$R^5$ is selected from the group consisting of H, $C_6$-$C_{20}$ aryl, $C_3$-$C_{12}$ carbocyclyl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:
Q-C(=O)-(PEG)-;
Q-C(=O)-(PEG)-C(=O)—;
Q-C(=O)-(PEG)-O—;
Q-C(=O)-(PEG)-C(=O)—(PEP)-;
Q-C(=O)-(PEG)-C(=O)$N(R^5)$—($C_1$-$C_{12}$ alkyldiyl)-;
Q-C(=O)-(PEG)-C(=O)$N(R^5)$—($C_1$-$C_{12}$ alkyldiyl)-$N(R^5)$C(=O)—($C_2$-$C_5$ monoheterocyclyldiyl)-;
Q-C(=O)-(PEG)-C(=O)$N(R^5)$—($C_1$-$C_{12}$ alkyldiyl)-(Mcgluc)-;
Q-C(=O)-(PEG)-C(=O)-(Mcgluc)-;
Q-C(=O)-(PEG)-C(=O)—(PEP)-$N(R^5)$—($C_1$-$C_{12}$ alkyldiyl)-;
Q-C(=O)-(PEG)-C(=O)—(PEP)-$N(R^5)$—($C_1$-$C_{12}$ alkyldiyl)-$N(R^5)$C(=O)—($C_2$-$C_5$ monoheterocyclyldiyl)-;
Q-C(=O)-(PEG)-$N(R^5)$—;
Q-C(=O)-(PEG)-$N(R^5)$C(=O)—;
Q-C(=O)-(PEG)-$N(R^5)$-(PEG)-C(=O)—(PEP)-;
Q-C(=O)-(PEG)-$N^+(R^5)_2$-(PEG)-C(=O)—(PEP)-;
Q-C(=O)-(PEG)-C(=O)—$N(R^5)$CH($AA_1$)C(=O)-(PEG)-C(=O)—(PEP)-;
Q-C(=O)-(PEG)-C(=O)—$N(R^5)$CH($AA_1$)C(=O)—$N(R^5)$—($C_1$-$C_{12}$ alkyldiyl)-;
Q-C(=O)-(PEG)-SS—($C_1$-$C_{12}$ alkyldiyl)-OC(=O)—;
Q-C(=O)-(PEG)-SS—($C_1$-$C_{12}$ alkyldiyl)-C(=O)—;
Q-C(=O)—($C_1$-$C_{12}$ alkyldiyl)-C(=O)—(PEP)-;
Q-C(=O)—($C_1$-$C_{12}$ alkyldiyl)-C(=O)—(PEP)-$N(R^5)$—($C_1$-$C_{12}$ alkyldiyl)-;
Q-C(=O)—($C_1$-$C_{12}$ alkyldiyl)-C(=O)—(PEP)-$N(R^5)$—($C_1$-$C_{12}$ alkyldiyl)-$N(R^5)$—C(=O);
Q-C(=O)—($C_1$-$C_{12}$ alkyldiyl)-C(=O)—(PEP)-$N(R^5)$—($C_1$-$C_{12}$ alkyldiyl)-$N(R^5)$C(=O)—($C_2$-$C_5$ monoheterocyclyldiyl)-;
Q-C(=O)—$CH_2CH_2OCH_2CH_2$—($C_1$-$C_{20}$ heteroaryldiyl)-$CH_2$O-(PEG)-C(=O)-(Mcgluc)-;
Q-C(=O)—$CH_2CH_2OCH_2CH_2$—($C_1$-$C_{20}$ heteroaryldiyl)-$CH_2$O-(PEG)-C(=O)-(Mcgluc)-$N(R^5)$—($C_1$-$C_{12}$ alkyldiyl)-$N(R^5)$C(=O)—($C_2$-$C_5$ monoheterocyclyldiyl)-; and
Q-$(CH_2)_m$—C(=O)—(PEP)-$N(R^5)$—($C_1$-$C_{12}$ alkyldiyl)-$N(R^5)$C(=O)—($C_2$-$C_5$ monoheterocyclyldiyl)-;

where PEG has the formula: —$(CH_2CH_2O)_n$—$(CH_2)_m$—;
m is an integer from 1 to 5, and n is an integer from 2 to 50;

PEP has the formula:

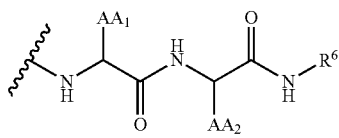

where $AA_1$ and $AA_2$ are independently selected from an amino acid side chain, or $AA_1$ or $AA_2$ and an adjacent nitrogen atom form a 5-membered ring proline amino acid, and the wavy line indicates a point of attachment and;

$R^6$ is selected from the group consisting of $C_6$-$C_{20}$ aryldiyl and $C_1$-$C_{20}$ heteroaryldiyl, substituted with —$CH_2O$—C(=O)— and optionally with:

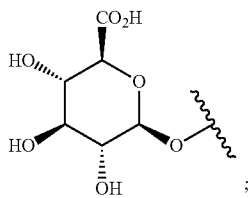 [SMILES: *O[C@@H]1O[C@H](C(=O)O)[C@@H](O)[C@H](O)[C@H]1O]

and

Mcgluc is selected from the groups:

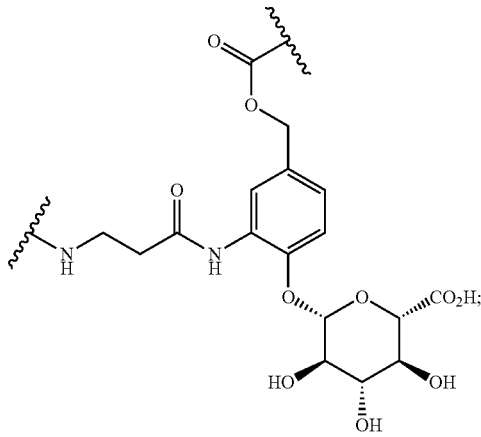

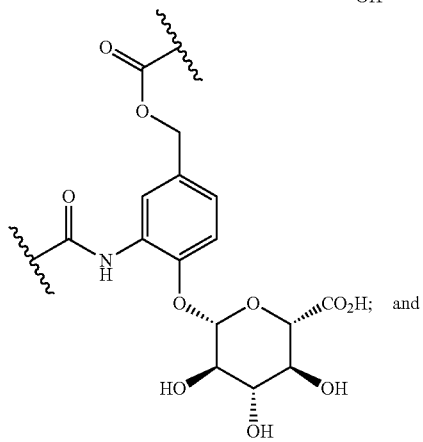

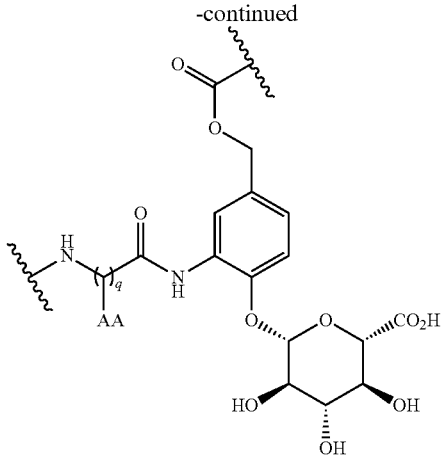

where q is 1 to 8, and AA is an amino acid side chain; and

Q is selected from the group consisting of N-hydroxysuccinimidyl, N-hydroxysulfosuccinimidyl, maleimide, and phenoxy substituted with one or more groups independently selected from F, Cl, $NO_2$, and $SO_3^-$;

where alkyl, alkyldiyl, alkenyl, alkenyldiyl, alkynyl, alkynyldiyl, aryl, aryldiyl carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH=$CH_2$, —C≡CH, —C≡$CCH_3$, —$CH_2CH_2CH_3$, —$CH(CH_3)_2$, —$CH_2CH(CH_3)_2$, —$CH_2OH$, —$CH_2OCH_3$, —$CH_2CH_2OH$, —$C(CH_3)_2OH$, —$CH(OH)CH(CH_3)_2$, —$C(CH_3)_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —$CH(CH_3)CN$, —$C(CH_3)_2CN$, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —$COCH(OH)CH_3$, —$CONH_2$, —$CONHCH_3$, —$CON(CH_3)_2$, —$C(CH_3)_2CONH_2$, —$NH_2$, —$NHCH_3$, —$N(CH_3)_2$, —$NHCOCH_3$, —$N(CH_3)COCH_3$, —$NHS(O)_2CH_3$, —$N(CH_3)C(CH_3)_2CONH_2$, —$N(CH_3)CH_2CH_2S(O)_2CH_3$, —NHC(=NH)H, —NHC(=NH)$CH_3$, —NHC(=NH)$NH_2$, —NHC(=O)$NH_2$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —$O(CH_2CH_2O)_n$—$(CH_2)_mCO_2H$, —$O(CH_2CH_2O)_n$H, —$OCH_2F$, —$OCHF_2$, —$OCF_3$, —OP(O)(OH)$_2$, —$S(O)_2N(CH_3)_2$, —$SCH_3$, —$S(O)_2CH_3$, and —$S(O)_3H$.

An exemplary embodiment of the thienoazepine-linker compound of Formula II includes wherein PEP has the formula:

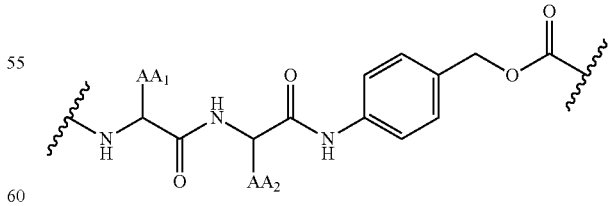

wherein $AA_1$ and $AA_2$ are independently selected from a side chain of a naturally-occurring amino acid.

An exemplary embodiment of the thienoazepine-linker compound of Formula II includes wherein $AA_1$ or $AA_2$ with an adjacent nitrogen atom form a 5-membered ring to form a proline amino acid.

An exemplary embodiment of the thienoazepine-linker compound of Formula II includes wherein PEP has the formula:

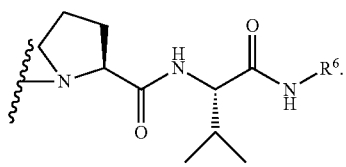

An exemplary embodiment of the thienoazepine-linker compound of Formula II includes wherein Mcgluc has the formula:

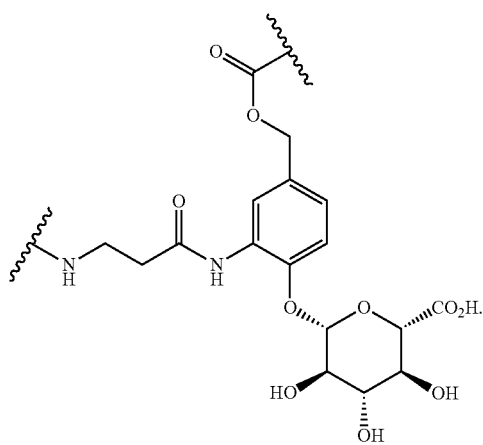 [SMILES: *NCCC(=O)Nc1cc(COC(*)=O)ccc1O[C@@H]1O[C@H](C(=O)O)[C@@H](O)[C@H](O)[C@H]1O]

An exemplary embodiment of the thienoazepine-linker compound of Formula II includes wherein $AA_1$ and $AA_2$ are independently selected from H, —$CH_3$, —$CH(CH_3)_2$, —$CH_2(C_6H_5)$, —$CH_2CH_2CH_2CH_2NH_2$, —$CH_2CH_2CH_2NHC(NH)NH_2$, —$CHCH(CH_3)CH_3$, —$CH_2SO_3H$, and —$CH_2CH_2CH_2NHC(O)NH_2$.

An exemplary embodiment of the thienoazepine-linker compound of Formula II includes wherein $AA_1$ is —$CH(CH_3)_2$, and $AA_2$ is —$CH_2CH_2CH_2NHC(O)NH_2$.

An exemplary embodiment of the thienoazepine-linker compound of Formula II includes wherein $AA_1$ and $AA_2$ are independently selected from GlcNAc aspartic acid, —$CH_2SO_3H$, and —$CH_2OPO_3H$.

An exemplary embodiment of the thienoazepine-linker compound of Formula II includes wherein $NR^5(C_2-C_5$ heteroaryl) of $R^1$ or $R^3$ is selected from:

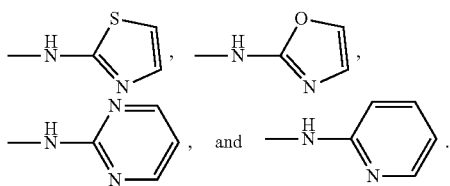

An exemplary embodiment of the thienoazepine-linker compound of Formula II includes wherein $X^1$ is a bond, and $R^1$ is H.

An exemplary embodiment of the thienoazepine-linker compound of Formula II includes wherein $X^2$ is a bond, and $R^2$ is $C_1$-$C_8$ alkyl.

An exemplary embodiment of the thienoazepine-linker compound of Formula II includes wherein $X^2$ and $X^3$ are each a bond, and $R^2$ and $R^3$ are independently selected from $C_1$-$C_8$ alkyl, —O—($C_1$-$C_{12}$ alkyl), —($C_1$-$C_{12}$ alkyldiyl)-$OR^5$, —($C_1$-$C_8$ alkyldiyl)-$N(R^5)CO_2R^5$, and —O—($C_1$-$C_{12}$ alkyl)-$N(R^5)CO_2R^5$.

An exemplary embodiment of the thienoazepine-linker compound of Formula II includes wherein $R^2$ and $R^3$ are each independently selected from —$CH_2CH_2CH_3$, —$OCH_2CH_3$, —$CH_2CH_2CF_3$, and —$CH_2CH_2CH_2OH$.

An exemplary embodiment of the thienoazepine-linker compound of Formula II includes wherein $R^2$ is $C_1$-$C_8$ alkyl and $R^3$ is —($C_1$-$C_8$ alkyldiyl)-$N(R^5)CO_2R^4$.

An exemplary embodiment of the thienoazepine-linker compound of Formula II includes wherein $R^2$ is —$CH_2CH_2CH_3$ and $R^3$ is —$CH_2CH_2CH_2NHCO_2$(t-Bu).

An exemplary embodiment of the thienoazepine-linker compound of Formula II includes wherein $R^2$ and $R^3$ are each —$CH_2CH_2CH_3$.

An exemplary embodiment of the thienoazepine-linker compound of Formula II includes wherein $X^3$—$R^3$ is selected from the group consisting of:

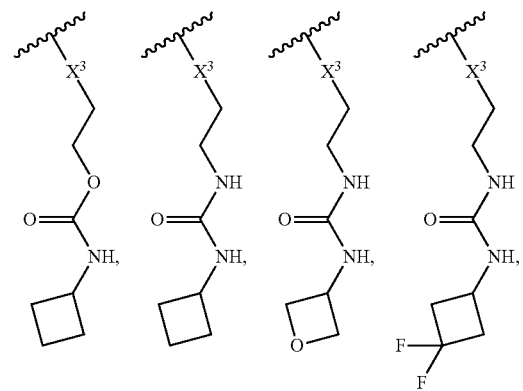

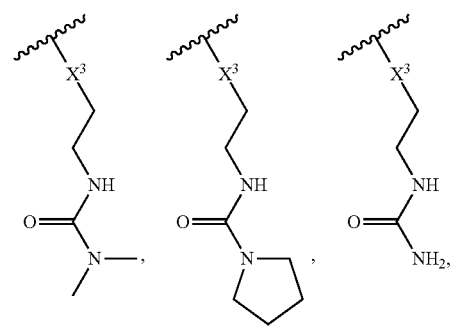

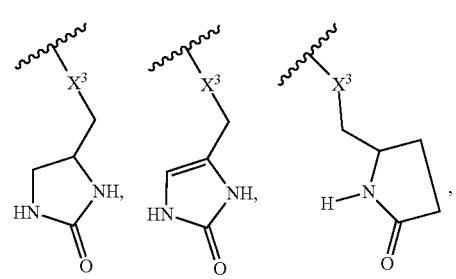

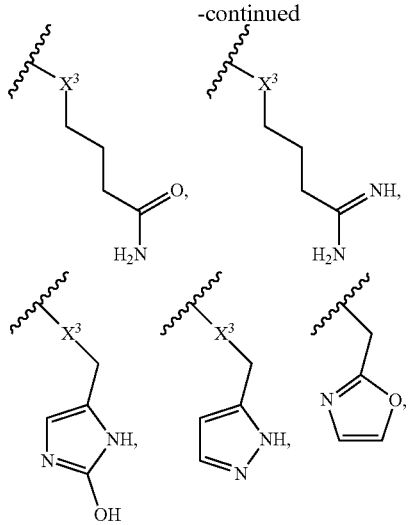

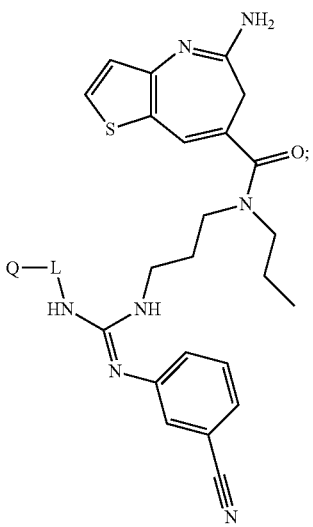

An exemplary embodiment of the thienoazepine-linker compound of Formula II includes wherein one of $R^2$ and $R^3$ is selected from:

- —($C_1$-$C_{12}$ alkyldiyl)-N($R^5$)—*;
- —($C_1$-$C_{12}$ alkyldiyl)-O—($C_1$-$C_{12}$ alkyldiyl)-N($R^5$)—*;
- —($C_1$-$C_{12}$ alkyldiyl)-N($R^5$)C(=N$R^5$)—N($R^5$)—*;
- —($C_1$-$C_{12}$ alkyldiyl)-($C_6$-$C_{20}$ aryldiyl)-($C_1$-$C_{12}$ alkyldiyl)-N($R^5$)—*;
- —($C_1$-$C_{12}$ alkyldiyl)-($C_6$-$C_{20}$ aryldiyl)-($C_1$-$C_{12}$ alkyldiyl)-N($R^5$)—C(=N$R^5$)N($R^5$)—*;
- —($C_2$-$C_6$ alkynyldiyl)-N($R^5$)—*; and
- —($C_2$-$C_6$ alkynyldiyl)-N($R^5$)C(=N$R^5$)N($R^5$)—*;

$X^2$ and $X^3$ are a bond, and where the asterisk * indicates the attachment site of L.

An exemplary embodiment of the thienoazepine-linker compound of Formula II includes wherein L is selected from the group consisting of:

- Q-C(=O)-(PEG)-;
- Q-C(=O)-(PEG)-C(=O)—;
- Q-C(=O)-(PEG)-O—;
- Q-C(=O)-(PEG)-N($R^5$)—; and
- Q-C(=O)-(PEG)-N($R^5$)C(=O)—.

An exemplary embodiment of the thienoazepine-linker compound of Formula II is selected from Formulae IIa-IIc:

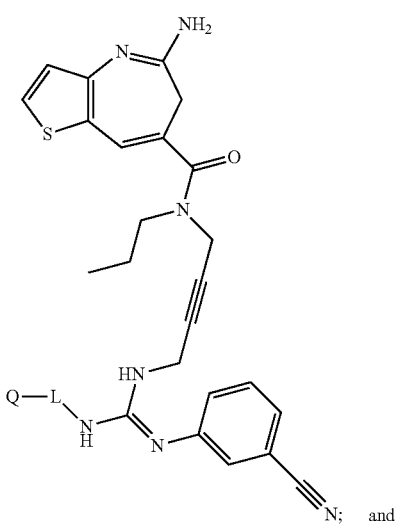

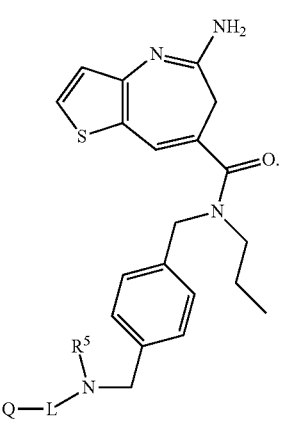

An exemplary embodiment of the thienoazepine-linker compound of Formula II is selected from Formulae IId-IIh:

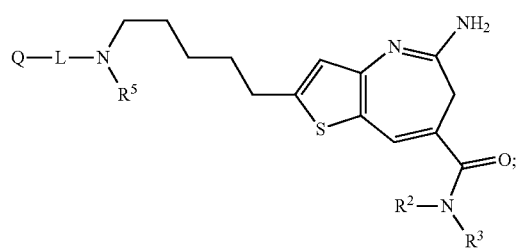 IId

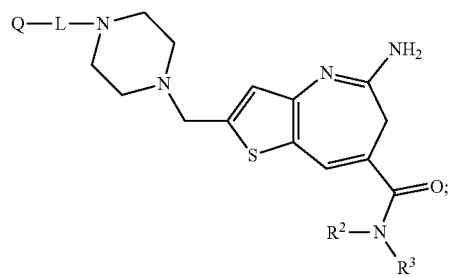 IIe

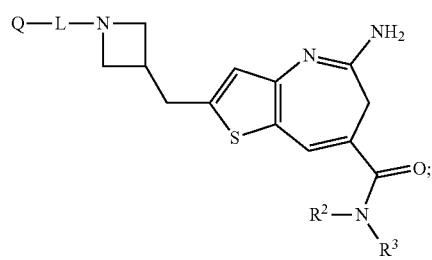 IIf

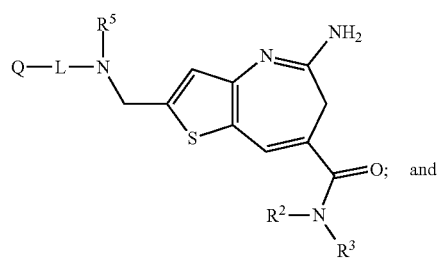 IIg

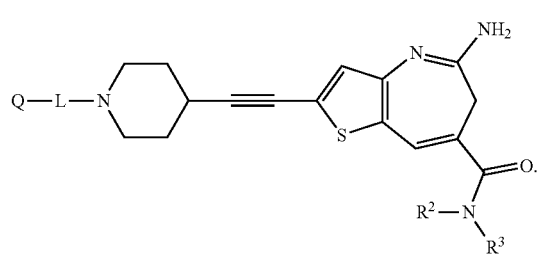 IIh

An exemplary embodiment of the thienoazepine-linker compound of Formula II includes wherein Q is selected from:

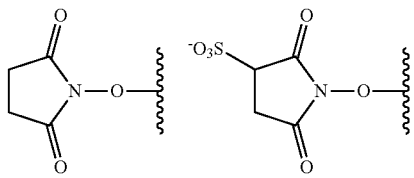

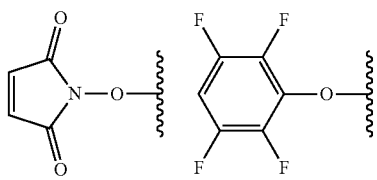

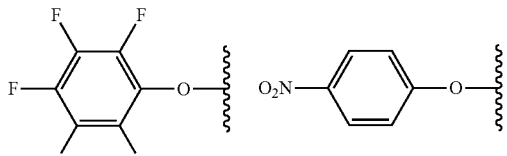

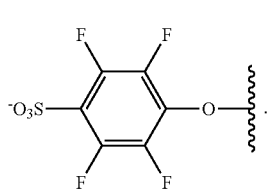

An exemplary embodiment of the thienoazepine-linker compound of Formula II includes wherein Q is phenoxy substituted with one or more F.

An exemplary embodiment of the thienoazepine-linker compound of Formula II includes wherein Q is 2,3,5,6-tetrafluorophenoxy.

An exemplary embodiment of the thienoazepine-linker (TAZ-L) compound is selected from Tables 2a-c. Each compound was synthesized, purified, and characterized by mass spectrometry and shown to have the mass indicated. Additional experimental procedures are found in the Examples. The thienoazepine-linker compounds of Tables 2a-c demonstrate the surprising and unexpected property of TLR8 agonist selectivity which may predict useful therapeutic activity to treat cancer and other disorders. The thienoazepine-linker compounds of Tables 2a-c are used in conjugation with antibodies by the methods of Example 201 to form the Immunoconjugates of Tables 3a-c.

Table 2a
Thienoazepine-linker (TAZ-L) Formula II compounds
| TAZ-L No. | Structure | MW |
|---|---|---|
| TAZ-L-1 | 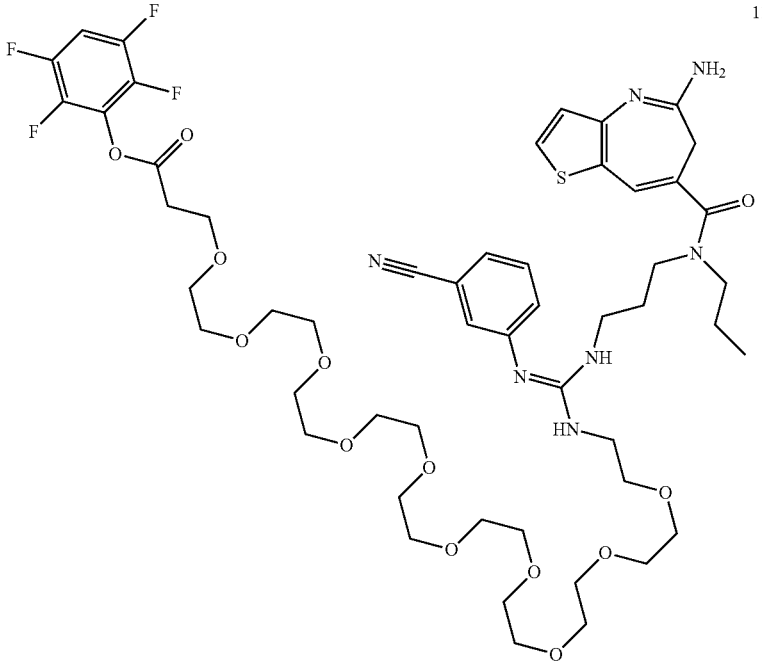 [SMILES: CCCN(CCCN/C(=N\c1cccc(C#N)c1)NCCOCCOCCOCCOCCOCCOCCOCCOCCOCCOCCC(=O)Oc1c(F)c(F)cc(F)c1F)C(=O)C1=Cc2sccc2N=C(N)C1] | 1110.2 |
| TAZ-L-2 | 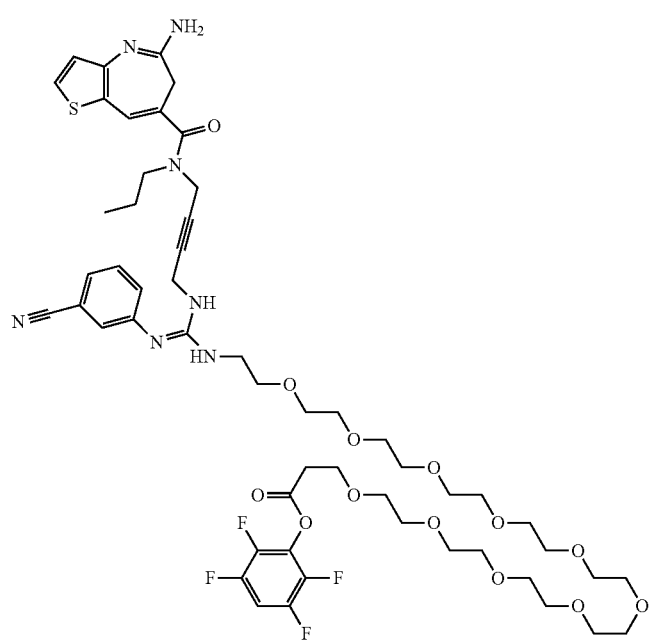 [SMILES: CCCN(CC#CCN/C(=N\c1cccc(C#N)c1)NCCOCCOCCOCCOCCOCCOCCOCCOCCOCCOCCC(=O)Oc1c(F)c(F)cc(F)c1F)C(=O)C1=Cc2sccc2N=C(N)C1] | 1120.2 |

Table 2a-continued
Thienoazepine-linker (TAZ-L) Formula II compounds
| TAZ-L No. | Structure | MW |
|---|---|---|
| TAZ-L-3 | 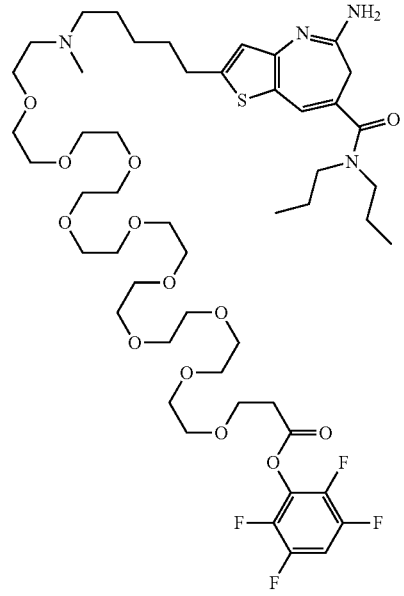 [SMILES: CCCN(CCC)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1051.2 |
| TAZ-L-4 | 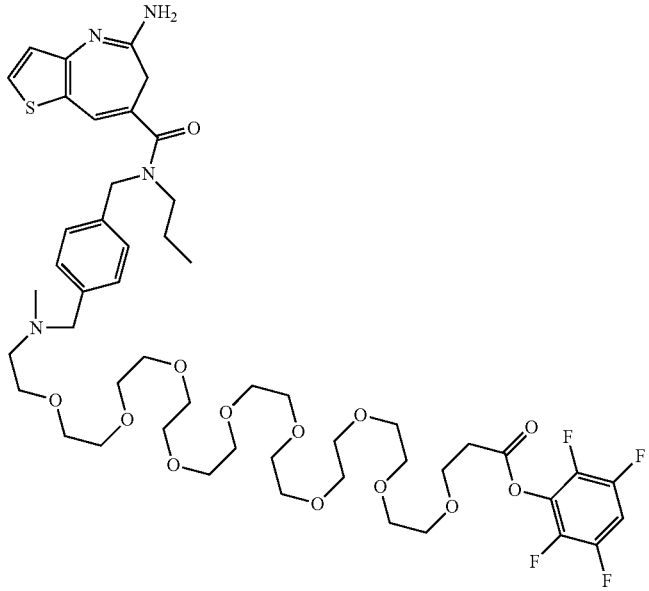 [SMILES: CCCN(Cc1ccc(CN(C)CCOCCOCCOCCOCCOCCOCCOCCOCCOCCOCCC(=O)Oc2c(F)c(F)cc(F)c2F)cc1)C(=O)C1=Cc2sccc2N=C(N)C1] | 1043.2 |

TABLE 2B
Thienoazepine-linker (TAZ-L) Formula II compounds
| TAZ-L No. | Structure | MW |
|---|---|---|
| TAZ-L-5 | 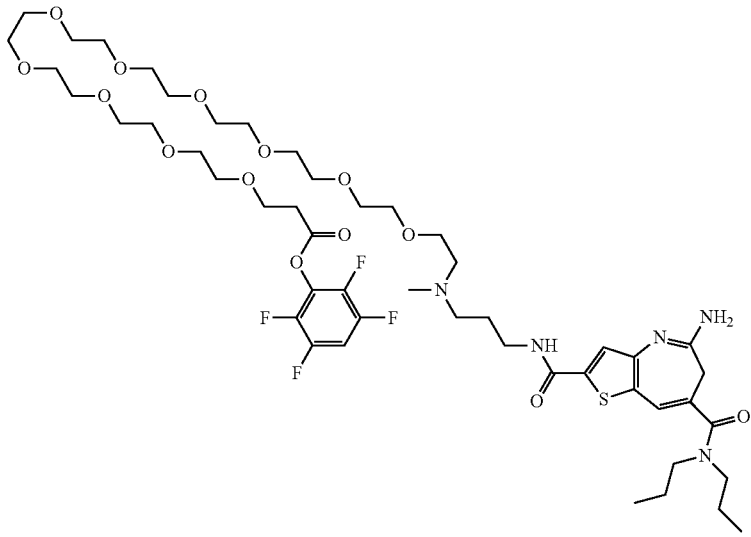 [SMILES: CCCN(CCC)C(=O)C1=Cc2sc(C(=O)NCCCN(C)CCOCCOCCOCCOCCOCCOCCOCCOCCOCCOCCC(=O)Oc3c(F)c(F)cc(F)c3F)cc2N=C(N)C1] | 1066.2 |
| TAZ-L-6 | 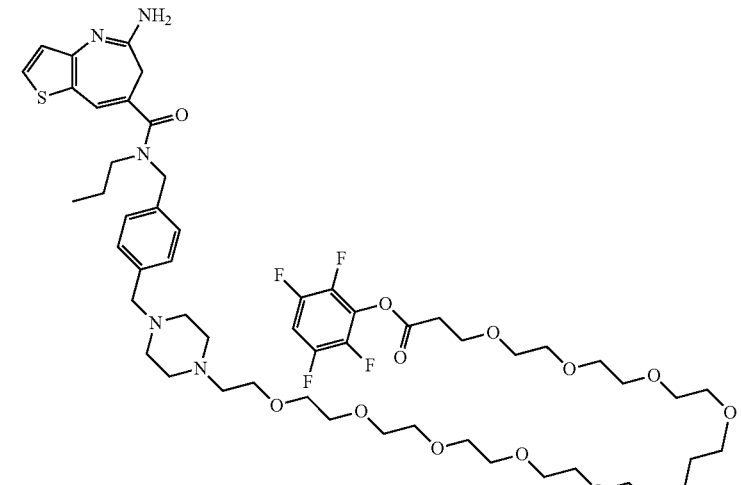 | 1098.3 |

TABLE 2B-continued

Thienoazepine-linker (TAZ-L) Formula II compounds

| TAZ-L No. | Structure | MW |
|---|---|---|
| TAZ-L-7 | 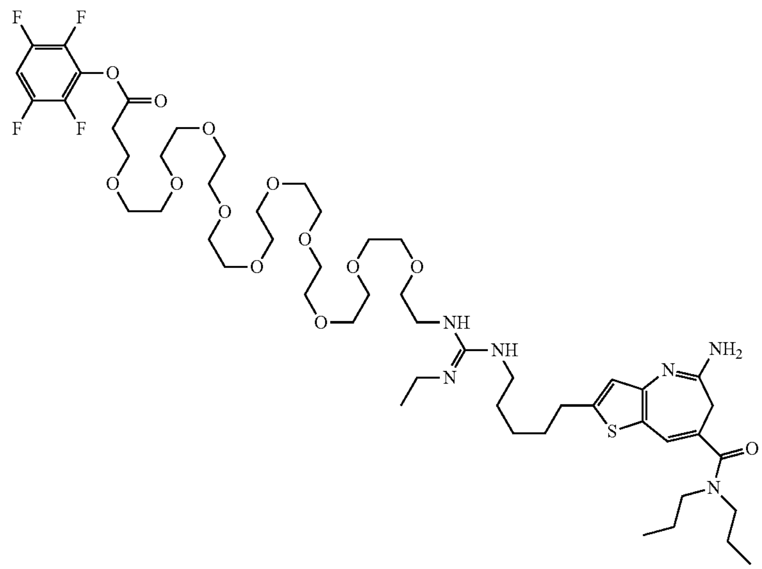 [SMILES: CCCN(CCC)C(=O)C1=Cc2sc(CCCCCN/C(=N/CC)NCCOCCOCCOCCOCCOCCOCCOCCOCCOCCOCCC(=O)Oc3c(F)c(F)cc(F)c3F)cc2N=C(N)C1] | 1107.3 |
| TAZ-L-8 | 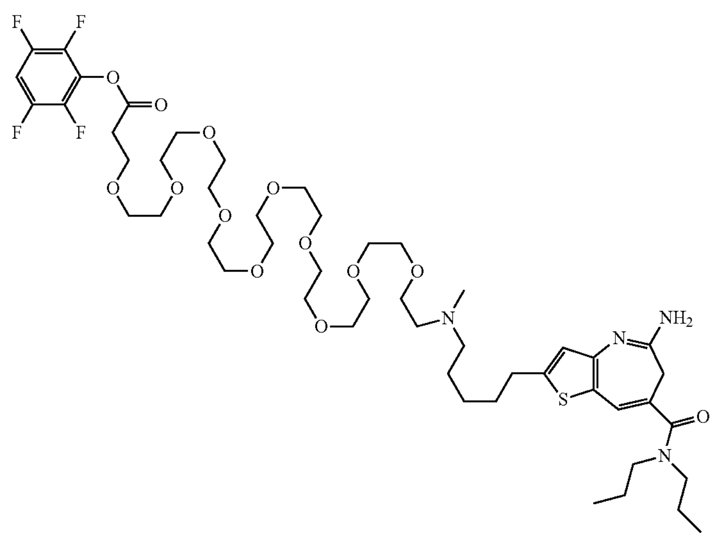 [SMILES: CCCN(CCC)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1037.2 |
| TAZ-L-9 | 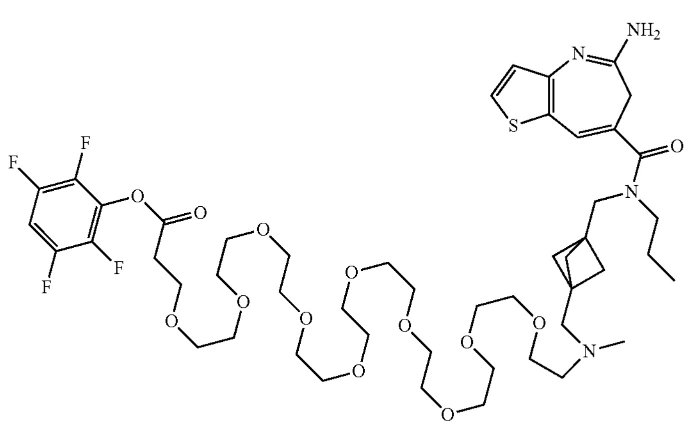 [SMILES: CCCN(CC12CC(CN(C)CCOCCOCCOCCOCCOCCOCCOCCOCCOCCOCCC(=O)Oc3c(F)c(F)cc(F)c3F)(C1)C2)C(=O)C1=Cc2sccc2N=C(N)C1] | 1033.2 |

TABLE 2B-continued

| Thienoazepine-linker (TAZ-L) Formula II compounds | | |
|---|---|---|
| TAZ-L No. | Structure | MW |
| TAZ-L-10 | | 1156.4 |
| TAZ-L-11 | | 1050.2 |
| TAZ-L-12 | | 1102.3 |

TABLE 2B-continued
Thienoazepine-linker (TAZ-L) Formula II compounds
| TAZ-L No. | Structure | MW |
|---|---|---|
| TAZ-L-13 | 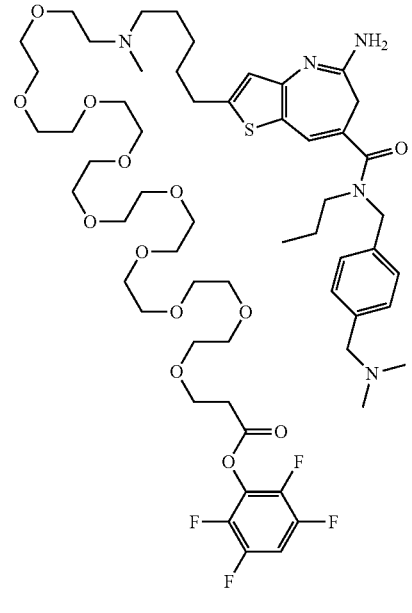 [SMILES: CCCN(Cc1ccc(CN(C)C)cc1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1156.4 |
| TAZ-L-14 | 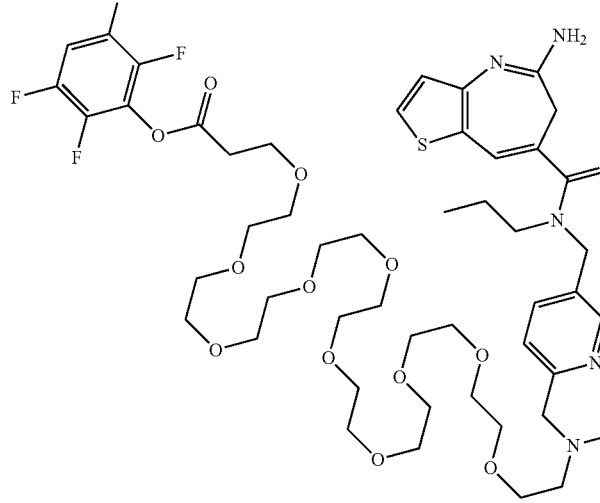 | 1044.2 |

TABLE 2B-continued

Thienoazepine-linker (TAZ-L) Formula II compounds

| TAZ-L No. | Structure | MW |
|---|---|---|
| TAZ-L -15 | 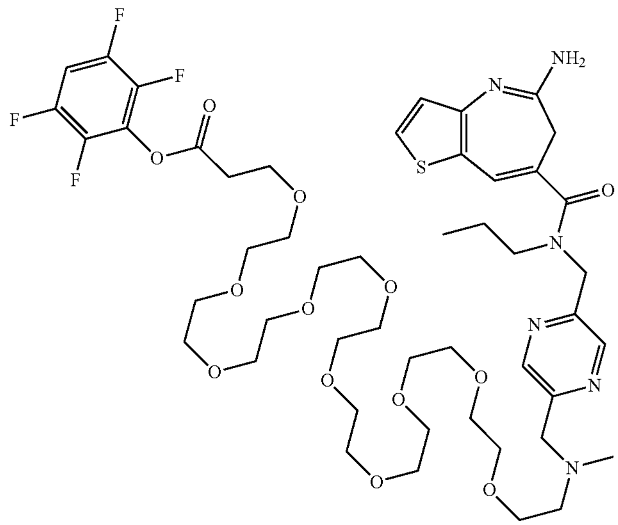 [SMILES: CCCN(Cc1cnc(CN(C)CCOCCOCCOCCOCCOCCOCCOCCOCCOCCOCCC(=O)Oc2c(F)c(F)cc(F)c2F)cn1)C(=O)C1=Cc2sccc2N=C(N)C1] | 1045.1 |
| TAZ-L -16 | 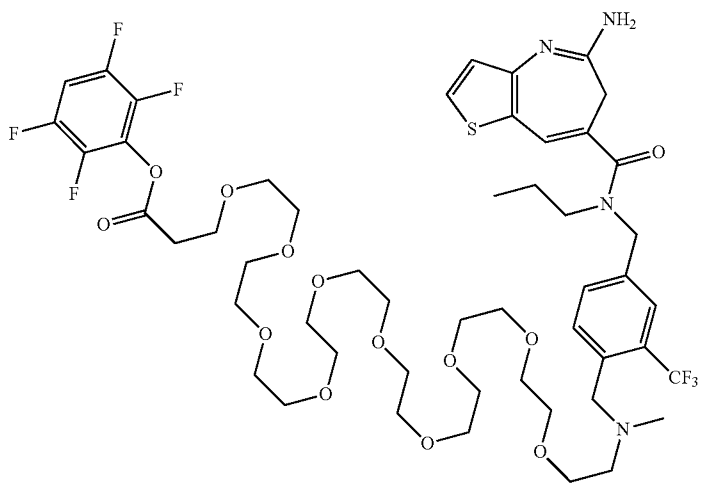 [SMILES: CCCN(Cc1ccc(CN(C)CCOCCOCCOCCOCCOCCOCCOCCOCCOCCOCCC(=O)Oc2c(F)c(F)cc(F)c2F)c(C(F)(F)F)c1)C(=O)C1=Cc2sccc2N=C(N)C1] | 1111.2 |

TABLE 2B-continued
Thienoazepine-linker (TAZ-L) Formula II compounds
| TAZ-L No. | Structure | MW |
|---|---|---|
| TAZ-L-17 | 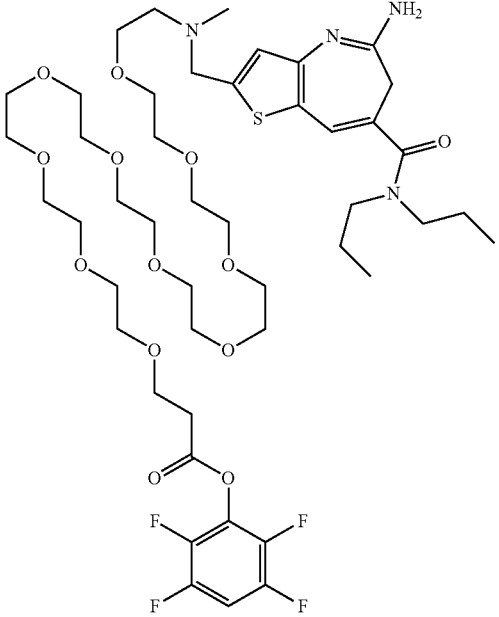 [SMILES: CCCN(CCC)C(=O)C1=Cc2sc(CN(C)CCOCCOCCOCCOCCOCCOCCOCCOCCOCCOCCC(=O)Oc3c(F)c(F)cc(F)c3F)cc2N=C(N)C1] | 995.13 |
| TAZ-L-18 | 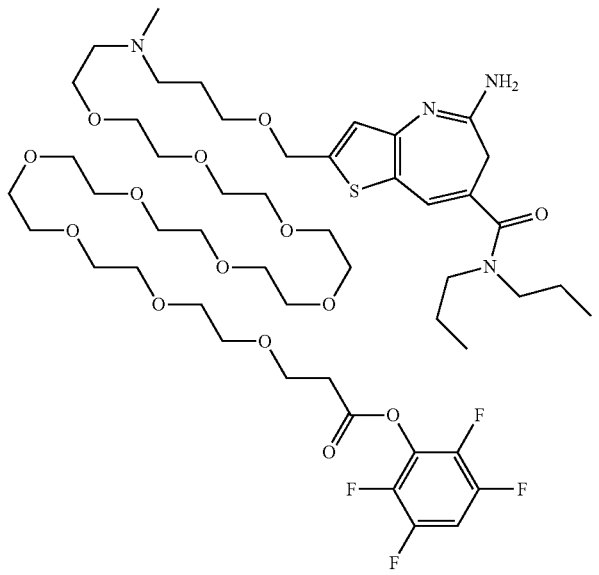 [SMILES: CCCN(CCC)C(=O)C1=Cc2sc(COCCCN(C)CCOCCOCCOCCOCCOCCOCCOCCOCCOCCOCCC(=O)Oc3c(F)c(F)cc(F)c3F)cc2N=C(N)C1] | 1053.2 |

TABLE 2B-continued

Thienoazepine-linker (TAZ-L) Formula II compounds

| TAZ-L No. | Structure | MW |
| --- | --- | --- |
| TAZ-L-19 | 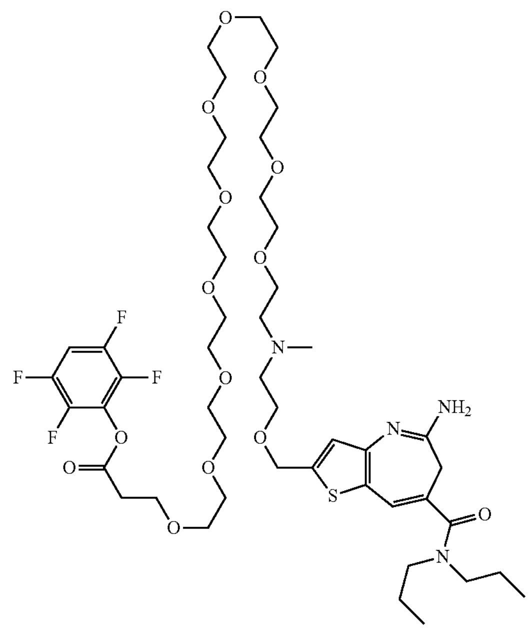 [SMILES: CCCN(CCC)C(=O)C1=Cc2sc(COCCN(C)CCOCCOCCOCCOCCOCCOCCOCCOCCOCCOCCC(=O)Oc3c(F)c(F)cc(F)c3F)cc2N=C(N)C1] | 1039.2 |
| TAZ-L-20 | 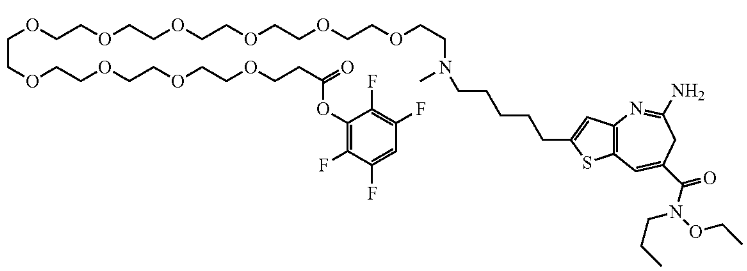 [SMILES: CCCN(OCC)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1053.2 |
| TAZ-L-21 | 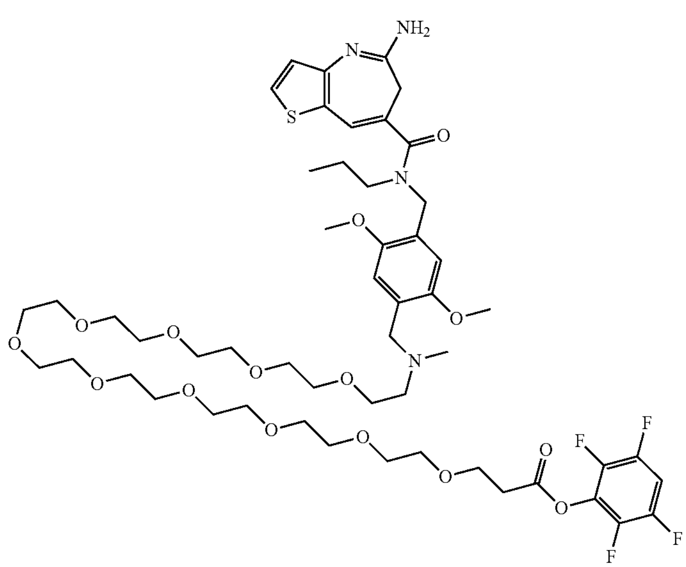 [SMILES: CCCN(Cc1cc(OC)c(CN(C)CCOCCOCCOCCOCCOCCOCCOCCOCCOCCOCCC(=O)Oc2c(F)c(F)cc(F)c2F)cc1OC)C(=O)C1=Cc2sccc2N=C(N)C1] | 1103.2 |

TABLE 2B-continued

Thienoazepine-linker (TAZ-L) Formula II compounds

| TAZ-L No. | Structure | MW |
|---|---|---|
| TAZ-L-22 | 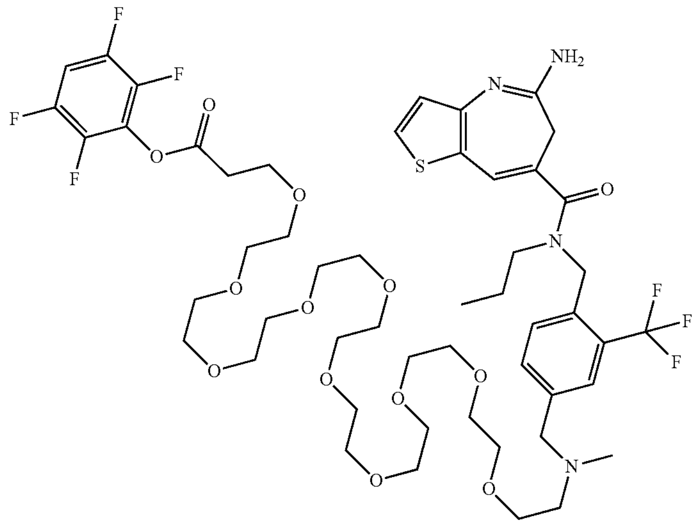 [SMILES: CCCN(Cc1ccc(CN(C)CCOCCOCCOCCOCCOCCOCCOCCOCCOCCOCCC(=O)Oc2c(F)c(F)cc(F)c2F)cc1C(F)(F)F)C(=O)C1=Cc2sccc2N=C(N)C1] | 1111.2 |
| TAZ-L-23 | 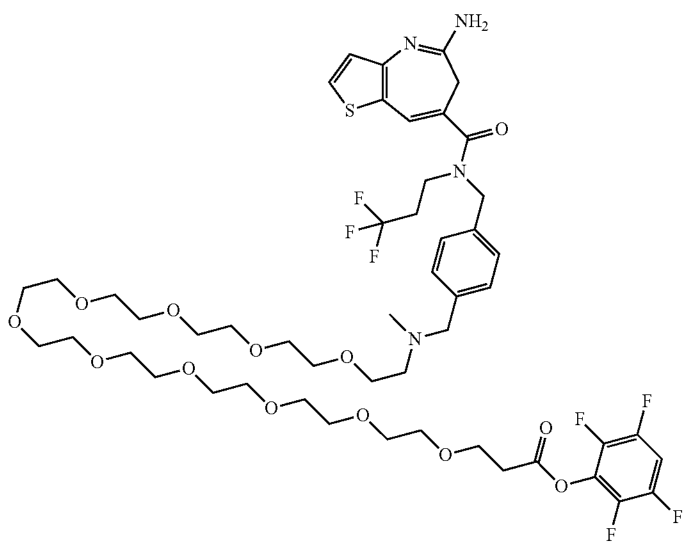 [SMILES: CN(CCOCCOCCOCCOCCOCCOCCOCCOCCOCCOCCC(=O)Oc1c(F)c(F)cc(F)c1F)Cc1ccc(CN(CCC(F)(F)F)C(=O)C2=Cc3sccc3N=C(N)C2)cc1] | 1097.1 |
| TAZ-L-24 | 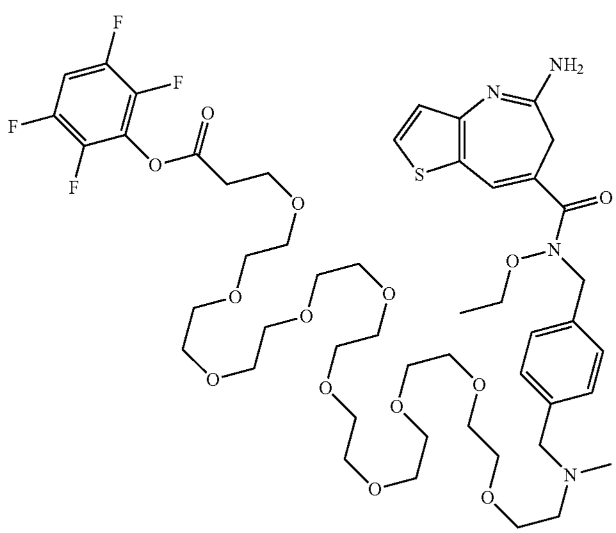 [SMILES: CCON(Cc1ccc(CN(C)CCOCCOCCOCCOCCOCCOCCOCCOCCOCCOCCC(=O)Oc2c(F)c(F)cc(F)c2F)cc1)C(=O)C1=Cc2sccc2N=C(N)C1] | 1045.1 |

TABLE 2B-continued
Thienoazepine-linker (TAZ-L) Formula II compounds
| TAZ-L No. | Structure | MW |
|---|---|---|
| TAZ-L-25 | 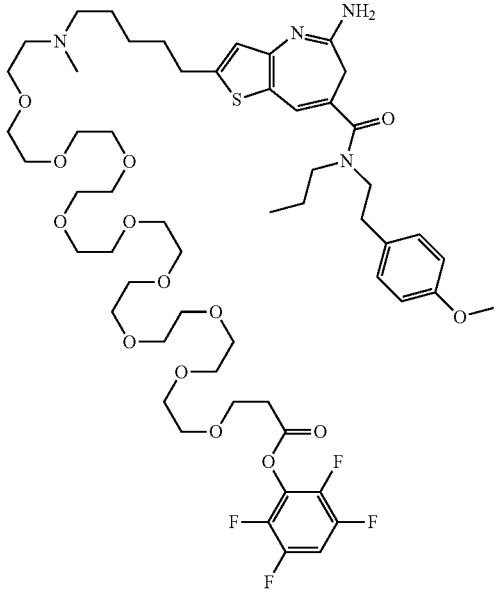 [SMILES: CCCN(CCc1ccc(OC)cc1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1143.3 |
| TAZ-L-26 | 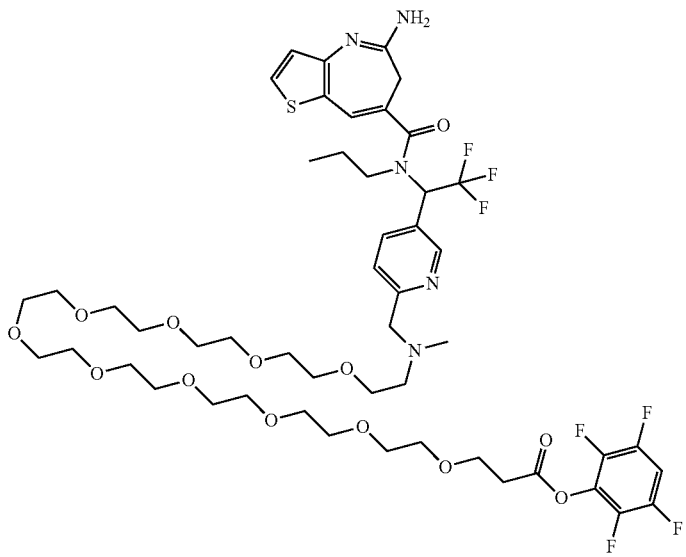 [SMILES: CCCN(C(=O)C1=Cc2sccc2N=C(N)C1)C(c1ccc(CN(C)CCOCCOCCOCCOCCOCCOCCOCCOCCOCCOCCC(=O)Oc2c(F)c(F)cc(F)c2F)nc1)C(F)(F)F] | 1112.2 |

TABLE 2B-continued

Thienoazepine-linker (TAZ-L) Formula II compounds

| TAZ-L No. | Structure | MW |
|---|---|---|
| TAZ-L-27 | 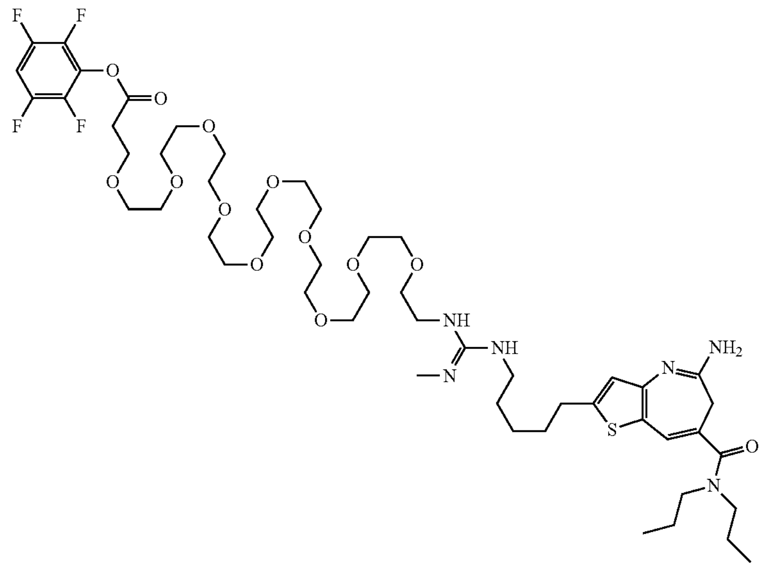 [SMILES: CCCN(CCC)C(=O)C1=Cc2sc(CCCCCN/C(=N/C)NCCOCCOCCOCCOCCOCCOCCOCCOCCOCCOCCC(=O)Oc3c(F)c(F)cc(F)c3F)cc2N=C(N)C1] | 1093.3 |
| TAZ-L-28 | 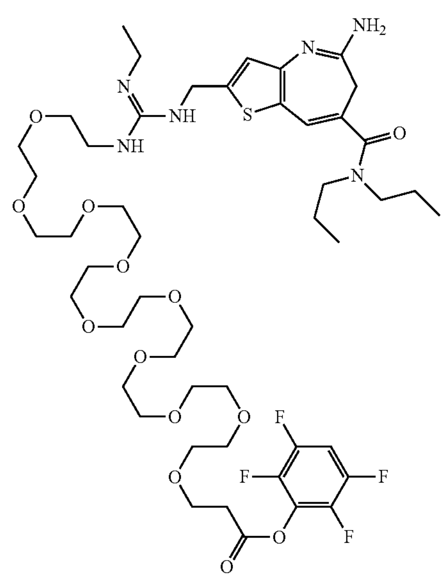 [SMILES: CCCN(CCC)C(=O)C1=Cc2sc(CN/C(=N\CC)NCCOCCOCCOCCOCCOCCOCCOCCOCCOCCOCCC(=O)Oc3c(F)c(F)cc(F)c3F)cc2N=C(N)C1] | 1051.2 |

TABLE 2B-continued

Thienoazepine-linker (TAZ-L) Formula II compounds

| TAZ-L No. | Structure | MW |
| --- | --- | --- |
| TAZ-L-29 | 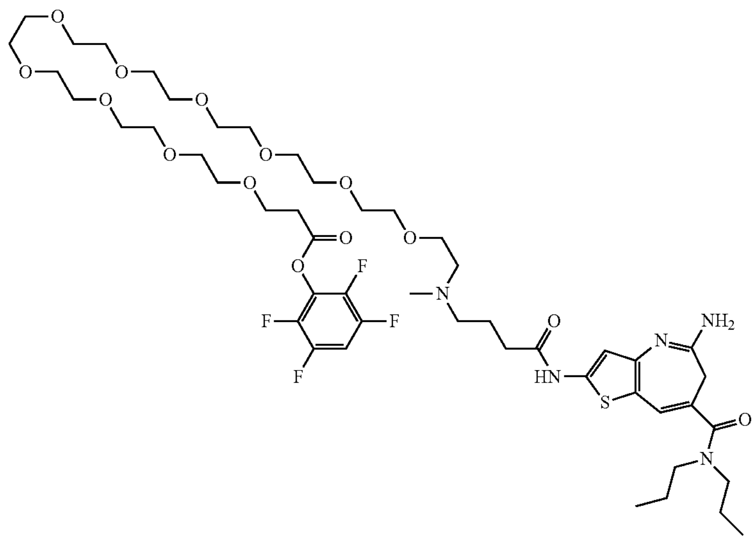 [SMILES: CCCN(CCC)C(=O)C1=Cc2sc(NC(=O)CCCN(C)CCOCCOCCOCCOCCOCCOCCOCCOCCOCCOCCC(=O)Oc3c(F)c(F)cc(F)c3F)cc2N=C(N)C1] | 1066.2 |
| TAZ-L-30 | 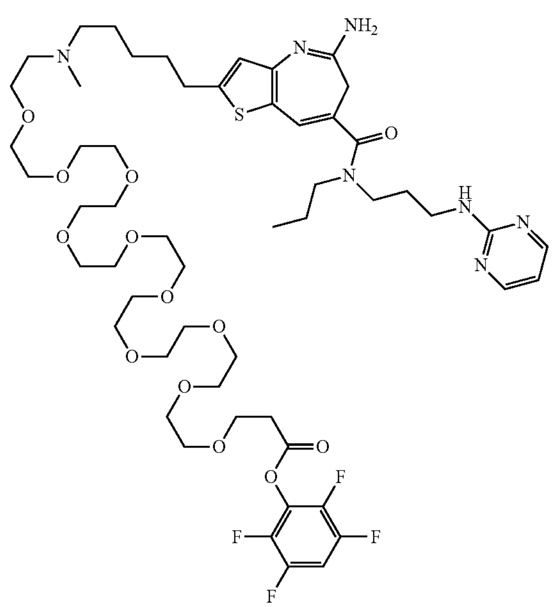 [SMILES: CCCN(CCCNc1ncccn1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1144.3 |
| TAZ-L-31 | 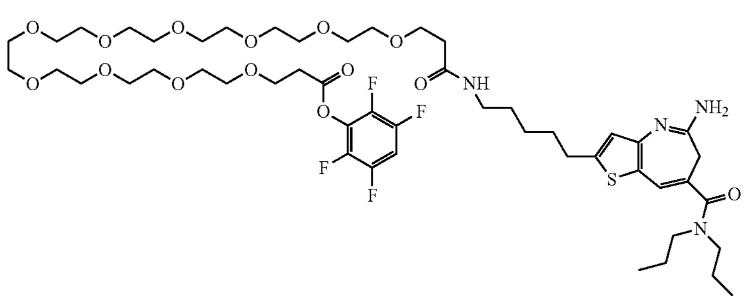 [SMILES: CCCN(CCC)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1065.2 |

TABLE 2B-continued
Thienoazepine-linker (TAZ-L) Formula II compounds
| TAZ-L No. | Structure | MW |
|---|---|---|
| TAZ-L-32 | 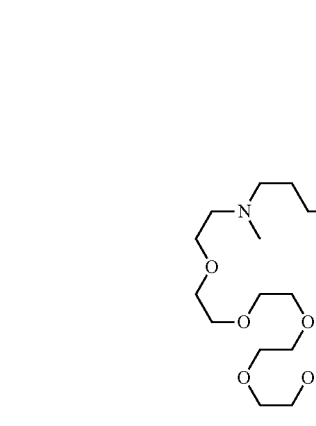 | 1178.4 |
| TAZ-L-33 | 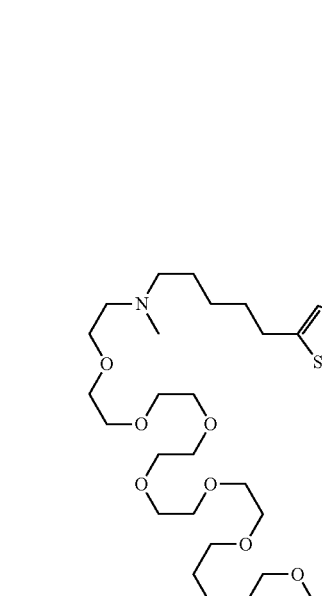 | 1131.3 |
| TAZ-L-34 | 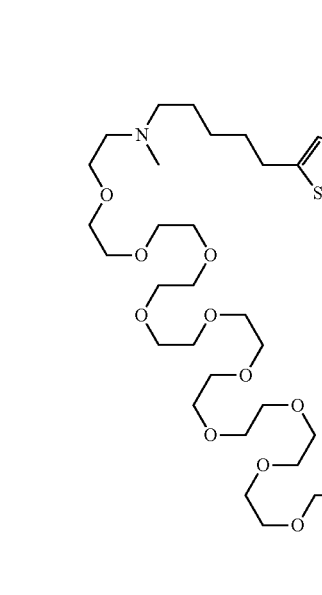 | 1164.4 |

TABLE 2B-continued
Thienoazepine-linker (TAZ-L) Formula II compounds
| TAZ-L No. | Structure | MW |
|---|---|---|
| TAZ-L-35 | 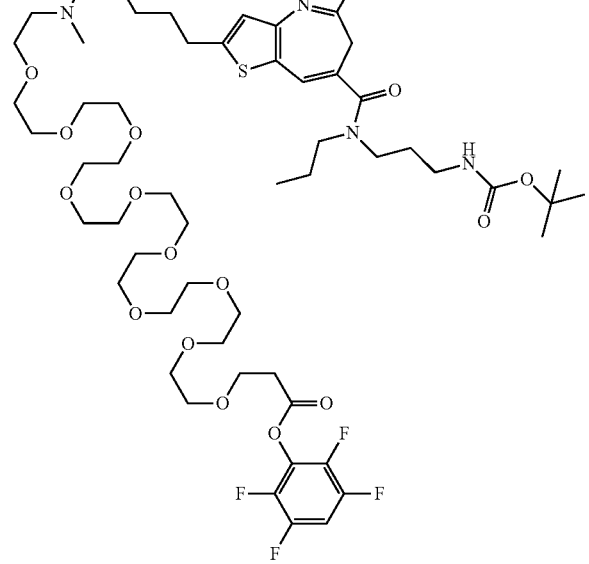 | 1166.4 |
| TAZ-L-36 | 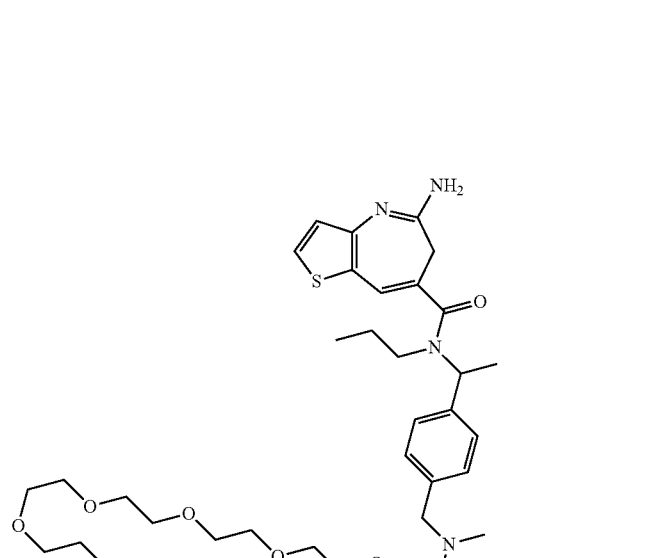 | 1057.2 |

TABLE 2B-continued
Thienoazepine-linker (TAZ-L) Formula II compounds
| TAZ-L No. | Structure | MW |
|---|---|---|
| TAZ-L-37 | 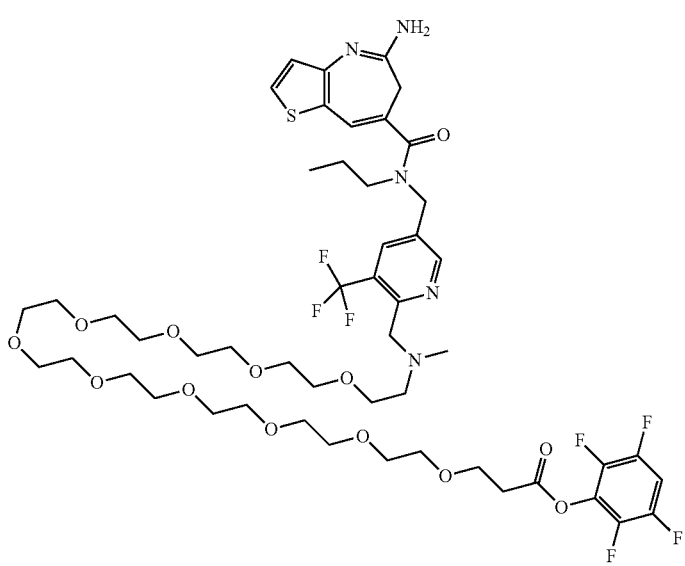 [SMILES: CCCN(Cc1cnc(CN(C)CCOCCOCCOCCOCCOCCOCCOCCOCCOCCOCCC(=O)Oc2c(F)c(F)cc(F)c2F)c(C(F)(F)F)c1)C(=O)C1=Cc2sccc2N=C(N)C1] | 1112.2 |
TABLE 2C
Thienoazepine-linker (TAZ-L) Formula II compounds
| TAZ-L No. | Structure | MW |
|---|---|---|
| TAZ-L-38 | 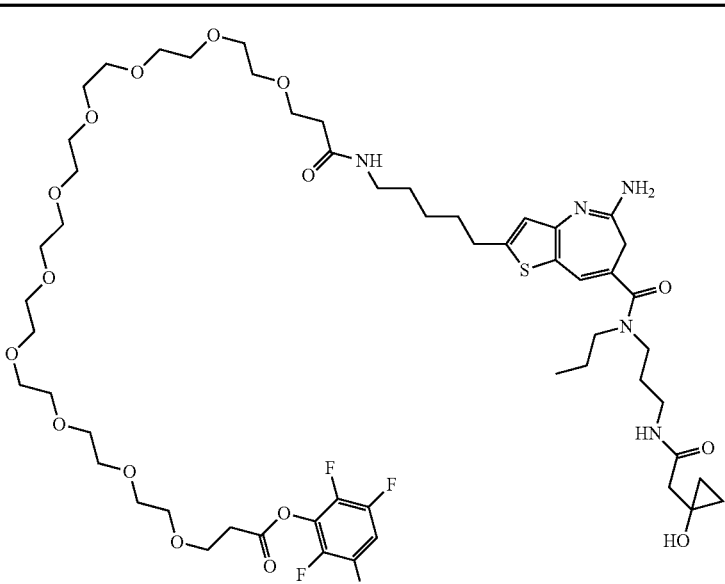 | 1178.3 |

TABLE 2C-continued
Thienoazepine-linker (TAZ-L) Formula II compounds
| TAZ-L No. | Structure | MW |
|---|---|---|
| TAZ-L-39 | 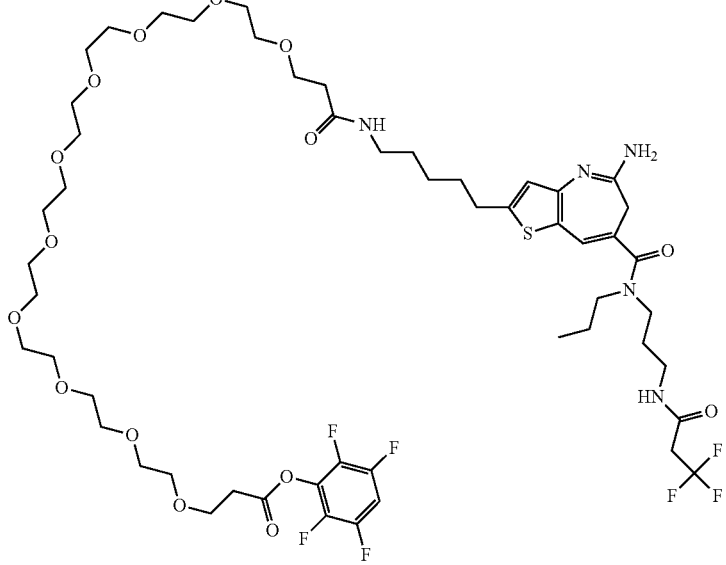 | 1190.3 |
| TAZ-L-40 | 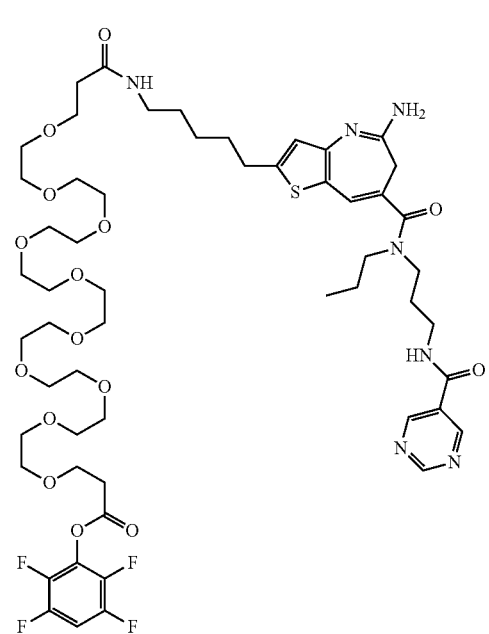 [SMILES: CCCN(CCCNC(=O)c1cncnc1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1186.3 |

TABLE 2C-continued

Thienoazepine-linker (TAZ-L) Formula II compounds

| TAZ-L No. | Structure | MW |
|---|---|---|
| TAZ-L-41 | 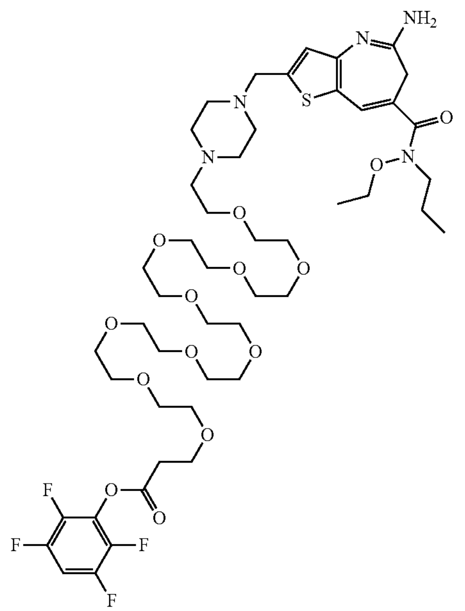 [SMILES: CCCN(OCC)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1052.2 |
| TAZ-L-42 | 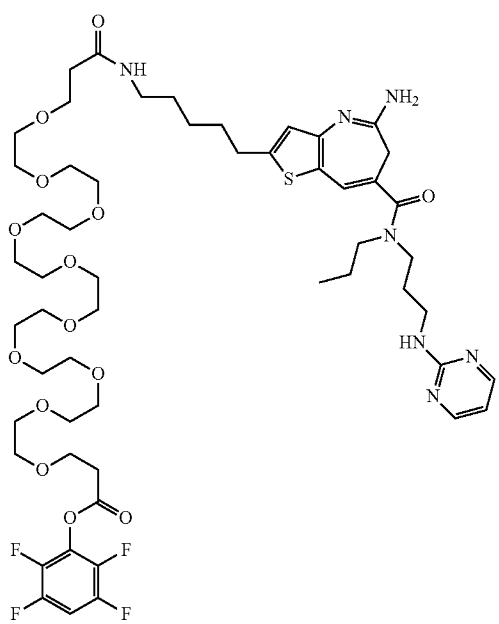 [SMILES: CCCN(CCCNc1ncccn1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1158.3 |

TABLE 2C-continued
Thienoazepine-linker (TAZ-L) Formula II compounds
| TAZ-L No. | Structure | MW |
|---|---|---|
| TAZ-L-43 | 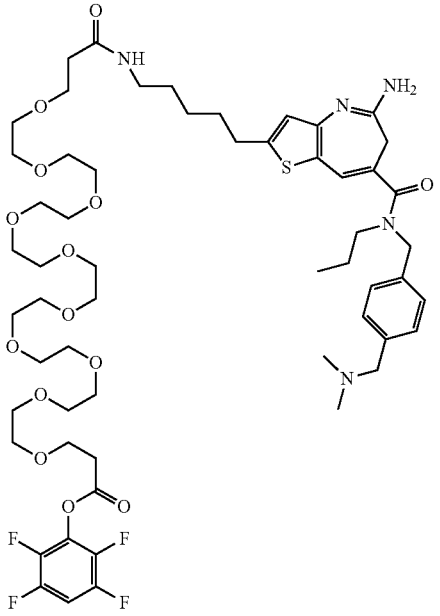 [SMILES: CCCN(Cc1ccc(CN(C)C)cc1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1170.4 |
| TAZ-L-44 | 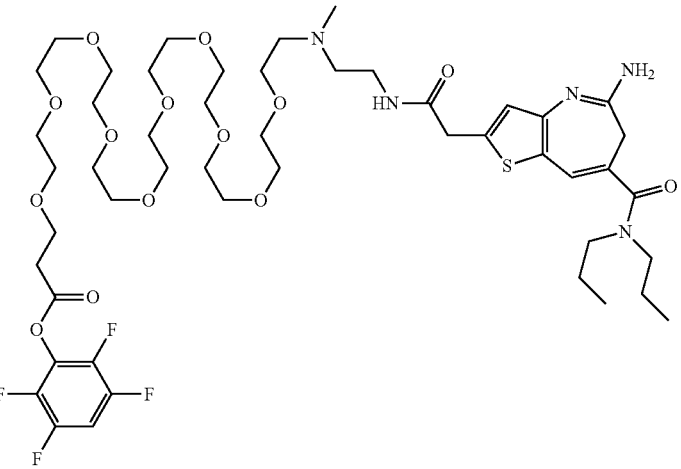 | 1066.2 |
| TAZ-L-45 | 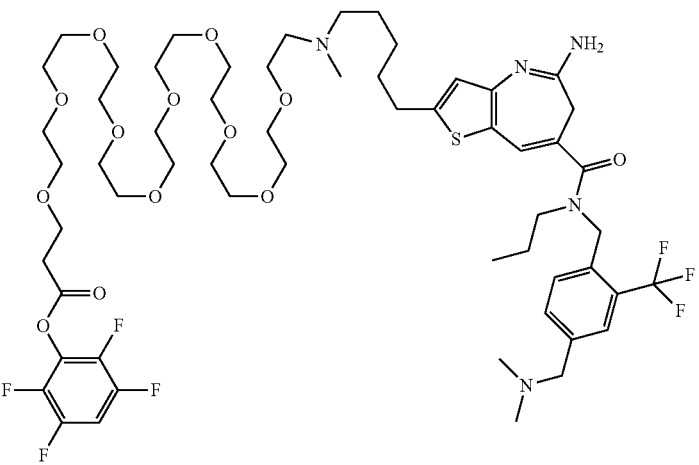 [SMILES: CCCN(Cc1ccc(CN(C)C)cc1C(F)(F)F)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1224.4 |

TABLE 2C-continued

Thienoazepine-linker (TAZ-L) Formula II compounds

| TAZ-L No. | Structure | MW |
|---|---|---|
| TAZ-L-46 | 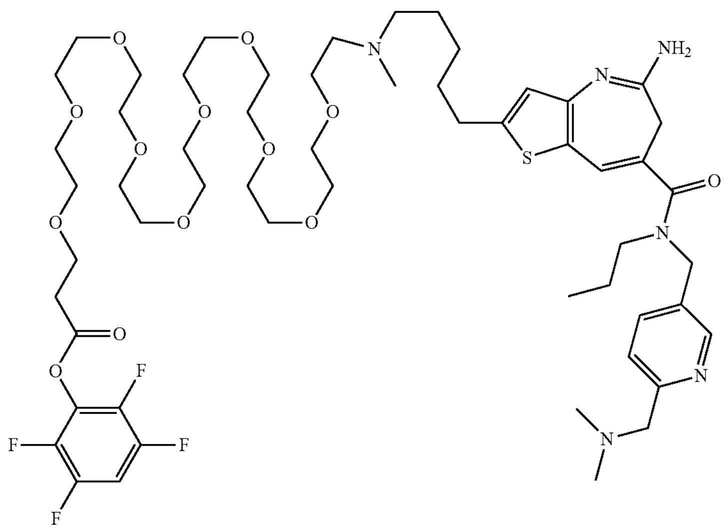 [SMILES: CCCN(Cc1ccc(CN(C)C)nc1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1157.4 |
| TAZ-L-47 | 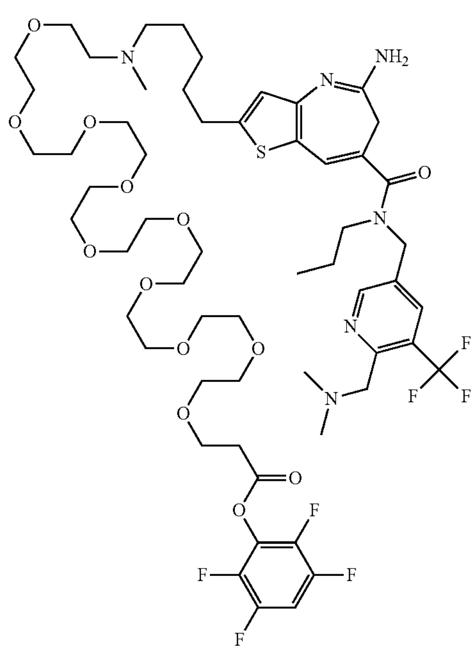 [SMILES: CCCN(Cc1cnc(CN(C)C)c(C(F)(F)F)c1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1225.4 |

TABLE 2C-continued

Thienoazepine-linker (TAZ-L) Formula II compounds

| TAZ-L No. | Structure | MW |
|---|---|---|
| TAZ-L-48 | 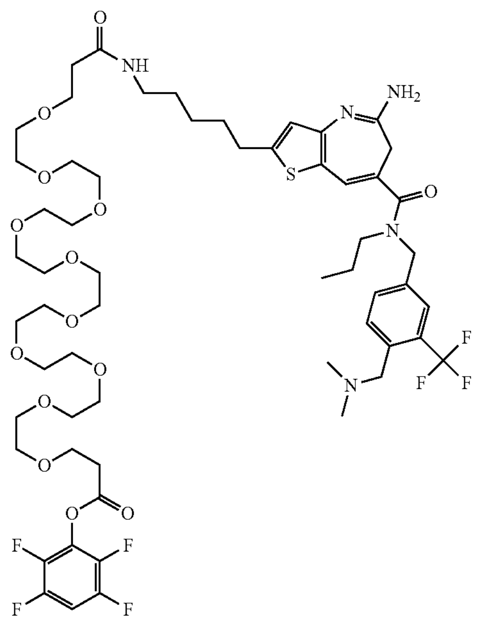 [SMILES: CCCN(Cc1ccc(CN(C)C)c(C(F)(F)F)c1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1238.4 |
| TAZ-L-49 | 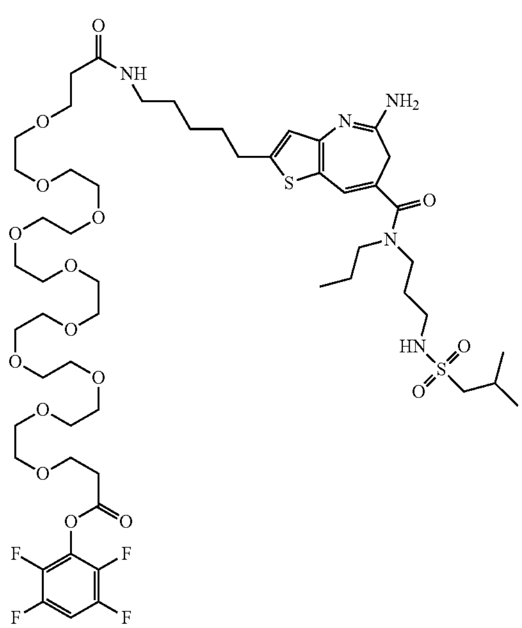 [SMILES: CCCN(CCCNS(=O)(=O)CC(C)C)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1200.4 |

TABLE 2C-continued
Thienoazepine-linker (TAZ-L) Formula II compounds
| TAZ-L No. | Structure | MW |
|---|---|---|
| TAZ-L-50 | 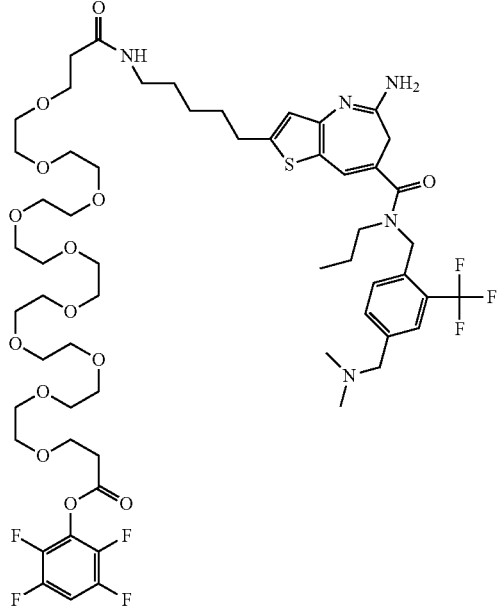 [SMILES: CCCN(Cc1ccc(CN(C)C)cc1C(F)(F)F)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1238.4 |
| TAZ-L-51 | 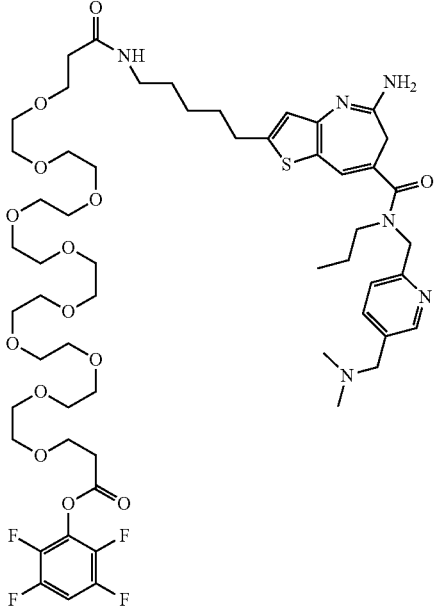 [SMILES: CCCN(Cc1ccc(CN(C)C)cn1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1171.3 |

TABLE 2C-continued
Thienoazepine-linker (TAZ-L) Formula II compounds
| TAZ-L No. | Structure | MW |
|---|---|---|
| TAZ-L-52 | 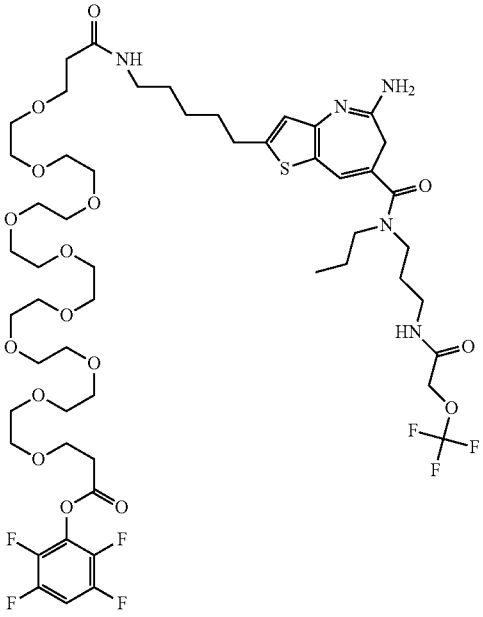 [SMILES: CCCN(CCCNC(=O)COC(F)(F)F)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1206.3 |
| TAZ-L-53 | 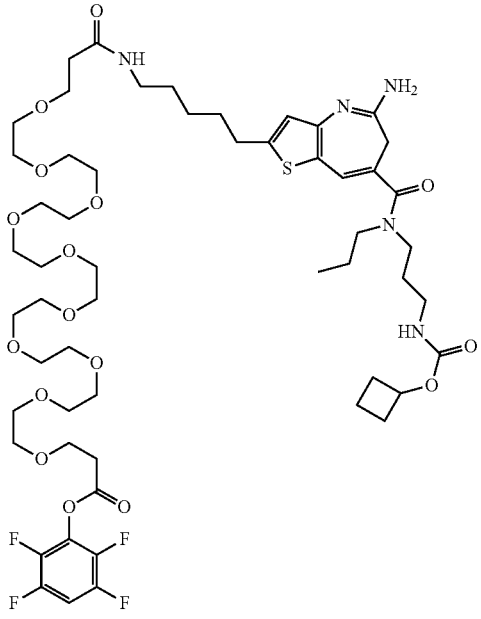 [SMILES: CCCN(CCCNC(=O)OC1CCC1)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1178.3 |

TABLE 2C-continued

Thienoazepine-linker (TAZ-L) Formula II compounds

| TAZ-L No. | Structure | MW |
|---|---|---|
| TAZ-L-54 | 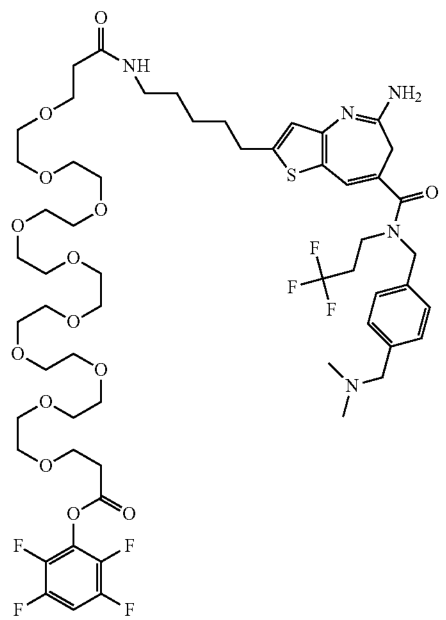 [SMILES: CN(C)Cc1ccc(CN(CCC(F)(F)F)C(=O)C2=Cc3sc(CCCCCNC(=O)CCOCCOCCOCCOCCOCCOCCOCCOCCOCCOCCC(=O)Oc4c(F)c(F)cc(F)c4F)cc3N=C(N)C2)cc1] | 1224.3 |
| TAZ-L-55 | 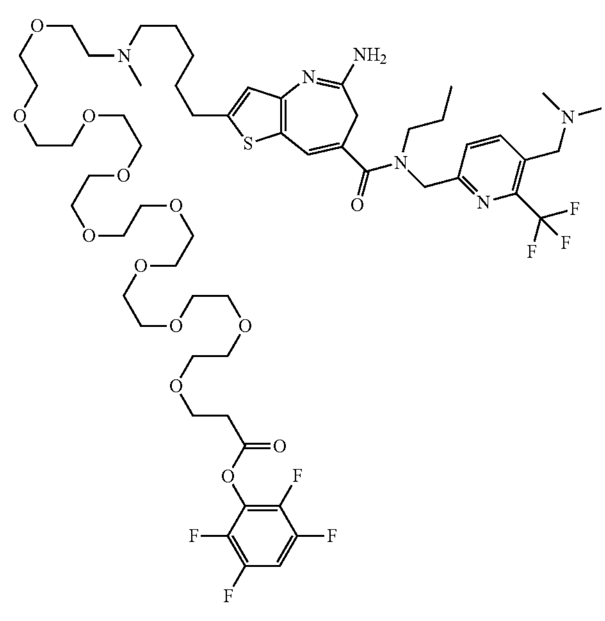 [SMILES: CCCN(Cc1ccc(CN(C)C)c(C(F)(F)F)n1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1225.4 |

TABLE 2C-continued
Thienoazepine-linker (TAZ-L) Formula II compounds
| TAZ-L No. | Structure | MW |
|---|---|---|
| TAZ-L-56 | 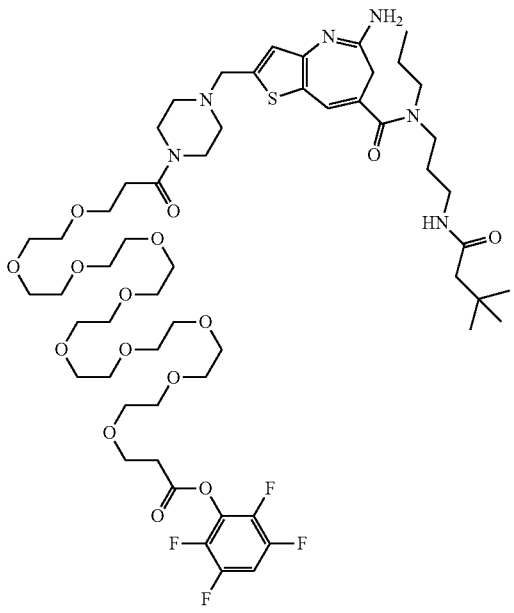 [SMILES: CCCN(CCCNC(=O)CC(C)(C)C)C(=O)C1=Cc2sc(CN3CCN(C(=O)CCOCCOCCOCCOCCOCCOCCOCCOCCOCCOCCC(=O)Oc4c(F)c(F)cc(F)c4F)CC3)cc2N=C(N)C1] | 1191.4 |
| TAZ-L-57 | 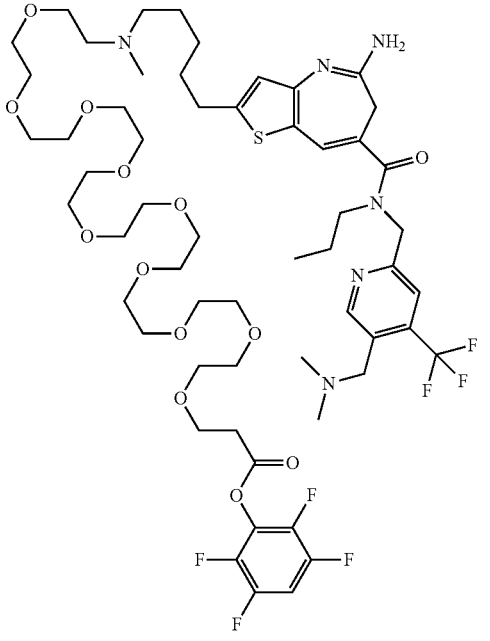 [SMILES: CCCN(Cc1cc(C(F)(F)F)c(CN(C)C)cn1)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1225.4 |

TABLE 2C-continued
Thienoazepine-linker (TAZ-L) Formula II compounds
| TAZ-L No. | Structure | MW |
|---|---|---|
| TAZ-L-58 | 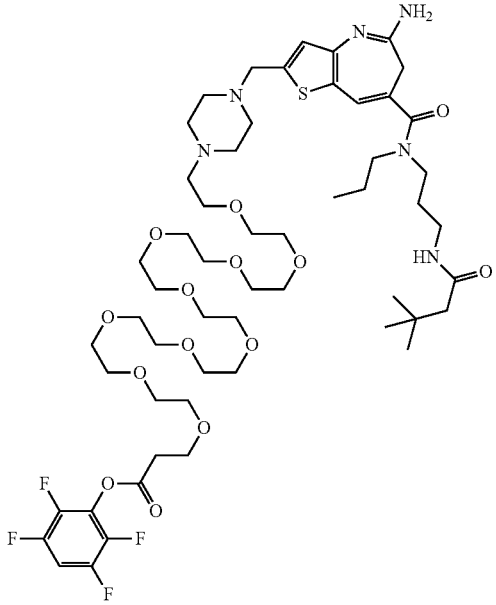 [SMILES: CCCN(CCCNC(=O)CC(C)(C)C)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1163.4 |
| TAZ-L-59 | 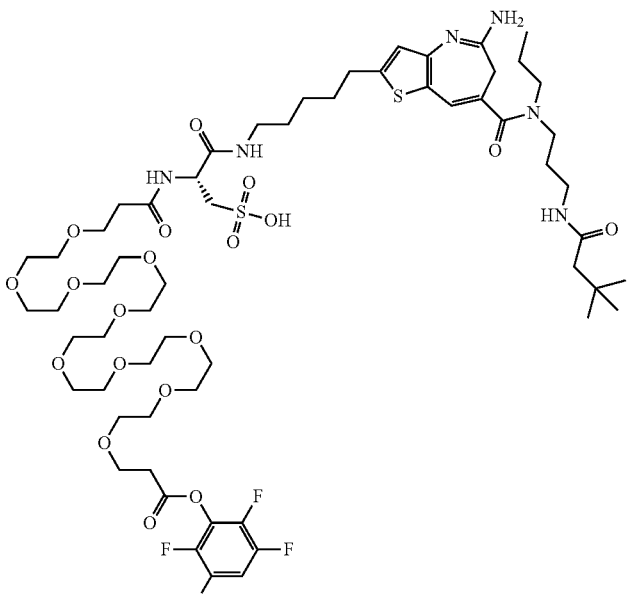 | 1329.5 |
| TAZ-L-60 | 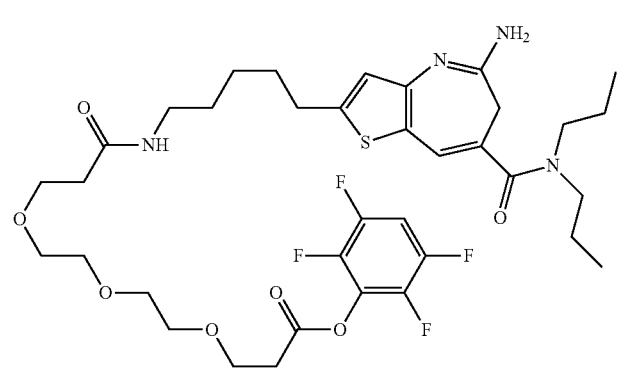 [SMILES: CCCN(CCC)C(=O)C1=Cc2sc(CCCCCNC(=O)CCOCCOCCOCCC(=O)Oc3c(F)c(F)cc(F)c3F)cc2N=C(N)C1] | 756.9 |

TABLE 2C-continued
Thienoazepine-linker (TAZ-L) Formula II compounds
| TAZ-L No. | Structure | MW |
|---|---|---|
| TAZ-L-61 | 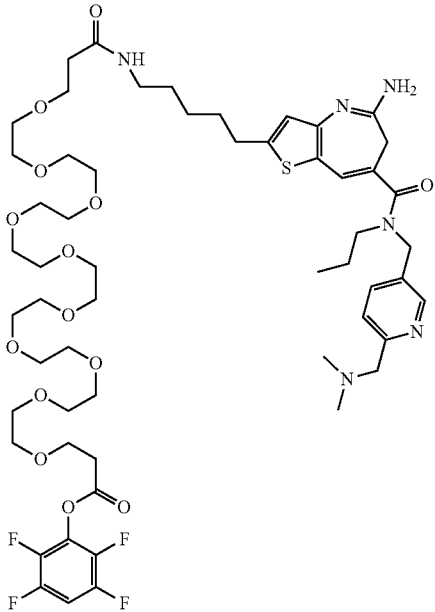 | 1171.3 |
| TAZ-L-62 | 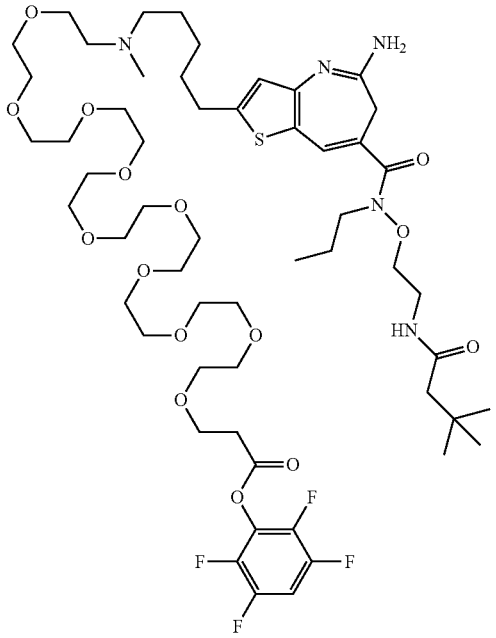 [SMILES: CCCN(OCCNC(=O)CC(C)(C)C)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 66.4 |

TABLE 2C-continued
Thienoazepine-linker (TAZ-L) Formula II compounds
| TAZ-L No. | Structure | MW |
|---|---|---|
| TAZ-L-63 | 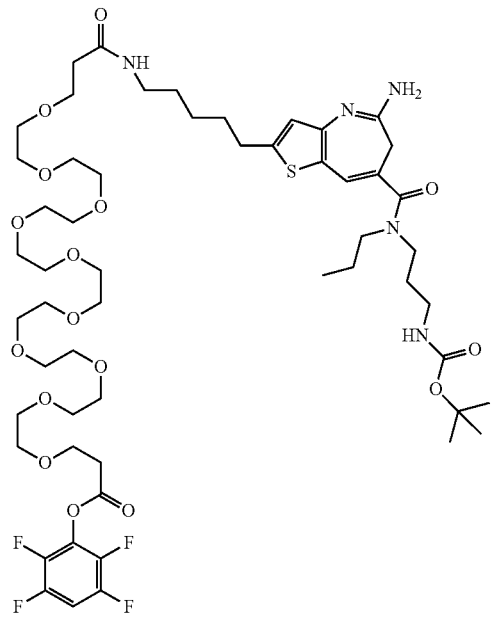 [SMILES: CCCN(CCCNC(=O)OC(C)(C)C)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1180.4 |
| TAZ-L-64 | 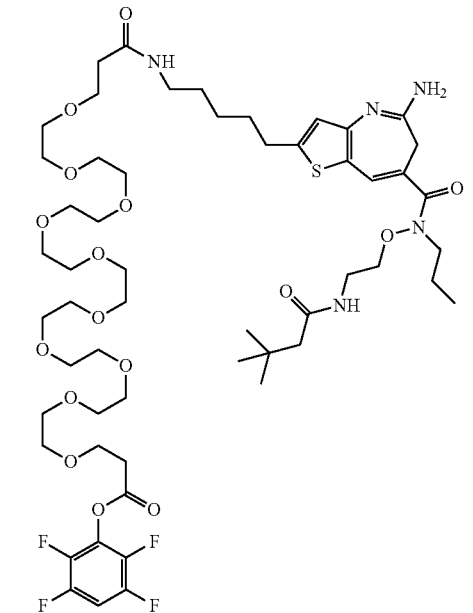 [SMILES: CCCN(OCCNC(=O)CC(C)(C)C)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1180.4 |

TABLE 2C-continued
Thienoazepine-linker (TAZ-L) Formula II compounds
| TAZ-L No. | Structure | MW |
|---|---|---|
| TAZ-L-65 | 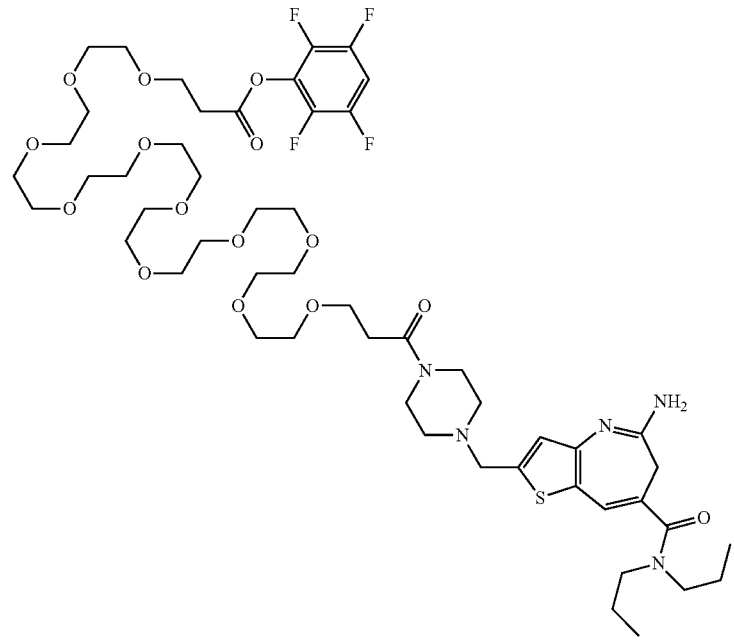 [SMILES: CCCN(CCC)C(=O)C1=Cc2sc(CN3CCN(C(=O)CCOCCOCCOCCOCCOCCOCCOCCOCCOCCOCCOCCC(=O)Oc4c(F)c(F)cc(F)c4F)CC3)cc2N=C(N)C1] | 1122.3 |
| TAZ-L-66 | 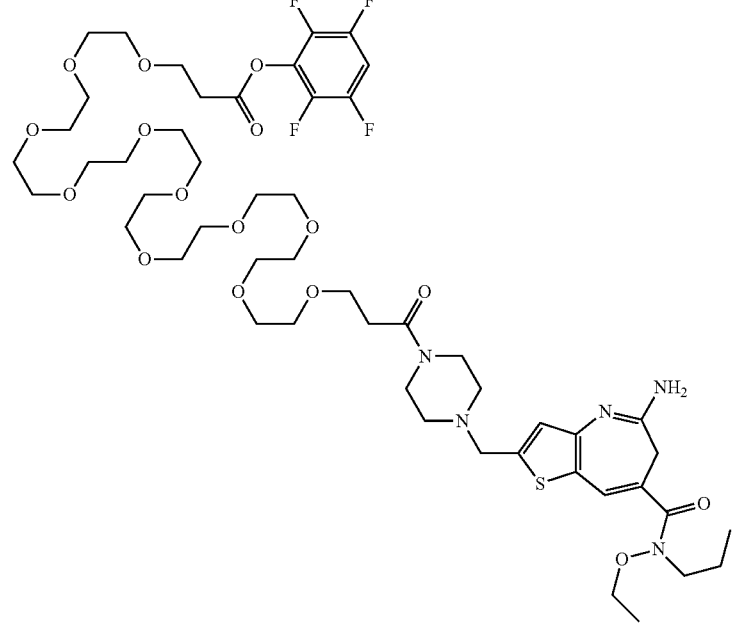 | 1124.2 |

TABLE 2C-continued

Thienoazepine-linker (TAZ-L) Formula II compounds

| TAZ-L No. | Structure | MW |
|---|---|---|
| TAZ-L-67 | 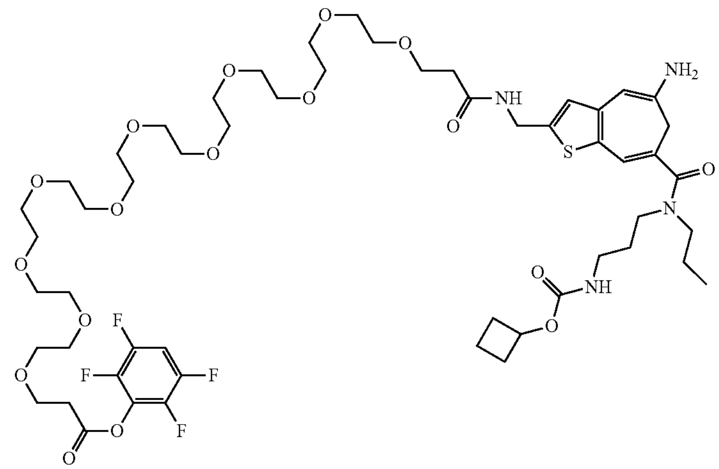 [SMILES: CCCN(CCCNC(=O)OC1CCC1)C(=O)C1=Cc2sc(CNC(=O)CCOCCOCCOCCOCCOCCOCCOCCOCCOCCOCCOCCC(=O)Oc3c(F)c(F)cc(F)c3F)cc2C=C(N)C1] | 1166.3 |
| TAZ-L-68 | 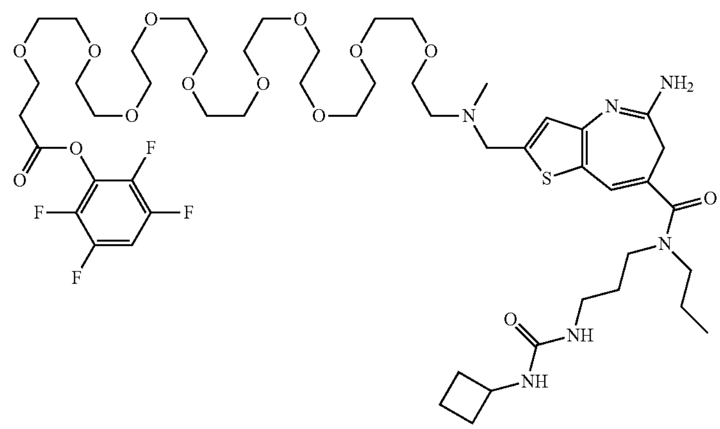 [SMILES: CCCN(CCCNC(=O)NC1CCC1)C(=O)C1=Cc2sc(CN(C)CCOCCOCCOCCOCCOCCOCCOCCOCCOCCOCCC(=O)Oc3c(F)c(F)cc(F)c3F)cc2N=C(N)C1] | 1108.2 |
| TAZ-L-69 | 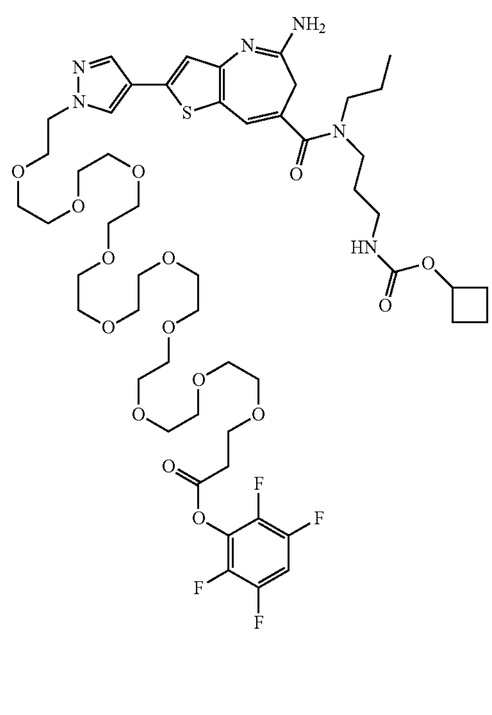 [SMILES: CCCN(CCCNC(=O)OC1CCC1)C(=O)C1=Cc2sc(-c3cnn(CCOCCOCCOCCOCCOCCOCCOCCOCCOCCOCCC(=O)Oc4c(F)c(F)cc(F)c4F)c3)cc2N=C(N)C1] | 1131.2 |

TABLE 2C-continued
Thienoazepine-linker (TAZ-L) Formula II compounds
| TAZ-L No. | Structure | MW |
|---|---|---|
| TAZ-L-70 | 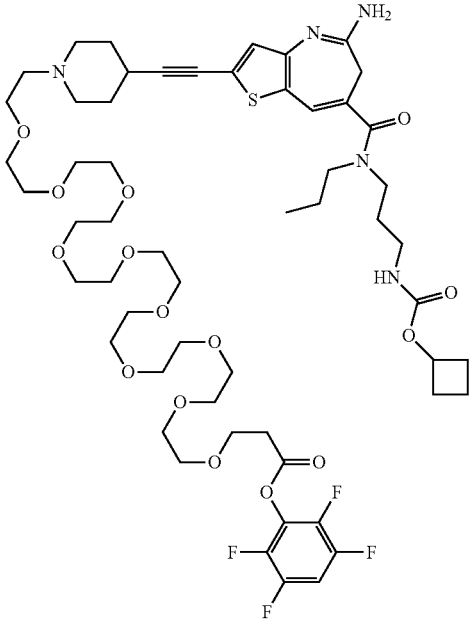 [SMILES: CCCN(CCCNC(=O)OC1CCC1)C(=O)C1=Cc2sc(C#CC3CCN(CCOCCOCCOCCOCCOCCOCCOCCOCCOCCOCCC(=O)Oc4c(F)c(F)cc(F)c4F)CC3)cc2N=C(N)C1] | 1172.3 |
| TAZ-L-71 | 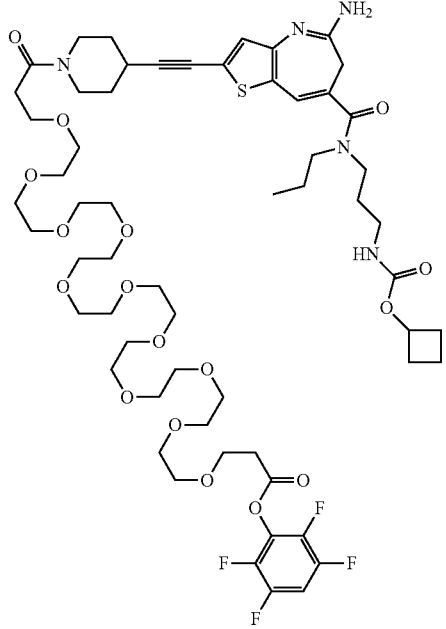 [SMILES: CCCN(CCCNC(=O)OC1CCC1)C(=O)C1=Cc2sc(C#CC3CCN(C(=O)CCOCCOCCOCCOCCOCCOCCOCCOCCOCCOCCOCCC(=O)Oc4c(F)c(F)cc(F)c4F)CC3)cc2N=C(N)C1] | 1244.4 |

TABLE 2C-continued

Thienoazepine-linker (TAZ-L) Formula II compounds

| TAZ-L No. | Structure | MW |
|---|---|---|
| TAZ-L-72 | 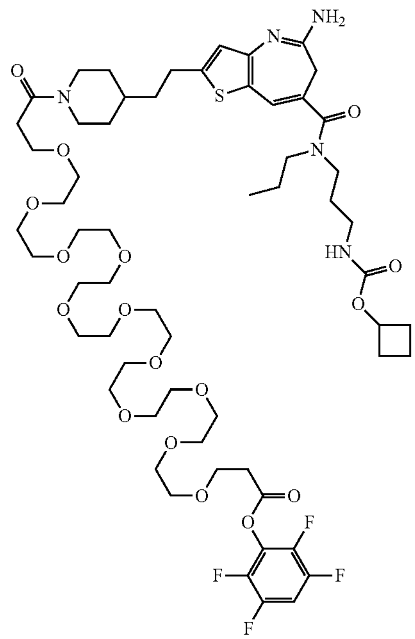 [SMILES: CCCN(CCCNC(=O)OC1CCC1)C(=O)C1=Cc2sc(CCC3CCN(C(=O)CCOCCOCCOCCOCCOCCOCCOCCOCCOCCOCCOCCC(=O)Oc4c(F)c(F)cc(F)c4F)CC3)cc2N=C(N)C1] | 1248.4 |
| TAZ-L-73 | 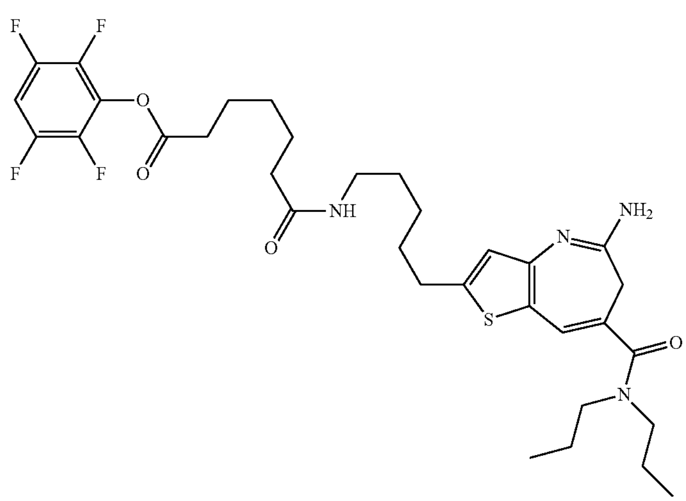 [SMILES: CCCN(CCC)C(=O)C1=Cc2sc(CCCCCNC(=O)CCCCCC(=O)Oc3c(F)c(F)cc(F)c3F)cc2N=C(N)C1] | 666.8 |

TABLE 2C-continued
Thienoazepine-linker (TAZ-L) Formula II compounds
| TAZ-L No. | Structure | MW |
|---|---|---|
| TAZ-L-74 | 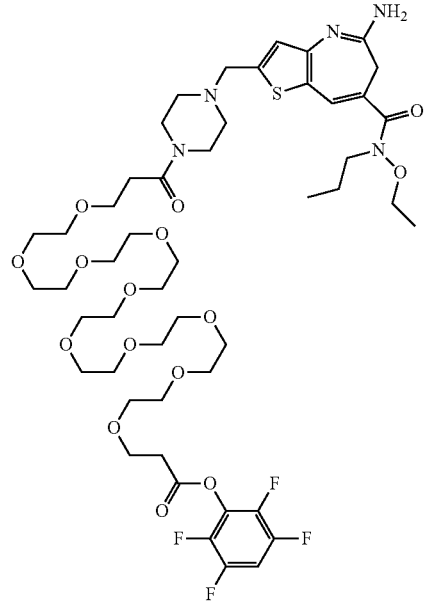 [SMILES: CCCN(CCC)C(=O)C1=Cc2sc(CN3CCN(C(=O)CCOCCOCCOCCOCCOCCOCCOCCOCCOCCOCCC(=O)Oc4c(F)c(F)cc(F)c4F)CC3)cc2N=C(N)C1] | 1080.2 |
| TAZ-L-75 | 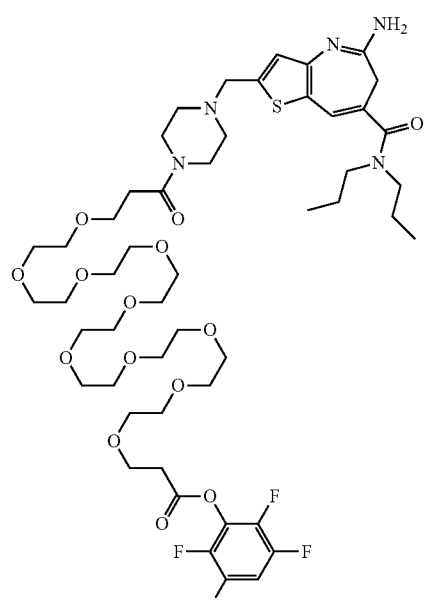 | 1078.2 |

TABLE 2C-continued
Thienoazepine-linker (TAZ-L) Formula II compounds
| TAZ-L No. | Structure | MW |
|---|---|---|
| TAZ-L-76 | 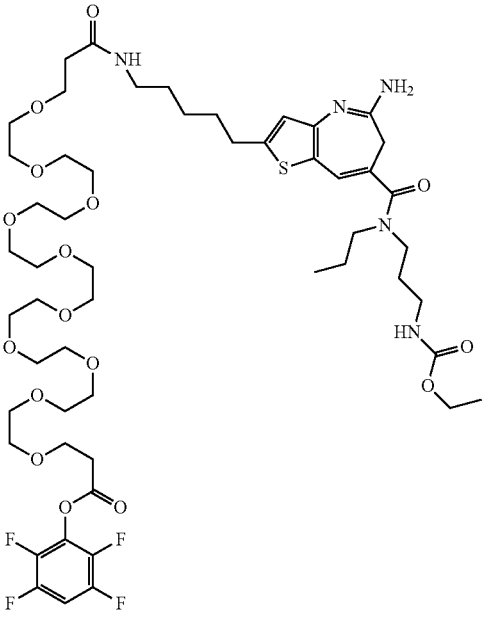 [SMILES: CCCN(CCCNC(=O)OCC)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1152.3 |
| TAZ-L-77 | 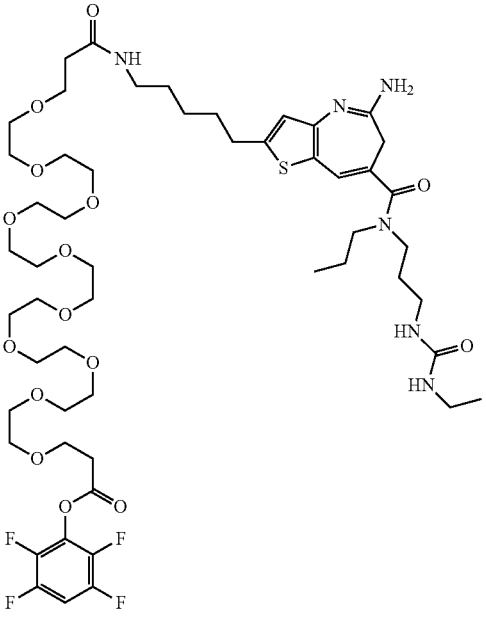 [SMILES: CCCN(CCCNC(=O)NCC)C(=O)C1=Cc2sc(CCCCCNC(=O)CCOCCOCCOCCOCCOCCOCCOCCOCCOCCOCCC(=O)Oc3c(F)c(F)cc(F)c3F)cc2N=C(N)C1] | 1151.3 |

TABLE 2C-continued
Thienoazepine-linker (TAZ-L) Formula II compounds
| TAZ-L No. | Structure | MW |
|---|---|---|
| TAZ-L-78 | 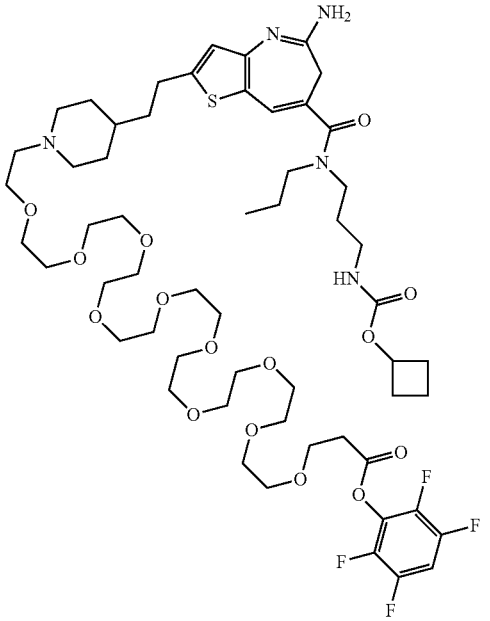 [SMILES: CCCN(CCCNC(=O)OC1CCC1)C(=O)C1=Cc2sc(CCC3CCN(CCOCCOCCOCCOCCOCCOCCOCCOCCOCCOCCC(=O)Oc4c(F)c(F)cc(F)c4F)CC3)cc2N=C(N)C1] | 1176.4 |
| TAZ-L-79 | 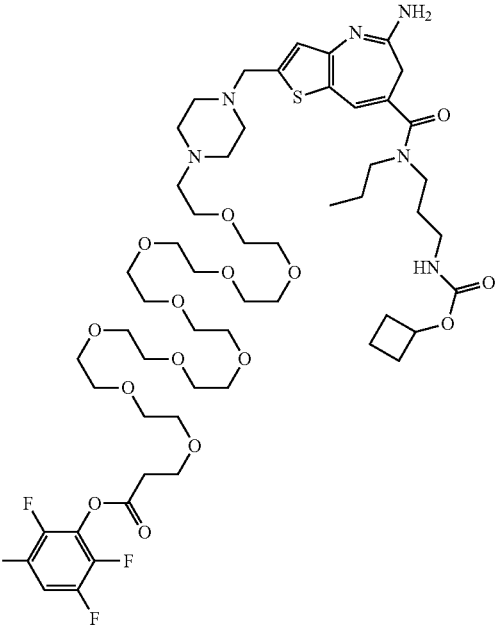 | 1163.3 |

TABLE 2C-continued

Thienoazepine-linker (TAZ-L) Formula II compounds

| TAZ-L No. | Structure | MW |
|---|---|---|
| TAZ-L-80 | 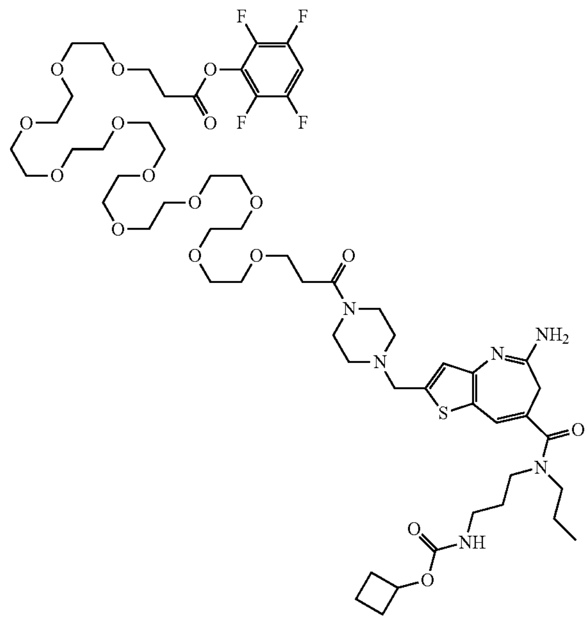 [SMILES: CCCN(CCCNC(=O)OC1CCC1)C(=O)C1=Cc2sc(CN3CCN(C(=O)CCOCCOCCOCCOCCOCCOCCOCCOCCOCCOCCOCCC(=O)Oc4c(F)c(F)cc(F)c4F)CC3)cc2N=C(N)C1] | 1235.4 |
| TAZ-L-81 | 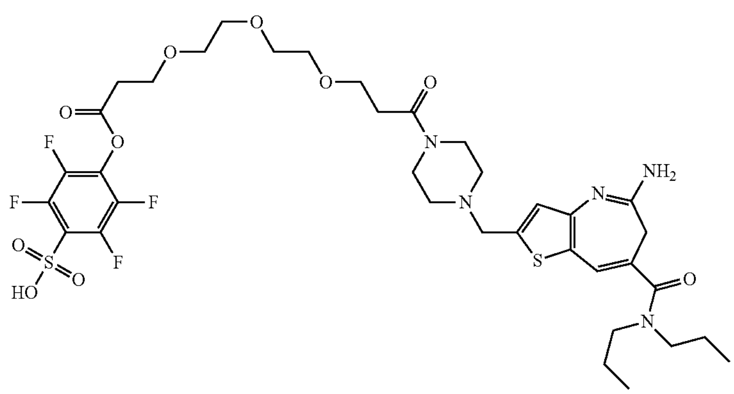 [SMILES: CCCN(CCC)C(=O)C1=Cc2sc(CN3CCN(C(=O)CCOCCOCCOCCC(=O)Oc4c(F)c(F)c(S(=O)(=O)O)c(F)c4F)CC3)cc2N=C(N)C1] | 849.9 |
| TAZ-L-82 | 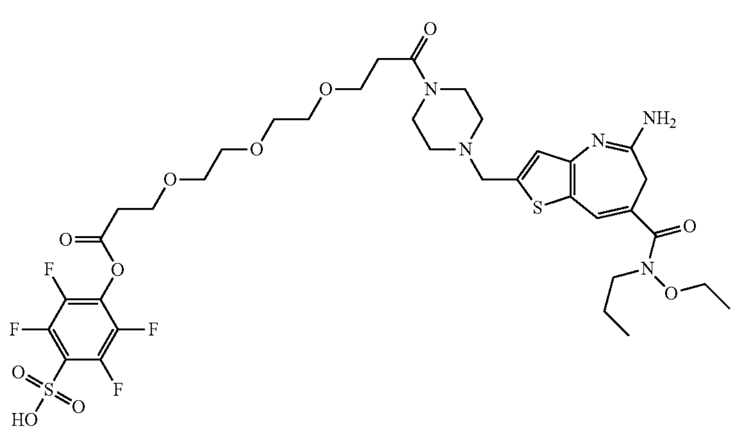 [SMILES: CCCN(OCC)C(=O)C1=Cc2sc(CN3CCN(C(=O)CCOCCOCCOCCC(=O)Oc4c(F)c(F)c(S(=O)(=O)O)c(F)c4F)CC3)cc2N=C(N)C1] | 851.9 |

TABLE 2C-continued
Thienoazepine-linker (TAZ-L) Formula II compounds
| TAZ-L No. | Structure | MW |
|---|---|---|
| TAZ-L-83 | 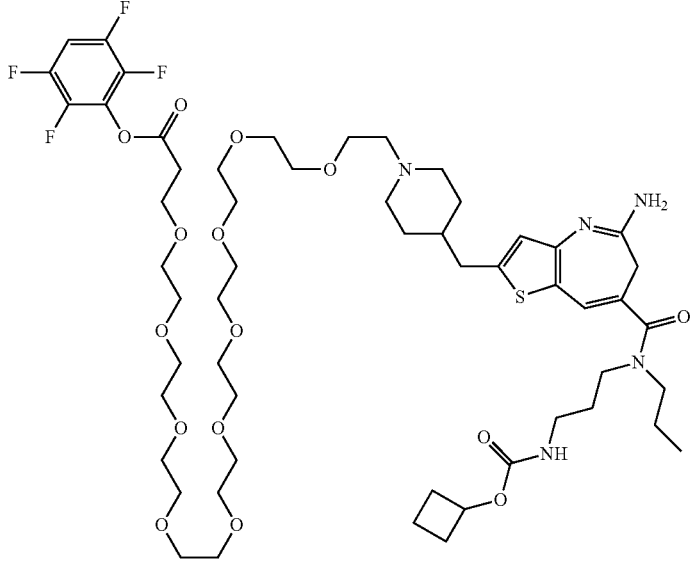 [SMILES: CCCN(CCCNC(=O)OC1CCC1)C(=O)C1=Cc2sc(CC3CCN(CCOCCOCCOCCOCCOCCOCCOCCOCCOCCOCCC(=O)Oc4c(F)c(F)cc(F)c4F)CC3)cc2N=C(N)C1] | 1162.3 |
| TAZ-L-84 | 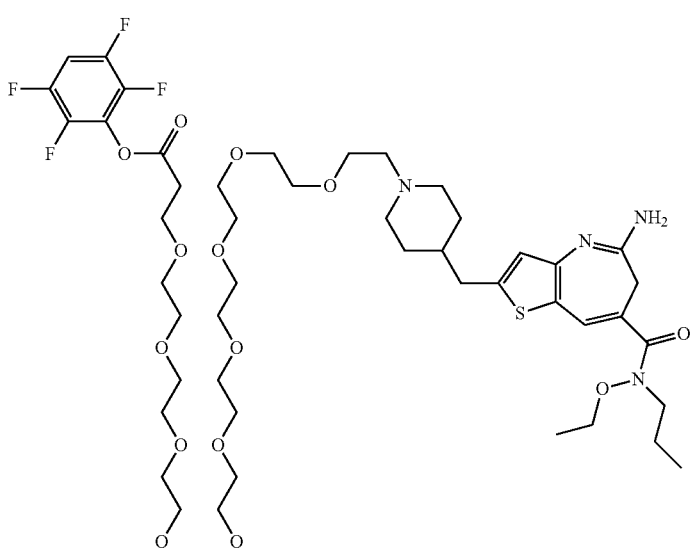 | 1051.2 |

TABLE 2C-continued
Thienoazepine-linker (TAZ-L) Formula II compounds
| TAZ-L No. | Structure | MW |
|---|---|---|
| TAZ-L-85 | 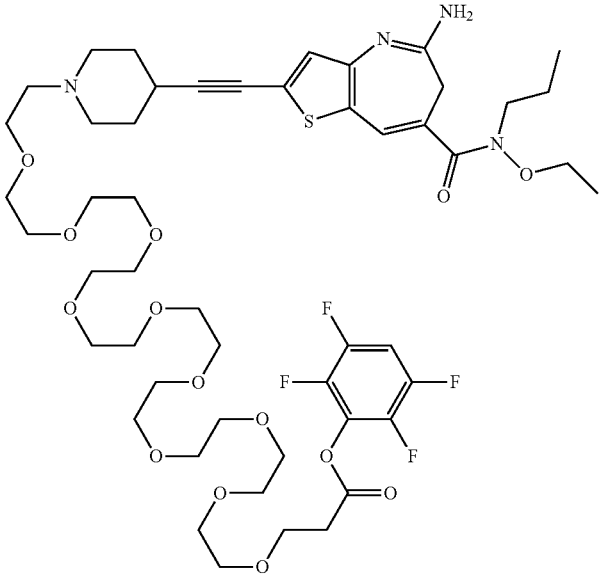 [SMILES: CCCN(OCC)C(=O)C1=Cc2sc(C#CC3CCN(CCOCCOCCOCCOCCOCCOCCOCCOCCOCCOCCC(=O)Oc4c(F)c(F)cc(F)c4F)CC3)cc2N=C(N)C1] | 1061.2 |
| TAZ-L-86 | 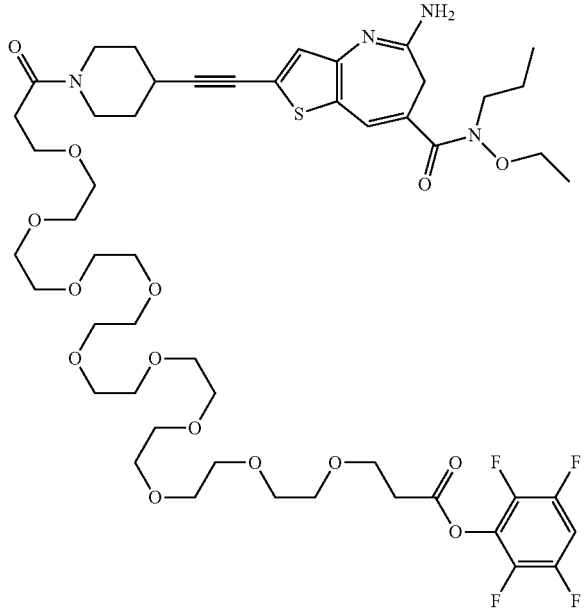 [SMILES: CCCN(OCC)C(=O)C1=Cc2sc(C#CC3CCN(C(=O)CCOCCOCCOCCOCCOCCOCCOCCOCCOCCOCCC(=O)Oc4c(F)c(F)cc(F)c4F)CC3)cc2N=C(N)C1] | 1089.2 |

TABLE 2C-continued
Thienoazepine-linker (TAZ-L) Formula II compounds
| TAZ-L No. | Structure | MW |
|---|---|---|
| TAZ-L-87 | 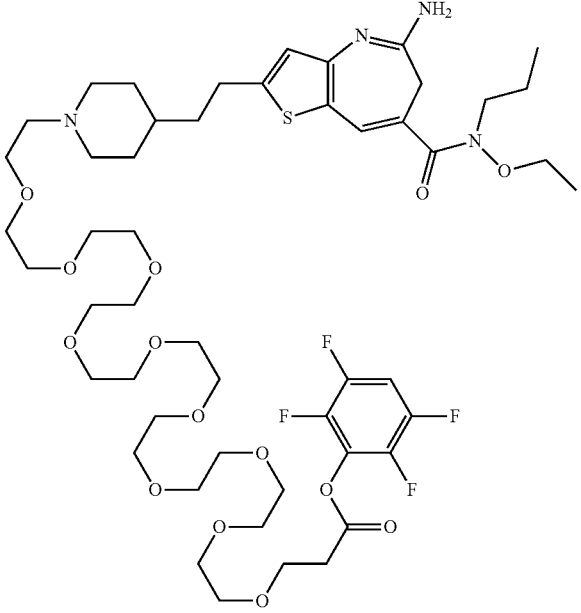 [SMILES: CCCN(OCC)C(=O)C1=Cc2sc(CCC3CCN(CCOCCOCCOCCOCCOCCOCCOCCOCCOCCOCCC(=O)Oc4c(F)c(F)cc(F)c4F)CC3)cc2N=C(N)C1] | 1065.2 |
| TAZ-L-88 | 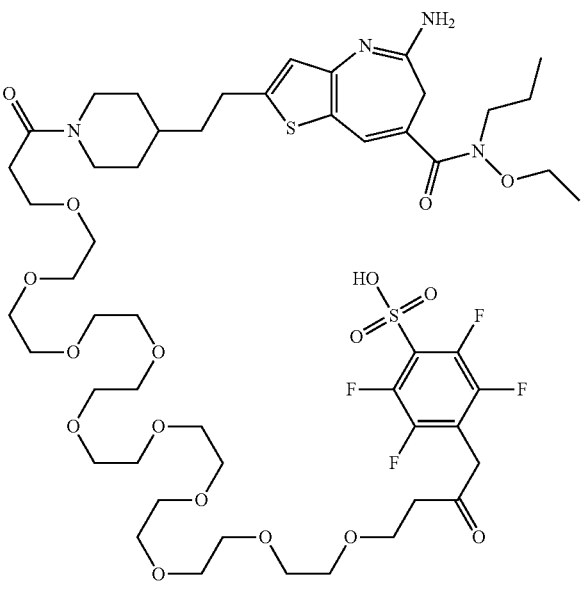 [SMILES: CCCN(OCC)C(=O)C1=Cc2sc(CCC3CCN(C(=O)CCOCCOCCOCCOCCOCCOCCOCCOCCOCCOCCC(=O)Cc4c(F)c(F)c(S(=O)(=O)O)c(F)c4F)CC3)cc2N=C(N)C1] | 1173.3 |

TABLE 2C-continued

Thienoazepine-linker (TAZ-L) Formula II compounds

| TAZ-L No. | Structure | MW |
|---|---|---|
| TAZ-L-89 | 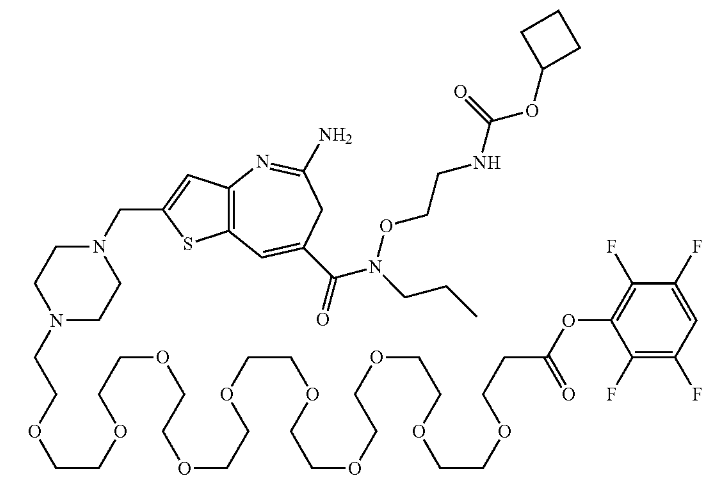 [SMILES: CCCN(OCCNC(=O)OC1CCC1)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1165.3 |
| TAZ-L-90 | 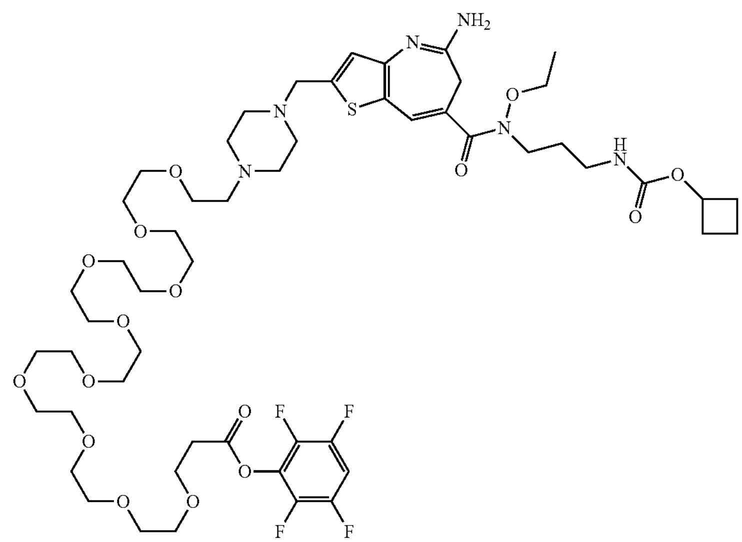 [SMILES: CCON(CCCNC(=O)OC1CCC1)C(=O)C1=Cc2sc(CN3CCN(CCOCCOCCOCCOCCOCCOCCOCCOCCOCCOCCC(=O)Oc4c(F)c(F)cc(F)c4F)CC3)cc2N=C(N)C1] | 1165.3 |
| TAZ-L-91 | 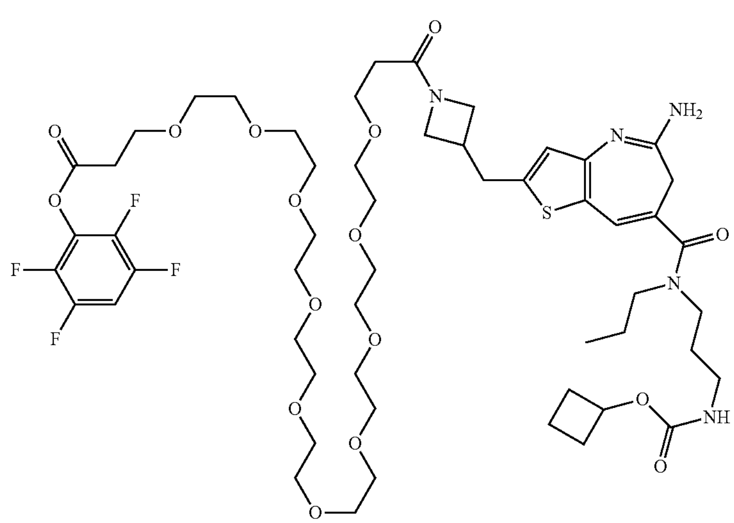 [SMILES: CCCN(CCCNC(=O)OC1CCC1)C(=O)C1=Cc2sc(CC3CN(C(=O)CCOCCOCCOCCOCCOCCOCCOCCOCCOCCOCCC(=O)Oc4c(F)c(F)cc(F)c4F)C3)cc2N=C(N)C1] | 1162.3 |

TABLE 2C-continued
Thienoazepine-linker (TAZ-L) Formula II compounds
| TAZ-L No. | Structure | MW |
|---|---|---|
| TAZ-L-92 | 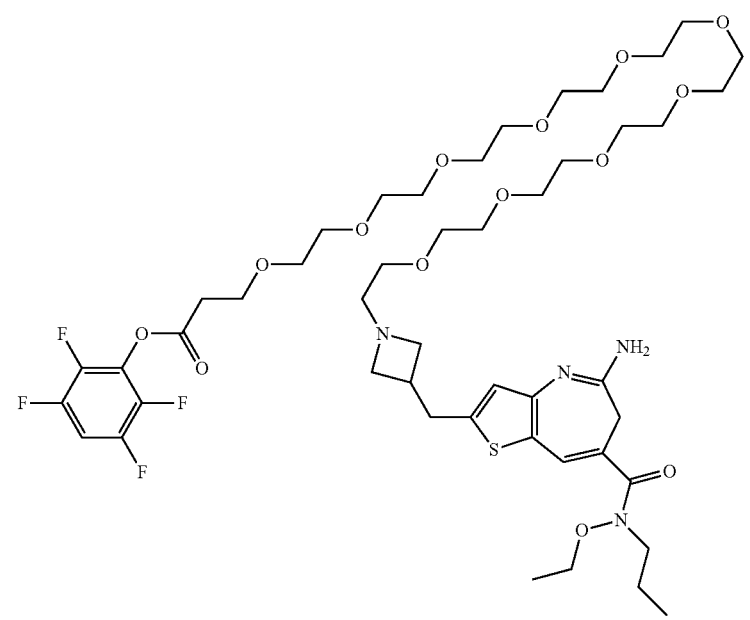 [SMILES: CCCN(OCC)C(=O)C1=Cc2sc(CC3CN(CCOCCOCCOCCOCCOCCOCCOCCOCCOCCOCCC(=O)Oc4c(F)c(F)cc(F)c4F)C3)cc2N=C(N)C1] | 1023.1 |
| TAZ-L-93 | 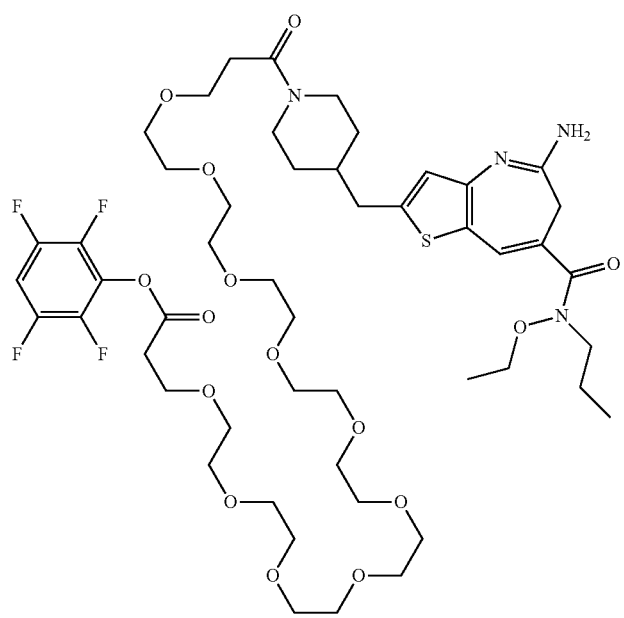 [SMILES: CCCN(OCC)C(=O)C1=Cc2sc(CC3CCN(C(=O)CCOCCOCCOCCOCCOCCOCCOCCOCCOCCOCCC(=O)Oc4c(F)c(F)cc(F)c4F)CC3)cc2N=C(N)C1] | 1079.2 |

TABLE 2C-continued
| Thienoazepine-linker (TAZ-L) Formula II compounds | | |
|---|---|---|
| TAZ-L No. | Structure | MW |
| TAZ-L-94 | 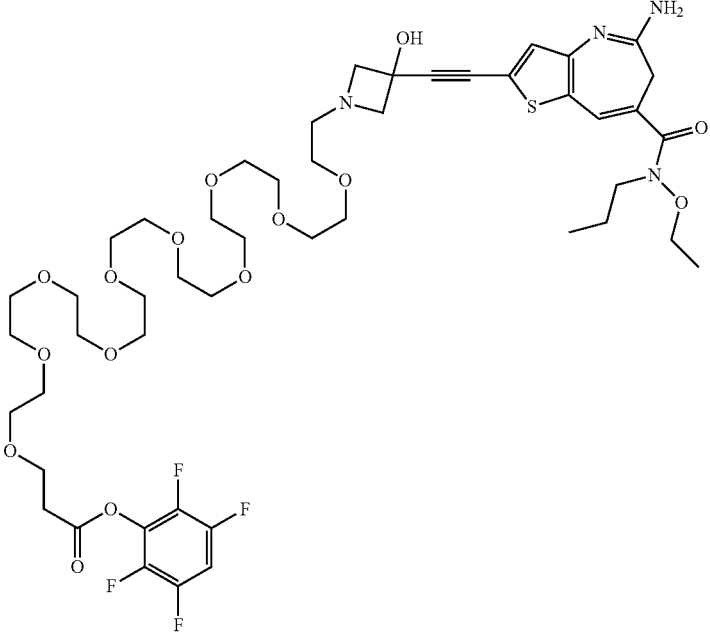 [SMILES: CCCN(OCC)C(=O)C1=Cc2sc(C#CC3(O)CN(CCOCCOCCOCCOCCOCCOCCOCCOCCOCCOCCC(=O)Oc4c(F)c(F)cc(F)c4F)C3)cc2N=C(N)C1] | 1049.1 |
| TAZ-L-95 | 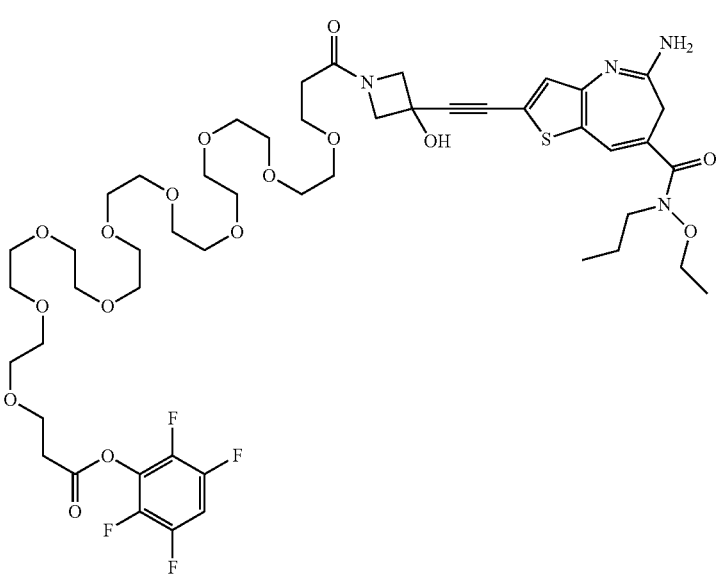 [SMILES: CCCN(OCC)C(=O)C1=Cc2sc(C#CC3(O)CN(C(=O)CCOCCOCCOCCOCCOCCOCCOCCOCCOCCOCCC(=O)Oc4c(F)c(F)cc(F)c4F)C3)cc2N=C(N)C1] | 1077.1 |

TABLE 2C-continued

Thienoazepine-linker (TAZ-L) Formula II compounds

| TAZ-L No. | Structure | MW |
|---|---|---|
| TAZ-L-96 | 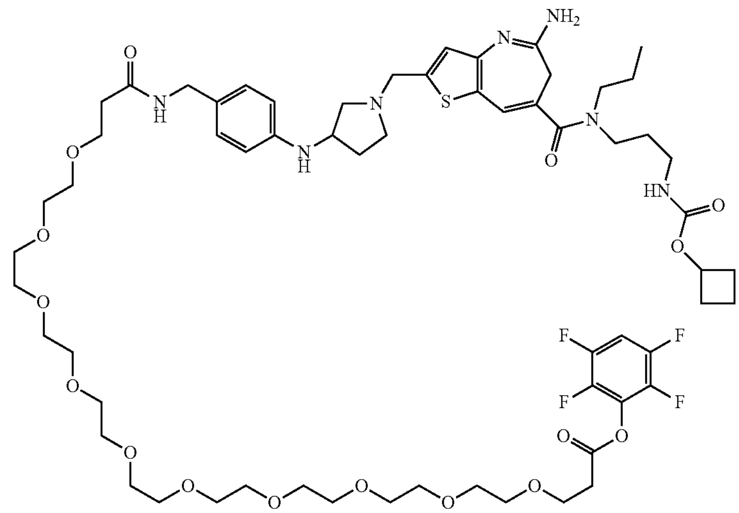 [SMILES: CCCN(CCCNC(=O)OC1CCC1)C(=O)C1=Cc2sc(CN3CCC(Nc4ccc(CNC(=O)CCOCCOCCOCCOCCOCCOCCOCCOCCOCCOCCC(=O)Oc5c(F)c(F)cc(F)c5F)cc4)C3)cc2N=C(N)C1] | 1296.5 |
| TAZ-L-97 | 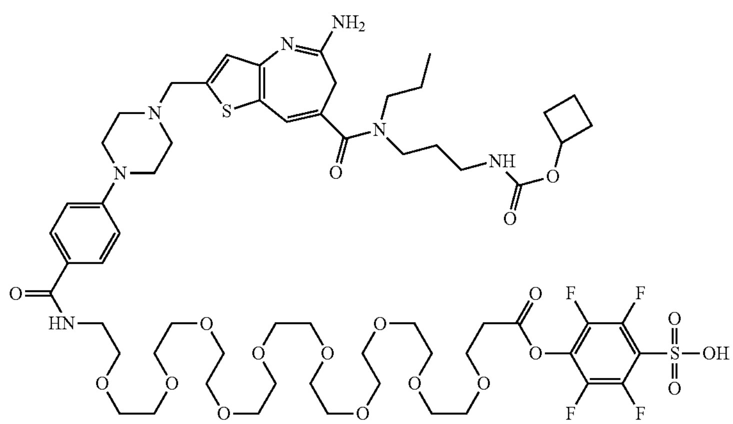 [SMILES: CCCN(CCCNC(=O)OC1CCC1)C(=O)C1=Cc2sc(CN3CCN(c4ccc(C(=O)NCCOCCOCCOCCOCCOCCOCCOCCOCCOCCOCCC(=O)Oc5c(F)c(F)c(S(=O)(=O)O)c(F)c5F)cc4)CC3)cc2N=C(N)C1] | 1362.5 |
| TAZ-L-98 | 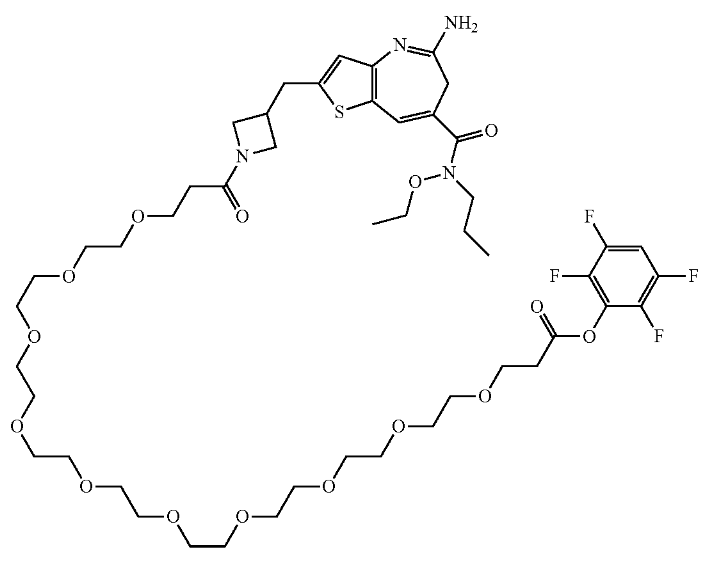 [SMILES: CCCN(OCC)C(=O)C1=Cc2sc(CC3CN(C(=O)CCOCCOCCOCCOCCOCCOCCOCCOCCOCCOCCC(=O)Oc4c(F)c(F)cc(F)c4F)C3)cc2N=C(N)C1] | 1051.2 |

TABLE 2C-continued

Thienoazepine-linker (TAZ-L) Formula II compounds

| TAZ-L No. | Structure | MW |
|---|---|---|
| TAZ-L-99 | 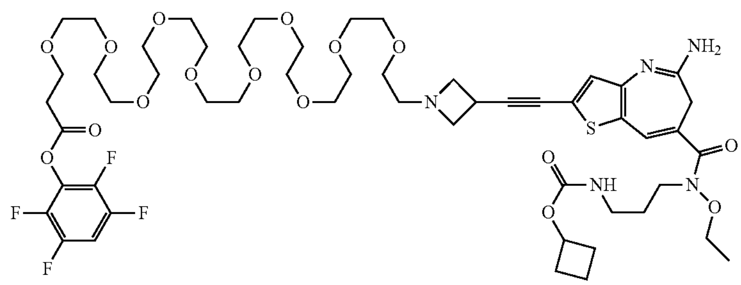 [SMILES: CCON(CCCNC(=O)OC1CCC1)C(=O)C1=Cc2sc(C#CC3CN(CCOCCOCCOCCOCCOCCOCCOCCOCCOCCOCCC(=O)Oc4c(F)c(F)cc(F)c4F)C3)cc2N=C(N)C1] | 1144.3 |
| TAZ-L-100 | 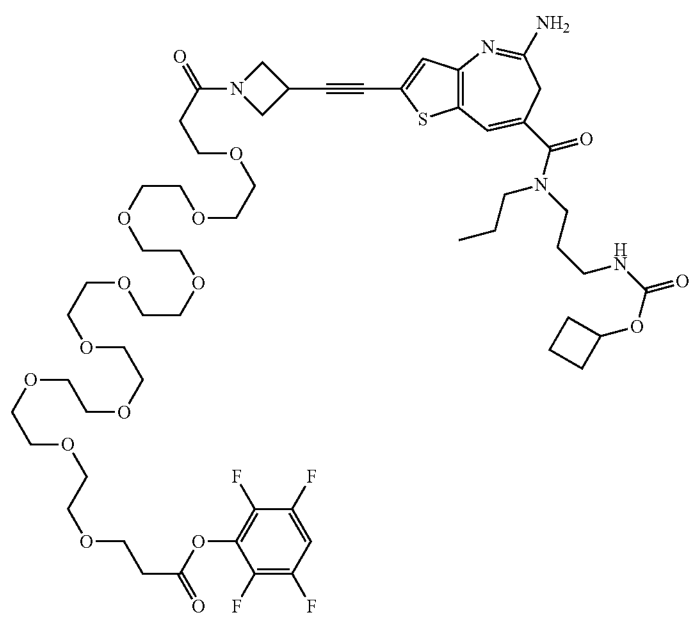 [SMILES: CCCN(CCCNC(=O)OC1CCC1)C(=O)C1=Cc2sc(C#CC3CN(C(=O)CCOCCOCCOCCOCCOCCOCCOCCOCCOCCOCCC(=O)Oc4c(F)c(F)cc(F)c4F)C3)cc2N=C(N)C1] | 1172.3 |
| TAZ-L-101 | 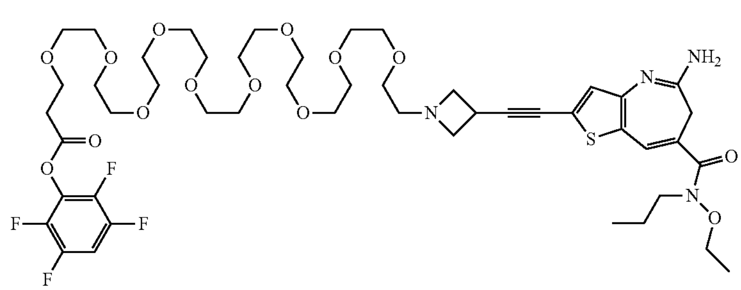 [SMILES: CCCN(OCC)C(=O)C1=Cc2sc(C#CC3CN(CCOCCOCCOCCOCCOCCOCCOCCOCCOCCOCCC(=O)Oc4c(F)c(F)cc(F)c4F)C3)cc2N=C(N)C1] | 1033.1 |

TABLE 2C-continued

Thienoazepine-linker (TAZ-L) Formula II compounds

| TAZ-L No. | Structure | MW |
| --- | --- | --- |
| TAZ-L-102 | 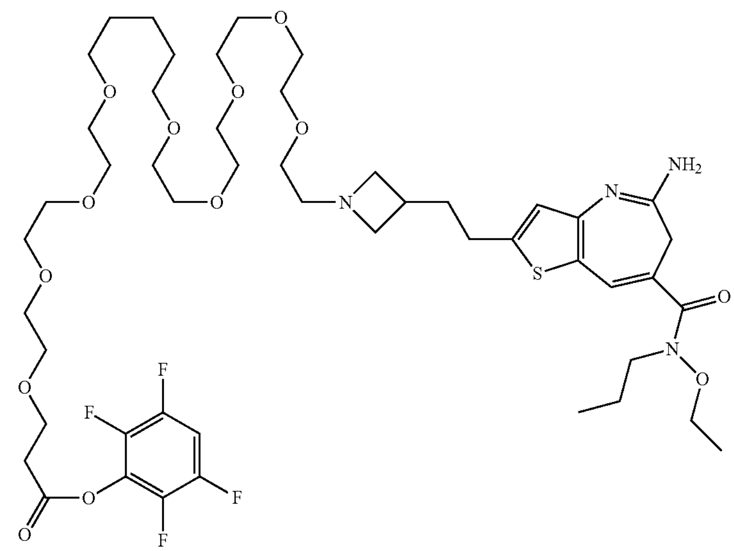 [SMILES: CCCN(OCC)C(=O)C1=Cc2sc(CCC3CN(CCOCCOCCOCCOCCOCCCCCOCCOCCOCCOCCC(=O)Oc4c(F)c(F)cc(F)c4F)C3)cc2N=C(N)C1] | 1037.2 |
| TAZ-L-103 | 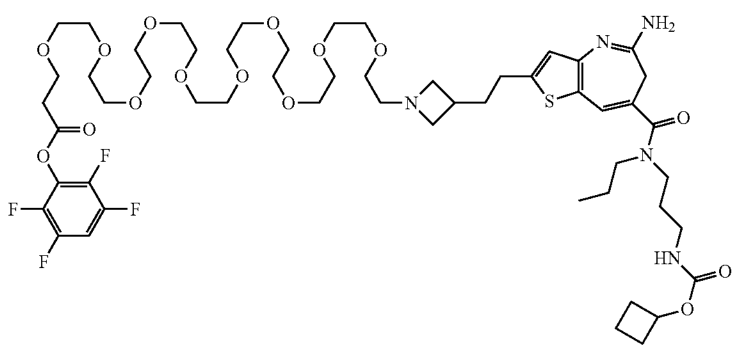 [SMILES: CCCN(CCCNC(=O)OC1CCC1)C(=O)C1=Cc2sc(CCC3CN(CCOCCOCCOCCOCCOCCOCCOCCOCCOCCOCCC(=O)Oc4c(F)c(F)cc(F)c4F)C3)cc2N=C(N)C1] | 1148.3 |
| TAZ-L-104 | 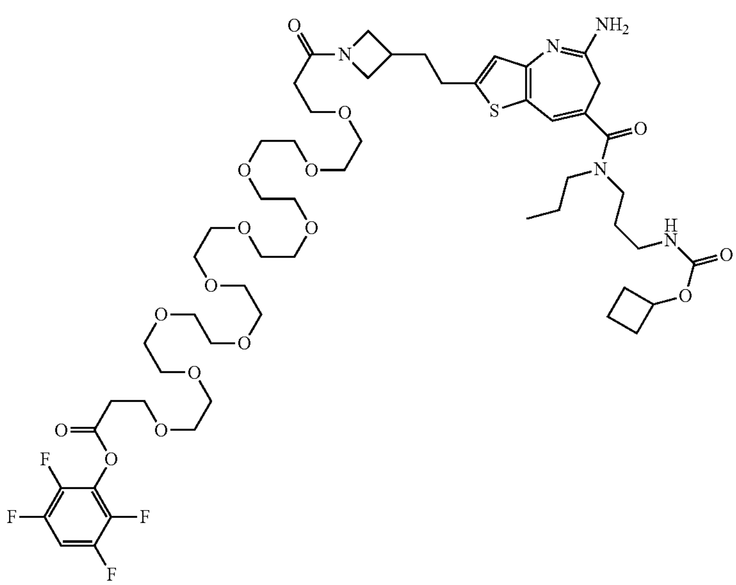 [SMILES: CCCN(CCCNC(=O)OC1CCC1)C(=O)C1=Cc2sc(CCC3CN(C(=O)CCOCCOCCOCCOCCOCCOCCOCCOCCOCCOCCC(=O)Oc4c(F)c(F)cc(F)c4F)C3)cc2N=C(N)C1] | 1176.3 |

TABLE 2C-continued
Thienoazepine-linker (TAZ-L) Formula II compounds
| TAZ-L No. | Structure | MW |
|---|---|---|
| TAZ-L-105 | 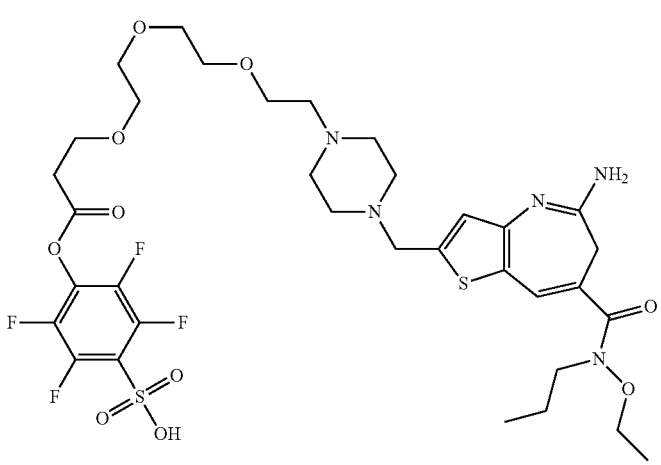 [SMILES: CCCN(OCC)C(=O)C1=Cc2sc(CN3CCN(CCOCCOCCOCCC(=O)Oc4c(F)c(F)c(S(=O)(=O)O)c(F)c4F)CC3)cc2N=C(N)C1] | 823.9 |
| TAZ-L-106 | 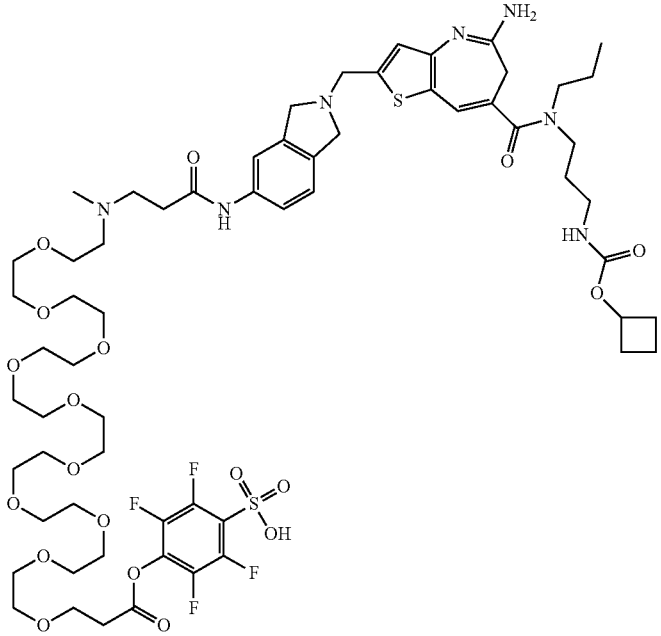 [SMILES: CCCN(CCCNC(=O)OC1CCC1)C(=O)C1=Cc2sc(CN3Cc4ccc(NC(=O)CCN(C)CCOCCOCCOCCOCCOCCOCCOCCOCCOCCOCCC(=O)Oc5c(F)c(F)c(S(=O)(=O)O)c(F)c5F)cc4C3)cc2N=C(N)C1] | 1376.5 |

TABLE 2C-continued
Thienoazepine-linker (TAZ-L) Formula II compounds
| TAZ-L No. | Structure | MW |
|---|---|---|
| TAZ-L-107 | 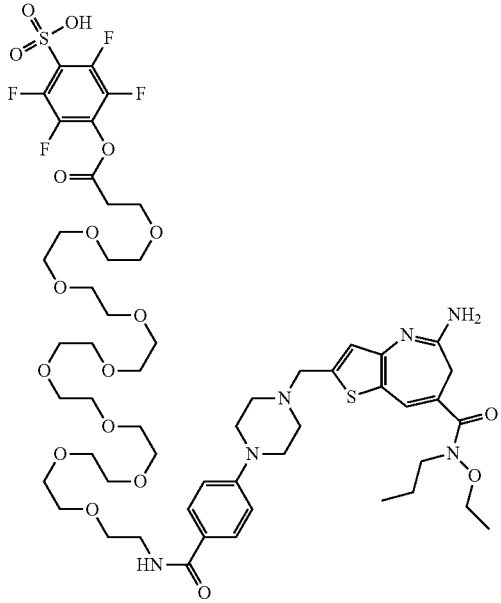 [SMILES: CCCN(OCC)C(=O)C1=Cc2sc(CN3CCN(c4ccc(C(=O)NCCOCCOCCOCCOCCOCCOCCOCCOCCOCCOCCC(=O)Oc5c(F)c(F)c(S(=O)(=O)O)c(F)c5F)cc4)CC3)cc2N=C(N)C1] | 1251.4 |
| TAZ-L-108 | 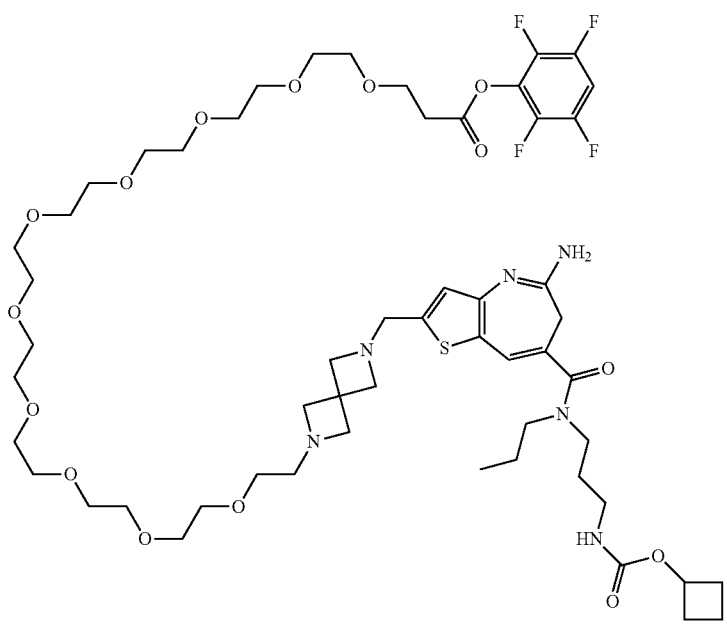 [SMILES: CCCN(CCCNC(=O)OC1CCC1)C(=O)C1=Cc2sc(CN3CC4(CN(CCOCCOCCOCCOCCOCCOCCOCCOCCOCCOCCC(=O)Oc5c(F)c(F)cc(F)c5F)C4)C3)cc2N=C(N)C1] | 1175.3 |

TABLE 2C-continued
Thienoazepine-linker (TAZ-L) Formula II compounds
| TAZ-L No. | Structure | MW |
|---|---|---|
| TAZ-L-109 | 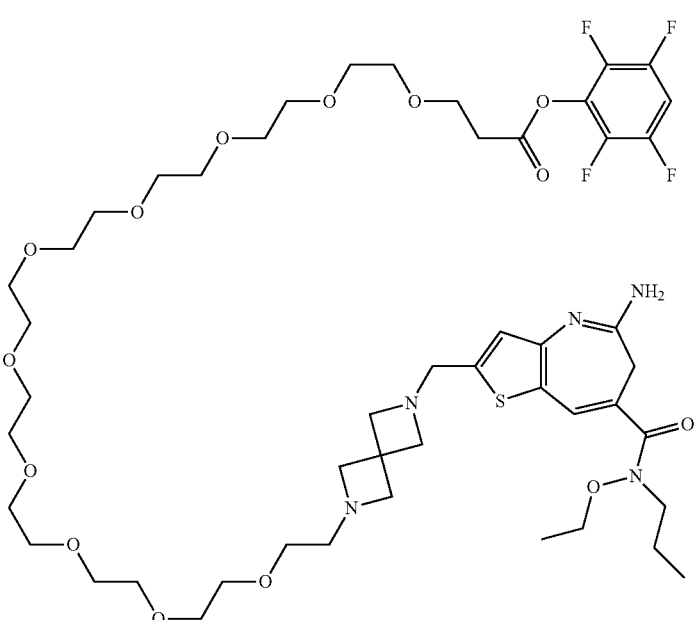 [SMILES: CCCN(OCC)C(=O)C1=Cc2sc(CN3CC4(CN(CCOCCOCCOCCOCCOCCOCCOCCOCCOCCOCCC(=O)Oc5c(F)c(F)cc(F)c5F)C4)C3)cc2N=C(N)C1] | 1064.2 |
| TAZ-L-110 | 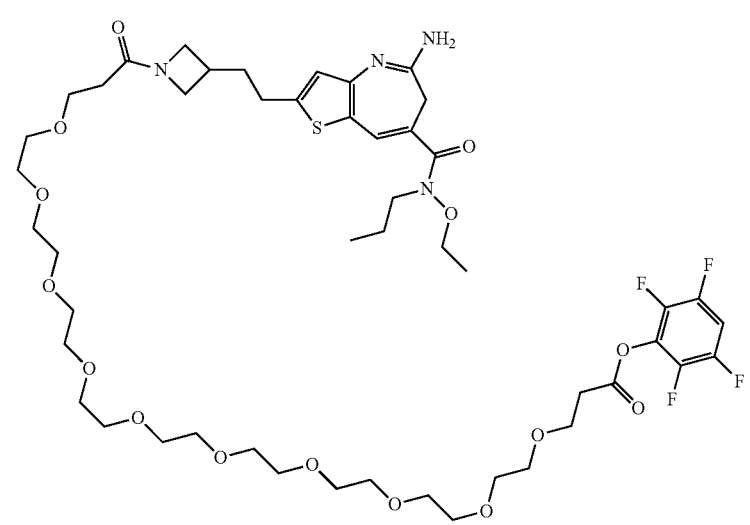 [SMILES: CCCN(OCC)C(=O)C1=Cc2sc(CCC3CN(C(=O)CCOCCOCCOCCOCCOCCOCCOCCOCCOCCOCCC(=O)Oc4c(F)c(F)cc(F)c4F)C3)cc2N=C(N)C1] | 1065.2 |

TABLE 2C-continued

Thienoazepine-linker (TAZ-L) Formula II compounds

| TAZ-L No. | Structure | MW |
|---|---|---|
| TAZ-L-111 | 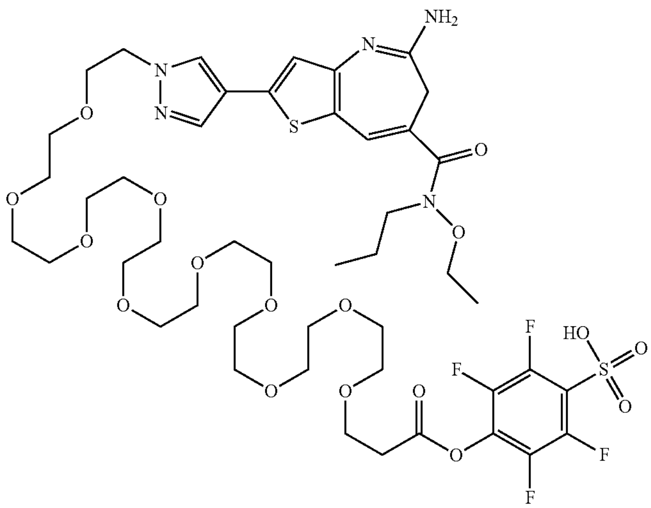 [SMILES: CCCN(OCC)C(=O)C1=Cc2sc(-c3cnn(CCOCCOCCOCCOCCOCCOCCOCCOCCOCCOCCC(=O)Oc4c(F)c(F)c(S(=O)(=O)O)c(F)c4F)c3)cc2N=C(N)C1] | 1100.2 |
| TAZ-L-112 | 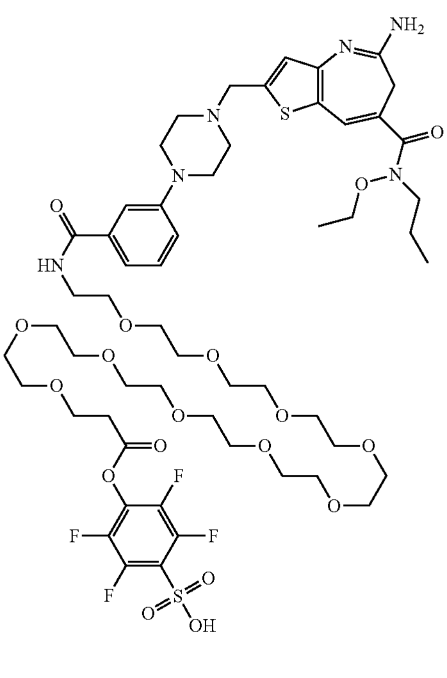 [SMILES: CCCN(OCC)C(=O)C1=Cc2sc(CN3CCN(c4cccc(C(=O)NCCOCCOCCOCCOCCOCCOCCOCCOCCOCCOCCC(=O)Oc5c(F)c(F)c(S(=O)(=O)O)c(F)c5F)c4)CC3)cc2N=C(N)C1] | 1251.4 |

TABLE 2C-continued
Thienoazepine-linker (TAZ-L) Formula II compounds
| TAZ-L No. | Structure | MW |
|---|---|---|
| TAZ-L-113 | 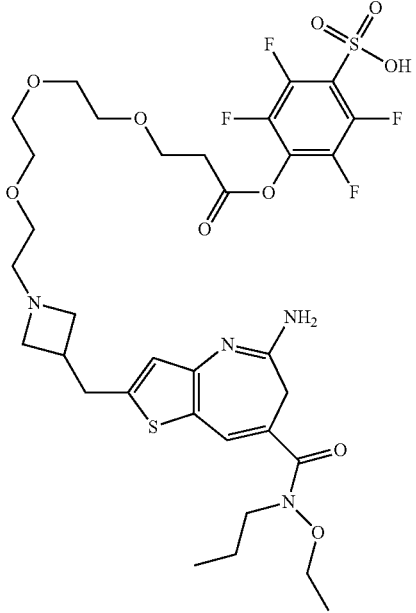 [SMILES: CCCN(OCC)C(=O)C1=Cc2sc(CC3CN(CCOCCOCCOCCC(=O)Oc4c(F)c(F)c(S(=O)(=O)O)c(F)c4F)C3)cc2N=C(N)C1] | 794.8 |
| TAZ-L-114 | 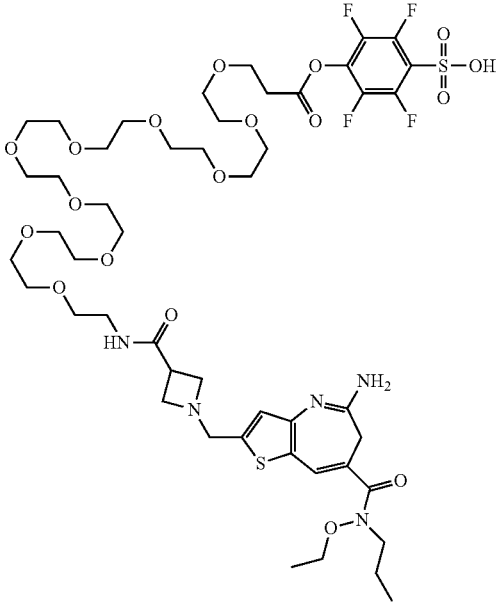 [SMILES: CCCN(OCC)C(=O)C1=Cc2sc(CN3CC(C(=O)NCCOCCOCCOCCOCCOCCOCCOCCOCCOCCOCCC(=O)Oc4c(F)c(F)c(S(=O)(=O)O)c(F)c4F)C3)cc2N=C(N)C1] | 1146.2 |

TABLE 2C-continued
Thienoazepine-linker (TAZ-L) Formula II compounds
| TAZ-L No. | Structure | MW |
|---|---|---|
| TAZ-L-115 | 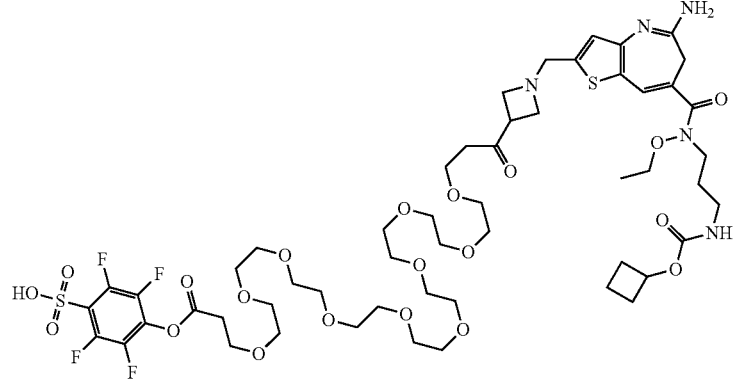 [SMILES: CCON(CCCNC(=O)OC1CCC1)C(=O)C1=Cc2sc(CN3CC(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1244.3 |
| TAZ-L-116 | 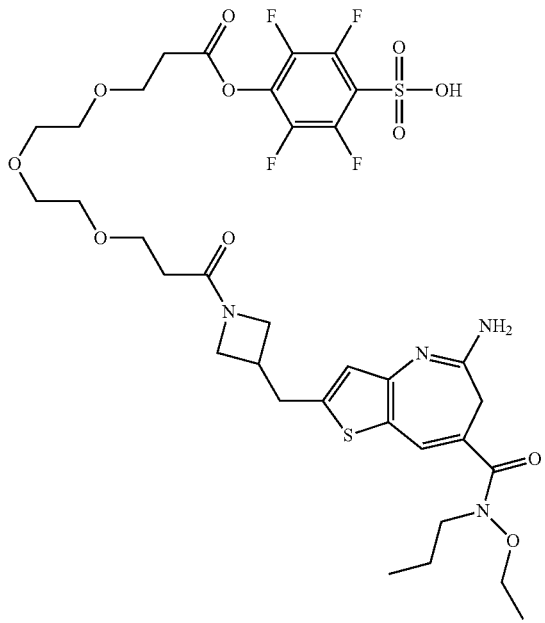 [SMILES: CCCN(OCC)C(=O)C1=Cc2sc(CC3CN(C(=O)CCOCCOCCOCCC(=O)Oc4c(F)c(F)c(S(=O)(=O)O)c(F)c4F)C3)cc2N=C(N)C1] | 822.8 |

TABLE 2C-continued

Thienoazepine-linker (TAZ-L) Formula II compounds

| TAZ-L No. | Structure | MW |
|---|---|---|
| TAZ-L-117 | 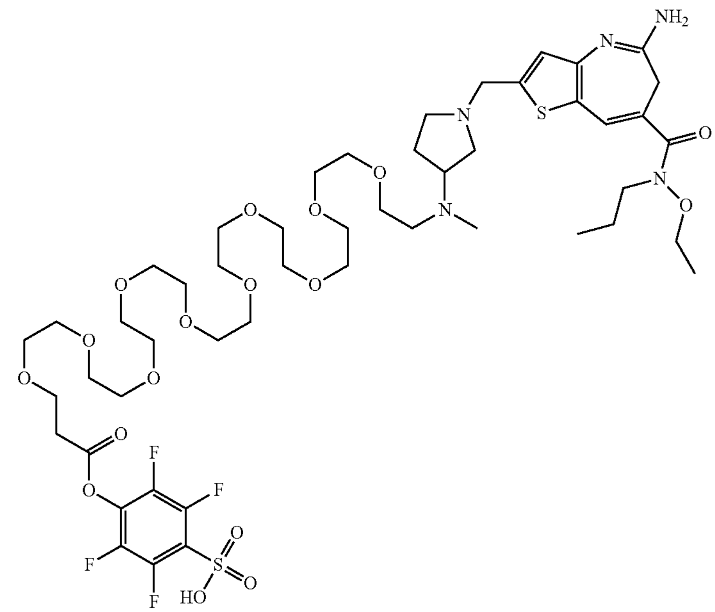 [SMILES: CCCN(OCC)C(=O)C1=Cc2sc(CN3CCC(N(C)CCOCCOCCOCCOCCOCCOCCOCCOCCOCCOCCC(=O)Oc4c(F)c(F)c(S(=O)(=O)O)c(F)c4F)C3)cc2N=C(N)C1] | 1146.3 |
| TAZ-L-118 | 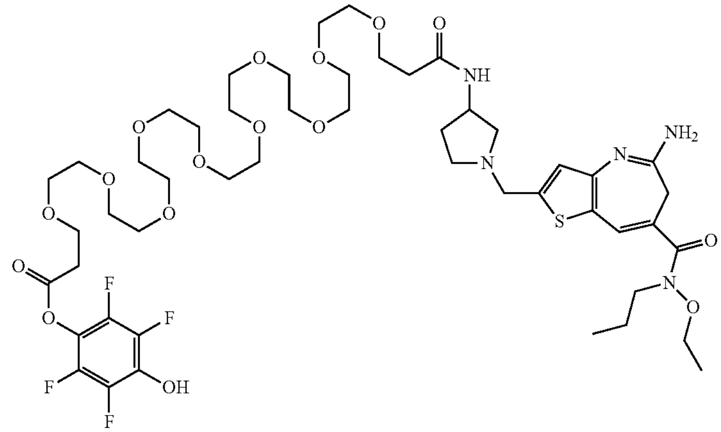 [SMILES: CCCN(OCC)C(=O)C1=Cc2sc(CN3CCC(NC(=O)CCOCCOCCOCCOCCOCCOCCOCCOCCOCCOCCC(=O)Oc4c(F)c(F)c(O)c(F)c4F)C3)cc2N=C(N)C1] | 1160.3 |
| TAZ-L-119 | 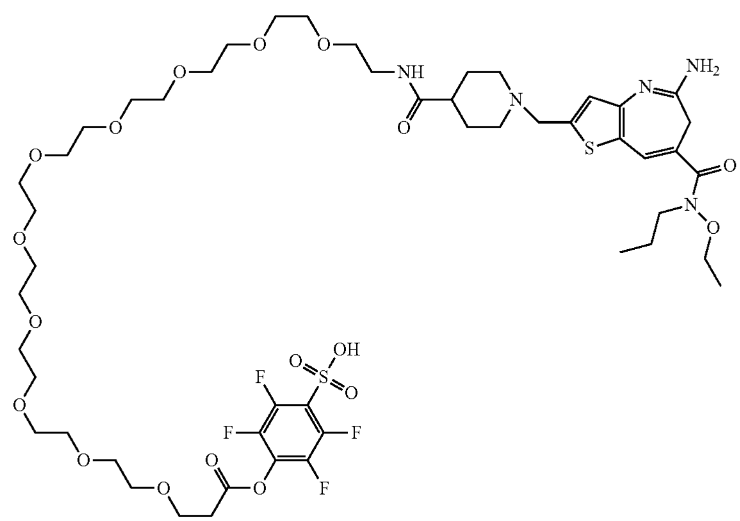 [SMILES: CCCN(OCC)C(=O)C1=Cc2sc(CN3CCC(C(=O)NCCOCCOCCOCCOCCOCCOCCOCCOCCOCCOCCC(=O)Oc4c(F)c(F)c(S(=O)(=O)O)c(F)c4F)CC3)cc2N=C(N)C1] | 1174.3 |

TABLE 2C-continued

Thienoazepine-linker (TAZ-L) Formula II compounds

| TAZ-L No. | Structure | MW |
|---|---|---|
| TAZ-L-120 | 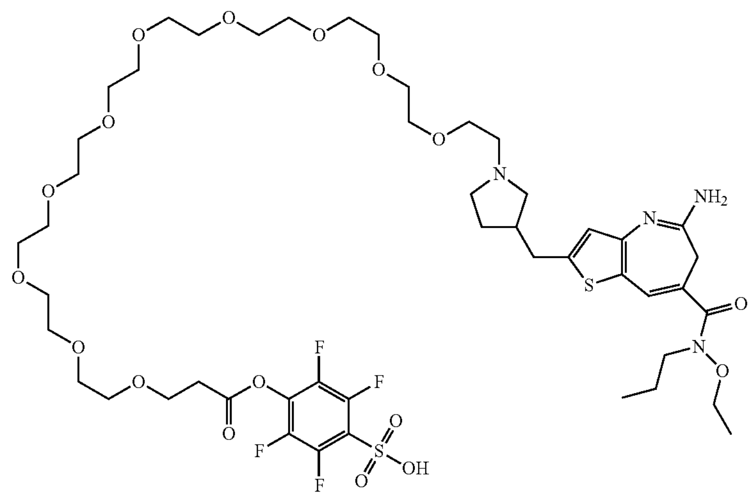 [SMILES: CCCN(OCC)C(=O)C1=Cc2sc(CC3CCN(CCOCCOCCOCCOCCOCCOCCOCCOCCOCCOCCC(=O)Oc4c(F)c(F)c(S(=O)(=O)O)c(F)c4F)C3)cc2N=C(N)C1] | 1117.2 |
| TAZ-L-121 | 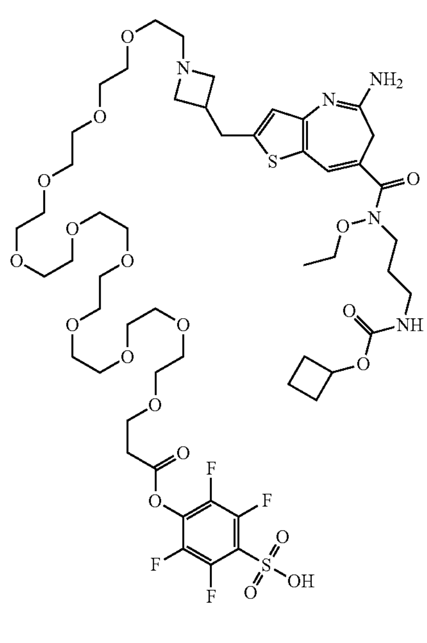 [SMILES: CCON(CCCNC(=O)OC1CCC1)C(=O)C1=Cc2sc(CC3CN(CCOCCOCCOCCOCCOCCOCCOCCOCCOCCOCCC(=O)Oc4c(F)c(F)c(S(=O)(=O)O)c(F)c4F)C3)cc2N=C(N)C1] | 1216.3 |

TABLE 2C-continued

Thienoazepine-linker (TAZ-L) Formula II compounds

| TAZ-L No. | Structure | MW |
|---|---|---|
| TAZ-L-122 | 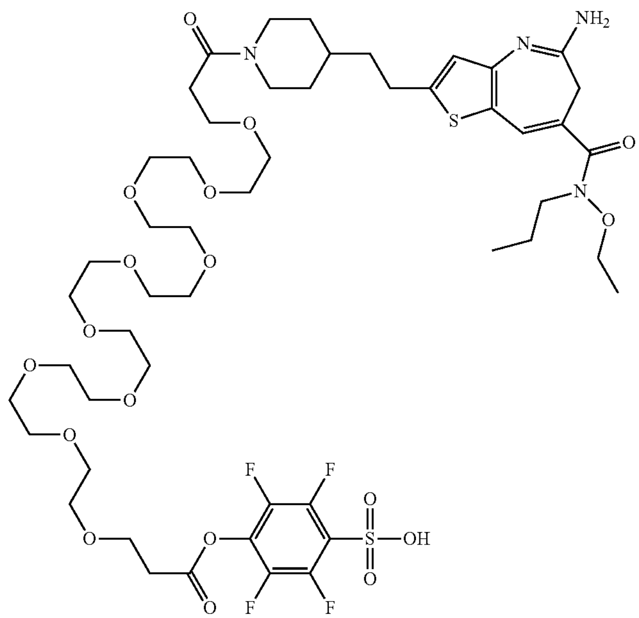 [SMILES: CCCN(OCC)C(=O)C1=Cc2sc(CCC3CCN(C(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1173.3 |
| TAZ-L-123 | 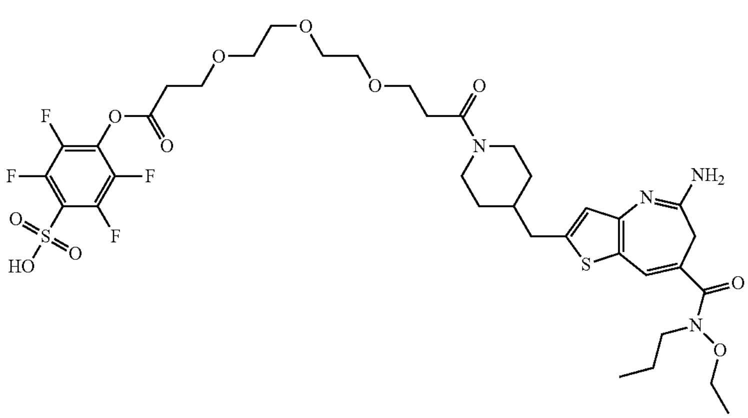 [SMILES: CCCN(OCC)C(=O)C1=Cc2sc(CC3CCN(C(=O)CCOCCOCCOCCC(=O)Oc4c(F)c(F)c(S(=O)(=O)O)c(F)c4F)CC3)cc2N=C(N)C1] | 850.9 |

TABLE 2C-continued
Thienoazepine-linker (TAZ-L) Formula II compounds
| TAZ-L No. | Structure | MW |
|---|---|---|
| TAZ-L-124 | 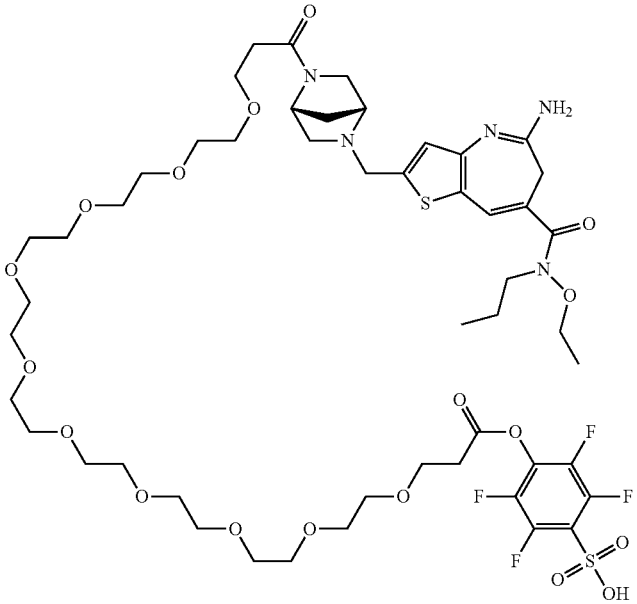 [SMILES: CCCN(OCC)C(=O)C1=Cc2sc(CN3C[C@H]4C[C@@H]3CN4C(=O)CCOCCOCCOCCOCCOCCOCCOCCOCCOCCOCCC(=O)Oc3c(F)c(F)c(S(=O)(=O)O)c(F)c3F)cc2N=C(N)C1] | 1172.3 |
| TAZ-L-125 | 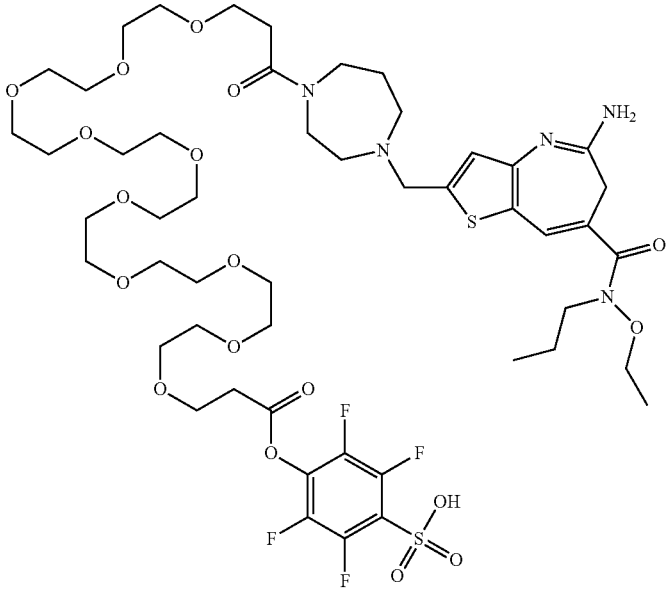 [SMILES: CCCN(OCC)C(=O)C1=Cc2sc(CN3CCCN(C(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1174.3 |

TABLE 2C-continued

Thienoazepine-linker (TAZ-L) Formula II compounds

| TAZ-L No. | Structure | MW |
|---|---|---|
| TAZ-L-126 | 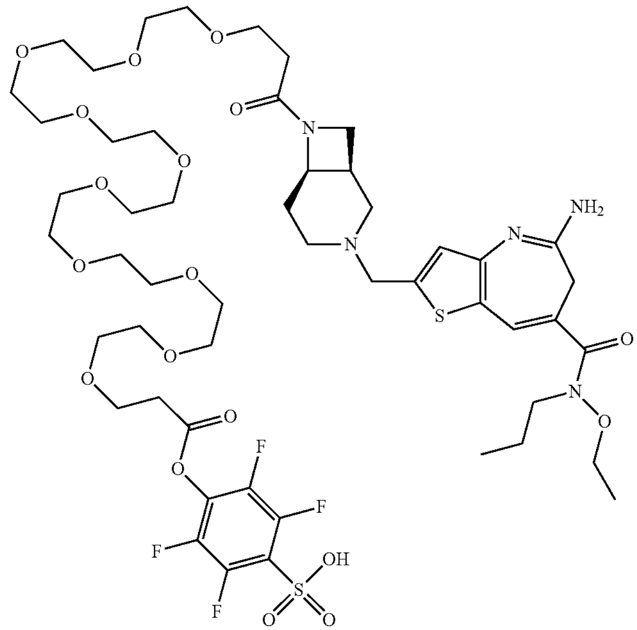 [SMILES: CCCN(OCC)C(=O)C1=Cc2sc(CN3CC[C@@H]4[C@H](C3)CN4C(=O)CCOCCOCCOCCOCCOCCOCCOCCOCCOCCOCCC(=O)Oc3c(F)c(F)c(S(=O)(=O)O)c(F)c3F)cc2N=C(N)C1] | 1186.3 |
| TAZ-L-127 | 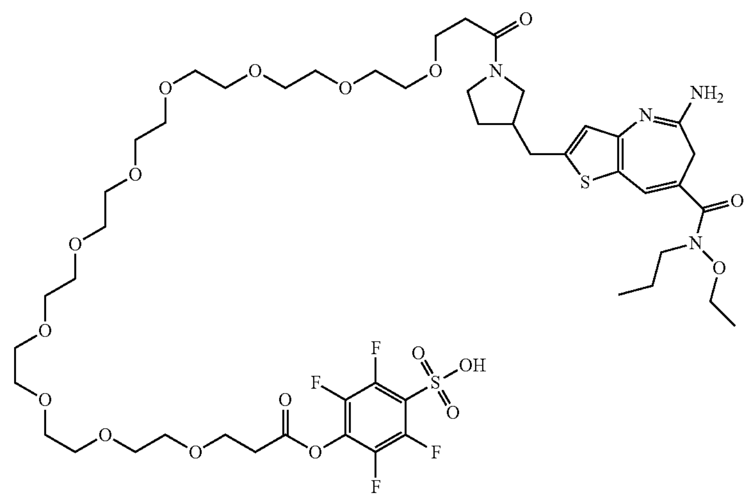 [SMILES: CCCN(OCC)C(=O)C1=Cc2sc(CC3CCN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1145.2 |
| TAZ-L-128 | 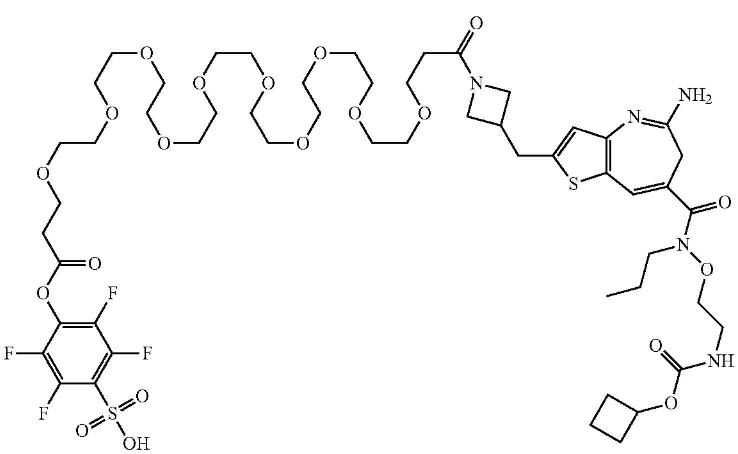 [SMILES: CCCN(OCCNC(=O)OC1CCC1)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1244.3 |

TABLE 2C-continued

Thienoazepine-linker (TAZ-L) Formula II compounds

| TAZ-L No. | Structure | MW |
|---|---|---|
| TAZ-L-129 | 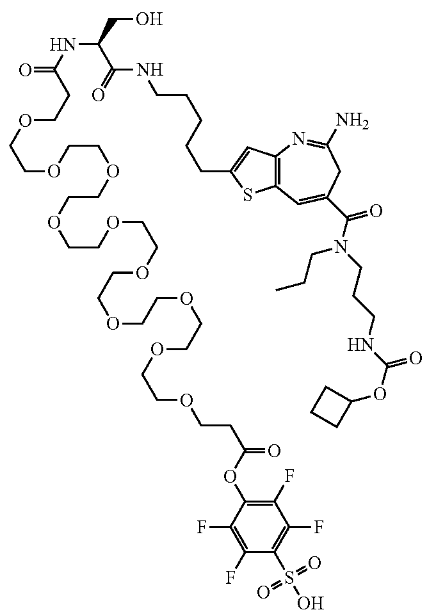 [SMILES: CCCN(CCCNC(=O)OC1CCC1)C(=O)C1=Cc2sc(CCCCCNC(=O)[C@H](CO)NC(=O)CCOCCOCCOCCOCCOCCOCCOCCOCCOCCOCCC(=O)Oc3c(F)c(F)c(S(=O)(=O)O)c(F)c3F)cc2N=C(N)C1] | 1409.5 |
| TAZ-L-130 | 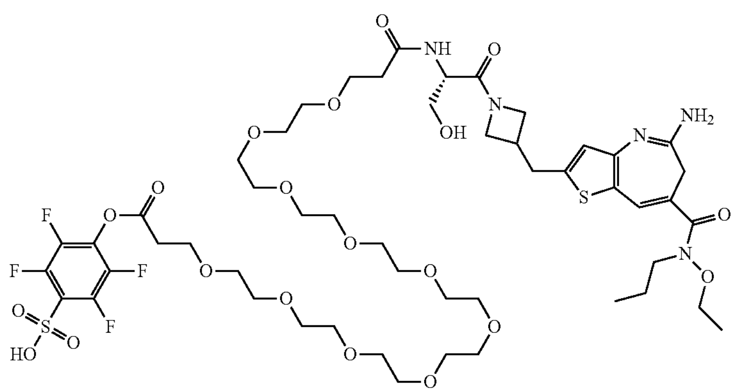 [SMILES: CCCN(OCC)C(=O)C1=Cc2sc(CC3CN(C(=O)[C@H](CO)NC(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1282.4 |
| TAZ-L-131 | 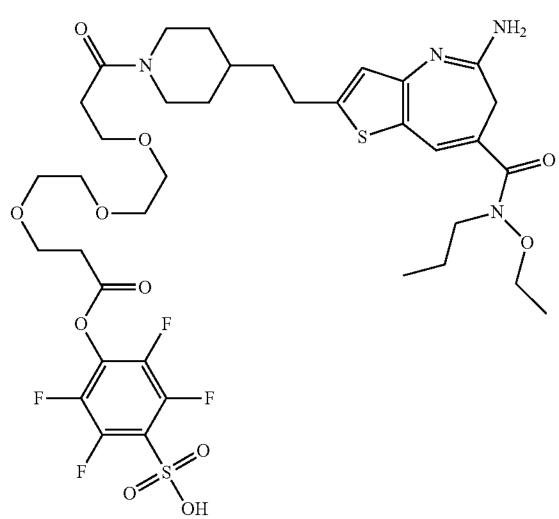 [SMILES: CCCN(OCC)C(=O)C1=Cc2sc(CCC3CCN(C(=O)CCOCCOCCOCCC(=O)Oc4c(F)c(F)c(S(=O)(=O)O)c(F)c4F)CC3)cc2N=C(N)C1] | 864.9 |

TABLE 2C-continued

Thienoazepine-linker (TAZ-L) Formula II compounds

| TAZ-L No. | Structure | MW |
|---|---|---|
| TAZ-L-132 | 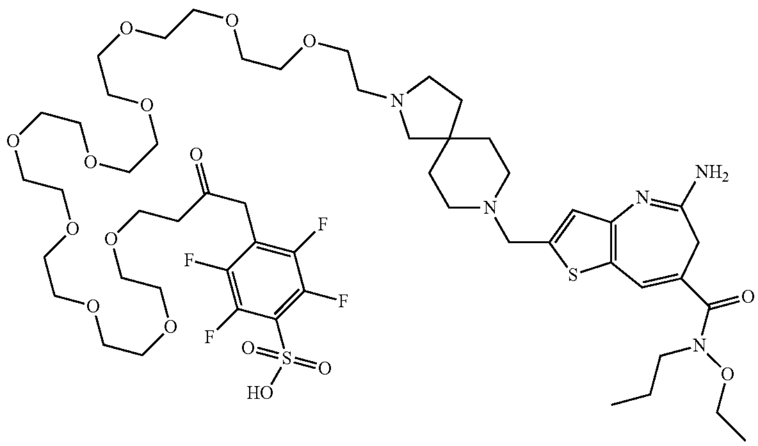 [SMILES: CCCN(OCC)C(=O)C1=Cc2sc(CN3CCC4(CC3)CCN(CCOCCOCCOCCOCCOCCOCCOCCOCCOCCOCCC(=O)Cc3c(F)c(F)c(S(=O)(=O)O)c(F)c3F)C4)cc2N=C(N)C1] | 1186.3 |
| TAZ-L-133 | 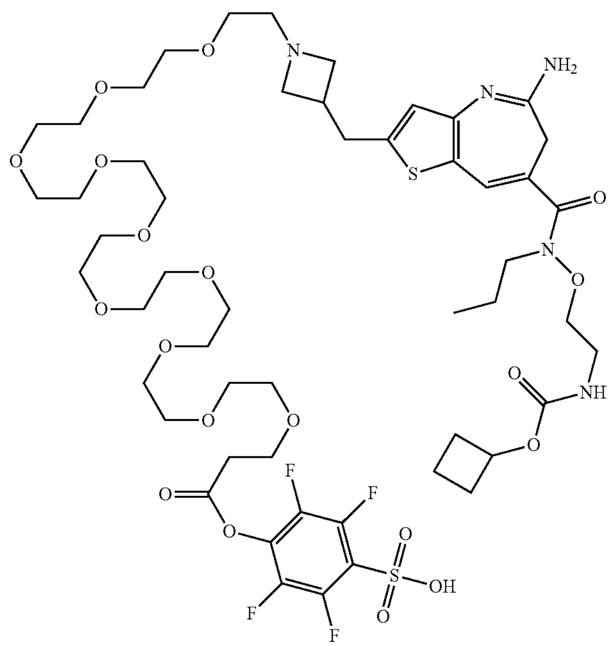 [SMILES: CCCN(OCCNC(=O)OC1CCC1)C(=O)C1=Cc2sc(CC3CN(CCOCCOCCOCCOCCOCCOCCOCCOCCOCCOCCC(=O)Oc4c(F)c(F)c(S(=O)(=O)O)c(F)c4F)C3)cc2N=C(N)C1] | 1216.3 |
| TAZ-L-134 | 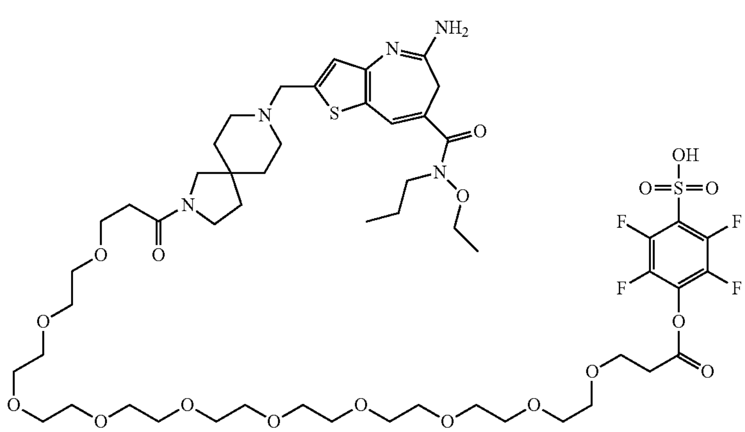 [SMILES: CCCN(OCC)C(=O)C1=Cc2sc(CN3CCC4(CC3)CCN(C(=O)CCOCCOCCOCCOCCOCCOCCOCCOCCOCCOCCC(=O)Oc3c(F)c(F)c(S(=O)(=O)O)c(F)c3F)C4)cc2N=C(N)C1] | 1214.3 |

TABLE 2C-continued
Thienoazepine-linker (TAZ-L) Formula II compounds
| TAZ-L No. | Structure | MW |
|---|---|---|
| TAZ-L-135 | 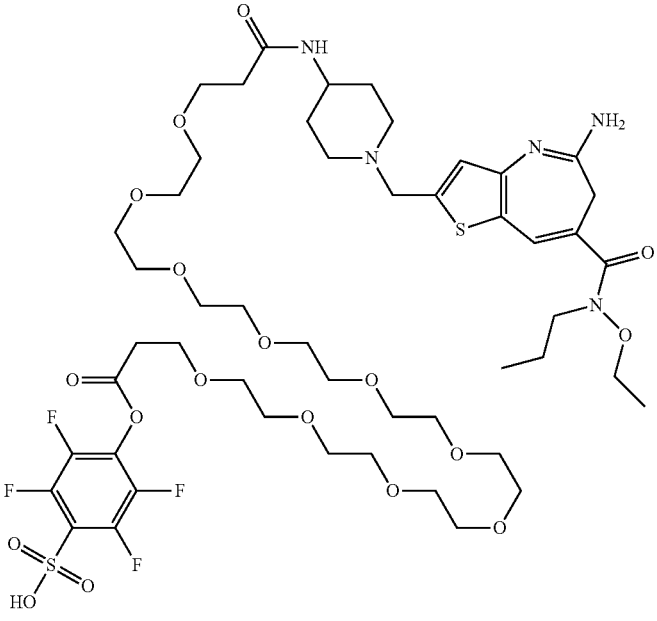 [SMILES: CCCN(OCC)C(=O)C1=Cc2sc(CN3CCC(NC(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1174.3 |
| TAZ-L-136 | 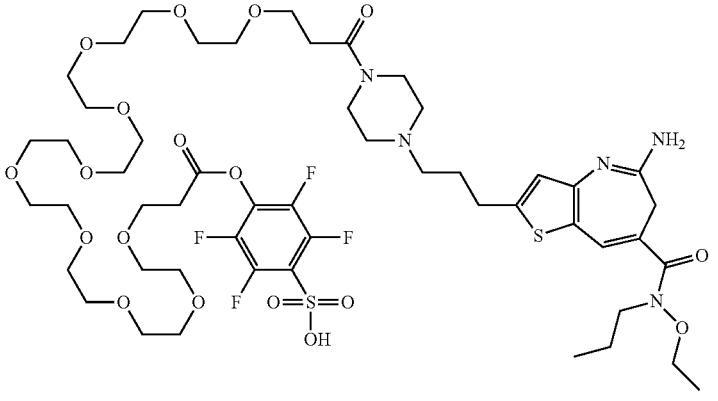 [SMILES: CCCN(OCC)C(=O)C1=Cc2sc(CCCN3CCN(C(=O)CCOCCOCCOCCOCCOCCOCCOCCOCCOCCOCCC(=O)Oc4c(F)c(F)c(S(=O)(=O)O)c(F)c4F)CC3)cc2N=C(N)C1] | 1188.3 |

TABLE 2C-continued
Thienoazepine-linker (TAZ-L) Formula II compounds
| TAZ-L No. | Structure | MW |
|---|---|---|
| TAZ-L-137 | 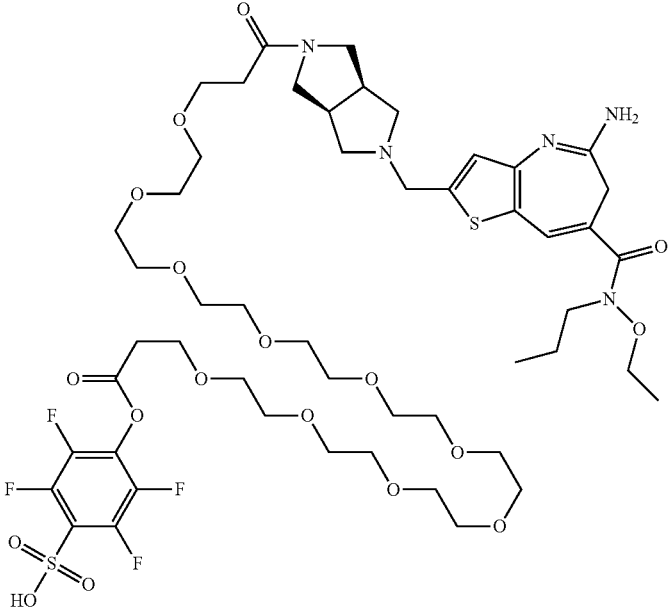 [SMILES: CCCN(OCC)C(=O)C1=Cc2sc(CN3C[C@@H]4CN(C(=O)CCOCCOCCOCCOCCOCCOCCOCCOCCOCCOCCC(=O)Oc5c(F)c(F)c(S(=O)(=O)O)c(F)c5F)C[C@@H]4C3)cc2N=C(N)C1] | 1186.3 |
| TAZ-L-138 | 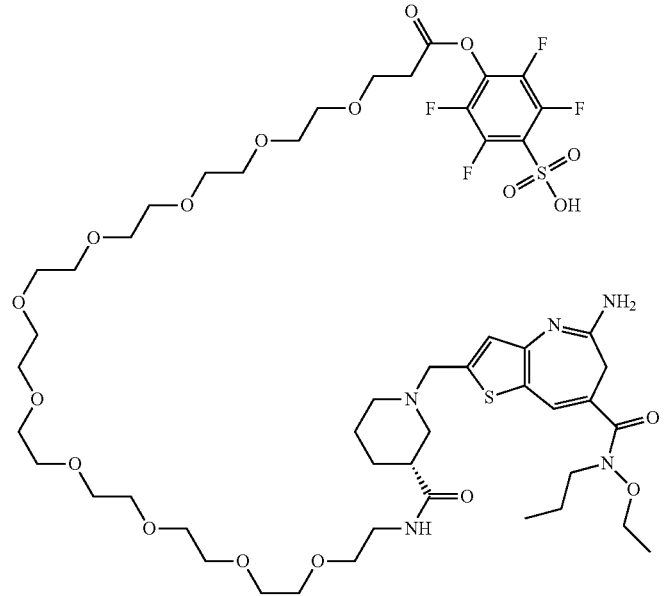 [SMILES: CCCN(OCC)C(=O)C1=Cc2sc(CN3CCC[C@@H](C(=O)NCCOCCOCCOCCOCCOCCOCCOCCOCCOCCOCCC(=O)Oc4c(F)c(F)c(S(=O)(=O)O)c(F)c4F)C3)cc2N=C(N)C1] | 1174.3 |

TABLE 2C-continued
Thienoazepine-linker (TAZ-L) Formula II compounds
| TAZ-L No. | Structure | MW |
|---|---|---|
| TAZ-L-139 | 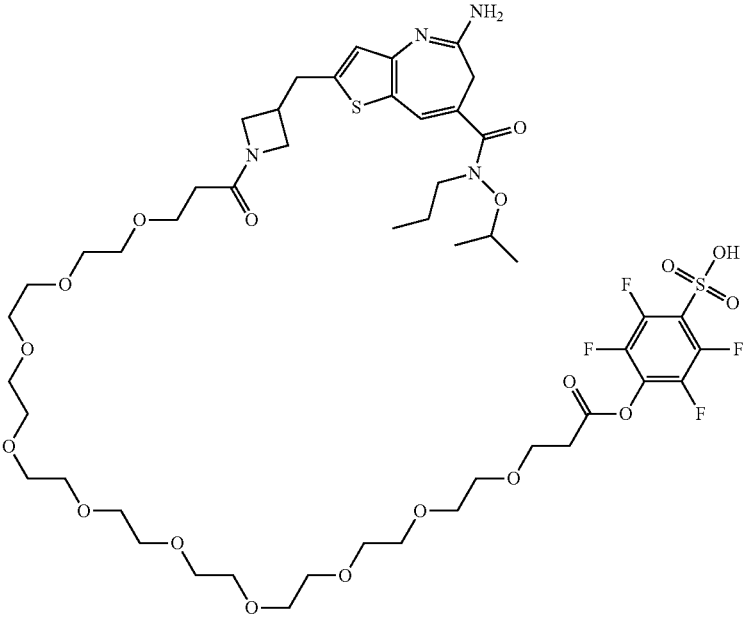 [SMILES: CCCN(OC(C)C)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1145.2 |
| TAZ-L-140 | 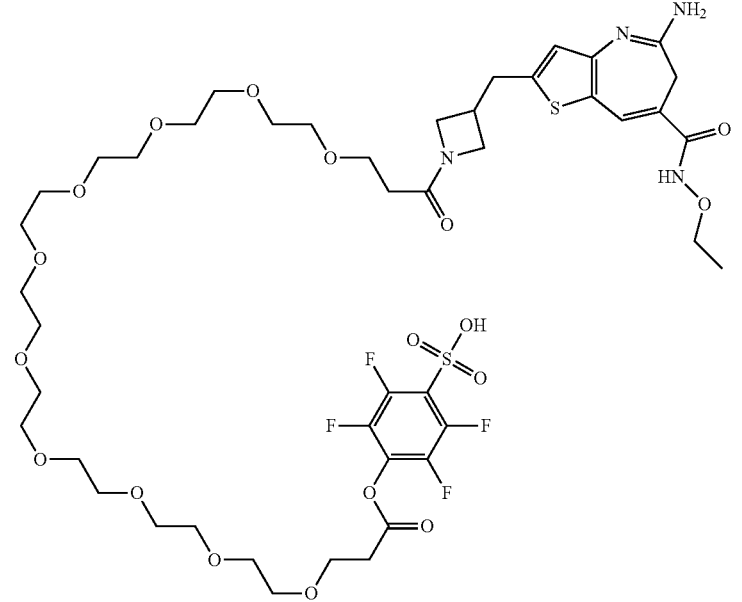 [SMILES: CCONC(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1089.1 |

TABLE 2C-continued

Thienoazepine-linker (TAZ-L) Formula II compounds

| TAZ-L No. | Structure | MW |
| --- | --- | --- |
| TAZ-L-141 | 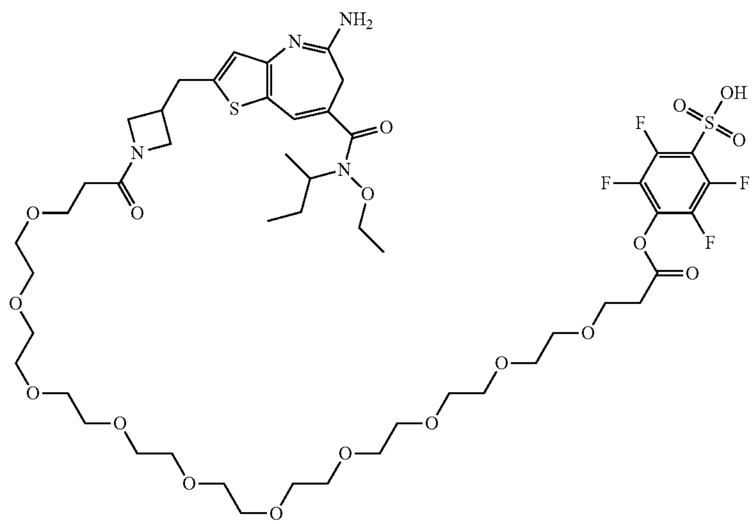 [SMILES: CCON(C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1)C(C)CC] | 1145.2 |
| TAZ-L-142 | 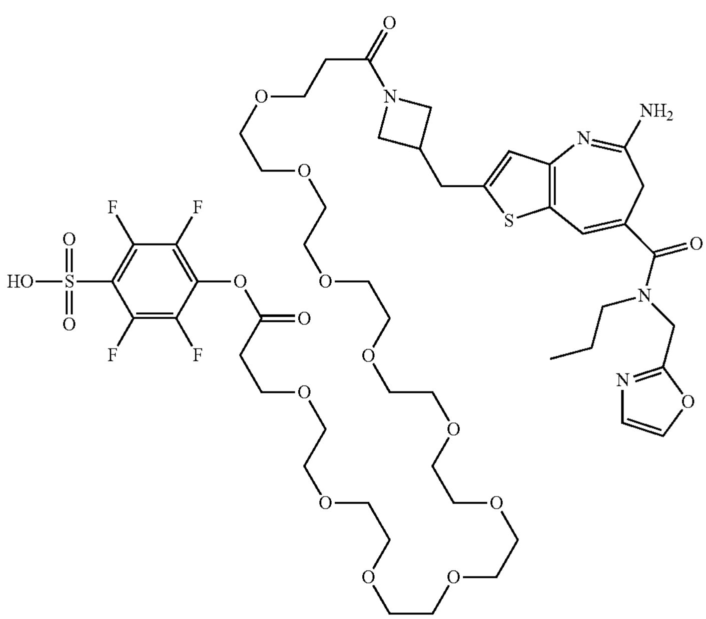 [SMILES: CCCN(Cc1ncco1)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1168.2 |

TABLE 2C-continued
Thienoazepine-linker (TAZ-L) Formula II compounds
| TAZ-L No. | Structure | MW |
| --- | --- | --- |
| TAZ-L-143 | 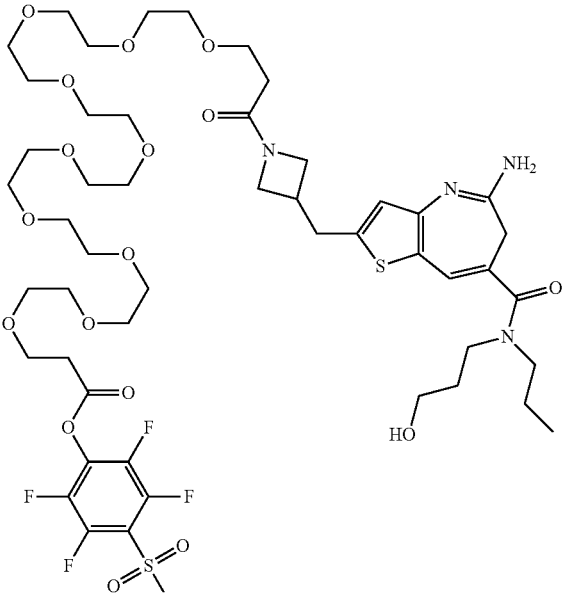 | 1145.2 |
| TAZ-L-144 | 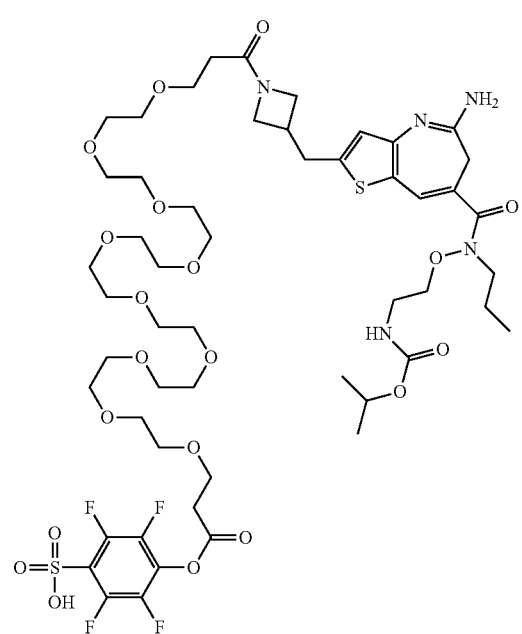 [SMILES: CCCN(OCCNC(=O)OC(C)C)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1232.3 |

TABLE 2C-continued

Thienoazepine-linker (TAZ-L) Formula II compounds

| TAZ-L No. | Structure | MW |
| --- | --- | --- |
| TAZ-L-145 | 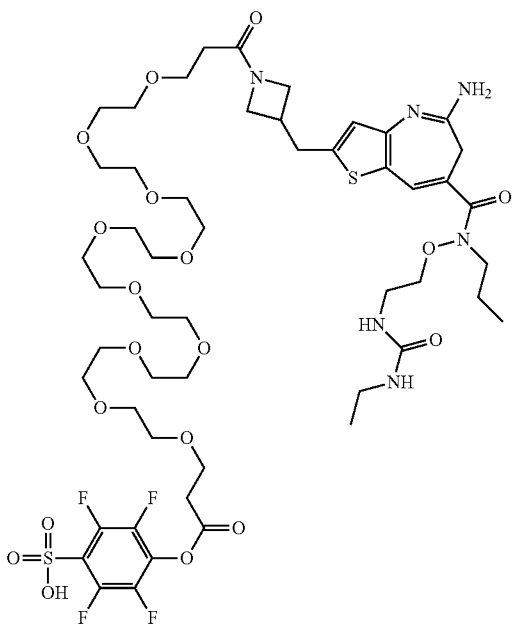 [SMILES: CCCN(OCCNC(=O)NCC)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1217.3 |
| TAZ-L-146 | 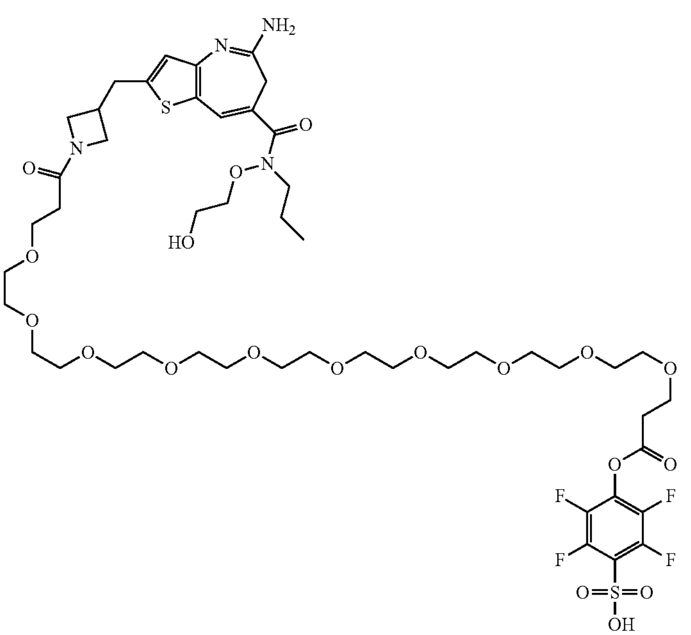 [SMILES: CCCN(OCCO)C(=O)C1=Cc2sc(CC3CN(C(=O)CCOCCOCCOCCOCCOCCOCCOCCOCCOCCOCCC(=O)Oc4c(F)c(F)c(S(=O)(=O)O)c(F)c4F)C3)cc2N=C(N)C1] | 1147.2 |

TABLE 2C-continued
Thienoazepine-linker (TAZ-L) Formula II compounds
| TAZ-L No. | Structure | MW |
|---|---|---|
| TAZ-L-147 | 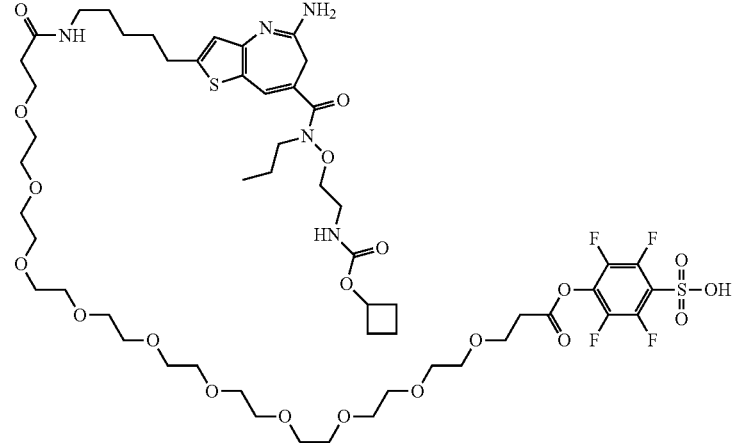 [SMILES: CCCN(OCCNC(=O)OC1CCC1)C(=O)C1=Cc2sc(CCCCCNC(=O)CCOCCOCCOCCOCCOCCOCCOCCOCCOCCOCCC(=O)Oc3c(F)c(F)c(S(=O)(=O)O)c(F)c3F)cc2N=C(N)C1] | 1260.4 |
| TAZ-L-148 | 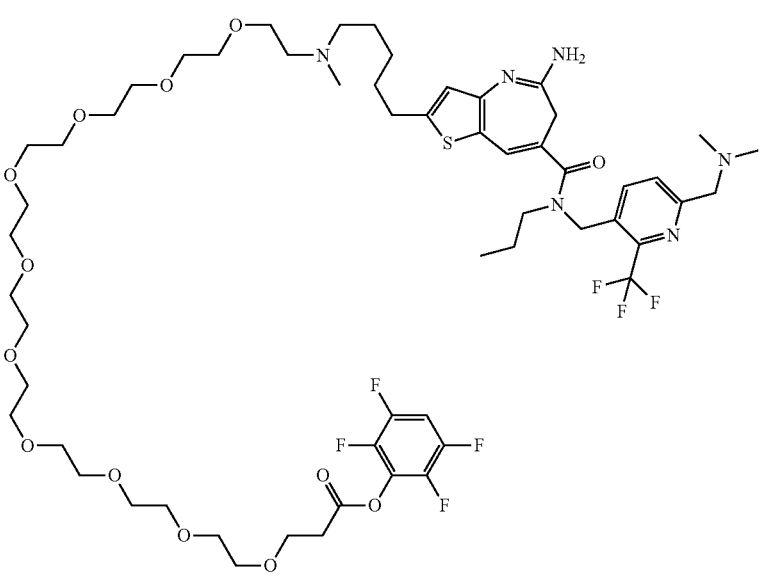 [SMILES: CCCN(Cc1ccc(CN(C)C)nc1C(F)(F)F)C(=O)C1=Cc2sc(CCCCCN(C)CCOCCOCCOCCOCCOCCOCCOCCOCCOCCOCCC(=O)Oc3c(F)c(F)cc(F)c3F)cc2N=C(N)C1] | 1225.4 |

TABLE 2C-continued
Thienoazepine-linker (TAZ-L) Formula II compounds
| TAZ-L No. | Structure | MW |
| --- | --- | --- |
| TAZ-L-149 | 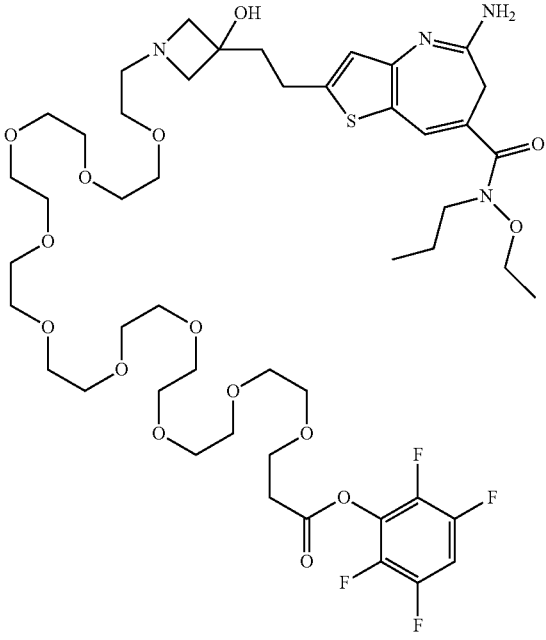 [SMILES: CCCN(OCC)C(=O)C1=Cc2sc(CCC3(O)CN(CCOCCOCCOCCOCCOCCOCCOCCOCCOCCOCCC(=O)Oc4c(F)c(F)cc(F)c4F)C3)cc2N=C(N)C1] | 1053.2 |
| TAZ-L-150 | 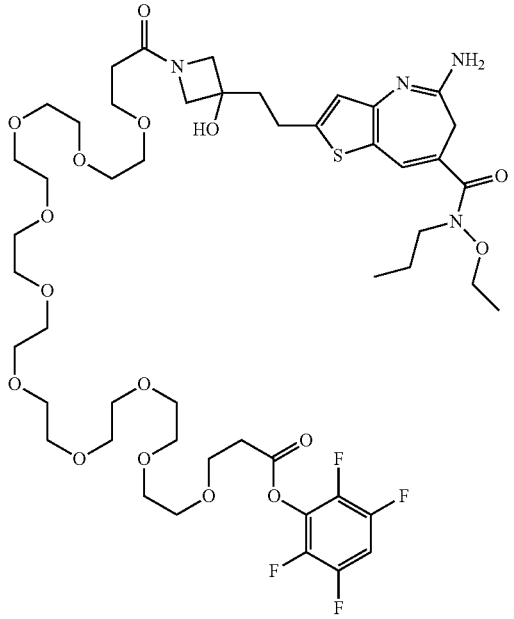 [SMILES: CCCN(OCC)C(=O)C1=Cc2sc(CCC3(O)CN(C(=O)CCOCCOCCOCCOCCOCCOCCOCCOCCOCCOCCC(=O)Oc4c(F)c(F)cc(F)c4F)C3)cc2N=C(N)C1] | 1081.2 |

Immunoconjugates

Exemplary embodiments of immunoconjugates comprise an antibody covalently attached to one or more 5-aminothienoazepine (TAZ) moieties by a linker, and having Formula I:

Ab-[L-TAZ]$_p$   I or a pharmaceutically acceptable salt thereof,
wherein:
Ab is the antibody;
p is an integer from 1 to 8;
TAZ is the 5-aminothienoazepine moiety having the formula:

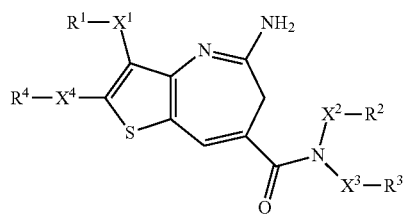

$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:
—($C_1$-$C_{12}$ alkyldiyl)-N($R^5$)—*;
—($C_1$-$C_{12}$ alkyldiyl)-N($R^5$)$_2$;
—($C_1$-$C_{12}$ alkyldiyl)-O$R^5$;
—($C_3$-$C_{12}$ carbocyclyl);
—($C_3$-$C_{12}$ carbocyclyl)-*;
—($C_3$-$C_{12}$ carbocyclyl)-($C_1$-$C_{12}$ alkyldiyl)-N$R^5$—*;
—($C_3$-$C_{12}$ carbocyclyl)-($C_1$-$C_{12}$ alkyldiyl)-N($R^5$)$_2$;
—($C_3$-$C_{12}$ carbocyclyl)-N$R^5$—C(=N$R^5$)N$R^5$—*;
—($C_6$-$C_{20}$ aryl);
—($C_6$-$C_{20}$ aryl)-*;
—($C_6$-$C_{20}$ aryldiyl)-N($R^5$)—*;
—($C_6$-$C_{20}$ aryldiyl)-($C_1$-$C_{12}$ alkyldiyl)-N($R^5$)—*;
—($C_6$-$C_{20}$ aryldiyl)-($C_1$-$C_{12}$ alkyldiyl)-($C_2$-$C_{20}$ heterocyclyldiyl)-*;
—($C_6$-$C_{20}$ aryldiyl)-($C_1$-$C_{12}$ alkyldiyl)-N($R^5$)$_2$;
—($C_6$-$C_{20}$ aryldiyl)-($C_1$-$C_{12}$ alkyldiyl)-N$R^5$—C(=N$R^{5a}$)N($R^5$)—*;
—($C_2$-$C_{20}$ heterocyclyl);
—($C_2$-$C_{20}$ heterocyclyl)-*;
—($C_2$-$C_9$ heterocyclyl)-($C_1$-$C_{12}$ alkyldiyl)-N$R^5$—*;
—($C_2$-$C_9$ heterocyclyl)-($C_1$-$C_{12}$ alkyldiyl)-N($R^5$)$_2$;
—($C_2$-$C_9$ heterocyclyl)-C(=O)—($C_1$-$C_{12}$ alkyldiyl)-N($R^5$)—*;
—($C_2$-$C_9$ heterocyclyl)-N$R^5$—C(=N$R^{5a}$)N$R^5$—*;
—($C_2$-$C_9$ heterocyclyl)-N$R^5$—($C_6$-$C_{20}$ aryldiyl)-($C_1$-$C_{12}$ alkyldiyl)-N($R^5$)—*;
—($C_2$-$C_9$ heterocyclyl)-($C_6$-$C_{20}$ aryldiyl)-*;
—($C_1$-$C_{20}$ heteroaryl);
—($C_1$-$C_{20}$ heteroaryl)-*;
—($C_1$-$C_{20}$ heteroaryl)-($C_1$-$C_{12}$ alkyldiyl)-N($R^5$)—*;
—($C_1$-$C_{20}$ heteroaryl)-($C_1$-$C_{12}$ alkyldiyl)-N($R^5$)$_2$;
($C_1$-$C_{20}$ heteroaryl)-N$R^5$—C(=N$R^{5a}$)N($R^5$)—*;
($C_1$-$C_{20}$ heteroaryl)-N($R^5$)C(=O)—($C_1$-$C_{12}$ alkyldiyl)-N($R^5$)—*;
—C(=O)—*;
—C(=O)—($C_1$-$C_{12}$ alkyldiyl)-N($R^5$)—*;
—C(=O)—($C_2$-$C_{20}$ heterocyclyldiyl)-*;
—C(=O)N($R^5$)$_2$;
—C(=O)N($R^5$)—*;
—C(=O)N($R^5$)—($C_1$-$C_{12}$ alkyldiyl)-N($R^5$)C(=O)$R^5$;
—C(=O)N($R^5$)—($C_1$-$C_{12}$ alkyldiyl)-N($R^5$)C(=O)N($R^5$)$_2$;
—C(=O)N$R^5$—($C_1$-$C_{12}$ alkyldiyl)-N($R^5$)CO$_2$$R^5$;
—C(=O)N$R^5$—($C_1$-$C_{12}$ alkyldiyl)-N($R^5$)C(=N$R^{5a}$)N($R^5$)$_2$;
—C(=O)N$R^5$—($C_1$-$C_{12}$ alkyldiyl)-N$R^5$C(=N$R^{5a}$)$R^5$;
—C(=O)N$R^5$—($C_1$-$C_8$ alkyldiyl)-N$R^5$($C_2$-$C_5$ heteroaryl);
—C(=O)N$R^5$—($C_1$-$C_{20}$ heteroaryldiyl)-N($R^5$)—*;
—C(=O)N$R^5$—($C_1$-$C_{20}$ heteroaryldiyl)-*;
—C(=O)N$R^5$—($C_1$-$C_{20}$ heteroaryldiyl)—($C_1$-$C_{12}$ alkyldiyl)-N($R^5$)$_2$;
—C(=O)N$R^5$—($C_1$-$C_{20}$ heteroaryldiyl)-($C_2$-$C_{20}$ heterocyclyldiyl)-C(=O)N$R^5$—($C_1$-$C_{12}$ alkyldiyl)-N$R^5$—*;
—N($R^5$)$_2$;
—N($R^5$)—*;
—N($R^5$)C(=O)$R^5$;
—N($R^5$)C(=O)—*;
—N($R^5$)C(=O)N($R^5$)$_2$;
—N($R^5$)C(=O)N($R^5$)—*;
—N($R^5$)CO$_2$$R^5$;
—N$R^5$C(=N$R^{5a}$)N($R^5$)$_2$;
—N$R^5$C(=N$R^{5a}$)N($R^5$)—*;
—N$R^5$C(=N$R^{5a}$)$R^5$;
—N($R^5$)C(=O)—($C_1$-$C_{12}$ alkyldiyl)-N($R^5$)—*;
—N($R^5$)—($C_2$-$C_5$ heteroaryl);
—N($R^5$)—S(=O)$_2$—($C_1$-$C_{12}$ alkyl);
—O—($C_1$-$C_{12}$ alkyl);
—O—($C_1$-$C_{12}$ alkyldiyl)-N($R^5$)$_2$;
—O—($C_1$-$C_{12}$ alkyldiyl)-N($R^5$)—*;
—S(=O)$_2$—($C_2$-$C_{20}$ heterocyclyldiyl)-*;
—S(=O)$_2$—($C_2$-$C_{20}$ heterocyclyldiyl)-($C_1$-$C_{12}$ alkyldiyl)-N($R^5$)$_2$;
—S(=O)$_2$—($C_2$-$C_{20}$ heterocyclyldiyl)-($C_1$-$C_{12}$ alkyldiyl)-N$R^5$—*; and
—S(=O)$_2$—($C_2$-$C_{20}$ heterocyclyldiyl)-($C_1$-$C_{12}$ alkyldiyl)-OH;

or $R^2$ and $R^3$ together form a 5- or 6-membered heterocyclyl ring;

$X^1$, $X^2$, $X^3$, and $X^4$ are independently selected from the group consisting of a bond, C(=O), C(=O)N($R^5$), O, N($R^5$), S, S(O)$_2$, and S(O)$_2$N($R^5$);

$R^5$ is selected from the group consisting of H, $C_6$-$C_{20}$ aryl, $C_3$-$C_{12}$ carbocyclyl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;

$R^{5a}$ is selected from the group consisting of $C_6$-$C_{20}$ aryl and $C_1$-$C_{20}$ heteroaryl;

where the asterisk * indicates the attachment site of L, and where one of $R^1$, $R^2$, $R^3$ and $R^4$ is attached to L;

L is the linker selected from the group consisting of:
—C(=O)-(PEG)-;
—C(=O)-(PEG)-C(=O)—;
—C(=O)-(PEG)-O—;
—C(=O)-(PEG)-C(=O)—(PEP)-;
—C(=O)-(PEG)-C(=O)N($R^5$)—($C_1$-$C_{12}$ alkyldiyl)-;
—C(=O)-(PEG)-C(=O)N($R^5$)—($C_1$-$C_{12}$ alkyldiyl)-N($R^5$)C(=O)—($C_2$-$C_5$ monoheterocyclyldiyl)-;
—C(=O)-(PEG)-C(=O)N($R^5$)—($C_1$-$C_{12}$ alkyldiyl)-(MCgluc)-;
—C(=O)-(PEG)-C(=O)-(MCgluc)-;
—C(=O)-(PEG)-C(=O)—(PEP)-N($R^5$)—($C_1$-$C_{12}$ alkyldiyl)-;

—C(=O)-(PEG)-C(=O)—(PEP)-N(R$^5$)—(C$_1$-C$_{12}$ alkyldiyl)-N(R$^5$)C(=O)—(C$_2$-C$_5$ monoheterocyclyldiyl)-;

—C(=O)-(PEG)-N(R$^5$)—;

—C(=O)-(PEG)-N(R$^5$)C(=O)—;

—C(=O)-(PEG)-N(R$^5$)-(PEG)-C(=O)—(PEP)-;

—C(=O)-(PEG)-N$^+$(R$^5$)$_2$-(PEG)-C(=O)—(PEP)-;

—C(=O)-(PEG)-C(=O)—N(R$^5$)CH(AA$_1$)C(=O)-(PEG)-C(=O)—(PEP)-;

—C(=O)-(PEG)-C(=O)—N(R$^5$)CH(AA$_1$)C(=O)—N(R$^5$)—(C$_1$-C$_{12}$ alkyldiyl)-;

—C(=O)-(PEG)-SS—(C$_1$-C$_{12}$ alkyldiyl)-OC(=O)—;

—C(=O)-(PEG)-SS—(C$_1$-C$_{12}$ alkyldiyl)-C(=O)—;

—C(=O)—(C$_1$-C$_{12}$ alkyldiyl)-C(=O)—(PEP)-;

—C(=O)—(C$_1$-C$_{12}$ alkyldiyl)-C(=O)—(PEP)-N(R$^5$)—(C$_1$-C$_{12}$ alkyldiyl)-;

—C(=O)—(C$_1$-C$_{12}$ alkyldiyl)-C(=O)—(PEP)-N(R$^5$)—(C$_1$-C$_{12}$ alkyldiyl)-N(R$^5$)—C(=O);

—C(=O)—(C$_1$-C$_{12}$ alkyldiyl)-C(=O)—(PEP)-N(R$^5$)—(C$_1$-C$_{12}$ alkyldiyl)-N(R$^5$)C(=O)—(C$_2$-C$_5$ monoheterocyclyldiyl)-;

—C(=O)—CH$_2$CH$_2$OCH$_2$CH$_2$—(C$_1$-C$_{20}$ heteroaryldiyl)-CH$_2$O-(PEG)-C(=O)-(MCgluc)-;

—C(=O)—CH$_2$CH$_2$OCH$_2$CH$_2$—(C$_1$-C$_{20}$ heteroaryldiyl)-CH$_2$O-(PEG)-C(=O)-(MCgluc)-N(R$^5$)—(C$_1$-C$_{12}$ alkyldiyl)-N(R$^5$)C(=O)—(C$_2$-C$_5$ monoheterocyclyldiyl)-; and -(succinimidyl)-(CH$_2$)$_m$—C(=O)—(PEP)-N(R$^5$)—(C$_1$-C$_{12}$ alkyldiyl)-N(R$^5$)C(=O)—(C$_2$-C$_5$ monoheterocyclyldiyl)-;

PEG has the formula: —(CH$_2$CH$_2$O)$_n$—(CH$_2$)$_m$—; m is an integer from 1 to 5, and n is an integer from 2 to 50;

PEP has the formula:

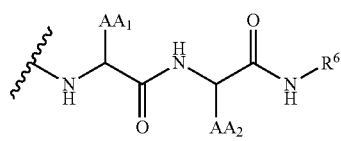

where AA$_1$ and AA$_2$ are independently selected from an amino acid side chain, or AA$_1$ or AA$_2$ and an adjacent nitrogen atom form a 5-membered ring proline amino acid, and the wavy line indicates a point of attachment;

R$^6$ is selected from the group consisting of C$_6$-C$_{20}$ aryldiyl and C$_1$-C$_{20}$ heteroaryldiyl, substituted with —CH$_2$O—C(=O)— and optionally with:

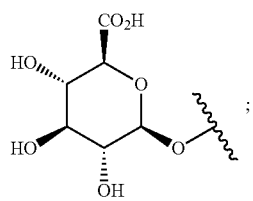 [SMILES: *O[C@@H]1O[C@H](C(=O)O)[C@@H](O)[C@H](O)[C@H]1O]

and

MCgluc is selected from the groups:

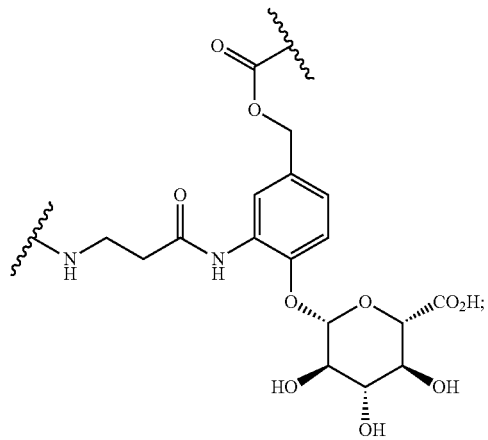

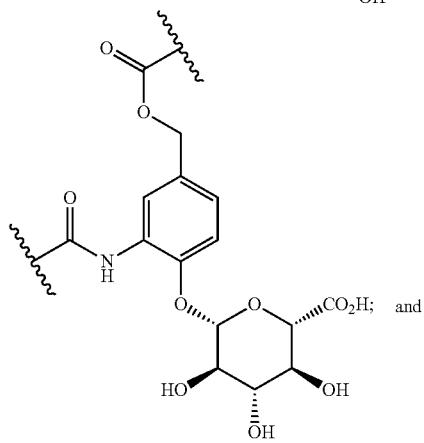

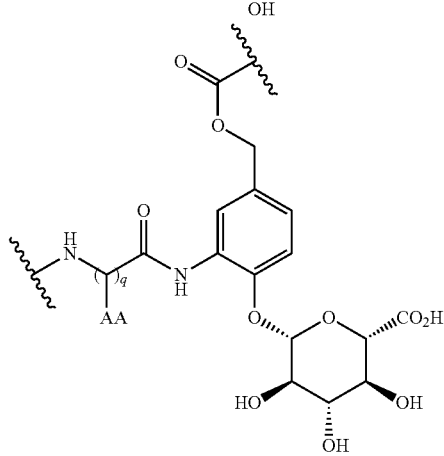

where q is 1 to 8, and AA is an amino acid side chain; and alkyl, alkyldiyl, alkenyl, alkenyldiyl, alkynyl, alkynyldiyl, aryl, aryldiyl, carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —CH$_3$, —CH$_2$CH$_3$, —CH=CH$_2$, —C≡CH, —C≡CCH$_3$, —CH$_2$CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CH$_2$NH$_2$, —CH$_2$NHSO$_2$CH$_3$, —CH$_2$NHCH$_3$, —CH$_2$N(CH$_3$)$_2$, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NHC(=NH)H, —NHC(=NH)CH$_3$, —NHC(=NH)NH$_2$, —NHC(=O)NH$_2$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —O(CH$_2$CH$_2$O)$_n$—(CH$_2$)$_m$CO$_2$H, —O(CH$_2$CH$_2$O)$_n$ H, —OCH$_2$F, —OCHF$_2$, —OCF$_3$, —OP(O)(OH)$_2$, —S(O)$_2$N(CH$_3$)$_2$, —SCH$_3$, —S(O)$_2$CH$_3$, and —S(O)$_3$H.

An exemplary embodiment of the immunoconjugate of Formula I includes wherein the antibody is an antibody construct that has an antigen binding domain that binds PD-L1.

An exemplary embodiment of the immunoconjugate of Formula I includes wherein the antibody is selected from the group consisting of atezolizumab, durvalumab, and avelumab, or a biosimilar or a biobetter thereof.

An exemplary embodiment of the immunoconjugate of Formula I includes wherein the antibody is an antibody construct that has an antigen binding domain that binds HER2.

An exemplary embodiment of the immunoconjugate of Formula I includes wherein the antibody is selected from the group consisting of trastuzumab and pertuzumab, or a biosimilar or a biobetter thereof.

An exemplary embodiment of the immunoconjugate of Formula I includes wherein the antibody is an antibody construct that has an antigen binding domain that binds CEA.

An exemplary embodiment of the immunoconjugate of Formula I includes wherein the antibody is labetuzumab, or a biosimilar or a biobetter thereof.

An exemplary embodiment of the immunoconjugate of Formula I includes wherein the antibody is an antibody construct that has an antigen binding domain that binds Caprin-1.

An exemplary embodiment of the immunoconjugate of Formula I includes wherein PEP has the formula:

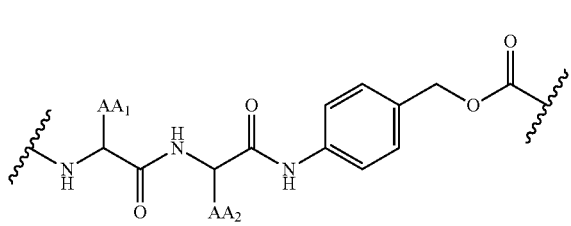

wherein AA$_1$ and AA$_2$ are independently selected from a side chain of a naturally-occurring amino acid.

An exemplary embodiment of the immunoconjugate of Formula I includes wherein AA$_1$ or AA$_2$ with an adjacent nitrogen atom form a 5-membered ring proline amino acid.

An exemplary embodiment of the immunoconjugate of Formula I includes wherein PEP has the formula:

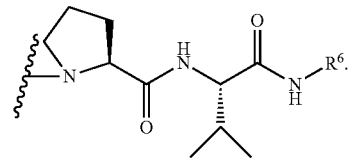

An exemplary embodiment of the immunoconjugate of Formula I includes wherein MCgluc has the formula:

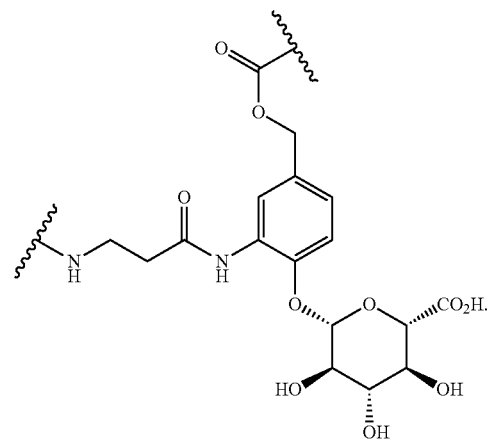 [SMILES: *NCCC(=O)Nc1cc(COC(*)=O)ccc1O[C@@H]1O[C@H](C(=O)O)[C@@H](O)[C@H](O)[C@H]1O]

An exemplary embodiment of the immunoconjugate of Formula I includes wherein AA$_1$ and AA$_2$ are independently selected from H, —CH$_3$, —CH(CH$_3$)$_2$, —CH$_2$(C$_6$H$_5$), —CH$_2$CH$_2$CH$_2$CH$_2$NH$_2$, —CH$_2$CH$_2$CH$_2$NHC(NH)NH$_2$, —CHCH(CH$_3$)CH$_3$, —CH$_2$SO$_3$H, and —CH$_2$CH$_2$CH$_2$NHC(O)NH$_2$.

An exemplary embodiment of the immunoconjugate of Formula I includes wherein AA$_1$ is —CH(CH$_3$)$_2$, and AA$_2$ is —CH$_2$CH$_2$CH$_2$NHC(O)NH$_2$.

An exemplary embodiment of the immunoconjugate of Formula I includes wherein AA$_1$ and AA$_2$ are independently selected from GlcNAc aspartic acid, —CH$_2$SO$_3$H, and —CH$_2$OPO$_3$H.

An exemplary embodiment of the immunoconjugate of Formula I includes wherein one of R$^1$ and R$^4$ is selected from the formulas:

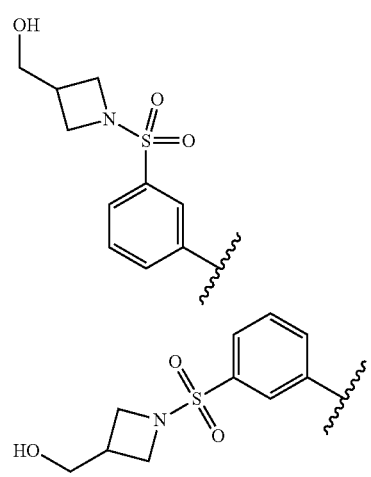

-continued

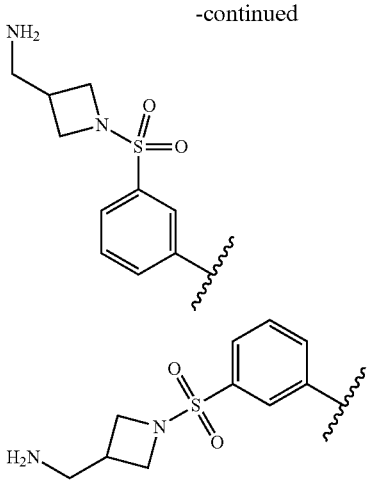

An exemplary embodiment of the immunoconjugate of Formula I includes wherein one of $R^1$ and $R^4$ is —C(=O)NR$^5$—(C$_1$-C$_{20}$ heteroaryldiyl)-(C$_2$-C$_{20}$ heterocyclyldiyl)-C(=O)NR$^5$—(C$_1$-C$_{12}$ alkyldiyl)-NR$^5$-L.

An exemplary embodiment of the immunoconjugate of Formula I includes wherein C$_1$-C$_{20}$ heteroaryldiyl is pyridindiyl and C$_2$-C$_{20}$ heterocyclyldiyl is piperidiyl.

An exemplary embodiment of the immunoconjugate of Formula I includes wherein one of $R^1$, $R^2$, $R^3$, and $R^4$ is —(C$_1$-C$_8$ alkyldiyl)-NR$^5$(C$_2$-C$_5$ heteroaryl);

An exemplary embodiment of the immunoconjugate of Formula I includes wherein NR$^5$(C$_2$-C$_5$ heteroaryl) of $R^1$, $R^2$, $R^3$, and $R^4$ is selected from:

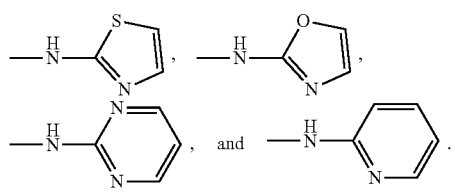

An exemplary embodiment of the immunoconjugate of Formula I includes wherein $X^1$ is a bond, and $R^1$ is H.

An exemplary embodiment of the immunoconjugate of Formula I includes wherein $X^2$ is a bond, and $R^2$ is C$_1$-C$_8$ alkyl.

An exemplary embodiment of the immunoconjugate of Formula I includes wherein $X^2$ and $X^3$ are each a bond, and $R^2$ and $R^3$ are independently selected from C$_1$-C$_8$ alkyl, —O—(C$_1$-C$_{12}$ alkyl), —(C$_1$-C$_{12}$ alkyldiyl)-OR$^5$, —(C$_1$-C$_8$ alkyldiyl)-N(R$^5$)CO$_2$R$^5$, and —O—(C$_1$-C$_{12}$ alkyl)-N(R$^5$)CO$_2$R$^5$.

An exemplary embodiment of the immunoconjugate of Formula I includes wherein $R^2$ and $R^3$ are each independently selected from —CH$_2$CH$_2$CH$_3$, —OCH$_2$CH$_3$, —CH$_2$CH$_2$CF$_3$, and —CH$_2$CH$_2$CH$_2$OH.

An exemplary embodiment of the immunoconjugate of Formula I includes wherein $R^2$ is C$_1$-C$_8$ alkyl and $R^3$ is —(C$_1$-C$_8$ alkyldiyl)-N(R$^5$)CO$_2$R$^4$.

An exemplary embodiment of the immunoconjugate of Formula I includes wherein $R^2$ is —CH$_2$CH$_2$CH$_3$ and $R^3$ is —CH$_2$CH$_2$CH$_2$NHCO$_2$(t-Bu).

An exemplary embodiment of the immunoconjugate of Formula I includes wherein $R^2$ and $R^3$ are each —CH$_2$CH$_2$CH$_3$.

An exemplary embodiment of the immunoconjugate of Formula I includes wherein $X^3$—$R^3$ is selected from the group consisting of:

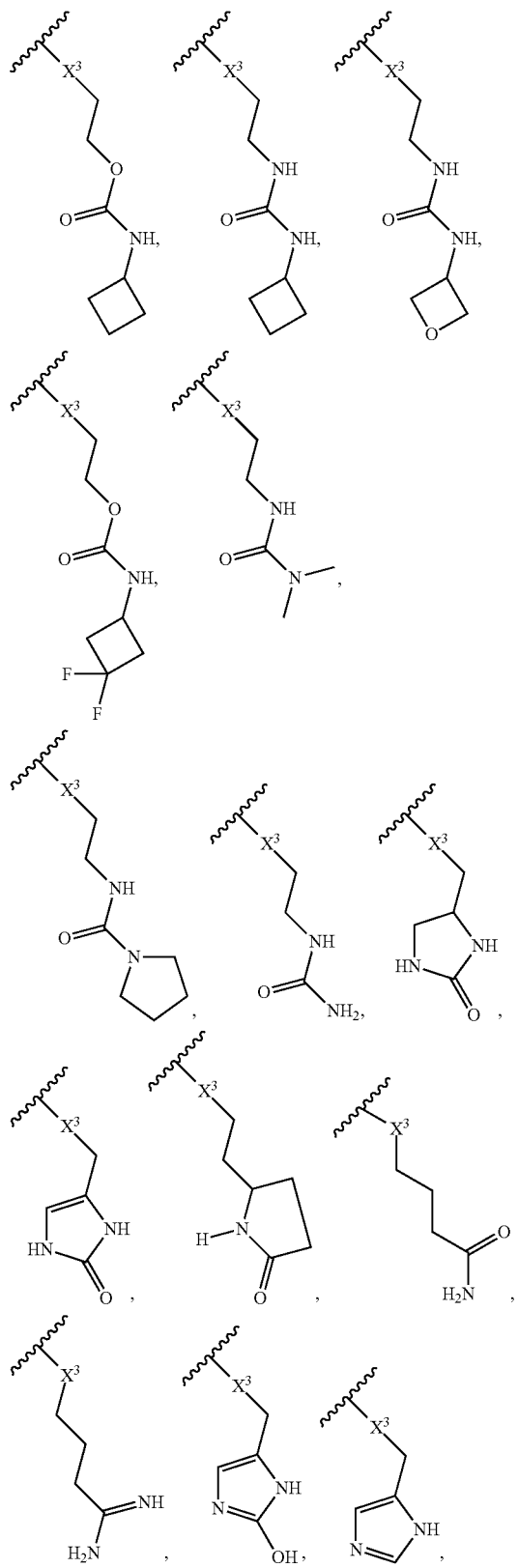

361

-continued

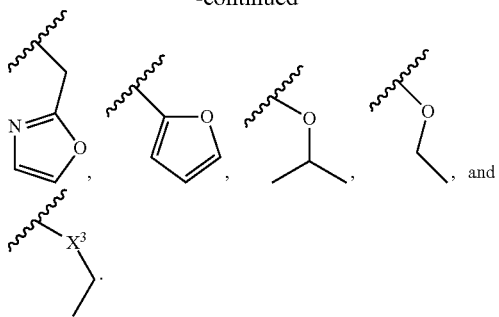

An exemplary embodiment of the immunoconjugate of Formula I includes wherein one of $R^2$ and $R^3$ is selected from:

- —($C_1$-$C_{12}$ alkyldiyl)-N($R^5$)—*;
- —($C_1$-$C_{12}$ alkyldiyl)-O—($C_1$-$C_{12}$ alkyldiyl)-N($R^5$)—*;
- —($C_1$-$C_{12}$ alkyldiyl)-N($R^5$)C(=N$R^5$)—N($R^5$)—*;
- —($C_1$-$C_{12}$ alkyldiyl)-($C_6$-$C_{20}$ aryldiyl)-($C_1$-$C_{12}$ alkyldiyl)-N($R^5$)—*;
- —($C_1$-$C_{12}$ alkyldiyl)-($C_6$-$C_{20}$ aryldiyl)-($C_1$-$C_{12}$ alkyldiyl)-N($R^5$)—C(=N$R^5$)N($R^5$)—*;
- —($C_2$-$C_6$ alkynyldiyl)-N($R^5$)—*; and
- —($C_2$-$C_6$ alkynyldiyl)-N($R^5$)C(=N$R^5$)N($R^5$)—*;

$X^2$ and $X^3$ are a bond, and where the asterisk * indicates the attachment site of L.

An exemplary embodiment of the immunoconjugate of Formula I includes wherein L is selected from the group consisting of:

- —C(=O)-(PEG)-;
- —C(=O)-(PEG)-C(=O)—;
- —C(=O)-(PEG)-O—;
- —C(=O)-(PEG)-N($R^5$)—; and
- —C(=O)-(PEG)-N($R^5$)C(=O)—.

An exemplary embodiment of the immunoconjugate of Formula I is selected from Formulae Ia-Ic:

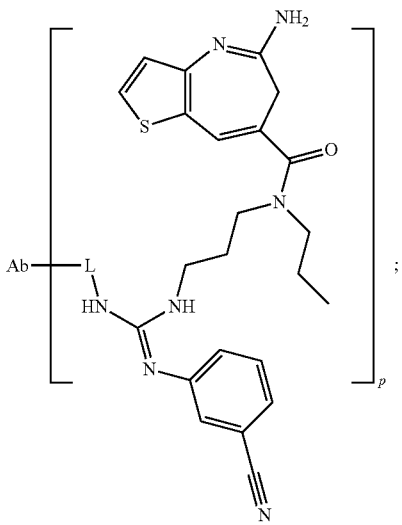

Ia

362

-continued

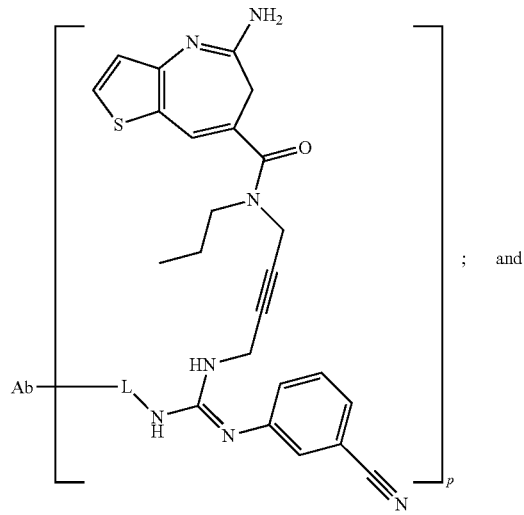

Ib

; and

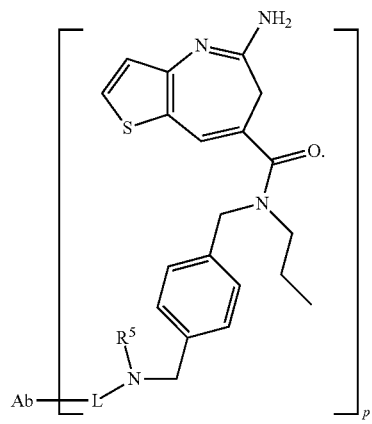

Ic

An exemplary embodiment of the immunoconjugate of Formula I is selected from Formulae Id-Ih:

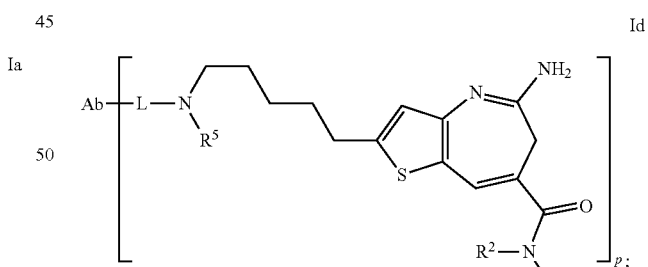

Id

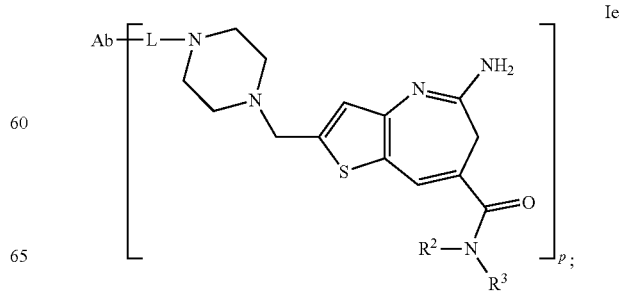

Ie

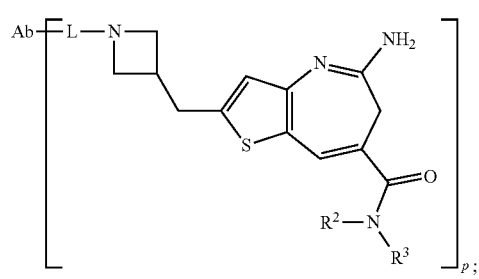

If

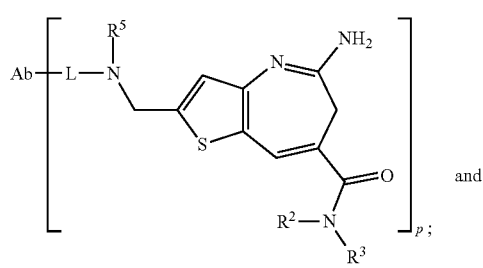

and Ig

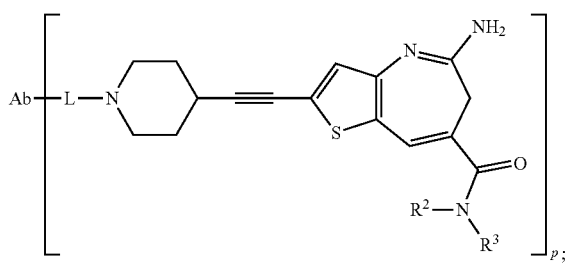

Ih

The invention includes all reasonable combinations, and permutations of the features, of the Formula I embodiments.

In certain embodiments, the immunoconjugate compounds of the invention include those with immunostimulatory activity. The antibody-drug conjugates of the invention selectively deliver an effective dose of a thienoazepine drug to tumor tissue, whereby greater selectivity (i.e., a lower efficacious dose) may be achieved while increasing the therapeutic index ("therapeutic window") relative to unconjugated thienoazepine.

Drug loading is represented by p, the number of TAZ moieties per antibody in an immunoconjugate of Formula I. Drug (TAZ) loading may range from 1 to about 8 drug moieties (D) per antibody. Immunoconjugates of Formula I include mixtures or collections of antibodies conjugated with a range of drug moieties, from 1 to about 8. In some embodiments, the number of drug moieties that can be conjugated to an antibody is limited by the number of reactive or available amino acid side chain residues such as lysine and cysteine. In some embodiments, free cysteine residues are introduced into the antibody amino acid sequence by the methods described herein. In such aspects, p may be 1, 2, 3, 4, 5, 6, 7, or 8, and ranges thereof, such as from 1 to 8 or from 2 to 5. In any such aspect, p and n are equal (i.e., p=n=1, 2, 3, 4, 5, 6, 7, or 8, or some range there between). Exemplary immunoconjugates of Formula I include, but are not limited to, antibodies that have 1, 2, 3, or 4 engineered cysteine amino acids (Lyon, R. et al. (2012) *Methods in Enzym.* 502:123-138). In some embodiments, one or more free cysteine residues are already present in an antibody forming intrachain disulfide bonds, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

For some immunoconjugates, p may be limited by the number of attachment sites on the antibody. For example, where the attachment is a cysteine thiol, as in certain exemplary embodiments described herein, an antibody may have only one or a limited number of cysteine thiol groups, or may have only one or a limited number of sufficiently reactive thiol groups, to which the drug may be attached. In other embodiments, one or more lysine amino groups in the antibody may be available and reactive for conjugation with an TAZ-linker compound of Formula II. In certain embodiments, higher drug loading, e.g. p>5, may cause aggregation, insolubility, toxicity, or loss of cellular permeability of certain antibody-drug conjugates. In certain embodiments, the average drug loading for an immunoconjugate ranges from 1 to about 8; from about 2 to about 6; or from about 3 to about 5. In certain embodiments, an antibody is subjected to denaturing conditions to reveal reactive nucleophilic groups such as lysine or cysteine.

The loading (drug/antibody ratio) of an immunoconjugate may be controlled in different ways, and for example, by: (i) limiting the molar excess of the TAZ-linker intermediate compound relative to antibody, (ii) limiting the conjugation reaction time or temperature, and (iii) partial or limiting reductive denaturing conditions for optimized antibody reactivity.

It is to be understood that where more than one nucleophilic group of the antibody reacts with a drug, then the resulting product is a mixture of immunoconjugate compounds with a distribution of one or more drug moieties attached to an antibody. The average number of drugs per antibody may be calculated from the mixture by a dual ELISA antibody assay, which is specific for antibody and specific for the drug. Individual immunoconjugate molecules may be identified in the mixture by mass spectroscopy and separated by HPLC, e.g. hydrophobic interaction chromatography (see, e.g., McDonagh et al. (2006) *Prot. Engr. Design & Selection* 19(7):299-307; Hamblett et al. (2004) *Clin. Cancer Res.* 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous immunoconjugate with a single loading value may be isolated from the conjugation mixture by electrophoresis or chromatography.

An exemplary embodiment of the immunoconjugate of Formula I is selected from the Tables 3a-c Immunoconjugates. Assessment of Immunoconjugate Activity In Vitro was conducted according to the methods of Example 203.

TABLE 3a

Immunoconjugates (IC)

| Immunoconjugate No. | TAZ-linker Table 2a/b | Ab Antigen | DAR | Myeloid TNFα Secretion EC50 [nM] |
|---|---|---|---|---|
| IC-1 | TAZ-L-1 | trastuzumab HER2 | 2.24 | >1000 |
| IC-2 | TAZ-L-3 | trastuzumab HER2 | 2.40 | 365 |
|  |  |  | 4.10 | 78 |
| IC-3 | TAZ-L-4 | trastuzumab HER2 | 2.57 | 612 |

TABLE 3b

Immunoconjugates (IC)

| Immunoconjugate No. | TAZ-linker Table 2a/b | Ab Antigen | DAR | Myeloid TNFα Secretion EC50 [nM] |
|---|---|---|---|---|
| IC-4 | TAZ-L-3 | avelumab PD-L1 | 2.46 | 58 |
| IC-5 | TAZ-L-4 | avelumab PD-L1 | 2.32 | >1000 |
| IC-6 | TAZ-L-5 | trastuzumab HER2 | 2.58 | Not Available |
| IC-7 | TAZ-L-6 | trastuzumab HER2 | 2.56 | Not Available |
| IC-8 | TAZ-L-3 | PDL1.24-G1f PD-L1 | 2.25 | Not Available |
| IC-9 | TAZ-L-3 | PDL1.85-G1f PD-L1 | 2.21 | Not Available |
| IC-10 | TAZ-L-7 | trastuzumab HER2 | 2.82 | 115 |
| IC-11 | TAZ-L-8 | trastuzumab HER2 | 2.54 | 455 |
| IC-12 | TAZ-L-3 | CEA.5-G1fhL2 CEACAM5 | 2.80 | Not Available |
| IC-13 | TAZ-L-9 | trastuzumab HER2 | 2.77 | >1000 |
| IC-14 | TAZ-L-10 | trastuzumab HER2 | 2.69 | 15 |
| IC-15 | TAZ-L-11 | trastuzumab HER2 | 2.74 | >1000 |
| IC-16 | TAZ-L-12 | trastuzumab HER2 | 2.79 | >1000 |
| IC-17 | TAZ-L-13 | trastuzumab HER2 | 2.52 | 23 |
| IC-18 | TAZ-L-15 | trastuzumab HER2 | 2.44 | >1000 |
| IC-19 | TAZ-L-14 | trastuzumab HER2 | 2.63 | >1000 |
| IC-20 | TAZ-L-19 | trastuzumab HER2 | 3.03 | >1000 |
| IC-21 | TAZ-L-16 | trastuzumab HER2 | 2.63 | 435 |
| IC-22 | TAZ-L-17 | trastuzumab HER2 | 2.72 | >1000 |
| IC-23 | TAZ-L-20 | trastuzumab HER2 | 2.67 | 504 |
| IC-24 | TAZ-L-25 | trastuzumab HER2 | 2.55 | 113 |
| IC-25 | TAZ-L-18 | trastuzumab HER2 | 2.52 | >1000 |
| IC-26 | TAZ-L-22 | trastuzumab HER2 | 2.47 | 469 |
| IC-27 | TAZ-L-23 | trastuzumab HER2 | 2.99 | >1000 |
| IC-28 | TAZ-L-30 | trastuzumab HER2 | 2.47 | 468 |
| IC-29 | TAZ-L-31 | trastuzumab HER2 | 1.94 | 907 |
| IC-30 | TAZ-L-32 | trastuzumab HER2 | 2.59 | 134 |
| IC-31 | TAZ-L-34 | trastuzumab HER2 | 3.13 | 388 |

TABLE 3b-continued

Immunoconjugates (IC)

| Immunoconjugate No. | TAZ-linker Table 2a/b | Ab Antigen | DAR | Myeloid TNFα Secretion EC50 [nM] |
|---|---|---|---|---|
| IC-32 | TAZ-L-28 | trastuzumab HER2 | 2.66 | Not available |

TABLE 3c

Immunoconjugates (IC)

| Immunoconjugate No. | TAZ-L Table 2c | Ab Antigen | DAR |
|---|---|---|---|
| IC-33 | TAZ-L-32 | rituximab CD20 | 2.28 |
| IC-34 | TAZ-L-29 | trastuzumab HER2 | 2.77 |
| IC-35 | TAZ-L-35 | trastuzumab HER2 | 2.56 |
| IC-36 | TAZ-L-27 | trastuzumab HER2 | 2.50 |
| IC-37 | TAZ-L-37 | trastuzumab HER2 | 2.55 |
| IC-38 | TAZ-L-32 | Tras-G1f-N297A | 3.06 |
| IC-39 | TAZ-L-32 | CEA. 9-G1fhL2 | 2.40 |
| IC-40 | TAZ-L-34 | CEA. 9-G1fhL2 | 2.52 |
| IC-41 | TAZ-L-38 | trastuzumab HER2 | 2.14 |
| IC-42 | TAZ-L-39 | trastuzumab HER2 | 2.18 |
| IC-43 | TAZ-L-43 | trastuzumab HER2 | 2.28 |
| IC-44 | TAZ-L-49 | trastuzumab HER2 | 2.68 |
| IC-45 | TAZ-L-40 | trastuzumab HER2 | 2.25 |
| IC-46 | TAZ-L-47 | trastuzumab HER2 | 2.37 |
| IC-47 | TAZ-L-48 | trastuzumab HER2 | 2.15 |
| IC-48 | TAZ-L-52 | trastuzumab HER2 | 2.38 |
| IC-49 | TAZ-L-32 | PDL 1.24-G1f | 2.73 |
| IC-50 | TAZ-L-42 | trastuzumab HER2 | 2.00 |
| IC-51 | TAZ-L-45 | trastuzumab HER2 | 2.17 |
| IC-52 | TAZ-L-46 | trastuzumab HER2 | 2.53 |
| IC-53 | TAZ-L-41 | trastuzumab HER2 | 2.14 |
| IC-54 | TAZ-L-44 | trastuzumab HER2 | 2.04 |
| IC-55 | TAZ-L-50 | trastuzumab HER2 | 2.10 |
| IC-56 | TAZ-L-51 | trastuzumab HER2 | 2.35 |
| IC-57 | TAZ-L-53 | trastuzumab HER2 | 2.14 |
| IC-58 | TAZ-L-56 | trastuzumab HER2 | 2.55 |
| IC-59 | TAZ-L-59 | trastuzumab HER2 | 2.39 |
| IC-60 | TAZ-L-58 | trastuzumab HER2 | 2.74 |
| IC-61 | TAZ-L-62 | trastuzumab HER2 | 2.55 |
| IC-62 | TAZ-L-63 | trastuzumab HER2 | 2.72 |
| IC-63 | TAZ-L-64 | trastuzumab HER2 | 2.57 |
| IC-64 | TAZ-L-60 | trastuzumab HER2 | 2.66 |

TABLE 3c-continued

Immunoconjugates (IC)

| Immunoconjugate No. | TAZ-L Table 2c | Ab Antigen | DAR |
|---|---|---|---|
| IC-65 | TAZ-L-61 | trastuzumab HER2 | 2.64 |
| IC-66 | TAZ-L-74 | trastuzumab HER2 | 2.08 |
| IC-67 | TAZ-L-75 | trastuzumab HER2 | 2.03 |
| IC-68 | TAZ-L-32 | CEA.5-G1f-G236AhL2 | 2.38 |
| IC-69 | TAZ-L-59 | CEA.9-G1fhL2 | 2.71 |
| IC-70 | TAZ-L-70 | trastuzumab HER2 | 2.67 |
| IC-71 | TAZ-L-71 | trastuzumab HER2 | 3.12 |
| IC-72 | TAZ-L-76 | trastuzumab HER2 | 1.94 |
| IC-73 | TAZ-L-77 | trastuzumab HER2 | 2.35 |
| IC-74 | TAZ-L-53 | CEA.9-G1fhL2 | 2.48 |
| IC-75 | TAZ-L-78 | trastuzumab HER2 | 2.65 |
| IC-76 | TAZ-L-79 | trastuzumab HER2 | 2.91 |
| IC-77 | TAZ-L-32 | PDL1.85-G1f | 2.9 |
| IC-78 | TAZ-L-72 | trastuzumab HER2 | 2.50 |
| IC-79 | TAZ-L-73 | trastuzumab HER2 | 2.64 |
| IC-80 | TAZ-L-80 | trastuzumab HER2 | 2.17 |
| IC-81 | TAZ-L-81 | trastuzumab HER2 | 2.49 |
| IC-82 | TAZ-L-53 | PDL1.85-G1f | 2.54 |
| IC-83 | TAZ-L-67 | trastuzumab HER2 | 2.03 |
| IC-84 | TAZ-L-68 | trastuzumab HER2 | 2.33 |
| IC-85 | TAZ-L-82 | trastuzumab HER2 | 2.97 |
| IC-86 | TAZ-L-83 | trastuzumab HER2 | 1.98 |
| IC-87 | TAZ-L-84 | trastuzumab HER2 | 2.27 |
| IC-88 | TAZ-L-148 | trastuzumab HER2 | 2.12 |
| IC-89 | TAZ-L-57 | trastuzumab HER2 | 1.93 |
| IC-90 | TAZ-L-85 | trastuzumab HER2 | 2.49 |
| IC-91 | TAZ-L-86 | trastuzumab HER2 | 2.55 |
| IC-92 | TAZ-L-87 | trastuzumab HER2 | 2.53 |
| IC-93 | TAZ-L-88 | trastuzumab HER2 | 1.71 |
| IC-94 | TAZ-L-149 | trastuzumab HER2 | 2.8 |
| IC-95 | TAZ-L-150 | trastuzumab HER2 | 2.5 |
| IC-96 | TAZ-L-53 | PDL1.24-G1f | 2.54 |
| IC-97 | TAZ-L-92 | trastuzumab HER2 | 2.72 |
| IC-98 | TAZ-L-93 | trastuzumab HER2 | 2.50 |
| IC-99 | TAZ-L-94 | trastuzumab HER2 | 2.79 |
| IC-100 | TAZ-L-95 | trastuzumab HER2 | 2.56 |
| IC-101 | TAZ-L-32 | mPD-L1 | 2.21 |
| IC-102 | TAZ-L-53 | mPD-L1 | 2.28 |
| IC-103 | TAZ-L-32 | rat IgG2b isotype control | 2.53 |
| IC-104 | TAZ-L-53 | rat IgG2b isotype control | 2.54 |
| IC-105 | TAZ-L-91 | trastuzumab HER2 | 2.3 |
| IC-106 | TAZ-L-90 | trastuzumab HER2 | 2.6 |
| IC-107 | TAZ-L-89 | trastuzumab HER2 | 2.8 |
| IC-108 | TAZ-L-69 | trastuzumab HER2 | 3.1 |
| IC-109 | TAZ-L-98 | trastuzumab HER2 | 2.58 |
| IC-110 | TAZ-L-101 | trastuzumab HER2 | 1.95 |
| IC-111 | TAZ-L-102 | trastuzumab HER2 | 2.28 |
| IC-112 | TAZ-L-105 | trastuzumab HER2 | 2.33 |
| IC-113 | TAZ-L-97 | trastuzumab HER2 | 2.48 |
| IC-114 | TAZ-L-103 | trastuzumab HER2 | 2.41 |
| IC-115 | TAZ-L-104 | trastuzumab HER2 | 2.97 |
| IC-116 | TAZ-L-32 | rituximab CD20 | |
| IC-117 | TAZ-L-53 | rituximab CD20 | 2.5 |
| IC-118 | TAZ-L-113 | trastuzumab HER2 | 2.3 |
| IC-119 | TAZ-L-114 | trastuzumab HER2 | 2.4 |
| IC-120 | TAZ-L-109 | trastuzumab HER2 | 2.4 |
| IC-121 | TAZ-L-115 | trastuzumab HER2 | 2.62 |
| IC-122 | TAZ-L-117 | trastuzumab HER2 | 2.76 |
| IC-123 | TAZ-L-118 | trastuzumab HER2 | 3.05 |
| IC-124 | TAZ-L-119 | trastuzumab HER2 | 2.86 |
| IC-125 | TAZ-L-110 | trastuzumab HER2 | 2.2 |
| IC-126 | TAZ-L-116 | trastuzumab HER2 | 2.0 |
| IC-127 | TAZ-L-123 | trastuzumab HER2 | 2.4 |
| IC-128 | TAZ-L-120 | trastuzumab HER2 | 3.25 |
| IC-129 | TAZ-L-127 | trastuzumab HER2 | 2.32 |
| IC-130 | TAZ-L-128 | trastuzumab HER2 | 2.56 |
| IC-131 | TAZ-L-131 | trastuzumab HER2 | 2.61 |
| IC-132 | TAZ-L-1347 | trastuzumab HER2 | 3.1 |
| IC-133 | TAZ-L-98 | rituximab CD20 | 2.32 |
| IC-134 | TAZ-L-98 | CEA.9-G1fhL2 | 2.46 |
| IC-135 | TAZ-L-124 | trastuzumab HER2 | 2.3 |
| IC-136 | TAZ-L-125 | trastuzumab HER2 | 2.6 |
| IC-137 | TAZ-L-130 | trastuzumab HER2 | 2.4 |
| IC-138 | TAZ-L-88 | trastuzumab HER2 | 1.9 |
| IC-139 | TAZ-L-132 | trastuzumab HER2 | 3.1 |
| IC-140 | TAZ-L-128 | CEA.9-G1fhL2 | 2.61 |
| IC-141 | TAZ-L-128 | rituximab CD20 | 2.08 |
| IC-142 | TAZ-L-128 | Tras-G1f-N297a | 2.13 |
| IC-143 | TAZ-L-134 | trastuzumab HER2 | 2.2 |
| IC-144 | TAZ-L-135 | trastuzumab HER2 | 2.2 |

TABLE 3c-continued

Immunoconjugates (IC)

| Immunoconjugate No. | TAZ-L Table 2c | Ab Antigen | DAR |
|---|---|---|---|
| IC-145 | TAZ-L-136 | trastuzumab HER2 | 2.5 |
| IC-146 | TAZ-L-139 | trastuzumab HER2 | 2.32 |
| IC-147 | TAZ-L-142 | trastuzumab HER2 | 2.33 |
| IC-148 | TAZ-L-129 | trastuzumab HER2 | 1.9 |
| IC-149 | TAZ-L-141 | trastuzumab HER2 | 2.8 |
| IC-150 | TAZ-L-144 | trastuzumab HER2 | 2.66 |
| IC-151 | TAZ-L-145 | trastuzumab HER2 | 2.55 |
| IC-152 | TAZ-L-144 | rituximab CD20 | 2.59 |
| IC-153 | TAZ-L-145 | rituximab CD20 | 2.46 |
| IC-154 | TAZ-L-144 | CEA.9-G1fhL2 | 2.55 |
| IC-155 | TAZ-L-145 | CEA.9-G1fhL2 | 2.49 |
| IC-156 | TAZ-L-147 | trastuzumab HER2 | 2.06 |
| IC-157 | TAZ-L-146 | trastuzumab HER2 | 2.44 |

Compositions of Immunoconjugates

The invention provides a composition, e.g., a pharmaceutically or pharmacologically acceptable composition or formulation, comprising a plurality of immunoconjugates as described herein and optionally a carrier therefor, e.g., a pharmaceutically or pharmacologically acceptable carrier. The immunoconjugates can be the same or different in the composition, i.e., the composition can comprise immunoconjugates that have the same number of adjuvants linked to the same positions on the antibody construct and/or immunoconjugates that have the same number of TAZ adjuvants linked to different positions on the antibody construct, that have different numbers of adjuvants linked to the same positions on the antibody construct, or that have different numbers of adjuvants linked to different positions on the antibody construct.

In an exemplary embodiment, a composition comprising the immunoconjugate compounds comprises a mixture of the immunoconjugate compounds, wherein the average drug (TAZ) loading per antibody in the mixture of immunoconjugate compounds is about 2 to about 5.

A composition of immunoconjugates of the invention can have an average adjuvant to antibody construct ratio (DAR) of about 0.4 to about 10. A skilled artisan will recognize that the number of thienoazepine adjuvants conjugated to the antibody construct may vary from immunoconjugate to immunoconjugate in a composition comprising multiple immunoconjugates of the invention and thus the adjuvant to antibody construct (e.g., antibody) ratio can be measured as an average which may be referred to as the drug to antibody ratio (DAR). The adjuvant to antibody construct (e.g., antibody) ratio can be assessed by any suitable means, many of which are known in the art.

The average number of adjuvant moieties per antibody (DAR) in preparations of immunoconjugates from conjugation reactions may be characterized by conventional means such as mass spectrometry, ELISA assay, and HPLC. The quantitative distribution of immunoconjugates in a composition in terms of p may also be determined. In some instances, separation, purification, and characterization of homogeneous immunoconjugates where p is a certain value from immunoconjugates with other drug loadings may be achieved by means such as reverse phase HPLC or electrophoresis.

In some embodiments, the composition further comprises one or more pharmaceutically or pharmacologically acceptable excipients. For example, the immunoconjugates of the invention can be formulated for parenteral administration, such as IV administration or administration into a body cavity or lumen of an organ. Alternatively, the immunoconjugates can be injected intra-tumorally. Compositions for injection will commonly comprise a solution of the immunoconjugate dissolved in a pharmaceutically acceptable carrier. Among the acceptable vehicles and solvents that can be employed are water and an isotonic solution of one or more salts such as sodium chloride, e.g., Ringer's solution. In addition, sterile fixed oils can conventionally be employed as a solvent or suspending medium. For this purpose, any bland fixed oil can be employed, including synthetic monoglycerides or diglycerides. In addition, fatty acids such as oleic acid can likewise be used in the preparation of injectables. These compositions desirably are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The composition can contain any suitable concentration of the immunoconjugate. The concentration of the immunoconjugate in the composition can vary widely, and will be selected primarily based on fluid volumes, viscosities, body weight, and the like, in accordance with the particular mode of administration selected and the patient's needs. In certain embodiments, the concentration of an immunoconjugate in a solution formulation for injection will range from about 0.1% (w/w) to about 10% (w/w).

Method of Treating Cancer with Immunoconjugates

The invention provides a method for treating cancer. The method includes administering a therapeutically effective amount of an immunoconjugate as described herein (e.g., as a composition as described herein) to a subject in need thereof, e.g., a subject that has cancer and is in need of treatment for the cancer. The method includes administering a therapeutically effective amount of an immunoconjugate (IC) selected from Tables 3a and 3b.

It is contemplated that the immunoconjugate of the present invention may be used to treat various hyperproliferative diseases or disorders, e.g. characterized by the overexpression of a tumor antigen. Exemplary hyperproliferative disorders include benign or malignant solid tumors and hematological disorders such as leukemia and lymphoid malignancies.

In another aspect, an immunoconjugate for use as a medicament is provided. In certain embodiments, the invention provides an immunoconjugate for use in a method of treating an individual comprising administering to the individual an effective amount of the immunoconjugate. In one such embodiment, the method further comprises administering to the individual an effective amount of at least one additional therapeutic agent, e.g., as described herein.

In a further aspect, the invention provides for the use of an immunoconjugate in the manufacture or preparation of a medicament. In one embodiment, the medicament is for treatment of cancer, the method comprising administering to an individual having cancer an effective amount of the medicament. In one such embodiment, the method further comprises administering to the individual an effective amount of at least one additional therapeutic agent, e.g., as described herein.

Carcinomas are malignancies that originate in the epithelial tissues. Epithelial cells cover the external surface of the body, line the internal cavities, and form the lining of glandular tissues. Examples of carcinomas include, but are not limited to, adenocarcinoma (cancer that begins in glandular (secretory) cells such as cancers of the breast, pancreas, lung, prostate, stomach, gastroesophageal junction, and colon) adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma; transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostrate, pancreas, colon, brain (usually as secondary metastases), lung, breast, and skin. In some embodiments, methods for treating non-small cell lung carcinoma include administering an immunoconjugate containing an antibody construct that is capable of binding PD-L1 (e.g., atezolizumab, durvalumab, avelumab, biosimilars thereof, or biobetters thereof). In some embodiments, methods for treating breast cancer include administering an immunoconjugate containing an antibody construct that is capable of binding PD-L1 (e.g., atezolizumab, durvalumab, avelumab, biosimilars thereof, or biobetters thereof). In some embodiments, methods for treating triple-negative breast cancer include administering an immunoconjugate containing an antibody construct that is capable of binding PD-L1 (e.g., atezolizumab, durvalumab, avelumab, biosimilars thereof, or biobetters thereof).

Soft tissue tumors are a highly diverse group of rare tumors that are derived from connective tissue. Examples of soft tissue tumors include, but are not limited to, alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DFSP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; pleomorphic adenoma of soft tissue; and neoplasias derived from fibroblasts, myofibroblasts, histiocytes, vascular cells/endothelial cells, and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to, askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; and undifferentiated pleomorphic sarcoma).

A teratoma is a type of germ cell tumor that may contain several different types of tissue (e.g., can include tissues derived from any and/or all of the three germ layers: endoderm, mesoderm, and ectoderm), including, for example, hair, muscle, and bone. Teratomas occur most often in the ovaries in women, the testicles in men, and the tailbone in children.

Melanoma is a form of cancer that begins in melanocytes (cells that make the pigment melanin). Melanoma may begin in a mole (skin melanoma), but can also begin in other pigmented tissues, such as in the eye or in the intestines.

Merkel cell carcinoma is a rare type of skin cancer that usually appears as a flesh-colored or bluish-red nodule on the face, head or neck. Merkel cell carcinoma is also called neuroendocrine carcinoma of the skin. In some embodiments, methods for treating Merkel cell carcinoma include administering an immunoconjugate containing an antibody construct that is capable of binding PD-L1 (e.g., atezolizumab, durvalumab, avelumab, biosimilars thereof, or biobetters thereof). In some embodiments, the Merkel cell carcinoma has metastasized when administration occurs.

Leukemias are cancers that start in blood-forming tissue, such as the bone marrow, and cause large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to, Acute myeloid leukemia (AML), Acute lymphoblastic leukemia (ALL), Chronic myeloid leukemia (CML), and Chronic lymphocytic leukemia (CLL).

Lymphomas are cancers that begin in cells of the immune system. For example, lymphomas can originate in bone marrow-derived cells that normally mature in the lymphatic system. There are two basic categories of lymphomas. One category of lymphoma is Hodgkin lymphoma (HL), which is marked by the presence of a type of cell called the Reed-Stemberg cell. There are currently 6 recognized types of HL. Examples of Hodgkin lymphomas include nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to, AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to, gliomas (e.g., glioblastomas, astrocytomas, oligodendrogliomas, ependymomas, and the like), meningiomas, pituitary adenomas, and vestibular schwannomas, primitive neuroectodermal tumors (medulloblastomas).

Immunoconjugates of the invention can be used either alone or in combination with other agents in a therapy. For instance, an immunoconjugate may be co-administered with at least one additional therapeutic agent, such as a chemotherapeutic agent. Such combination therapies encompass combined administration (where two or more therapeutic agents are included in the same or separate formulations), and separate administration, in which case, administration of the immunoconjugate can occur prior to, simultaneously, and/or following, administration of the additional therapeutic agent and/or adjuvant. Immunoconjugates can also be used in combination with radiation therapy.

The immunoconjugates of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Atezolizumab, durvalumab, avelumab, biosimilars thereof, and biobetters thereof are known to be useful in the treatment of cancer, particularly breast cancer, especially triple negative (test negative for estrogen receptors, progesterone receptors, and excess HER2 protein) breast cancer, bladder cancer, and Merkel cell carcinoma. The immunoconjugate described herein can be used to treat the same types of cancers as atezolizumab, durvalumab, avelumab, biosimilars thereof, and biobetters thereof, particularly breast cancer, especially triple negative (test negative for estrogen receptors, progesterone receptors, and excess HER2 protein) breast cancer, bladder cancer, and Merkel cell carcinoma.

The immunoconjugate is administered to a subject in need thereof in any therapeutically effective amount using any suitable dosing regimen, such as the dosing regimens utilized for atezolizumab, durvalumab, avelumab, biosimilars thereof, and biobetters thereof. For example, the methods can include administering the immunoconjugate to provide a dose of from about 100 ng/kg to about 50 mg/kg to the subject. The immunoconjugate dose can range from about 5 mg/kg to about 50 mg/kg, from about 10 µg/kg to about 5 mg/kg, or from about 100 µg/kg to about 1 mg/kg. The immunoconjugate dose can be about 100, 200, 300, 400, or 500 µg/kg. The immunoconjugate dose can be about 1, 2, 3, 4, 5, 6, 7, 8, 9, or 10 mg/kg. The immunoconjugate dose can also be outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

In another aspect, the invention provides a method for preventing cancer. The method comprises administering a therapeutically effective amount of an immunoconjugate (e.g., as a composition as described above) to a subject. In certain embodiments, the subject is susceptible to a certain cancer to be prevented. For example, the methods can include administering the immunoconjugate to provide a dose of from about 100 ng/kg to about 50 mg/kg to the subject. The immunoconjugate dose can range from about 5 mg/kg to about 50 mg/kg, from about 10 µg/kg to about 5 mg/kg, or from about 100 µg/kg to about 1 mg/kg. The immunoconjugate dose can be about 100, 200, 300, 400, or 500 µg/kg. The immunoconjugate dose can be about 1, 2, 3, 4, 5, 6, 7, 8, 9, or 10 mg/kg. The immunoconjugate dose can also be outside of these ranges, depending on the particular conjugate as well as the type and severity of the cancer being treated. Frequency of administration can range from a single dose to multiple doses per week, or more frequently. In some embodiments, the immunoconjugate is administered from about once per month to about five times per week. In some embodiments, the immunoconjugate is administered once per week.

Some embodiments of the invention provide methods for treating cancer as described above, wherein the cancer is breast cancer. Breast cancer can originate from different areas in the breast, and a number of different types of breast cancer have been characterized. For example, the immunoconjugates of the invention can be used for treating ductal carcinoma in situ; invasive ductal carcinoma (e.g., tubular carcinoma; medullary carcinoma; mucinous carcinoma; papillary carcinoma; or cribriform carcinoma of the breast); lobular carcinoma in situ; invasive lobular carcinoma; inflammatory breast cancer; and other forms of breast cancer such as triple negative (test negative for estrogen receptors, progesterone receptors, and excess HER2 protein) breast cancer. In some embodiments, methods for treating breast cancer include administering an immunoconjugate containing an antibody construct that is capable of binding HER2 (e.g. trastuzumab, pertuzumab, biosimilars, or biobetters thereof) and PD-L1 (e.g., atezolizumab, durvalumab, avelumab, biosimilars, or biobetters thereof). In some embodiments, methods for treating colon cancer lung cancer, renal cancer, pancreatic cancer, gastric cancer, and esophageal cancer include administering an immunoconjugate containing an antibody construct that is capable of binding CEA, or tumors over-expressing CEA (e.g. labetuzumab, biosimilars, or biobetters thereof).

375

In some embodiments, the cancer is susceptible to a pro-inflammatory response induced by TLR7 and/or TLR8.

EXAMPLES

Preparation of thienoazepine compounds (TAZ) and intermediates

Example 1 Synthesis of 5-amino-2-bromo-N,N-dipropyl-6H-thieno[3,2-b]azepine-7-carboxamide, TAZ-1

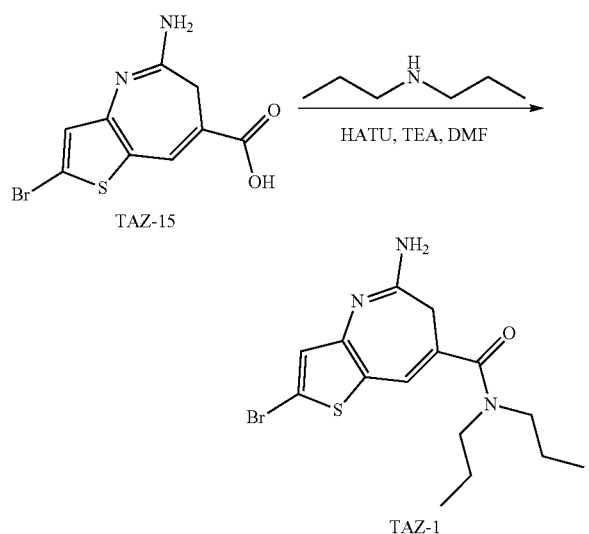

To a solution of 5-amino-2-bromo-6H-thieno[3,2-b]azepine-7-carboxylic acid, TAZ-15 (70 mg, 244 μmol (micromoles), 1 eq) in DMF (1 mL) was added 1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium, HATU (110 mg, 293 μmol, 1.2 eq), N-propylpropan-1-amine (74.0 mg, 731 μmol, 100 μL (microliters), 3 eq) and triethylamine, Et$_3$N (49.0 mg, 488 μmol, 67.8 μL, 2 eq). The mixture was stirred at 25° C. for 1 h. The mixture was filtered and purified by prep-HPLC (column: Nano-micro Kromasil C18 100*30 mm 8 um; mobile phase: [water (0.1% TFA)-ACN]; B %: 20%-50%, 10 min) to give TAZ-1 (27 mg, 72.91 μmol, 29.9% yield) as white solid. $^1$H NMR (CDCl$_3$, 400 MHz) δ11.66 (s, 1H), 7.75 (s, 1H), 7.22 (s, 1H), 6.79 (s, 1H), 3.40 (s, 4H), 3.28 (s, 2H), 1.68-1.57 (m, 4H), 0.91 (t, J=7.2 Hz, 6H). LC/MS [M+H] 370.0 (calculated); LC/MS [M+H] 370.0 (observed).

376

Example 2 Synthesis of 5-amino-N,N-dipropyl-6H-thieno[3,2-b]azepine-7-carboxamide, TAZ-2

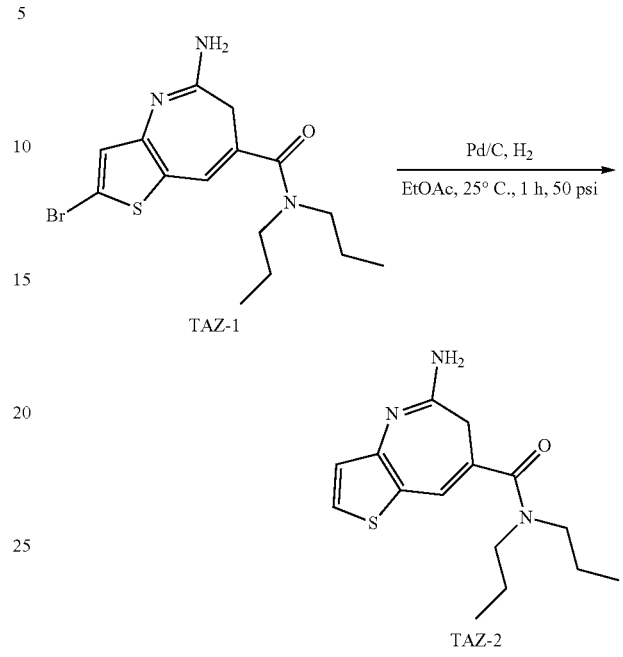

To a solution of 5-amino-2-bromo-N,N-dipropyl-6H-thieno[3,2-b]azepine-7-carboxamide, TAZ-1 (70 mg, 189 μmol, 1 eq) in ethylacetate, EtOAc (5 mL) was added palladium on carbon, Pd/C (10 mg, 189 μmol, 20% purity, 1 eq) The suspension was degassed under vacuum and purged with H$_2$ several time and then stirred under H$_2$ (50 psi) at 25° C. for 1 h. The mixture was filtered and concentrated. The residue was purified by prep-HPLC (column: Nano-micro Kromasil C18 100*30 mm 8 um; mobile phase: [water (0.1% TFA)-ACN]; B %: 15%-40%, 10 min) to give TAZ-2 (12 mg, 41.18 μmol, 21.78% yield) as white solid. $^1$H NMR (MeOD-d$_4$, 400 MHz) δ7.71 (d, J=5.6 Hz, 1H), 7.15-7.09 (m, 2H), 3.44-3.40 (m, 4H), 3.36 (s, 2H), 1.72-1.61 (m, 4H), 0.98-0.84 (m, 6H). LC/MS [M+H] 292.1 (calculated); LC/MS [M+H] 292.1 (observed)

Example 3 Synthesis of tert-butyl (2-(1-(5-(5-amino-7-(dipropylcarbamoyl)-6H-thieno[3,2-b]azepine-2-carboxamido)pyridin-2-yl)piperidine-4-carboxamido)ethyl)carbamate, TAZ-3

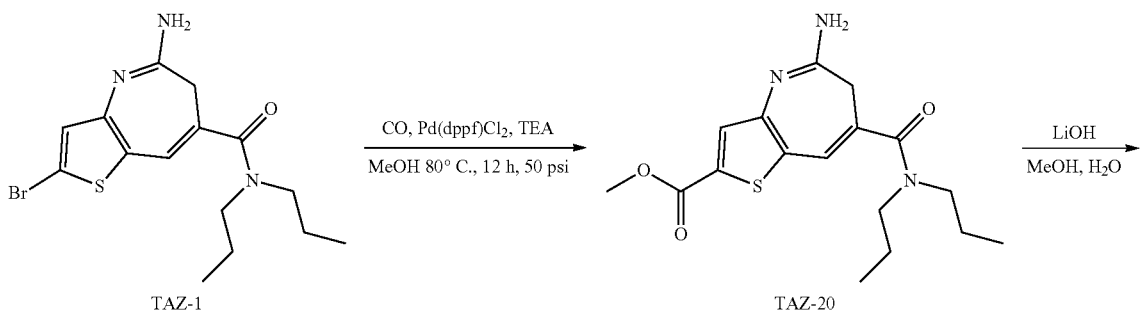

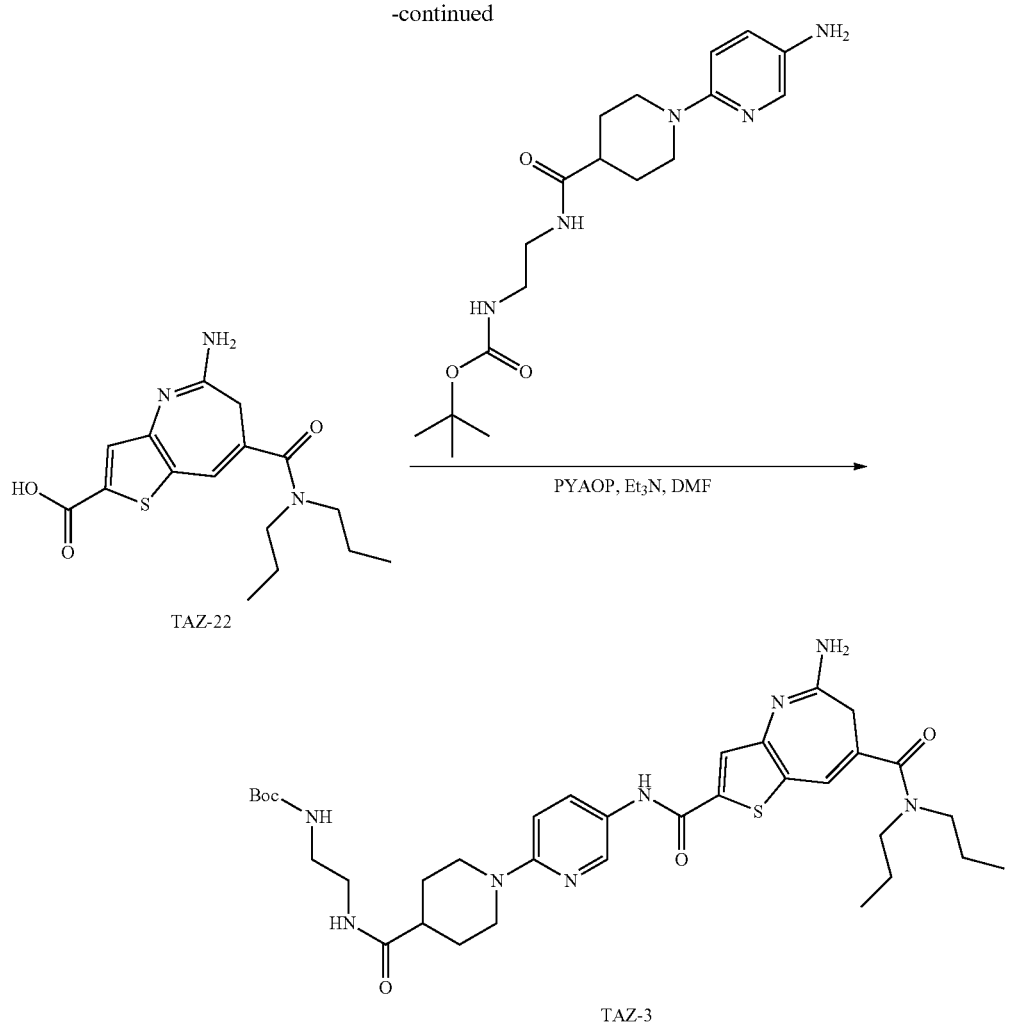

Preparation of methyl 5-amino-7-(dipropylcarbamoyl)-6H-thieno [3,2-b]azepine-2-carboxylate, TAZ-20

To a solution of 5-amino-2-bromo-N,N-dipropyl-6H-thieno[3,2-b]azepine-7-carboxamide, TAZ-1 (0.5 g, 1.30 mmol, 1 eq) in MeOH (5 mL) was added $Et_3N$ (409 mg, 4.05 mmol, 564 μL, 3 eq) and [1,1'-bis(diphenylphosphino)ferrocene]palladium(II) dichloride, $Pd(dppf)Cl_2$ (99.0 mg, 135 μmol, 0.1 eq) under $N_2$. The suspension was degassed under vacuum and purged with carbon monoxide, CO several times. The mixture was stirred under CO (50 psi) at 80° C. for 12 h. The mixture was filtered and concentrated to give TAZ-20 (0.5 g, crude) as red solid. $^1$H NMR (MeOD-$d_4$, 400 MHz) δ7.51 (s, 1H), 6.91 (s, 1H), 3.87 (s, 3H), 3.43-3.35 (m, 4H), 3.35 (s, 2H), 1.73-1.60 (m, 4H), 0.97-0.83 (m, 6H).

Preparation of 5-amino-7-(dipropylcarbamoyl)-6H-thieno[3,2-b] azepine-2-carboxylic Acid, TAZ-22

To a solution of methyl 5-amino-7-(dipropylcarbamoyl)-6H-thieno[3,2-b] azepine-2-carboxylate, TAZ-20 (450 mg, 1.29 mmol, 1 eq) in MeOH (10 mL) and $H_2O$ (10 mL) was added $LiOH.H_2O$ (270 mg, 6.44 mmol, 5 eq), and then stirred at 25° C. for 2 h. The reaction mixture was concentrated under reduced pressure to remove MeOH. The residue was diluted with $H_2O$ 30 mL and extracted with EtOAc (10 mL×2). The aqueous phase pH was adjusted to about 4 with aq (aqueous) HCl (1M) and extracted with EtOAc (10 mL×3). The organic layer was washed with brine (10 mL), dried over $Na_2SO_4$, filtered and concentrated to give TAZ-22 (0.2 g, 596.27 μmol, 46.30% yield) as light yellow solid. $^1$H NMR (DMSO-$d_6$, 400 MHz) δ7.49 (s, 1H), 6.99 (s, 1H), 3.32-3.28 (m, 4H), 3.16 (s, 2H), 1.61-1.46 (m, 4H), 0.82 (br s, 6H).

Preparation of tert-butyl (2-(1-(5-(5-amino-7-(dipropylcarbamoyl)-6H-thieno[3,2-b]azepine-2-carboxamido)pyridin-2-yl)piperidine-4-carboxamido)ethyl) carbamate, TAZ-3

To a solution of 5-amino-7-(dipropylcarbamoyl)-6H-thieno[3,2-b]azepine-2-carboxylic acid (150 mg, 447 μmol, 1 eq) in DMF (2 mL) was added 7-Aza-benzotriazol-1-yloxy-tripyrrolidino-phosphonium hexafluorophosphate, PYAOP (256 mg, 491.9 μmol, 1.1 eq), $Et_3N$ (45.0 mg, 447.2 μmol, 62.25 μL, 1 eq) and tert-butyl N-[2-[[1-(5-amino-2-pyridyl)piperidine-4-carbonyl]amino]ethyl]carbamate (195. mg, 536.6 μmol, 1.2 eq) and it was stirred at 25° C. for 12 h. The mixture was filtered and purified by prep-HPLC (column: Welch Xtimate C18 150*25 mm*5 um; mobile phase: [water (10 mM NH4HCO3)-ACN]; B %: 30%-60%, 10.5 min) to give TAZ-3 (62 mg, 91.06 μmol, 20.36% yield) as grayness solid. ¹H NMR (MeOD-d₄, 400 MHz) δ8.35 (d, J=2.0 Hz, 1H), 7.89-7.82 (m, 1H), 7.60 (s, 1H), 7.51 (s, 1H), 6.93 (s, 1H), 6.91-6.84 (m, 1H), 4.28 (d, J=12.8 Hz, 2H), 3.44-3.35 (m, 4H), 3.27-3.21 (m, 2H), 3.18-3.12 (m, 2H), 2.97 (s, 2H), 2.88 (t, J=11.6 Hz, 2H), 2.48-2.32 (m, 1H), 1.90-1.80 (m, 2H), 1.79-1.56 (m, 6H), 1.43 (s, 9H), 0.90 (s, 6H). LC/MS [M+H] 681.3 (calculated); LC/MS [M+H] 681.4 (observed).

Example 4 Synthesis of 5-amino-2-[3-[3-(hydroxymethyl)azetidin-1-yl]sulfonylphenyl]-N,N-dipropyl-6H-thieno[3,2-b]azepine-7-carboxamide, TAZ-4

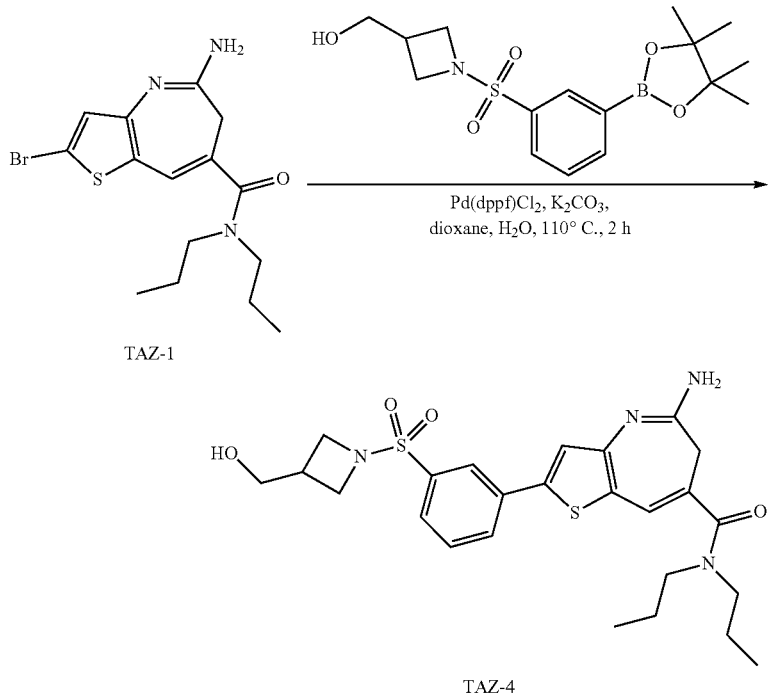

To a solution of 5-amino-2-bromo-N,N-dipropyl-6H-thieno[3,2-b]azepine-7-carboxamide, TAZ-1 (71.0 mg, 192 μmol, 1.1 eq) in dioxane (1 mL) and H₂O (0.5 mL) was added [1-[3-(4,4,5,5-tetramethyl-1,3,2-dioxaborolan-2-yl)phenyl]sulfonylazetidin-3-yl]methanol (62.0 mg, 174 μmol, 1 eq), K₂CO₃ (48.0 mg, 348 μmol, 2 eq) and [1,1'-bis(diphenylphosphino)ferrocene]palladium(1) dichloride, Pd(dppf)Cl₂ (6.0 mg, 8.7 μmol, 0.05 eq) at 25° C. under N₂ and then stirred at 110° C. for 2 h. The mixture was filtered and concentrated. The residue was purified by prep-HPLC (column: Welch Xtimate C18 150*25 mm*5 um; mobile phase: [water (10 mM NH4HCO3)-ACN]; B %: 30%-60%, 10.5 min) to give TAZ-4 (22 mg, 42.58 μmol, 24.45% yield) as light yellow solid. ¹H NMR (MeOD-d₄, 400 MHz) δ8.04-7.97 (m, 2H), 7.79-7.75 (m, 1H), 7.73-7.67 (m, 1H), 7.31 (s, 1H), 6.92 (s, 1H), 3.85 (t, J=8.2 Hz, 2H), 3.62-3.56 (m, 2H), 3.45-3.37 (m, 6H), 2.99 (s, 2H), 2.63-2.52 (m, 1H), 1.71-1.59 (m, 4H), 0.99-0.83 (m, 6H). LC/MS [M+H] 517.2 (calculated); LC/MS [M+H] 517.2 (observed)

Example 5 Synthesis of [4-[[(2S)-2-[[(2S)-2-(9H-fluoren-9-ylmethoxycarbonylamino)-3-methyl-butanoyl]amino]-5-ureido-pentanoyl]amino]phenyl]methyl N-[2-[[1-[5-[[5-amino-7-(dipropylcarbamoyl)-6H-thieno[3,2-b]azepine-2-carbonyl]amino]-2-pyridyl]piperidine-4-carbonyl]amino]ethyl]carbamate, TAZ-5

-continued
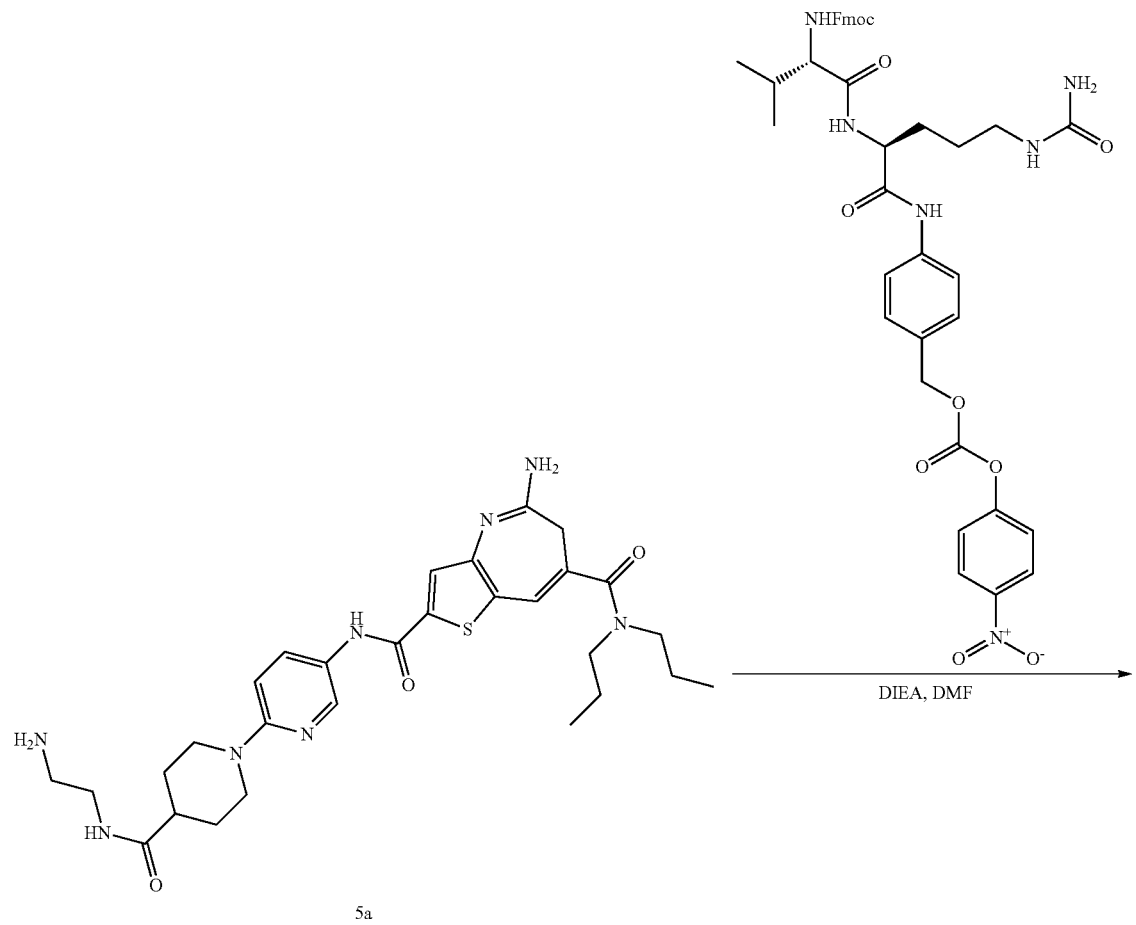
5a
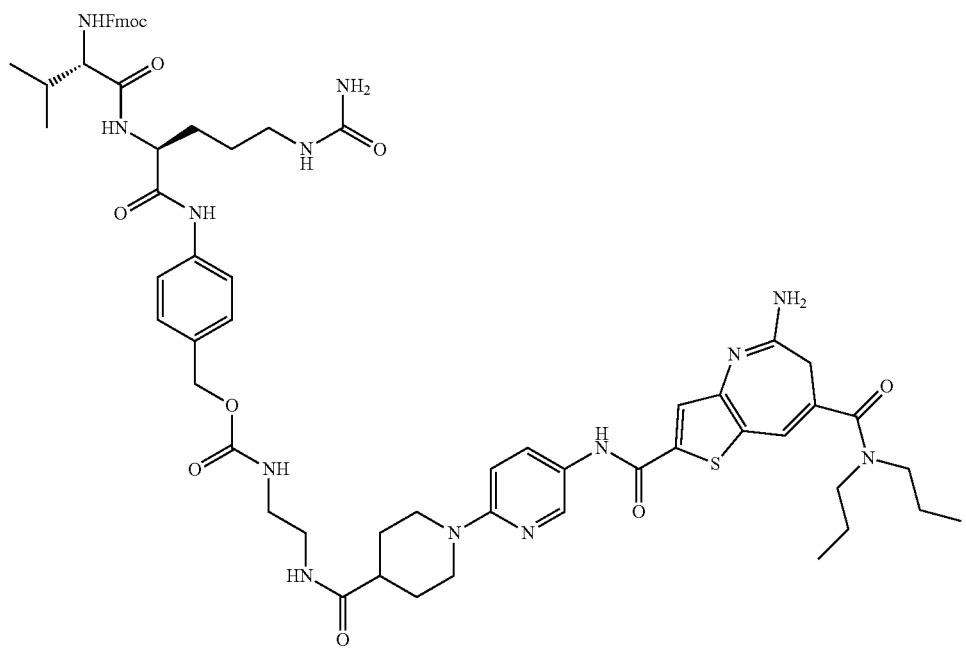
TAZ-5

Preparation of 5-amino-N2-[6-[4-(2-aminoethylcarbamoyl)-1-piperidyl]-3-pyridyl]-N7,N7-dipropyl-6H-thieno[3,2-b]azepine-2,7-dicarboxamide, 5a To a solution of tert-butyl N-[2-[[1-[5-[[5-amino-7-(dipropylcarbamoyl)-6H-thieno[3,2-b] azepine-2-carbonyl]amino]-2-pyridyl]piperidine-4-carbonyl]amino]ethyl]carbamate, TAZ-3 (50 mg, 73.4 μmol, 1 eq) in DCM (1 mL) was added TFA (84.0 mg, 734 μmol, 54.0 μL, 10 eq). The mixture was stirred at 30° C. for 2 h. The mixture was filtered and concentrated and then lyophilization to give 5a (59 mg, 72.95 μmol, 99.34% yield, 2TFA) as grayness solid. $^1$H NMR (MeOD-d$_4$, 400 MHz) δ8.62 (d, J=2.4 Hz, 1H), 8.17 (dd, J=9.6, 2.8 Hz, 1H), 7.89 (s, 1H), 7.43 (d, J=9.6 Hz, 1H), 7.16 (s, 1H), 4.21 (d, J=13.6 Hz, 2H), 3.52-3.39 (m, 8H), 3.36-3.31 (m, 2H), 3.07 (t, J=6.0 Hz, 2H), 2.68-2.61 (m, 1H), 2.07-2.00 (m, 2H), 1.90-1.78 (m, 2H), 1.67 (dq, J=14.8, 7.2 Hz, 4H), 0.93 (s, 6H).

Preparation of TAZ-5

To a solution of 5a (50 mg, 61.8 μmol, 1 eq, 2TFA) in DMF (1 mL) was added DIEA (32.0 mg, 247.2 μmol, 43.0 μL, 4 eq) and [4-[[(2S)-2-[[(2S)-2-(9H-fluoren-9-yl-methoxycarbonylamino)-3-methyl-butanoyl]amino]-5-ureido-pentanoyl]amino]phenyl]methyl (4-nitrophenyl) carbonate (52.0 mg, 68.0 μmol, 1.1 eq) and then stirred at 25° C. for 1 h. The mixture was filtered and purified by prep-HPLC (column: Nano-micro Kromasil C18 100*30 mm 8 um; mobile phase: [water (0.1% TFA)-ACN]; B %: 25%-45%, 10 min) to give TAZ-5 (36 mg, 27.2 μmol, 44.03% yield, TFA) as light yellow solid. $^1$H NMR (MeOD-d$_4$, 400 MHz) δ8.58 (s, 1H), 8.07 (br d, J=10.4 Hz, 1H), 7.93 (br s, 1H), 7.86-7.72 (m, 3H), 7.63 (br t, J=7.2 Hz, 2H), 7.57 (br d, J=8.2 Hz, 2H), 7.41-7.34 (m, 2H), 7.33-7.25 (m, 4H), 7.13 (s, 1H), 5.03 (br s, 2H), 4.41-4.29 (m, 3H), 4.23-4.15 (m, 1H), 4.13-4.03 (m, 2H), 3.98-3.91 (m, 1H), 3.51-3.34 (m, 5H), 3.25-3.07 (m, 9H), 2.52-2.31 (m, 1H), 2.08 (br d, J=7.6 Hz, 1H), 1.99-1.36 (m, 12H), 1.04-0.82 (m, 12H). LC/MS [M+H] 1208.6 (calculated); LC/MS [M+H] 1208.5 (observed).

Example 6 Synthesis of tert-butyl N-[5-[5-amino-7-(dipropylcarbamoyl)-6H-thieno[3,2-b]azepin-2-yl]pent-4-ynyl] carbamate, TAZ-6

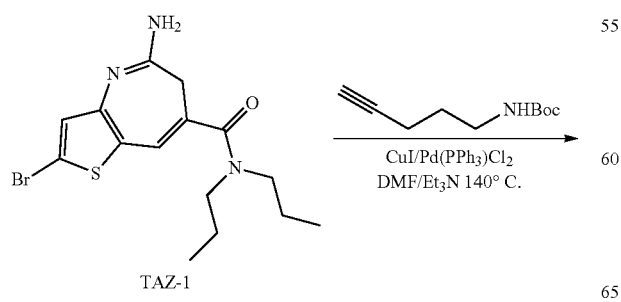

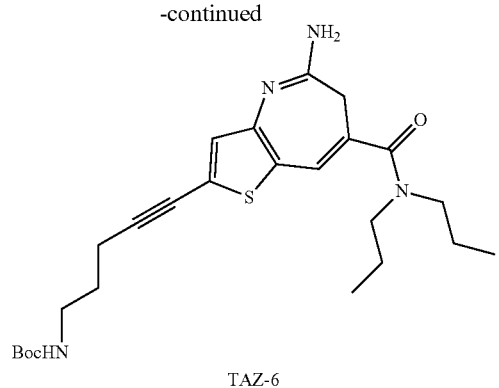

TAZ-6

A mixture of 5-amino-2-bromo-N,N-dipropyl-6H-thieno[3,2-b]azepine-7-carboxamide, TAZ-1 (20 mg, 54.0 μmol, 1 eq), tert-butyl N-pent-4-ynylcarbamate (29.69 mg, 162 μmol, 3 eq), Pd(PPh$_3$)$_2$Cl$_2$ (1.90 mg, 2.70 μmol, 0.05 eq), CuI (2.06 mg, 10.8 μmol, 0.2 eq) and PPh$_3$ (2.83 mg, 10.8 μmol, 0.2 eq) in TEA (0.2 mL) and DMF (0.6 mL) was degassed and purged with N$_2$ for 3 times, and then stirred at 140° C. for 3 h under N$_2$. The reaction mixture was quenched by addition of H$_2$O (5 mL) at 0° C., and then extracted with EtOAc (5 mL×3). The combined organic layers were washed with brine (5 mL×3), dried over Na$_2$SO$_4$, filtered and concentrated under reduced pressure. The residue was purified by prep-TLC (SiO$_2$, EtOAc:MeOH=10:1) to give TAZ-6 (8 mg, 16.9 μmol, 31.34% yield) as yellow solid. $^1$H NMR (MeOD-d$_4$, 400 MHz) δ6.87 (s, 1H), 6.79 (s, 1H), 3.42-3.34 (m, 4H), 3.31 (s, 2H), 3.17 (t, J=6.8 Hz, 2H), 2.48 (t, J=7.2 Hz, 2H), 1.75 (q, J=7.2 Hz, 2H), 1.69-1.56 (m, 4H), 1.44 (s, 9H), 0.92-0.87 (m, 6H). LC/MS [M+H] 473.2 (calculated); LC/MS [M+H] 473.2 (observed)

Example 7 Synthesis of 5-amino-2-methyl-N,N-dipropyl-6H-thieno[3,2-b]azepine-7-carboxamide, TAZ-7

To a solution of 5-amino-2-bromo-N,N-dipropyl-6H-thieno[3,2-b]azepine-7-carboxamide, TAZ-1 (30 mg, 81.0 µmol, 1 eq) in DMF (1 mL) was added methylboronic acid (73.0 mg, 1.22 mmol, 15 eq), $K_2CO_3$ (22.0 mg, 162.03 µmol, 2 eq) and [1,1'-bis(diphenylphosphino)ferrocene]palladium (II) dichloride, Pd(dppf)$Cl_2$ (2.96 mg, 4.05 µmol, 0.05 eq) under $N_2$ and then stirred at 100° C. for 3 h. The mixture was filtered and concentrated. The residue was purified by prep-HPLC (column: Nano-micro Kromasil C18 100*30 mm 8 um; mobile phase: [water (0.1% TFA)-ACN]; B %: 10%-40%, 10 min) to give TAZ-7 (8 mg, 26.19 µmol, 32.33% yield) as white solid. $^1$H NMR (MeOD-$d_4$, 400 MHz) δ7.00 (s, 1H) 6.83 (s, 1H) 3.43 (br t, J=7.2 Hz, 4H) 3.34 (s, 2H) 2.53 (s, 3H) 1.69-1.60 (m, 4H) 0.98-0.85 (m, 6H). LC/MS [M+H] 306.2 (calculated); LC/MS [M+H] 306.2 (observed).

Example 8 Synthesis of tert-butyl N-[3-[(5-amino-6H-thieno[3,2-b]azepine-7-carbonyl)-propyl-amino]propyl]carbamate, TAZ-8

Example 9 Synthesis of tert-butyl N-[3-[(5-amino-2-bromo-6H-thieno[3,2-b]azepine-7-carbonyl)-propyl-amino]propyl]carbamate, TAZ-9

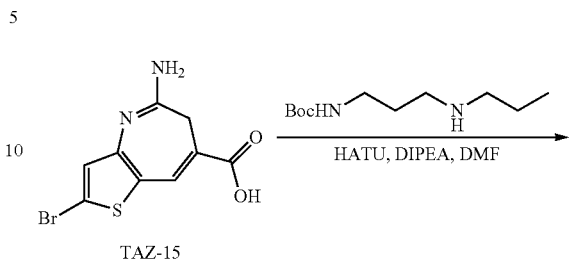

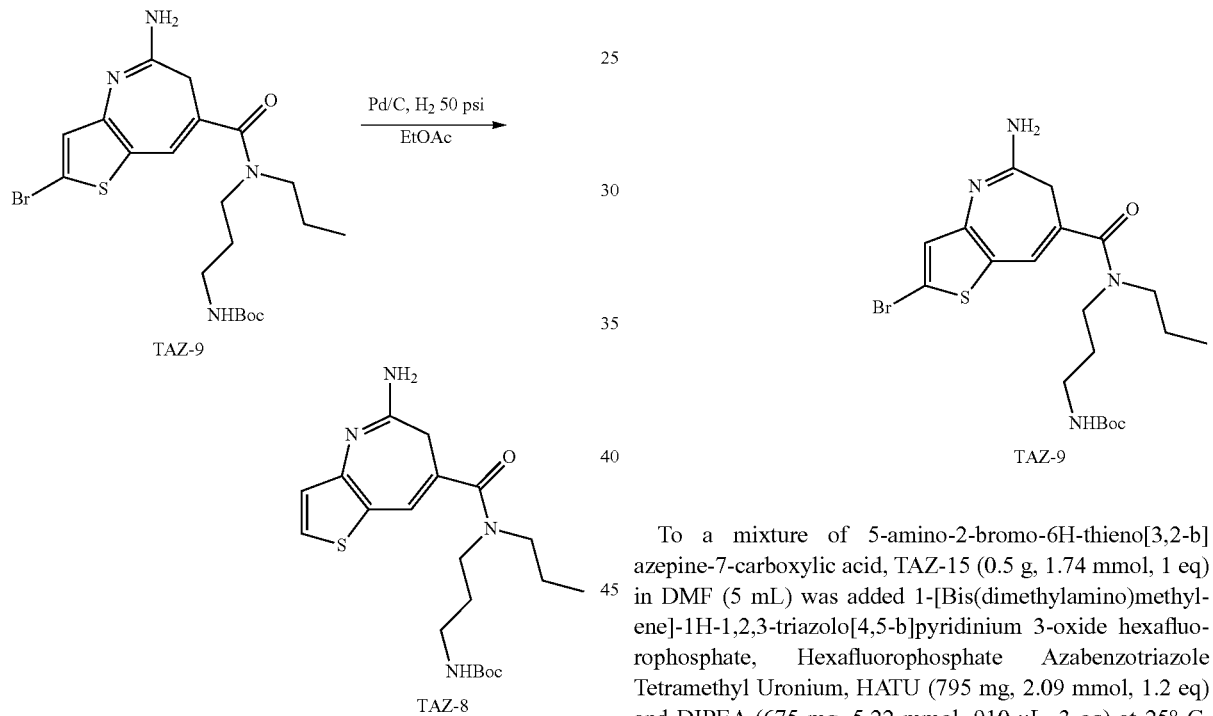

To a solution of tert-butyl N-[3-[(5-amino-2-bromo-6H-thieno[3,2-b]azepine-7-carbonyl)-propyl-amino]propyl]carbamate, TAZ-9 (0.72 g, 1.48 mmol, 1 eq) in EtOAc (10 mL) was added palladium on carbon, Pd/C (10%, 0.2 g) under $N_2$. The suspension was degassed under vacuum and purged with $H_2$ several times, and then stirred under hydrogen gas, $H_2$ (50 psi) at 25° C. for 12 h. The reaction mixture was filtered and concentrated under reduced pressure. The residue was purified by column chromatography (SiO$_2$, EtOAc:EtOH=1:0 to 3:1) to give TAZ-8 (0.4 g, 984 µmol, 66.34% yield) as a light yellow solid. $^1$H NMR (MeOD, 400 MHz) δ7.67 (d, J=5.6 Hz, 1H), 7.13-7.05 (m, 2H), 3.50 (t, J=7.6 Hz, 2H), 3.44 (t, J=7.6 Hz, 2H), 3.30-3.24 (m, 2H), 3.07 (s, 2H), 1.84-1.78 (m, 2H), 1.72-1.61 (m, 2H), 1.41 (s, 9H), 0.93-0.88 (m, 3H). LC/MS [M+H] 407.2 (calculated); LC/MS [M+H] 407.2 (observed).

To a mixture of 5-amino-2-bromo-6H-thieno[3,2-b]azepine-7-carboxylic acid, TAZ-15 (0.5 g, 1.74 mmol, 1 eq) in DMF (5 mL) was added 1-[Bis(dimethylamino)methylene]-1H-1,2,3-triazolo[4,5-b]pyridinium 3-oxide hexafluorophosphate, Hexafluorophosphate Azabenzotriazole Tetramethyl Uronium, HATU (795 mg, 2.09 mmol, 1.2 eq) and DIPEA (675 mg, 5.22 mmol, 910 µL, 3 eq) at 25° C. After 15 min, tert-butyl N-[3-(propylamino)propyl]carbamate (489.70 mg, 2.26 mmol, 1.3 eq) was added at 25° C., and then stirred for 1 h. The reaction mixture was quenched by addition of $H_2O$ (30 mL) at 0° C., and then extracted with EtOAc (15 mL×3). The combined organic layers were washed with brine (10 mL×3), dried over $Na_2SO_4$, filtered and concentrated under reduced pressure. The residue was purified by column chromatography (SiO$_2$, Petroleum ether/Ethyl acetate=1/0 to 0/1) and (SiO$_2$, EtOAc:MeOH=1:0 to 5:1) to give TAZ-9 (0.73 g, 1.50 mmol, 86.36% yield) as a light yellow solid. $^1$H NMR (MeOD, 400 MHz) δ6.95 (s, 1H), 6.86 (s, 1H), 3.50-3.43 (m, 2H), 3.42-3.35 (m, 2H), 3.07-3.01 (m, 4H), 1.84-1.74 (m, 2H), 1.69-1.57 (m, 2H), 1.41 (s, 9H), 0.91-0.86 (m, 3H). LC/MS [M+H] 485.1 (calculated); LC/MS [M+H] 485.1 (observed).

Example 10 Synthesis of tert-butyl N-[4-[(5-amino-2-bromo-6H-thieno[3,2-b]azepine-7-carbonyl)-propyl-amino]but-2-ynyl]carbamate, TAZ-10

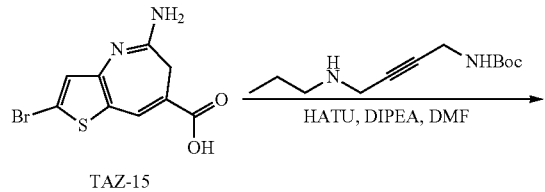

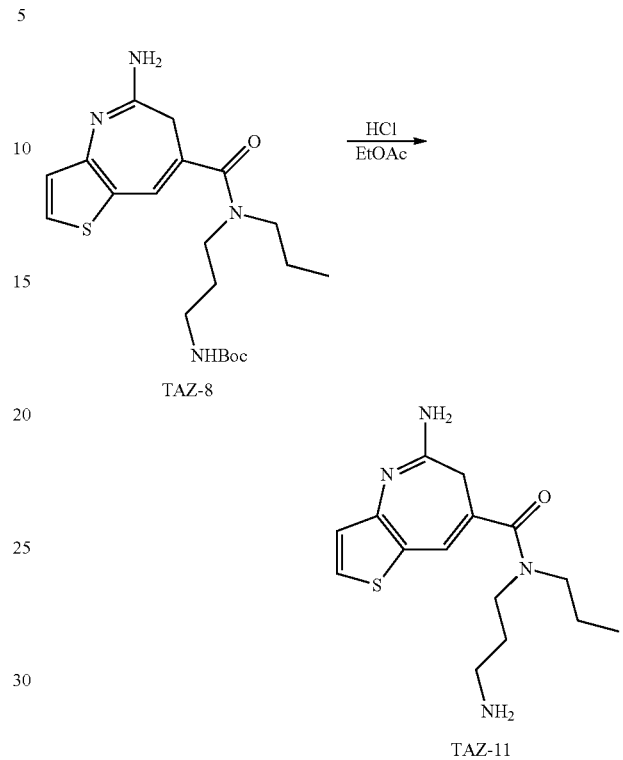

To a solution of 5-amino-2-bromo-6H-thieno[3,2-b]azepine-7-carboxylic acid, TAZ-15 (0.2 g, 697 μmol, 1 eq) in DMF (4 mL) was added HATU (318 mg, 836 μmol, 1.2 eq) and DIPEA (270 mg, 2.09 mmol, 3 eq) at 25° C. After 15 min, tert-butyl N-[4-(propylamino)but-2-ynyl]carbamate (205 mg, 906 μmol, 1.3 eq) was added at 25° C. and then stirred at 25° C. for 1 h. The reaction mixture was quenched by addition of H$_2$O (20 mL) at 0° C., and then extracted with EtOAc (10 mL×3). The combined organic layers were washed with brine (5 mL×3), dried over Na$_2$SO$_4$, filtered and concentrated under reduced pressure. The residue was purified by column chromatography (SiO$_2$, Petroleum ether/Ethyl acetate=1/0 to 0/1) to give TAZ-10 (150 mg, 302.77 μmol, 43.47% yield) as a yellow solid. $^1$H NMR (MeOD, 400 MHz) δ7.20-7.18 (m, 2H), 4.29 (s, 2H), 3.84 (s, 2H), 3.58-3.50 (m, 2H), 3.40 (s, 2H), 1.76-1.66 (m, 2H), 1.43 (s, 9H), 0.94 (t, J=7.2 Hz, 3H). LC/MS [M+H] 495.1 (calculated); LC/MS [M+H] 495.1 (observed).

Example 11 Synthesis of 5-amino-N-(3-aminopropyl)-N-propyl-6H-thieno[3,2-b]azepine-7-carboxamide, TAZ-11

To a solution of tert-butyl N-[3-[(5-amino-6H-thieno[3,2-b]azepine-7-carbonyl)-propyl-amino]propyl]carbamate, TAZ-8 (1.4 g, 3.44 mmol, 1 eq) in EtOAc (10 mL) and MeOH (1 mL) was added HCl/EtOAc (4 M, 20 mL, 23.23 eq) at 25° C. and then stirred for 0.5 h. The reaction mixture was concentrated under reduced pressure to give TAZ-11 (1.28 g, crude, HCl) as a light yellow solid. $^1$H NMR (MeOD-d$_4$, 400 MHz) δ7.74 (d, J=5.6 Hz, 1H), 7.20 (s, 1H), 7.15 (d, J=5.6 Hz, 1H), 3.59 (t, J=6.8 Hz, 2H), 3.49 (t, J=7.2 Hz, 2H), 3.41 (s, 2H), 3.00 (t, J=7.2 Hz, 2H), 2.08-1.97 (m, 2H), 1.75-1.62 (m, 2H), 0.91 (t, J=7.2 Hz, 3H). LC/MS [M+H] 307.2 (calculated); LC/MS [M+H] 307.1 (observed).

Example 12 Synthesis of 5-amino-2-[1-[3-(hydroxymethyl)azetidin-1-yl]sulfonylpyrazol-4-yl]-N,N-dipropyl-6H-thieno[3,2-b]azepine-7-carboxamide, TAZ-12

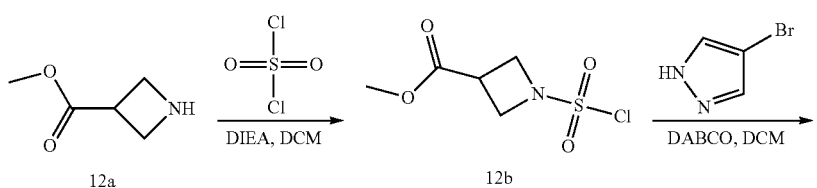

-continued

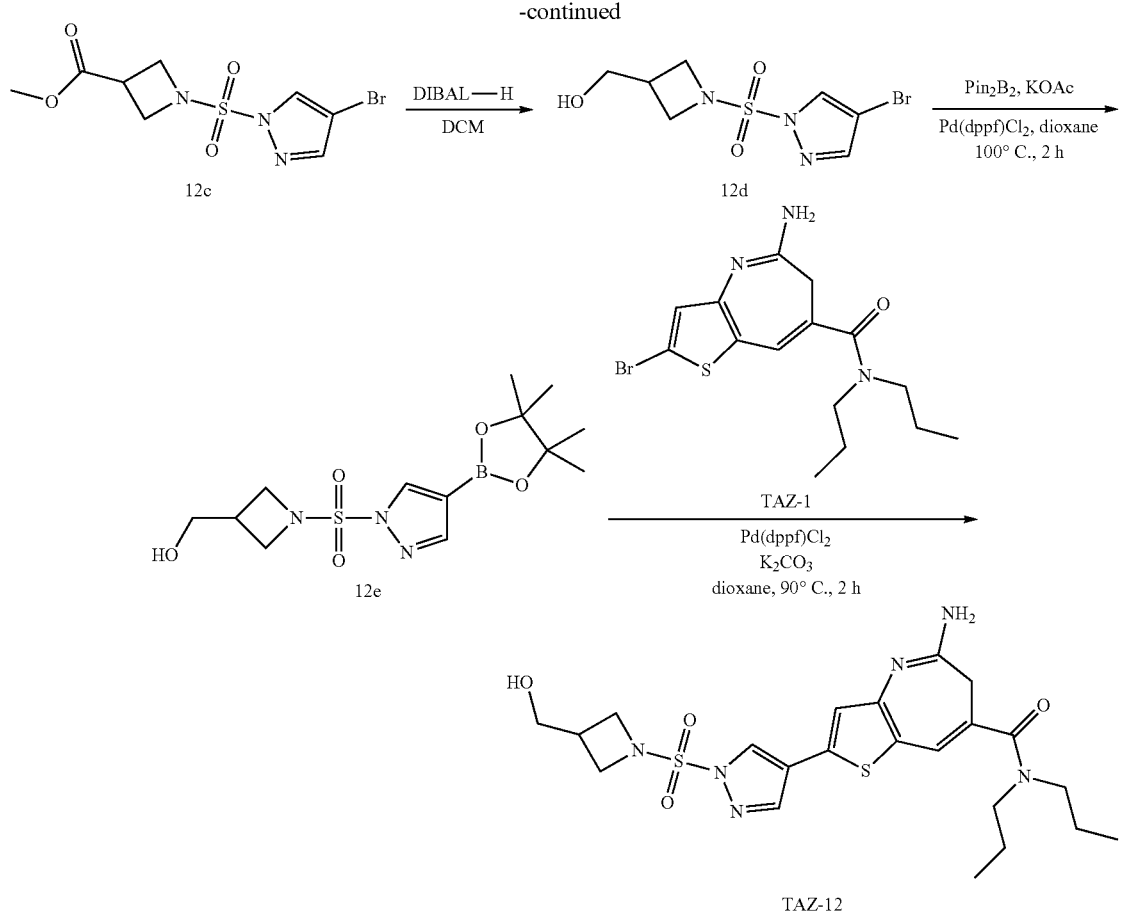

Preparation of methyl 1-chlorosulfonylazetidine-3-carboxylate, 12b

To a mixture of sulfuryl chloride (3.34 g, 24.7 mmol, 2.47 mL, 1.5 eq) in DCM (50 mL) was added a solution of methyl azetidine-3-carboxylate, 12a (2.5 g, 16.49 mmol, 1 eq, HCl) and DIEA (8.53 g, 65.97 mmol, 11.49 mL, 4 eq) in DCM (30 mL) at −78° C. and then stirred for 2 h at this temperature. The mixture was diluted with water and extracted with EtOAc (60 mL×3). The organic layer was washed with the brine, dried over $Na_2SO_4$, filtered and concentrated. The residue was purified by silica gel chromatography (Petroleum ether/Ethyl acetate=1/0, 0/1) to afford 12b (2.75 g, 12.87 mmol, 78.05% yield) as colorless oil. $^1$H NMR ($CDCl_3$, 400 MHz) δ4.36-4.25 (m, 4H), 3.80 (s, 3H), 3.57-3.47 (m, 1H).

Preparation of methyl 1-(4-bromopyrazol-1-yl)sulfonylazetidine-3-carboxylate, 12c To a mixture of 4-bromo-1H-pyrazole (1.58 g, 10.77 mmol, 1.0 eq) in DCM (40 mL) was added DABCO (1.57 g, 14.0 mmol, 1.54 mL, 1.3 eq) and 12b (2.3 g, 10.8 mmol, 1.0 eq) in one portion at 25° C. and it was stirred for 2 h. The mixture was diluted with water and extracted with EtOAc (50 mL×3). The organic layer was washed with brine, dried over $Na_2SO_4$, filtered and concentrated. The residue was purified by silica gel chromatography (Petroleum ether/Ethyl acetate=1/0, 3/1) to afford 12c (3 g, 9.25 mmol, 85.97% yield) as yellow oil. $^1$H NMR ($CDCl_3$, 400 MHz) δ8.03 (s, 1H), 7.77 (s, 1H), 4.32-4.27 (m, 4H), 3.73 (s, 3H), 3.41-3.34 (m, 1H).

Preparation of [1-(4-bromopyrazol-1-yl)sulfonylazetidin-3-yl]methanol, 12d

To a solution of 12c (3.3 g, 10.2 mmol, 1 eq) in DCM (50 mL) was added DIBAL-H (1 M, 40.7 mL, 4 eq) slowly at 0° C. under $N_2$, and then stirred at this temperature for 2 h. The mixture was quenched with water (1.5 mL) and dried over $Na_2SO_4$, filtered and concentrated to obtain 12d (1.19 g, crude) as yellow oil. $^1$H NMR ($CDCl_3$, 400 MHz) δ8.04 (s, 1H), 7.77 (s, 1H), 4.18-4.14 (t, J=8.4 Hz, 2H), 3.96 (dd, J=5.6, 8.4 Hz, 2H), 3.66 (d, J=5.6 Hz, 2H).

Preparation of [1-[4-(4,4,5,5-tetramethyl-1,3,2-dioxaborolan-2-yl)pyrazol-1-yl]sulfonylazetidin-3-yl]methanol, 12e To a mixture of 12d (0.1 g, 338 μmol, 1.0 eq) in dioxane (2 mL) was added $Pin_2B_2$ (129 mg, 507 μmol, 1.5 eq), potassium acetate, KOAc (66.3 mg, 675 μmol, 2.0 eq) and Pd(dppf)Cl$_2$ (12.4 mg, 16.9 μmol, 0.05 eq) in one portion at 25° C. under $N_2$ and it was stirred at 100° C. for 2 h. Then the mixture was diluted with water and extracted with EtOAc (10 mL×3). The organic layer was washed with brine, dried over $Na_2SO_4$, filtered and concentrated to give 12e (0.1 g, crude) as black oil.

Preparation of TAZ-12

To a mixture of 5-amino-2-bromo-N,N-dipropyl-6H-thieno[3,2-b]azepine-7-carboxamide, TAZ-1 (54 mg, 146 μmol, 1.0 eq) and 12e (50 mg, 146 μmol, 1.0 eq) in dioxane (2 mL) and H$_2$O (0.2 mL) was added K$_2$CO$_3$ (60.4 mg, 437 μmol, 3.0 eq) and Pd(dppf)Cl$_2$ (5.3 mg, 7.28 μmol, 0.05 eq) in one portion at 25° C. under N$_2$. The mixture was stirred at 90° C. for 2 h. Then the reaction was diluted with water and extracted with EtOAc (10 mL×3). The organic layer was washed with brine, dried over Na$_2$SO$_4$, filtered and concentrated. The residue was further purification by prep-HPLC (column: Phenomenex Gemini-NX C18 75*30 mm*3 um; mobile phase: [water (10 mM NH$_4$HCO$_3$)-ACN]; B %: 30%-50%, 10.5 min) to give 5-amino-2-[1-[3-(hydroxymethyl)azetidin-1-yl]sulfonylpyrazol-4-yl]-N,N-dipropyl-6H-thieno[3,2-b]azepine-7-carboxamide (9 mg, 17.8 μmol, 12.19% yield) as white solid. $^1$H NMR (MeOD, 400 MHz) δ8.56 (s, 1H), 8.28 (s, 1H), 7.42 (s, 1H), 7.38-7.35 (m, 2H), 6.85 (s, 1H), 4.13 (t, J=8.8 Hz, 2H), 3.89 (dd, J=6.0, 8.4 Hz, 2H), 3.49 (d, J=6.0 Hz, 2H), 3.43-3.37 (m, 4H), 2.97 (s, 2H), 2.72-2.67 (m, 1H), 1.69-1.61 (m, 4H), 0.93-0.87 (m, 6H). LC/MS [M+H]507.2 (calculated); LC/MS [M+H] 507.2 (observed).

Example 13 Synthesis of tert-butyl N-[5-[5-amino-7-(dipropylcarbamoyl)-6H-thieno[3,2-b]azepin-2-yl]pentyl]carbamate, TAZ-13

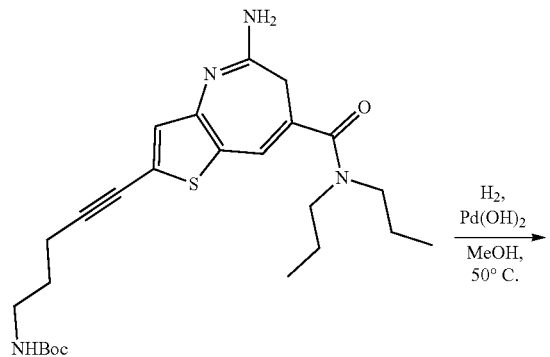

TAZ-6

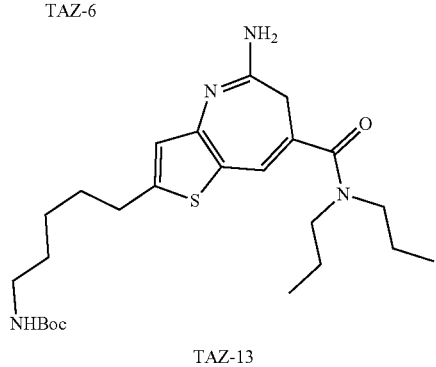

TAZ-13

To a solution of tert-butyl N-[5-[5-amino-7-(dipropylcarbamoyl)-6H-thieno[3,2-b]azepin-2-yl] pent-4-ynyl]carbamate, TAZ-6 (0.8 g, 1.69 mmol, 1.0 eq) in MeOH (30 mL) was added Pd(OH)$_2$/C (10%, 0.3 g) under N$_2$. The suspension was degassed under vacuum and purged with H$_2$ several times. The mixture was stirred under H$_2$ (50 psi) at 25° C. for 12 hours. The reaction mixture was filtered and concentrated. The residue was purified by flash silica gel chromatography (ISCO®; 20 g SepaFlash® Silica Flash Column, Eluent of 0~100% Ethyl acetate/Petroleum ether gradient @ 60 mL/min) to give TAZ-13 (0.6 g, 1.26 mmol, 74.37% yield) as yellow oil. $^1$H NMR (MeOD, 400 MHz) δ6.80 (s, 1H), 6.62 (s, 1H), 3.43-3.35 (m, 4H), 3.03 (t, J=7.2 Hz, 2H), 2.91 (s, 2H), 2.78 (t, J=7.2 Hz, 2H), 1.69-1.60 (m, 6H), 1.50-1.40 (m, 13H), 0.92-0.87 (m, 6H). LC/MS [M+H] 477.3 (calculated); LC/MS [M+H] 477.3 (observed)

Example 14 Synthesis of 5-amino-2-(5-aminopentyl)-N,N-dipropyl-6H-thieno [3,2-b]azepine-7-carboxamide, TAZ-14

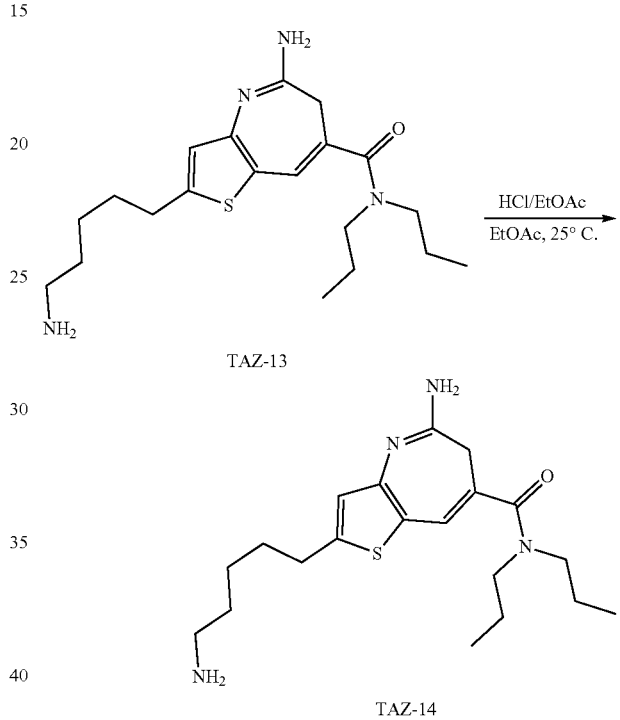

To a solution of tert-butyl N-[5-[5-amino-7-(dipropylcarbamoyl)-6H-thieno[3,2-b]azepin-2-yl]pentyl]carbamate, TAZ-13 (0.31 g, 650 μmol, 1.0 eq) in EtOAc (10 mL) was added HCl/EtOAc (4 M, 4.88 mL, 30.0 eq) at 25° C. and then stirred for 1 hour at this temperature. The mixture was concentrated under reduced pressure to give TAZ-14 (0.26 g, 630 μmol, 96.80% yield, HCl) as yellow solid. $^1$H NMR (MeOD, 400 MHz) δ7.02 (s, 1H), 6.92 (s, 1H), 3.45-3.43 (m, 4H), 3.35 (s, 2H), 2.98-2.86 (m, 4H), 1.82-1.62 (m, 8H), 1.55-1.45 (m, 2H), 0.92-0.87 (m, 6H). LC/MS [M+H] 377.2 (calculated); LC/MS [M+H] 377.2 (observed).

Example 15 Synthesis of 5-amino-2-bromo-6H-thieno[3,2-b]azepine-7-carboxylic Acid, TAZ-15

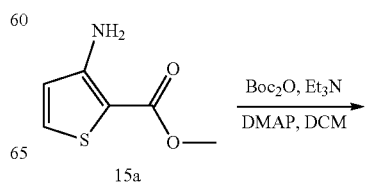

15a

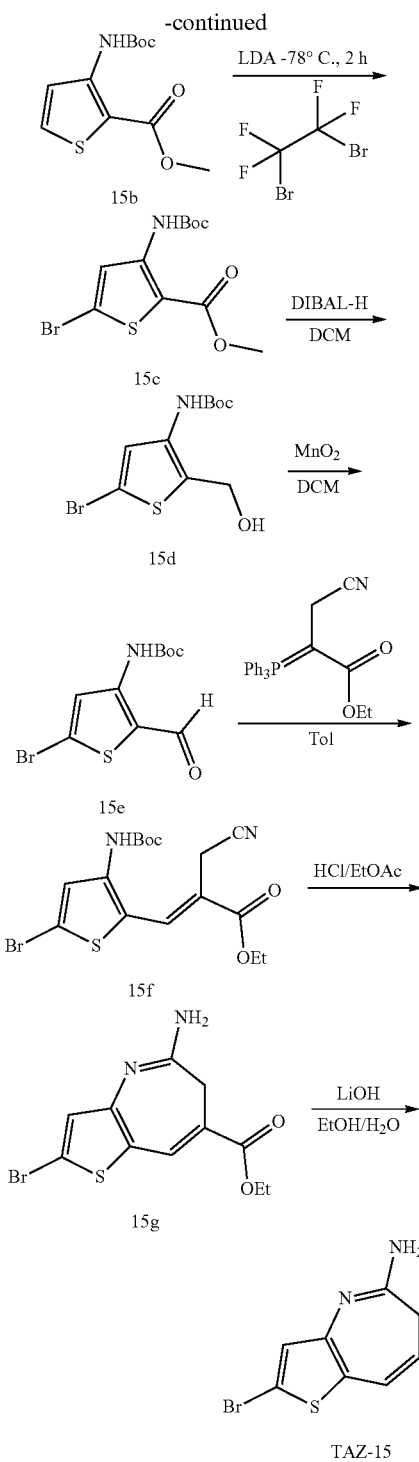

Preparation of methyl 3-(tert-butoxycarbonylamino)thiophene-2-carboxylate, 15b To a solution of methyl 3-aminothiophene-2-carboxylate, 15a (19 g, 121 mmol, 1 eq) and Et₃N (14.7 g, 145 mmol, 20.2 mL, 1.2 eq) in DCM (100 mL) was added Boc₂O (29.0 g, 133 mmol, 30.5 mL, 1.1 eq) in DCM (50 mL) dropwise at 25° C., then DMAP (738 mg, 6.0 mmol, 0.05 eq) was added to the mixture. The resulting mixture was stirred at 25° C. for 3 h. The mixture was diluted with water (100 mL) and extracted with DCM (50 mL×3). The organic layer was washed with brine (30 mL), dried over Na₂SO₄, filtered and concentrated. The residue was purified by flash silica gel chromatography (ISCO®; 20 g SepaFlash® Silica Flash Column, Eluent of 0~20% Ethyl acetate/Petroleum ether gradient @ 45 mL/min) to give 15b (12 g, 46.64 mmol, 38.58% yield) as white solid. ¹H NMR (CDCl₃, 400 MHz) δ9.36 (s, 1H), 7.89 (d, J=5.6 Hz 1H), 7.42 (d, J=5.6 Hz, 1H), 3.88 (s, 3H), 1.53 (s, 9H).

Preparation of methyl 5-bromo-3-(tert-butoxycarbonylamino)thiophene-2-carboxylate, 15c To a solution of 15b (8.9 g, 34.6 mmol, 1 eq) in THF (50 mL) was added LDA (2 M, 60.0 mL, 3.5 eq) at −78° C., the mixture was stirred for 1 h at −78° C., then 1,2-dibromo-1,1,2,2-tetrafluoro-ethane (53.92 g, 207.54 mmol, 6 eq) was added and then stirred for 1 h at this temperature. The mixture was poured into cold ammonium chloride solution (100 mL) while stirring vigorously, and extracted with EtOAc (50 mL×3). The organic layer was washed with brine (50 mL), dried over Na₂SO₄, filtered and concentrated. The residue was purified by flash silica gel chromatography (ISCO®; 10 g SepaFlash® Silica Flash Column, Eluent of 0~20% Ethyl acetate/Petroleum ether gradient @ 45 mL/min) to give 15c (4 g, 11.90 mmol, 34.40% yield) as off-white solid. ¹H NMR (CDCl₃, 400 MHz) δ9.33 (s, 1H), 7.97 (s, 1H), 3.86 (s, 3H), 1.54 (s, 9H)

Preparation of tert-butyl N-[5-bromo-2-(hydroxymethyl)-3-thienyl]carbamate, 15d To a solution of 15c (4 g, 11.9 mmol, 1 eq) in DCM (60 mL) was added DIBAL-H (1 M, 59.0 mL, 5 eq) at 0° C. under N₂ and then stirred at 25° C. for 2 h. The reaction mixture was quenched by addition of H₂O 1 mL at 0° C., and then added 15% NaOH (0.5 mL) and H₂O (1 mL) at 0° C. The mixture was stirred for 30 min at 25° C., filtered and the cake was washed with EtOAc (50 mL), the filtrate was concentrated to give 15d (3 g, 9.7 mmol, 81.82% yield) as yellow solid. ¹H NMR (CDCl₃, 400 MHz) δ7.21 (s, 1H), 6.68 (s, 1H), 4.60 (s, 2H), 1.51 (s, 9H).

Preparation of tert-butyl N-(5-bromo-2-formyl-3-thienyl)carbamate, 15e

To a solution of 15d (3 g, 9.73 mmol, 1 eq) in DCM (30 mL) was added MnO₂ (8.5 g, 97.34 mmol, 10 eq) at 25° C. The mixture was stirred at 50° C. for 12 h. The mixture was filtered and concentrated to give 15e (1.5 g, 4.90 mmol, 50.33% yield) as yellow solid. ¹H NMR (CDCl₃, 400 MHz) δ9.82 (s, 1H), 9.51 (s, 1H), 8.03 (s, 1H), 1.53 (s, 9H).

Preparation of ethyl (E)-3-[5-bromo-3-(tert-butoxycarbonylamino)-2-thienyl]-2-(cyanomethyl)prop-2-enoate, 15f To a solution of 15e (1.5 g, 4.90 mmol, 1 eq) in toluene (15 mL) was added ethyl 3-cyano-2-(triphenyl-phosphanylidene)propanoate (2.5 g, 6.4 mmol, 1.3 eq) at 25° C., and then stirred at 75° C. for 2 h. The mixture was concentrated and the residue was purified by flash silica gel chromatography (ISCO®; 2 g SepaFlash® Silica Flash Column, Eluent of 0~80% Ethyl acetate/Petroleum ether gradient @ 45 mL/min) to give 15f (1.65 g, 3.97 mmol, 81.10% yield) as yellow solid. ¹H NMR (CDCl₃, 400 MHz) δ7.81 (s, 1H), 7.73 (s, 1H), 6.72 (s, 1H), 4.35 (q, J=7.2 Hz, 2H), 3.68 (s, 2H), 1.54 (s, 9H), 1.39 (t, J=7.2 Hz, 3H).

Preparation of ethyl 5-amino-2-bromo-6H-thieno[3,2-b]azepine-7-carboxylate, 15g

To a solution of 15f (1.3 g, 3.13 mmol, 1 eq) in EtOAc (10 mL) was added HCl/EtOAc (4 M, 13.00 mL, 16.6 eq) at 25° C. The mixture was stirred at 25° C. for 2 h and then concentrated to give 15g (1 g, crude) was obtained as yellow solid. $^1$H NMR (DMSO-$d_6$, 400 MHz) δ10.13 (s, 1H), 9.29 (s, 1H), 7.91 (s, 1H), 7.37 (s, 1H), 4.24 (q, J=7.2 Hz, 2H), 3.52 (s, 2H), 1.28 (t, J=7.2 Hz, 3H).

Preparation of 5-amino-2-bromo-6H-thieno[3,2-b]azepine-7-carboxylic Acid, TAZ-15

To a solution of 15g (1 g, 3.17 mmol, 1 eq) in EtOH (10 mL) and H$_2$O (1 mL) was added LiOH.H$_2$O (665 mg, 15.8 mmol, 5 eq) and then stirred at 25° C. for 12 h. The reaction mixture was concentrated under reduced pressure to remove EtOH. The residue was diluted with H$_2$O (30 mL), and then the pH of mixture was adjusted to 4 by aq HCl (1 M), and extracted with EtOAc (20 mL×3). The organic layer was washed with brine (10 mL), dried over Na$_2$SO$_4$, filtered and concentrated to give TAZ-15 (0.85 g, 2.96 mmol, 93.30% yield) as yellow solid. $^1$H NMR (DMSO-$d_6$, 400 MHz) δ7.65 (s, 1H), 7.34 (br s, 2H), 6.97 (s, 1H), 2.97 (s, 2H).

Example 16 Synthesis of tert-butyl N-[4-[(5-amino-6H-thieno[3,2-b]azepine-7-carbonyl)-propyl-amino]but-2-ynyl]carbamate, TAZ-16

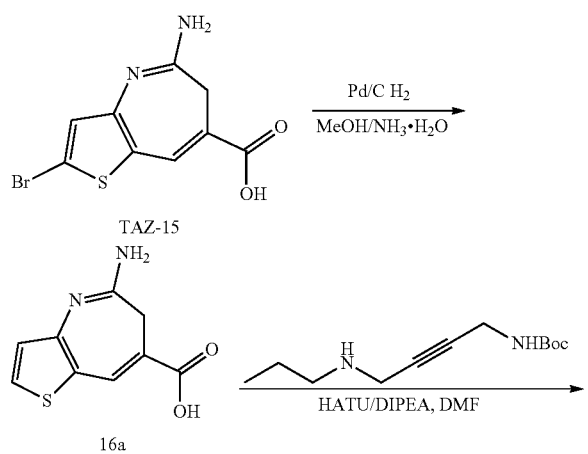

Preparation of 5-amino-6H-thieno[3,2-b]azepine-7-carboxylic acid, 16a

To a solution of 5-amino-2-bromo-6H-thieno[3,2-b]azepine-7-carboxylic acid, TAZ-15 (1 g, 3.48 mmol, 1 eq) in MeOH (20 mL) was added Pd/C (10%, 0.2 g) and aqueous ammonium hydroxide, NH$_3$.H$_2$O (4.88 g, 34.8 mmol, 5.37 mL, 25% purity, 10 eq) under N$_2$. The suspension was degassed under vacuum and purged with H$_2$ several times, and then stirred under H$_2$ (50 psi) at 25° C. for 12 h. The reaction mixture was filtered through Celite® (Johns Manville) and the pH of filtrate was adjusted to ~6 with 2 N HCl at 0° C., and then concentrated under reduced pressure to remove MeOH. The solid was filtered and dried under reduced pressure to give 16a (0.54 g, 2.59 mmol, 74.46% yield) as a light yellow solid. $^1$H NMR (DMSO-$d_6$, 400 MHz) δ7.71 (s, 1H), 7.61 (d, J=5.2 Hz, 1H), 6.98 (br s, 2H), 6.83 (d, J=5.2 Hz, 1H), 2.91 (s, 2H).

Preparation of TAZ-16

To a solution of 16a (0.33 g, 1.58 mmol, 1 eq) in DMF (4 mL) was added HATU (662.82 mg, 1.74 mmol, 1.1 eq) and DIPEA (1.02 g, 7.92 mmol, 1.38 mL, 5 eq) at 0° C. After 10 min, tert-butyl N-[4-(propylamino)but-2-ynyl]carbamate (394.51 mg, 1.74 mmol, 1.1 eq) was added at 0° C., and then the resulting mixture was stirred at 25° C. for 30 min. The reaction mixture was quenched by addition of H$_2$O (30 mL) at 0° C., and then extracted with EtOAc (15 mL×3). The combined organic layers were washed with brine (5 mL×3), dried over Na$_2$SO$_4$, filtered and concentrated under reduced pressure. The residue was purified by prep-HPLC (TFA condition; column: Phenomenex Luna C18 100*30 mm*5 um; mobile phase: [water (0.1% TFA)-ACN]; B %: 15%-45%, 10 min) to give TAZ-16 (0.185 g, 444.14 μmol, 28.03% yield) as a light yellow solid. $^1$H NMR (MeOD, 400 MHz) δ7.74 (d, J=5.6 Hz, 1H), 7.29 (s, 1H), 7.13 (d, J=5.6 Hz, 1H), 4.30 (s, 2H), 3.84 (s, 2H), 3.54-3.52 (m, 2H), 3.38 (s, 2H), 1.76-1.67 (m, 2H), 1.43 (s, 9H), 0.94 (t, J=7.6 Hz, 3H). LC/MS [M+H] 417.2 (calculated); LC/MS [M+H] 417.2 (observed).

Example 17 Synthesis of 5-amino-N-(4-aminobut-2-ynyl)-N-propyl-6H-thieno[3,2-b]azepine-7-carboxamide, TAZ-17

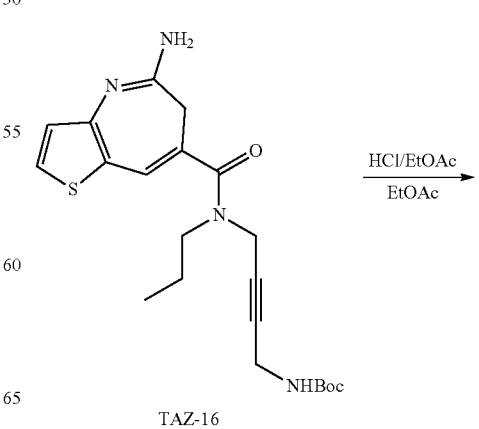

-continued

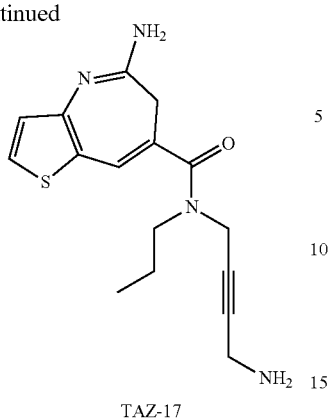
TAZ-17

To a solution of tert-butyl N-[4-[(5-amino-6H-thieno[3,2-b]azepine-7-carbonyl)-propyl-amino]but-2-ynyl]carbamate, TAZ-16 (0.45 g, 1.08 mmol, 1 eq) in EtOAc (2 mL) was added HCl/EtOAc (4 M, 15.00 mL, 55 eq) at 25° C. and then stirred for 0.5 h at this temperature. The reaction mixture was concentrated under reduced pressure to give TAZ-17 (496 mg, crude, HCl) as a light yellow solid. $^1$H NMR (MeOD, 400 MHz) δ7.76 (d, J=5.6 Hz, 1H), 7.23 (s, 1H), 7.15 (d, J=5.6 Hz, 1H), 4.40 (s, 2H), 3.87 (s, 2H), 3.57 (t, J=7.2 Hz, 2H), 3.40 (s, 2H), 1.81-1.65 (m, 2H), 0.95 (t, J=7.6 Hz, 3H). LC/MS [M+H] 317.1 (calculated); LC/MS [M+H] 317.1 (observed).

Example 18 Synthesis of 5-amino-2-phenyl-N,N-dipropyl-6H-thieno[3,2-b]azepine-7-carboxamide, TAZ-18

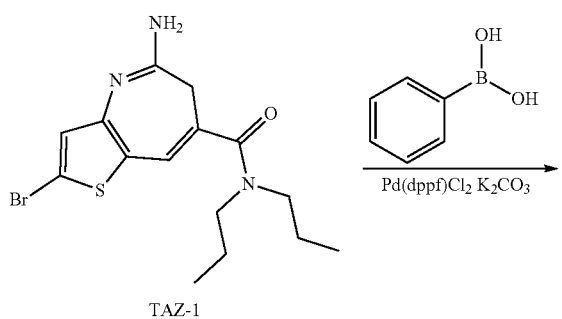

To a mixture of phenylboronic acid (34.5 mg, 283 μmol, 1.5 eq), K$_2$CO$_3$ (52.0 mg, 378 μmol, 2.0 eq) and 5-amino-2-bromo-N,N-dipropyl-6H-thieno[3,2-b]azepine-7-carboxamide, TAZ-1 (70.0 mg, 190 μmol, 1.0 eq) in dioxane (2 mL) and H$_2$O (0.2 mL) was added Pd(dppf)Cl$_2$ (7.0 mg, 9.45 μmol, 0.05 eq) at 25° C. under N$_2$ and then stirred at 100° C. for 1 hours. The mixture was filtered and purified by prep-HPLC (column: Nano-micro Kromasil C18 100*30 mm 8 um; mobile phase: [water (0.1% TFA)-ACN]; B %: 25%-50%, 10 min) to afford TAZ-18 (54 mg, 147 μmol, 77.7% yield) as white solid. $^1$H NMR (MeOD, 400 MHz) δ7.69 (d, J=7.2 Hz, 2H), 7.49-7.37 (m, 4H), 7.11 (s, 1H), 3.54-3.38 (m, 6H), 1.68 (sxt, J=7.4 Hz, 4H), 0.99-0.92 (m, 6H). LC/MS [M+H] 368.2 (calculated); LC/MS [M+H] 368.1 (observed).

Example 19 Synthesis of 5-amino-N,N-dipropyl-2-(1-((2-(trimethylsilyl)ethoxy)methyl)-1H-pyrazol-4-yl)-6H-thieno[3,2-b]azepine-7-carboxamide, TAZ-19

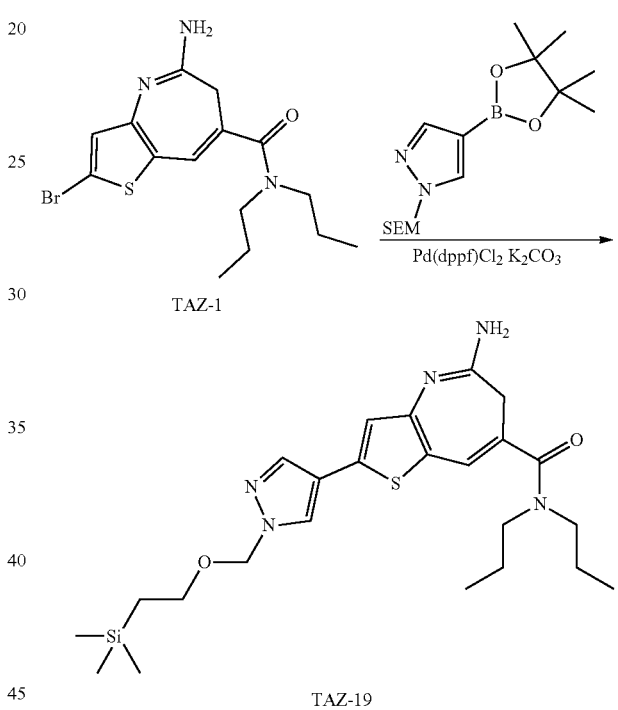
TAZ-19

To a mixture of 5-amino-2-bromo-N,N-dipropyl-6H-thieno[3,2-b]azepine-7-carboxamide, TAZ-1 (100 mg, 270 μmol, 1.0 eq), K$_2$CO$_3$ (75.0 mg, 540 μmol, 2.0 eq) and trimethyl-[2-[[4-(4,4,5,5-tetramethyl-1,3,2-dioxaborolan-2-yl)pyrazol-1-yl]methoxy]ethyl]silane (96 mg, 297 μmol, 1.1 eq) in dioxane (3 mL) and H$_2$O (0.2 mL) was added Pd(dppf)Cl$_2$ (9.88 mg, 13.50 μmol, 0.05 eq) at 25° C. under N$_2$ and then stirred at 95° C. for 1 hours. The mixture was filtered and concentrated in vacuum. The residue was purified by prep-HPLC (column: Phenomenex Gemini-NX C18 75*30 mm*3 um; mobile phase: [water (10 mM NH$_4$HCO$_3$)-ACN]; B %: 40%-60%, 10.5 min) to afford TAZ-19 (80 mg, 164 μmol, 60.7% yield) as light yellow solid. $^1$H NMR (MeOD, 400 MHz) δ8.09 (s, 1H), 7.80 (s, 1H), 6.97 (s, 1H), 6.85 (s, 1H), 5.45 (s, 2H), 3.61 (t, J=8.0 Hz, 2H), 3.46-3.36 (m, 4H), 2.96 (s, 2H), 1.72-1.57 (m, 4H), 0.90 (t, J=8.0 Hz, 8H), 0.00 (s, 9H). LC/MS [M+H] 488.2 (calculated); LC/MS [M+H] 488.2 (observed).

Example 20 Synthesis of methyl 5-amino-7-(dipropylcarbamoyl)-6H-thieno[3,2-b]azepine-2-carboxylate, TAZ-20

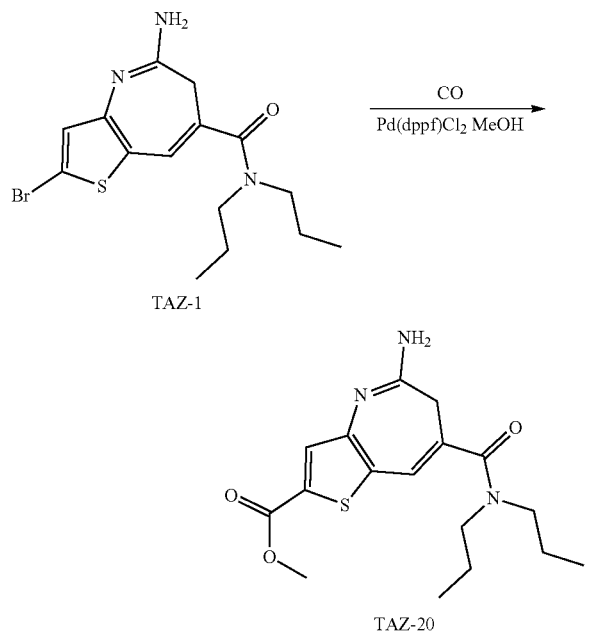

To a solution of 5-amino-2-bromo-N,N-dipropyl-6H-thieno[3,2-b]azepine-7-carboxamide, TAZ-1 (1.2 g, 3.24 mmol, 1.0 eq) and Et$_3$N (984 mg, 9.72 mmol, 1.35 mL, 3 eq) in MeOH (20 mL) was added Pd(dppf)Cl$_2$ (118.56 mg, 162.03 μmol, 0.05 eq) under N$_2$. The suspension was degassed under vacuum and purged with CO several times. The mixture was stirred under CO (50 psi) at 80° C. for 12 hours. The mixture was filtered and concentrated in vacuum to afford TAZ-20 (1.1 g, 3.15 mmol, 97.14% yield) as white solid. $^1$H NMR (MeOD, 400 MHz) δ7.72 (s, 1H), 7.14 (s, 1H), 3.92 (s, 3H), 3.58-3.37 (m, 6H), 1.69-1.62 (m, 4H), 0.99-0.90 (m, 6H). LC/MS [M+H] 350.2 (calculated); LC/MS [M+H] 350.2 (observed).

Example 21 Synthesis of 5-amino-N,N-dipropyl-2-(1H-pyrazol-4-yl)-6H-thieno[3,2-b]azepine-7-carboxamide, TAZ-21

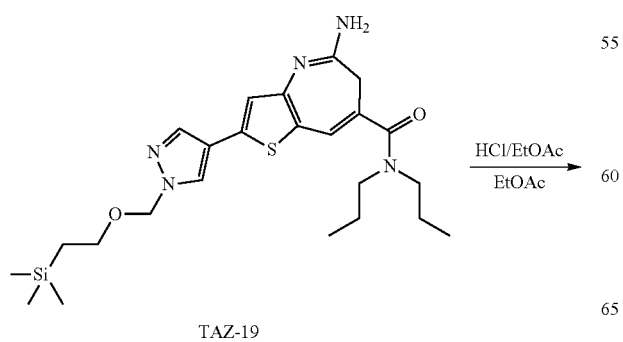

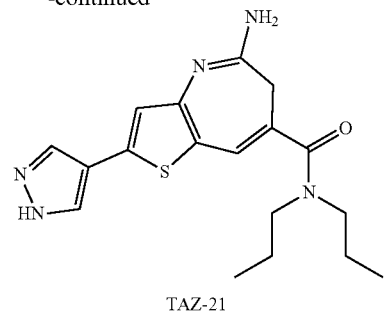

To a mixture of 5-amino-N,N-dipropyl-2-[1-(2-trimethylsilylethoxymethyl) pyrazol-4-yl]-6H-thieno[3,2-b]azepine-7-carboxamide, TAZ-19 (66.0 mg, 135 μmol, 1.0 eq) in MeOH (4 mL) was added HCl/MeOH (4 M, 338 μL, 10.0 eq) at 25° C. and then stirred for 12 hours at this temperature. The mixture was concentrated in vacuum, and the residue was purified by prep-HPLC (column: Phenomenex Gemini-NX C18 75*30 mm*3 um; mobile phase: [water (10 mM NH$_4$HCO$_3$)-ACN]; B %: 20%-50%, 10.5 min) to afford TAZ-21 (22 mg, 61.5 μmol, 45.5% yield) as white solid. $^1$H NMR (MeOD, 400 MHz) δ7.87 (s, 2H), 6.95 (s, 1H), 6.85 (s, 1H), 3.44-3.35 (m, 4H), 2.96 (s, 2H), 1.66-1.60 (m, 4H), 0.99-0.89 (m, 6H). LC/MS [M+H] 358.2 (calculated); LC/MS [M+H] 358.2 (observed).

Example 22 Synthesis of 5-amino-7-(dipropylcarbamoyl)-6H-thieno[3,2-b]azepine-2-carboxylic Acid, TAZ-22

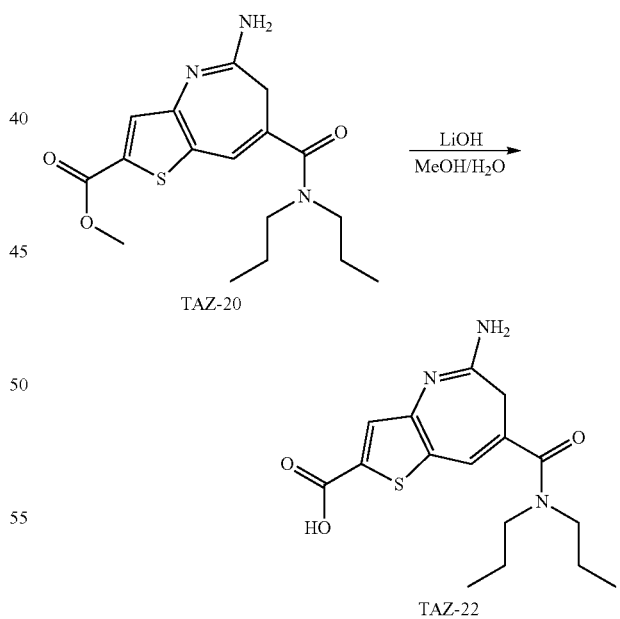

To a mixture of methyl 5-amino-7-(dipropylcarbamoyl)-6H-thieno[3,2-b]azepine-2-carboxylate, TAZ-20 (1.1 g, 3.15 mmol, 1.0 eq) in MeOH (20 mL) was added LiOH.H$_2$O (396 mg, 9.44 mmol, 3.0 eq) in H$_2$O (5 mL) at 25° C. and then stirred for 2 hours at this temperature. The mixture was quenched with aq HCl (4 M) until pH to 5, off-white solid precipitated from the mixture and then filtered to give TAZ-22 (0.85 g, 2.53 mmol, 80.5% yield) as off white solid. ¹H NMR (MeOD, 400 MHz) δ7.41 (s, 1H), 6.92 (s, 1H), 3.37-3.25 (m, 4H), 3.05 (s, 2H), 1.61-1.45 (m, 4H), 0.86-0.75 (m, 6H). LC/MS [M+H] 336.1 (calculated); LC/MS [M+H] 336.1 (observed).

Example 23 Synthesis of 5-amino-N2-phenyl-N7,N7-dipropyl-6H-thieno [3,2-b]azepine-2,7-dicarboxamide, TAZ-23

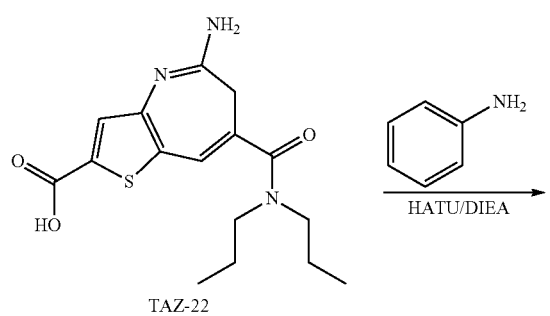

Example 24 Synthesis of 5-amino-N2-ethyl-N7,N7-dipropyl-6H-thieno[3,2-b]azepine-2,7-dicarboxamide, TAZ-24

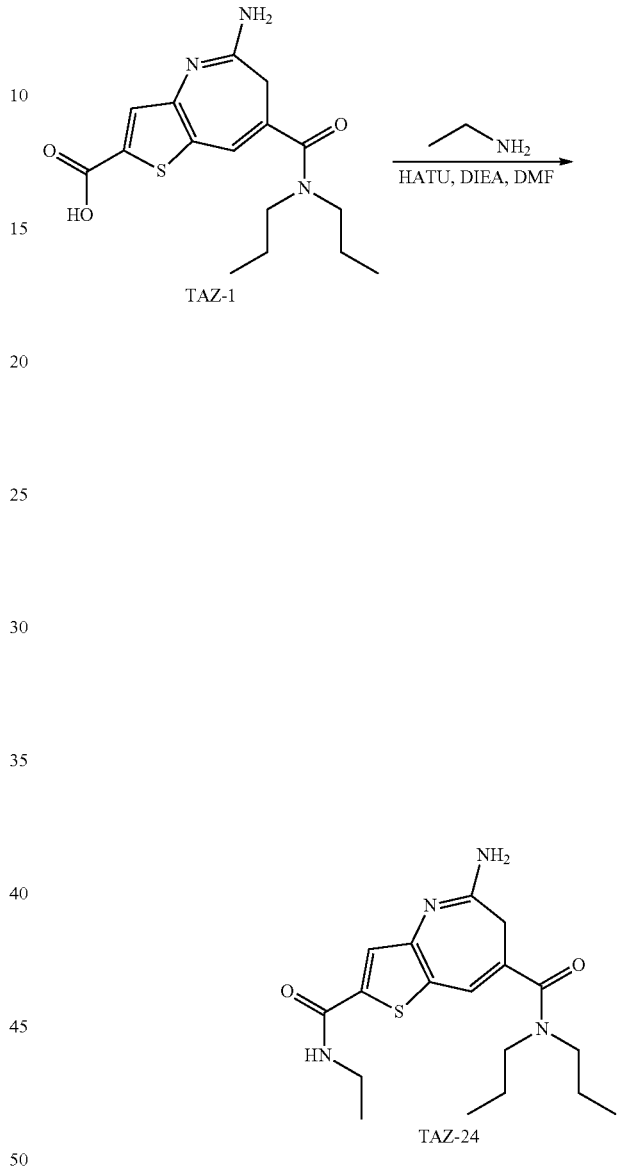

To a mixture of 5-amino-7-(dipropylcarbamoyl)-6H-thieno[3,2-b]azepine-2-carboxylic acid, TAZ-22 (50 mg, 150 μmol, 1.0 eq) HATU (62 mg, 164 μmol, 1.1 eq) and DIEA (58 mg, 447 μmol, 3.0 eq) in DMF (1 mL) was added aniline (28 mg, 298 μmol, 2.0 eq) at 25° C. and then stirred at 25° C. for 30 min. The mixture was filtered and purified by prep-HPLC (column: Nano-micro Kromasil C18 100*30 mm 8 um; mobile phase: [water (0.1% TFA)-ACN]; B %: 10%-40%, 10 min) to give TAZ-23 (34 mg, 82.8 μmol, 55.6% yield) as white solid. ¹H NMR (MeOD, 400 MHz) δ7.87 (s, 1H), 7.67 (d, J=8.0 Hz, 2H), 7.38 (t, J=8.0 Hz, 2H), 7.18 (d, J=8.0 Hz, 1H), 7.15 (s, 1H), 3.49-3.42 (m, 6H), 1.70-1.65 (m, 4H), 0.98-0.90 (m, 6H). LC/MS [M+H]411.2 (calculated); LC/MS [M+H] 411.1 (observed).

To a mixture of 5-amino-7-(dipropylcarbamoyl)-6H-thieno[3,2-b]azepine-2-carboxylic acid, TAZ-1 (50 mg, 149 μmol, 1.0 eq), HATU (62.4 mg, 164 μmol, 1.1 eq) and DIEA (58 mg, 447 μmol, 3.0 eq) in DMF (1 mL) was added ethanamine (20 mg, 298 μmol, 2.0 eq) at 25° C. and then stirred for 0.5 hours at this temperature. The mixture was filtered and purified by prep-HPLC (column: Nano-micro Kromasil C18 100*30 mm 8 um; mobile phase: [water (0.1% TFA)-ACN]; B %: 5%-35%, 10 min). Afforded TAZ-24 (28 mg, 77.2 μmol, 51.8% yield) as white solid. ¹H NMR (MeOD, 400 MHz) δ7.62 (s, 1H), 7.13 (s, 2H), 3.54-3.35 (m, 8H), 1.73-1.61 (m, 4H), 1.23 (t, J=7.2 Hz, 3H), 0.97-0.90 (m, 6H). LC/MS [M+H] 363.2 (calculated); LC/MS [M+H] 363.2 (observed).

Example 25 Synthesis of 3-[2-[2-[2-[2-[2-[2-[2-[2-[2-[5-[5-amino-7-(dipropylcarbamoyl)-6H-thieno[3,2-b]azepin-2-yl]pentyl-methylamino]ethoxy]ethoxy]ethoxy]ethoxy]ethoxy]ethoxy]ethoxy]ethoxy]propanoic Acid, TAZ-25
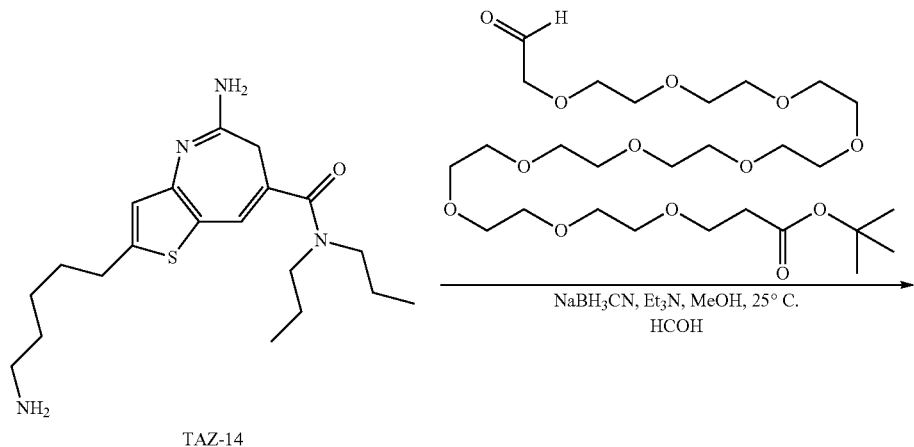
TAZ-14
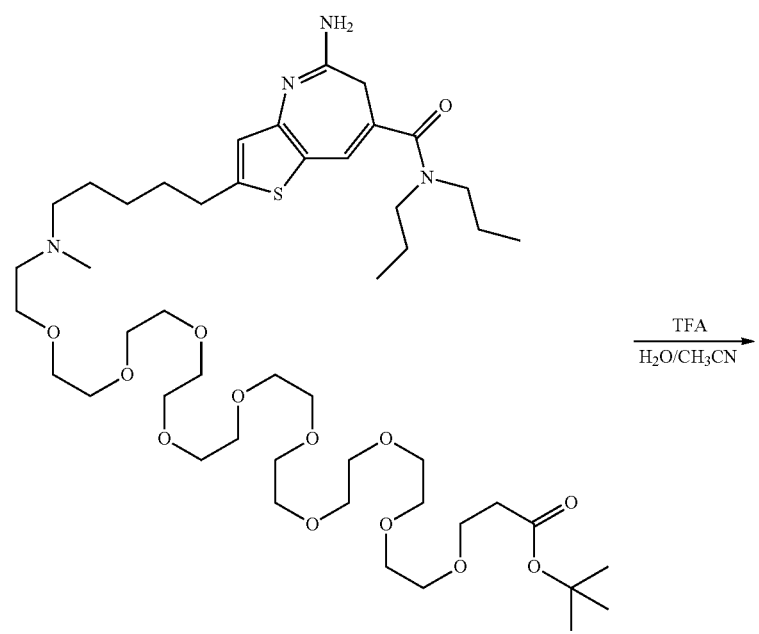
25a

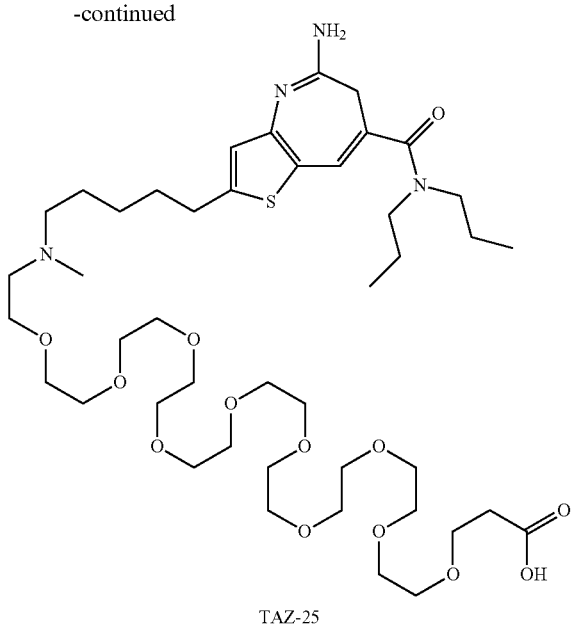

TAZ-25

Preparation of tert-butyl 3-[2-[2-[2-[2-[2-[2-[2-[2-[2-[2-[5-[5-amino-7-(dipropylcarbamoyl)-6H-thieno[3,2-b]azepin-2-yl]pentyl-methylamino]ethoxy]ethoxy]ethoxy]ethoxy]ethoxy]ethoxy]ethoxy]ethoxy]ethoxy]propanoate, 25a To a solution of 5-amino-2-(5-aminopentyl)-N,N-dipropyl-6H-thieno[3,2-b]azepine-7-carboxamide, TAZ-14 (0.2 g, 484 μmol, 1.0 eq, HCl) in MeOH (80 mL) was added Et$_3$N (73.5 mg, 726 μmol, 101 μL, 1.5 eq) and tert-butyl 3-[2-[2-[2-[2-[2-[2-[2-[2-[2-(2-oxoethoxy) ethoxy]ethoxy]ethoxy]ethoxy]ethoxy]ethoxy]ethoxy]ethoxy]propanoate (368.1 mg, 629 μmol, 1.3 eq) at 25° C. The mixture was stirred at 25° C. for 10 min, then NaBH$_3$CN (60.8 mg, 968 μmol, 2.0 eq) was added and it was stirred at the same temperature for 16 hours. Formaldehyde (117.9 mg, 1.45 mmol, 108 μL, 3.0 eq) was added followed by NaBH$_3$CN (60.9 mg, 968 μmol, 2.0 eq) and then stirred at 25° C. for 2 hours. The mixture was concentrated and the residue was purified by prep-HPLC (column: Xtimate C18 100*30 mm*3 um; mobile phase: [water (0.1% TFA)-ACN]; B %: 15%-50%, 10 min) to give 25a (0.4 g, 416.98 μmol, 86.11% yield) as colorless oil.

Preparation of TAZ-25

To a solution of 25a (0.39 g, 406 μmol, 1.0 eq) in H$_2$O (20 mL) was added TFA (927 mg, 8.13 mmol, 602 μL, 20 eq) at 25° C. The mixture was stirred at 85° C. for 1 hour and then concentrated under reduced pressure at 50° C. The residue purified by prep-HPLC (column: Nano-micro Kromasil C18 100*30 mm 8 um; mobile phase: [water (0.1% TFA)-ACN]; B %: 10%-30%, 15 min) to afford TAZ-25 (0.18 g, 199.30 μmol, 49.02% yield) as light yellow oil. $^1$H NMR (MeOD, 400 MHz) δ7.02 (s, 1H), 6.90 (s, 1H), 3.84-3.82 (m, 2H), 3.75-3.59 (m, 41H), 3.45-3.42 (m, 4H), 3.35 (s, 2H), 2.96-2.87 (m, 5H), 2.54 (t, J=6.4 Hz, 2H), 1.84-1.76 (m, 4H), 1.71-1.60 (m, 4H), 1.54-1.44 (m, 2H), 0.94-0.89 (m, 6H). LC/MS [M+H] 903.5 (calculated); LC/MS [M+H] 903.5 (observed).

Example 26 Synthesis of 5-amino-2-benzyl-N,N-dipropyl-6H-thieno[3,2-b] azepine-7-carboxamide, TAZ-26

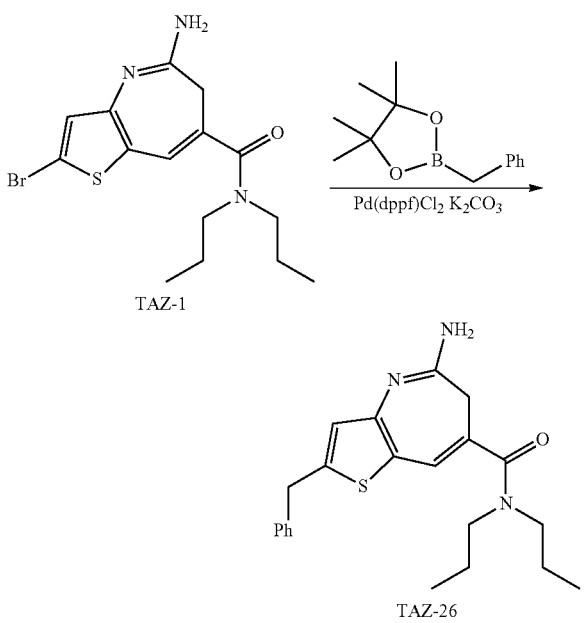

To a mixture of 5-amino-2-bromo-N,N-dipropyl-6H-thieno[3,2-b]azepine-7-carboxamide, TAZ-1 (0.11 g, 297 μmol, 1.0 eq), K$_2$CO$_3$ (82 mg, 594 μmol, 2 eq) and 2-benzyl-4,4,5,5-tetramethyl-1,3,2-dioxaborolane (324 mg, 1.49 mmol, 5.0 eq) in DMF (3 mL) and H$_2$O (0.2 mL) was added Pd(dppf)Cl$_2$ (11 mg, 14.8 μmol, 0.05 eq) at 25° C. under N$_2$. The mixture was stirred at 120° C. for 2 hours and then filtered and concentrated. The residue was purified by prep-HPLC (column: Xtimate C18 100*30 mm*3 um; mobile phase: [water (0.1% TFA)-ACN]; B %: 25%-45%, 10 min)

to give TAZ-26 (16 mg, 41.9 μmol, 14.1% yield) as light yellow solid. ¹H NMR (MeOD, 400 MHz) δ7.40-7.21 (m, 5H), 6.98 (s, 1H), 6.88 (s, 1H), 4.17 (s, 2H), 3.41 (t, J=7.6 Hz, 4H), 3.34 (s, 2H), 1.66-1.62 (m, 4H), 0.96-0.86 (m, 6H). LC/MS [M+H]382.2 (calculated); LC/MS [M+H] 382.1 (observed).

Example 27 Synthesis of 5-amino-N7,N7-dipropyl-N2-pyrimidin-5-yl-6H-thieno[3,2-b]azepine-2,7-dicarboxamide, TAZ-27

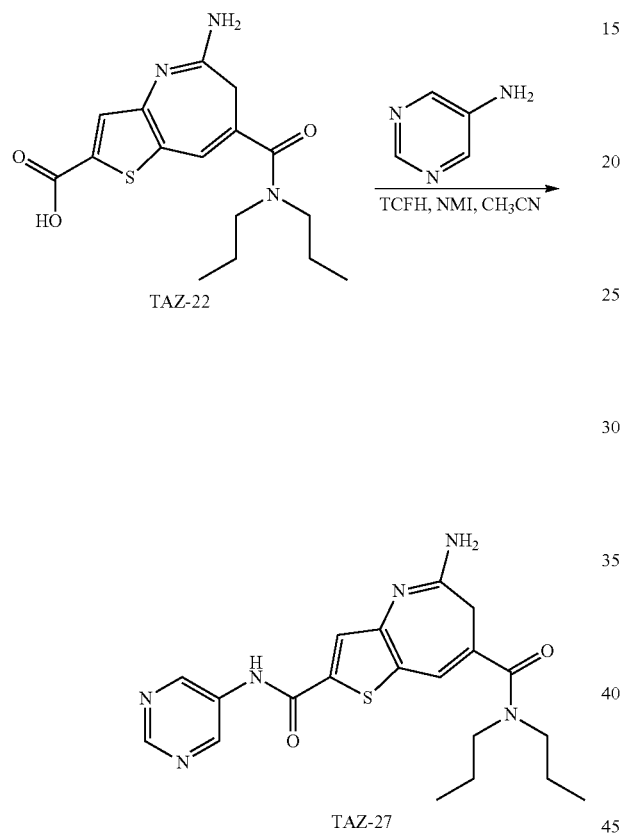

To a mixture of 5-amino-7-(dipropylcarbamoyl)-6H-thieno[3,2-b]azepine-2-carboxylic acid, TAZ-22 (50 mg, 149 μmol, 1 eq), pyrimidin-5-amine (18.4 mg, 194 μmol, 1.3 eq) and 1-methylimidazole (42.8 mg, 522 μmol, 3.5 eq) in CH₃CN (2 mL) was added chloro-N,N,N',N'-tetramethyl-formamidinium hexafluorophosphate, TCFH (50.19 mg, 179 μmol, 1.2 eq) at 25° C., and then stirred for 16 h at this temperature. The reaction mixture was quenched by addition of H₂O (10 mL) at 0° C., and then extracted with EtOAc (10 mL×3). The combined organic layers were washed with brine (5 mL), dried over Na₂SO₄, filtered and concentrated under reduced pressure. The residue was purified by prep-HPLC (TFA condition; column: Phenomenex Luna C18 100*30 mm*5 um; mobile phase: [water (0.1% TFA)-ACN]; B %: 10%-40%, 10 min) to give TAZ-27 (13 mg, 31.5 μmol, 21.14% yield) as off-white solid. ¹H NMR (MeOD, 400 MHz) δ9.17 (s, 2H), 8.94 (s, 1H), 7.90 (s, 1H), 7.18 (s, 1H), 3.54-3.40 (m, 6H), 1.76-1.59 (m, 4H), 0.99-0.90 (m, 6H). LC/MS [M+H] 413.2 (calculated); LC/MS [M+H] 413.1 (observed).

Example 28 Synthesis of 2-amino-N,N-dipropyl-3H-benzo[4,5]thieno[3,2-b]azepine-4-carboxamide, TAZ-28

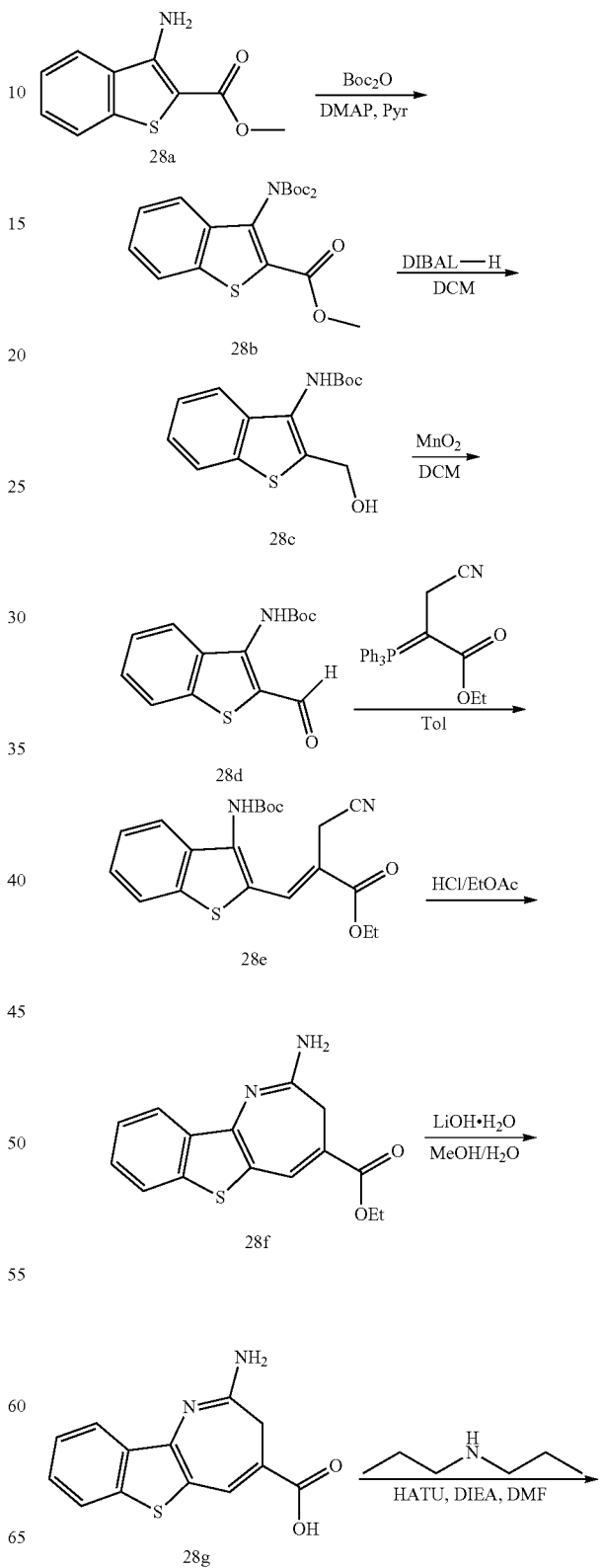

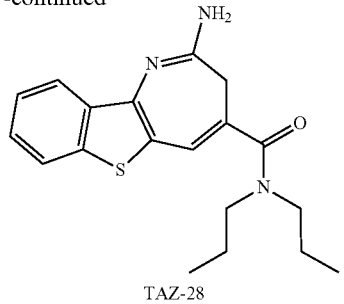

TAZ-28

Preparation of methyl 3-[bis(tert-butoxycarbonyl)amino]benzothiophene-2-carboxylate, 28b To a mixture of methyl 3-aminobenzothiophene-2-carboxylate, 28a (3 g, 14.5 mmol, 1.0 eq) in pyridine, Pyr (30 mL) was added DMAP (177 mg, 1.45 mmol, 0.1 eq). Then a solution of Boc$_2$O (6.32 g, 29.0 mmol, 6.65 mL, 2.0 eq) in pyridine (10 mL) was added to the mixture slowly at 0° C. and then stirred at 25° C. for 16 h. The mixture was concentrated in vacuum. The residue was dissolved in EtOAc (20 ml) and washed successively with aqueous sat. NaHCO$_3$ and brine. The mixture was dried over Na$_2$SO$_4$, filtered and concentrated. The residue was purified by silica gel chromatography (Petroleum ether/Ethyl acetate=1/0, 5/1) to afford methyl 3-[bis(tert-butoxycarbonyl)amino]benzothiophene-2-carboxylate (5.6 g, 13.7 mmol, 94.94% yield) as yellow solid. $^1$H NMR (CDCl$_3$, 400 MHz) δ7.83 (d, J=7.6 Hz, 1H), 7.68 (d, J=7.6 Hz, 1H), 7.52-7.42 (m, 2H), 3.94 (s, 3H), 1.35 (s, 18H).

Preparation of tert-butyl N-[2-(hydroxymethyl)benzothiophen-3-yl]carbamate, 28c To a mixture of 28b (3.8 g, 9.33 mmol, 1.0 eq) in DCM (40 mL) was added DIBAL-H (1 M, 37.3 mL, 4.0 eq) slowly at 0° C. under N$_2$ and then stirred at the same temperature for 2 h. The reaction was quenched with water (2 mL) and dried over Na$_2$SO$_4$, filtered and concentrated. The residue was purified by silica gel chromatography (Petroleum ether/Ethyl acetate=1/0, 3/1) to afford 28c (2.3 g, 8.23 mmol, 88.29% yield) as yellow solid. $^1$H NMR (CDCl$_3$, 400 MHz) δ7.83-7.78 (m, 1H), 7.63 (dd, J=2.0, 6.8 Hz, 1H), 7.43-7.35 (m, 2H), 4.75 (d, J=6.4 Hz, 2H), 1.55 (s, 9H).

Preparation of tert-butyl N-(2-formylbenzothiophen-3-yl)carbamate, 28d

To a solution of 28c (1.8 g, 6.44 mmol, 1.0 eq) in DCM (30 mL) was added MnO$_2$ (4.48 g, 51.6 mmol, 8.0 eq) in one portion at 25° C. and then stirred for 12 h. The reaction was filtered and concentrated. The residue was purified by column chromatography (SiO$_2$, Petroleum ether/Ethyl acetate=1/0 to 5/1) to afford 28d (1.2 g, 4.33 mmol, 67.15% yield) as yellow solid. $^1$H NMR (CDCl$_3$, 400 MHz) δ10.07 (s, 1H), 8.22 (s, 1H), 8.10 (d, J=8.0 Hz, 1H), 7.83 (d, J=8.0 Hz, 1H), 7.55-7.50 (m, 1H), 7.47-7.43 (m, 1H), 1.57 (s, 9H).

Preparation of ethyl (E)-3-[3-(tert-butoxycarbonylamino)benzothiophen-2-yl]-2-(cyanomethyl)prop-2-enoate, 28e To a solution of 28d (0.6 g, 2.16 mmol, 1.0 eq) and ethyl 3-cyano-2-(triphenyl-phosphanylidene)propanoate (1.09 g, 2.81 mmol, 1.3 eq) in toluene (15 mL) at 25° C. and it was stirred at 80° C. for 12 h. Then the mixture was concentrated. The residue was diluted with water and extracted with EtOAc (30 mL×3). The organic layer was washed with brine, dried over Na$_2$SO$_4$, filtered and concentrated. The residue was purified by silica gel chromatography (Petroleum ether/Ethyl acetate=1/0, 5/1) to afford 28e (0.6 g, 1.55 mmol, 71.88% yield) as yellow solid. $^1$H NMR (DMSO, 400 MHz) δ8.08 (d, J=7.2 Hz, 1H), 8.00 (s, 1H), 7.78 (d, J=7.2 Hz, 1H), 7.56-7.47 (m, 2H), 4.28 (q, J=7.2 Hz, 2H), 3.90 (s, 2H), 1.47 (s, 9H), 1.29 (t, J=7.2 Hz, 3H).

Preparation of ethyl 2-amino-3H-benzothiopheno[3,2-b]azepine-4-carboxylate, 28f To a solution of 28e (0.2 g, 518 μmol, 1.0 eq) in EtOAc (2 mL) was added HCl/EtOAc (10 mL) in one portion at 25° C. and it was stirred at 50° C. for 12 h. The mixture was concentrated to give 28f (0.25 g, crude) as green solid.

Preparation of 2-amino-3H-benzothiopheno[3,2-b]azepine-4-carboxylic Acid, 28g To a mixture of 28f (0.25 g, 774 μmol, 1.0 eq) in MeOH (6 mL) was added a solution of LiOH.H$_2$O (162 mg, 3.87 mmol, 5.0 eq) in H$_2$O (1 mL) at 25° C. The mixture was stirred at 50° C. for 12 h. The mixture was quenched with aq. HCl (1M) until pH to 5, and then concentrated to remove MeOH. The desired solid precipitated from the mixture and then filtered to obtain 28g (0.15 g, crude) as yellow solid

Preparation of 2-amino-N,N-dipropyl-3H-benzo[4,5]thieno[3,2-b]azepine-4-carboxamide, TAZ-28

To a mixture of 28 gm (0.05 g, 194 μmol, 1.0 eq) in DMF (2 mL) was added HATU (88.3 mg, 232 μmol, 1.2 eq) and DIEA (125 mg, 968 μmol, 169 μL, 5.0 eq) and it was stirred at 25° C. for 2 min. N-propylpropan-1-amine (25.5 mg, 252 μmol, 34.7 μL, 1.3 eq) was added to the mixture and then stirred for 1 h. The reaction mixture was filtered and purified by prep-HPLC (column: Nano-micro Kromasil C18 100*30 mm 8 um; mobile phase: [water (0.1% TFA)-ACN]; B %: 15%-45%, 10 min) to give TAZ-28 (19 mg, 55.64 μmol, 28.74% yield) as white solid. $^1$H NMR (MeOD, 400 MHz) δ8.00-7.92 (m, 2H), 7.58-7.53 (m, 2H), 7.18 (s, 1H), 3.48 (s, 6H), 1.74-1.65 (m, 4H), 0.94 (s, 6H). LC/MS [M+H] 342.2 (calculated); LC/MS [M+H] 342.2 (observed).

Example 29 Synthesis of tert-butyl (4-((5-amino-N-propyl-6H-thieno[3,2-b]azepine-7-carboxamido)methyl)benzyl)carbamate, TAZ-29

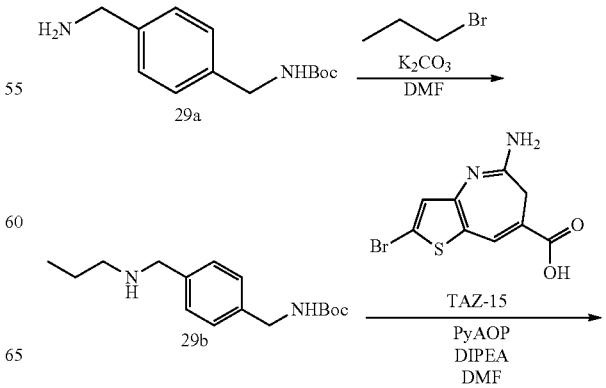

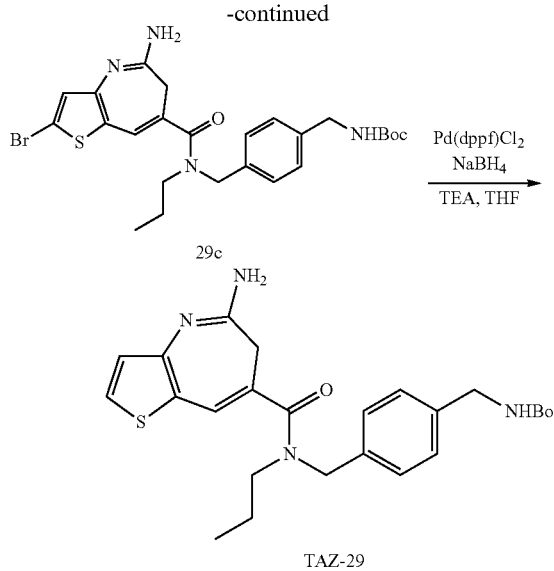

29c

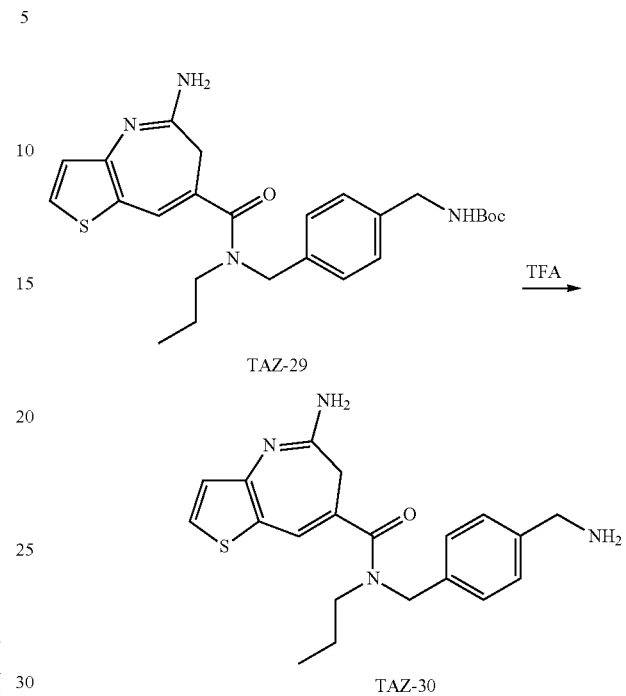

TAZ-29

TAZ-30

Preparation of tert-butyl (4-((propylamino)methyl)benzyl)carbamate, 29b tert-Butyl (4-(aminomethyl)benzyl)carbamate, 29a (0.98 g, 4.15 mmol, 1 eq.) was dissolved in 10 ml DMF. Potassium carbonate (2.9 g, 20.7 mmol, 5 eq.) was added, followed by propyl bromide (0.38 ml, 4.15 mmol, 1 eq.). The reaction mixture was stirred for 2 hours, then filtered, concentrated, and purified by reverse-phase chromatography to give 29b (0.36 g, 1.29 mmol, 31%). LC/MS [M+H] 279.21 (calculated); LC/MS [M+H] 279.24 (observed).

Preparation of tert-butyl (4-((5-amino-2-bromo-N-propyl-6H-thieno[3,2-b]azepine-7-carboxamido)methyl)benzyl)carbamate, 29c 5-amino-2-bromo-6H-thieno[3,2-b]azepine-7-carboxylic acid, TAZ-15 (0.330 g, 1.15 mmol, 1 eq.) and 29b (0.32 g, 1.15 mmol, 1 eq.) were suspended in 5 ml DMF. DIPEA (1.2 ml, 6.9 mmol, 6 eq.) was added, followed by 7-aza-benzo-triazol-1-yloxy-tripyrrolidino-phosphonium hexafluorophosphate, PyAOP (0.90 g, 1.72 mmol, 1.5 eq.). The reaction was monitored by LCMS. Upon consumption of starting material, the reaction mixture was added to 100 ml water, filtered, and the precipitate purified by flash chromatography (MeOH/DCM with 1% TEA) to give 29c (0.35 g, 0.64 mmol, 56%). LC/MS [M+H] 547.14/549.14 (calculated); LC/MS [M+H] 547.40/549.35 (observed).

Preparation of TAZ-29

Intermediate 29c (0.35 g, 0.64 mmol, 1 eq.) was dissolved in 5 ml THF. Triethylamine (0.89 ml, 6.4 mmol, 10 eq.) and [1,1'-bis(diphenylphosphino)ferrocene]palladium(II) dichloride, Pd(dppf)Cl$_2$ (0.023 g, 0.032 mmol, 0.05 eq.) were added, followed by sodium borohydride (0.12 g, 3.2 mmol, 5 eq.). After 2 hours, another portion of sodium borohydride was added (0.073 g, 1.9 mmol, 3 eq.) and the reaction stirred for 30 minutes. The reaction mixture was concentrated and purified by HPLC to give TAZ-29 (0.129 g, 0.28 mmol, 43%). LC/MS [M+H] 469.23 (calculated); LC/MS [M+H] 469.42 (observed).

Example 30 Synthesis of 5-amino-N-(4-(aminomethyl)benzyl)-N-propyl-6H-thieno[3,2-b]azepine-7-carboxamide, TAZ-30 tert-Butyl (4-((5-amino-N-propyl-6H-thieno[3,2-b]azepine-7-carboxamido)methyl)benzyl)carbamate, TAZ-29 (0.129 g, 0.28 mmol, 1 eq.) was dissolved in 100 μl TFA. After 15 minutes, the product was concentrated and purified by HPLC to give TAZ-30 (0.063 g, 0.17 mmol, 61%). LC/MS [M+H] 547.14/549.14 (calculated); LC/MS [M+H] 547.40/549.35 (observed).

Example 52 Synthesis of 5-amino-N-[[4-(aminomethyl)-2-(trifluoromethyl)phenyl]methyl]-N-propyl-6H-thieno[3,2-b]azepine-7-carboxamide, TAZ-52

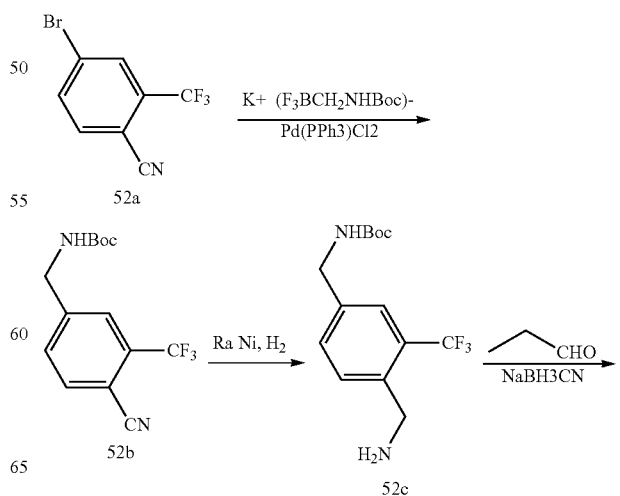

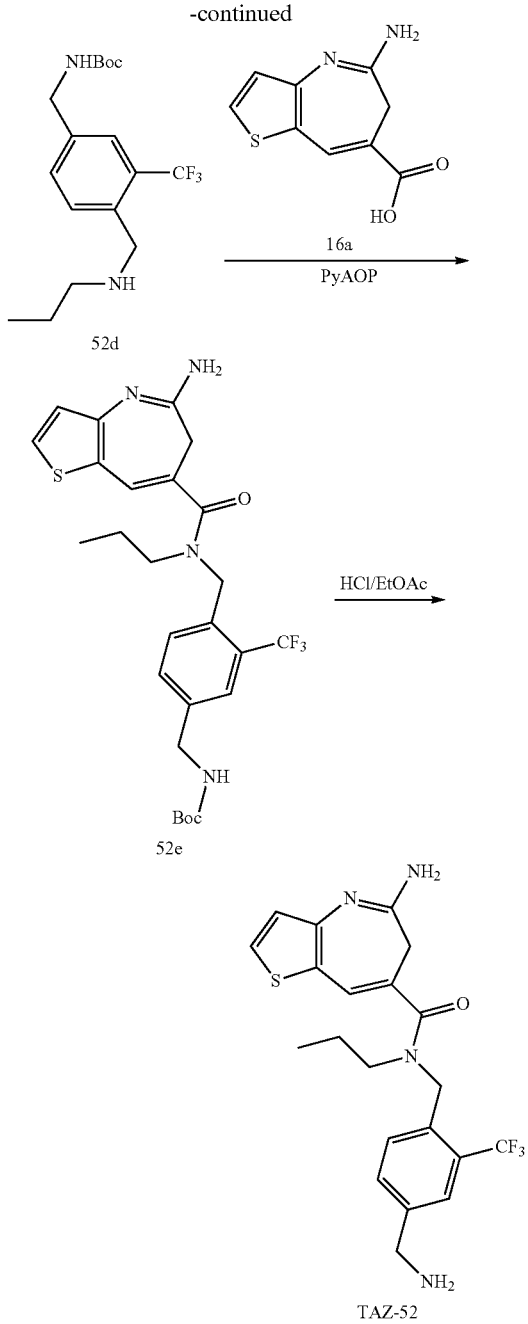

Preparation of tert-butyl N-[[4-cyano-3-(trifluoromethyl)phenyl]methyl]carbamate, 52b To a mixture of 4-bromo-2-(trifluoromethyl)benzonitrile, 52a (0.5 g, 2.00 mmol, 1.0 eq), potassium; (tert-butoxycarbonylamino)methyl-trifluoro-boranuide, also known as potassium (((tert-butoxycarbonyl)amino)methyl)trifluoroborate, CAS Reg. No. 1314538-55-0 (711 mg, 3.00 mmol, 1.5 eq) and Na$_2$CO$_3$ (678 mg, 6.40 mmol, 3.2 eq) in EtOH (20 mL) and H$_2$O (4 mL) was added Pd(PPh$_3$)$_2$Cl$_2$ (154 mg, 219 umol, 0.11 eq) under N$_2$. The suspension was degassed under vacuum and purged with N$_2$ several times and then stirred at 80° C. for 12 hours. The reaction was concentrated in vacuum to give a residue. The residue was poured into ice water (5 mL) and stirred for 5 min. The aqueous phase was extracted with ethyl acetate (5 mL×3). The combined organic phase was washed with brine (20 mL×2), dried with anhydrous Na$_2$SO$_4$, filtered and concentrated in vacuum. The residue was purified by silica gel chromatography (Petroleum ether/Ethyl acetate=10/1, 1/1) to afford 52b (0.5 g, 1.67 mmol, 83.2% yield) as yellow oil. $^1$H NMR (MeOD, 400 MHz) δ7.95 (d, J=6.8 Hz, 1H), 7.81 (s, 1H), 7.71 (d, J=6.8 Hz, 1H), 4.36 (s, 2H), 1.45 (s, 9H).

Preparation of tert-butyl N-[[4-(aminomethyl)-3-(trifluoromethyl)phenyl]methyl]carbamate, 52c To a solution of 52b (0.5 g, 1.67 mmol, 1.0 eq) in MeOH (10 mL) was added NH$_3$.H$_2$O (17 mg, 166 umol, 33% purity, 0.1 eq) and Raney-Ni (1.43 g, 1.67 mmol, 10% purity, 1.0 eq) at 25° C. under N$_2$. The suspension was degassed under vacuum and purged with H$_2$ several times, and then stirred under H$_2$ (50 psi) at 25° C. for 10 hours. Then it was filtered and the filtrate was concentrated in vacuum. The residue was purified by silica gel chromatography (Petroleum ether/Ethyl acetate=10/1, 1/1) to afford 52c (200 mg, 657.23 umol, 39.47% yield) as yellow oil. $^1$H NMR (MeOD, 400 MHz) δ 6.99-6.92 (m, 2H), 6.89-6.86 (m, 1H), 3.62 (s, 2H), 2.66 (s, 2H), 0.80 (s, 9H)

Preparation of tert-butyl N-[[4-(propylaminomethyl)-3-(trifluoromethyl) phenyl]methyl]carbamate, 52d To a mixture of 52c (190 mg, 624 umol, 1 eq) in MeOH (2 mL) and THF (2 mL) was added propanal (47 mg, 812 umol, 1.3 eq), after 30 min, NaBH$_3$CN (117 mg, 1.87 mmol, 3.0 eq) and AcOH (3 mg, 62 umol, 3 uL, 0.1 eq) was added at 25° C., and then stirred for 2 hours. The mixture was concentrated in vacuum. The residue was purified by prep-HPLC (column: Phenomenex Gemini-NX C18 75*30 mm*3 um; mobile phase: [water (10 mM NH$_4$HCO$_3$)-ACN]; B %: 30%-60%, 12 min) to afford 52d (100 mg, 277 umol, 44.39% yield, 96% purity) as white solid. $^1$H NMR (MeOD, 400 MHz) δ7.65-7.57 (m, 2H), 7.53-7.50 (m, 1H), 4.27 (s, 2H), 3.91 (s, 2H), 2.58 (t, J=7.6 Hz, 2H), 1.63-1.59 (m, 2H), 1.45 (s, 9H), 0.93 (t, J=7.2 Hz, 3H)

Preparation of tert-butyl N-[[4-[[(5-amino-6H-thieno[3,2-b]azepine-7-carbonyl)-propyl-amino]methyl]-3-(trifluoromethyl)phenyl]methyl]carbamate, 52e To a solution of 5-amino-6H-thieno[3,2-b]azepine-7-carboxylic acid, 16a (24.0 mg, 115 umol, 1.0 eq) in DMF (1 mL) was added DIEA (74 mg, 577 umol, 100 uL, 5 eq) and PyAOP (66 mg, 127 umol, 1.1 eq) in one portion at 25° C., and it was stirred for 30 min, then 52d (60 mg, 173.22 umol, 1.5 eq) was added and then stirred for another 2 hours. After that, the reaction was concentrated and purified by prep-HPLC (column: Phenomenex Synergi C18 150*25*10 um; mobile phase: [water (0.1% TFA)-ACN]; B %: 25%-50%, 10 min) to afford 52e (15 mg, 27.95 umol, 24.21% yield) as white solid. $^1$H NMR (MeOD, 400 MHz) δ7.75-7.68 (m, 1H), 7.65 (s, 1H), 7.57 (d, J=7.6 Hz, 1H), 7.44 (d, J=7.6 Hz, 1H), 7.30-7.10 (m, 2H), 4.92 (s, 2H), 4.29 (s, 2H), 3.48 (t, J=7.2 Hz, 2H), 3.32 (s, 2H), 1.66-1.64 (m, 2H), 1.45 (s, 9H), 0.94-0.86 (m, 3H). LC/MS [M+H] 537.2 (calculated); LC/MS [M+H] 537.1 (observed).

Preparation of TAZ-52

To a solution of 52e (10 mg, 18.6 umol, 1.0 eq) in EtOAc (2 mL) was added HCl/EtOAc (4 M, 140 uL, 30 eq) in one portion at 25° C. The mixture was stirred at 25° C. for 3 hours. Followed, the mixture was concentrated to afford TAZ-52 (8 mg, 18.3 umol, 98.35% yield) as yellow solid. ¹H NMR (MeOD, 400 MHz) δ7.80 (s, 1H), 7.70-7.63 (m, 2H), 7.51 (d, J=7.6 Hz, 1H), 7.20-7.17 (m, 1H), 7.03 (d, J=4.0 Hz, 1H), 4.85 (s, 2H), 4.13 (s, 2H), 3.45-3.37 (m, 2H), 3.31 (s, 2H), 1.62-1.50 (m, 2H), 0.87-0.68 (m, 3H). LC/MS [M+H] 437.2 (calculated); LC/MS [M+H] 437.1 (observed).

Example 54 Synthesis of 5-amino-N-[[4-(aminomethyl)-2-(trifluoromethyl)phenyl]methyl]-N-propyl-6H-thieno[3,2-b] azepine-7-carboxamide, TAZ-54

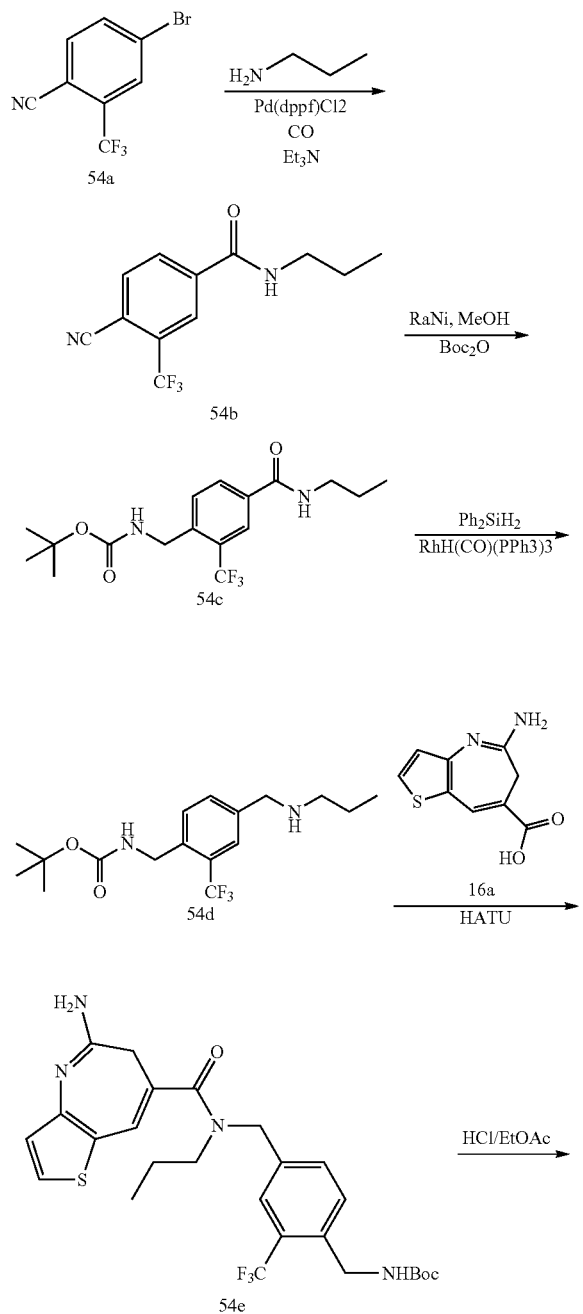

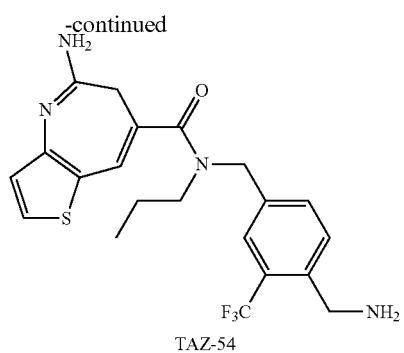

TAZ-54

Preparation of 4-cyano-N-propyl-2-(trifluoro methyl)benzamide, 54b

To a solution of 4-bromo-3-(trifluoromethyl)benzonitrile, 54a (4.00 g, 16.0 mmol, 1.0 eq) in DMF (20 mL) was added propan-1-amine (2.84 g, 48.0 mmol, 3.95 mL, 3.0 eq), Et₃N (4.86 g, 48.0 mmol, 6.68 mL, 3.0 eq) and Pd(dppf)Cl₂ (585 mg, 800 umol, 0.05 eq) under N₂. The suspension was degassed under vacuum and purged with CO several times, and the mixture was stirred under CO (50 psi) at 80° C. for 15 hours. Water (50 mL) was added to the mixture and the aqueous phase was extracted with ethyl acetate (30 mL*3), the combined organic phase was washed with brine (50 mL), dried with anhydrous Na₂SO₄, filtered and concentrated in vacuum. The residue was purified by silica gel chromatography (column height: 250 mm, diameter: 100 mm, 100-200 mesh silica gel, Petroleum ether/Ethyl acetate=10/1, 1/1) to afford 54b (4.00 g, 15.6 mmol, 97.5% yield) as white solid. ¹H NMR (400 MHz, CDCl₃) δ8.13 (s, 1H), 8.01 (d, J=8.0 Hz, 1H), 7.85 (d, J=8.0 Hz, 1H), 6.49 (br s, 1H), 3.37 (q, J=7.2 Hz, 2H), 1.66-1.54 (m, 2H), 0.92 (t, J=7.2 Hz, 3H)

Preparation of tert-butyl N-[[4-(propyl carbamoyl)-3-(trifluoromethyl)phenyl]methyl]carbamate, 54c To a solution of 54b (2.30 g, 8.98 mmol, 1.0 eq) in MeOH (30 mL) was added Raney Ni (0.5 g, 1.0 eq) and Boc₂O (9.80 g, 44.8 mmol, 10.3 mL, 5.0 eq) at 25° C. under N₂. The suspension was degassed under vacuum and purged with H₂ several times. The mixture was stirred under H₂ (50 psi) at 25° C. for 5 hours. The reaction mixture was filtered and the filtrate was concentrated in vacuum. The residue was purified by silica gel chromatography (column height: 250 mm, diameter: 100 mm, 100-200 mesh silica gel, Petroleum ether/Ethyl acetate=10/1, 1/1) to afford 54c (2.50 g, 6.94 mmol, 77.2% yield) as white solid. ¹H NMR (400 MHz, CDCl₃) δ 8.04 (s, 1H), 7.89 (d, J=8.0 Hz, 1H), 7.63 (d, J=8.0 Hz, 1H), 6.26 (s, 1H), 5.02 (s, 1H), 4.53 (d, J=6.0 Hz, 2H), 3.44 (q, J=6.8 Hz, 2H), 1.70-1.62 (m, 2H), 1.46 (s, 9H), 1.00 (t, J=7.6 Hz, 3H).

Preparation of tert-butyl N-[[4-(propylaminomethyl)-3-(trifluoro methyl)phenyl]methyl]carbamate, 54d To a mixture of 54c (1.03 g, 2.86 mmol, 1.0 eq) and RhH(CO)(PPh₃)₃ (263 mg, 286 umol, 0.1 eq) in THF (30 mL) was added diphenylsilane (3.16 g, 17.1 mmol, 3.16 mL, 6.0 eq) in one portion at 20° C. under N₂, and then stirred at 20° C. for 8 hours. The reaction mixture was concentrated in vacuum, the residue was purified by silica gel chromatography (column height: 250 mm, diameter: 100 mm, 100-200 mesh silica gel, Petroleum ether/Ethyl acetate=10/1, 0/1 to Ethyl acetate/Methanol=5/1) to afford 54d (0.4 g, 1.15 mmol, 40.40% yield) as yellow oil. $^1$H NMR (400 MHz, MeOD) δ7.89 (s, 1H), 7.77 (d, J=8.0 Hz, 1H), 7.66 (d, J=8.0 Hz, 1H), 4.48 (s, 2H), 4.29 (s, 2H), 3.08-3.01 (m, 2H), 1.82-1.71 (m, 2H), 1.48 (s, 9H), 1.05 (t, J=7.6 Hz, 3H)

Preparation of tert-butyl N-[[4-[[(5-amino-6H-thieno[3,2-b]azepine-7-carbonyl)-propyl-amino]methyl]-3-(trifluoromethyl)phenyl]methyl]carbamate, 54e To a solution of 5-amino-6H-thieno[3,2-b]azepine-7-carboxylic acid, 16a (12.0 mg, 57.7 umol, 1.0 eq) in DMF (1 mL) was added HATU (19.7 mg, 52.0 umol, 0.9 eq) and Et$_3$N (17.53 mg, 173 umol, 24.1 uL, 3.0 eq) at 20° C. under N$_2$, the mixture was stirred at 20° C. for 10 min, then 54d (20 mg, 57.7 umol, 1.0 eq) was added and then stirred at 20° C. for 2 hours. The reaction mixture was filtered, the filtrate was purified by prep-HPLC (column: Phenomenex Synergi C18 150*25*10 um; mobile phase: [water (0.1% TFA)-ACN]; B %: 30%-55%, 10 min) to afford 54e (5.00 mg, 7.47 umol, 12.9% yield, 97.1% purity, TFA) as white solid. $^1$H NMR (400 MHz, MeOD) δ7.74 (d, J=5.6 Hz, 1H), 7.60-7.52 (m, 3H), 7.22 (s, 1H), 7.12 (br d, J=5.6 Hz, 1H), 4.82 (br s, 2H), 4.45 (s, 2H), 3.51 (br t, J=7.2 Hz, 2H), 3.42-3.35 (m, 2H), 1.75-1.64 (m, 2H), 1.49 (s, 9H), 0.96-0.90 (m, 3H). LC/MS [M+H] 537.2 (calculated); LC/MS [M+H] 537.1 (observed).

Preparation of TAZ-54

To a solution of 54e (50.0 mg, 93.2 umol, 1.0 eq) in EtOAc (1 mL) was added HCl/EtOAc (4 M, 2.33 mL, 100 eq) at 20° C. and then stirred at 20° C. for 2 hours. The reaction mixture was concentrated in vacuum and freeze-drying to afford TAZ-54 (30.0 mg, 62.8 umol, 67.4% yield, 99.0% purity, HCl) as yellow solid. $^1$H NMR (400 MHz, MeOD) δ7.67 (br s, 1H), 7.65-7.61 (m, 3H), 7.10 (s, 1H), 7.04 (d, J=5.2 Hz, 1H), 4.75 (s, 2H), 4.22 (s, 2H), 3.45-3.38 (m, 2H), 3.29 (br s, 2H), 1.63-1.52 (m, 2H), 0.79 (br t, J=7.2 Hz, 3H). LC/MS [M+H] 437.2 (calculated); LC/MS [M+H] 437.1 (observed).

Example 65 Synthesis of 5-amino-2-[5-(dimethylamino)pentyl]-N-[[4-(methylaminomethyl)phenyl]methyl]-N-propyl-6H-thieno[3,2-b]azepine-7-carboxamide, TAZ-65

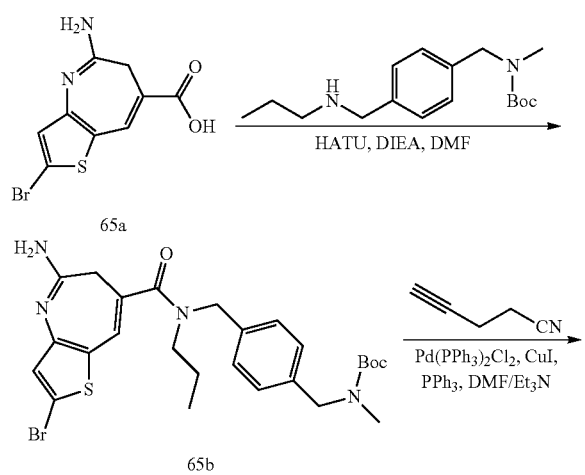

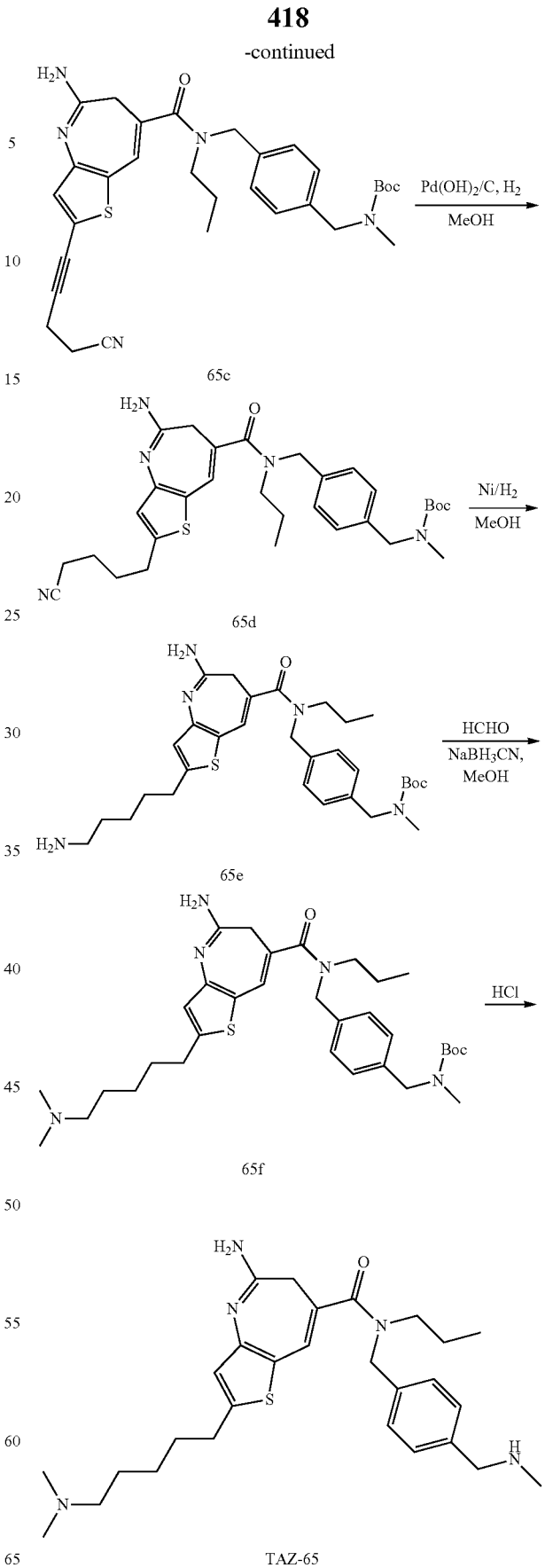

Preparation of tert-butyl N-[[4-[[(5-amino-2-bromo-6H-thieno[3,2-b]azepine-7-carbonyl)-propyl-amino]methyl]phenyl]methyl]-N-methyl-carbamate, 65b To a solution of 5-amino-2-bromo-6H-thieno[3,2-b]azepine-7-carboxylic acid, 65a (1.0 g, 3.48 mmol, 1.0 eq) in DMF (20 mL) was added HATU (1.46 g, 3.83 mmol, 1.1 eq), DIEA (1.35 g, 10.45 mmol, 1.82 mL, 3.0 eq) and tert-butyl N-methyl-N-[[4-(propylaminomethyl) phenyl]methyl]carbamate (1.07 g, 3.66 mmol, 1.05 eq), and then stirred for 1 hr at 25° C. The reaction mixture was quenched by addition $H_2O$ (100 mL) and then extracted with EtOAc (100 mL×3). The combined organic layers were washed with brine (20 mL×2), dried over $Na_2SO_4$, filtered and concentrated. Finally, the residue was purified by column chromatography ($SiO_2$, Petroleum ether/Ethyl acetate=200/1 to 0/1) to give 65b (1.80 g, 3.21 mmol, 92.04% yield) as yellow oil. $^1$H NMR ($CDCl_3$, 400 MHz) δ7.25-7.15 (m, 4H), 6.92 (s, 1H), 6.77 (s, 1H), 4.72 (s, 2H), 4.42 (s, 2H), 3.40 (t, J=7.2 Hz, 2H), 2.86 (s, 2H), 2.81 (s, 3H), 1.69-1.58 (m, 2H), 1.49 (s, 9H), 0.89 (t, J=7.2 Hz, 3H).

Preparation of tert-butyl N-[[4-[[[5-amino-2-(4-cyanobut-1-ynyl)-6H-thieno[3,2-b]azepine-7-carbonyl]-propyl-amino]methyl]phenyl]methyl]-N-methyl-carbamate, 65c To a mixture of 65b (2.25 g, 4.01 mmol, 1.0 eq) and pent-4-ynenitrile (951 mg, 12.0 mmol, 3.0 eq) in TEA (13.2 mL) and DMF (44 mL) was added $Pd(PPh_3)_2Cl_2$ (140.6 mg, 200.34 umol, 0.050 eq), CuI (152.6 mg, 801.38 umol, 0.20 eq) and $PPh_3$ (210 mg, 801 umol, 0.20 eq) at 15° C. and then stirred for 3 hrs at 140° C. under $N_2$ atmosphere. The reaction mixture was quenched by addition $H_2O$ (220 mL) at 25° C., and then extracted with DCM/isopropanol=3/1 (200 mL×3). The combined organic layers were washed with $H_2O$ (40 mL×4), dried over $Na_2SO_4$, filtered and concentrated. The residue was purified by column chromatography ($SiO_2$, Petroleum ether/Ethyl acetate=200/1 to 0/1 to Ethyl acetate/MeOH=50/1 to 5/1) to give 65c (1.62 g, 2.89 mmol, 72.23% yield) as yellow oil. $^1$H NMR ($CDCl_3$, 400 MHz) δ 7.21-7.20 (m, 4H), 7.00 (s, 1H), 6.81 (s, 1H), 4.73 (s, 2H), 4.42 (s, 2H), 3.40 (t, J=6.4 Hz, 2H), 2.83-2.81 (m, 7H), 2.68-2.65 (m, 2H), 1.64-1.62 (m, 2H), 1.49 (s, 9H), 0.89 (t, J=7.2 Hz, 3H)

Preparation of tert-butyl N-[[4-[[[5-amino-2-(4-cyanobutyl)-6H-thieno[3,2-b]azepine-7-carbonyl]-propyl-amino]methyl]phenyl]methyl]-N-methyl-carbamate, 65d To a solution of 65c (1.47 g, 2.63 mmol, 1.0 eq) in MeOH (30 mL) was added $Pd(OH)_2/C$ (369 mg, 262 umol, 10% purity, 0.10 eq) under N2 atmosphere. The suspension was degassed and purged with $H_2$ for 3 times. The mixture was stirred under $H_2$ (50 Psi) at 25° C. for 12 hrs. The reaction mixture was filtered and the filtrate was concentrated to give 65d (1.15 g, 2.04 mmol, 77.67% yield) as yellow oil. $^1$H NMR ($CDCl_3$, 400 MHz) δ7.21-7.19 (m, 4H), 6.86 (s, 1H), 6.67 (s, 1H), 4.74 (s, 2H), 4.42 (s, 2H), 3.40 (t, J=6.4 Hz, 2H), 2.86-2.82 (m, 5H), 2.37 (t, J=6.8 Hz, 2H), 1.88-1.83 (m, 2H), 1.78-1.74 (m, 2H), 1.64-1.61 (m, 2H), 1.49 (m, 9H), 0.89 (t, J=7.6 Hz, 3H).

Preparation of tert-butyl N-[[4-[[[5-amino-2-(5-aminopentyl)-6H-thieno[3,2-b]azepine-7-carbonyl]-propyl-amino]methyl]phenyl]methyl]-N-methyl-carbamate, 65e To a solution of 65d (1.15 g, 2.04 mmol, 1.0 eq) in MeOH (23 mL) was added $NH_3 \cdot H_2O$ (2.86 g, 20.4 mmol, 3.14 mL, 25% purity, 10 eq) and Ni (100 mg) under N2. The suspension was degassed under vacuum and purged with $H_2$ several times. The mixture was stirred under $H_2$ (50 psi) at 25° C. for 3 hrs. The reaction mixture was filtered and the filtrate was concentrated to give 65e (1.03 g, 1.81 mmol, 88.93% yield) as yellow oil.

Preparation of tert-butyl N-[[4-[[[5-amino-2-[5-(dimethylamino)pentyl]-6H-thieno[3,2-b]azepine-7-carbonyl]-propyl-amino]methyl]phenyl]methyl]-N-methyl-carbamate, 65f To a solution of 65e (300 mg, 528 umol, 1.0 eq) in MeOH (8 mL) was added AcOH (3.1 mg, 52.8 umol, 0.10 eq), HCHO (171.5 mg, 2.11 mmol, 157.3 uL, 37% purity, 4.0 eq) and $NaBH_3CN$ (99.6 mg, 1.59 mmol, 3.0 eq), and then stirred for 1 hr at 25° C. The mixture was quenched by addition $H_2O$ (10 mL) and concentrated to remove MeOH. The aqueous phase was extracted with DCM/isopropanol=3/1 (10 mL×3). The combined organic layers were dried over $Na_2SO_4$, filtered and concentrated to give 65f (314 mg, crude) as yellow oil.

Preparation of TAZ-65

To a solution of 65f (50 mg, 83.9 umol, 1.0 eq) in $H_2O$ (0.5 mL) was added HCl (12 M, 140 uL, 20.0 eq) and then stirred for 1 hr at 80° C. The mixture was concentrated in vacuum. The residue was purified by Prep-HPLC (column: Phenomenex Synergi C18 150*25*10 um; mobile phase: [water (0.1% TFA)-ACN]; B %: 5%-35%, 10 min) to give TAZ-65 (10 mg, 13.74 umol, 16.37% yield, 99.44% purity, 2TFA) as colorless oil. $^1$H NMR (MeOD, 400 MHz) δ 7.50-7.40 (m, 4H), 7.09 (s, 1H), 6.89 (s, 1H), 4.78 (s, 2H), 4.19 (s, 2H), 3.45-3.35 (m, 4H), 3.32 (s, 2H), 3.14-3.10 (m, 2H), 2.88 (s, 6H), 2.72 (s, 3H), 1.80-1.74 (m, 4H), 1.66-1.64 (m, 2H), 1.49-1.47 (m, 2H), 0.89-0.86 (m, 3H). LC/MS [M+H] 496.3 (calculated); LC/MS [M+H] 496.3 (observed).

Example 109 Synthesis of 5-amino-2-(5-aminopentyl)-N-(3-(3,3-dimethylbutanamido)propyl)-N-propyl-6H-thieno[3,2-b]azepine-7-carboxamide, TAZ-109

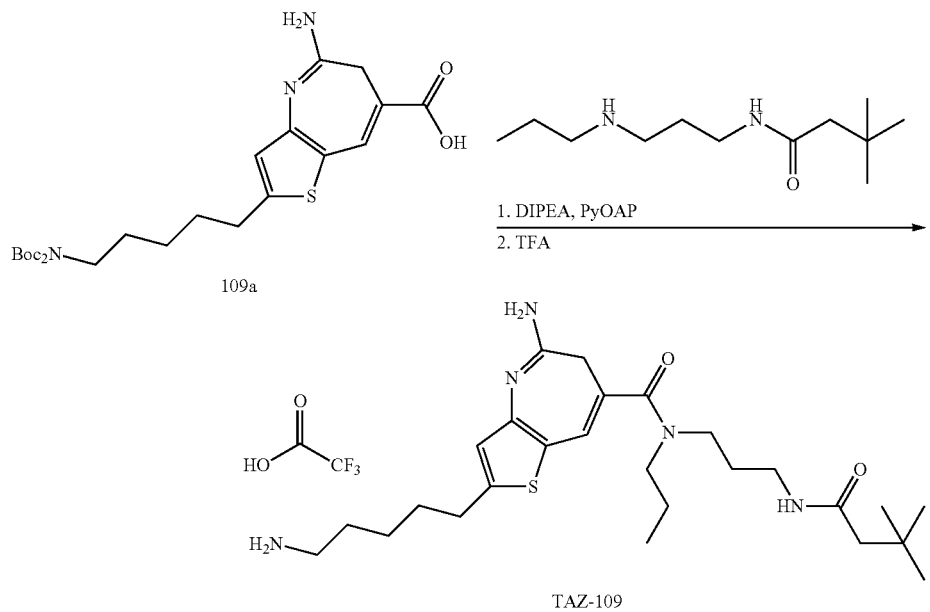

5-amino-2-(5-(bis(tert-butoxycarbonyl)amino)pentyl)-6H-thieno[3,2-b]azepine-7-carboxylic acid, 109a (115 mg, 0.23 mmol, 1 eq.) and 3,3-dimethyl-N-(3-(propylamino)propyl)butanamide (50 mg, 0.23, 1 eq.) were taken up in 8:3 ACN:DCM (2.75 ml). DIPEA (0.121 ml, 0.7 mmol, 3 eq.) was added, followed by 7-Aza-benzotriazol-1-yloxy-tripyrrolidino-phosphonium hexafluorophosphate, PyAOP (0.122 m, 0.23 mmol, 1 eq.). The solution was stirred at ambient temperature. Upon completion by LCMS, the reaction mixture was concentrated and purified by HPLC to afford [amide], which was subsequently dissolved in minimal TFA and allowed to stand for 15 minutes. The solution was concentrated and triturated with diethyl ether to afford TAZ-109 as the trifluoroacetate salt (61.4 mg, 0.102 mmol, 44%). LC/MS [M+H] 490.32 (calculated); LC/MS [M+H] 490.39 (observed).

Example 133 Synthesis of tert-butyl (3-(5-amino-2-(5-aminopentyl)-N-propyl-6H-thieno[3,2-b]azepine-7-carboxamido)propyl)carbamate, TAZ-133

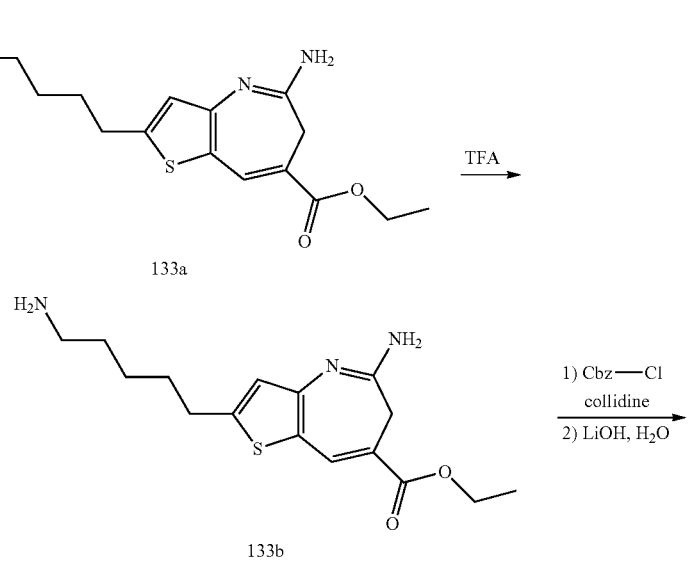

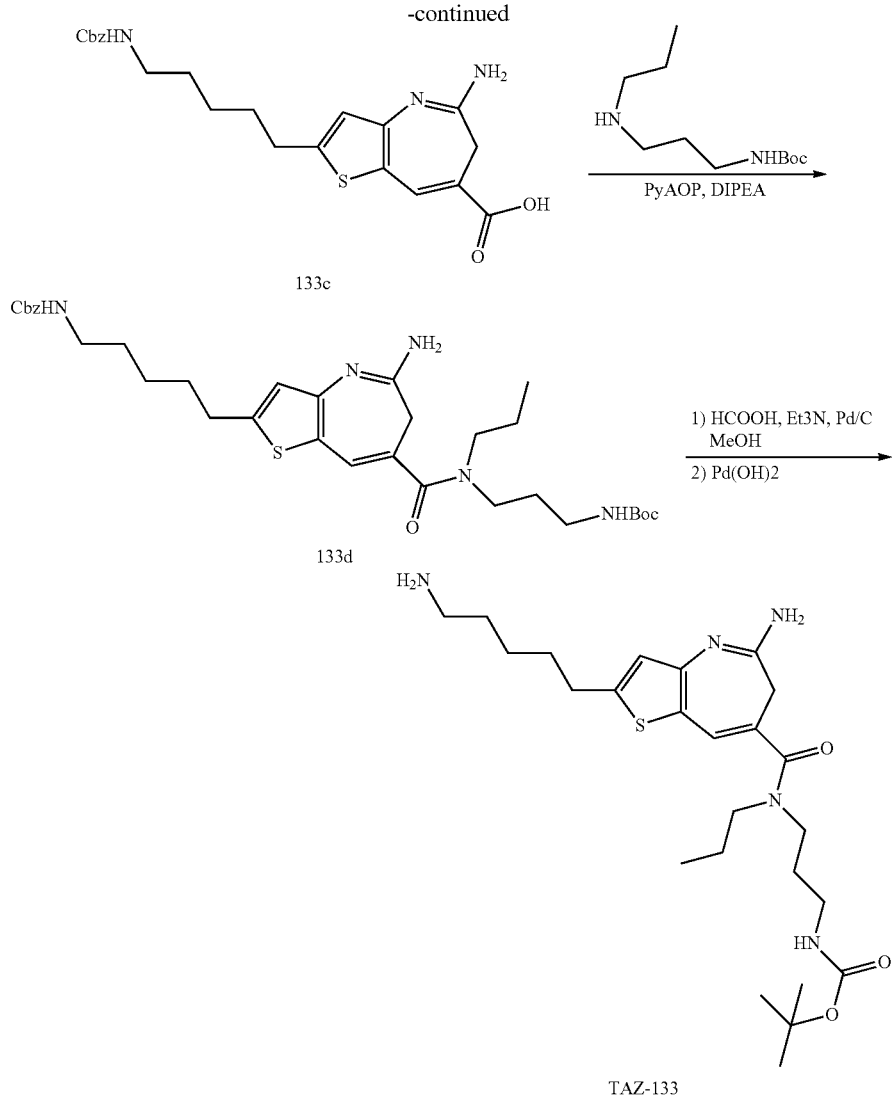

TAZ-133

Preparation of 5-(5-amino-7-(ethoxycarbonyl)-6H-thieno[3,2-b]azepin-2-yl)pentan-1-aminium trifluoroacetate, 133b Ethyl 5-amino-2-(5-(bis(tert-butoxycarbonyl)amino)pentyl)-6H-thieno[3,2-b]azepine-7-carboxylate, 133a (0.188 g, 0.36 mmol, 1 equiv.) was dissolved in minimal TFA. Upon complete deprotection, the solution was concentrated and the product precipitated from diethyl ether to give 133b (0.082 g, 0.188 mmol, 52%) as a yellow powder. LC/MS [M+H] 322.16 (calculated); LC/MS [M+H] 322.25 (observed).

Preparation of 5-amino-2-(5-(((benzyloxy)carbonyl)amino)pentyl)-6H-thieno[3,2-b]azepine-7-carboxylic Acid, 133c Intermediate 133b (0.296 g, 0.68 mmol, 1 equiv.) was suspended in 2 ml DMF. Collidine (0.27 ml, 2 mmol, 3 equiv.) was added, followed by benzyl chloroformate, Cbz-Cl, CAS Reg. No. 501-53-1 (0.1 ml, 0.68 mmol, 1 equiv.). The reaction was monitored by LCMS. Upon consumption of the amine starting material, the reaction was concentrated and redissolved in 7 ml 3:1:3 THF:MeOH:water. Lithium hydroxide (0.16 g, 6.8 mmol, 10 equiv.) was added and the reaction stirred at room temperature. Upon completion, the reaction mixture was concentrated and purified by reverse-phase HPLC to give 133c (0.246 g, 0.58 mmol, 85%). LC/MS [M+H]428.16 (calculated); LC/MS [M+H] 428.32 (observed).

Preparation of benzyl (5-(5-amino-7-((3-((tert-butoxycarbonyl)amino)propyl)(propyl)carbamoyl)-6H-thieno[3,2-b]azepin-2-yl)pentyl)carbamate, 133d Intermediate 133c (0.29 g, 0.68 mol, 1 equiv.) and tert-butyl (3-(propylamino)propyl)carbamate (0.225 g, 1.0 mmol, 1.53 equiv.) were dissolved in 1 ml DMF. Diisopropylethylamine, DIPEA (0.59 ml, 1.0 mmol, 1.53 equiv.) was added, followed by PyAOP (0.541 g, 1.0 mmol, 1.53 equiv.). The reaction was stirred at room temperature, then concentrated and purified by reverse-phase flash chromatography to give 133d (0.201 g, 0.32 mmol, 47%). LC/MS [M+H] 626.34 (calculated); LC/MS [M+H] 626.51 (observed).

Preparation of TAZ-133

Intermediate 133d (0.2 g, 0.32 mmol, 1 equiv.) was dissolved in 2 ml MeOH. Triethylamine (0.1 ml) and formic acid (0.049 ml, 1.29 mmol, 4 equiv.) were added, followed by 10% w/w Pd/C (0.04 g). The stirred reaction was heated to 60° C. After one hour, 20% w/w Pd(OH)$_2$ (0.02 g) was added. Upon completion, the reaction was filtered, concentrated, and purified by HPLC to give TAZ-133 0.139 g, 0.28 mmol, 88%). LC/MS [M+H] 492.30 (calculated); LC/MS [M+H] 492.45 (observed).

Example 176 Synthesis of 5-amino-N-ethoxy-2-[2-(4-piperidyl)ethyl]-N-propyl-6H-thieno[3,2-b]azepine-7-carboxamide, TAZ-176

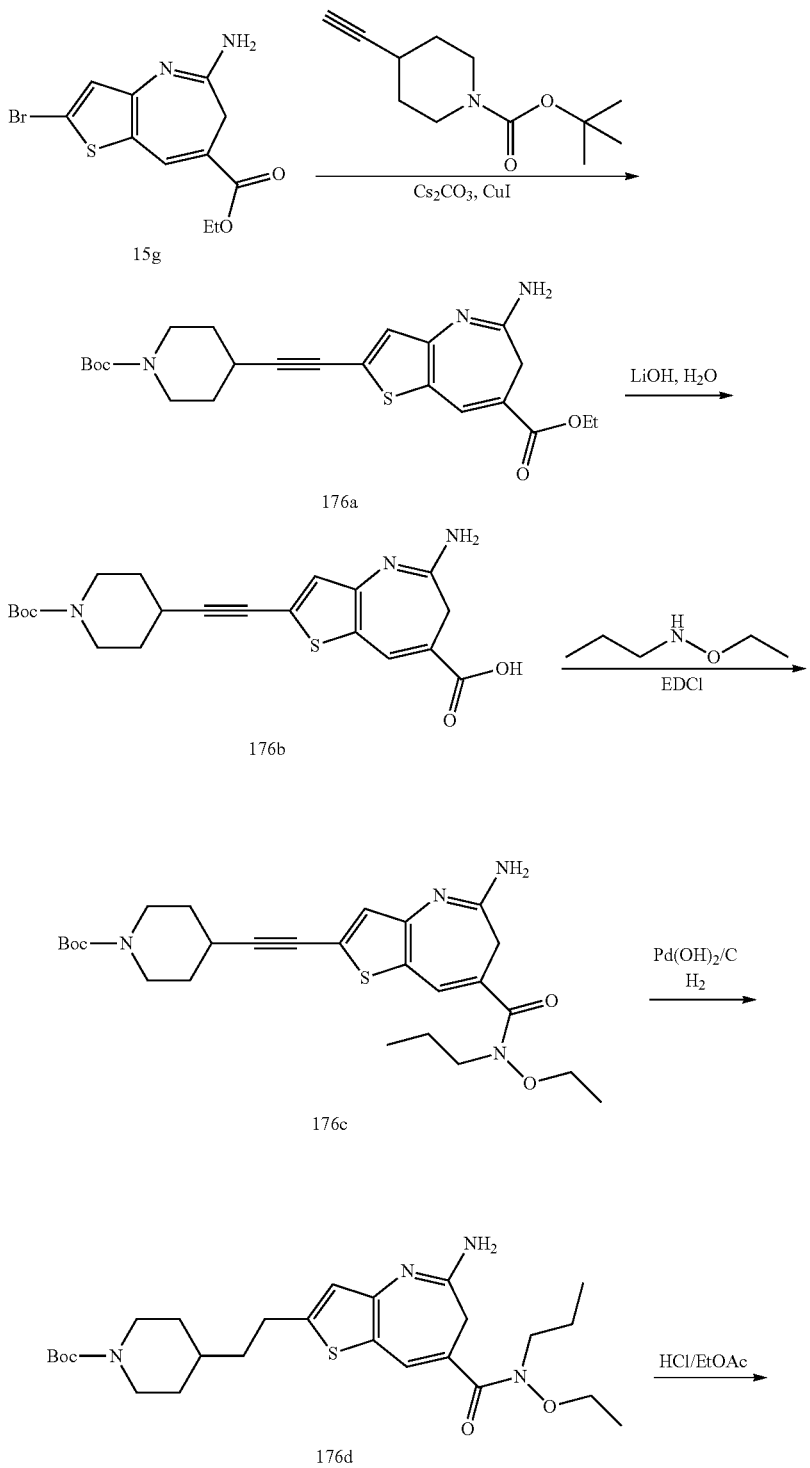

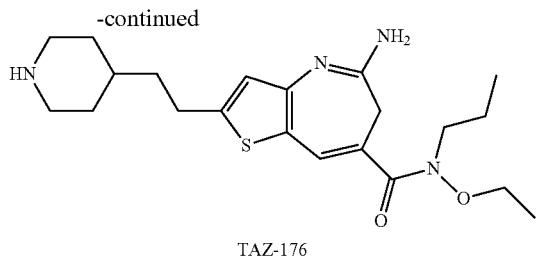

TAZ-176

Preparation of ethyl 5-amino-2-[2-(1-tert-butoxycarbonyl-4-piperidyl)ethynyl]-6H-thieno[3,2-b]azepine-7-carboxylate, 176a To a mixture of ethyl 5-amino-2-bromo-6H-thieno[3,2-b]azepine-7-carboxylate, 15g (2 g, 6.35 mmol, 1.0 eq) in $CH_3CN$ (60 mL) was added tert-butyl 4-ethynylpiperidine-1-carboxylate (1.73 g, 8.25 mmol, 1.3 eq), $Cs_2CO_3$ (6.20 g, 19.0 mmol, 3.0 eq), CuI (242 mg, 1.27 mmol, 0.2 eq) and $Pd(PPh_3)_2Cl_2$ (445 mg, 635 umol, 0.1 eq) in one portion at 25° C. under $N_2$ and it was stirred at 100° C. for 2 h. The mixture was concentrated to give a residue. The residue was purified by silica gel chromatography (column height: 250 mm, diameter: 100 mm, 100-200 mesh silica gel, Petroleum ether/Ethyl acetate=1/0, 10/1) to afford 176a (3.5 g, crude) as yellow solid.

Preparation of 5-amino-2-[2-(1-tert-butoxycarbonyl-4-piperidyl) ethynyl]-6H-thieno[3,2-b]azepine-7-carboxylic Acid, 176b To a mixture of 176a (3.5 g, 7.89 mmol, 1.0 eq) in EtOH (50 mL) and $H_2O$ (8 mL) was added $LiOH.H_2O$ (1.32 g, 31.6 mmol, 4.0 eq) in one portion at 25° C. and it was stirred at 30° C. for 2 h. The mixture was concentrated and the residue was diluted with water (30 mL). Then the mixture was filtered. The filter cake was triturated with $CH_3CN$ at 25° C. for 0.5 h, then filtered to afford 176b (2.3 g, 5.54 mmol, 70.2% yield) as yellow solid.

Preparation of tert-butyl 4-[2-[5-amino-7-[ethoxy(propyl)carbamoyl]-6H-thieno[3,2-b]azepin-2-yl]ethynyl]piperidine-1-carboxylate, 176c To a mixture of 176b (1 g, 2.41 mmol, 1.0 eq) in DCM (10 mL) and DMA (10 mL) was added N-ethoxypropan-1-amine (353 mg, 2.53 mmol, 1.05 eq, HCl) and EDCI (1.85 g, 9.63 mmol, 4.0 eq) in one portion at 25° C. and it was stirred at 25° C. for 1 h. The mixture was concentrated to remove DCM, the residue was diluted with water (50 mL) and the pH of the mixture was adjusted to about 8 with sat, $NaHCO_3$, and then extracted with EtOAc (30 mL×3). The organic layer was washed with brine, dried over $Na_2SO_4$, filtered and concentrated. The residue was purified by silica gel chromatography (column height: 250 mm, diameter: 100 mm, 100-200 mesh silica gel, Ethyl acetate/MeOH=1/0, 10/1) to afford 176c (0.63 g, 1.26 mmol, 52.3% yield) as light yellow solid. $^1$H NMR (MeOD, 400 MHz) δ7.27 (s, 1H), 6.88 (s, 1H), 3.89 (q, J=7.2 Hz, 2H), 3.74-3.70 (m, 2H), 3.69 (t, J=6.8 Hz, 2H), 3.25-3.19 (m, 3H), 2.99 (s, 2H), 1.89-1.85 (m, 2H), 1.79-1.67 (m, 2H), 1.65-1.59 (m, 2H), 1.47 (s, 9H), 1.15 (t, J=7.2 Hz, 3H), 0.95 (t, J=7.6 Hz, 3H). LC/MS [M+H] 501.2 (calculated); LC/MS [M+H] 501.1 (observed).

Preparation of tert-butyl 4-[2-[5-amino-7-[ethoxy(propyl) carbamoyl]-6H-thieno[3,2-b]azepin-2-yl]ethyl]piperidine-1-carboxylate, 176d To a solution of 176c (0.45 g, 899 umol, 1.0 eq) in MeOH (15 mL) was added $Pd(OH)_2/C$ (0.2 g, 10% purity) under $N_2$. The suspension was degassed under vacuum and purged with $H_2$ several times. The mixture was stirred under $H_2$ (50 psi) at 25° C. for 12 hours. The mixture was filtered and concentrated. The residue was purified by silica gel chromatography (column height: 250 mm, diameter: 100 mm, 100-200 mesh silica gel, Petroleum ether/Ethyl acetate=1/0, 0/1) to afford 176d (0.3 g, 594 umol, 66.13% yield) as light yellow solid. $^1$H NMR (MeOD, 400 MHz) δ7.32 (s, 1H), 6.65 (s, 1H), 4.06 (d, J=13.2 Hz, 2H), 3.89 (q, J=7.2 Hz, 2H), 3.69 (t, J=7.2 Hz, 2H), 2.98 (s, 2H), 2.85 (t, J=7.6 Hz, 2H), 2.73 (s, 2H), 1.77-1.73 (m, 4H), 1.69-1.60 (m, 2H), 1.58-1.50 (m, 1H), 1.45 (s, 9H), 1.16 (t, J=7.2 Hz, 3H), 1.13-1.05 (m, 2H), 0.95 (t, J=7.6 Hz, 3H). LC/MS [M+H] 501.2 (calculated); LC/MS [M+H] 505.3 (observed).

Preparation of TAZ-176

To a mixture of 176d (0.3 g, 594 umol, 1.0 eq) in EtOAc (5 mL) was added HCl/EtOAc (4 M, 10 mL) in one portion at 25° C. and it was stirred at 25° C. for 0.5 h. The mixture was concentrated to give TAZ-176 (0.3 g, crude, HCl) as a yellow solid. $^1$H NMR (MeOD, 400 MHz) δ7.45 (s, 1H), 6.93 (s, 1H), 3.93 (q, J=7.2 Hz, 2H), 3.72 (t, J=7.2 Hz, 2H), 3.45-3.37 (m, 4H), 3.05-2.91 (m, 4H), 2.02 (d, J=13.6 Hz, 2H), 1.80-1.65 (m, 5H), 1.52-1.35 (m, 2H), 1.18 (t, J=7.2 Hz, 3H), 0.97 (t, J=7.6 Hz, 3H). LC/MS [M+H] 405.2 (calculated); LC/MS [M+H] 405.1 (observed).

Example 183 Synthesis of 5-amino-2-(azetidin-3-ylmethyl)-N-ethoxy-N-propyl-6H-thieno[3,2-b]azepine-7-carboxamide, TAZ-183

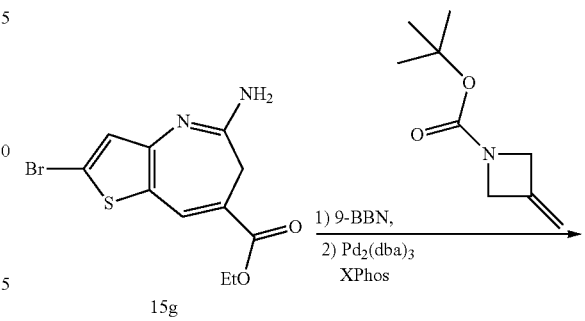

-continued

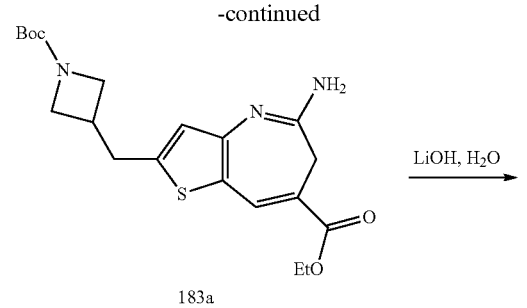

183a

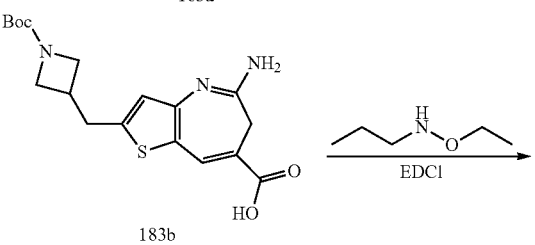

183b

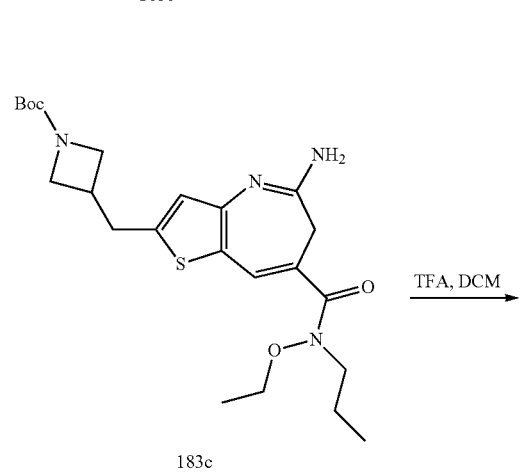

183c

TAZ-183

Preparation of ethyl 5-amino-2-[(1-tert-butoxycarbonyl azetidin-3-yl)methyl]-6H-thieno[3,2-b]azepine-7-carboxylate, 183a tert-Butyl 3-methyleneazetidine-1-carboxylate (2.25 g, 13.3 mmol, 2 eq) was treated with a 9-BBN (0.5 M, 53.3 mL, 4 eq) in THE (50 mL) and the mixture was heated at 70° C. for 4 hrs. The resulting mixture was transferred into a stirred mixture of ethyl 5-amino-2-bromo-6H-thieno[3,2-b]azepine-7-carboxylate, 15g (2.1 g, 6.66 mmol, 1 eq), Pd₂(dba)₃ (610 mg, 666 umol, 0.1 eq), XPhos (953 mg, 2.00 mmol, 0.3 eq) and Na₂CO₃ (2.12 g, 20.0 mmol, 3 eq) in dioxane (50 mL) and H₂O (5 mL). The resulting mixture was stirred at 100° C. for 12 hr under N₂, and then filtered, the filtrate was concentrated to remove THE and dioxane, EtOAc (100 mL) and water (100 mL) was poured into the mixture. The organic layer was washed with brine, dried over anhydrous Na₂SO₄, concentrated to give a residue. The residue was purified by column chromatography (SiO₂, Petroleum ether/Ethyl acetate=1:0 to 0:1, then EtOAc:MeOH=10:1) to give 183a (2 g, 2.47 mmol, 37.0% yield) as yellow solid.

Preparation of 5-amino-2-[(1-tert-butoxycarbonylazetidin-3-yl)methyl]-6H-thieno[3,2-b]azepine-7-carboxylic Acid, 183b To a mixture of 183a (2 g, 4.93 mmol, 1 eq) in THE (10 mL) and H₂O (10 mL) was added LiOH.H₂O (621 mg, 14.8 mmol, 3 eq), and then stirred at 15° C. for 3 hr. The mixture was concentrated to remove THF, then the pH of the aqueous phase was adjusted to ~7 with HCl (4M). The desired solid precipitated from the mixture, and filtered to give 183b (1.5 g, 3.97 mmol, 80.6% yield) as yellow solid. ¹H NMR (400 MHz, DMSO-d₆) δ7.65 (s, 1H), 6.94 (s, 2H), 6.66 (s, 1H), 4.05-3.93 (m, 2H), 3.70-3.55 (m, 2H), 3.07 (d, J=7.6 Hz, 2H), 2.88 (s, 2H), 2.80-2.65 (m, 1H), 1.43 (s, 9H).

Preparation of tert-butyl 3-[[5-amino-7-[ethoxy(propyl)carbamoyl]-6H-thieno[3,2-b]azepin-2-yl]methyl]azetidine-1-carboxylate, 183c To a mixture of 183b (0.2 g, 530 umol, 1 eq) and N-ethoxypropan-1-amine (96.2 mg, 689 umol, 1.3 eq, HCl) in DMA (3 mL) and DCM (3 mL) was added EDCI (406 mg, 2.12 mmol, 4 eq), and then stirred at 15° C. for 2 hr. The mixture was concentrated to give a residue. The residue was purified by Prep-HPLC (column: Phenomenex Synergi C18 150*25*10 um; mobile phase: [water (0.1% TFA)-ACN]; B %: 25%-55%, 8 min) to give 183c (130 mg, 273 umol, 51.6% yield, 97.2% purity) as light-yellow solid. ¹H NMR (400 MHz, MeOD) δ7.47 (s, 1H), 6.93 (s, 1H), 4.07 (br t, J=8.4 Hz, 2H), 3.95 (q, J=7.2 Hz, 2H), 3.82-3.63 (m, 4H), 3.44 (s, 2H), 3.18 (d, J=7.6 Hz, 2H), 3.02-2.81 (m, 1H), 1.76 (sxt, J=7.2 Hz, 2H), 1.45 (s, 9H), 1.20 (t, J=7.2 Hz, 3H), 0.99 (t, J=7.2 Hz, 3H). LC/MS [M+H] 463.2 (calculated); LC/MS [M+H] 463.1 (observed).

Preparation of TAZ-183

To a mixture of 183c (0.11 g, 238 umol, 1 eq) in DCM (10 mL) was added TFA (1.54 g, 13.5 mmol, 1 mL, 56.8 eq). The mixture was stirred at 15° C. for 1 hr. The pH of the mixture was adjusted to ~7 with saturated aqueous solution of NaHCO₃, then extracted with DCM/i-PrOH (3:1, 10 mL*3). The organic layer was dried over Na₂SO₄, concentrated to give TAZ-183 (60 mg, 151 umol, 63.3% yield, 90.95% purity) as light yellow solid. ¹H NMR (400 MHz, MeOD) δ7.20 (s, 1H), 6.63 (s, 1H), 4.04 (br t, J=9.6 Hz, 2H), 3.83-3.75 (m, 4H), 3.59 (t, J=7.2 Hz, 2H), 3.36-3.30 (m, 1H), 3.05 (d, J=7.6 Hz, 2H), 2.88 (s, 2H), 1.62 (sxt, J=7.2 Hz, 2H), 1.08-1.00 (m, 3H), 0.85 (t, J=7.2 Hz, 3H). LC/MS [M+H] 363.2 (calculated); LC/MS [M+H]363.1 (observed).

431

Example 185 Synthesis of cyclobutyl N-[3-[[5-amino-2-(4-piperidylmethyl)-6H-thieno[3,2-b]azepine-7-carbonyl]-propyl-amino]propyl]carbamate, TAZ-185

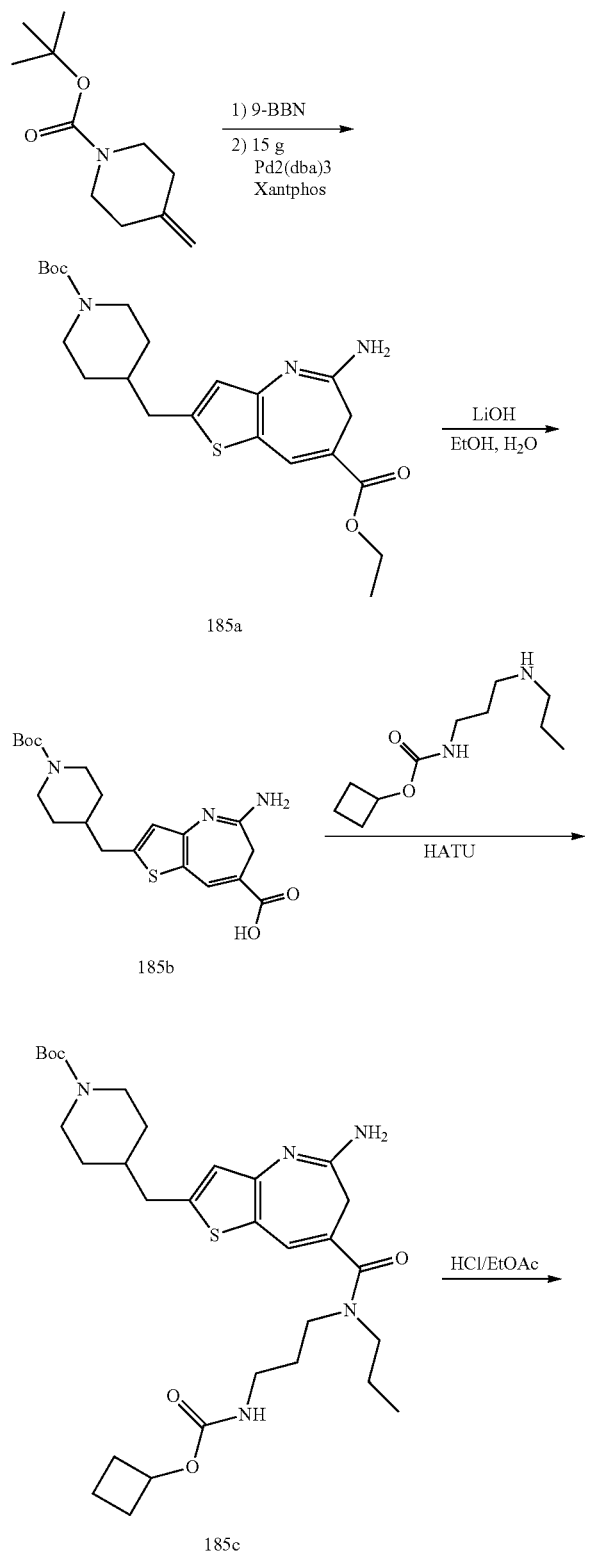

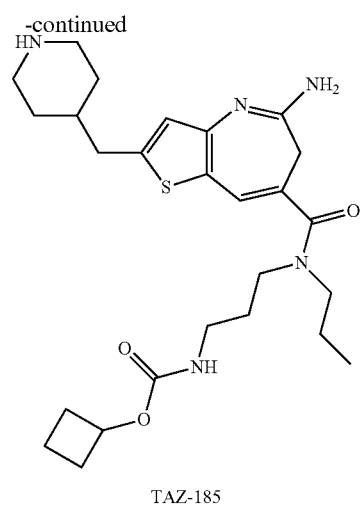

TAZ-185

Preparation of ethyl 5-amino-2-[(1-tert-butoxycarbonyl-4-piperidyl) methyl]-6H-thieno[3,2-b]azepine-7-carboxylate, 185a A mixture of tert-butyl 4-methylenepiperidine-1-carboxylate (4.51 g, 22.8 mmol, 2.0 eq) and 9-BBN (1 M, 57.1 mL, 5.0 eq) was heated to 70° C. and stirred at 70° C. for 2 hours, then ethyl 5-amino-2-bromo-6H-thieno[3,2-b]azepine-7-carboxylate, 15g (3.60 g, 11.4 mmol, 1.0 eq), Xantphos (1.59 g, 2.74 mmol, 0.24 eq), $Pd_2(dba)_3$ (836 mg, 913 umol, 0.08 eq), $K_2CO_3$ (4.74 g, 34.2 mmol, 3.0 eq), $H_2O$ (5 mL) and dioxane (50 mL) was added to this mixture after it was cooled to 20° C., then the mixture was stirred at 100° C. for 4 hours under $N_2$. Water (200 mL) was added and the aqueous phase was extracted with ethyl acetate (50 mL*4), the combined organic phase was washed with brine (100 mL*1), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=10/1, 0/1) to afford 185a (1.8 g, 4.15 mmol, 36.35% yield) as brown oil.

Preparation of 5-amino-2-[(1-tert-butoxycarbonyl-4-piperidyl)methyl]-6H-thieno[3,2-b]azepine-7-carboxylic Acid, 185b To a solution of L-185a (1.80 g, 4.15 mmol, 1.0 eq) in EtOH (3 mL) and $H_2O$ (5 mL) was added $LiOH \cdot H_2O$ (696 mg, 16.6 mmol, 4.0 eq) in one portion at 20° C. under $N_2$, and then stirred at 20° C. for 4 hours. The reaction mixture was quenched with HCl (4 M) until pH=6, then EtOH was removed in vacuum. The precipitation was filtered and dried to afford 185b (1.20 g, 2.96 mmol, 71.2% yield) as yellow solid. $^1$H NMR (400 MHz, DMSO-$d_6$) δ7.61 (s, 1H), 6.58 (s, 1H), 3.86 (d, 2.0 Hz, 2H), 2.92 (s, 2H), 2.65 (d, J=6.4 Hz, 2H), 1.65-1.60 (m, 3H), 1.35 (s, 9H), 1.07-0.96 (m, 2H)

Preparation of tert-butyl 4-[[5-amino-7-[3-(cyclobutoxycarbonylamino) propyl-propyl-carbamoyl]-6H-thieno[3,2-b]azepin-2-yl]methyl]piperidine-1-carboxylate, 185c To a mixture of L-185b (200 mg, 493 umol, 1.0 eq) and cyclobutyl N-[3-(propylamino) propyl]carbamate (148 mg, 591 umol, 1.2 eq, HCl) in DMF (2 mL) was added HATU (187 mg, 493 umol, 1.0 eq) and DIEA (191 mg, 1.48 mmol, 257 uL, 3.0 eq) in one portion at 20° C. under $N_2$, the mixture was stirred at 20° C. for 1 hours. Water (10 mL) was added and the aqueous phase was extracted with ethyl acetate (10 mL*3), the combined organic phase was washed with brine (15 mL*2), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=5/1, 0/1 to Ethyl acetate/Methanol=10/1) to afford 185c (180 mg, 299 umol, 60.6% yield) as brown solid. $^1$H NMR (400 MHz, MeOD) δ6.88 (s, 1H), 6.68 (s, 1H), 4.88-4.80 (m, 1H), 4.08 (d, J=12.4 Hz, 2H), 3.49 (t, J=7.2 Hz, 2H), 3.41 (t, J=7.6 Hz, 2H), 3.11 (s, 2H), 2.75 (d, J=6.8 Hz, 3H), 2.36-2.23 (m, 2H), 1.86-1.59 (m, 10H), 1.47 (s, 9H), 1.22-1.09 (m, 2H), 0.90 (t, J=4.0, 3H)

Preparation of TAZ-185

To a solution of 185c (180 mg, 299 umol, 1.0 eq) in EtOAc (1 mL) was added HCl/EtOAc (4 M, 3.74 mL, 50 eq) in one portion at 20° C. under $N_2$, and then stirred at 20° C. for 1 hour. The reaction mixture was concentrated in vacuum to afford TAZ-185 (140 mg, 260 umol, 86.98% yield, HCl) as yellow oil.

Example 198 Synthesis of 5-amino-N-ethoxy-2-(4-piperidylmethyl)-N-propyl-6H-thieno[3,2-b]azepine-7-carboxamide, TAZ-198

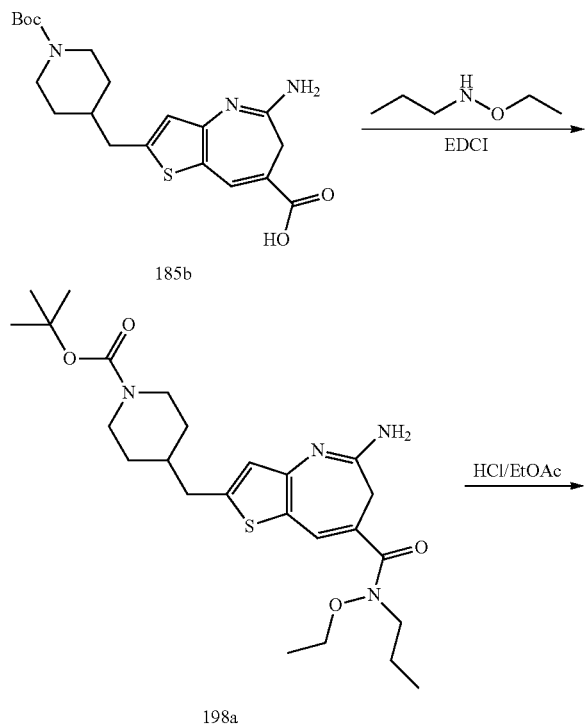

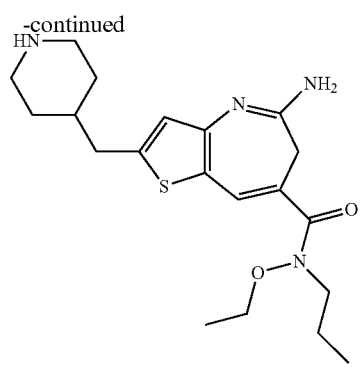

TAZ-198

Preparation of tert-butyl 4-[[5-amino-7-[ethoxy(propyl)carbamoyl]-6H-thieno[3,2-b]azepin-2-yl]methyl]piperidine-1-carboxylate, 198a To a mixture of 5-amino-2-[(1-tert-butoxycarbonyl-4-piperidyl)methyl]-6H-thieno[3,2-b]azepine-7-carboxylic acid, 185b (200 mg, 493 umol, 1.0 eq) and N-ethoxypropan-1-amine (82.6 mg, 591 umol, 1.2 eq, HCl) in DMA (1 mL) and DCM (2 mL) was added EDCI (378 mg, 1.97 mmol, 4.0 eq) at 20° C. under $N_2$, and then stirred at 20° C. for 2 hours. DCM (2 mL) was removed in vacuum, then the aqueous phase was quenched with aq $NaHCO_3$ until pH=8, the water phase was extracted with EtOAc (15 mL*3), the combined organic phase was washed with brine (15 mL), dried with anhydrous $Na_2SO_4$, filtered and concentrated in vacuum. The residue was purified by silica gel chromatography (column height: 250 mm, diameter: 100 mm, 100-200 mesh silica gel, Petroleum ether/Ethyl acetate=5/1, 0/1 to Ethyl acetate/Methanol=10/1) to afford 198a (150 mg, 305 umol, 61.9% yield) as brown solid. $^1$H NMR (400 MHz, MeOD) δ7.35 (s, 1H), 6.68 (s, 1H), 4.08 (d, J=13.2 Hz, 2H), 3.90 (q, J=7.2 Hz, 2H), 3.71 (t, J=7.2 Hz, 2H), 3.33 (s, 2H), 3.08 (d, J=8.0 Hz 2H), 2.76 (d, J=6.8 Hz, 3H), 1.80-1.70 (m, 5H), 1.47 (s, 9H), 1.20-1.10 (m, 5H), 0.97 (t, J=7.2 Hz, 3H)

Preparation of TAZ-198

To a solution of 198a (150 mg, 305 umol, 1.0 eq) in EtOAc (1 mL) was added HCl/EtOAc (4 M, 3.82 mL, 50 eq) at 20° C. under $N_2$, the mixture was stirred at 20° C. for 1 hour. The reaction mixture was concentrated in vacuum to afford TAZ-198 (100 mg, 234 umol, 76.6% yield, HCl) as yellow oil.

Example 238 Synthesis of cyclobutyl N-[2-[[5-amino-2-(azetidin-3-ylmethyl)-6H-thieno[3,2-b]azepine-7-carbonyl]-propyl-amino] oxyethyl]carbamate, TAZ-238

Preparation of tert-butyl 3-[[5-amino-7-[2-(cyclobutoxycarbonylamino)ethoxy-propyl-carbamoyl]-6H-thieno[3,2-b]azepin-2-yl]methyl]azetidine-1-carboxylate, 238a To a solution of 5-amino-2-[(1-tert-butoxycarbonylazetidin-3-yl)methyl]-6H-thieno[3,2-b]azepine-7-carboxylic acid, 261a (200 mg, 529.86 umol, 1 eq) and cyclobutyl N-[2-(propylaminooxy)ethyl]carbamate (174.09 mg, 688.82 umol, 1.3 eq, HCl) in DCM (2 mL) and DMA (2 mL) was added EDCI (304.72 mg, 1.59 mmol, 3 eq) at 0° C., and then stirred at 25° C. for 1 hr. The reaction mixture was concentrated under reduced pressure to give a residue. The residue was diluted with H₂O (10 mL) and the pH of the mixture was adjusted to ~9 with aq. Na₂CO₃ at 0° C. and it was extracted with EtOAc (10 mL*3). The combined organic layers were washed with brine (5 mL*3), dried over Na₂SO₄, filtered and concentrated under reduced pressure to give a residue. The residue was purified by column chromatography (SiO₂, Petroleum ether/Ethyl acetate=1/0 to 0/1) and then (SiO2, EtOAc:MeOH=1:0 to 3:1) to give 238a (0.2 g, 347.39 umol, 65.56% yield) as a yellow solid. ¹H NMR (MeOD, 400 MHz) δ7.32 (s, 1H), 6.69 (s, 1H), 4.81 (s, 1H), 4.08-3.99 (m, 2H), 3.89 (t, J=5.2 Hz, 2H), 3.72-3.62 (m, 4H), 3.29-3.25 (m, 2H), 3.09 (d, J=7.6 Hz, 2H), 3.02 (s, 2H), 2.95-2.83 (m, 1H), 2.32-2.21 (m, 2H), 2.05-1.94 (m, 2H), 1.77-1.54 (m, 4H), 1.45-1.40 (m, 9H), 0.94 (t, J=7.6 Hz, 3H). LC/MS [M+H] 576.3 (calculated); LC/MS [M+H] 576.3 (observed).

Preparation of TAZ-238

To a mixture of 238a (0.31 g, 538 umol, 1.0 eq) in DCM (6 mL) was added TFA (1.23 g, 10.8 mmol, 797 uL, 20.0 eq) in one portion at 25° C. and then stirred at 25° C. for 2 h. The mixture was concentrated to give a residue, the residue was diluted with H₂O (15 mL), the mixture was extracted with MTBE (10 mL*2) to remove excess TFA, the aqueous phase was freeze-dried to afford TAZ-238 (0.38 g, 521 umol, 96.7% yield, 96.4% purity, TFA salt) as yellow solid. ¹H NMR (MeOD, 400 MHz) δ7.47 (s, 1H), 6.96 (s, 1H), 4.81-4.74 (m, 1H), 4.22-4.13 (m, 2H), 3.96-3.86 (m, 4H), 3.71 (t, J=7.2 Hz, 2H), 3.41 (s, 2H), 3.29-3.22 (m, 5H), 2.25 (d, J=7.2 Hz, 2H), 2.03-1.89 (m, 2H), 1.80-1.55 (m, 4H), 0.96 (t, J=7.6 Hz, 3H). LC/MS [M+H] 476.2 (calculated); LC/MS [M+H] 476.1 (observed).

Example 253 Synthesis of 5-amino-2-(azetidin-3-ylmethyl)-N-isopropoxy-N-propyl-6H-thieno[3,2-b]azepine-7-carboxamide, TAZ-253

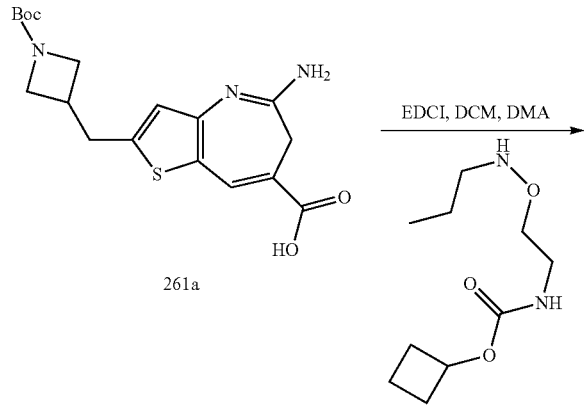
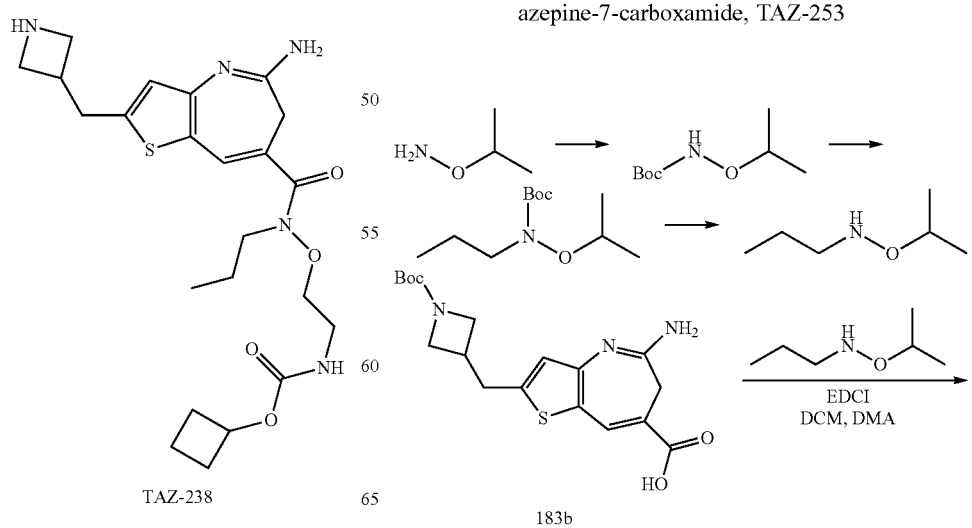

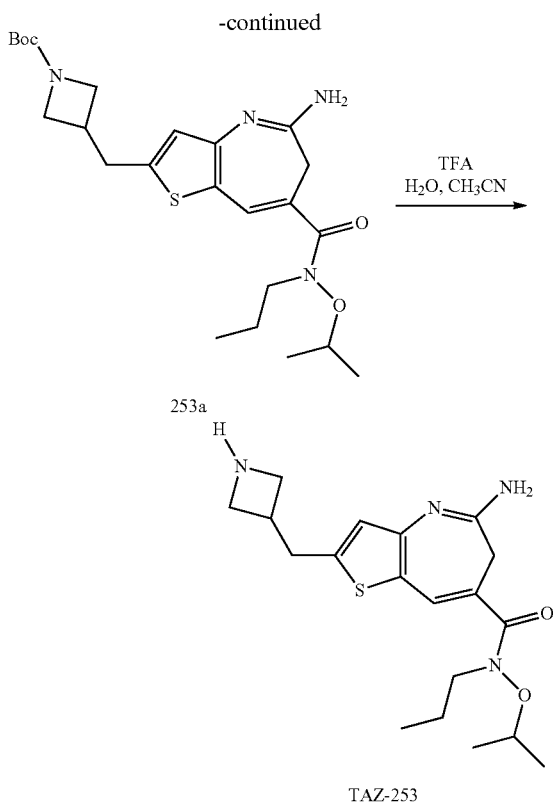

acetate=0:1-1:1. tert-butyl N-isopropoxy-N-propyl-carbamate (3.8 g, crude) was obtained as colorless oil. $^1$H NMR (MeOD, 400 MHz) δ4.12-4.02 (m, 1H), 3.39 (t, J=7.2 Hz, 2H), 1.70-1.61 (m, 2H), 1.49 (s, 9H), 1.21 (d, J=6.0 Hz, 6H), 0.90 (t, J=7.2 Hz, 3H).

To a solution of tert-butyl N-isopropoxy-N-propyl-carbamate (3.2 g, 14.7 mmol, 1 eq) in EtOAc (5 mL) was added HCl/EtOAc (4 M, 55.2 mL, 15 eq), and then stirred at 20° C. for 2 h. The reaction mixture was concentrated under reduced pressure to give a residue. N-isopropoxypropan-1-amine (1.61 g, 10.48 mmol, 71.16% yield, HCl) was obtained as colorless oil. $^1$H NMR (MeOD, 400 MHz) δ4.76-4.67 (m, 1H), 3.23-3.16 (m, 2H), 2.00-1.89 (m, 2H), 1.41 (d, J=6.2 Hz, 6H), 1.03 (t, J=7.6 Hz, 3H).

Preparation of tert-butyl 3-[[5-amino-7-[isopropoxy (propyl)carbamoyl]-6H-thieno[3,2-b]azepin-2-yl] methyl]azetidine-1-carboxylate, 253a To a mixture of 5-amino-2-[(1-tert-butoxycarbonylazetidin-3-yl)methyl]-6H-thieno [3,2-b]azepine-7-carboxylic acid, 183b (400 mg, 1.06 mmol, 1 eq) and N-isopropoxypropan-1-amine (244 mg, 1.59 mmol, 1.50 eq, HCl) in DMA (2 mL) and DCM (2 mL) was added EDCI (610 mg, 3.18 mmol, 3 eq), and then stirred at 20° C. for 1 h. The reaction mixture was added H$_2$O (20 mL) and then the pH of the mixture was adjusted to ~8 with aq NaHCO$_3$, extracted with EtOAc (30 mL×3), the combined organic phase was washed with brine (10 mL×3), dried with anhydrous Na$_2$SO$_4$, filtered and concentrated in vacuum. The crude product was purified by silica gel chromatography eluted with (Ethyl acetate:Methanol=1:0, 5:1) to give 253a (410 mg, 860 umol, 81.17% yield) as a light yellow solid. $^1$H NMR (MeOD, 400 MHz) δ7.34 (s, 1H), 6.73 (s, 1H), 4.20-4.15 (m, 1H), 4.09-4.00 (m, 2H), 3.74-3.63 (m, 4H), 3.06 (d, J=8.0 Hz, 2H), 2.95 (s, 2H), 2.90-2.84 (m, 1H), 1.76-1.67 (m, 2H), 1.43 (s, 9H), 1.17 (d, J=6.2 Hz, 6H), 0.94 (t, J=7.6 Hz, 3H).

Preparation of TAZ-253

To a solution of 253a (410 mg, 860 umol, 1 eq) in CH$_3$CN (2 mL) and H$_2$O (2 mL) was added TFA (785 mg, 6.88 mmol, 510 uL, 8 eq), and then stirred at 80° C. for 2 h under N$_2$ atmosphere. The reaction mixture was concentrated under reduced pressure to remove CH$_3$CN, the aqueous phase was extracted with and MTBE (15 mL×3) to remove excess TFA, the water phase was freeze-dried to give TAZ-253 (320 mg, 850 umol, 98.80% yield) as a light yellow solid. $^1$H NMR (MeOD, 400 MHz) δ7.43 (s, 1H), 6.95 (s, 1H), 4.27-4.20 (m, 1H), 4.20-4.14 (m, 2H), 3.97-3.87 (m, 2H), 3.73 (br t, J=7.2 Hz, 2H), 3.40 (s, 2H), 3.30-3.25 (m, 3H), 1.81-1.69 (m, 2H), 1.18 (d, J=6.2 Hz, 6H), 0.96 (t, J=7.4 Hz, 3H). LC/MS [M+H] 377.2 (calculated); LC/MS [M+H] 377.1 (observed).

Preparation of N-isopropoxypropan-1-amine

To a solution of O-isopropylhydroxylamine (2 g, 17.9 mmol, 1 eq, HCl) in THF (15 mL) was added a solution of NaHCO$_3$ (3.01 g, 35.8 mmol, 1.39 mL, 2 eq) in H$_2$O (5 mL) and tert-butoxycarbonyl tert-butyl carbonate (5.87 g, 26.9 mmol, 6.18 mL, 1.5 eq), and then stirred at 20° C. for 2 h under N$_2$ atmosphere. H$_2$O (50 mL) was added to the mixture and then extracted with EtOAc (80 mL×3), the combined organic phase was washed with brine (50 mL×3), dried with anhydrous Na$_2$SO$_4$, filtered and concentrated in vacuum. The crude product was purified by silica gel chromatography eluted with (Petroleum ether:Ethyl acetate=1:0, 1:1). tert-Butyl N-isopropoxycarbamate (2.81 g, 16.0 mmol, 89.46% yield) was obtained as light yellow oil. $^1$H NMR (MeOD, 400 MHz) δ7.00 (br s, 1H), 4.10-1.00 (m, 1H), 1.49 (s, 9H), 1.22 (d, J=6.4 Hz, 6H).

To a solution of tert-butyl N-isopropoxycarbamate (2.80 g, 15.9 mmol, 1 eq) in DMF (10 mL) was added NaH (959 mg, 23.9 mmol, 60% purity, 1.5 eq) at 0° C. under N$_2$ and it was stirred for 0.5 h, and then 1-iodopropane (5.43 g, 32.0 mmol, 3.12 mL, 2 eq) was added. The mixture was stirred at 25° C. for 2 h under N$_2$ atmosphere. The reaction mixture was quenched at 0° C. by the addition of (50 mL) sat. NH$_4$Cl solution, then extracted with EtOAc (80 mL×3), the combined organic phase was washed with brine (30 mL×3), dried with anhydrous Na$_2$SO$_4$, filtered and concentrated in vacuum. The crude product was purified by silica gel chromatography eluted with Petroleum ether/Ethyl

Example 260 Synthesis of isopropyl N-[2-[[5-amino-2-(azetidin-3-ylmethyl)-6H-thieno [3,2-b]azepine-7-carbonyl]-propyl-amino] oxyethyl]carbamate, TAZ-260

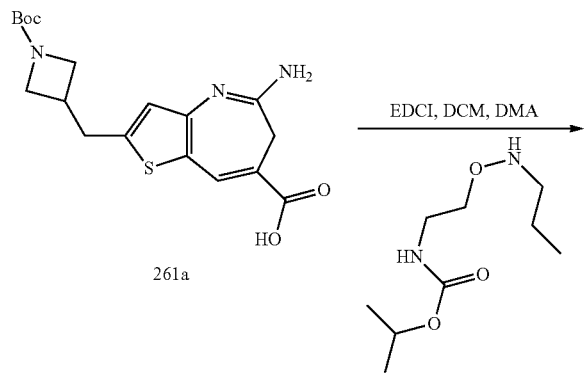

Preparation of tert-butyl 3-[[5-amino-7-[2-(isopropoxycarbonylamino) ethoxy-propyl-carbamoyl]-6H-thieno[3,2-b] azepin-2-yl]methyl]azetidine-1-carboxylate, 260a To a mixture of isopropyl N-[2-(propylaminooxy)ethyl] carbamate (158 mg, 654 umol, 1.3 eq, HCl) and 5-amino-2-[(1-tert-butoxycarbonylazetidin-3-yl)methyl]-6H-thieno [3,2-b]azepine-7-carboxylic acid, 261a (0.19 g, 503 umol, 1.0 eq) in DCM (4 mL) and DMA (0.5 mL) was added EDCI (289 mg, 1.51 mmol, 3.0 eq) in one portion at 25° C. and then stirred at 25° C. for 0.5 h. The mixture was concentrated to remove DCM. Then the mixture was diluted with water (20 mL), the pH of the aqueous phase was adjusted to ~8 with sat. NaHCO₃ and then the mixture was extracted with EtOAc (20 mL×3). The organic layer was washed with brine, dried over Na₂SO₄, filtered and concentrated. The residue was purified by silica gel chromatography (column height: 250 mm, diameter: 100 mm, 100-200 mesh silica gel, Ethyl acetate/MeOH=1/0, 10/1) to afford 260a (0.18 g, 319 umol, 63.44% yield) as yellow oil. $^1$H NMR (MeOH, 400 MHz) δ7.30 (s, 1H), 6.67 (s, 1H), 4.83-4.75 (m, 1H), 4.07-4.03 (m, 2H), 3.89 (t, J=5.4 Hz, 2H), 3.68 (t, J=7.0 Hz, 4H), 3.30-3.26 (m, 2H), 3.08 (d, J=7.6 Hz, 2H), 3.00 (s, 2H), 2.90-2.85 (m, 1H), 1.76-1.67 (m, 2H), 1.43 (s, 9H), 1.18 (d, J=6.0 Hz, 6H), 0.94 (t, J=7.2 Hz, 3H).

Preparation of TAZ-260

To a mixture of 260a (0.18 g, 319 umol, 1.0 eq) in CH₃CN (2 mL) and H₂O (2 mL) was added TFA (291 mg, 2.55 mmol, 189 uL, 8.0 eq) at 25° C. and it was stirred at 80° C. for 0.5 h. The mixture was concentrated to remove CH₃CN. Then the mixture was extracted with MTBE (10 mL×3) to remove excess TFA. The water phase was freeze-dried to give TAZ-260 (0.25 g, 310.30 umol, 97.18% yield, TFA salt) as a yellow solid. $^1$H NMR (MeOH, 400 MHz) δ7.47 (s, 1H), 6.96 (s, 1H), 4.81-4.76 (m, 1H), 4.23-4.09 (m, 2H), 3.98-3.86 (m, 4H), 3.71 (t, J=6.8 Hz, 2H), 3.41 (s, 2H), 3.29-3.18 (m, 5H), 1.83-1.64 (m, 2H), 1.25-1.12 (m, 6H), 0.96 (t, J=7.6 Hz, 3H). LC/MS [M+H] 464.2 (calculated); LC/MS [M+H] 464.1 (observed).

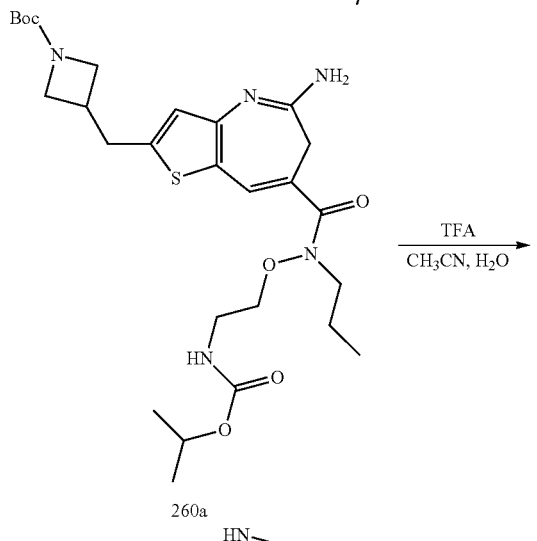

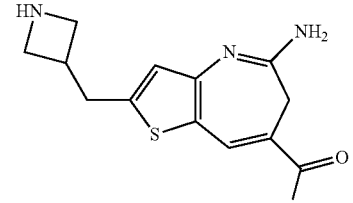

Example 261 Synthesis of 5-amino-2-(azetidin-3-ylmethyl)-N-[2-(ethylcarbamoylamino)ethoxy]-N-propyl-6H-thieno[3,2-b]azepine-7-carboxamide, TAZ-261

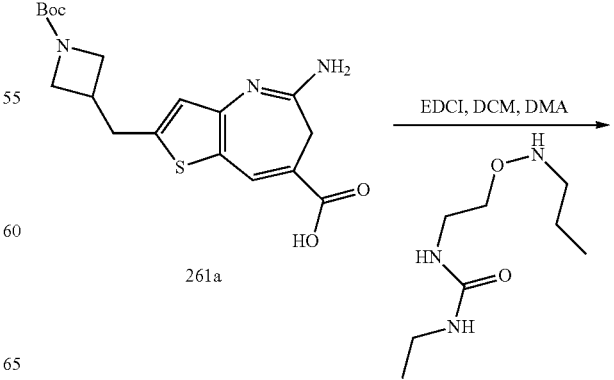

-continued

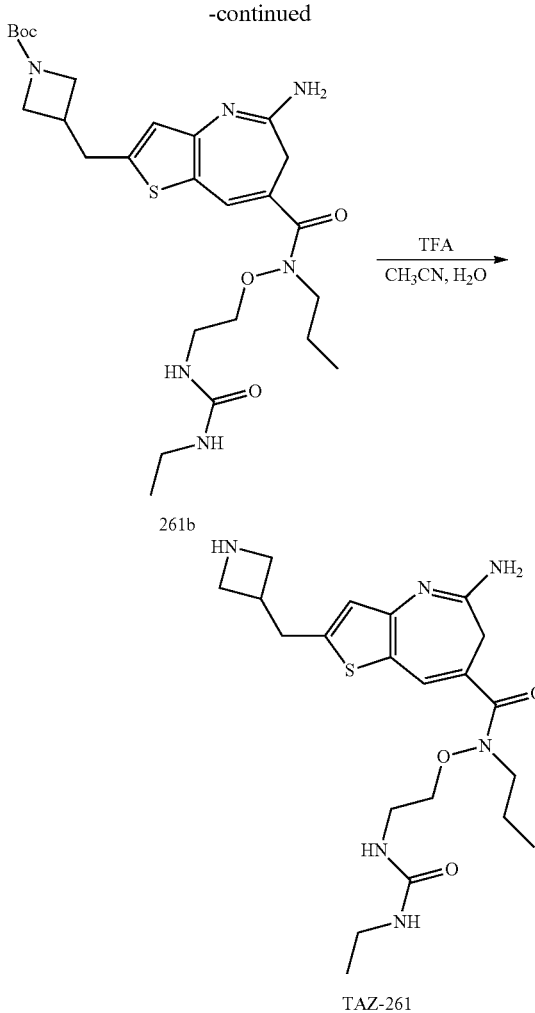

acid, 261a (230 mg, 607.76 umol, 1 eq) and 1-ethyl-3-[2-(propylaminooxy)ethyl]urea (192 mg, 851 umol, 1.4 eq, HCl) in DCM (3.00 mL) and DMA (3.00 mL) was added EDCI (350 mg, 1.82 mmol, 3 eq), and then stirred at 25° C. for 1 h. The mixture was concentrated to remove DCM and diluted with water (20 mL) and the pH of the mixture was adjusted about 9 by sat, $Na_2CO_3$ and extracted with EtOAc (20 mL×3). The organic layer was washed with brine (20 mL×3), dried over $Na_2SO_4$, filtered and concentrated. The residue was purified by flash silica gel chromatography (ISCO®; 0.5 g SepaFlash® Silica Flash Column, Eluent of 0~30% Ethyl acetate/MeOH @ 35 mL/min) to give 261b (270 mg, 492 umol, 80.97% yield) as light yellow solid. $^1$H NMR (MeOD, 400 MHz) δ7.29 (s, 1H), 6.68 (s, 1H), 4.10-4.00 (m, 2H), 3.88 (t, J=5.2 Hz, 2H), 3.74-3.61 (m, 4H), 3.29 (br s, 2H), 3.12-3.05 (m, 4H), 3.01 (s, 2H), 2.95-2.83 (m, 1H), 1.72 (sxt, J=7.2 Hz, 2H), 1.43 (s, 9H), 1.06 (t, J=7.2 Hz, 3H), 0.94 (t, J=7.6 Hz, 3H).

Preparation of TAZ-261

To a solution of 261b (270 mg, 492 umol, 1 eq) in $CH_3CN$ (3.00 mL) and $H_2O$ (3.00 mL) was added TFA (449 mg, 3.94 mmol, 291 uL, 8 eq), and then stirred at 80° C. for 1 h. The mixture was concentrated and diluted with water (20 mL) and extracted with MTBE (20 mL×2) to remove excess TFA and the aqueous phase was freeze-dried to give TAZ-261 (300 mg, 443.38 umol, 90.10% yield, 2TFA) as light yellow solid. $^1$H NMR (MeOD, 400 MHz) δ7.45 (s, 1H), 6.96 (s, 1H), 4.21-4.13 (m, 2H), 3.97-3.86 (m, 4H), 3.71 (t, J=7.2 Hz, 2H), 3.42 (s, 2H), 3.30-3.20 (m, 3H), 3.06 (q, J=7.2 Hz, 2H), 1.80-1.68 (m, 2H), 1.05 (t, J=7.2 Hz, 3H), 0.96 (t, J=7.6 Hz, 3H). LC/MS [M+H] 449.2 (calculated); LC/MS [M+H] 449.1 (observed).

Preparation of tert-butyl 3-[[5-amino-7-[2-(ethylcarbamoylamino)ethoxy-propyl-carbamoyl]-6H-thieno[3,2-b]azepin-2-yl]methyl]azetidine-1-carboxylate, 261b To a solution of 2-[(1-tert-butoxycarbonylazetidin-3-yl)methyl]-5-amino-6H-thieno[3,2-b]azepine-7-carboxylic Example L-1 Synthesis of 2,3,5,6-tetrafluorophenyl (E)-40-(5-amino-6H-thieno[3,2-b]azepine-7-carbonyl)-35-((3-cyanophenyl)imino)-4,7,10,13,16,19,22,25,28,31-decaoxa-34,36,40-triazatritetracontanoate, TAZ-L-1

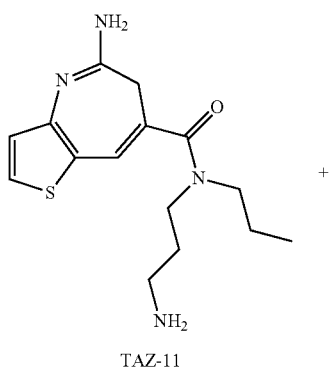

TAZ-11

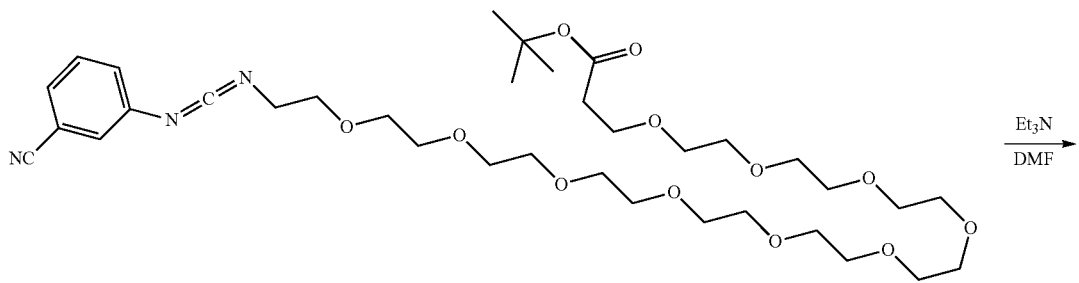
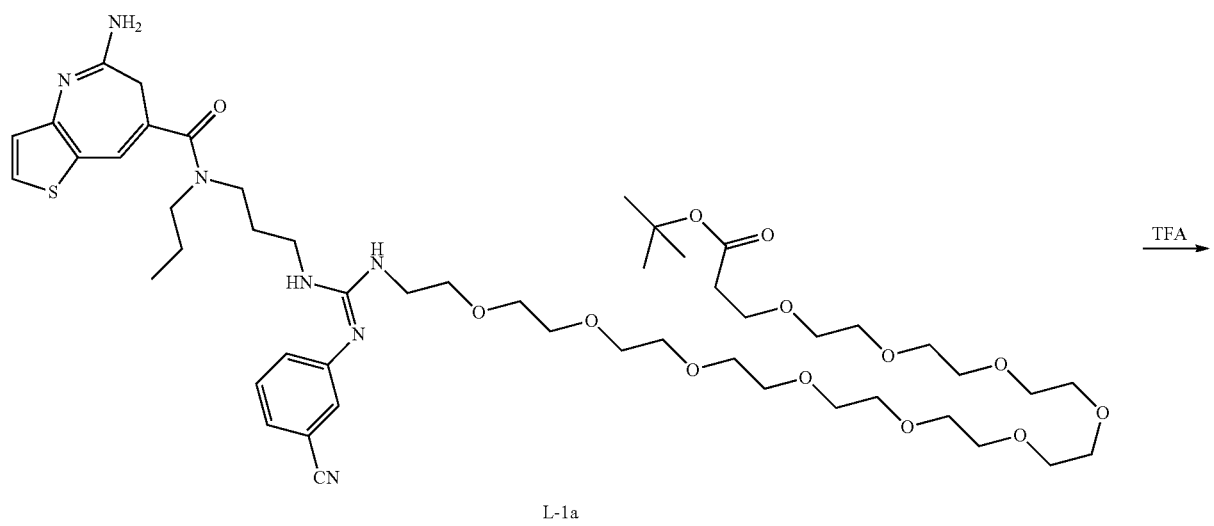
L-1a
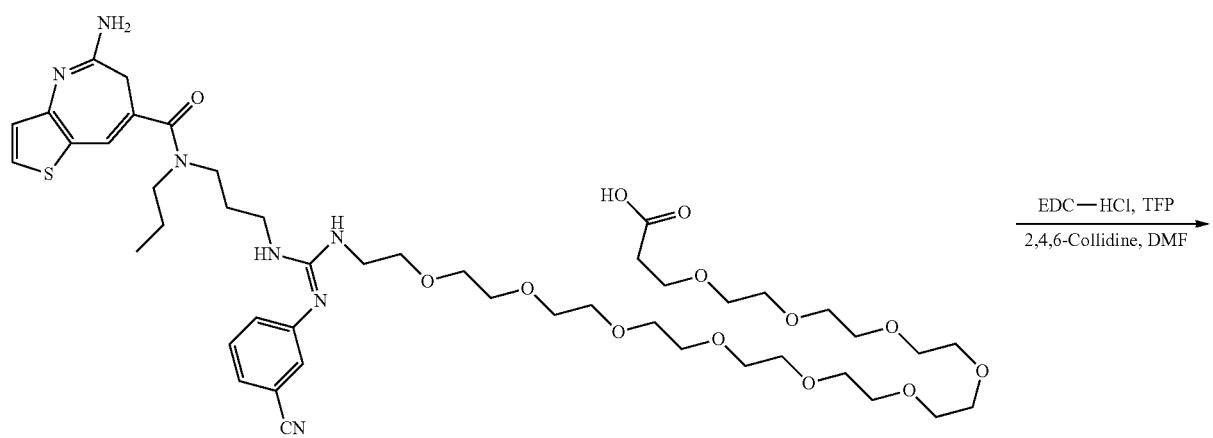
L-1b

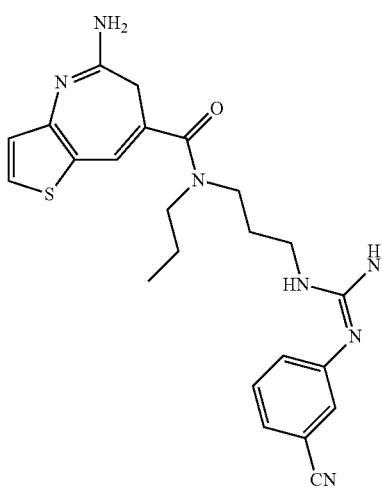
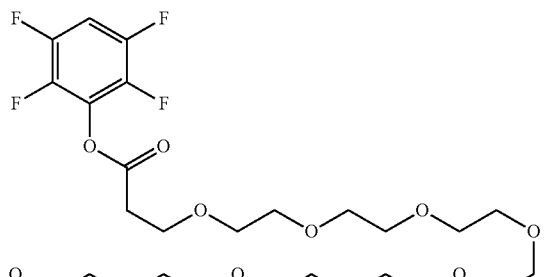

TAZ-L-1

Preparation of tert-butyl (E)-40-(5-amino-6H-thieno[3,2-b]azepine-7-carbonyl)-35-((3-cyanophenyl)imino)-4,7,10,13,16,19,22,25,28,31-decaoxa-34,36,40-triazatritetracontanoate, L-1a TAZ-11 (0.05 g, 0.16 mmol, 1 eq.) and tert-butyl 1-((3-cyanophenyl)imino)-5,8,11,14,17,20,23,26,29,32-decaoxa-2-azapentatriacont-1-en-35-oate, PEG10-diimide (0.116 g, 0.16 mmol, 1 eq.) were dissolved in DMF. Triethylamine (0.068 ml, 0.49 mmol, 3 eq.) was added, and the reaction was stirred at ambient temperature. Upon consumption of amine starting material, the reaction was concentrated and purified by HPLC to give L-1a (0.102 g, 0.10 mmol, 62%). LC/MS [M+H] 1018.55 (calculated); LC/MS [M+H] 1018.91 (observed).

Preparation of (E)-40-(5-amino-6H-thieno[3,2-b]azepine-7-carbonyl)-35-((3-cyanophenyl)imino)-4,7,10,13,16,19,22,25,28,31-decaoxa-34,36,40-triazatritetracontanoic Acid, L-1b L-1a (0.102 g, 0.100 mmol, 1 eq.) was dissolved in 100 μl TFA. After 15 minutes, the product was triturated with diethyl ether and then concentrated under vacuum to give L-1b (94.4 mg, 0.98 mmol, 98%). LC/MS [M+H] 962.49 (calculated); LC/MS [M+H] 962.85 (observed).

Preparation of TAZ-L-1

L-1b (0.094 g, 0.098 mmol, 1 eq.) and 2,3,5,6-tetrafluorophenol, TFP (0.033 g, 0.20 mmol, 2 eq.) were dissolved in DMF. Collidine (0.064 ml, 0.49 mmol, 5 eq.) was added, followed by 1-ethyl-3-(3-dimethylaminopropyl)carbodiimide hydrochloride, EDC-HCl (0.038 g, 0.20 mmol, 2 eq.). The reaction was stirred at room temperature until complete, then purified by HPLC to give TAZ-L-1 (0.057 g, 0.051 mmol, 52%). LC/MS [M+H] 1110.48 (calculated); LC/MS [M+H] 1110.87 (observed).

Example L-2 Synthesis of 2,3,5,6-tetrafluorophenyl (E)-41-(5-amino-6H-thieno[3,2-b]azepine-7-carbonyl)-35-((3-cyanophenyl)imino)-4,7,10,13,16,19,22,25,28,31-decaoxa-34,36,41-triazatetratetracont-38-ynoate, TAZ-L-2

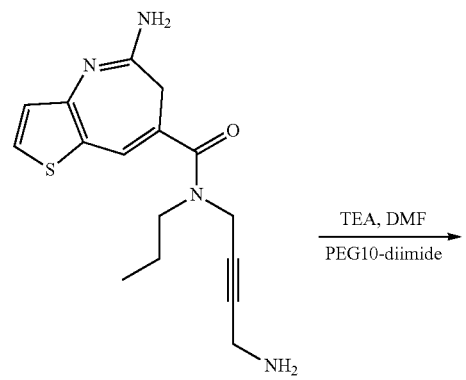

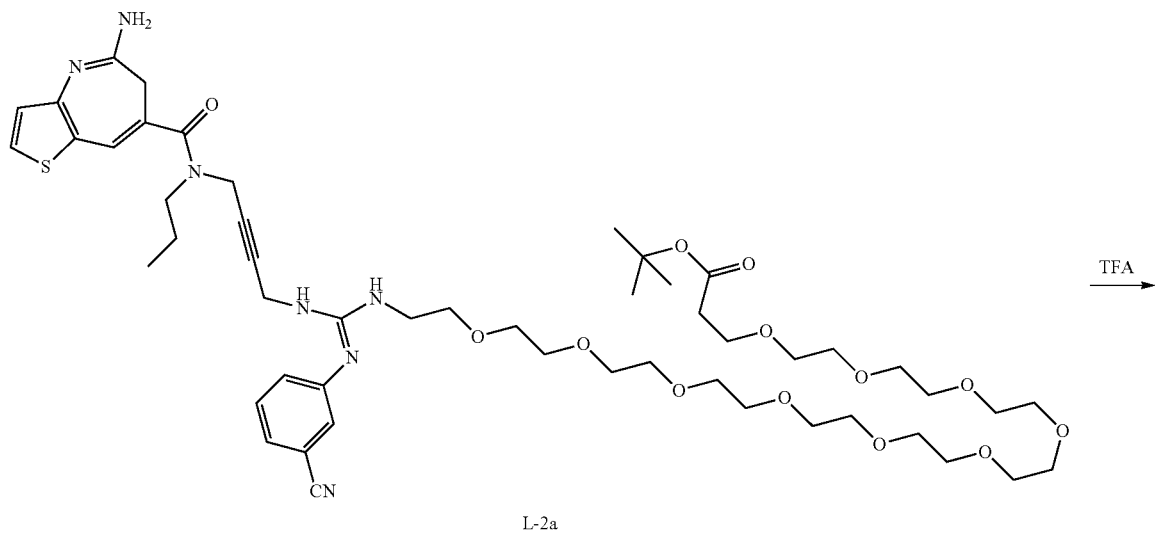
L-2a
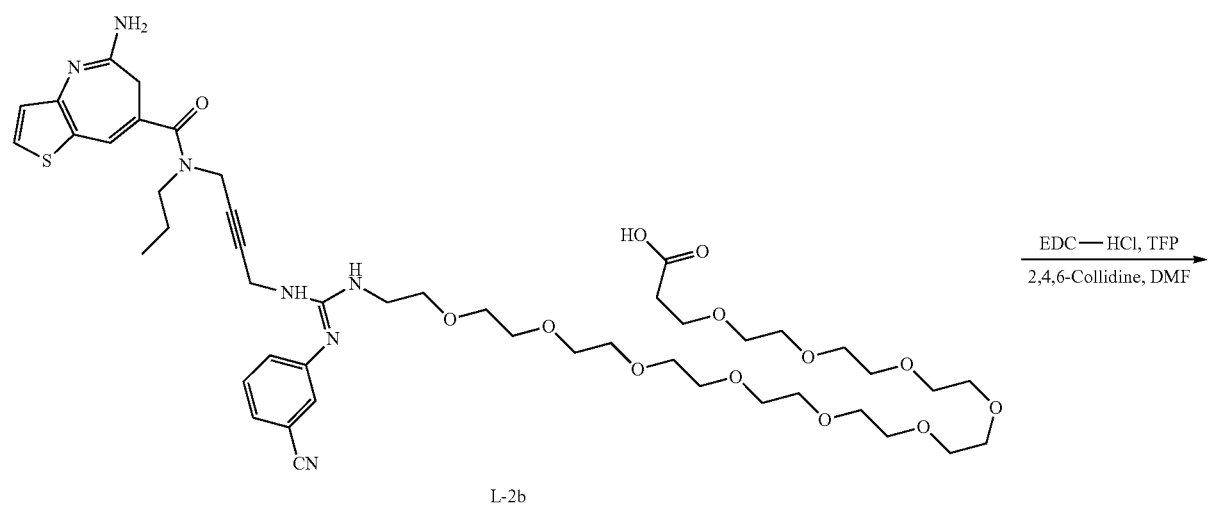
L-2b

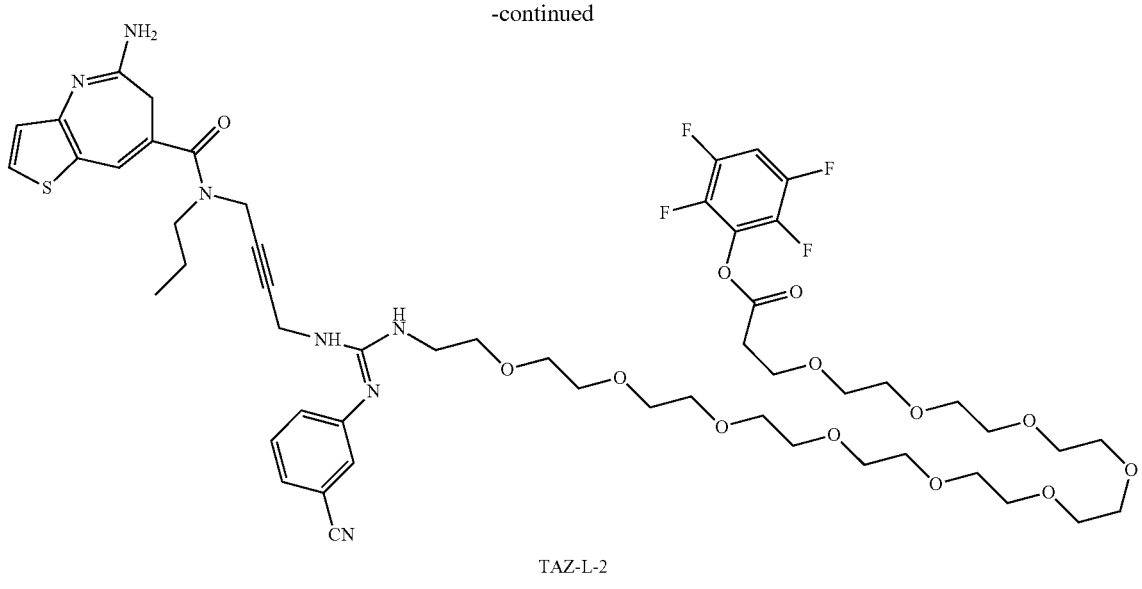

TAZ-L-2

Preparation of tert-butyl (E)-41-(5-amino-6H-thieno
[3,2-b]azepine-7-carbonyl)-35-((3-cyanophenyl)
imino)-4,7,10,13,16,19,22,25,28,31-decaoxa-34,36,
41-triazatetratetracont-38-ynoate, L-2a TAZ-17 (0.05 g, 0.16 mmol, 1 eq.) and tert-butyl 1-((3-cyanophenyl)imino)-5,8,11,14,17,20,23,26,29,32-decaoxa-2-azapentatriacont-1-en-35-oate, PEG10-diimide (0.112 g, 0.16 mmol, 1 eq.) were dissolved in DMF. Triethylamine (0.066 ml, 0.47 mmol, 3 eq.) was added, and the reaction was stirred at ambient temperature. Upon consumption of amine starting material, the reaction was concentrated and purified by HPLC to give L-2a (0.120 g, 0.12 mmol, 74%). LC/MS [M+H] 1028.54 (calculated); LC/MS [M+H] 1028.92 (observed).

Preparation of (E)-41-(5-amino-6H-thieno[3,2-b]
azepine-7-carbonyl)-35-((3-cyanophenyl)imino)-4,7,
10,13,16,19,22,25,28,31-decaoxa-34,36,41-triazatet-
ratetracont-38-ynoic Acid, L-2b L-2a (0.120 g, 0.12 mmol, 1 eq.) was dissolved in 100 µl TFA. After 15 minutes, the product was concentrated and purified by HPLC to give L-2b (84.9 mg, 0.087 mmol, 75%). LC/MS [M+H] 972.47 (calculated); LC/MS [M+H] 972.83 (observed).

Preparation of TAZ-L-2

L-2b (0.085 g, 0.087 mmol, 1 eq.) and TFP (0.029 g, 0.17 mmol, 2 eq.) were dissolved in DMF. Collidine (0.058 ml, 0.44 mmol, 5 eq.) was added, followed by 1-ethyl-3-(3-dimethylaminopropyl)carbodiimide hydrochloride, EDC-HCl (0.033 g, 0.17 mmol, 2 eq.). The reaction was stirred at room temperature until complete, then purified by HPLC to give TAZ-L-2 (0.057 g, 0.055 mmol, 62%). LC/MS [M+H] 1120.47 (calculated); LC/MS [M+H] 1120.85 (observed).

Example L-3 Synthesis of 2,3,5,6-tetrafluorophenyl
39-(5-amino-7-(dipropylcarbamoyl)-6H-thieno[3,2-
b]azepin-2-yl)-34-methyl-4,7,10,13,16,19,22,25,28,
31-decaoxa-34-azanonatriacontanoate, TAZ-L-3

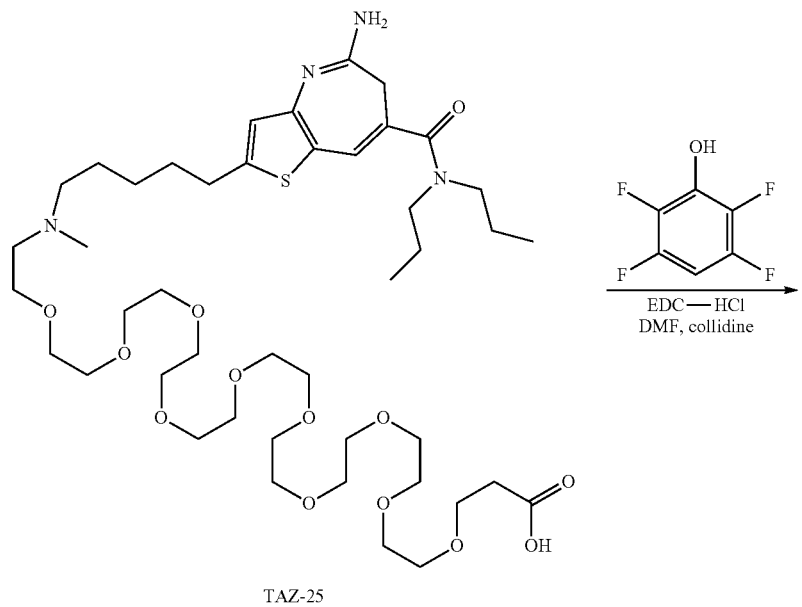

TAZ-25

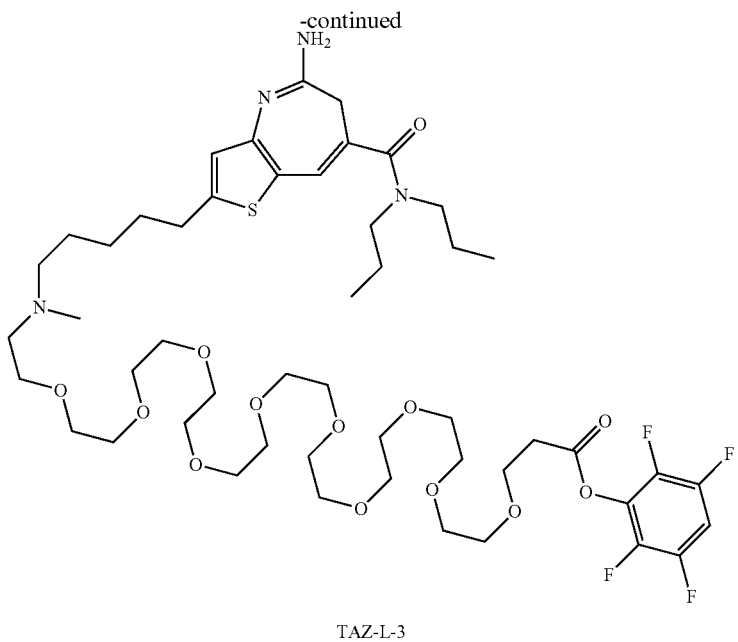

TAZ-L-3

TAZ-25 (0.18 g, 0.20 mmol, 1 eq.) and TFP (0.066 g, 0.40 mmol, 2 eq.) were dissolved in 1 ml DMF. Collidine (0.13 ml, 1.0 mmol, 5 eq.) was added, followed by 1-ethyl-3-(3-dimethylaminopropyl)carbodiimide hydrochloride, EDC-HCl (0.115 g, 0.60 mmol, 3 eq.). The reaction was stirred at room temperature until complete, then purified by HPLC to give TAZ-L-3 (0.103 g, 0.098 mmol, 49%). LC/MS [M+H] 1051.53 (calculated); LC/MS [M+H] 1051.74 (observed).

Example L-4 Synthesis of 2,3,5,6-tetrafluorophenyl 1-(4-((5-amino-N-propyl-6H-thieno[3,2-b]azepine-7-carboxamido)methyl)phenyl)-2-methyl-5,8,11,14,17,20,23,26,29,32-decaoxa-2-azapentatriacontan-35-oate, TAZ-L-4

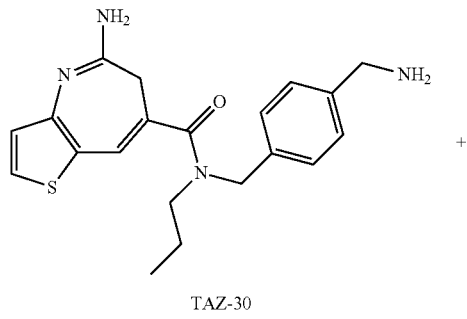

TAZ-30

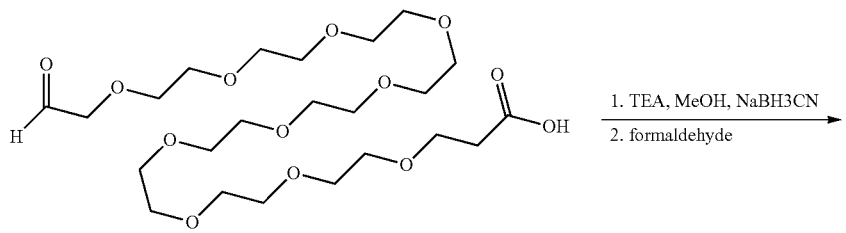

1. TEA, MeOH, NaBH3CN
2. formaldehyde

-continued

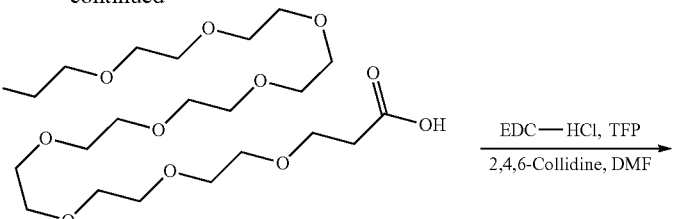
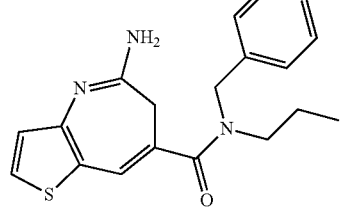

L-4a

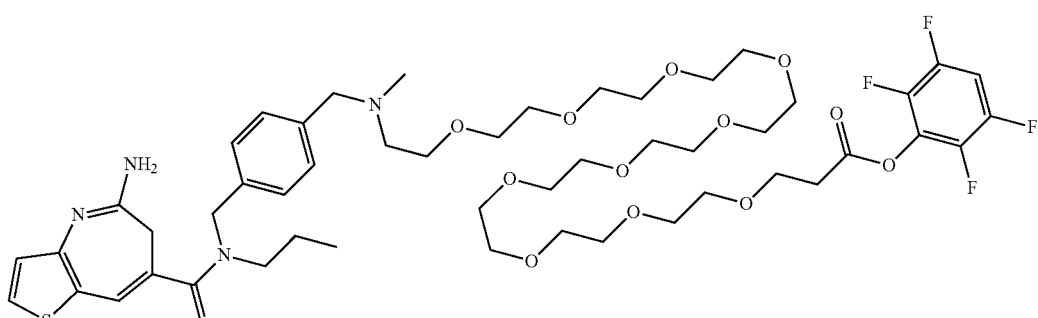

TAZ-L-4

Preparation of 1-(4-((5-amino-N-propyl-6H-thieno [3,2-b]azepine-7-carboxamido)methyl)phenyl)-2-methyl-5,8,11,14,17,20,23,26,29,32-decaoxa-2-aza-pentatriacontan-35-oic Acid, L-4a 5-Amino-N-(4-(aminomethyl)benzyl)-N-propyl-6H-thieno[3,2-b]azepine-7-carboxamide, TAZ-30 (0.063 g, 0.17 mmol, 1 eq.) and 1-oxo-3,6,9,12,15,18,21,24,27,30-decaoxatritriacontan-33-oic acid (0.09 g, 0.17 mmol, 1 eq.) were dissolved in methanol. Triethylamine (0.14 ml, 1.0 mmol, 6 eq.) was added, followed by sodium cyanoborohydride (0.032 g, 0.51 mmol, 3 eq.). The reaction was monitored by LCMS. After 2 hours, formaldehyde (14 µl, 0.17 mmol, 37% w/w solution in water, 1 eq.) was added and the reaction stirred for an additional 30 minutes. Upon consumption of amine, the reaction was concentrated and purified by HPLC to give L-4a (0.045 g, 0.050 mmol, 29%). LC/MS [M+H] 895.47 (calculated); LC/MS [M+H] 895.80 (observed).

Preparation of TAZ-L-4

Intermediate L-4a (0.045 g, 0.05 mmol, 1 eq.) and TFP (0.017 g, 0.10 mmol, 2 eq.) were dissolved in 1 ml DMF. Collidine (0.033 ml, 0.25 mmol, 5 eq.) was added, followed by 1-ethyl-3-(3-dimethylaminopropyl)carbodiimide hydrochloride, EDC-HCl (0.029 g, 0.15 mmol, 3 eq.). The reaction was stirred at room temperature until complete, then purified by HPLC to give TAZ-L-4 (0.031 g, 0.030 mmol, 59%). LC/MS [M+H] 1043.47 (calculated); LC/MS [M+H] 1043.79 (observed).

Example L-10 Synthesis of (2,3,5,6-tetrafluorophenyl) 3-[2-[2-[2-[2-[2-[2-[2-[2-[2-[2-[[4-[[[5-amino-2-[5-(dimethylamino)pentyl]-6H-thieno[3,2-b] azepine-7-carbonyl]-propyl-amino]methyl]phenyl] methyl-methylamino]ethoxy]ethoxy]ethoxy]ethoxy] ethoxy]ethoxy]ethoxy]ethoxy]ethoxy] propanoate, TAZ-L-10

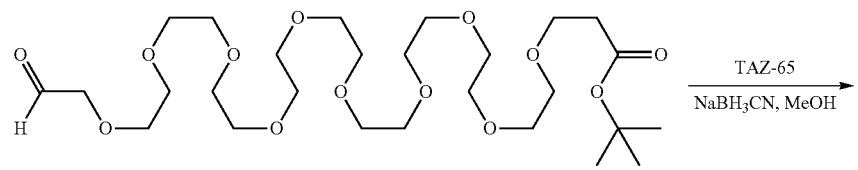

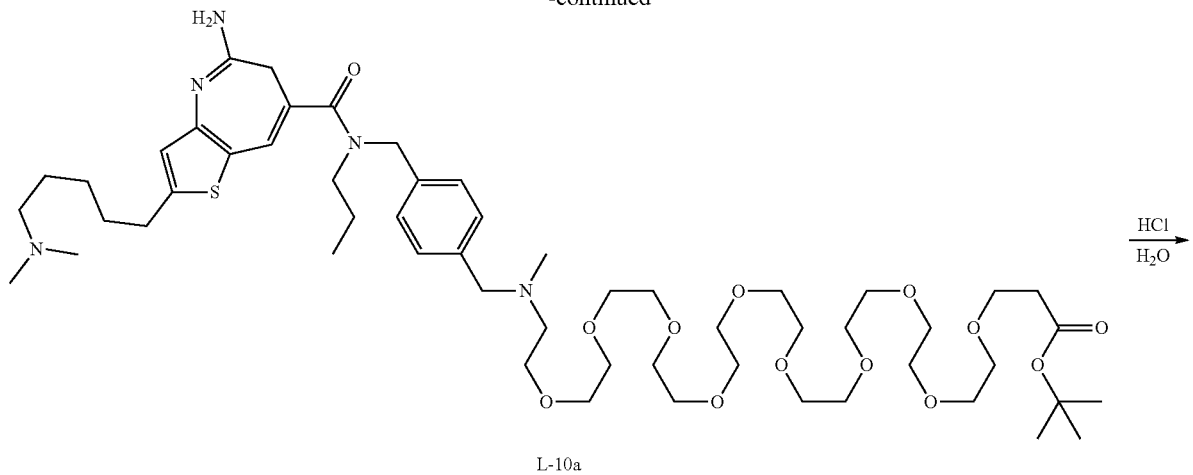

L-10a

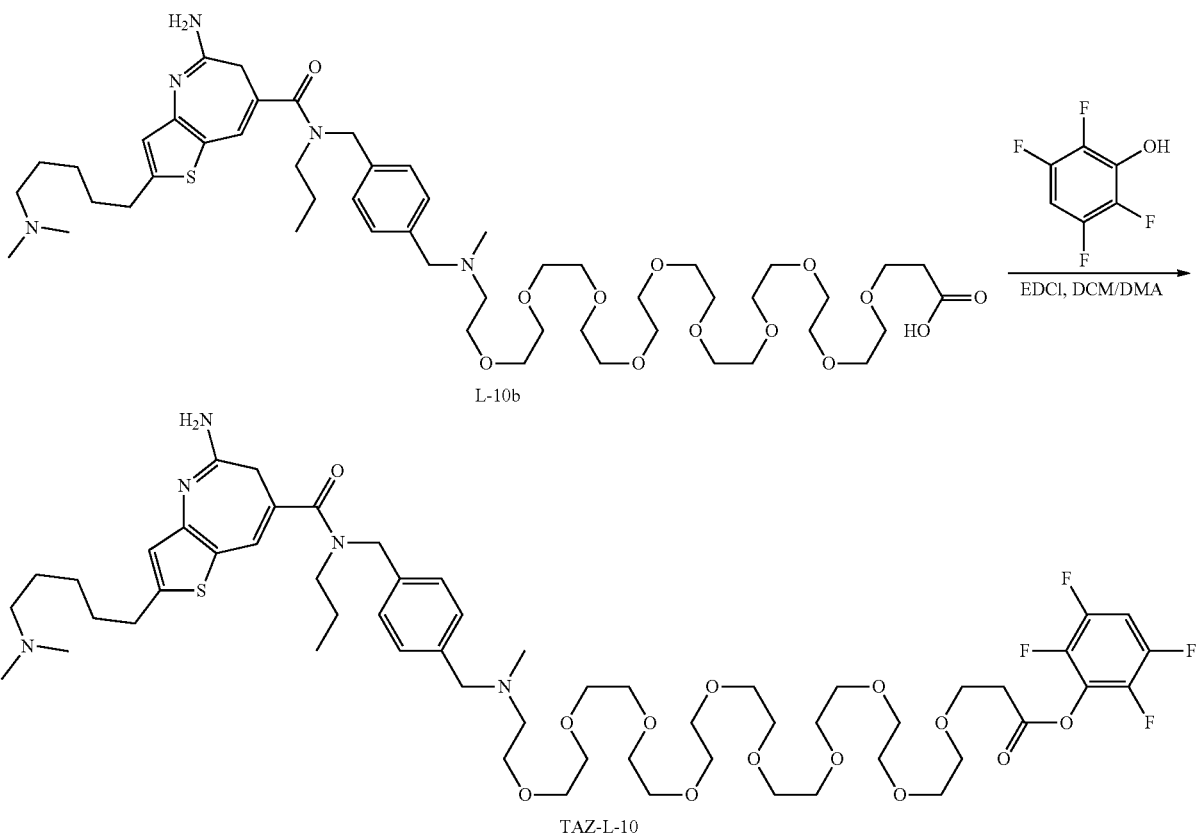

Preparation of tert-butyl 3-[2-[2-[2-[2-[2-[2-[2-[2-[2-[2-[[4-[[[5-amino-2-[5-(dimethylamino)pentyl]-6H-thieno[3,2-b]azepine-7-carbonyl]-propyl-amino]methyl]phenyl]methyl-methylamino]ethoxy]ethoxy]ethoxy]ethoxy]ethoxy]ethoxy]ethoxy]ethoxy]ethoxy]propanoate, L-10a To a solution of 5-amino-2-[5-(dimethylamino)pentyl]-N-[[4-(methylaminomethyl)phenyl]methyl]-N-propyl-6H-thieno[3,2-b]azepine-7-carboxamide, TAZ-65 (300 mg, 527 umol, 1.0 eq, 2 HCl) in MeOH (10 mL) was added tert-butyl 3-[2-[2-[2-[2-[2-[2-[2-[2-(2-oxoethoxy) ethoxy]ethoxy]ethoxy]ethoxy]ethoxy]ethoxy]ethoxy]ethoxy]propanoate (617 mg, 1.06 mmol, 2.0 eq), AcOH (3.1 mg, 52.7 umol, 0.10 eq) and NaBH₃CN (66.3 mg, 1.06 mmol, 2.0 eq). The mixture was stirred for 12 hrs at 25° C. and then it was concentrated and purified by prep-HPLC (column: Nano-micro Kromasil C18 100*40 mm 10 um; mobile phase: [water (0.1% TFA)-ACN]; B %: 5%-45%, 8 min) to give L-10a (350 mg, 328 umol, 62.33% yield) as colorless oil.

Preparation of 3-[2-[2-[2-[2-[2-[2-[2-[2-[2-[2-[[4-[[[5-amino-2-[5-(dimethylamino)pentyl]-6H-thieno[3,2-b]azepine-7-carbonyl]-propyl-amino]methyl]phenyl]methyl-methylamino]ethoxy]ethoxy]ethoxy]ethoxy]ethoxy]ethoxy]ethoxy]ethoxy]ethoxy]propanoic Acid, L-10b To a mixture of L-10a (100 mg, 84.8 umol, 1.0 eq, TFA) in H$_2$O (2 mL) was added HCl (12 M, 141 uL, 20.0 eq) at 25° C., and then stirred at 80° C. for 1 hr. The mixture was concentrated to afford L-10b (80.0 mg, 76.6 umol, 90.2% yield, HCl) as light yellow oil.

Preparation of TAZ-L-10

To a mixture of L-10b (50.0 mg, 49.6 umol, 1.0 eq) in DCM (2 mL) and DMA (0.1 mL) was added 1-ethyl-3-(3-dimethylaminopropyl)carbodiimide hydrochloride, EDCI (95.0 mg, 495 umol, 10.0 eq) at 15° C. and then stirred for 0.5 hr. The mixture was concentrated in vacuum to give a residue. The residue was purified by prep-HPLC (column: Phenomenex Synergi C18 150*25*10 um; mobile phase: [water (0.1% TFA)-ACN]; B %: 25%-50%, 8 min) to obtain TAZ-L-10 (21.0 mg, 16.5 umol, 34.5% yield, TFA) as light yellow oil. $^1$H NMR (MeOD, 400 MHz) δ 7.57-7.50 (m, 2H), 7.48-7.43 (m, 3H), 7.12 (s, 1H), 6.92 (s, 1H), 4.80 (s, 2H), 4.50-4.32 (m, 2H), 3.90-3.87 (m, 4H), 3.70-3.59 (m, 38H), 3.38-3.40 (m, 6H), 3.01-2.99 (m, 2H), 2.90-2.98 (m, 2H), 2.90 (s, 9H), 1.79-1.78 (m, 4H), 1.70-1.65 (m, 2H), 1.52-1.49 (m, 2H), 0.93-0.87 (m, 3H). LC/MS [M+H] 1156.6 (calculated); LC/MS [M+H] 1156.6 (observed).

Example L-13 Synthesis of (2,3,5,6-tetrafluorophenyl) 3-[2-[2-[2-[2-[2-[2-[2-[2-[2-[5-[5-amino-7-[[4-[(dimethylamino)methyl]phenyl]methyl-propyl-carbamoyl]-6H-thieno[3,2-b]azepin-2-yl]pentyl-methylamino]ethoxy]ethoxy]ethoxy]ethoxy]ethoxy]ethoxy]ethoxy]ethoxy]ethoxy]propanoate, TAZ-L-13

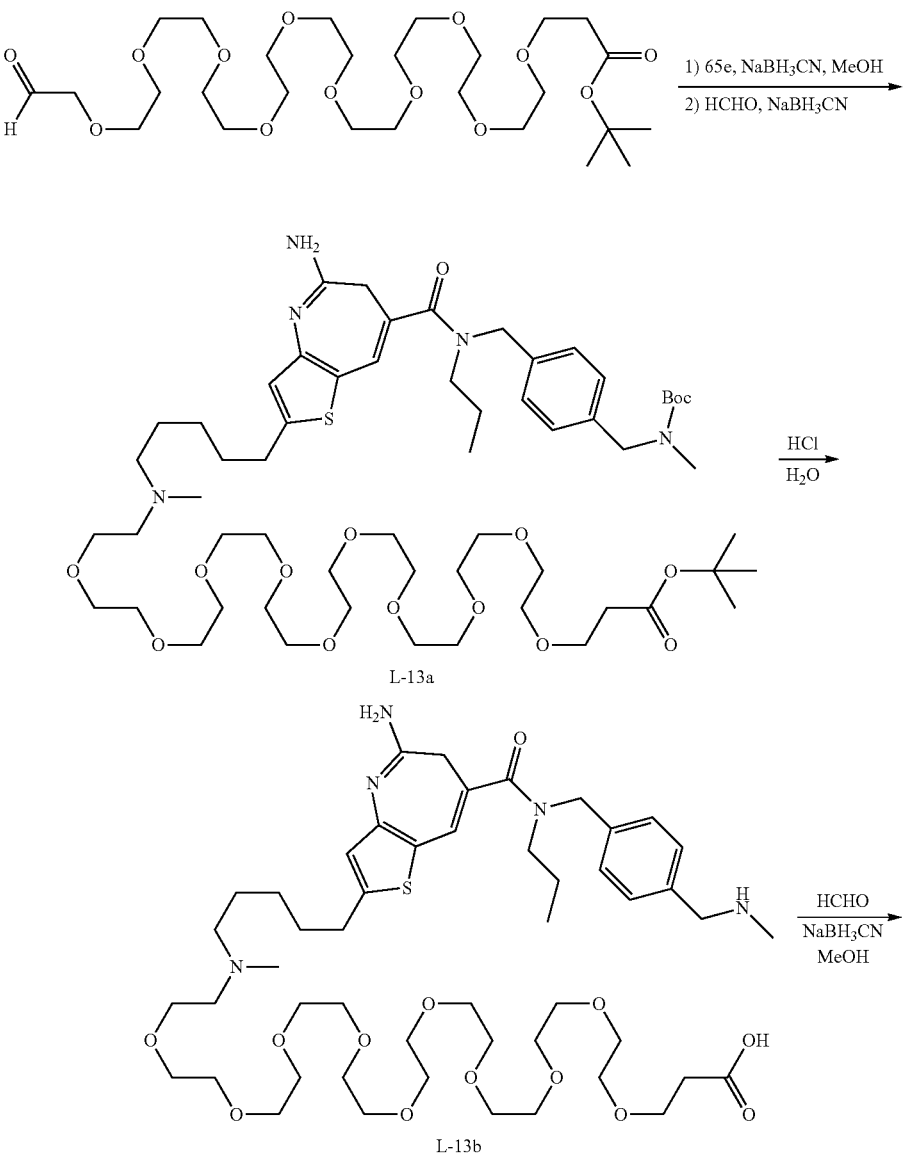

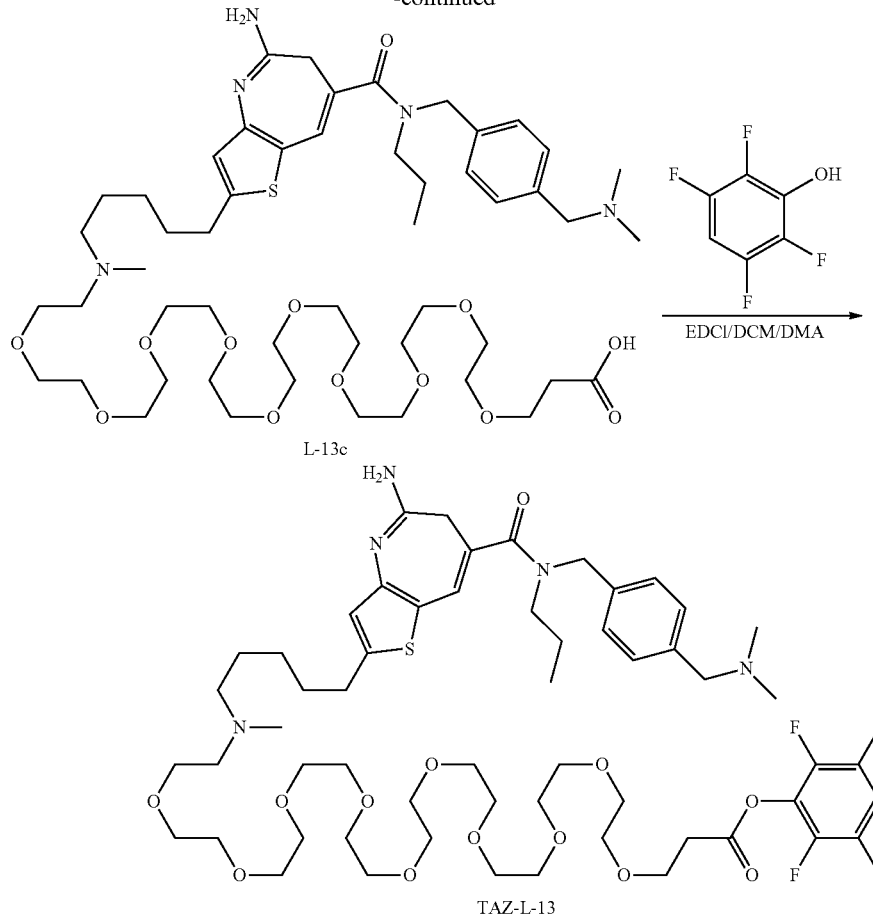

Preparation of tert-butyl 3-[2-[2-[2-[2-[2-[2-[2-[2-[2-[2-[5-[5-amino-7-[[4-[[tert-butoxycarbonyl(methyl)amino]methyl]phenyl]methyl-propyl-carbamoyl]-6H-thieno[3,2-b]azepin-2-yl]pentyl-methylamino]ethoxy]ethoxy]ethoxy]ethoxy]ethoxy]ethoxy]ethoxy]ethoxy]ethoxy]propanoate, L-13a To a solution of tert-butyl N-[[4-[[[5-amino-2-(5-aminopentyl)-6H-thieno[3,2-b]azepine-7-carbonyl]-propyl-amino]methyl]phenyl]methyl]-N-methyl-carbamate, 65e (130 mg, 229 umol, 1.0 eq) in MeOH (50 mL) was added AcOH (13.7 mg, 228.96 umol, 13.0 uL, 1 eq) tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]propanoate (200 mg, 343 umol, 1.50 eq) and NaBH$_3$CN (43.1 mg, 687 umol, 3.0 eq), and then stirred for 12 hrs at 25° C. Formaldehyde, HCHO (56 mg, 674 umol, 37% purity, 3.0 eq) and NaBH$_3$CN (22.0 mg, 343 umol, 1.5 eq) were added to the mixture and then stirred for another 2 hrs at 25° C. The reaction mixture was quenched by addition H$_2$O 2 mL and it was concentrated in vacuum to give a residue. The residue was purified by prep-HPLC (column: Phenomenex luna C18 250*50 mm*10 um; mobile phase: [water (0.1% TFA)-ACN]; B %: 30%-60%, 10 min) to give L-13a (100 mg, 86.92 umol, 38% yield) as colorless oil.

Preparation of 3-[2-[2-[2-[2-[2-[2-[2-[2-[2-[2-[5-[5-amino-7-[[4-(methylaminomethyl)phenyl]methyl-propyl-carbamoyl]-6H-thieno[3,2-b]azepin-2-yl]pentyl-methylamino]ethoxy]ethoxy]ethoxy]ethoxy]ethoxy]ethoxy]ethoxy]ethoxy]ethoxy]ethoxy]propanoic Acid, L-13b To a solution of L-13a (100 mg, 86.9 umol, 1.0 eq) in H$_2$O (0.5 mL) was added HCl (12 M, 145 uL, 20.0 eq) and then stirred for 0.5 h at 80° C. The reaction mixture was concentrated under pressure to give L-13b (92 mg, crude) as colorless oil.

Preparation of 3-[2-[2-[2-[2-[2-[2-[2-[2-[2-[2-[5-[5-amino-7-[[4-[(dimethylamino)methyl]phenyl]methyl-propyl-carbamoyl]-6H-thieno[3,2-b]azepin-2-yl]pentyl-methylamino]ethoxy]ethoxy]ethoxy]ethoxy]ethoxy]ethoxy]ethoxy]ethoxy]ethoxy]ethoxy]propanoic Acid, L-13c To a mixture of HCHO, formaldehyde (30.4 mg, 375 umol, 37% purity, 5.0 eq) and L-13b (80 mg, 74.9 umol, 1.0 eq, 2HCl) in MeOH (1 mL) was added NaBH$_3$CN (9.4 mg, 150 umol, 2.0 eq) at 15° C. and then stirred at 15° C. for 1 hr. The mixture was filtered and the filtrate was purified by prep-HPLC (column: Phenomenex luna C18 80*40 mm*3 um; mobile phase: [water (0.04% HCl)-ACN]; B %: 5%-35%, 7 min) to obtain L-13c (55 mg, 50.87 umol, 67.86% yield, 2HCl) as colorless oil. $^1$H NMR (MeOD, 400

MHz) δ 7.56 (d, J=8.0 Hz, 2H), 7.48 (d, J=7.2 Hz, 2H), 7.13 (s, 1H), 6.95 (s, 1H), 4.83 (s, 2H), 4.35 (s, 2H), 3.76-3.70 (m, 2H), 3.70-3.62 (m, 40H), 3.50-3.47 (m, 6H), 3.35-3.28 (m, 2H), 2.94-2.91 (m, 5H), 2.88 (s, 6H), 2.56 (t, J=6.4 Hz, 2H), 1.82-1.81 (m, 3H), 1.69-1.65 (m, 2H), 1.53-1.49 (m, 2H), 0.91 (t, J=7.2 Hz, 3H)

Preparation of TAZ-L-13

To a mixture of L-13c (50 mg, 49.6 umol, 1.0 eq) in DCM (2 mL) and DMA (0.1 mL) was added 1-ethyl-3-(3-dimethylaminopropyl)carbodiimide hydrochloride, EDCI (95.0 mg, 496 umol, 10.0 eq) at 15° C. and then stirred at 15° C. for 0.5 hr. The mixture was concentrated under reduced pressure to give a residue. The residue was purified by prep-HPLC (column: Phenomenex Synergi C18 150*25*10 um; mobile phase: [water (0.1% TFA)-ACN]; B %: 20%- 40%, 10 min) to afford TAZ-L-13 (23 mg, 19.89 umol, 40.11% yield) as light yellow oil. $^1$H NMR (MeOD, 400 MHz) δ 7.53-7.51 (m, 2H), 7.46-7.40 (m, 3H), 7.11 (s, 1H), 6.92 (s, 1H), 4.80 (s, 2H), 4.33 (s, 2H), 3.89 (t, J=6.4 Hz, 2H), 3.89-3.85 (m, 2H), 3.70-3.63 (m, 38H), 3.54-3.42 (m, 4H), 3.39 (s, 2H), 2.99 (t, J=6.0 Hz, 2H), 2.94-2.91 (m, 5H), 2.87 (s, 6H), 1.80 (d, J=6.4 Hz, 4H), 1.69-1.64 (m, 2H), 1.52-1.50 (m, 2H), 0.90 (t, J=6.8 Hz, 3H). LC/MS [M+H] 1156.6 (calculated); LC/MS [M+H] 1156.6 (observed).

Example L-16 Synthesis of (2,3,5,6-tetrafluorophenyl) 3-[2-[2-[2-[2-[2-[2-[2-[2-[2-[4-[[(5-amino-6H-thieno [3,2-b]azepine-7-carbonyl)-propyl-amino] methyl]-2-(trifluoromethyl)phenyl]methyl-methylamino]ethoxy]ethoxy]ethoxy]ethoxy]ethoxy] ethoxy]ethoxy]ethoxy]ethoxy]propanoate, TAZ-L-16

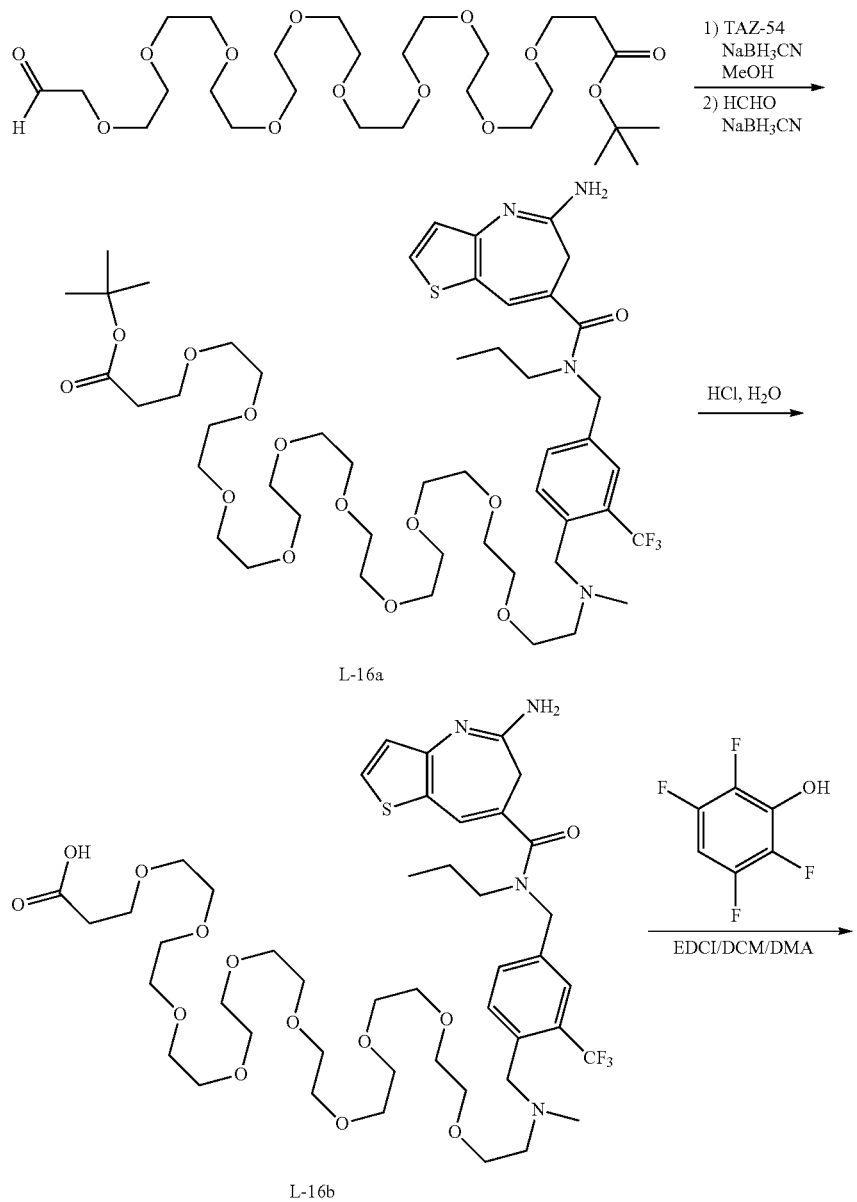

-continued

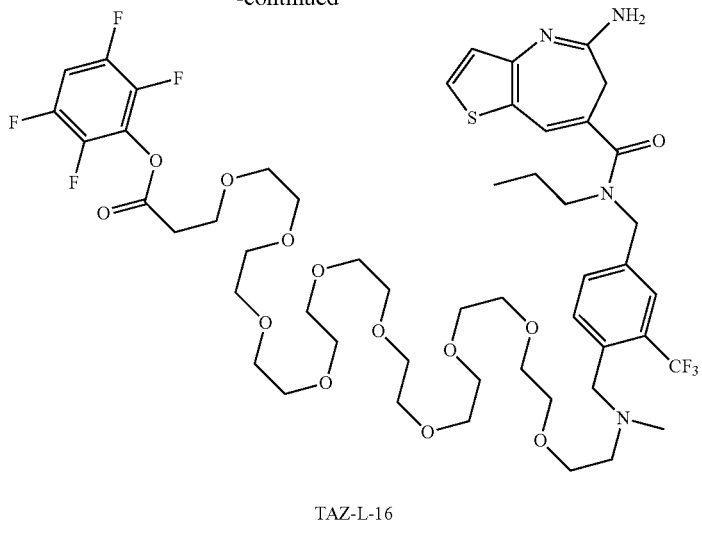

TAZ-L-16

Preparation of tert-butyl 3-[2-[2-[2-[2-[2-[2-[2-[2-[2-[2-[[4-[[(5-amino-6H-thieno[3,2-b]azepine-7-carbonyl)-propyl-amino]methyl]-2-(trifluoromethyl)phenyl]methyl-methylamino]ethoxy]ethoxy]ethoxy]ethoxy]ethoxy]ethoxy]ethoxy]ethoxy]ethoxy]propanoate, L-16a To a mixture of 5-amino-N-[[4-(aminomethyl)-3-(trifluoromethyl)phenyl]methyl]-N-propyl-6H-thieno[3,2-b]azepine-7-carboxamide, TAZ-54 (80.0 mg, 145 umol, 1.0 eq, TFA) and tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]propanoate (110 mg, 189 umol, 1.3 eq) in MeOH (20 mL) was added NaBH$_3$CN (22.8 mg, 363 umol, 2.5 eq) at 20° C. and then stirred 20 hrs at this temperature. HCHO (70.7 mg, 872 umol, 64.9 uL, 37% purity, 6.0 eq) and NaBH$_3$CN (22.8 mg, 363 umol, 2.5 eq) was added to the mixture, and it was stirred at 20° C. for another 1 hour. The reaction mixture was concentrated in vacuum and purified by prep-HPLC (column: Nano-micro Kromasil C18 100*40 mm 10 um; mobile phase: [water (0.1% TFA)-ACN]; B %: 3%-40%, 8 min) to afford L-16a (88.0 mg, 86.3 umol, 59.4% yield) as colorless oil. $^1$H NMR (400 MHz, MeOD) δ7.90-7.83 (m, 2H), 7.83-7.78 (m, 1H), 7.76 (d, J=5.2 Hz, 1H), 7.22 (d, J=6.4 Hz, 1H), 7.16 (d, J=4.8 Hz, 1H), 4.73-4.55 (m, 2H), 3.93-3.84 (m, 2H), 3.71-3.70 (m, 4H), 3.68-3.57 (m, 38H), 3.49 (s, 2H), 3.41 (s, 2H), 2.95 (s, 3H), 2.48 (t, J=6.0 Hz, 2H), 1.75-1.67 (m, 2H), 1.47 (s, 9H), 0.93 (br t, J=7.6 Hz, 3H).

Preparation of 3-[2-[2-[2-[2-[2-[2-[2-[2-[2-[[4-[[(5-amino-6H-thieno[3,2-b]azepine-7-carbonyl)-propyl-amino]methyl]-2-(trifluoromethyl)phenyl]methyl-methylamino]ethoxy]ethoxy]ethoxy]ethoxy]ethoxy]ethoxy]ethoxy]ethoxy]ethoxy]propanoic Acid, L-16b To a solution of L-16a (78.0 mg, 76.5 umol, 1.0 eq) in H$_2$O (0.5 mL) and MeCN (0.1 mL) was added HCl (12 M, 191 uL, 30 eq) at 20° C. under N$_2$, the mixture was heated to 80° C. and then stirred for 1 hour. The reaction mixture was concentrated in vacuum to afford L-16b (70.0 mg, 72.6 umol, 94.9% yield) as colorless oil.

Preparation of TAZ-L-16

To a mixture of L-16b (60 mg, 62.3 umol, 1 eq) and 2,3,5,6-tetrafluorophenol (51.7 mg, 311 umol, 5.0 eq) in DCM (1 mL) and DMA (0.1 mL) was added EDCI (59.7 mg, 311 umol, 5.0 eq) at 20° C. under N$_2$, and then stirred at 20° C. for 1 hour. The reaction mixture was concentrated in vacuum. The residue was purified by prep-HPLC (column: Phenomenex Synergi C18 150*25*10 um; mobile phase: [water (0.1% TFA)-ACN]; B %: 25%-50%, 7 min) to afford TAZ-L-16 (15 mg, 13.5 umol, 21.67% yield) as colorless oil. $^1$H NMR (400 MHz, MeOD) δ7.88-7.83 (m, 2H), 7.82-7.78 (m, 1H), 7.76 (d, J=5.6 Hz, 1H), 7.48-7.41 (m, 1H), 7.22 (s, 1H), 7.16 (d, J=5.6 Hz, 1H), 4.96 (s, 2H), 3.92-3.87 (m, 4H), 3.71-3.58 (m, 38H), 3.52-3.48 (m, 2H), 3.41 (s, 2H), 3.34 (s, 2H), 2.99 (t, J=6.0 Hz, 2H), 2.95 (s, 3H), 1.75-1.66 (m, 2H), 0.92 (t, J=7.2 Hz, 3H). LC/MS [M+H] 1111.5 (calculated); LC/MS [M+H] 1111.5 (observed).

Example L-22 Synthesis of (2,3,5,6-tetrafluorophenyl) 3-[2-[2-[2-[2-[2-[2-[2-[2-[2-[[4-[[(5-amino-6H-thieno [3,2-b]azepine-7-carbonyl)-propyl-amino] methyl]-3-(trifluoromethyl)phenyl]methyl-methylamino]ethoxy]ethoxy]ethoxy]ethoxy]ethoxy]ethoxy]ethoxy]ethoxy]ethoxy]ethoxy]propanoate, TAZ-L-22

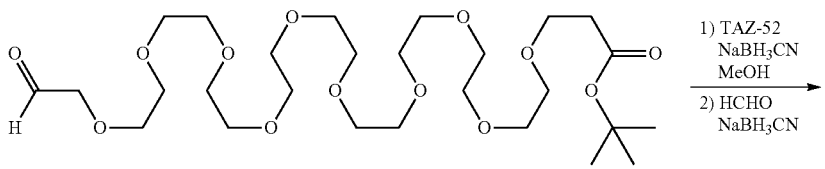

-continued
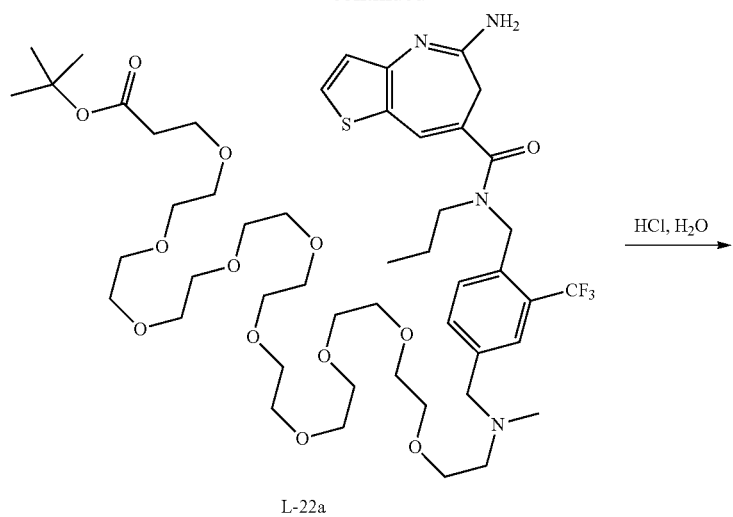
L-22a
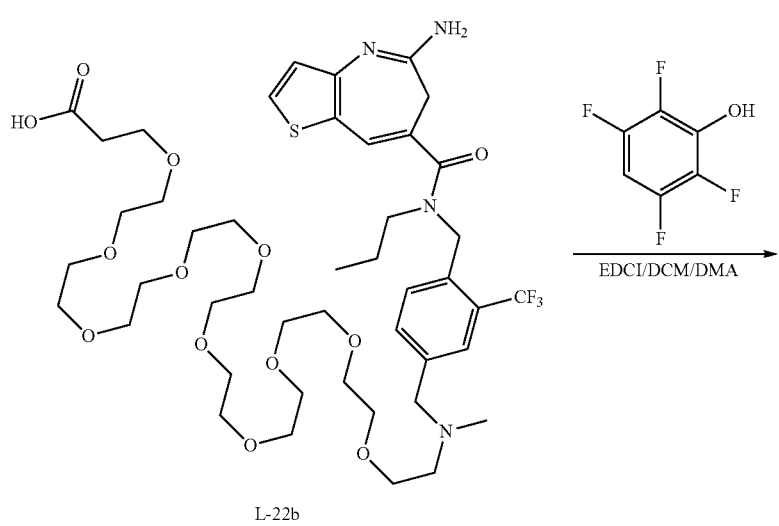
L-22b
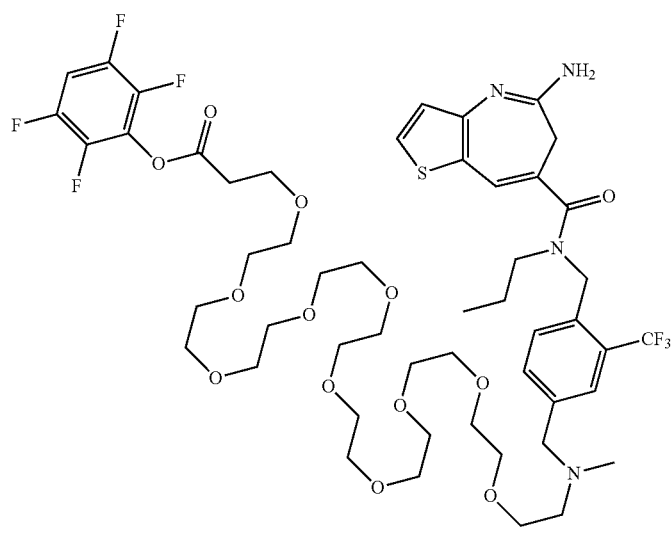
TAZ-L-22

Preparation of tert-butyl 3-[2-[2-[2-[2-[2-[2-[2-[2-[2-[2-[[4-[[(5-amino-6H-thieno[3,2-b]azepine-7-carbonyl)-propyl-amino]methyl]-3-(trifluoromethyl)phenyl]methyl-methylamino]ethoxy]ethoxy]ethoxy]ethoxy]ethoxy]ethoxy]ethoxy]ethoxy]ethoxy]propanoate, L-22a To a mixture of tert-butyl 3-[2-[2-[2-[2-[2-[2-[2-[2-[2-(2-oxoethoxy)ethoxy]ethoxy]ethoxy] ethoxy]ethoxy]ethoxy]ethoxy]ethoxy]propanoate (51.9 mg, 89 umol, 1.4 eq) in MeOH (3 mL) was added 5-amino-N-[[4-(aminomethyl)-2-(trifluoromethyl)phenyl]methyl]-N-propyl-6H-thieno[3,2-b]azepine-7-carboxamide, TAZ-52 (30 mg, 63 umol, 1.0 eq, HCl) at 25° C. The mixture was stirred for 10 min, then NaBH₃CN (7.97 mg, 126.86 umol, 2 eq) was added and it was stirred at 25° C. for 23 hours, then formaldehyde (15.44 mg, 190.29 umol, 14.17 uL, 3 eq) and NaBH₃CN (7.97 mg, 126.86 umol, 2 eq) was added and the reaction was stirred for another 1 hour. Followed, the reaction mixture was concentrated and purified by prep-HPLC (column: Phenomenex Luna C18 150*30 mm*5 um; mobile phase: [water (0.1% TFA)-ACN]; B %: 25%-55%, 10 min) to give L-22a (60 mg, crude) as colorless oil.

Preparation of 3-[2-[2-[2-[2-[2-[2-[2-[2-[2-[2-[[4-[[(5-amino-6H-thieno[3,2-b]azepine-7-carbonyl)-propyl-amino]methyl]-3-(trifluoromethyl)phenyl]methyl-methylamino]ethoxy]ethoxy]ethoxy]ethoxy]ethoxy]ethoxy]ethoxy]ethoxy]ethoxy]propanoic Acid, L-22b To a mixture of L-22a (60 mg, 58.87 umol, 1 eq) in H₂O (0.5 mL) was added HCl (12 M, 150 uL, 30 eq) in one portion at 15° C. and then stirred at 80° C. for 2 hours. The mixture was concentrated in vacuum to obtain L-22b (45 mg, 45.02 umol, 76.47% yield, HCl) as light yellow oil.

Preparation of TAZ-L-22

To a mixture of L-22b (40 mg, 40 umol, 1.0 eq, HCl) in DCM (0.2 mL) and DMA (0.02 mL) was added 2,3,5,6-tetrafluorophenol (53.2 mg, 320 umol, 8.0 eq) and EDCI (76.7 mg, 400 umol, 10 eq) at 15° C., and then stirred for 30 min. The reaction was concentrated under reduced pressure at 30° C. and purified by prep-HPLC (column: Phenomenex Synergi C18 150*25*10 um; mobile phase: [water (0.1% TFA)-ACN]; B %: 20%-50%, 8 min) to afford TAZ-L-22 (24.7 mg, 22.23 umol, 55.55% yield) as light yellow oil. $^1$H NMR (MeOD, 400 MHz) δ7.98 (s, 1H), 7.86-7.84 (m, 1H), 7.76-7.72 (m, 1H), 7.65 (d, J=8.0 Hz, 1H), 7.48-7.39 (m, 1H), 7.14 (d, J=5.2 Hz, 1H), 4.96 (s, 2H), 4.70-4.41 (m, 2H), 3.92-3.82 (m, 4H), 3.70-3.54 (m, 38H), 3.44-3.40 (m, 4H), 3.34 (s, 2H), 2.97 (t, J=6.0 Hz, 2H), 2.91 (s, 3H), 1.75-1.59 (m, 2H), 0.91 (t, J=6.8 Hz, 3H). LC/MS [M+H] 1111.5 (calculated); LC/MS [M+H] 1111.4 (observed).

Example L-32 Synthesis of 2,3,5,6-tetrafluorophenyl 40-(5-amino-7-((3-(3,3-dimethylbutanamido)propyl)(propyl)carbamoyl)-6H-thieno[3,2-b]azepin-2-yl)-34-oxo-4,7,10,13,16,19,22,25,28,31-decaoxa-35-azatetracontanoate, TAZ-L-32

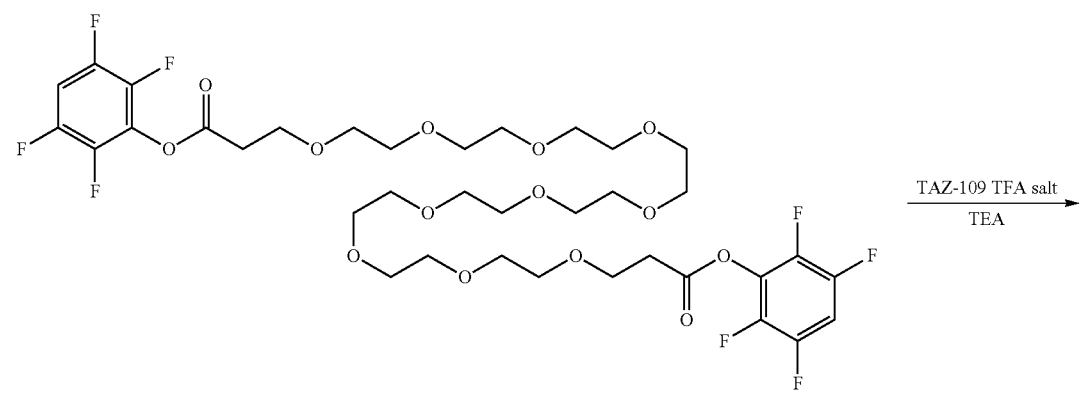

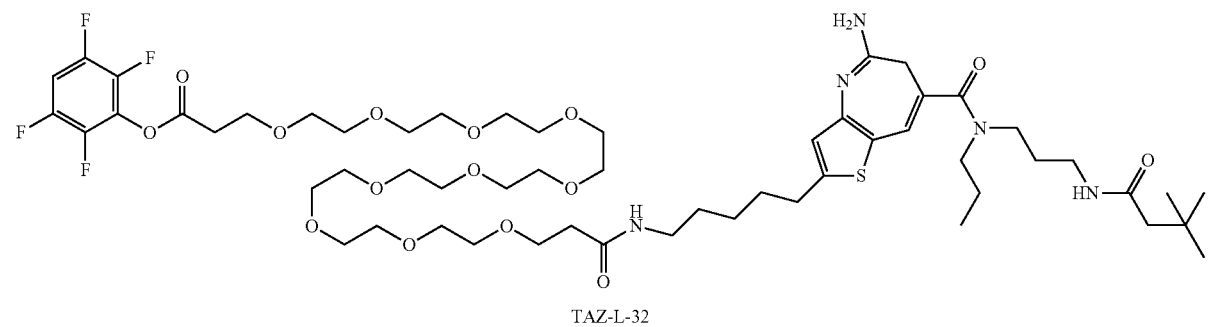

TAZ-L-32

Bis(2,3,5,6-tetrafluorophenyl) 4,7,10,13,16,19,22,25,28,31-decaoxatetratriacontanedioate (10 mg, 0.12 mmol, 1 eq.) was dissolved in 0.5 ml acetonitrile, ACN. To this solution was added dropwise a solution of the trifluoroacetate salt of 5-amino-2-(5-aminopentyl)-N-(3-(3,3-dimethylbutanamido)propyl)-N-propyl-6H-thieno[3,2-b]azepine-7-carboxamide, TAZ-109 (7.4 mg, 0.012 mmol, 1 eq.) and triethylamine, TEA (0.01 ml, 0.073 mmol, 6 eq.) in 1 ml ACN. Upon completion, the reaction was purified by HPLC to TAZ-L-32 as a colorless glass (4 mg, 0.03 mmol, 28%). LC/MS [M+H] 1178.59 (calculated); LC/MS [M+H] 1178.83 (observed).

Example L-34 Synthesis of 2,3,5,6-tetrafluorophenyl 39-(5-amino-7-((3-(3,3-dimethylbutanamido)propyl)(propyl)carbamoyl)-6H-thieno[3,2-b]azepin-2-yl)-34-methyl-4,7,10,13,16,19,22,25,28,31-decaoxa-34-azanonatriacontanoate, TAZ-L-34

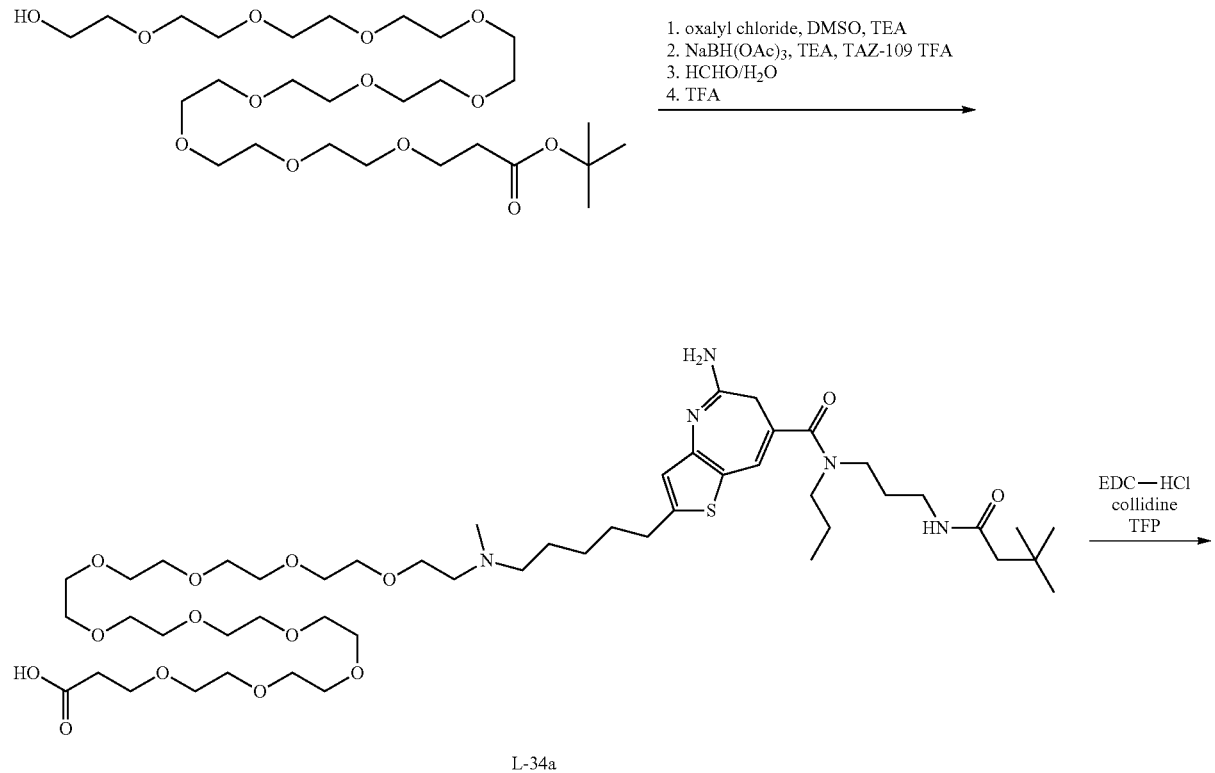

L-34a

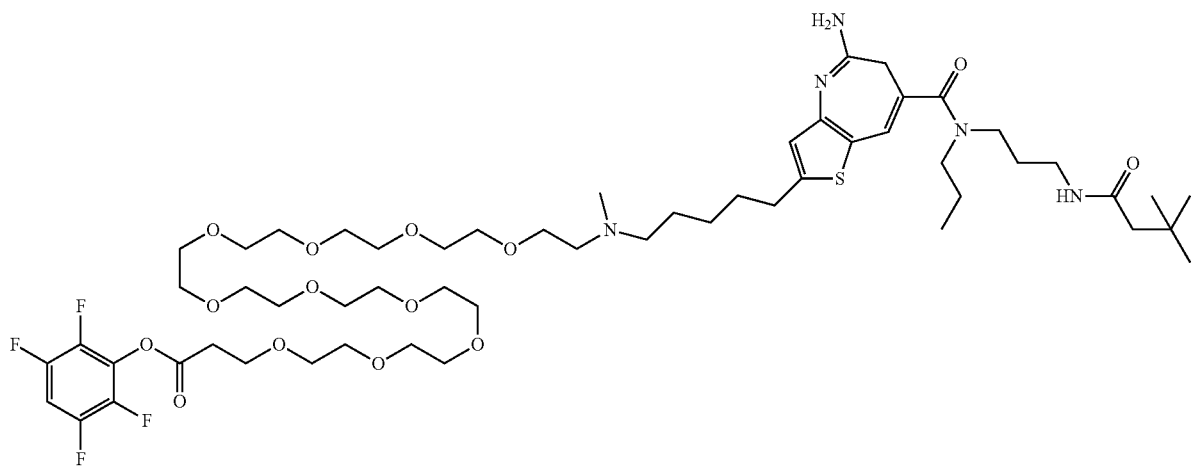

TAZ-L-34

Preparation of 39-(5-amino-7-((3-(3,3-dimethylbu-tanamido)propyl)(propyl)carbamoyl)-6H-thieno[3,2-b]azepin-2-yl)-34-methyl-4,7,10,13,16,19,22,25,28,31-decaoxa-34-azanonatriacontanoic Acid, L-34a Oxalyl chloride (0.023 ml, 0.27 mmol, 3 eq.) was dissolved in 2.5 ml DCM at −78° C. dimethylsulfoxide, DMSO (0.038 ml, 0.54 mmol, 6 eq.) was added dropwise. The reaction was stirred at −78° C. for 15 minutes, then tert-butyl 1-hydroxy-3,6,9,12,15,18,21,24,27,30-decaoxatritriacontan-33-oate (0.052 g, 0.089 mmol, 1 eq.) was added dropwise as a solution in 0.5 ml DCM. The reaction was stirred 30 minutes at −78° C., and then triethylamine, TEA (0.112 ml, 0.80 mmol, 9 eq.) was added dropwise. The reaction was stirred 30 more minutes at −78° C., then removed from cooling and allowed to warm to ambient temperature over 30 minutes to form the crude aldehyde intermediate. The trifluoroacetate salt of 5-amino-2-(5-aminopentyl)-N-(3-(3,3-dimethylbutanamido)propyl)-N-propyl-6H-thieno[3,2-b]azepine-7-carboxamide, TAZ-109 (0.054 g, 0.089 mmol, 1 eq.) and sodium triacetoxyborohydride, STAB (0.186 g, 0.88 mmol, 9.8 eq.) were suspended in 2 ml DCM with an additional 0.05 ml TEA. The crude aldehyde solution was added to the stirring solution. The reaction was stirred at room temperature for 3 hours, and then formaldehyde (0.0073 g, 0.089 mmol, 1 eq., 37 wt. % in $H_2O$) added. After 15 minutes, the reaction was concentrated and purified by HPLC to give as a colorless residue, which was dissolved in minimal TFA and allowed to stand for 15 minutes. The solution was then concentrated and triturated with diethyl ether to give L-34a (0.042 g, 0.041 mmol, 46%). LC/MS [M+H] 1016.62 (calculated); LC/MS [M+H] 1016.95 (observed).

Preparation of TAZ-L-34

Intermediate L-34a (0.042 g, 0.041 mmol, 1 eq.) and 2,3,5,6-tetrafluorophenol, TFP (0.014 g, 0.082 mmol, 2 eq.) were dissolved in 3 ml ACN. Collidine (0.054 ml, 0.406 mmol, 9.83 eq.) was added, followed by 1-ethyl-3-(3-dimethylaminopropyl)carbodiimide hydrochloride, EDC-HCl (0.017 g, 0.088 mmol, 2.13 eq.). The reaction was stirred at room temperature and monitored by LCMS, then diluted with 2 ml $H_2O$ and purified by HPLC to give TAZ-L-34 (0.0198 g, 0.017 mmol, 41%). LC/MS [M+H] 1164.61 (calculated); LC/MS [M+H]1164.81 (observed).

Example L-52 Synthesis of 2,3,5,6-tetrafluorophenyl 40-(5-amino-7-(propyl(3-(2-(trifluoromethoxy)acetamido)propyl)carbamoyl)-6H-thieno[3,2-b]azepin-2-yl)-34-oxo-4,7,10,13,16,19,22,25,28,31-decaoxa-35-azatetracontanoate, TAZ-L-52

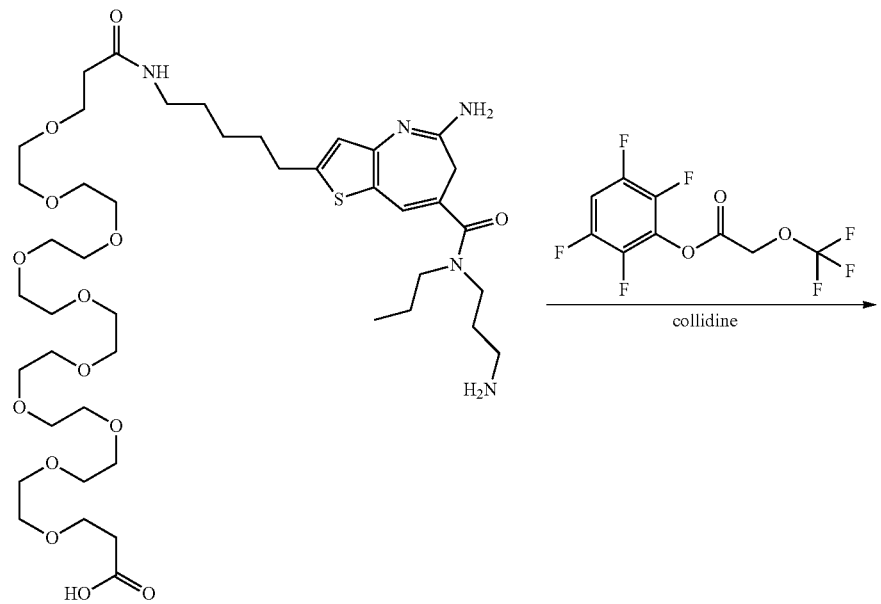

L-53b

-continued

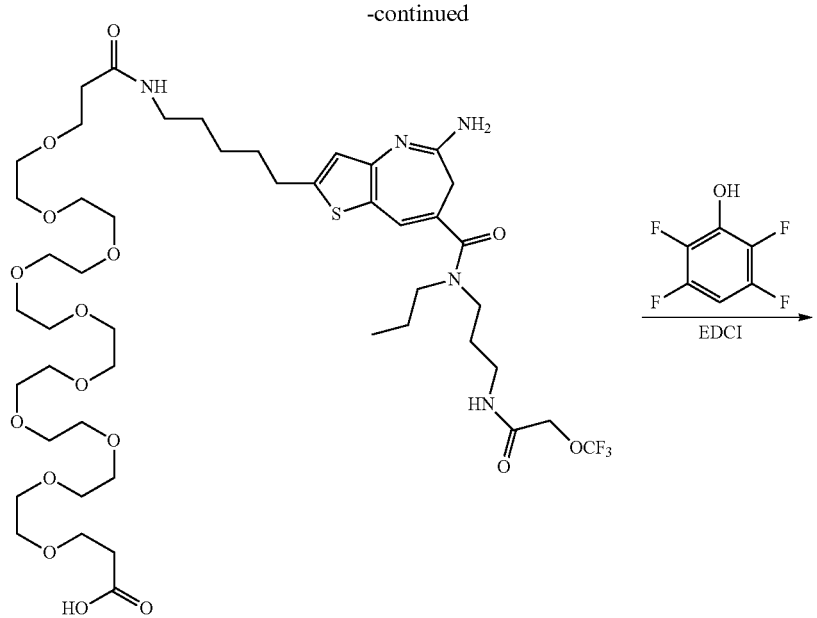

L-52a

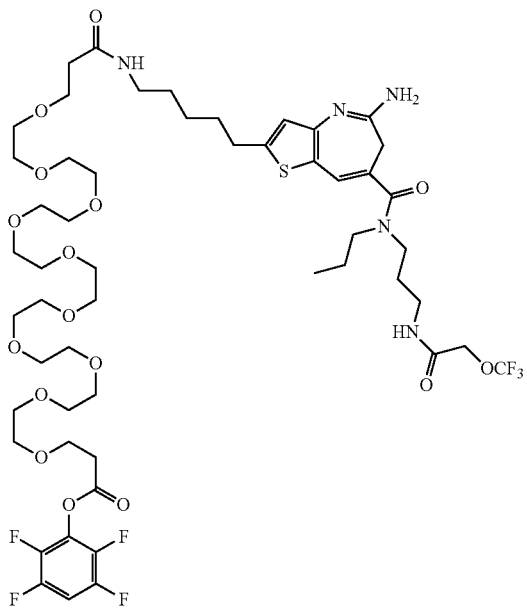

TAZ-L-52

Preparation of 40-(5-amino-7-(propyl(3-(2-(trifluoromethoxy)acetamido)propyl)carbamoyl)-6H-thieno[3,2-b]azepin-2-yl)-34-oxo-4,7,10,13,16,19,22,25,28,31-decaoxa-35-azatetracontanoic Acid, L-52a 2,3,5,6-Tetrafluorophenyl 2-(trifluoromethoxy)acetate (0.012 g, 0.041 mmol, 1 equiv.) and 3-(5-amino-2-(1-carboxy-33-oxo-3,6,9,12,15,18,21,24,27,30-decaoxa-34-azanonatriacontan-39-yl)-N-propyl-6H-thieno[3,2-b]azepine-7-carboxamido)propan-1-aminium trifluoroacetate, L-53b (0.038 g, 0.041 mmol, 1 equiv.) were combined in acetonitrile. Collidine (0.027 ml, 0.205 mmol, 5 equiv.) was added, and the reaction monitored by HPLC. Upon completion, the reaction was concentrated and purified by HPLC to give L-52a (0.07 g, 0.066 mmol, 160%) as a syrup containing a significant amount of residual collidine. The crude material was carried on to the next step without further purification. LC/MS [M+H] 1058.52 (calculated); LC/MS [M+H] 1058.84 (observed).

Preparation of TAZ-L-52

Intermediate L-52a (0.07 g, 0.066 mmol, 1 equiv.) and 2,3,5,6-tetrafluorophenol (0.011 g, 0.66 mmol, 1 equiv.) were dissolved in 1 ml acetonitrile. Collidine (0.017 ml, 0.16 mmol, 2 equiv.) was added, followed by EDC (0.013 g, 0.66 mmol, 1 equiv.). The reaction was stirred at room temperature and monitored by LCMS, then diluted with water and purified by reverse-phase HPLC to give TAZ-L-52 (0.095 g, 0.075 mmol, 49%). LC/MS [M+H] 1206.51 (calculated); LC/MS [M+H] 1206.51 (observed).

Example L-53 Synthesis of 2,3,5,6-tetrafluorophenyl 40-(5-amino-7-((3-((cyclobutoxycarbonyl)amino)propyl)(propyl)carbamoyl)-6H-thieno[3,2-b]azepin-2-yl)-34-oxo-4,7,10,13,16,19,22,25,28,31-decaoxa-35-azatetracontanoate, TAZ-L-53

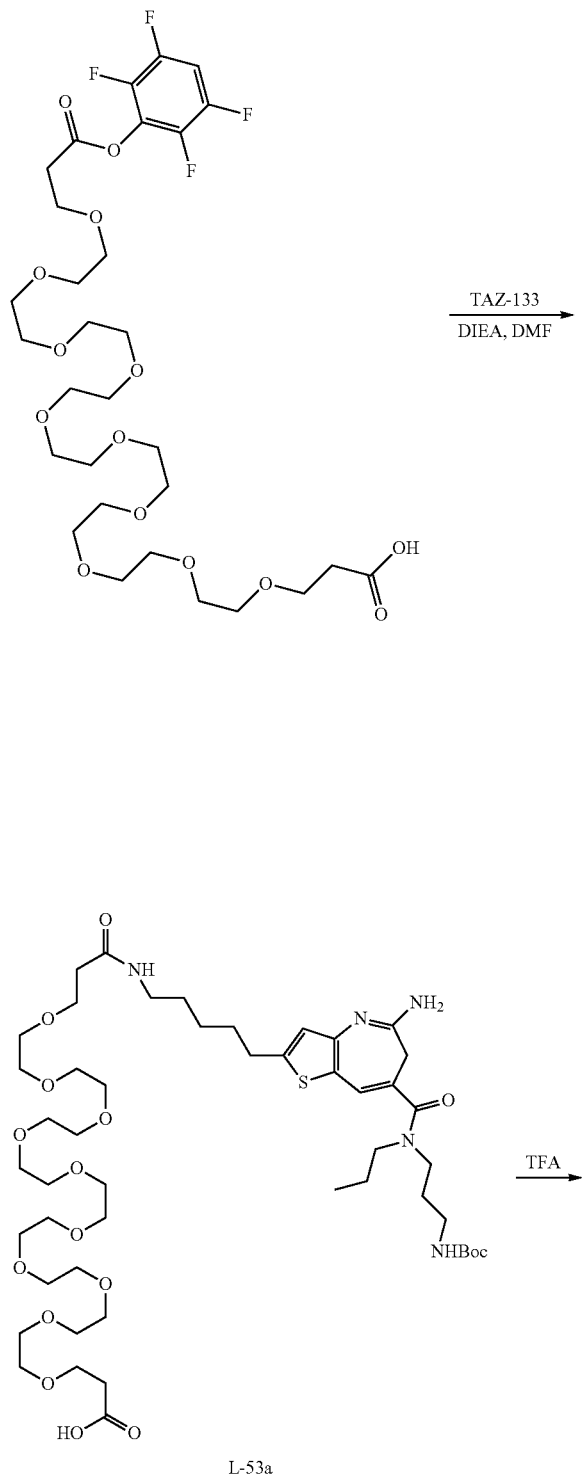

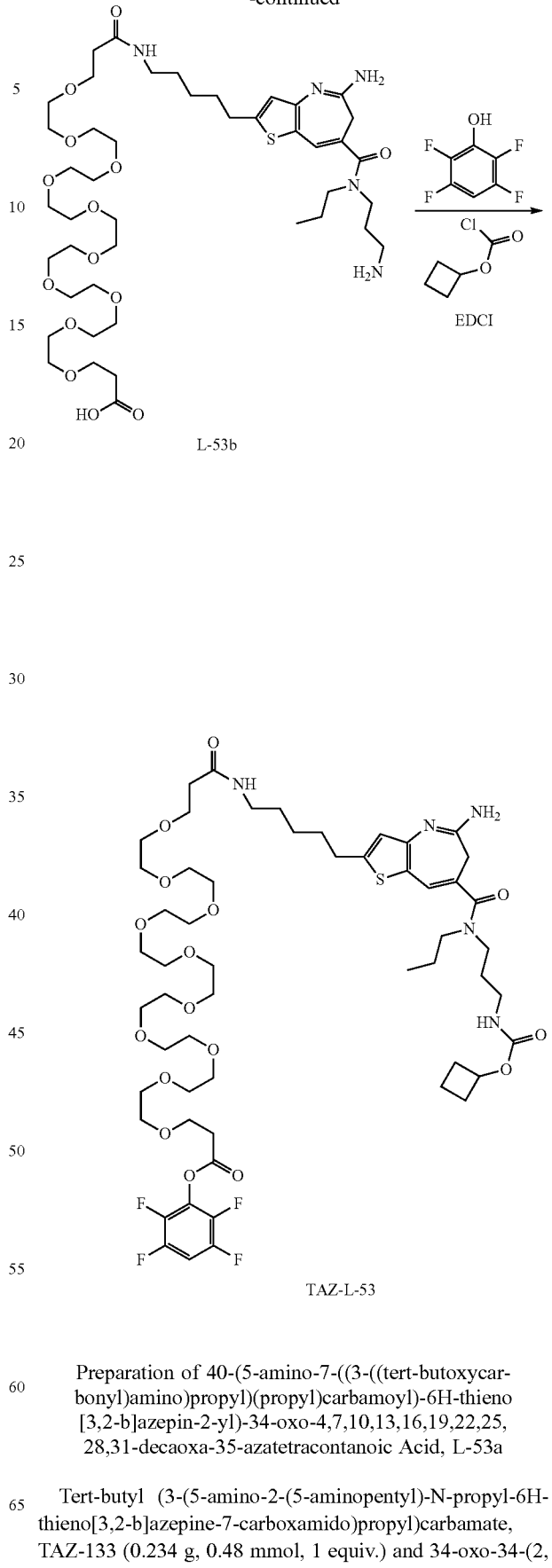

Preparation of 40-(5-amino-7-((3-((tert-butoxycarbonyl)amino)propyl)(propyl)carbamoyl)-6H-thieno[3,2-b]azepin-2-yl)-34-oxo-4,7,10,13,16,19,22,25,28,31-decaoxa-35-azatetracontanoic Acid, L-53a Tert-butyl (3-(5-amino-2-(5-aminopentyl)-N-propyl-6H-thieno[3,2-b]azepine-7-carboxamido)propyl)carbamate, TAZ-133 (0.234 g, 0.48 mmol, 1 equiv.) and 34-oxo-34-(2, 3,5,6-tetrafluorophenoxy)-4,7,10,13,16,19,22,25,28,31-decaoxatetratriacontanoic acid (0.34 g, 0.48 mmol, 1 equiv.) were dissolved in DMF. Triethylamine (0.33 g, 2.4 mmol, 5 equiv.) was added and the reaction stirred at room temperature. Upon consumption of amine starting material, the reaction was diluted with water and purified by reverse-phase HPLC to give L-53a (0.385 g, 0.40 mmol, 84%). LC/MS [M+H] 1032.58 (calculated); LC/MS [M+H] 1032.89 (observed).

Preparation of 3-(5-amino-2-(1-carboxy-33-oxo-3,6,9,12,15,18,21,24,27,30-decaoxa-34-azanonatriacontan-39-yl)-N-propyl-6H-thieno[3,2-b]azepine-7-carboxamido)propan-1-aminium trifluoroacetate, L-53b Intermediate L-53a (0.27 g, 0.26 mmol, 1 equiv.) was dissolved in minimal TFA and allowed to stand at room temperature. Upon complete consumption of starting material, the reaction was concentrated and triturated with diethyl ether to give L-53b (0.268 g, 0.256 mmol, 98%). LC/MS [M+H] 932.53 (calculated); LC/MS [M+H] 932.81 (observed).

Preparation of TAZ-L-53

Cyclobutyl chloroformate (0.1 ml, 0.094 mmol, 1.24 equiv.), 2,3,5,6-tetrafluorophenol (0.065 g, 0.39 mmol, 5 equiv.), and collidine (0.103 ml, 0.78 mmol, 10 equiv.) were dissolved in 1 ml acetonitrile and allowed to stand for one hour. Intermediate L-53b (0.073 g, 0.078 mmol, 1 equiv.) was dissolved in this reaction mixture and the reaction monitored by LCMS. EDC (0.03 g, 0.157 mmol, 2 equiv.) was added to the solution upon consumption of the amine, and the reaction stirred at room temperature. Upon completion, the reaction was concentrated and purified by HPLC to give TAZ-L-53 (0.027 g, 0.023 mmol, 29%). LC/MS [M+H] 1178.56 (calculated); LC/MS [M+H] 1178.85 (observed).

Example L-59 Synthesis of (R)-2-((5-(5-amino-7-((3-(3,3-dimethylbutanamido)propyl)(propyl)carbamoyl)-6H-thieno[3,2-b]azepin-2-yl)pentyl)carbamoyl)-4,37-dioxo-37-(2,3,5,6-tetrafluorophenoxy)-7,10,13,16,19,22,25,28,31,34-decaoxa-3-azaheptatriacontane-1-sulfonic Acid, TAZ-L-59

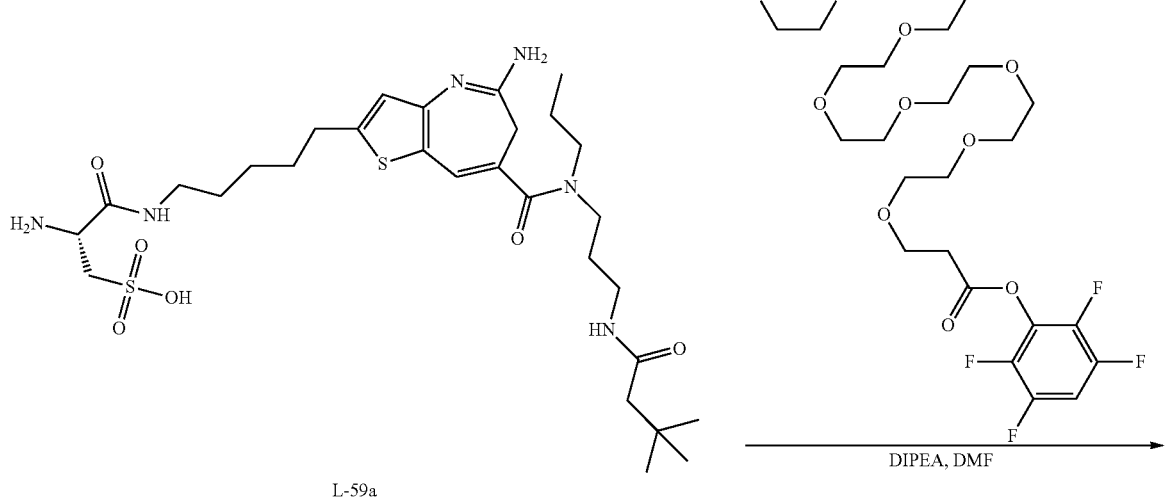

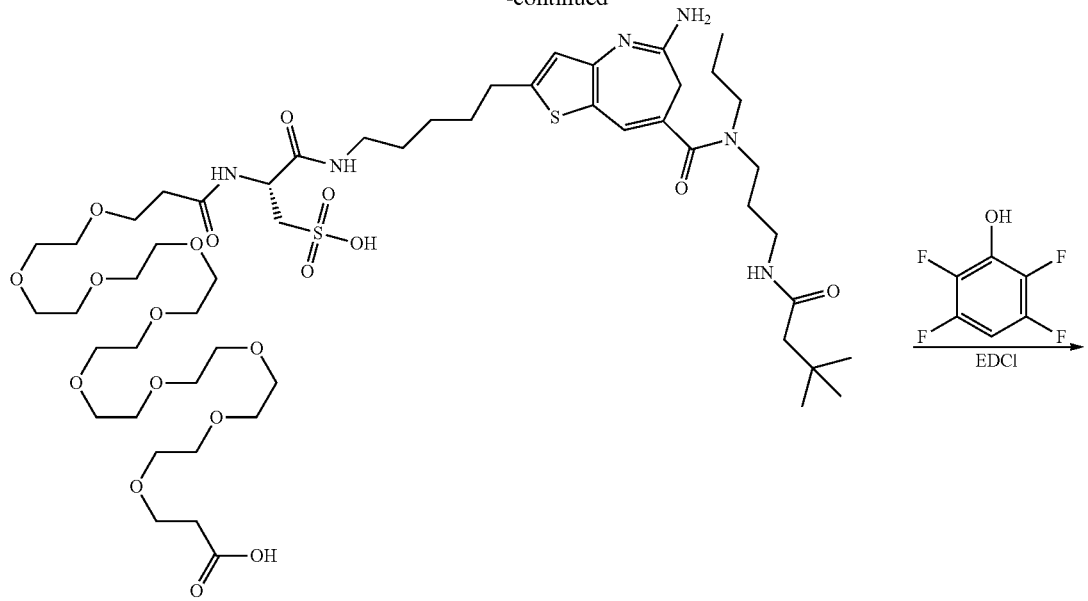

L-59b

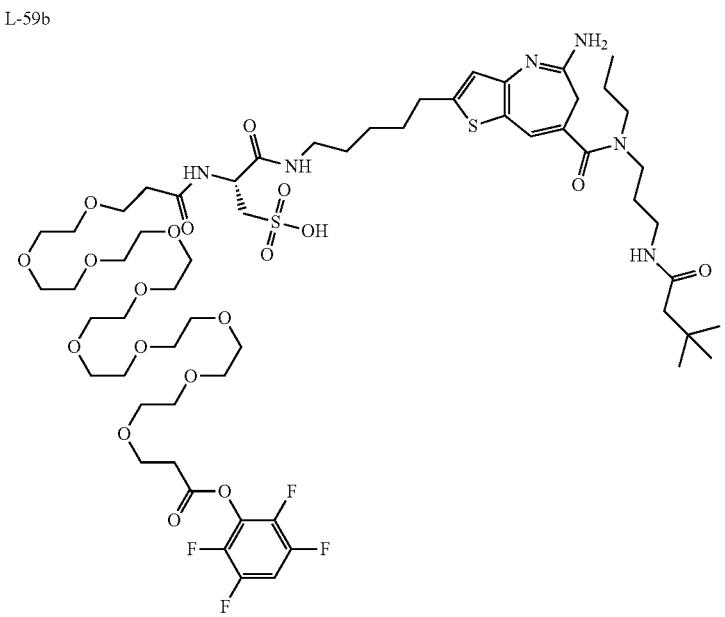

TAZ-L-59

Preparation of (R)-43-(5-amino-7-((3-(3,3-dimethylbutanamido)propyl)(propyl)carbamoyl)-6H-thieno[3,2-b]azepin-2-yl)-34,37-dioxo-36-(sulfomethyl)-4,7,10,13,16,19,22,25,28,31-decaoxa-35,38-diazatritetracontanoic Acid, L-59b (R)-2-amino-3-((5-(5-amino-7-((3-(3,3-dimethylbutanamido)propyl)(propyl)carbamoyl)-6H-thieno[3,2-b]azepin-2-yl)pentyl)amino)-3-oxopropane-1-sulfonic acid, L-59a (0.034 g, 0.053 mmol, 1 equiv.) was dissolved in DMF (1.5 ml). To this solution were added DIPEA (0.046 ml, 0.265 mmol, 5 equiv.), followed by 34-oxo-34-(2,3,5,6-tetrafluorophenoxy)-4,7,10,13,16,19,22,25,28,31-decaoxatetratriacontanoic acid (0.037 g, 0.053 mmol, 1 equiv.). The reaction was heated to 40° C. for 20 minutes, then cooled to room temperature and purified by reverse-phase HPLC to give L-59b (0.036 g, 0.30 mmol, 58%) as a yellow film. LC/MS [M+H]1181.59 (calculated); LC/MS [M+H] 1181.87 (observed).

Preparation of TAZ-L-59

Intermediate L-59b (0.036 g, 0.03 mmol, 1 equiv.) was dissolved in DMF. To this solution were added 2,3,5,6-tetrafluorophenol (0.02 g, 0.09 mmol, 3 equiv.), collidine (0.02 ml, 0.15 mmol, 5 equiv.), and EDCI (0.02 g, 0.09 mmol, 3 equiv.). The reaction was monitored by LCMS, and then concentrated and purified by HPLC to give TAZ-L-59 (0.034 g, 0.031 mmol, 84%). LC/MS [M+H] 1329.59 (calculated); LC/MS [M+H] 1329.88 (observed).

Example L-83 Synthesis of (2,3,5,6-tetrafluorophenyl)3-[2-[2-[2-[2-[2-[2-[2-[2-[2-[4-[[5-amino-7-[3-(cyclobutoxycarbonylamino)propyl-propyl-carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]propanoate, TAZ-L-83
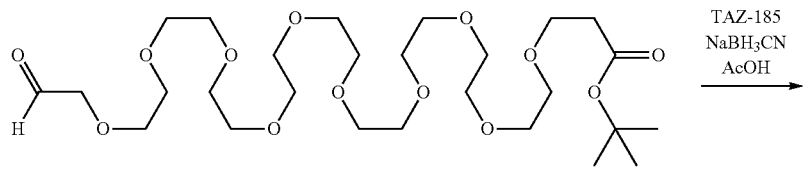
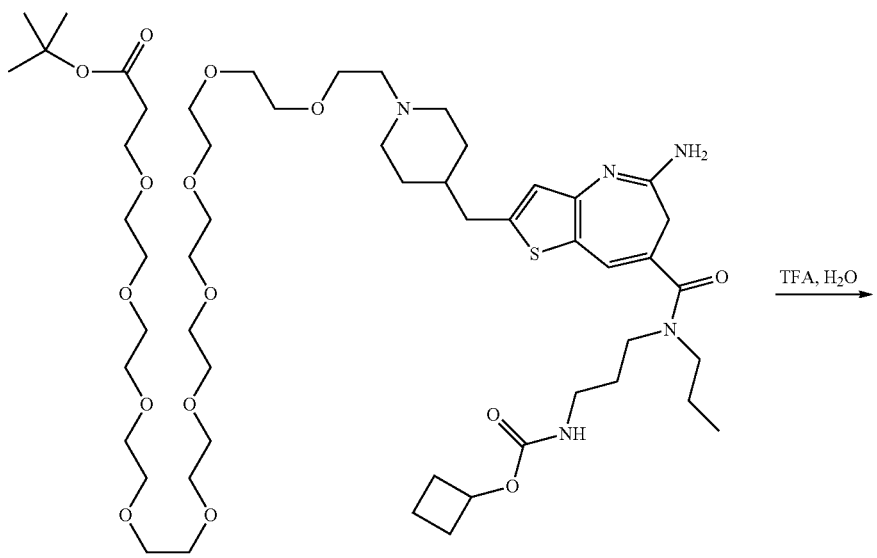
L-83a

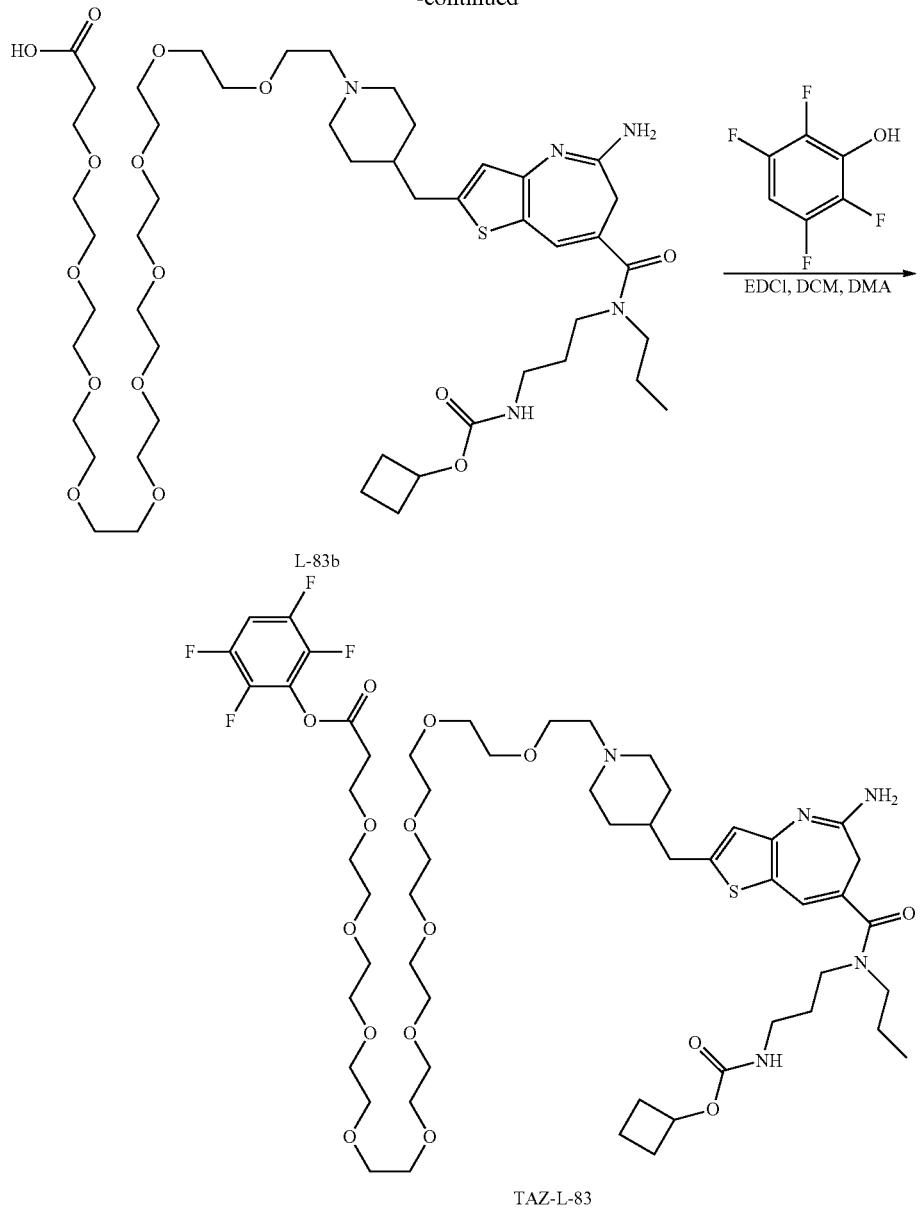

TAZ-L-83

Preparation of tert-butyl 3-[2-[2-[2-[2-[2-[2-[2-[2-[2-[2-[4-[[5-amino-7-[3-(cyclobutoxycarbonylamino) propyl-propyl-carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]propanoate, L-83a To a mixture of cyclobutyl N-[3-[[5-amino-2-(4-piperidylmethyl)-6H-thieno[3,2-b]azepine-7-carbonyl]-propylamino]propyl]carbamate, TAZ-185 (75.0 mg, 149 umol, 1.0 eq) and tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]propanoate (437 mg, 747 umol, 5.0 eq) in MeOH (5 mL) was added NaBH₃CN (37.5 mg, 598 umol, 4.0 eq) in one portion at 20° C. under N₂, and then stirred at 20° C. for 40 hours. The reaction mixture was concentrated in vacuum and the residue was purified by prep-HPLC (column: Phenomenex Synergi C18 150*30 mm*4 um; mobile phase: [water (0.1% TFA)-ACN]; B %: 20%-50%, 8 min) to afford L-83a (100 mg, 93.4 umol, 62.5% yield) as colorless oil. $^1$H NMR (400 MHz, MeOD) δ7.08 (s, 1H), 6.96 (s, 1H), 4.85-4.80 (m, 1H), 3.85 (d, J=4.8 Hz, 2H), 3.75-3.57 (m, 40H), 3.56-3.43 (m, 6H), 3.38 (s, 2H), 3.11 (dd, J=4.0, 5.4 Hz, 2H), 3.08-2.97 (m, 2H), 2.91 (d, J=6.4 Hz, 2H), 2.36-2.23 (m, 2H), 2.10-1.92 (m, 5H), 1.87-1.75 (m, 3H), 1.72-1.54 (m, 5H), 1.47 (s, 9H), 0.93 (s, 3H)

Preparation of 3-[2-[2-[2-[2-[2-[2-[2-[2-[2-[4-[[5-amino-7-[3-(cyclobutoxycarbonylamino)propyl-propyl-carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]propanoic Acid, L-83b To a solution of L-83a (100 mg, 93.4 umol, 1.0 eq) in MeCN (0.5 mL) and H₂O (2 mL) was added HCl (12 M, 233 uL, 30 eq) in one portion at 20° C. under N₂, and then stirred at 80° C. for 1 hour. The reaction mixture was concentrated in vacuum to afford L-83b (80.0 mg, 78.8 umol, 84.4% yield) as colorless oil.

Preparation of TAZ-L-83

To a mixture of L-83b (80.0 mg, 78.8 umol, 1.0 eq) and 2,3,5,6-tetrafluorophenol (131 mg, 788 umol, 10 eq) in DCM (2 mL) and DMA (0.5 mL) was added EDCI (151 mg, 788 umol, 10 eq) in one portion at 20° C. under N₂, the mixture was stirred at 20° C. for 1 hour. DCM (2 mL) was removed in vacuum and the mixture was filtered, the filtrate was purified by prep-HPLC (column: Phenomenex Synergi C18 150*30 mm*4 um; mobile phase: [water (0.1% TFA)-ACN]; B %: 20%-50%, 8 min) to afford TAZ-L-83 (43.0 mg, 36.3 umol, 46.0% yield, 98.20% purity) as colorless oil. ¹H NMR (400 MHz, MeOD) δ7.49-7.42 (m, 1H), 7.07 (s, 1H), 6.95 (s, 1H), 3.89 (t, J=6.0 Hz, 2H), 3.87-3.83 (m, 2H), 3.70-3.46 (m, 42H), 3.37 (s, 2H), 3.17-3.08 (m, 3H), 3.00 (t, J=6.0 Hz, 4H), 2.91 (d, J=6.8 Hz, 2H), 2.34-2.25 (m, 2H), 2.09-1.96 (m, 5H), 1.87-1.58 (m, 8H), 0.92 (t, J=4.0 Hz, 3H). LC/MS [M+H] 1162.6 (calculated); LC/MS [M+H] 1162.4 (observed).

Example L-84 Synthesis of (2,3,5,6-tetrafluorophenyl)3-[2-[2-[2-[2-[2-[2-[2-[2-[2-[2-[4-[[5-amino-7-[ethoxy(propyl)carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]propanoate, TAZ-L-84

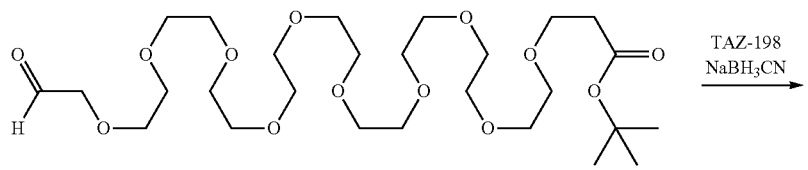

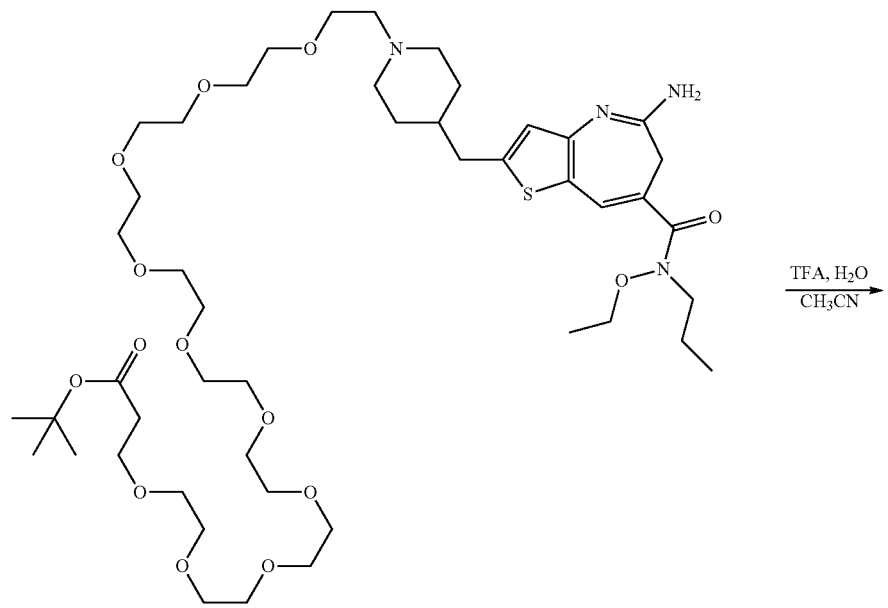

L-84a

-continued

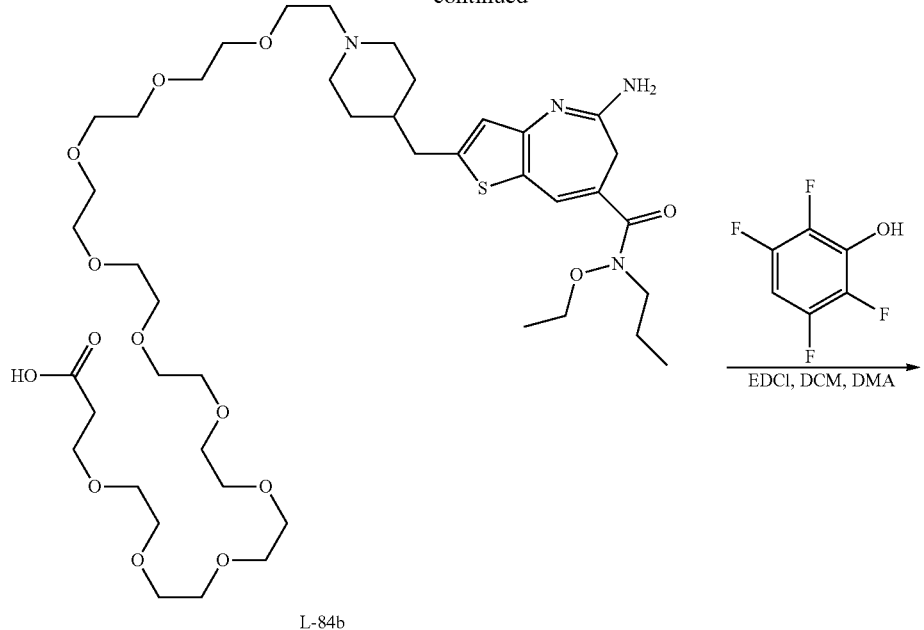

L-84b

TAZ-L-84

Preparation of tert-butyl 3-[2-[2-[2-[2-[2-[2-[2-[2-[2-[2-[4-[[5-amino-7-[ethoxy(propyl)carbamoyl]-6H-thieno[3,2-b]azepin-2-yl]methyl]-1-piperidyl]ethoxy]ethoxy]ethoxy]ethoxy]ethoxy]ethoxy]ethoxy]ethoxy]ethoxy]propanoate, L-84a To a mixture of 5-amino-N-ethoxy-2-(4-piperidylmethyl)-N-propyl-6H-thieno[3,2-b]azepine-7-carboxamide, TAZ-198 (60.0 mg, 153 umol, 1.0 eq) and tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]propanoate (449 mg, 768 umol, 5.0 eq) in MeOH (5 mL) was added NaBH$_3$CN (28.9 mg, 460 umol, 3.0 eq) in one portion at 20° C. under N$_2$, and then stirred at 20° C. for 40 hours. The reaction mixture was concentrated in vacuum and the residue was purified by prep-HPLC (column: Phenomenex Synergi C18 150*30 mm*4 um; mobile phase: [water (0.1% TFA)-ACN]; B %: 20%-45%, 8 min) to afford L-84a (100 mg, 104 umol, 67.8% yield) as colorless oil. $^1$H NMR (400 MHz, MeOD) δ7.48 (s, 1H), 6.97 (s, 1H), 3.95 (q, J=7.2 Hz, 2H), 3.85 (d, J=4.4 Hz, 2H), 3.77-3.65 (m, 40H), 3.45 (s, 2H), 3.01 (d, J=12.4 Hz, 2H), 2.92 (d, J=6.4 Hz, 2H), 2.49 (t, J=6.4 Hz, 2H), 2.05-2.00 (m, 3H), 1.82-1.72 (m, 2H), 1.66-1.54 (m, 2H), 1.47 (s, 9H), 1.20 (t, J=7.2 Hz, 3H), 1.00 (t, J=7.2 Hz, 3H).

Preparation of 3-[2-[2-[2-[2-[2-[2-[2-[2-[2-[2-[4-[[5-amino-7-[ethoxy(propyl)carbamoyl]-6H-thieno [3,2-b]azepin-2-yl]methyl]-1-piperidyl]ethoxy]ethoxy] ethoxy]ethoxy]ethoxy]ethoxy]ethoxy]ethoxy] ethoxy]ethoxy]propanoic Acid, L-84b To a solution of L-84a (100 mg, 104 umol, 1.0 eq) in MeCN (0.5 mL) and H₂O (2 mL) was added HCl (12 M, 260.62 uL, 30 eq) in one portion at 20° C. under N₂, and then stirred at 80° C. for 1 hour. The reaction mixture was concentrated in vacuum. to afford L-84b (80 mg, 88.58 umol, 84.97% yield) as colorless oil.

Preparation of TAZ-L-84

To a mixture of L-84b (80 mg, 88.5 umol, 1.0 eq) and 2,3,5,6-tetrafluorophenol (147 mg, 885 umol, 10 eq) in DCM (2 mL) and DMA (0.5 mL) was added EDCI (84.9 mg, 442 umol, 5.0 eq) in one portion at 20° C. under N₂, the mixture was stirred at 20° C. for 1 hour. DCM (2 mL) was removed in vacuum and the mixture was filtered, the residue was purified by prep-HPLC (column: Phenomenex Synergi C18 150*30 mm*4 um; mobile phase: [water (0.1% TFA)-ACN]; B %: 20%-50%, 8 min) to afford TAZ-L-84 (37 mg, 35.09 umol, 39.61% yield, 99.68% purity) as colorless oil. $^1$H NMR (400 MHz, MeOD) δ7.48 (s, 1H), 7.46-7.41 (m, 1H), 6.96 (s, 1H), 3.95 (q, J=6.8 Hz, 3H), 3.89 (t, J=6.0 Hz, 2H), 3.87-3.83 (m, 2H), 3.71-3.61 (m, 40H), 3.44 (s, 2H), 3.37-3.34 (m, 3H), 3.05-2.95 (m, 5H), 2.91 (d, J=6.4 Hz, 2H), 2.05-1.95 (m, 2H), 1.82-1.72 (m, 2H), 1.66-1.54 (m, 2H), 1.20 (t, J=7.2 Hz, 3H), 0.99 (t, J=7.2 Hz, 3H). LC/MS [M+H] 1151.5 (calculated); LC/MS [M+H] 1151.3 (observed).

Example L-87 Synthesis of (2,3,5,6-tetrafluorophenyl) 3-[2-[2-[2-[2-[2-[2-[2-[2-[2-[2-[4-[2-[5-amino-7-[ethoxy(propyl)carbamoyl]-6H-thieno[3,2-b]azepin-2-yl]ethyl]-1-piperidyl]ethoxy]ethoxy]ethoxy] ethoxy]ethoxy]ethoxy]ethoxy]ethoxy] ethoxy]propanoate, TAZ-L-87

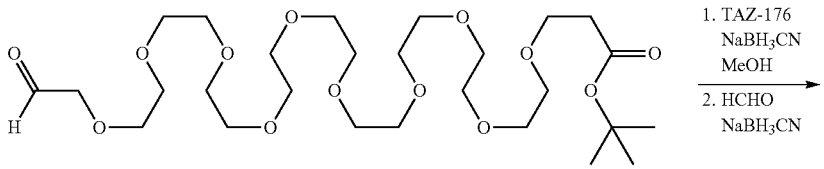

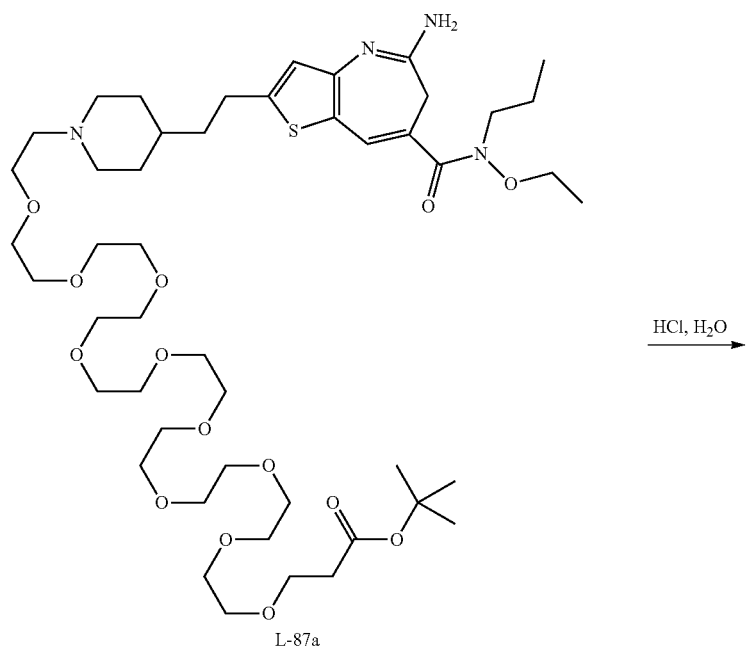

L-87a

-continued
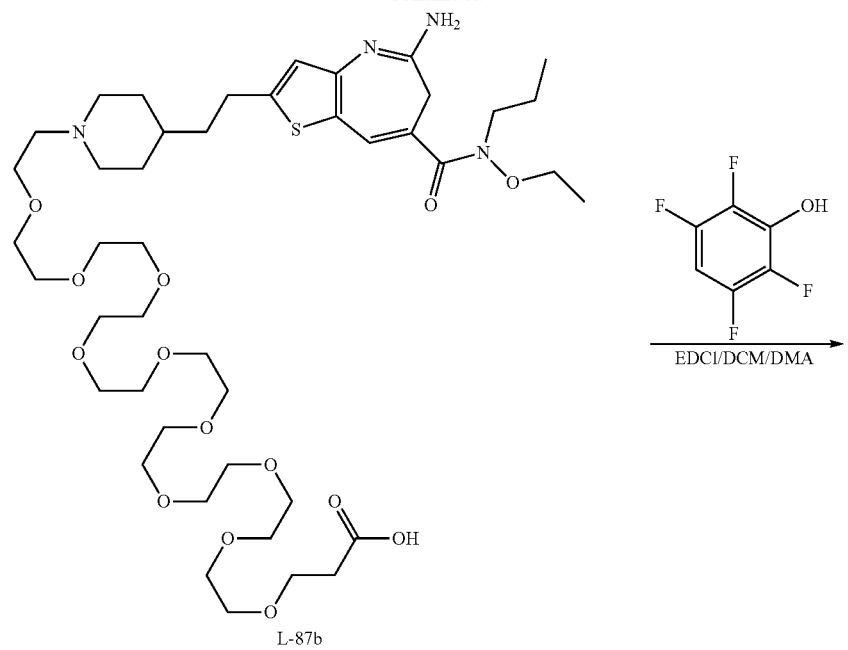
L-87b
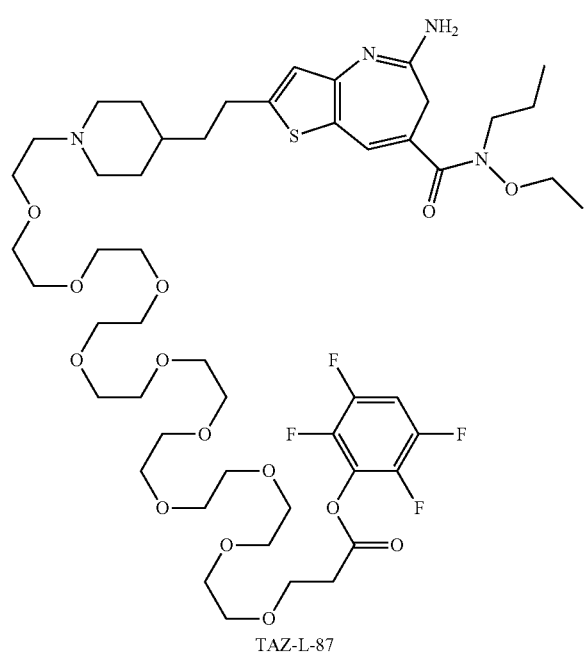 [SMILES: CCCN(OCC)C(=O)C1=Cc2sc(CCC3CCN(CCOCCOCCOCCOCCOCCOCCOCCOCCOCCOCCC(=O)Oc4c(F)c(F)cc(F)c4F)CC3)cc2N=C(N)C1]
TAZ-L-87

Preparation of tert-butyl 3-[2-[2-[2-[2-[2-[2-[2-[2-[2-[2-[4-[2-[5-amino-7-[ethoxy (propyl)carbamoyl]-6H-thieno[3,2-b]azepin-2-yl]ethyl]-1-piperidyl] ethoxy]ethoxy]ethoxy]ethoxy]ethoxy]ethoxy] ethoxy]ethoxy]ethoxy]propanoate, L-87a To a mixture of 5-amino-N-ethoxy-2-[2-(4-piperidyl) ethyl]-N-propyl-6H-thieno[3,2-b]azepine-7-carboxamide, TAZ-176 (0.15 g, 340 umol, 1.0 eq, HCl) in MeOH (3 mL) was added tert-butyl 3-[2-[2-[2-[2-[2-[2-[2-[2-[2-(2-oxoethoxy)ethoxy]ethoxy]ethoxy]ethoxy]ethoxy]ethoxy]ethoxy] ethoxy]ethoxy]propanoate (597 mg, 1.02 mmol, 3.0 eq) and NaBH$_3$CN (42.8 mg, 680 umol, 2.0 eq) in one portion at 25° C. and it was stirred at 25° C. for 12 h. The mixture was concentrated to give a residue. The residue was purified by prep-HPLC (column: Phenomenex luna C18 100*40 mm*5 um; mobile phase: [water (0.1% TFA)-ACN]; B %: 12%-42%, 8 min) to give L-87a (0.18 g, 165.55 umol, 48.67% yield, TFA) as yellow oil. $^1$H NMR (MeOD, 400 MHz) δ7.45 (s, 1H), 6.94 (s, 1H), 3.96-3.90 (m, 2H), 3.86-3.82 (m, 2H), 3.75-3.71 (m, 2H), 3.70-3.67 (m, 6H), 3.66-3.59 (m, 36H), 3.42 (s, 2H), 3.06-2.90 (m, 4H), 2.47 (t, J=6.2 Hz, 2H), 2.13-2.00 (m, 2H), 1.87-1.60 (m, 6H), 1.60-1.48 (m, 2H), 1.45 (s, 10H), 1.18 (t, J=7.2 Hz, 3H), 0.97 (t, J=7.6 Hz, 3H).

Preparation of 3-[2-[2-[2-[2-[2-[2-[2-[2-[2-[4-[2-[5-amino-7-[ethoxy(propyl)carbamoyl]-6H-thieno[3, 2-b]azepin-2-yl]ethyl]-1-piperidyl]ethoxy]ethoxy] ethoxy]ethoxy]ethoxy]ethoxy]ethoxy]ethoxy] ethoxy]ethoxy]propanoic Acid, L-87b To a mixture of L-87a (0.18 g, 166 umol, 1.0 eq, TFA) in H$_2$O (2.5 mL) and CH$_3$CN (0.3 mL) was added HCl (12 M, 345 uL, 25.0 eq) in one portion at 25° C. and it was stirred at 80° C. for 1 h. The mixture was concentrated to give L-87b (0.15 g, crude, HCl) as yellow oil.

Preparation of TAZ-L-87

To a mixture of L-87b (0.05 g, 52.4 umol, 1.0 eq, HCl) in DCM (1 mL) and DMA (0.2 mL) was added 2,3,5,6-tetrafluorophenol (69.7 mg, 419 umol, 8.0 eq) and EDCI (101 mg, 524 umol, 10.0 eq) in one portion at 25° C. and it was stirred at 25° C. for 0.5 h. The mixture was concentrated to give a residue. The residue was purified by prep-HPLC (column: Phenomenex Synergi C18 150*30 mm*4 um; mobile phase: [water (0.1% TFA)-ACN]; B %: 20%-50%, 8 min) to give TAZ-L-87 (14.5 mg, 12.30 umol, 23.45% yield, TFA) as yellow oil. $^1$H NMR (MeOD, 400 MHz) δ7.49-7.38 (m, 2H), 6.92 (s, 1H), 3.93 (q, J=8 Hz, 2H), 3.87 (t, J=6.0 Hz, 2H), 3.85-3.81 (m, 2H), 3.74-3.70 (m, 2H), 3.69-3.61 (m, 40H), 3.42 (s, 2H), 3.03-2.91 (m, 6H), 2.07 (d, J=13.6 Hz, 2H), 1.79-1.66 (m, 5H), 1.58-1.43 (m, 2H), 1.18 (t, J=7.2 Hz, 3H), 0.97 (t, J=7.6 Hz, 3H). LC/MS [M+H] 1065.5 (calculated); LC/MS [M+H] 1065.4 (observed).

Example L-88 Synthesis of (2,3,5,6-tetrafluorophenyl) 3-[2-[2-[2-[2-[2-[2-[2-[2-[3-[4-[2-[5-amino-7-[ethoxy(propyl)carbamoyl]-6H-thieno[3,2-b]azepin-2-yl]ethyl]-1-piperidyl]-3-oxo-propoxy]ethoxy] ethoxy]ethoxy]ethoxy]ethoxy]ethoxy]ethoxy] ethoxy]ethoxy]propanoate, TAZ-L-88

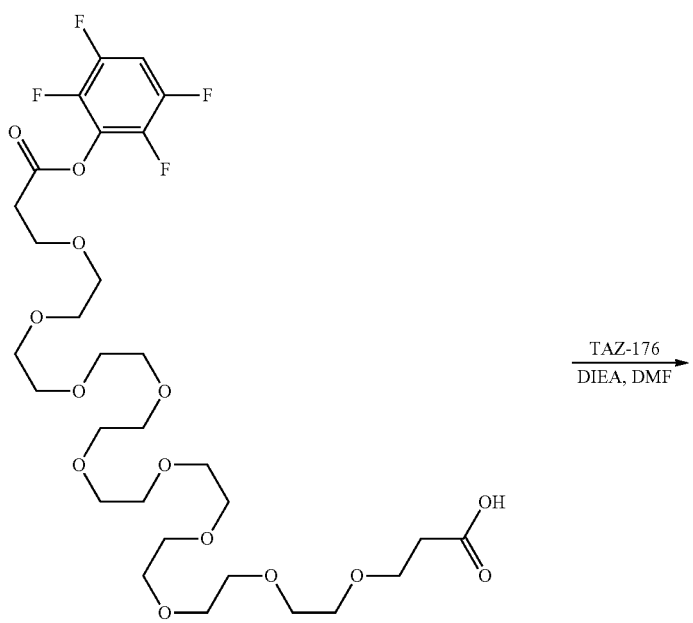

TAZ-176
―――――→
DIEA, DMF

-continued
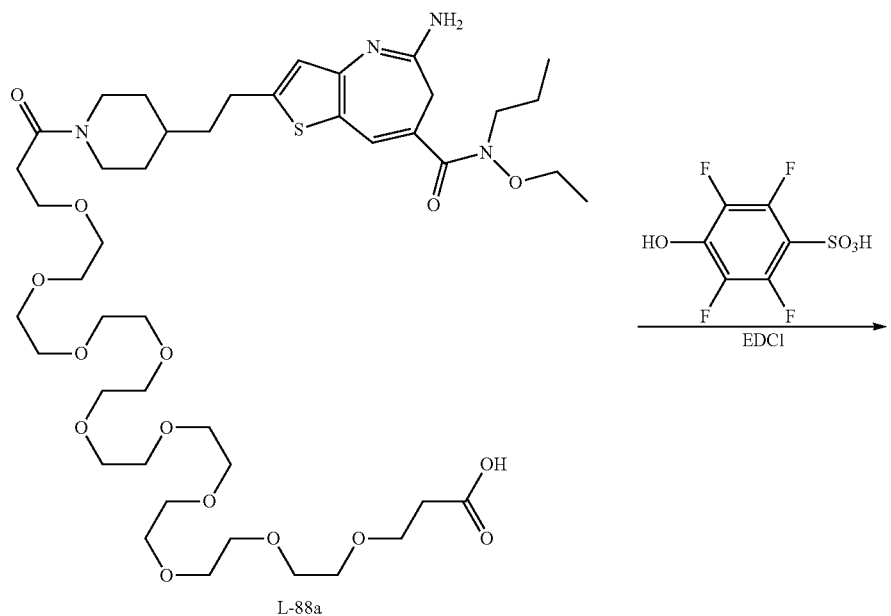
L-88a
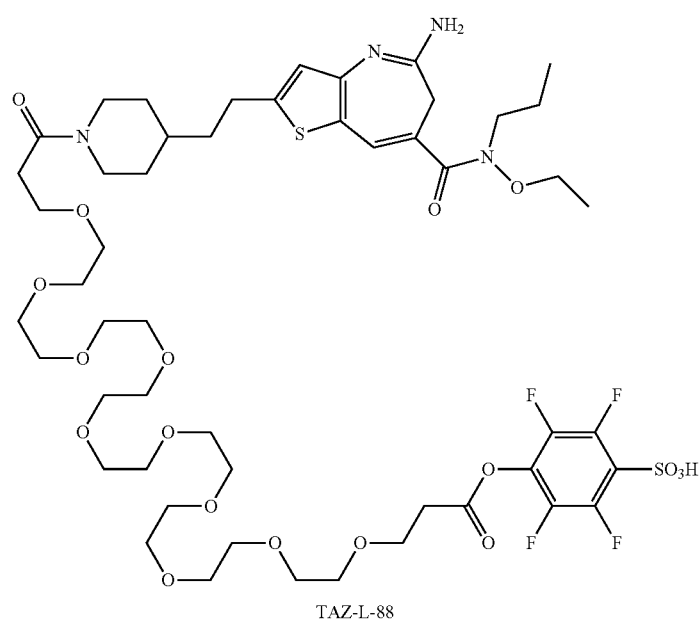
TAZ-L-88

Preparation of 3-[2-[2-[2-[2-[2-[2-[2-[2-[2-[3-[4-[2-[5-amino-7-[ethoxy(propyl) carbamoyl]-6H-thieno[3,2-b]azepin-2-yl]ethyl]-1-piperidyl]-3-oxo-propoxy]ethoxy]ethoxy]ethoxy]ethoxy]ethoxy]ethoxy]ethoxy]ethoxy]propanoic Acid, L-88a To a mixture of 5-amino-N-ethoxy-2-[2-(4-piperidyl)ethyl]-N-propyl-6H-thieno[3,2-b]azepine-7-carboxamide, TAZ-176 (60.0 mg, 136 umol, 1.0 eq, HCl) and 3-[2-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]propanoic acid (106 mg, 150 umol, 1.1 eq) in DMF (0.5 mL) was added DIEA (52.8 mg, 408 umol, 71.1 uL, 3.0 eq) in one portion at 25° C. and it was stirred at 25° C. for 0.5 h. Then the mixture was filtered and purified by prep-HPLC (column: Welch Xtimate C18 150*25 mm*5 um; mobile phase: [water (0.04% HCl)-ACN]; B %: 20%-35%, 8 min) to give L-88a (40 mg, 42.32 umol, 31.11% yield) as yellow oil.

Preparation of TAZ-L-88

To a mixture of L-88a (40 mg, 40.8 umol, 1.0 eq) in DCM (1 mL) and DMA (0.2 mL) was added 2,3,5,6-tetrafluorophenol (54.1 mg, 326 umol, 8.0 eq) and EDCI (78.1 mg, 407 umol, 10.0 eq) in one portion at 25° C. and it was stirred at 25° C. for 0.5 h. The mixture was concentrated to give a residue, and the residue was purified by prep-HPLC (column: Phenomenex Synergi C18 150*30 mm*4 um; mobile phase: [water (0.1% TFA)-ACN]; B %: 30%-60%, 8 min) to give TAZ-L-88 (36.2 mg, 33.11 umol, 81.26% yield) as yellow oil. $^1$H NMR (MeOD, 400 MHz) δ7.46 (s, 1H), 7.45-7.39 (m, 1H), 6.90 (s, 1H), 4.53 (d, J=13.2 Hz, 1H), 4.04 (d, J=13.6 Hz, 1H), 3.93 (q, J=7.2 Hz, 2H), 3.87 (t, J=6.0 Hz, 2H), 3.77-3.69 (m, 4H), 3.66-3.60 (m, 36H), 3.42 (s, 2H), 3.06 (t, J=12.0 Hz, 1H), 2.98 (t, J=6.0 Hz, 2H), 2.93 (t, J=7.6 Hz, 2H), 2.78-2.51 (m, 3H), 1.89-1.63 (m, 7H), 1.30-1.07 (m, 5H), 0.97 (t, J=7.6 Hz, 3H). LC/MS [M+H] 1093.5 (calculated); LC/MS [M+H] 1093.4 (observed).

Example L-92 Synthesis of (2,3,5,6-tetrafluorophenyl) 3-[2-[2-[2-[2-[2-[2-[2-[2-[2-[3-[[5-amino-7-[ethoxy(propyl)carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]propanoate, TAZ-L-92

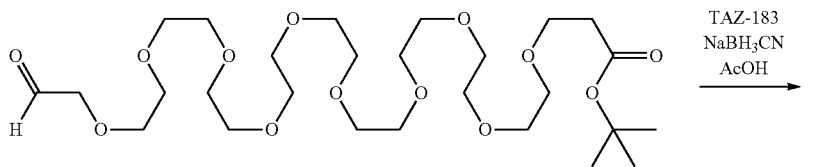

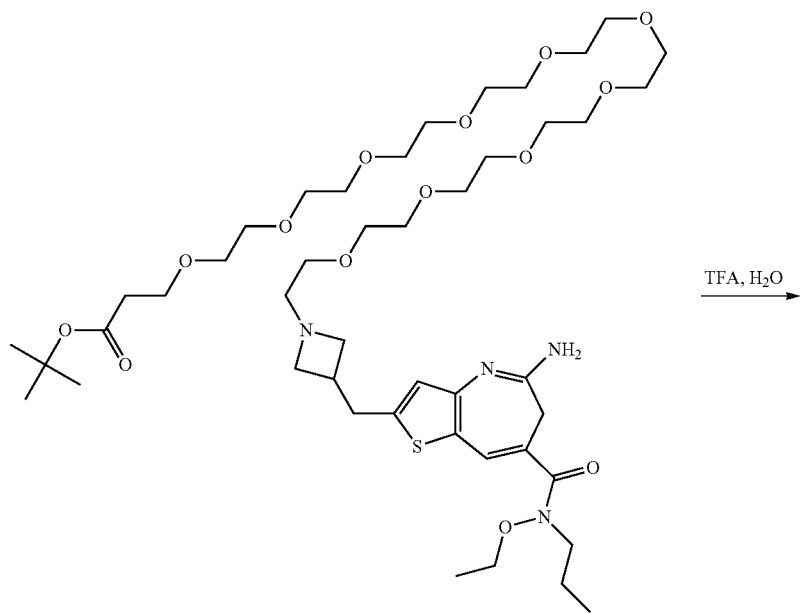

L-92a

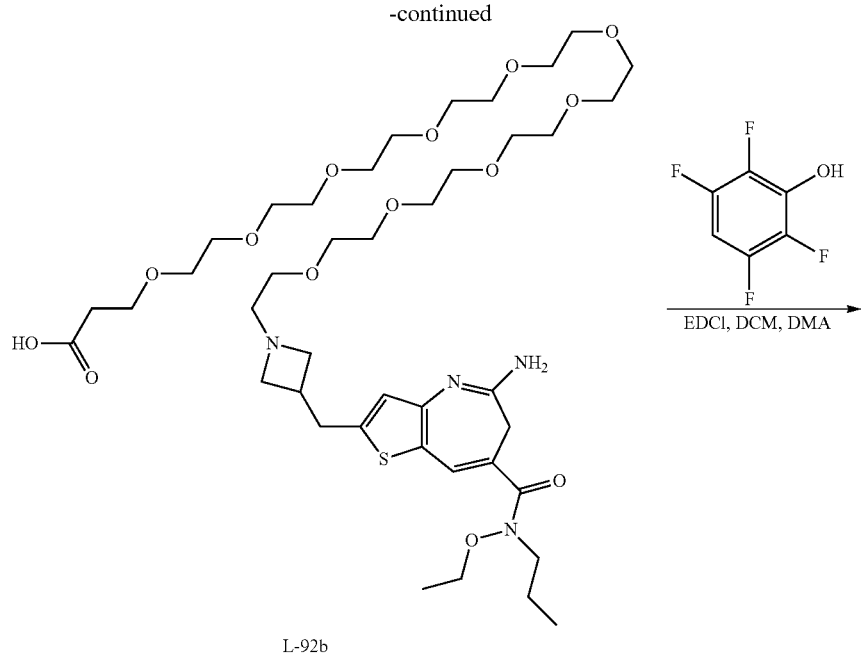

L-92b

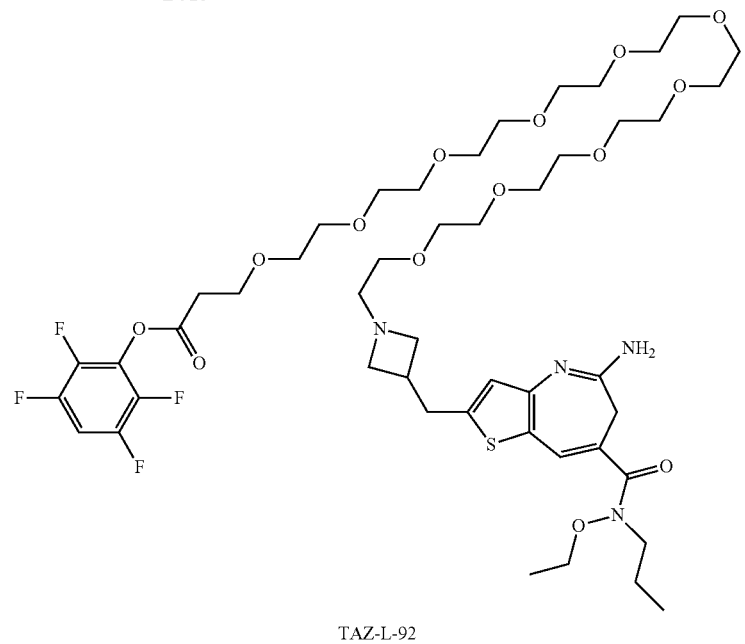 [SMILES: CCCN(OCC)C(=O)C1=Cc2sc(CC3CN(CCOCCOCCOCCOCCOCCOCCOCCOCCOCCOCCC(=O)Oc4c(F)c(F)cc(F)c4F)C3)cc2N=C(N)C1]

TAZ-L-92

Preparation of tert-butyl 3-[2-[2-[2-[2-[2-[2-[2-[2-[2-[2-[3-[[5-amino-7-[ethoxy(propyl)carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]propanoate, L-92a To a mixture of 5-amino-2-(azetidin-3-ylmethyl)-N-ethoxy-N-propyl-6H-thieno [3,2-b]azepine-7-carboxamide, TAZ-183 (0.06 g, 166 umol, 1 eq) and tert-butyl 3-[2-[2-[2-[2-[2-[2-[2-[2-[2-(2-oxoethoxy)ethoxy]ethoxy]ethoxy]ethoxy]ethoxy]ethoxy]ethoxy]ethoxy]propanoate (290 mg, 497 umol, 3 eq) in MeOH (5 mL) was added NaBH$_3$CN (20.8 mg, 331 umol, 2 eq) and AcOH (9.94 mg, 166 umol, 1 eq), and then stirred at 15° C. for 10 hr. The mixture was concentrated to give a residue. The residue was purified prep-HPLC (TFA)(column: Phenomenex Synergi C18 150*30 mm*4 um; mobile phase: [water (0.1% TFA)-ACN]; B %: 20%-45%, 8 min) to give L-92a (20 mg, 19.1 umol, 11.6% yield, TFA) as yellow solid.

Preparation of 3-[2-[2-[2-[2-[2-[2-[2-[2-[2-[2-[3-[[5-amino-7-[ethoxy(propyl)carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]propanoic Acid, L-92b To a mixture of L-92a (20 mg, 19.1 umol, 1 eq, TFA) in H$_2$O (0.5 mL) was add TFA (10.9 mg, 95.7 umol, 5 eq) at 25° C., and then stirred at 80° C. for 4 hr. The mixture was concentrated to give a residue. The residue was purified by prep-HPLC (column: Phenomenex Gemini-NX C18 75*30 mm*3 um; mobile phase: [water (10 mM NH4HCO3)-ACN]; B %: 25%-45%, 6 min) to give L-92b (13 mg, 14.9 umol, 77.6% yield) as colorless oil.

Preparation of TAZ-L-92

To a mixture of L-92b (12 mg, 13.7 umol, 1 eq) and 2,3,5,6-tetrafluorophenol (18.2 mg, 110 umol, 8 eq) in DCM (1 mL) and DMA (0.1 mL) was added EDCI (26.3 mg, 137 umol, 10 eq), and then stirred at 15° C. for 0.5 hr. The mixture was concentrated to give a residue. The residue was purified by prep-HPLC (column: Phenomenex Synergi C18 150*30 mm*4 um; mobile phase: [water (0.1% TFA)-ACN]; B %: 20%-50%, 8 min) to give TAZ-L-92 (6.3 mg, 5.54 umol, 40.4% yield, 100% purity, TFA) as colorless oil. $^1$H NMR (400 MHz, MeOD) δ7.57-7.32 (m, 2H), 6.98 (br s, 1H), 4.43-3.79 (m, 8H), 3.77-3.52 (m, 40H), 3.44 (s, 2H), 3.33-3.26 (m, 4H), 3.18-3.11 (m, 1H), 3.00 (t, J=6.0 Hz, 2H), 1.83-1.68 (m, 2H), 1.20 (t, J=7.2 Hz, 3H), 0.99 (t, J=7.6 Hz, 3H). LC/MS [M+H] 1023.5 (calculated); LC/MS [M+H] 1023.3 (observed).

Example L-93 Synthesis of (2,3,5,6-tetrafluorophenyl) 3-[2-[2-[2-[2-[2-[2-[2-[2-[3-[4-[[5-amino-7-[ethoxy(propyl)carbamoyl]-6H-thieno[3,2-b]azepin-2-yl]methyl]-1-piperidyl]-3-oxo-propoxy]ethoxy] ethoxy]ethoxy]ethoxy]ethoxy]ethoxy] ethoxy]ethoxy]propanoate, TAZ-L-93

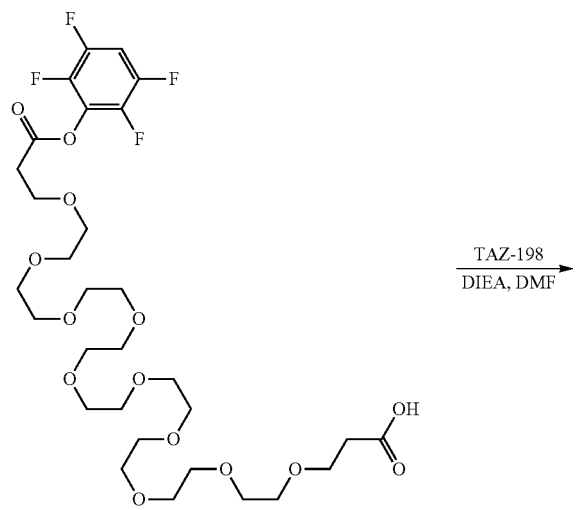

TAZ-198
────────→
DIEA, DMF

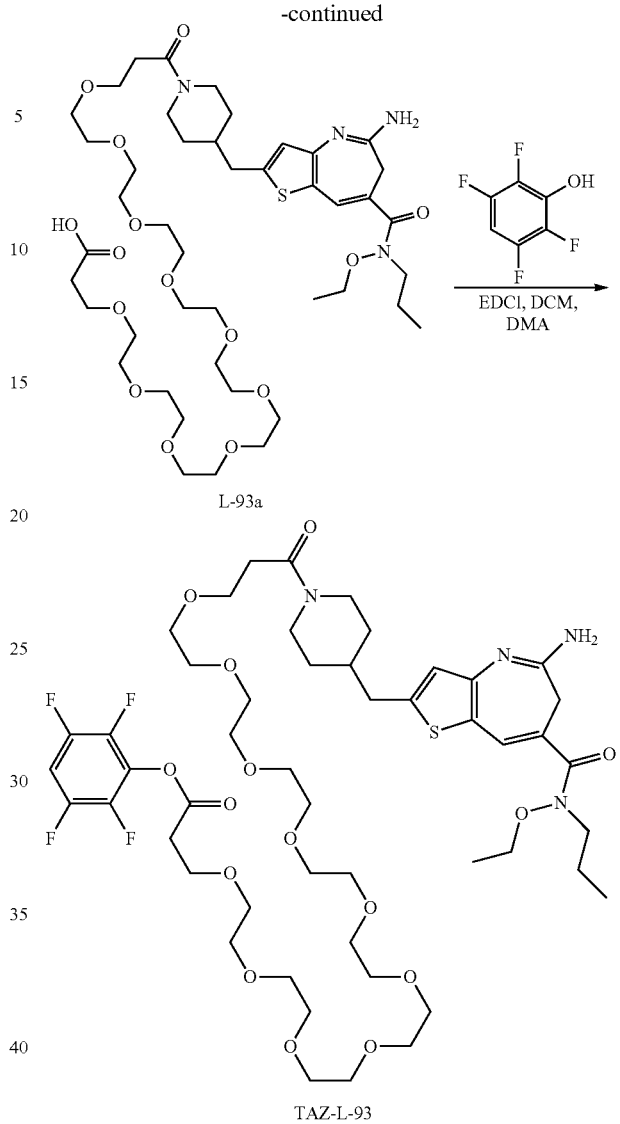

Preparation of 3-[2-[2-[2-[2-[2-[2-[2-[2-[3-[4-[[5-amino-7-[ethoxy(propyl) carbamoyl]-6H-thieno[3,2-b]azepin-2-yl]methyl]-1-piperidyl]-3-oxo-propoxy] ethoxy]ethoxy]ethoxy]ethoxy]ethoxy]ethoxy] ethoxy]ethoxy]propanoic Acid, L-93a To a mixture of 5-amino-N-ethoxy-2-(4-piperidylmethyl)-N-propyl-6H-thieno[3,2-b]azepine-7-carboxamide, TAZ-198 (30.0 mg, 70.3 umol, 1.0 eq, HCl) and 3-[2-[2-[2-[2-[2-[2-[2-[2-[3-oxo-3-(2,3,5,6-tetrafluorophenoxy) propoxy]ethoxy]ethoxy]ethoxy]ethoxy]ethoxy]ethoxy] ethoxy]ethoxy]propanoic acid (54.6 mg, 77.3 umol, 1.1 eq) in DMF (0.5 mL) was added DIEA (27.2 mg, 210 umol, 36.7 uL, 3.0 eq) in one portion at 20° C. under N$_2$, and then stirred at 20° C. for 1 hour. The reaction mixture was filtered and the filtrate was purified by prep-HPLC (column: Xtimate C18 100*30 mm*3 um; mobile phase: [water (0.04% HCl)-ACN]; B %: 22%-45%, 8 min) to afford L-93a (60.0 mg, 64.4 umol, 91.7% yield) as colorless oil.

Preparation of TAZ-L-93

To a mixture of L-93a (60.0 mg, 64.4 umol, 1.0 eq) and 2,3,5,6-tetrafluorophenol (107 mg, 644 umol, 10 eq) in DCM (2 mL) and DMA (0.5 mL) was added EDCI (123.53 mg, 644.37 umol, 10 eq) in one portion at 20° C. under $N_2$, and then stirred at 20° C. for 1 hour. The reaction mixture was filtered and the filtrate was purified by prep-HPLC (column: Phenomenex Synergi C18 150*30 mm*4 um; mobile phase: [water (0.1% TFA)-ACN]; B %: 30%-55%, 8 min) to afford TAZ-L-93 (44.2 mg, 40.2 umol, 62.4% yield, 98.2% purity) as colorless oil. $^1$H NMR (400 MHz, MeOD) δ7.49 (s, 1H), 7.47-7.41 (m, 1H), 6.92 (s, 1H), 4.56 (d, J=12.8 Hz, 1H), 4.06 (d, J=13.6 Hz, 1H), 3.95 (q, J=7.2 Hz, 2H), 3.89 (t, J=6.0 Hz, 2H), 3.80-3.71 (m, 4H), 3.70-3.58 (m, 36H), 3.45 (s, 2H), 3.10 (t, J=12.0 Hz, 1H), 3.00 (t, J=6.0 Hz, 2H), 2.86 (d, J=7.0 Hz, 2H), 2.77-2.57 (m, 3H), 1.95-1.90 (m, 1H), 1.80-1.75 (m, 4H), 1.35-1.20 (m, 5H), 0.99 (t, J=7.2 Hz, 3H). LC/MS [M+H] 1079.5 (calculated); LC/MS [M+H] 1079.4 (observed).

Example L-98 Synthesis of (2,3,5,6-tetrafluorophenyl)3-[2-[2-[2-[2-[2-[2-[2-[2-[2-[3-[3-[[5-amino-7-[ethoxy(propyl)carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoate, TAZ-L-98

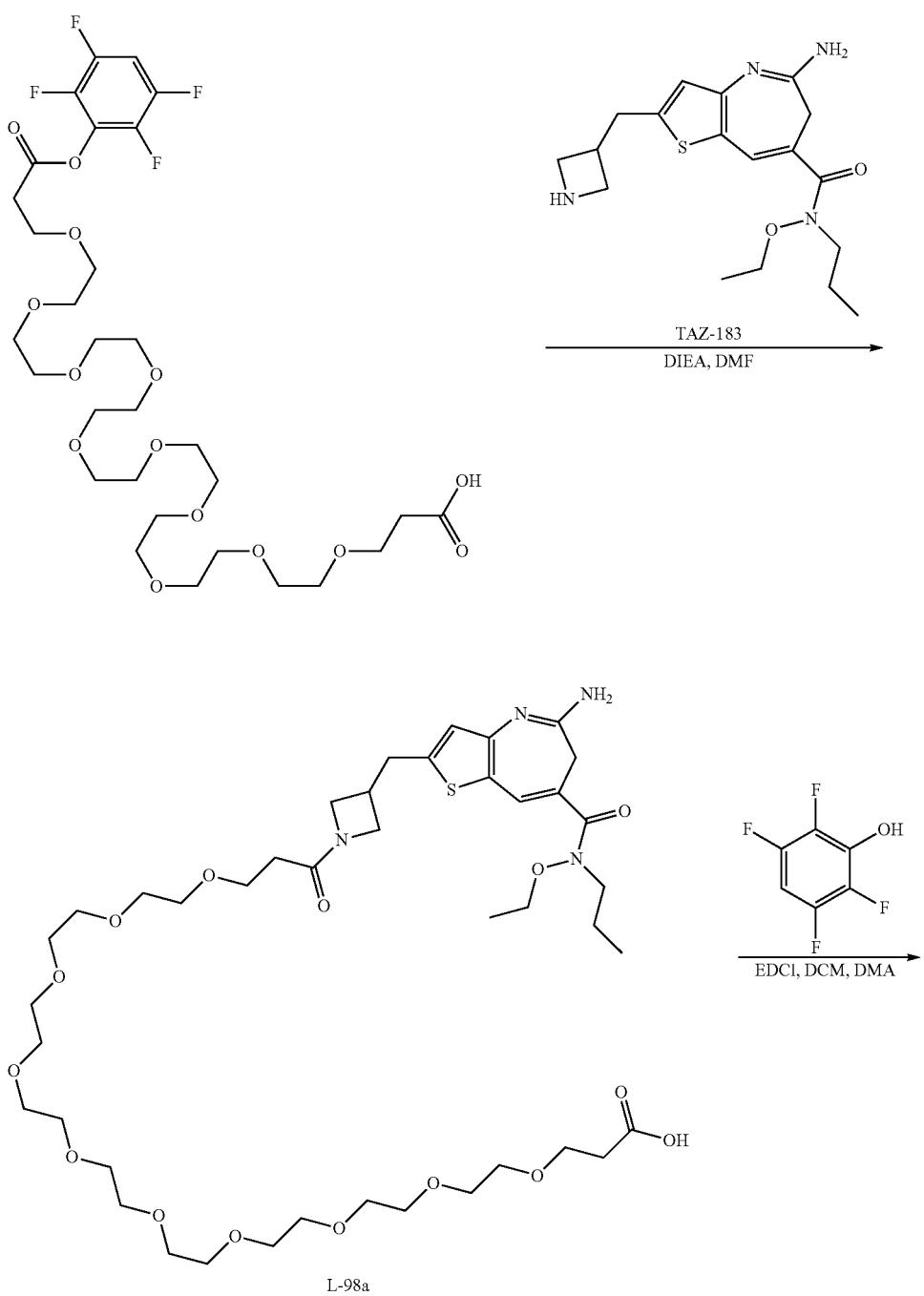

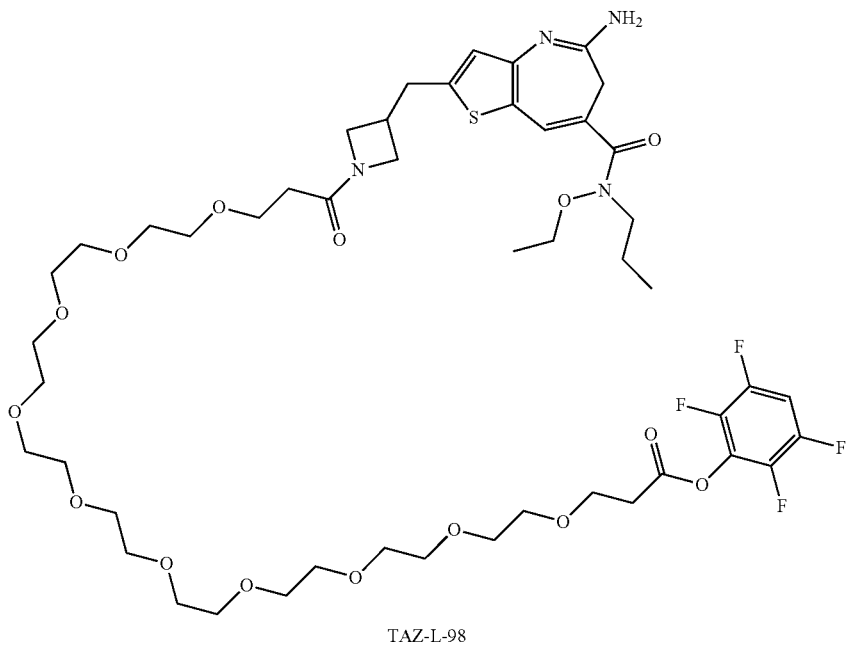

TAZ-L-98

Preparation of 3-[2-[2-[2-[2-[2-[2-[2-[2-[2-[3-[3-[[5-amino-7-[ethoxy(propyl)carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoic Acid, L-98a To a mixture of 5-amino-2-(azetidin-3-ylmethyl)-N-ethoxy-N-propyl-6H-thieno[3,2-b]azepine-7-carboxamide, TAZ-183 (150 mg, 315 umol, 1 eq, TFA) and DIEA (102 mg, 787 umol, 137 uL, 2.5 eq) in DMF (2 mL) was added 3-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]propanoic acid (223 mg, 315 umol, 1 eq), and then stirred at 20° C. for 0.5 hr. The mixture was concentrated to give a residue. The residue was purified by Prep-HPLC (column: Waters Xbridge Prep OBD C18 150*40 mm*10 um; mobile phase: [water (10 mM NH$_4$HCO$_3$)-ACN]; B %: 5%-40%, 8 min) to give L-98a (0.08 g, 88.6 umol, 28.1% yield) as yellow oil.

Preparation of TAZ-L-98

To a mixture of L-98a (0.08 g, 88.6 umol, 1 eq) and 2,3,5,6-tetrafluorophenol (118 mg, 709 umol, 8 eq) in DCM (3 mL) and DMA (0.3 mL) was added EDCI (170 mg, 886 umol, 10 eq). The mixture was stirred at 15° C. for 0.5 hr. The mixture was concentrated to give a residue. The residue was purified by Prep-HPLC (column: Phenomenex Synergi C18 150*25*10 um; mobile phase: [water (0.1% TFA)-ACN]; B %: 25%-50%, 10 min and column: Phenomenex Synergi C18 150*25*10 um; mobile phase: [water (0.1% TFA)-ACN]; B %: 25%-50%, 8 min) to give TAZ-L-98 (34.3 mg, 31.9 umol, 36.0% yield, 97.7% purity) as colorless oil. $^1$H NMR (400 MHz, MeOD) δ7.49-7.38 (m, 2H), 6.92 (s, 1H), 4.42-4.35 (m, 1H), 4.10 (t, J=9.2 Hz, 1H), 4.06-3.97 (m, 1H), 3.93 (q, J=7.2 Hz, 2H), 3.89-3.85 (m, 2H), 3.73-3.69 (m, 4H), 3.66-3.51 (m, 37H), 3.40 (s, 2H), 3.19 (br d, J=7.6 Hz, 2H), 2.99-2.96 (m, 3H), 2.48-2.24 (m, 2H), 1.74 (q, J=7.2 Hz, 2H), 1.18 (t, J=7.2 Hz, 3H), 0.97 (t, J=7.2 Hz, 3H). LC/MS [M+H]1051.5 (calculated); LC/MS [M+H] 1051.3 (observed).

Example L-128 Synthesis of 4-[3-[2-[2-[2-[2-[2-[2-[2-[2-[2-[3-[3-[[5-amino-7-[2-(cyclobutoxycarbonylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoyloxy]-2,3,5,6-tetrafluoro-benzenesulfonic Acid, TAZ-L-128
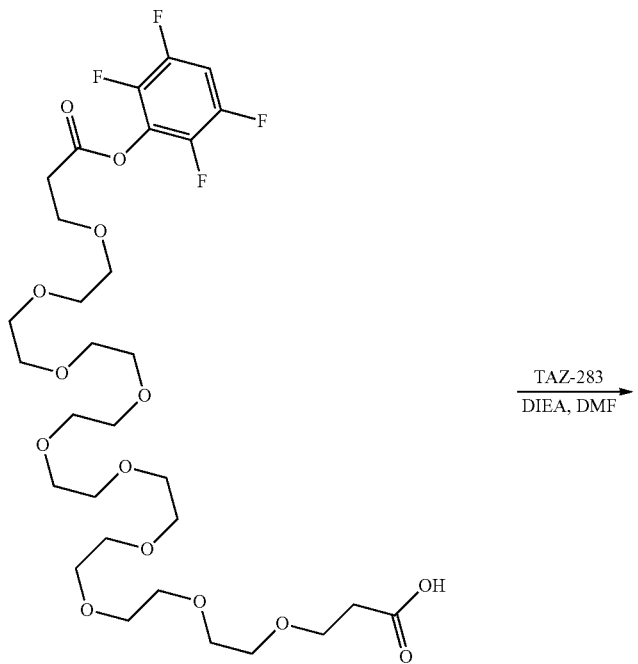
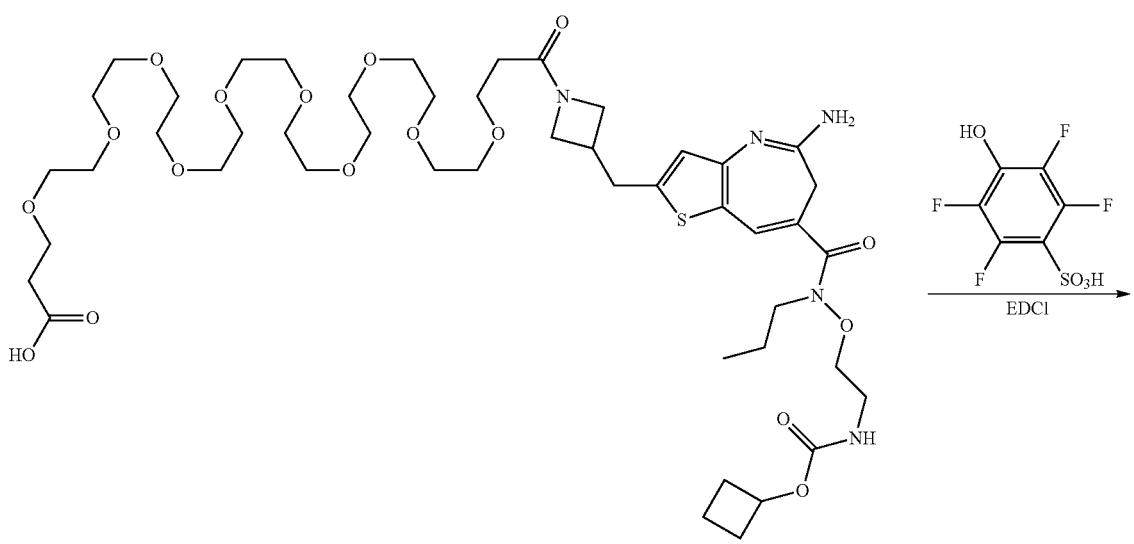
128a

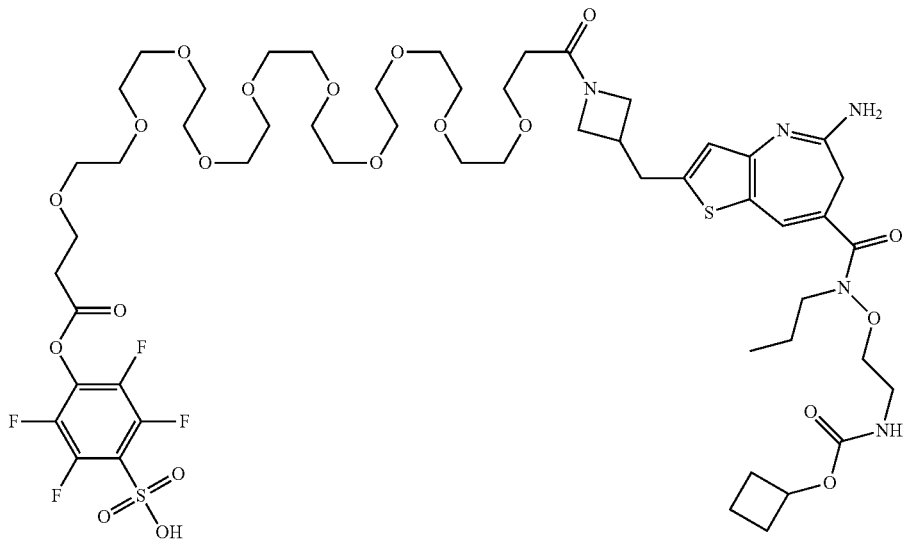

TAZ-128

Preparation of 3-[2-[2-[2-[2-[2-[2-[2-[2-[2-[3-[3-[[5-amino-7-[2-(cyclobutoxycarbonylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoic Acid, 128a To a mixture of cyclobutyl N-[2-[[5-amino-2-(azetidin-3-ylmethyl)-6H-thieno[3,2-b]azepine-7-carbonyl]-propyl-amino]oxyethyl]carbamate, TAZ-238 (0.12 g, 171 umol, 1.0 eq, TFA) in DMF (2 mL) was added DIEA (66.1 mg, 512 umol, 89.1 uL, 3.0 eq) and 3-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]propanoic acid (121 mg, 171 umol, 1.0 eq) in one portion at 0° C. and then stirred at 0° C. for 0.5 h. The mixture was filtered and purified by prep-HPLC (column: Welch Xtimate C18 100*25 mm*3 um; mobile phase: [water (0.05% HCl)-ACN]; B %: 20%-40%, 8 min) to give 128a (45 mg, 42.8 umol, 25.1% yield, HCl) as yellow oil. $^1$H NMR (MeOD, 400 MHz) δ7.51 (s, 1H), 6.96 (s, 1H), 4.81-4.76 (m, 1H), 4.40 (t, J=8.4 Hz, 1H), 4.11 (t, J=9.2 Hz, 1H), 4.03 (dd, J=5.6, 8.8 Hz, 1H), 3.92 (t, J=5.2 Hz, 2H), 3.77-3.68 (m, 7H), 3.66-3.55 (m, 36H), 3.42 (s, 2H), 3.30-2.25 (m, 2H), 3.20 (d, J=8.0 Hz, 2H), 3.06-2.89 (m, 1H), 2.54 (t, J=6.4 Hz, 2H), 2.44-2.31 (m, 2H), 2.30-2.20 (m, 2H), 2.05-1.90 (m, 2H), 1.80-1.68 (m, 3H), 1.66-1.52 (m, 1H), 0.96 (t, J=7.6 Hz, 3H)

Preparation of TAZ-128

To a mixture of 128a (40 mg, 38.0 umol, 1.0 eq, HCl) and sodium 2,3,5,6-tetrafluoro-4-hydroxy-benzenesulfonate (50.9 mg, 190 umol, 5.0 eq) in DCM (1.5 mL) and DMA (0.2 mL) was added EDCI (51.0 mg, 266 umol, 7.0 eq) in one portion at 25° C. and then stirred at 25° C. for 0.5 h. Then the mixture was concentrated. The residue was purified by prep-HPLC (column: Phenomenex Synergi C18 150*25*10 um; mobile phase: [water (0.1% TFA)-ACN]; B %: 15%-45%, 8 min) to give TAZ-128 (35.2 mg, 28.3 umol, 74.5% yield) as yellow solid. $^1$H NMR (MeOD, 400 MHz) δ7.49 (s, 1H), 6.96 (s, 1H), 4.79-4.73 (m, 1H), 4.43-4.35 (m, 1H), 4.16-3.98 (m, 2H), 3.97-3.83 (m, 4H), 3.77-3.67 (m, 5H), 3.66-3.57 (m, 34H), 3.42 (s, 2H), 3.30-3.25 (m, 4H), 3.19 (d, J=8.0 Hz, 2H), 2.98 (t, J=5.6 Hz, 3H), 2.44-2.19 (m, 4H), 2.03-1.89 (m, 2H), 1.80-1.54 (m, 4H), 0.96 (t, J=7.6 Hz, 3H). LC/MS [M+H] 1244.5 (calculated); LC/MS [M+H]1244.2 (observed).

Example L-131 Synthesis of 4-[3-[2-[2-[3-[4-[2-[5-amino-7-[ethoxy(propyl)carbamoyl]-6H-thieno[3,2-b]azepin-2-yl]ethyl]-1-piperidyl]-3-oxo-propoxy]ethoxy]ethoxy]propanoyloxy]-2,3,5,6-tetrafluoro-benzenesulfonic Acid, TAZ-L-131

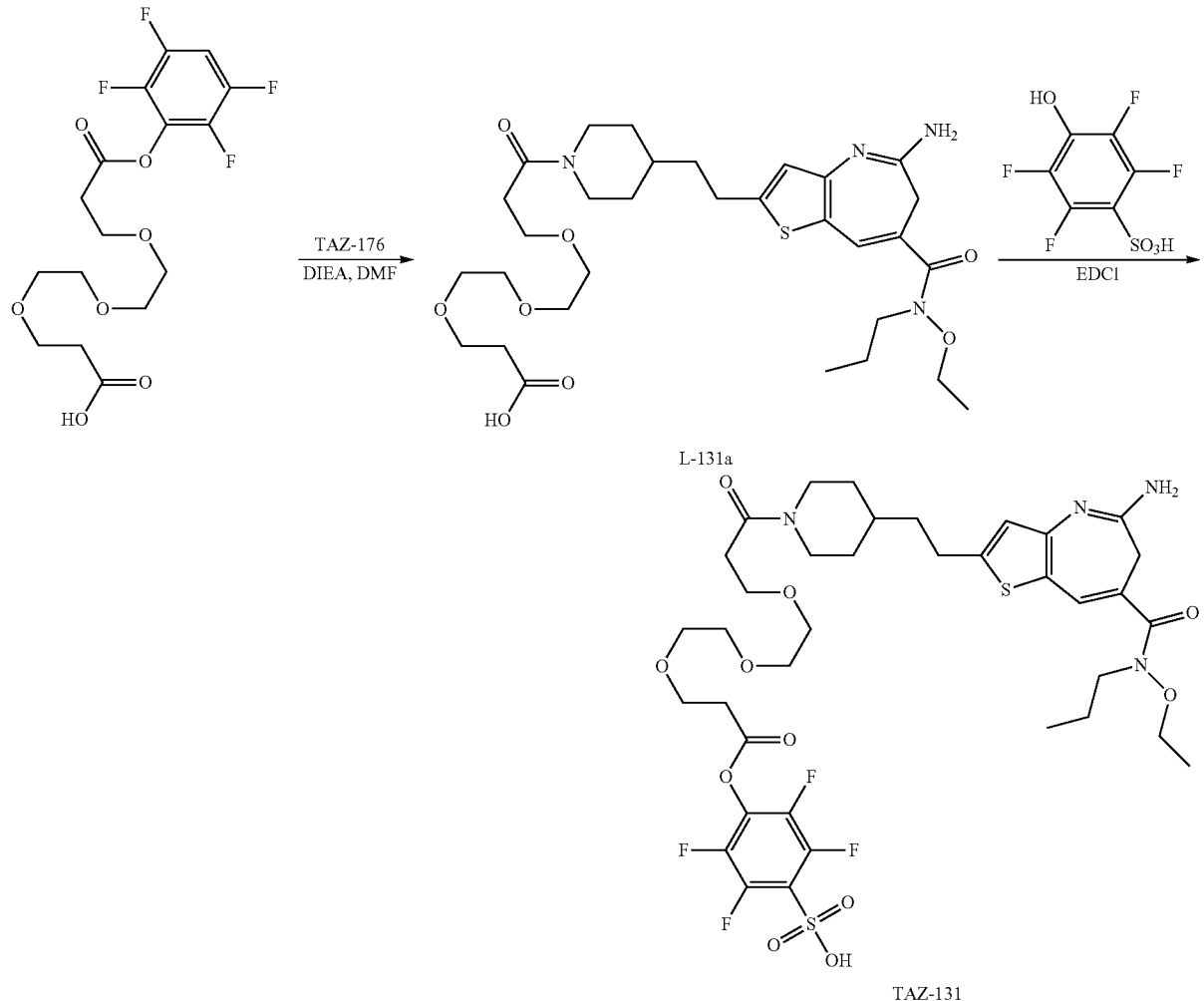 [SMILES: O=C(O)CCOCCOCCOCCC(=O)Oc1c(F)c(F)cc(F)c1F ; CCCN(OCC)C(=O)C1=Cc2sc(CCC3CCN(C(=O)CCOCCOCCOCCC(=O)O)CC3)cc2N=C(N)C1 ; O=S(=O)(O)c1c(F)c(F)c(O)c(F)c1F ; CCCN(OCC)C(=O)C1=Cc2sc(CCC3CCN(C(=O)CCOCCOCCOCCC(=O)Oc4c(F)c(F)c(S(=O)(=O)O)c(F)c4F)CC3)cc2N=C(N)C1]

Preparation of 3-[2-[2-[3-[4-[2-[5-amino-7-[ethoxy(propyl)carbamoyl]-6H-thieno [3,2-b]azepin-2-yl]ethyl]-1-piperidyl]-3-oxo-propoxy]ethoxy]ethoxy]propanoic Acid, L-131a To a mixture of 5-amino-N-ethoxy-2-[2-(4-piperidyl)ethyl]-N-propyl-6H-thieno[3,2-b]azepine-7-carboxamide, TAZ-176 (0.1 g, 227 umol, 1.0 eq, HCl) in DMF (2 mL) was added DIEA (87.9 mg, 680 umol, 118 uL, 3.0 eq) and 3-[2-[2-[3-oxo-3-(2,3,5,6-tetrafluorophenoxy)propoxy]ethoxy]ethoxy]propanoic acid (90.3 mg, 227 umol, 1.0 eq) in one portion at 0° C. and it was stirred at 0° C. for 0.5 h. The mixture was purified by prep-HPLC (column: Welch Xtimate C18 100*25 mm*3 um; mobile phase: [water (0.05% HCl)-ACN]; B %: 15%-35%, 8 min) to give L-131a (0.06 g, 94.22 umol, 41.55% yield) as yellow oil. ¹H NMR (MeOD, 400 MHz) δ7.46 (s, 1H), 6.89 (s, 1H), 4.54 (d, J=13.6 Hz, 1H), 4.04 (d, J=13.6 Hz, 1H), 3.93 (q, J=7.2 Hz, 2H), 3.77-3.69 (m, 6H), 3.63-3.58 (m, 8H), 3.42 (s, 2H), 3.15-3.01 (m, 1H), 2.94 (t, J=7.6 Hz, 2H), 2.75-2.51 (m, 5H), 1.88-1.78 (m, 2H), 1.78-1.71 (m, 2H), 1.70-1.65 (m, 2H), 1.29-1.07 (m, 5H), 0.97 (t, J=7.6 Hz, 3H).

Preparation of TAZ-L-131

To a mixture of L-131a (0.06 g, 89.1 umol, 1.0 eq, HCl) and sodium 2,3,5,6-tetrafluoro-4-hydroxy-benzenesulfonate (95.6 mg, 356 umol, 4.0 eq) in DCM (1.5 mL) and DMA (0.3 mL) was added EDCI (103 mg, 535 umol, 6.0 eq) in one portion at 25° C. and it was stirred at 25° C. for 0.5 h. The mixture was concentrated to give a residue, and the residue was purified by prep-HPLC (column: Phenomenex Synergi C18 150*25*10 um; mobile phase: [water (0.2% FA)-ACN]; B %: 20%-45%, 8 min) to give TAZ-L-131 (31.7 mg, 36.65 umol, 41.13% yield) as white solid. ¹H NMR (MeOD, 400 MHz) δ7.43 (s, 1H), 6.88 (s, 1H), 4.51 (d, J=13.2 Hz, 1H), 4.01 (d, J=13.6 Hz, 1H), 3.96-3.84 (m, 4H), 3.78-3.69 (m, 4H), 3.68-3.54 (m, 8H), 3.42 (s, 2H), 3.07-3.01 (m, 1H), 2.98 (t, J=5.6 Hz, 2H), 2.88 (t, J=7.2 Hz, 2H), 2.74-2.53 (m, 3H), 1.84-1.68 (m, 4H), 1.68-1.55 (m, 3H), 1.25-1.03 (m, 5H), 0.97 (t, J=7.6 Hz, 3H). LC/MS [M+H] 865.3 (calculated); LC/MS [M+H] 865.3 (observed).
Example L-133 Synthesis of 4-[3-[2-[2-[2-[2-[2-[2-[2-[2-[2-[2-[3-[[5-amino-7-[2-(cyclobutoxycarbonylamino)ethoxy-propyl-carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]ethoxy]propanoyloxy]-2,3,5,6-tetrafluorobenzenesulfonic Acid, TAZ-L-133
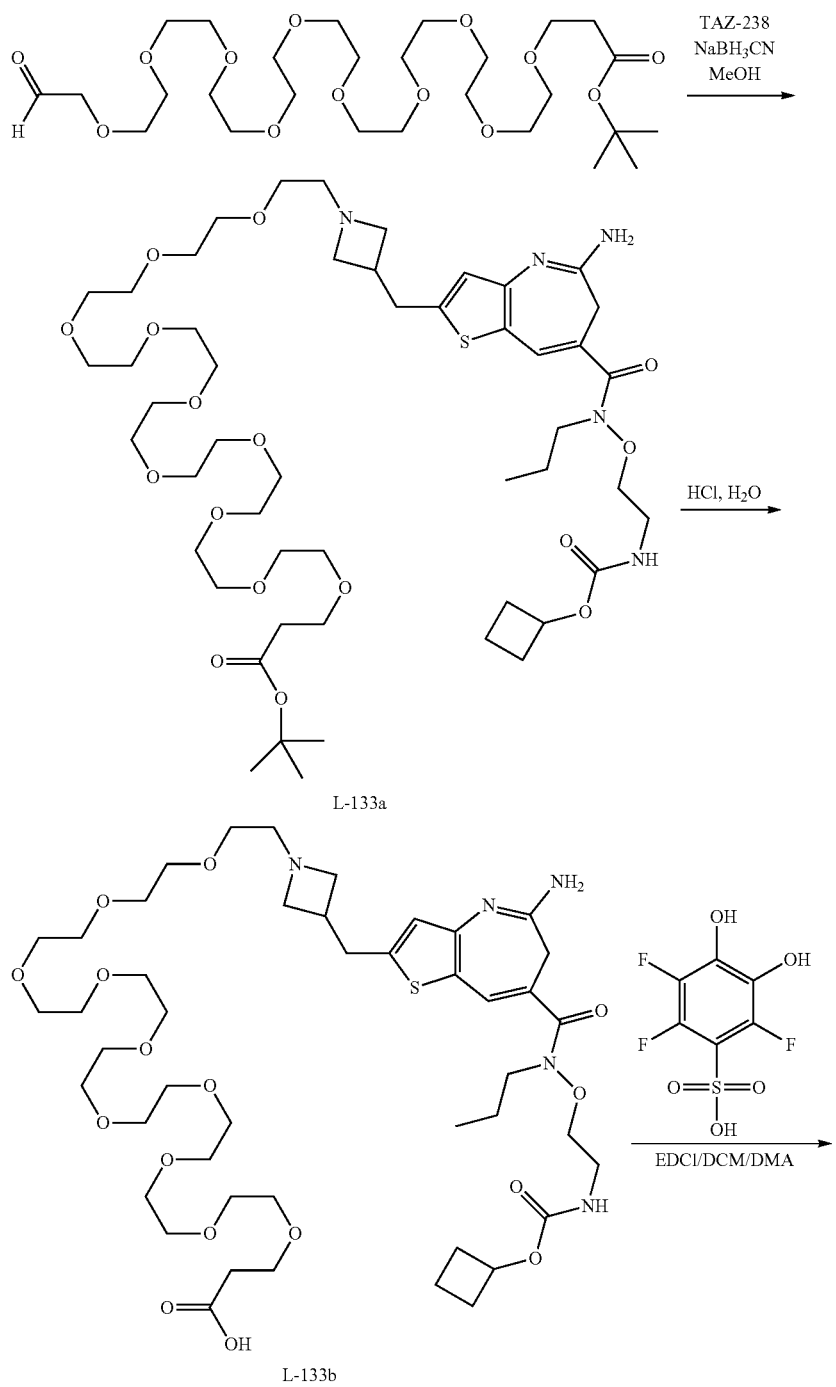

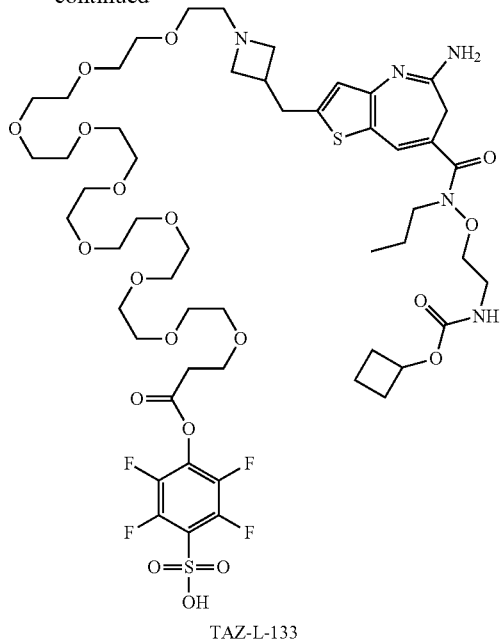

TAZ-L-133

Preparation of tert-butyl 3-[2-[2-[2-[2-[2-[2-[2-[2-[2-[2-[3-[[5-amino-7-[2-(cyclobutoxycarbonylamino)ethoxy-propyl-carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]propanoate, L-133a To a mixture of cyclobutyl N-[2-[[5-amino-2-(azetidin-3-ylmethyl)-6H-thieno[3,2-b]azepine-7-carbonyl]-propyl-amino]oxyethyl]carbamate, TAZ-238 (0.14 g, 199 umol, 1.0 eq, TFA) and tert-butyl 3-[2-[2-[2-[2-[2-[2-[2-[2-[2-(2-oxo-ethoxy)ethoxy]ethoxy]ethoxy]ethoxy]ethoxy]ethoxy]ethoxy]ethoxy]propanoate (151 mg, 259 umol, 1.3 eq) in MeOH (3 mL) was added NaBH₃CN (25.0 mg, 398 umol, 2.0 eq) in one portion at 25° C. and then stirred at 25° C. for 12 h. The mixture was concentrated. The residue was purified by prep-HPLC (column: Phenomenex Synergi C18 150*25*10 um; mobile phase: [water (0.1% TFA)-ACN]; B %: 20%-50%, 8 min) to give L-133a (0.2 g, 173 umol, 86.8% yield, TFA) as yellow oil. ¹H NMR (MeOD, 400 MHz) δ7.49 (s, 1H), 6.98 (s, 1H), 4.85-4.80 (m, 1H), 4.44-4.25 (m, 2H), 4.18-3.97 (m, 2H), 3.92 (t, J=5.2 Hz, 2H), 3.74-3.67 (m, 6H), 3.66-3.61 (m, 40H), 3.42 (s, 2H), 3.28-3.23 (m, 3H), 2.47 (td, J=1.6, 6.4 Hz, 2H), 2.31-2.19 (m, 2H), 2.02-1.91 (m, 2H), 1.76-1.71 (m, 3H), 1.67-1.54 (m, 1H), 1.45 (s, 9H), 0.96 (t, J=7.6 Hz, 3H).

Preparation of 3-[2-[2-[2-[2-[2-[2-[2-[2-[2-[2-[3-[[5-amino-7-[2-(cyclobutoxycarbonylamino)ethoxy-propyl-carbamoyl]-6H-thieno[3,2-b]azepin-2-yl]methyl]azetidin-1-yl]ethoxy]ethoxy]ethoxy]ethoxy]ethoxy]ethoxy]ethoxy]ethoxy]ethoxy]propanoic Acid, L-133b To a mixture of L-133a (0.2 g, 173 umol, 1.0 eq, TFA) in H₂O (3 mL) and CH₃CN (0.5 mL) was added HCl (12 M, 216 uL, 15.0 eq) in one portion at 25° C. and then stirred at 80° C. for 0.5 h. The mixture was concentrated. The residue was purified by prep-HPLC (column: Welch Xtimate C18 100*25 mm*3 um; mobile phase: [water (0.05% HCl)-ACN]; B %: 10%-30%, 8 min) to give L-133b (40 mg, 39.0 umol, 22.6% yield, HCl) as yellow oil.

Preparation of TAZ-L-133

To a mixture of L-133b (40 mg, 39.0 umol, 1.0 eq, HCl) and sodium 2,3,5,6-tetrafluoro-4-hydroxy-benzenesulfonate (41.9 mg, 156 umol, 4.0 eq) in DCM (1 mL) and DMA (0.1 mL) was added EDCI (52.4 mg, 273 umol, 7.0 eq) in one portion at 25° C. and then stirred at 25° C. for 0.5 h. The mixture was filtered and concentrated. The residue was purified by prep-HPLC (column: Phenomenex Synergi C18 150*25*10 um; mobile phase: [water (0.1% TFA)-ACN]; B %: 10%-30%, 8 min) to give TAZ-L-133 (14.7 mg, 12.1 umol, 30.9% yield) as yellow oil. ¹H NMR (MeOD, 400 MHz) δ7.48 (s, 1H), 7.02-6.96 (m, 1H), 4.84-4.84 (m, 1H), 4.41-4.25 (m, 2H), 4.15-4.14 (m, 1H), 4.19-3.97 (m, 2H), 3.95-3.84 (m, 4H), 3.76-3.68 (m, 4H), 3.68-3.58 (m, 38H), 3.52-3.44 (m, 2H), 3.42 (s, 2H), 3.28-3.21 (m, 3H), 2.99 (t, J=5.6 Hz, 2H), 2.25 (q, J=8.4 Hz, 2H), 2.04-1.90 (m, 2H), 1.80-1.54 (m, 4H), 0.96 (t, J=7.6 Hz, 3H). LC/MS [M+H] 1216.5 (calculated); LC/MS [M+H] 1216.6 (observed).

Example L-139 Synthesis of 4-[3-[2-[2-[2-[2-[2-[2-[2-[2-[2-[3-[3-[[5-amino-7-[isopropoxy(propyl)carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoyloxy]-2,3,5,6-tetrafluoro-benzenesulfonic Acid, TAZ-L-139
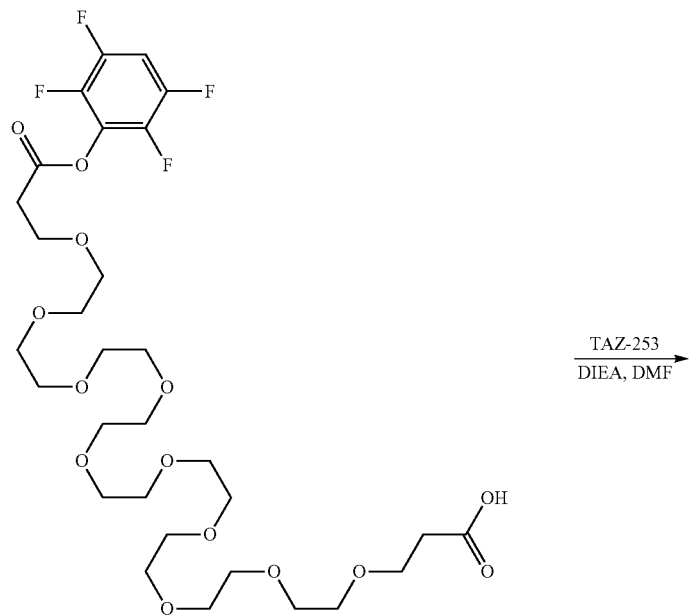
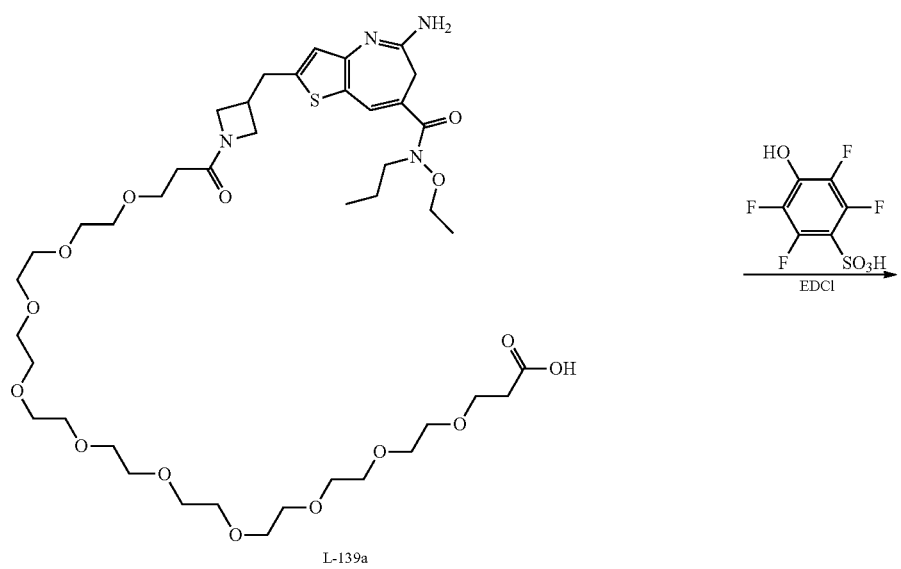

-continued

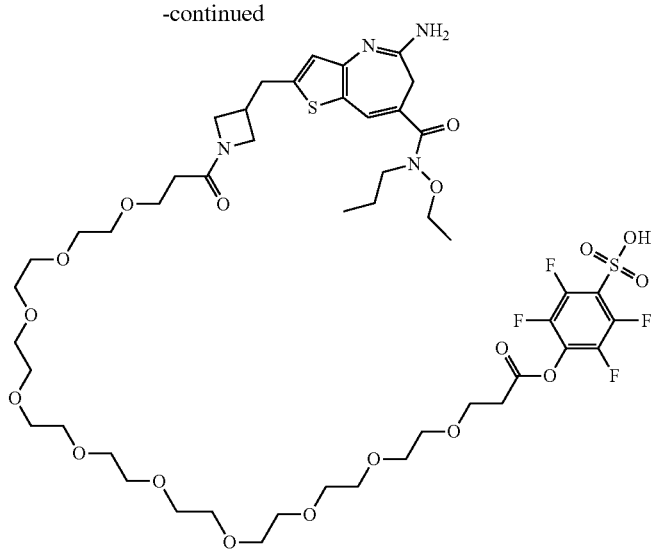

TAZ-L-139

Preparation of 3-[2-[2-[2-[2-[2-[2-[2-[2-[2-[3-[3-[[5-amino-7-[isopropoxy(propyl) carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoic Acid, L-139a To a mixture of 5-amino-2-(azetidin-3-ylmethyl)-N-isopropoxy-N-propyl-6H-thieno[3,2-b]azepine-7-carboxamide, TAZ-253 (100 mg, 204 umol, 1 eq, TFA) and 3-[2-[2-[2-[2-[2-[2-[2-[2-[3-oxo-3-(2,3,5,6-tetrafluorophenoxy)propoxy]ethoxy]ethoxy]ethoxy]ethoxy]ethoxy]ethoxy]ethoxy]ethoxy]propanoic acid (158 mg, 224 umol, 1.1 eq) in THF (3 mL) was added Et₃N (61.9 mg, 612 umol, 85.1 uL, 3 eq), and then stirred at 20° C. for 1 h. The residue was poured into water (5 mL) and the pH of the mixture was adjusted to about 6 with 1M HCl. The aqueous phase was extracted with ethyl acetate (8 mL×1)-discarded, the aqueous phase was further extracted with dichloromethane/isopropyl alcohol=3:1 (8 mL×3), the combined organic phase was dried with anhydrous Na₂SO₄, filtered and concentrated in vacuum to give L-139a (150 mg, 164 umol, 80.23% yield) as a light yellow oil.

Preparation of TAZ-L-139

To a solution of L-139a (100 mg, 109 umol, 1 eq) in DCM (1.5 mL) and DMA (0.5 mL) was added sodium 2,3,5,6-tetrafluoro-4-hydroxy-benzenesulfonate (117 mg, 436 umol, 4 eq) and EDCI (83.6 mg, 436 umol, 4 eq), and then stirred at 20° C. for 2 h. The reaction mixture was filtered and concentrated under residue pressure. The residue was purified by prep-HPLC (column: Phenomenex Synergi C18 150*25*10 um; mobile phase: [water (0.1% TFA)-ACN]; B %: 15%-35%, 8 min) to give TAZ-L-139 (69.7 mg, 55.3 umol, 50.76% yield, TFA) as a light yellow solid. ¹H NMR (MeOD, 400 MHz) δ7.45 (s, 1H), 6.96 (s, 1H), 4.85-4.80 (m, 1H), 4.39 (t, J=8.6 Hz, 1H), 4.26-4.20 (m, 1H), 4.11 (t, J=9.2 Hz, 1H), 4.02 (dd, J=5.2, 8.5 Hz, 1H), 3.87 (t, J=5.8 Hz, 2H), 3.82-3.67 (m, 6H), 3.66-3.58 (m, 34H), 3.42 (s, 2H), 3.18 (d, J=7.8 Hz, 2H), 3.05-2.95 (m, 3H), 2.42-2.31 (m, 2H), 1.79-1.69 (m, 2H), 1.18 (d, J=6.2 Hz, 6H), 0.95 (t, J=7.4 Hz, 3H). LC/MS [M+H] 1145.4 (calculated); LC/MS [M+H] 1145.4 (observed).

Example L-144 Synthesis of 4-[3-[2-[2-[2-[2-[2-[2-[2-[2-[2-[3-[3-[[5-amino-7-[2-(isopropoxycarbonylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoyloxy]-2,3,5,6-tetrafluoro-benzenesulfonic Acid, TAZ-L-144

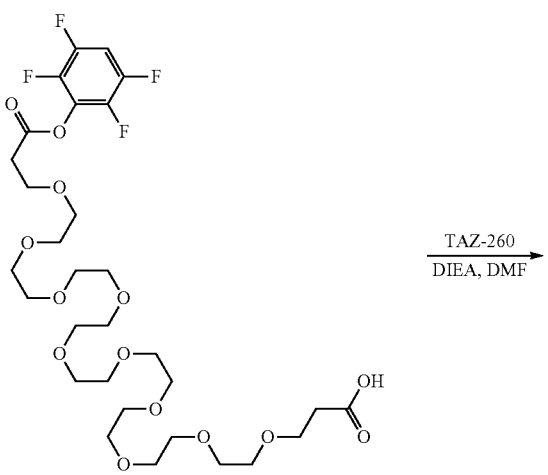

TAZ-260
DIEA, DMF

-continued

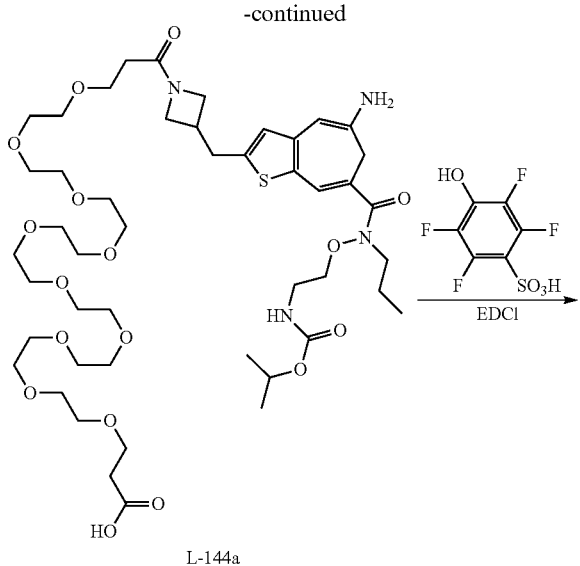

L-144a

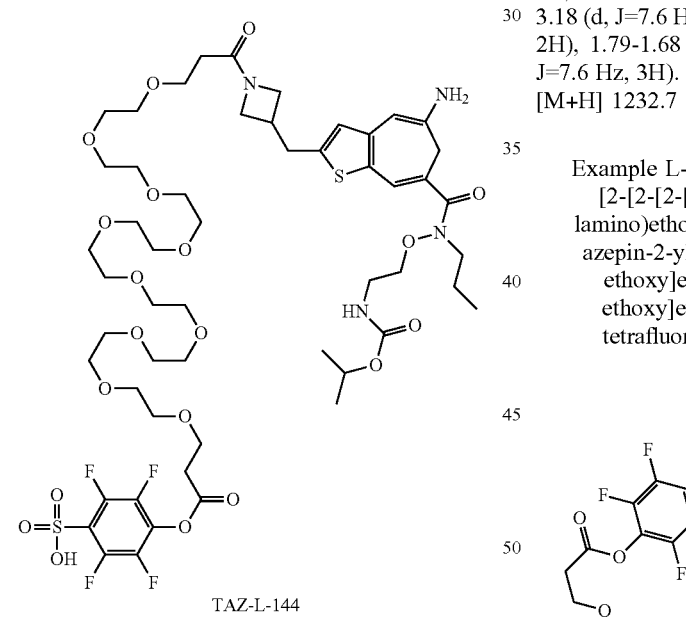

TAZ-L-144

Preparation of 3-[2-[2-[2-[2-[2-[2-[2-[2-[2-[3-[3-[[5-amino-7-[2-(isopropoxycarbonylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoic Acid, L-144a To a mixture of isopropyl N-[2-[[5-amino-2-(azetidin-3-ylmethyl)-6H-thieno[3,2-b]azepine-7-carbonyl]-propyl-amino]oxyethyl]carbamate, TAZ-260 (0.13 g, 161 umol, 1.0 eq, TFA salt) in THF (4 mL) was added Et₃N (49.0 mg, 484 umol, 67.4 uL, 3.0 eq) and 3-[2-[2-[2-[2-[2-[2-[2-[2-[3- oxo-3-(2,3,5,6-tetrafluorophenoxy)propoxy]ethoxy]ethoxy]ethoxy]ethoxy]ethoxy]ethoxy]ethoxy]ethoxy]propanoic acid (114 mg, 161 umol, 1.0 eq) in one portion at 0° C. and then stirred at 0° C. for 0.5 h. The mixture was diluted with water (5 mL) and the pH of the mixture was adjusted to ~6 with TFA. Then it was extracted with EtOAc (10 mL)-discarded. The water phase was further extracted with DCM:i-PrOH=3:1 (10 mL×3). The organic layer was dried over Na₂SO₄, filtered and concentrated to give L-144a (0.21 g, crude, 3TFA) as yellow oil.

Preparation of TAZ-L-144

To a mixture of L-144a (0.2 g, 199 umol, 1.0 eq) in DCM (3 mL) and DMA (0.3 mL) was added sodium; 2,3,5,6-tetrafluoro-4-hydroxy-benzenesulfonate (267 mg, 996 umol, 5.0 eq) and EDCI (267 mg, 1.39 mmol, 7.0 eq) in one portion at 25° C. and then stirred at 25° C. for 0.5 h. The mixture was concentrated to give a residue. The residue was purified by prep-HPLC (column: Phenomenex Synergi C18 150*25*10 um; mobile phase: [water (0.1% TFA)-ACN]; B %: 15%-40%, 8 min) to give TAZ-L-144 (98.2 mg, 79.69 umol, 40.01% yield) as light yellow oil. ¹H NMR (MeOH, 400 MHz) δ7.49 (s, 1H), 6.96 (s, 1H), 4.82-4.74 (m, 1H), 4.39 (t, J=8.8 Hz, 1H), 4.11 (t, J=9.2 Hz, 1H), 4.03 (dd, J=5.6, 9.2 Hz, 1H), 3.93 (t, J=5.2 Hz, 2H), 3.87 (t, J=6.0 Hz, 2H), 3.76-3.69 (m, 5H), 3.68-3.52 (m, 38H), 3.43 (s, 2H), 3.18 (d, J=7.6 Hz, 2H), 2.98 (t, J=6.0 Hz, 3H), 2.43-2.30 (m, 2H), 1.79-1.68 (m, 2H), 1.17 (d, J=6.4 Hz, 6H), 0.95 (t, J=7.6 Hz, 3H). LC/MS [M+H] 1232.5 (calculated); LC/MS [M+H] 1232.7 (observed).

Example L-145 Synthesis of 4-[3-[2-[2-[2-[2-[2-[2-[2-[2-[2-[3-[3-[[5-amino-7-[2-(ethylcarbamoylamino)ethoxy-propyl-carbamoyl]-6H-thieno[3,2-b]azepin-2-yl]methyl]azetidin-1-yl]-3-oxo-propoxy]ethoxy]ethoxy]ethoxy]ethoxy]ethoxy]ethoxy]ethoxy]ethoxy]propanoyloxy]-2,3,5,6-tetrafluoro-benzenesulfonic Acid, TAZ-L-145

523
-continued

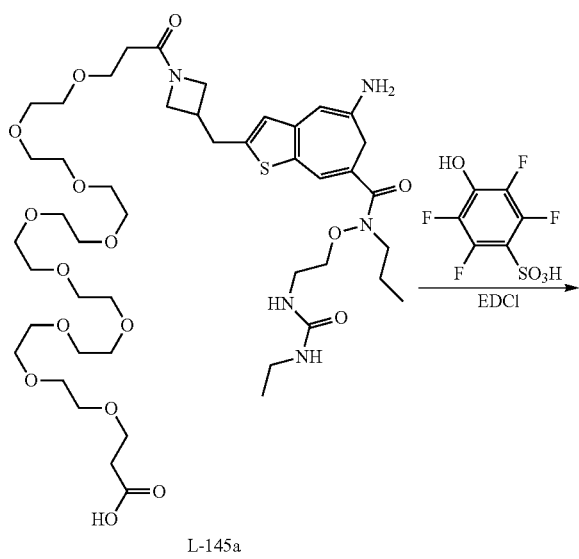

L-145a

Preparation of 3-[2-[2-[2-[2-[2-[2-[2-[2-[2-[3-[3-[[5-amino-7-[2-(ethylcarbamoylamino)ethoxy-propyl-carbamoyl]-6H-thieno[3,2-b]azepin-2-yl]methyl] azetidin-1-yl]-3-oxo-propoxy]ethoxy]ethoxy] ethoxy]ethoxy]ethoxy]ethoxy]ethoxy]ethoxy] propanoic Acid, L-145a To a solution of 5-amino-2-(azetidin-3-ylmethyl)-N-[2-(ethylcarbamoylamino) ethoxy]-N-propyl-6H-thieno[3,2-b]azepine-7-carboxamide, TAZ-261 (120 mg, 177 umol, 1 eq, TFA) in THF (3.00 mL) was added Et₃N (54.0 mg, 532 umol, 3 eq) and 3-[2-[2-[2-[2-[2-[2-[2-[2-[2-[3-oxo-3-(2,3,5,6-tetrafluorophenoxy)propoxy]ethoxy]ethoxy]ethoxy] ethoxy]ethoxy]ethoxy]ethoxy]ethoxy]propanoic acid (125 mg, 177 umol, 1 eq), and then stirred at 0° C. for 1 h. The mixture was diluted with water (10 mL) and the pH of the mixture was adjusted to about pH 6 by TFA and extracted with MTBE (10 mL)-discarded and the water phase was further extracted with DCM:i-PrOH=3:1 (20 mL×3). The organic layer was washed with brine (30 mL×3), dried over Na₂SO₄, filtered and concentrated to give L-145a (170 mg, 172 umol, 96.90% yield) as light yellow oil.

Preparation of TAZ-L-145

To a solution of L-145a (170 mg, 172 umol, 1 eq) and sodium 2,3,5,6-tetrafluoro-4-hydroxybenzenesulfonate (184 mg, 687 umol, 4 eq) in DCM (3.00 mL) and DMA (0.15 mL) was added EDCI (132 mg, 687 umol, 4 eq), and then stirred at 25° C. for 1 h. The mixture was concentrated to give a residue. The residue was purified by prep-HPLC (column: Phenomenex Synergi C18 150*25*10 um; mobile phase: [water (0.1% TFA)-ACN]; B %: 20%-40%, 8 min) to give TAZ-L-145 (103 mg, 77.37 umol, 45.02% yield, TFA) as light yellow oil. ¹H NMR (MeOD, 400 MHz) δ7.47 (s, 1H), 6.95 (s, 1H), 4.39 (t, J=8.5 Hz, 1H), 4.11 (t, J=9.0 Hz, 1H), 4.02 (dd, J=5.3, 8.8 Hz, 1H), 3.89 (td, J=5.6, 13.9 Hz, 4H), 3.76-3.68 (m, 6H), 3.67-3.56 (m, 36H), 3.44 (s, 2H), 3.18 (d, J=7.5 Hz, 2H), 3.07 (q, J=7.3 Hz, 3H), 2.98 (t, J=5.9 Hz, 2H), 2.44-2.30 (m, 2H), 1.79-1.69 (m, 2H), 1.05 (t, J=7.2 Hz, 3H), 0.96 (t, J=7.4 Hz, 3H). LC/MS [M+H] 1217.5 (calculated); LC/MS [M+H] 1217.6 (observed).

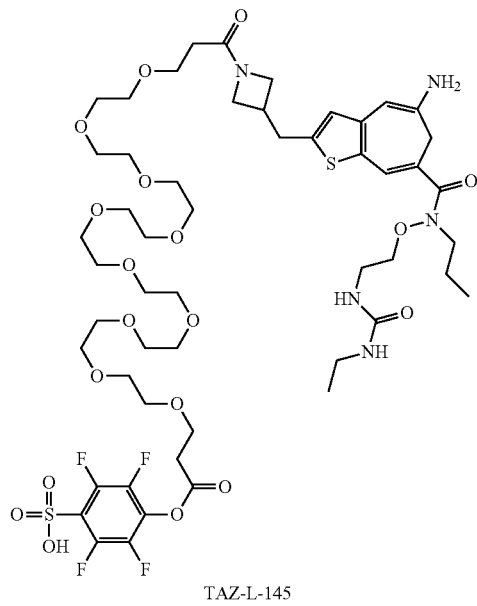

TAZ-L-145

Example L-147 Synthesis of 4-((40-(5-amino-7-((2-((cyclobutoxycarbonyl)amino)ethoxy)(propyl)carbamoyl)-6H-thieno[3,2-b]azepin-2-yl)-34-oxo-4,7,10,13,16,19,22,25,28,31-decaoxa-35-azatetracontanoyl)oxy)-2,3,5,6-tetrafluorobenzenesulfonic Acid, TAZ-L-147
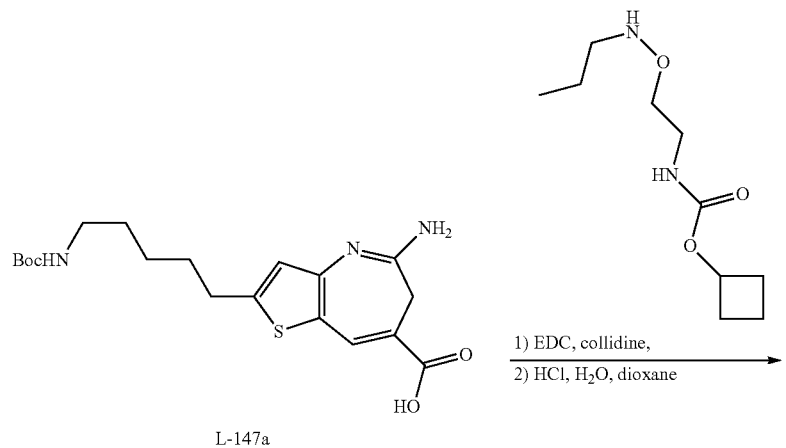
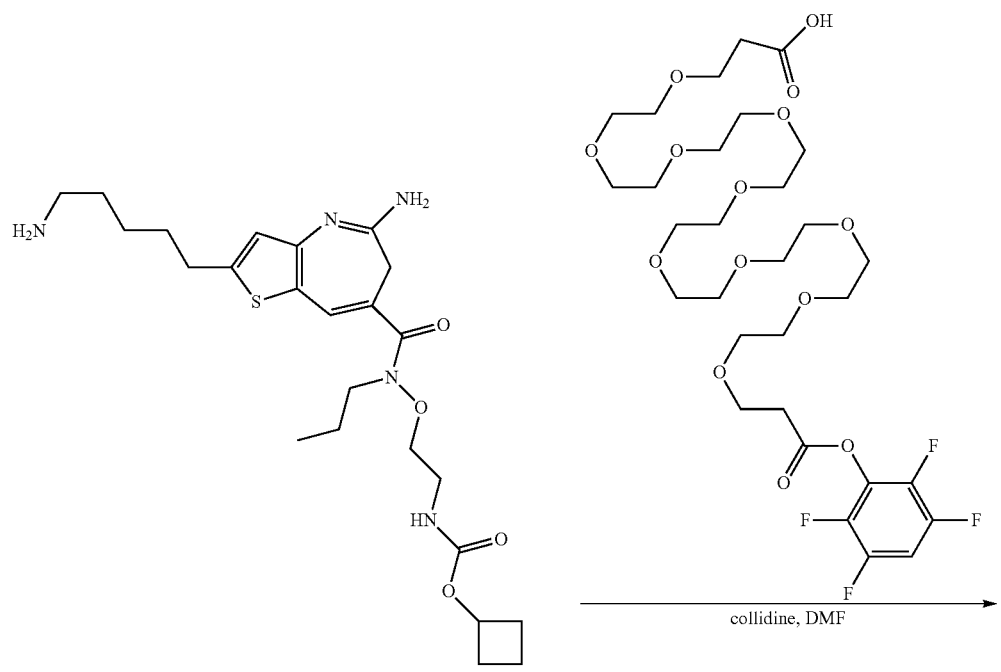

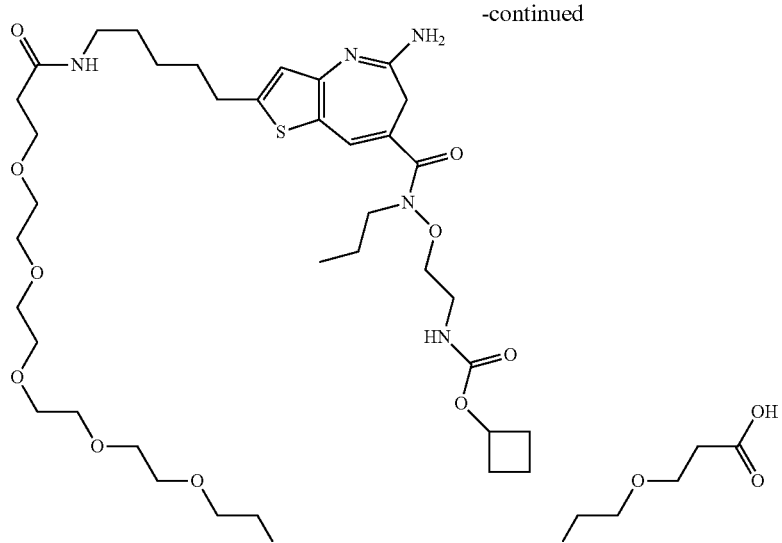

L-147c

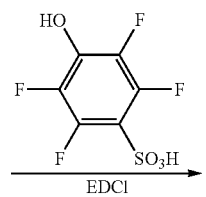

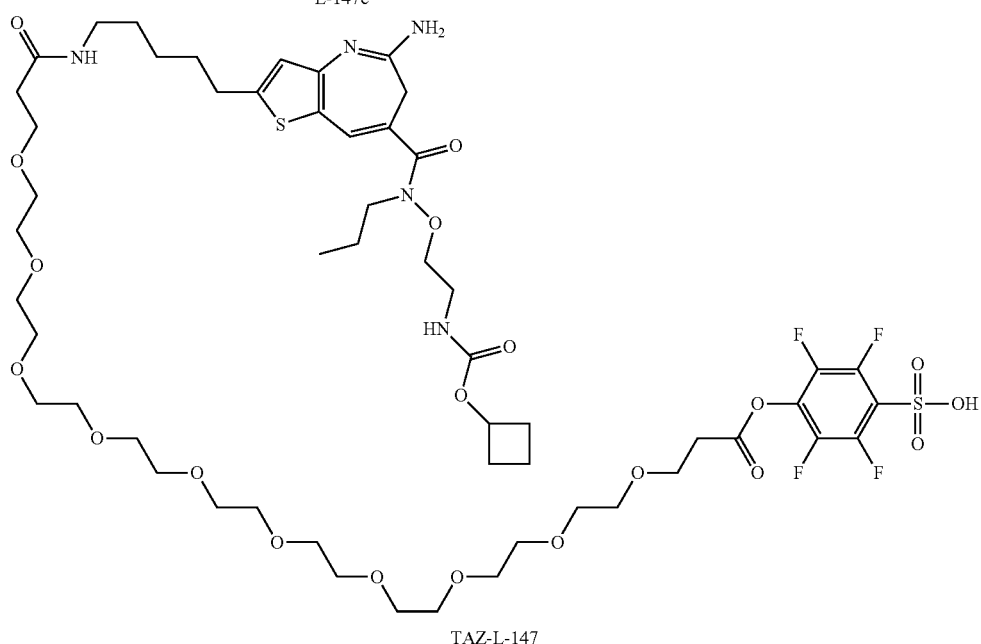

TAZ-L-147

Preparation of 5-(5-amino-7-((2-((cyclobutoxycarbonyl)amino)ethoxy)(propyl)carbamoyl)-6H-thieno[3,2-b]azepin-2-yl)pentan-1-aminium chloride, L-147b 5-Amino-2-(5-((tert-butoxycarbonyl)amino)pentyl)-6H-thieno[3,2-b]azepine-7-carboxylic acid, L-147a (0.78 g, 1.98 mmol, 1 equiv.) and cyclobutyl (2-((propylamino)oxy)ethyl)carbamate (0.5 g, 1.98 mmol, 1 equiv.) were combined in DMF. Collidine (0.52 ml, 3.9 mmol, 1.98 equiv.) was added, followed by EDCI, also known as EDC, 1-ethyl-3-(3-dimethylaminopropyl)carbodiimide, CAS Reg. No. 1892-57-5 (0.38 g, 1.98 mmol, 1 equiv.). The reaction monitored by LCMS, then concentrated and purified by reverse-phase flash chromatography. Combined fractions were lyophilized, then taken up in 4 N HCl/dioxane. The deprotected product was purified by reverse-phase flash chromatography to give L-147b (0.8 g, 1.51 mmol, 82%). LC/MS [M+H] 492.26 (calculated); LC/MS [M+H] 492.45 (observed).

Preparation of 40-(5-amino-7-((2-((cyclobutoxycarbonyl)amino)ethoxy)(propyl)carbamoyl)-6H-thieno[3,2-b]azepin-2-yl)-34-oxo-4,7,10,13,16,19,22,25,28,31-decaoxa-35-azatetracontanoic Acid, L-147c Intermediate L-147b (0.148 g, 0.3 mmol, 1 equiv.) and 34-oxo-34-(2,3,5,6-tetrafluorophenoxy)-4,7,10,13,16,19,22,25,28,31-decaoxatetratriacontanoic acid (0.23 g, 0.32 mmol, 1.07 equiv.) were dissolved in 3 ml DMF. Collidine (0.2 ml, 1.5 mmol, 5 equiv.) was added, and the reaction stirred at ambient temperature. The reaction was purified by reverse-phase HPLC to give L-147c (0.16 g, 0.16 mmol, 52%). LC/MS [M+H] 1032.54 (calculated); LC/MS [M+H] 1032.81 (observed).

Preparation of TAZ-L-147

Intermediate L-147c (0.16 g, 0.155 mmol, 1 equiv.) and 2,3,5,6-tetrafluoro-4-hydroxybenzenesulfonic acid (0.083 g, 0.31 mmol, 2 equiv.) were dissolved in 2 ml DMF. Collidine (0.1 ml, 0.78 mmol, 5 equiv.) was added, followed by EDC (0.045 g, 0.23 mmol, 1.5 equiv.). The reaction was stirred at room temperature and monitored by LCMS, then diluted with water and purified by reverse-phase HPLC to give TAZ-L-147 (0.095 g, 0.075 mmol, 49%). LC/MS [M+H] 1260.49 (calculated); LC/MS [M+H] 1260.70 (observed).

Example 201 Preparation of Immunoconjugates (IC)

In an exemplary procedure, an antibody is buffer exchanged into a conjugation buffer containing 100 mM boric acid, 50 mM sodium chloride, 1 mM ethylenediaminetetraacetic acid at pH 8.3, using G-25 SEPHADEX™ desalting columns (Sigma-Aldrich, St. Louis, Mo.). The eluates are then each adjusted to a concentration of about 1-10 mg/ml using the buffer and then sterile filtered. The antibody is pre-warmed to 20-30° C. and rapidly mixed with 2-20 (e.g., 7-10) molar equivalents of thienoazepine-linker (TAZ-L) compound of Formula II. The reaction is allowed to proceed for about 16 hours at 30° C. and the immunoconjugate (IC) is separated from reactants by running over two successive G-25 desalting columns equilibrated in phosphate buffered saline (PBS) at pH 7.2 to provide the Immunoconjugate (IC) of Table 3. Adjuvant-antibody ratio (DAR) is determined by liquid chromatography mass spectrometry analysis using a C4 reverse phase column on an ACQUITY™ UPLC H-class (Waters Corporation, Milford, Mass.) connected to a XEVO™ G2-XS TOF mass spectrometer (Waters Corporation).

For conjugation, the antibody may be dissolved in a aqueous buffer system known in the art that will not adversely impact the stability or antigen-binding specificity of the antibody. Phosphate buffered saline may be used. The thienoazepine-linker (TAZ-L) intermediate compound is dissolved in a solvent system comprising at least one polar aprotic solvent as described elsewhere herein. In some such aspects, thienoazepine-linker (TAZ-L) intermediate is dissolved to a concentration of about 5 mM, about 10 mM, about 20 mM, about 30 mM, about 40 mM or about 50 mM, and ranges thereof such as from about 5 mM to about 50 mM or from about 10 mM to about 30 mM in pH 8 Tris buffer (e.g., 50 mM Tris). In some aspects, the thienoazepine-linker intermediate is dissolved in DMSO (dimethylsulfoxide), DMA (dimethylacetamide) or acetonitrile, or another suitable dipolar aprotic solvent.

Alternatively in the conjugation reaction, an equivalent excess of thienoazepine-linker (TAZ-L) intermediate solution may be diluted and combined with antibody solution. The thienoazepine-linker intermediate solution may suitably be diluted with at least one polar aprotic solvent and at least one polar protic solvent, examples of which include water, methanol, ethanol, n-propanol, and acetic acid. The molar equivalents of thienoazepine-linker intermediate to antibody may be about 1.5:1, about 3:1, about 5:1, about 10:1, about 15:1, or about 20:1, and ranges thereof, such as from about 1.5:1 to about 20:1 from about 1.5:1 to about 15:1, from about 1.5:1 to about 10:1, from about 3:1 to about 15:1, from about 3:1 to about 10:1, from about 5:1 to about 15:1 or from about 5:1 to about 10:1. The reaction may suitably be monitored for completion by methods known in the art, such as LC-MS. The conjugation reaction is typically complete in a range from about 1 hour to about 16 hours. After the reaction is complete, a reagent may be added to the reaction mixture to quench the reaction. If antibody thiol groups are reacting with a thiol-reactive group such as maleimide of the thienoazepine-linker intermediate, unreacted antibody thiol groups may be reacted with a capping reagent. An example of a suitable capping reagent is ethylmaleimide.

Following conjugation, the immunoconjugates may be purified and separated from unconjugated reactants and/or conjugate aggregates by purification methods known in the art such as, for example and not limited to, size exclusion chromatography, hydrophobic interaction chromatography, ion exchange chromatography, chromatofocusing, ultrafiltration, centrifugal ultrafiltration, tangential flow filtration, and combinations thereof. For instance, purification may be preceded by diluting the immunoconjugate, such in 20 mM sodium succinate, pH 5. The diluted solution is applied to a cation exchange column followed by washing with, e.g., at least 10 column volumes of 20 mM sodium succinate, pH 5. The conjugate may be suitably eluted with a buffer such as PBS.

Example 202 HEK Reporter Assay

HEK293 reporter cells expressing human TLR7 or human TLR8 were purchased from Invivogen and vendor protocols were followed for cellular propagation and experimentation. Briefly, cells were grown to 80-85% confluence at 5% $CO_2$ in DMEM supplemented with 10% FBS, Zeocin, and Blasticidin. Cells were then seeded in 96-well flat plates at $4\times10^4$ cells/well with substrate containing HEK detection medium and immunostimulatory molecules. Activity was measured using a plate reader at 620-655 nm wavelength.

Example 203 Assessment of Immunoconjugate Activity In Vitro

This example shows that Immunoconjugates of the invention are effective at eliciting myeloid activation, and therefore are useful for the treatment of cancer.

Isolation of Human Antigen Presenting Cells: Human myeloid antigen presenting cells (APCs) were negatively selected from human peripheral blood obtained from healthy blood donors (Stanford Blood Center, Palo Alto, Calif.) by density gradient centrifugation using a ROSETTESEP™ Human Monocyte Enrichment Cocktail (Stem Cell Technologies, Vancouver, Canada) containing monoclonal antibodies against CD14, CD16, CD40, CD86, CD123, and HLA-DR. Immature APCs were subsequently purified to >90% purity via negative selection using an EASYSEP™ Human Monocyte Enrichment Kit (Stem Cell Technologies) without CD16 depletion containing monoclonal antibodies against CD14, CD16, CD40, CD86, CD123, and HLA-DR.

Myeloid APC Activation Assay: $2\times10^5$ APCs were incubated in 96-well plates (Corning, Corning, N.Y.) containing iscove's modified dulbecco's medium, IMDM (Lonza) supplemented with 10% FBS, 100 U/mL penicillin, 100 µg/mL (micrograms per milliliter) streptomycin, 2 mM L-glutamine, sodium pyruvate, non-essential amino acids, and where indicated, various concentrations of unconjugated (naked) PD-L1 or HER2 antibodies and immunoconjugates of the invention (as prepared according to the Example above). Trastuzumab and avelumab were used as the antibody constructs. Cell-free supernatants were analyzed after 18 hours via ELISA to measure TNFα secretion as a readout of a proinflammatory response.

All references, including publications, patent applications, and patents, cited herein are hereby incorporated by reference to the same extent as if each reference were individually and specifically indicated to be incorporated by reference and were set forth in its entirety herein.

The invention claimed is:

1. A 5-aminothienoazepine-linker compound of Formula II:

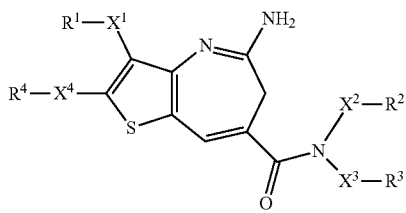

where one of $R^1$, $R^2$, $R^3$, and $R^4$ is attached to L;
$R^1$, $R^2$, $R^3$, and $R^4$ are independently selected from the group consisting of H, $C_1$-$C_{12}$ alkyl, $C_2$-$C_6$ alkenyl, $C_2$-$C_6$ alkynyl, $C_3$-$C_{12}$ carbocyclyl, $C_6$-$C_{20}$ aryl, $C_2$-$C_9$ heterocyclyl, and $C_1$-$C_{20}$ heteroaryl, where alkyl, alkenyl, alkynyl, carbocyclyl, aryl, heterocyclyl, and heteroaryl are independently and optionally substituted with one or more groups selected from:
—($C_1$-$C_{12}$ alkyldiyl)-N($R^5$)—*;
—($C_1$-$C_{12}$ alkyldiyl)-N($R^5$)$_2$;
—($C_1$-$C_{12}$ alkyldiyl)-O$R^5$;
—($C_3$-$C_{12}$ carbocyclyl);
—($C_3$-$C_{12}$ carbocyclyl)-*;
—($C_3$-$C_{12}$ carbocyclyl)-($C_1$-$C_{12}$ alkyldiyl)-N$R^5$—*;
—($C_3$-$C_{12}$ carbocyclyl)-($C_1$-$C_{12}$ alkyldiyl)-N($R^5$)$_2$;
—($C_3$-$C_{12}$ carbocyclyl)-N$R^5$—C(=N$R^5$)N$R^5$—*;
—($C_6$-$C_{20}$ aryl);
—($C_6$-$C_{20}$ aryl)-*;
—($C_6$-$C_{20}$ aryldiyl)-N($R^5$)—*;
—($C_6$-$C_{20}$ aryldiyl)-($C_1$-$C_{12}$ alkyldiyl)-N($R^5$)—*;
—($C_6$-$C_{20}$ aryldiyl)-($C_1$-$C_{12}$ alkyldiyl)-($C_2$-$C_{20}$ heterocyclyldiyl)-*;
—($C_6$-$C_{20}$ aryldiyl)-($C_1$-$C_{12}$ alkyldiyl)-N($R^5$)$_2$;
—($C_6$-$C_{20}$ aryldiyl)-($C_1$-$C_{12}$ alkyldiyl)-N$R^5$—C(=N$R^{5a}$)N($R^5$)—*;
—($C_2$-$C_{20}$ heterocyclyl);
—($C_2$-$C_{20}$ heterocyclyl)-*;
—($C_2$-$C_9$ heterocyclyl)-($C_1$-$C_{12}$ alkyldiyl)-N$R^5$—*;
—($C_2$-$C_9$ heterocyclyl)-($C_1$-$C_{12}$ alkyldiyl)-N($R^5$)$_2$;
—($C_2$-$C_9$ heterocyclyl)-C(=O)—($C_1$-$C_{12}$ alkyldiyl)-N($R^5$)—*;
—($C_2$-$C_9$ heterocyclyl)-N$R^5$—C(=N$R^{5a}$)N$R^5$—*;
—($C_2$-$C_9$ heterocyclyl)-N$R^5$—($C_6$-$C_{20}$ aryldiyl)-($C_1$-$C_{12}$ alkyldiyl)-N($R^5$)—*;
—($C_2$-$C_9$ heterocyclyl)-($C_6$-$C_{20}$ aryldiyl)-*;
—($C_1$-$C_{20}$ heteroaryl);
—($C_1$-$C_{20}$ heteroaryl)-*;
—($C_1$-$C_{20}$ heteroaryl)-($C_1$-$C_{12}$ alkyldiyl)-N($R^5$)—*;
—($C_1$-$C_{20}$ heteroaryl)-($C_1$-$C_{12}$ alkyldiyl)-N($R^5$)$_2$;
—($C_1$-$C_{20}$ heteroaryl)-N$R^5$—C(=N$R^{5a}$)N($R^5$)—*;

—($C_1$-$C_{20}$ heteroaryl)-N($R^5$)C(=O)—($C_1$-$C_{12}$ alkyldiyl)-N($R^5$)—*;
—C(=O)—*;
—C(=O)—($C_1$-$C_{12}$ alkyldiyl)-N($R^5$)—*;
—C(=O)—($C_2$-$C_{20}$ heterocyclyldiyl)-*;
—C(=O)N($R^5$)$_2$;
—C(=O)N($R^5$)—*;
—C(=O)N($R^5$)—($C_1$-$C_{12}$ alkyldiyl)-N($R^5$)C(=O)$R^5$;
—C(=O)N($R^5$)—($C_1$-$C_{12}$ alkyldiyl)-N($R^5$)C(=O)N($R^5$)$_2$;
—C(=O)N$R^5$—($C_1$-$C_{12}$ alkyldiyl)-N($R^5$)CO$_2R^5$;
—C(=O)N$R^5$—($C_1$-$C_{12}$ alkyldiyl)-N($R^5$)C(=N$R^{5a}$)N($R^5$)$_2$;
—C(=O)N$R^5$—($C_1$-$C_{12}$ alkyldiyl)-N$R^5$C(=N$R^{5a}$)$R^5$;
—C(=O)N$R^5$—($C_1$-$C_8$ alkyldiyl)-N$R^5$($C_2$-$C_5$ heteroaryl);
—C(=O)N$R^5$—($C_1$-$C_{20}$ heteroaryldiyl)-N($R^5$)—*;
—C(=O)N$R^5$—($C_1$-$C_{20}$ heteroaryldiyl)-*;
—C(=O)N$R^5$—($C_1$-$C_{20}$ heteroaryldiyl)-($C_1$-$C_{12}$ alkyldiyl)-N($R^5$)$_2$;
—C(=O)N$R^5$—($C_1$-$C_{20}$ heteroaryldiyl)-($C_2$-$C_{20}$ heterocyclyldiyl)-C(=O)N$R^5$—($C_1$-$C_{12}$ alkyldiyl)-N$R^5$—*;
—N($R^5$)$_2$;
—N($R^5$)—*;
—N($R^5$)C(=O)$R^5$;
—N($R^5$)C(=O)—*;
—N($R^5$)C(=O)N($R^5$)$_2$;
—N($R^5$)C(=O)N($R^5$)—*;
—N($R^5$)CO$_2R^5$;
—N$R^5$C(=N$R^{5a}$)N($R^5$)$_2$;
—N$R^5$C(=N$R^{5a}$)N($R^5$)—*;
—N$R^5$C(=N$R^{5a}$)$R^5$;
—N($R^5$)C(=O)—($C_1$-$C_{12}$ alkyldiyl)-N($R^5$)—*;
—N($R^5$)—($C_2$-$C_5$ heteroaryl);
—N($R^5$)—S(=O)$_2$—($C_1$-$C_{12}$ alkyl);
—O—($C_1$-$C_{12}$ alkyl);
—O—($C_1$-$C_{12}$ alkyldiyl)-N($R^5$)$_2$;
—O—($C_1$-$C_{12}$ alkyldiyl)-N($R^5$)—*;
—S(=O)$_2$—($C_2$-$C_{20}$ heterocyclyldiyl)-*;
—S(=O)$_2$—($C_2$-$C_{20}$ heterocyclyldiyl)-($C_1$-$C_{12}$ alkyldiyl)-N($R^5$)$_2$;
—S(=O)$_2$—($C_2$-$C_{20}$ heterocyclyldiyl)-($C_1$-$C_{12}$ alkyldiyl)-N$R^5$—*; and
—S(=O)$_2$—($C_2$-$C_{20}$ heterocyclyldiyl)-($C_1$-$C_{12}$ alkyldiyl)-OH;
or $R^2$ and $R^3$ together form a 5- or 6-membered heterocyclyl ring;
$X^1$, $X^2$, $X^3$, and $X^4$ are independently selected from the group consisting of a bond, C(=O), C(=O)N($R^5$), O, N($R^5$), S, S(O)$_2$, and S(O)$_2$N($R^5$);
$R^5$ is selected from the group consisting of H, $C_6$-$C_{20}$ aryl, $C_3$-$C_{12}$ carbocyclyl, $C_6$-$C_{20}$ aryldiyl, $C_1$-$C_{12}$ alkyl, and $C_1$-$C_{12}$ alkyldiyl, or two $R^5$ groups together form a 5- or 6-membered heterocyclyl ring;
$R^{5a}$ is selected from the group consisting of $C_6$-$C_{20}$ aryl and $C_1$-$C_{20}$ heteroaryl;
where the asterisk * indicates the attachment site of L, and where one of $R^1$, $R^2$, $R^3$ and $R^4$ is attached to L;
L is the linker selected from the group consisting of:
Q-C(=O)-(PEG)-;
Q-C(=O)-(PEG)-C(=O)—;
Q-C(=O)-(PEG)-O—;
Q-C(=O)-(PEG)-C(=O)—(PEP)-;
Q-C(=O)-(PEG)-C(=O)N($R^5$)—($C_1$-$C_{12}$ alkyldiyl)-;
Q-C(=O)-(PEG)-C(=O)N($R^5$)—($C_1$-$C_{12}$ alkyldiyl)-N($R^5$)C(=O)—($C_2$-$C_5$ monoheterocyclyldiyl)-;
Q-C(=O)-(PEG)-C(=O)N($R^5$)—($C_1$-$C_{12}$ alkyldiyl)-(MCgluc)-;
Q-C(=O)-(PEG)-C(=O)-(MCgluc)-;
Q-C(=O)-(PEG)-C(=O)—(PEP)-N($R^5$)—($C_1$-$C_{12}$ alkyldiyl)-;
Q-C(=O)-(PEG)-C(=O)—(PEP)-N($R^5$)—($C_1$-$C_{12}$ alkyldiyl)-N($R^5$)C(=O)—($C_2$-$C_5$ monoheterocyclyldiyl)-;
Q-C(=O)-(PEG)-N($R^5$)—;
Q-C(=O)-(PEG)-N($R^5$)C(=O)—;
Q-C(=O)-(PEG)-N($R^5$)-(PEG)-C(=O)—(PEP)-;
Q-C(=O)-(PEG)-N$^+$($R^5$)$_2$-(PEG)-C(=O)—(PEP)-;
Q-C(=O)-(PEG)-C(=O)—N($R^5$)CH(AA$_1$)C(=O)-(PEG)-C(=O)—(PEP)-;
Q-C(=O)-(PEG)-C(=O)—N($R^5$)CH(AA$_1$)C(=O)—N($R^5$)—($C_1$-$C_{12}$ alkyldiyl)-;
Q-C(=O)-(PEG)-SS—($C_1$-$C_{12}$ alkyldiyl)-OC(=O)—;
Q-C(=O)-(PEG)-SS—($C_1$-$C_{12}$ alkyldiyl)-C(=O)—;
Q-C(=O)—($C_1$-$C_{12}$ alkyldiyl)-C(=O)—(PEP)-;
Q-C(=O)—($C_1$-$C_{12}$ alkyldiyl)-C(=O)—(PEP)-N($R^5$)—($C_1$-$C_{12}$ alkyldiyl)-;
Q-C(=O)—($C_1$-$C_{12}$ alkyldiyl)-C(=O)—(PEP)-N($R^5$)—($C_1$-$C_{12}$ alkyldiyl)-N($R^5$)—C(=O);
Q-C(=O)—($C_1$-$C_{12}$ alkyldiyl)-C(=O)—(PEP)-N($R^5$)—($C_1$-$C_{12}$ alkyldiyl)-N($R^5$)C(=O)—($C_2$-$C_5$ monoheterocyclyldiyl)-;
Q-C(=O)—CH$_2$CH$_2$OCH$_2$CH$_2$—($C_1$-$C_{20}$ heteroaryldiyl)-CH$_2$O-(PEG)-C(=O)-(MCgluc)-;
Q-C(=O)—CH$_2$CH$_2$OCH$_2$CH$_2$—($C_1$-$C_{20}$ heteroaryldiyl)-CH$_2$O-(PEG)-C(=O)-(MCgluc)-N($R^5$)—($C_1$-$C_{12}$ alkyldiyl)-N($R^5$)C(=O)—($C_2$-$C_5$ monoheterocyclyldiyl)-; and
Q-(CH$_2$)$_m$—C(=O)—(PEP)-N($R^5$)—($C_1$-$C_{12}$ alkyldiyl)-N($R^5$)C(=O)—($C_2$-$C_5$ monoheterocyclyldiyl)-;
where PEG has the formula: —(CH$_2$CH$_2$O)$_n$—(CH$_2$)$_m$—;
m is an integer from 1 to 5, and n is an integer from 2 to 50;
PEP has the formula:

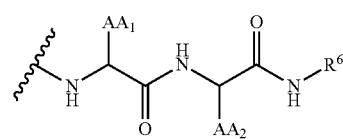

where AA$_1$ and AA$_2$ are independently selected from an amino acid side chain, or AA$_1$ or AA$_2$ and an adjacent nitrogen atom form a 5-membered ring proline amino acid, and the wavy line indicates a point of attachment and;
$R^6$ is selected from the group consisting of $C_6$-$C_{20}$ aryldiyl and $C_1$-$C_{20}$ heteroaryldiyl, substituted with —CH$_2$O—C(=O)— and optionally with:

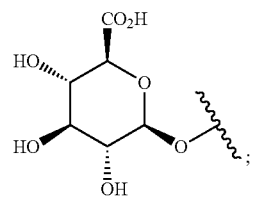 [SMILES: *O[C@@H]1O[C@H](C(=O)O)[C@@H](O)[C@H](O)[C@H]1O]

and

MCgluc is selected from the groups:

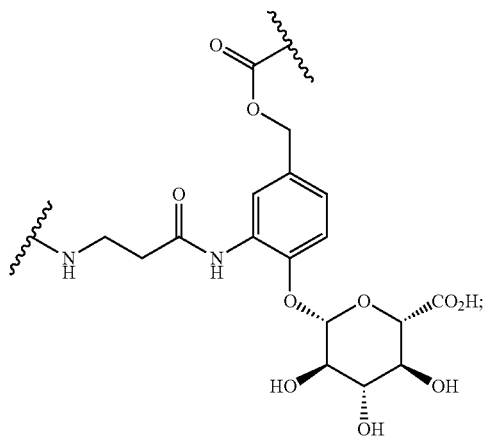

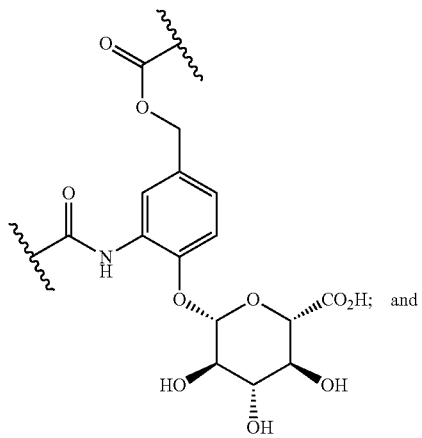

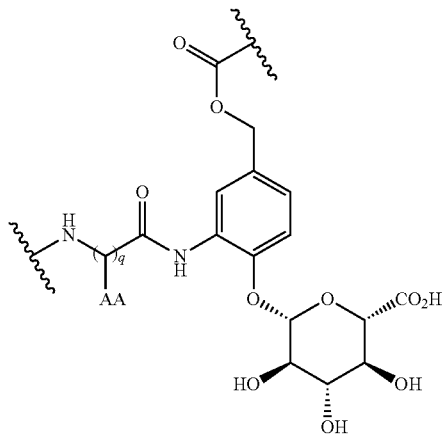

where q is 1 to 8, and AA is an amino acid side chain; and Q is selected from the group consisting of N-hydroxysuccinimidyl, N-hydroxysulfosuccinimidyl, maleimide, and phenoxy substituted with one or more groups independently selected from F, Cl, $NO_2$, and $SO_3^-$;

where alkyl, alkyldiyl, alkenyl, alkenyldiyl, alkynyl, alkynyldiyl, aryl, aryldiyl carbocyclyl, carbocyclyldiyl, heterocyclyl, heterocyclyldiyl, heteroaryl, and heteroaryldiyl are independently and optionally substituted with one or more groups independently selected from F, Cl, Br, I, —CN, —$CH_3$, —$CH_2CH_3$, —CH=$CH_2$, —C≡CH, —C≡$CCH_3$, —$CH_2CH_2CH_3$, —CH($CH_3$)$_2$, —$CH_2CH(CH_3)_2$, —$CH_2OH$, —$CH_2OCH_3$, —$CH_2CH_2OH$, —C($CH_3$)$_2$OH, —CH(OH)CH($CH_3$)$_2$, —C($CH_3$)$_2CH_2OH$, —$CH_2CH_2SO_2CH_3$, —$CH_2OP(O)(OH)_2$, —$CH_2F$, —$CHF_2$, —$CF_3$, —$CH_2CF_3$, —$CH_2CHF_2$, —CH($CH_3$)CN, —C($CH_3$)$_2$CN, —$CH_2CN$, —$CH_2NH_2$, —$CH_2NHSO_2CH_3$, —$CH_2NHCH_3$, —$CH_2N(CH_3)_2$, —$CO_2H$, —$COCH_3$, —$CO_2CH_3$, —$CO_2C(CH_3)_3$, —COCH(OH)$CH_3$, —$CONH_2$, —$CONHCH_3$, —CON($CH_3$)$_2$, —C($CH_3$)$_2CONH_2$, —$NH_2$, —$NHCH_3$, —N($CH_3$)$_2$, —$NHCOCH_3$, —N($CH_3$)$COCH_3$, —NHS(O)$_2CH_3$, —N($CH_3$)C($CH_3$)$_2CONH_2$, —N($CH_3$)$CH_2CH_2S(O)_2CH_3$, —NHC(=NH)H, —NHC(=NH)$CH_3$, —NHC(=NH)$NH_2$, —NHC(=O)$NH_2$, —$NO_2$, =O, —OH, —$OCH_3$, —$OCH_2CH_3$, —$OCH_2CH_2OCH_3$, —$OCH_2CH_2OH$, —$OCH_2CH_2N(CH_3)_2$, —O($CH_2CH_2O)_n$—($CH_2)_mCO_2H$, —O($CH_2CH_2O)_nH$, —$OCH_2F$, —$OCHF_2$, —$OCF_3$, —OP(O)(OH)$_2$, —S(O)$_2$N($CH_3$)$_2$, —$SCH_3$, —S(O)$_2CH_3$, and —S(O)$_3H$.

2. The 5-amino-thienoazepine-linker compound of claim 1, wherein PEP has the formula:

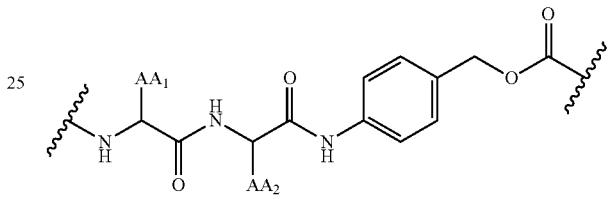

wherein $AA_1$ and $AA_2$ are independently selected from a side chain of a naturally-occurring amino acid.

3. The 5-amino-thienoazepine-linker compound of claim 2 wherein $AA_1$ or $AA_2$ with an adjacent nitrogen atom form a 5-membered ring to form a proline amino acid.

4. The 5-amino-thienoazepine-linker compound of claim 1 wherein PEP has the formula:

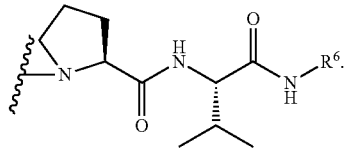

5. The 5-amino-thienoazepine-linker compound of claim 1 wherein MCgluc has the formula:

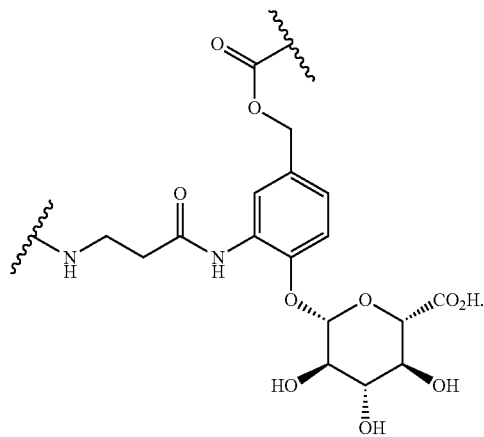 [SMILES: *NCCC(=O)Nc1cc(COC(*)=O)ccc1O[C@@H]1O[C@H](C(=O)O)[C@@H](O)[C@H](O)[C@H]1O]

6. The 5-amino-thienoazepine-linker compound of claim 1 wherein $AA_1$ and $AA_2$ are independently selected from H, —$CH_3$, —$CH_2CH(CH_3)_2$, —$CH_2(C_6H_5)$, —$CH_2CH_2CH_2CH_2NH_2$, —$CH_2CH_2CH_2NHC(NH)NH_2$, —$CHCH(CH_3)CH_3$, —$CH_2SO_3H$, and —$CH_2CH_2CH_2NHC(O)NH_2$.

7. The 5-amino-thienoazepine-linker compound of claim 6 wherein $AA_1$ is —$CH_2CH(CH_3)_2$, and $AA_2$ is —$CH_2CH_2CH_2NHC(O)NH_2$.

8. The 5-amino-thienoazepine-linker compound of claim 2 wherein $AA_1$ and $AA_2$ are independently selected from GlcNAc aspartic acid, —$CH_2SO_3H$, and —$CH_2OPO_3H$.

9. The 5-amino-thienoazepine-linker compound of claim 1 wherein $X^1$ is a bond, and $R^1$ is H.

10. The 5-amino-thienoazepine-linker compound of claim 1 wherein $X^2$ is a bond, and $R^2$ is $C_1$-$C_8$ alkyl.

11. The 5-amino-thienoazepine-linker compound of claim 1 wherein $X^2$ and $X^3$ are each a bond, and $R^2$ and $R^3$ are independently selected from $C_1$-$C_8$ alkyl, —O—($C_1$-$C_{12}$ alkyl), —($C_1$-$C_{12}$ alkyldiyl)-$OR^5$, —($C_1$-$C_8$ alkyldiyl)—N($R^5$)$CO_2R^5$, and —O—($C_1$-$C_{12}$ alkyl)—N($R^5$)$CO_2R^5$.

12. The 5-amino-thienoazepine-linker compound of claim 11 wherein $R^2$ and $R^3$ are each independently selected from —$CH_2CH_2CH_3$, —$OCH_2CH_3$, —$CH_2CH_2CF_3$, and —$CH_2CH_2CH_2OH$.

13. The 5-amino-thienoazepine-linker compound of claim 11 wherein $R^2$ is $C_1$-$C_8$ alkyl and $R^3$ is —($C_1$-$C_8$ alkyldiyl)—N($R^5$)$CO_2R^4$.

14. The 5-amino-thienoazepine-linker compound of claim 13 wherein $R^2$ is —$CH_2CH_2CH_3$ and $R^3$ is —$CH_2CH_2CH_2NHCO_2$(t-Bu).

15. The 5-amino-thienoazepine-linker compound of claim 12 wherein $R^2$ and $R^3$ are each —$CH_2CH_2CH_3$.

16. The 5-amino-thienoazepine-linker compound of claim 1 wherein $X^3$—$R^3$ is selected from the group consisting of:

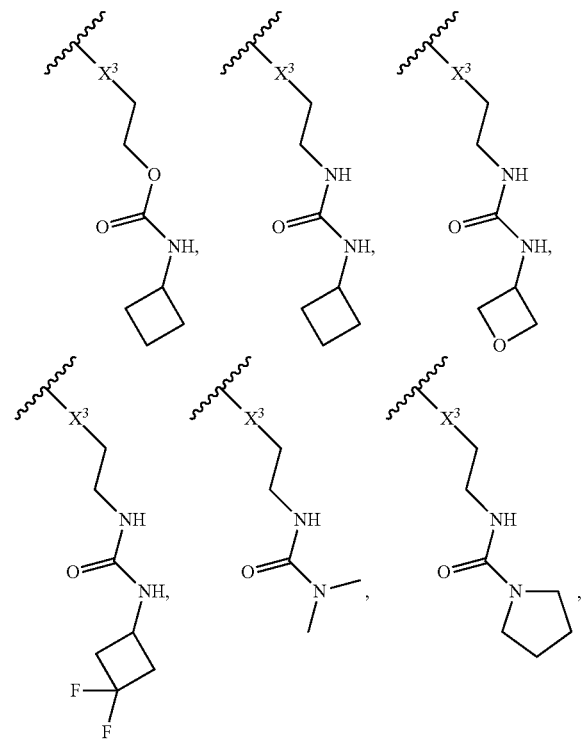

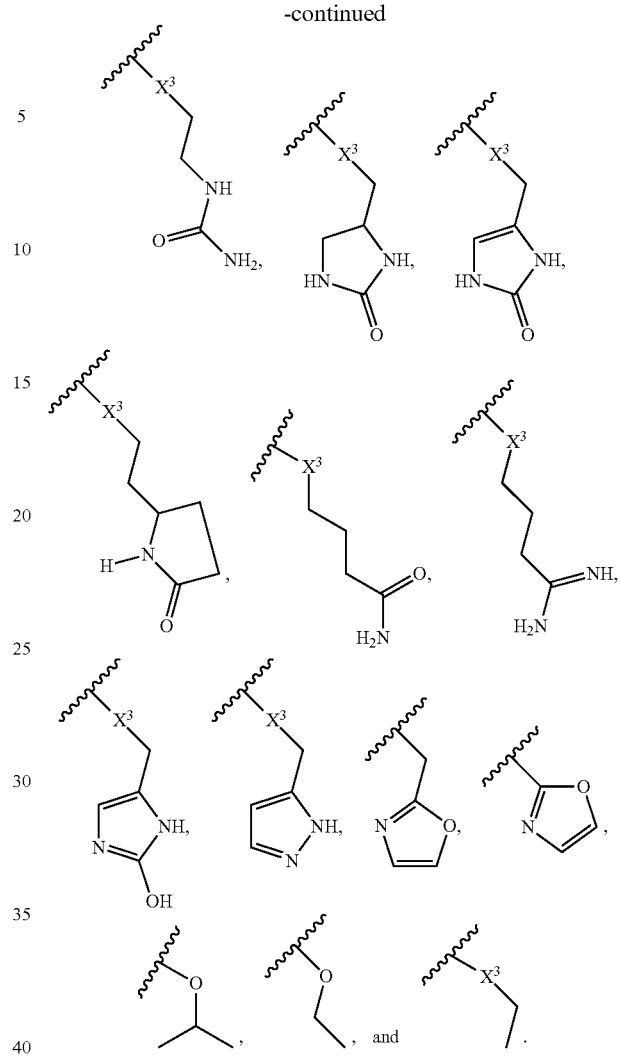

17. The 5-amino-thienoazepine-linker compound of claim 1 wherein one of $R^2$ and $R^3$ is selected from:
—($C_1$-$C_{12}$ alkyldiyl)-N($R^5$)—*;
—($C_1$-$C_{12}$ alkyldiyl)-O—($C_1$-$C_{12}$ alkyldiyl)-N($R^5$)—*;
—($C_1$-$C_{12}$ alkyldiyl)-N($R^5$)C(=N$R^5$)—N($R^5$)—*;
—($C_1$-$C_{12}$ alkyldiyl)-($C_6$-$C_{20}$ aryldiyl)-($C_1$-$C_{12}$ alkyldiyl)-N($R^5$)—*;
—($C_1$-$C_{12}$ alkyldiyl)-($C_6$-$C_{20}$ aryldiyl)-($C_1$-$C_{12}$ alkyldiyl)-N($R^5$)—C(=N$R^5$)N($R^5$)—*;
—($C_2$-$C_6$ alkynyldiyl)-N($R^5$)—*; and
—($C_2$-$C_6$ alkynyldiyl)-N($R^5$)C(=N$R^5$)N($R^5$)—*;
$X^2$ and $X^3$ are a bond, and where the asterisk * indicates the attachment site of L.

18. The 5-amino-thienoazepine-linker compound of claim 1 wherein L is selected from the group consisting of:
Q-C(=O)-(PEG)-;
Q-C(=O)-(PEG)-C(=O)—;
Q-C(=O)-(PEG)-O—;
Q-C(=O)-(PEG)-N($R^5$)—; and
Q-C(=O)-(PEG)-N($R^5$)C(=O)—.

19. The 5-amino-thienoazepine-linker compound of claim 1 selected from Formulae IIa-IIc:

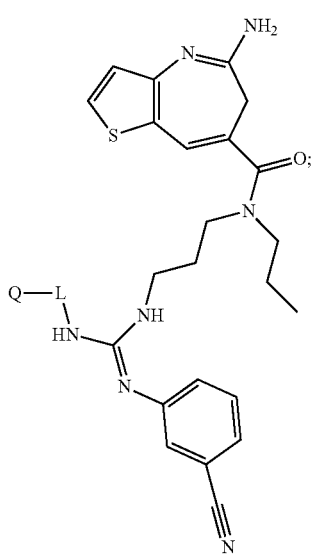
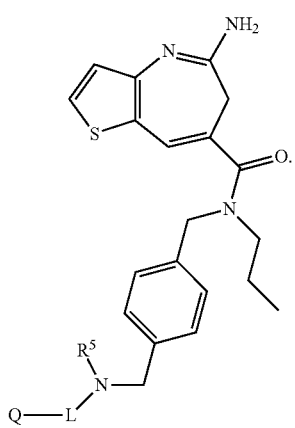
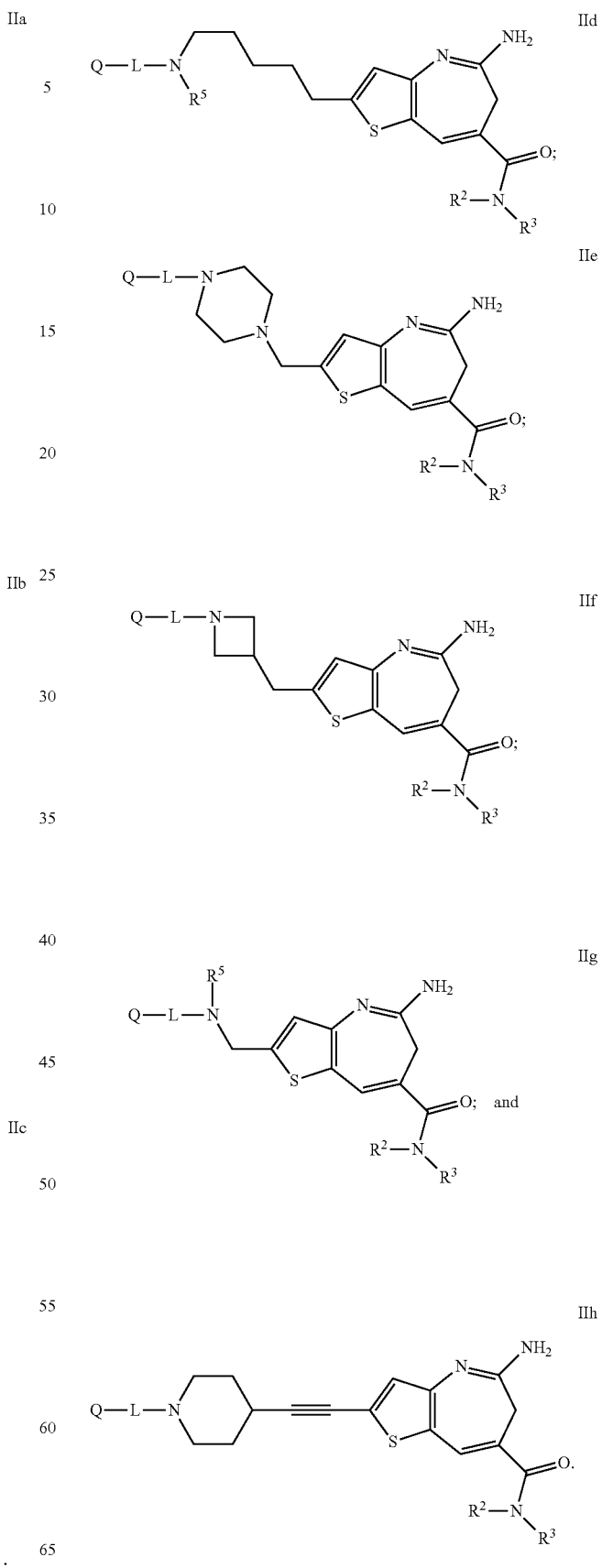
20. The 5-amino-thienoazepine-linker compound of claim 1 selected from Formulae IId-IIh:

21. The 5-amino-thienoazepine-linker compound of claim 20 wherein $R^2$ and $R^3$ are independently selected from $C_1$-$C_8$ alkyl, —O—($C_1$-$C_{12}$ alkyl), —($C_1$-$C_{12}$ alkyldiyl)-$OR^5$, —($C_1$-$C_8$ alkyldiyl)-$N(R^5)CO_2R^5$, and —O—($C_1$-$C_{12}$ alkyl)-$N(R^5)CO_2R^5$.

22. The 5-amino-thienoazepine-linker compound of claim 21 wherein $R^2$ and $R^3$ are each independently selected from —$CH_2CH_2CH_3$, —$OCH_2CH_3$, —$CH_2CH_2CF_3$, and —$CH_2CH_2CH_2OH$.

23. The 5-amino-thienoazepine-linker compound of claim 1 wherein Q is selected from:

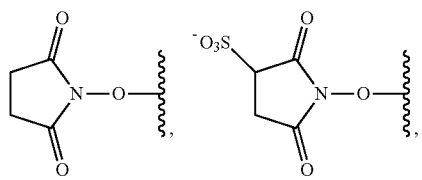

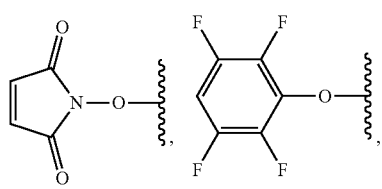

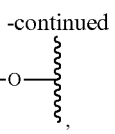

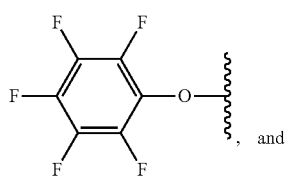, and

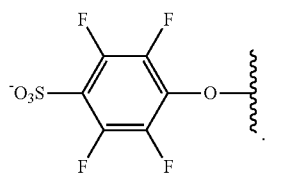.

24. The 5-amino-thienoazepine-linker compound of claim 1 wherein Q is phenoxy substituted with one or more F.

25. The 5-amino-thienoazepine-linker compound of claim 24 wherein Q is 2,3,5,6-tetrafluorophenoxy.

26. The 5-amino-thienoazepine-linker compound of claim 1 selected from the group consisting of:

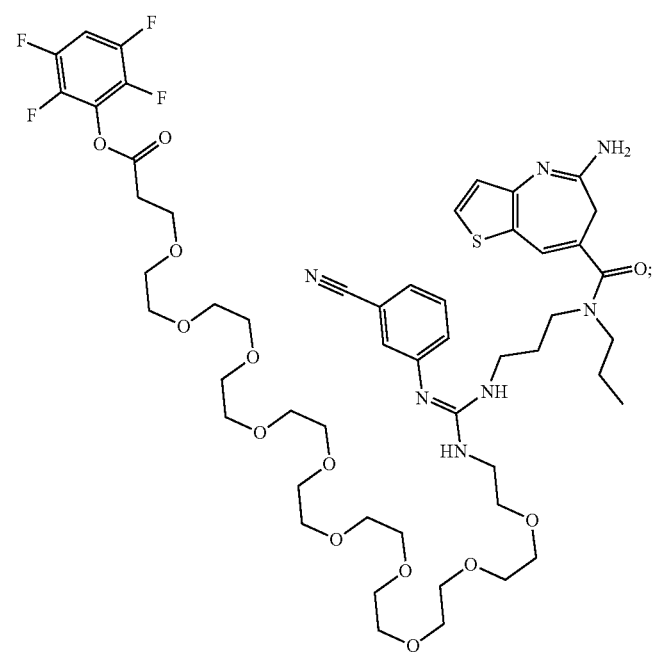

837 838
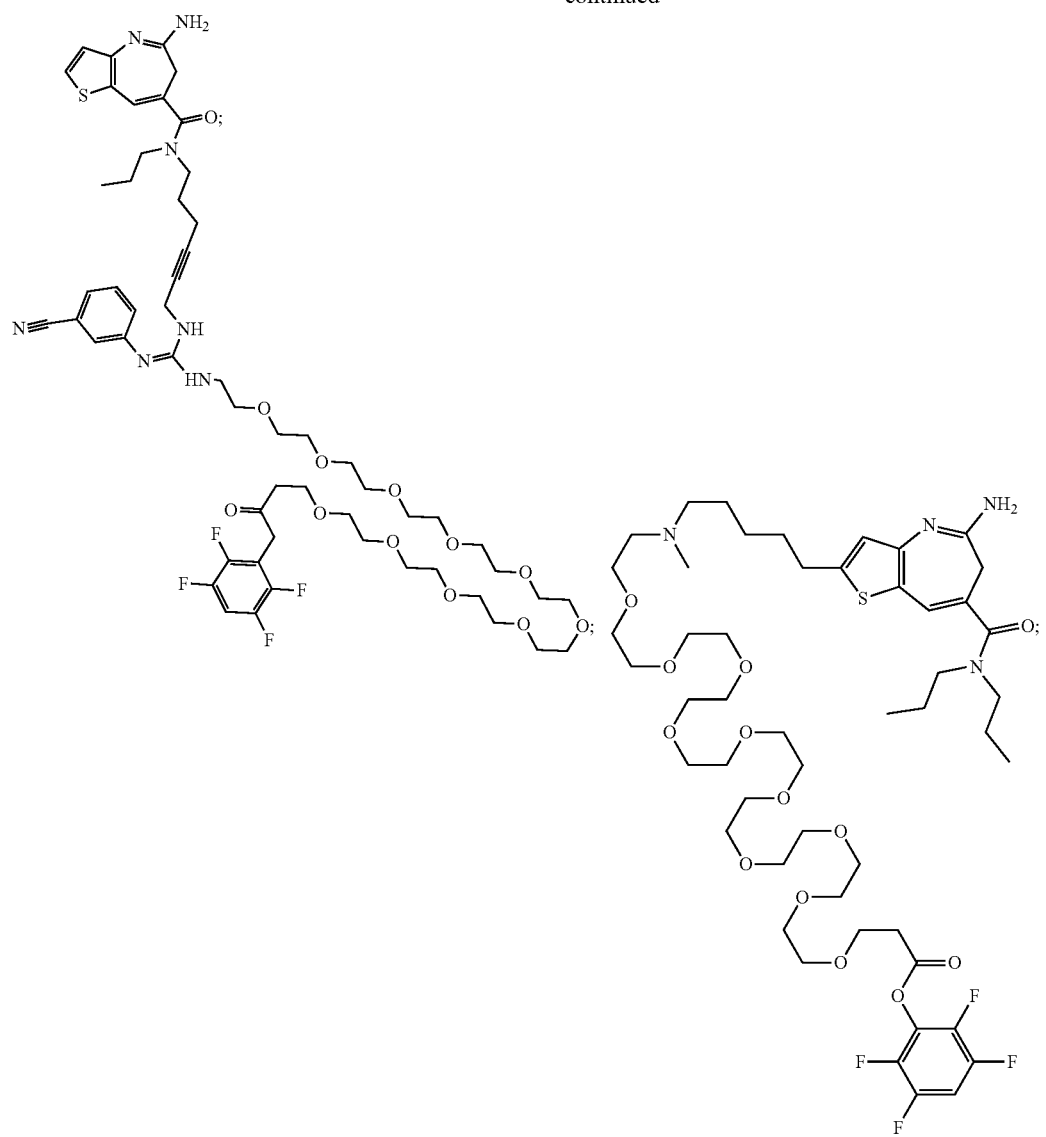

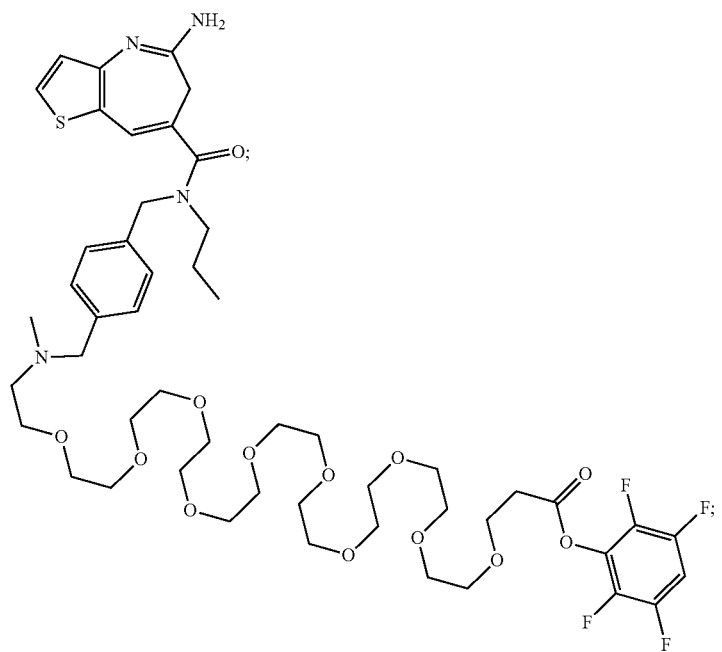
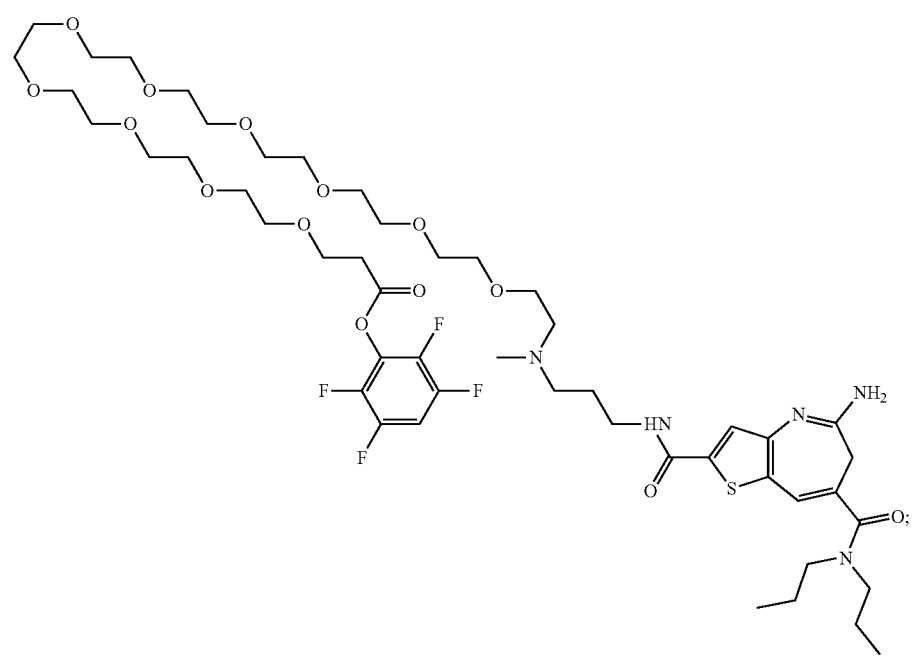

-continued
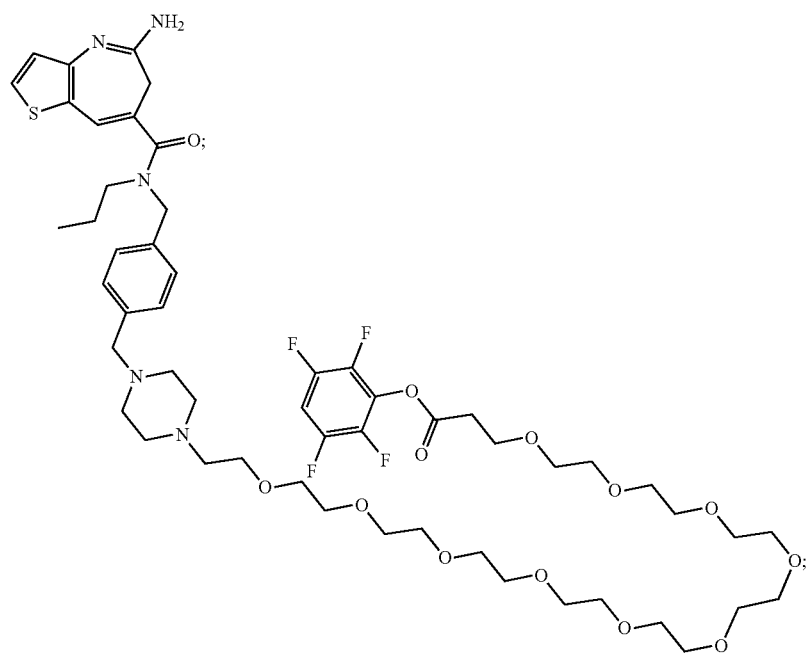
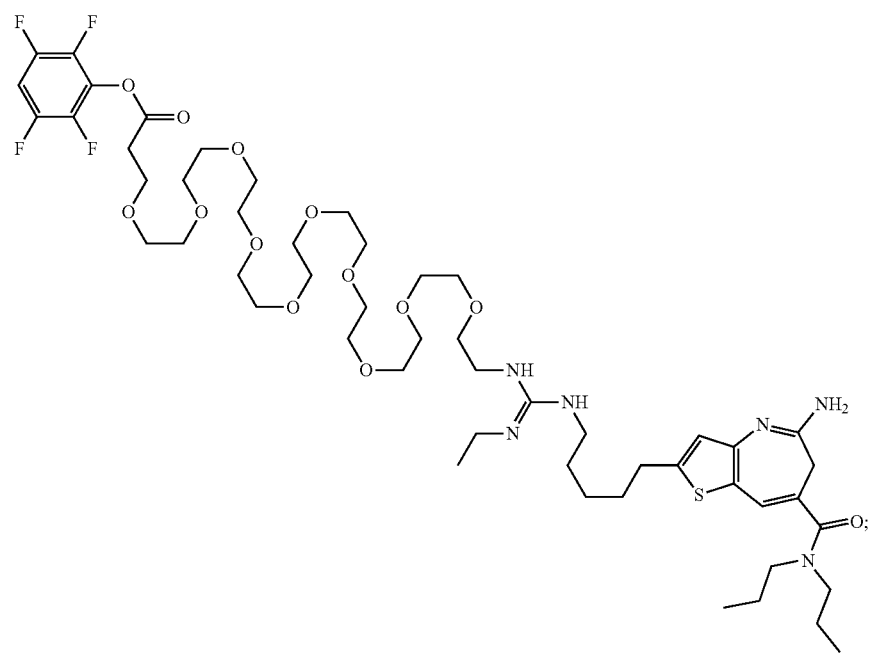

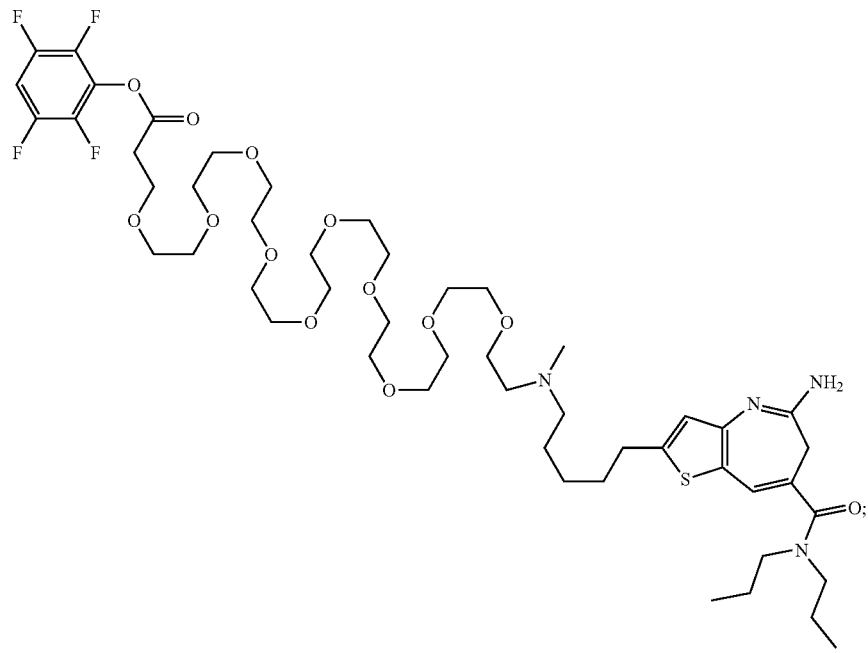
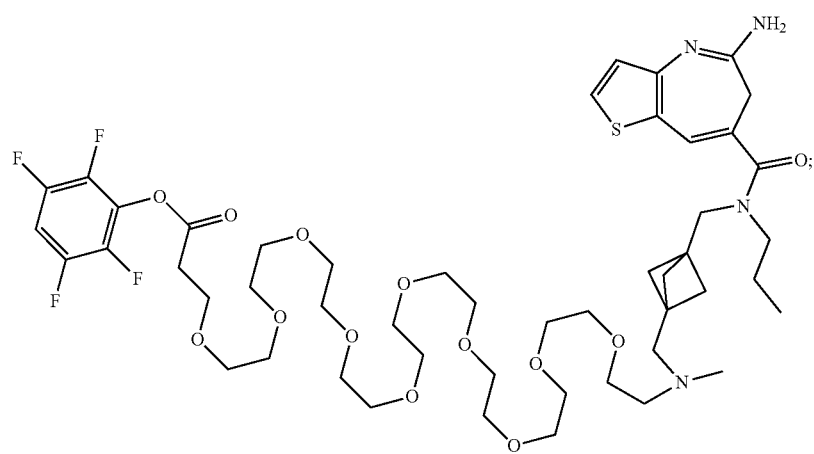

-continued
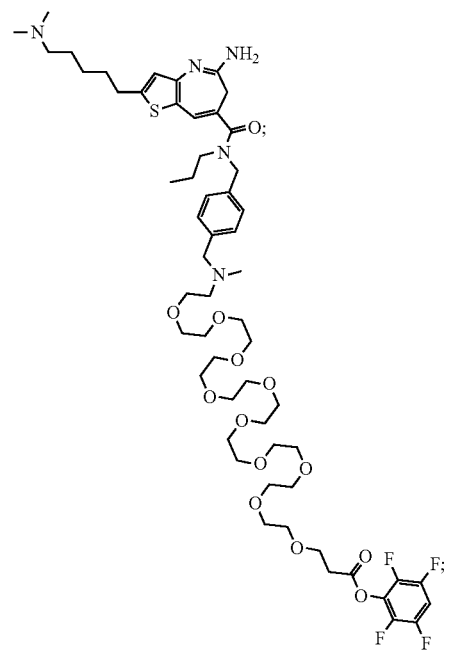
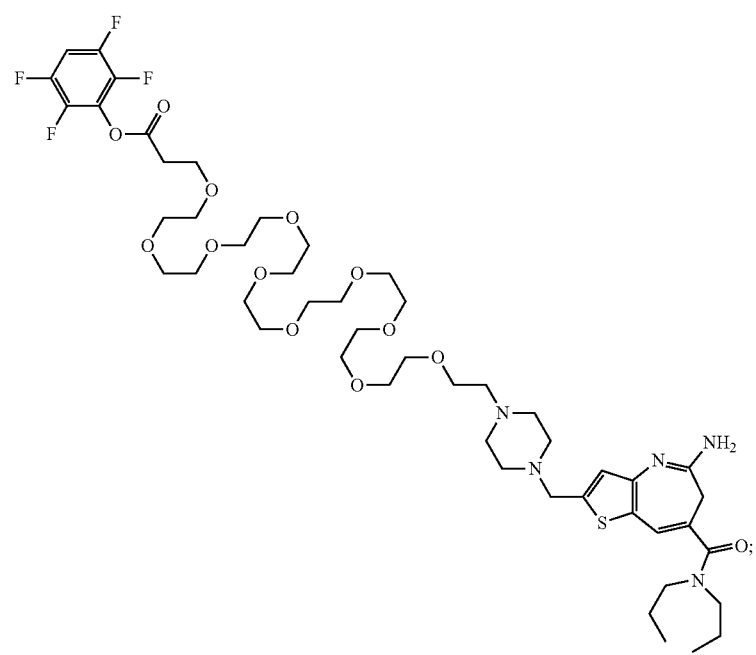

847
-continued
848
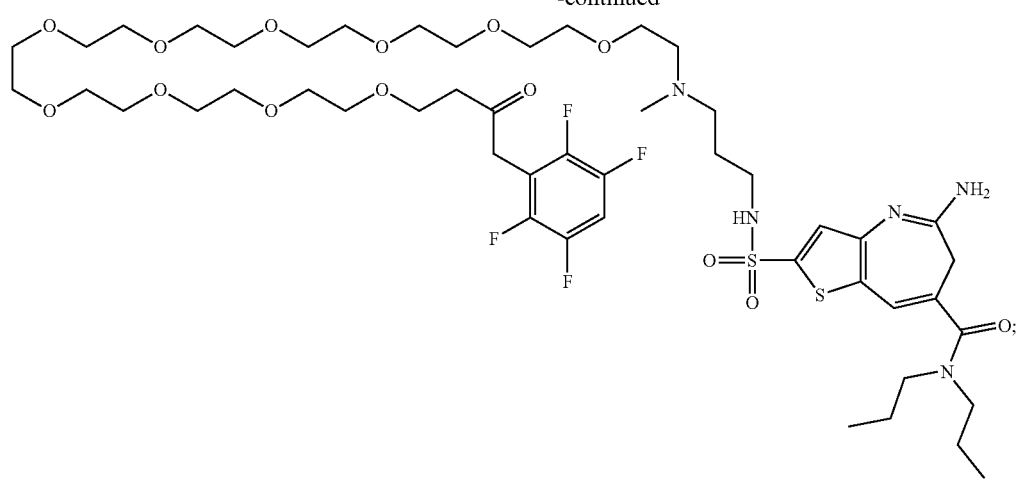
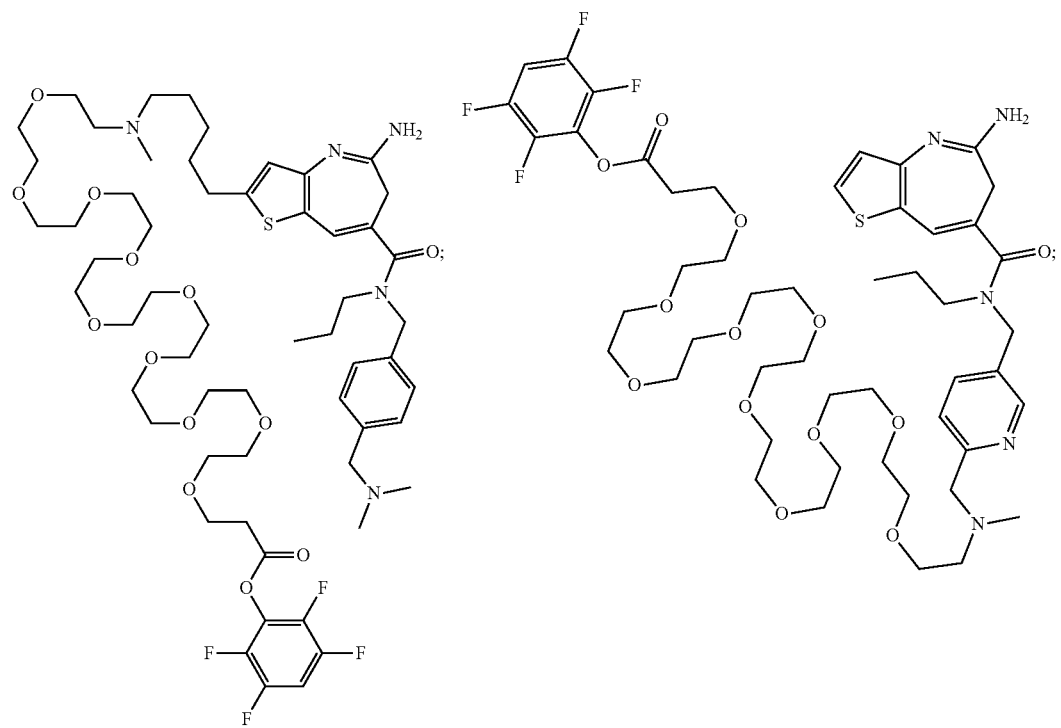

849
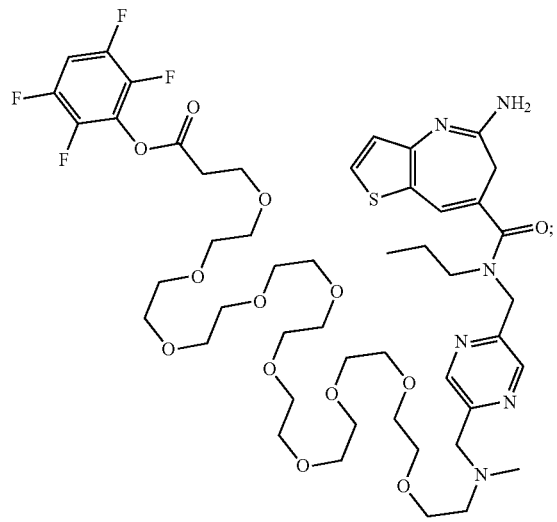
850
-continued
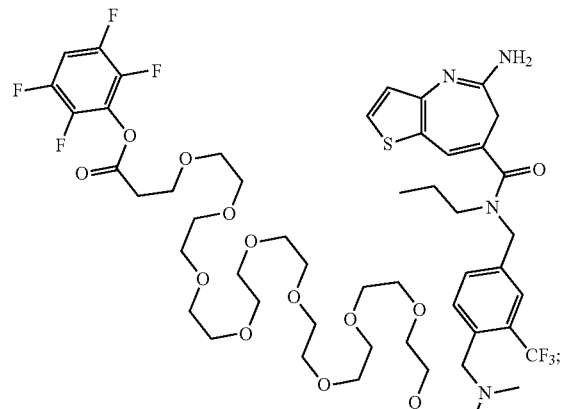
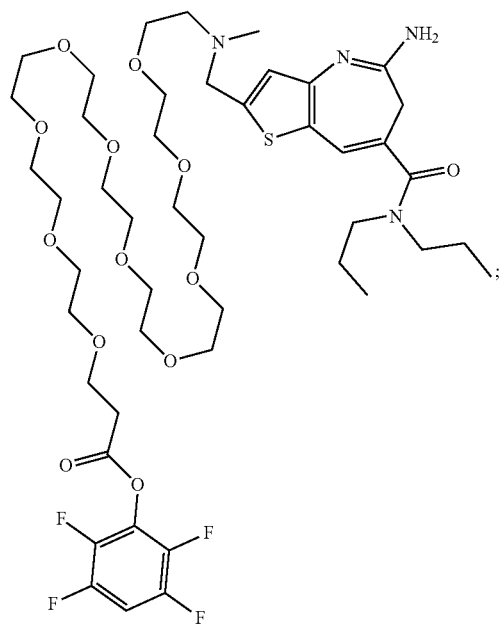

851 852
-continued
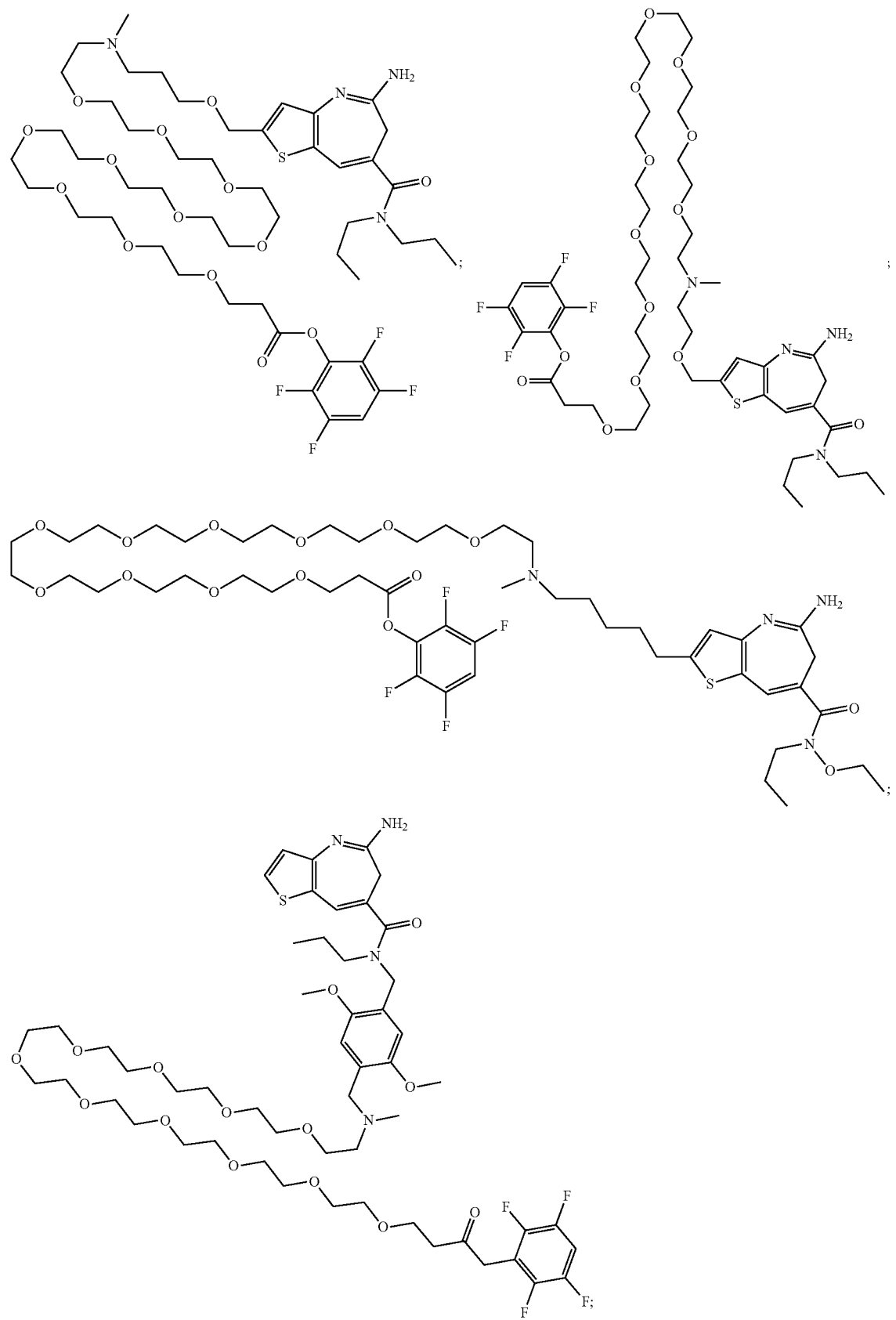

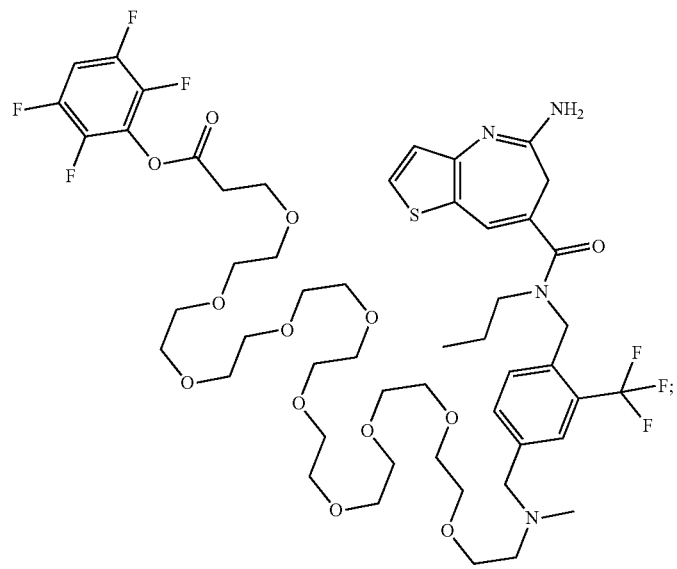
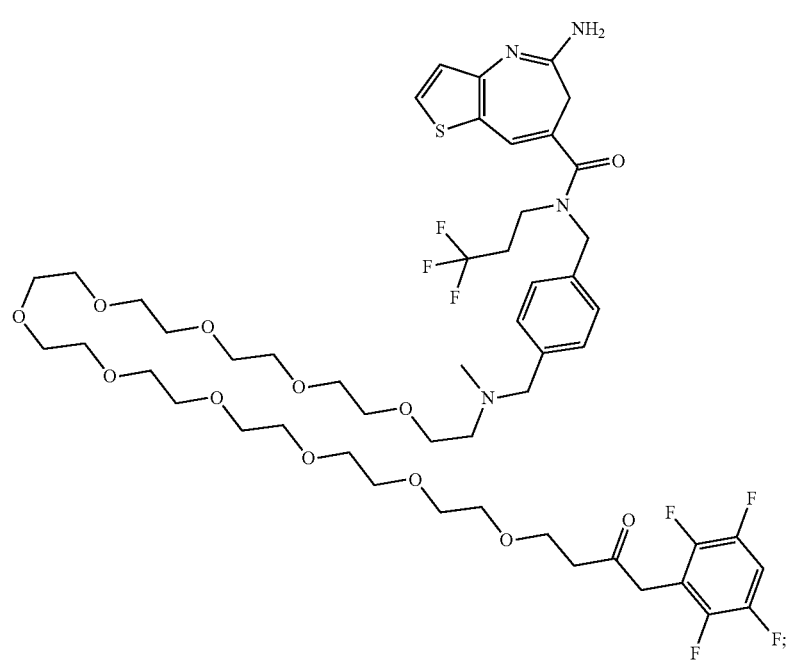

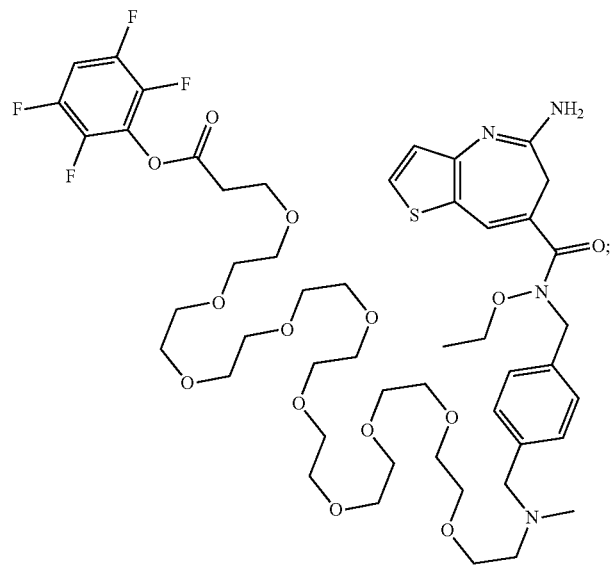
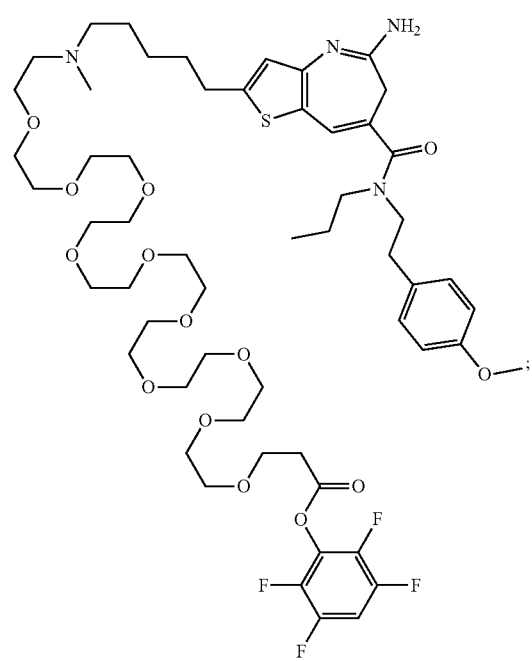

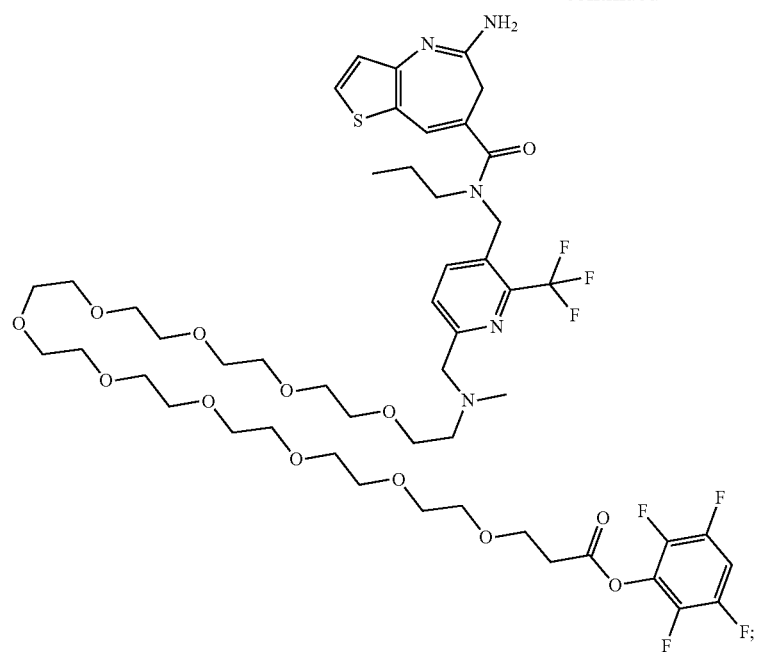
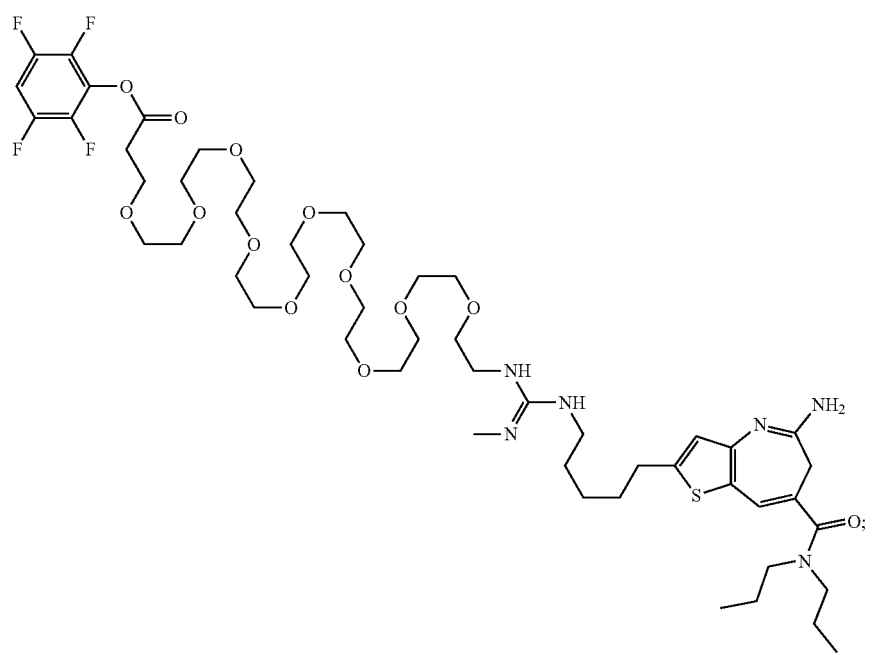

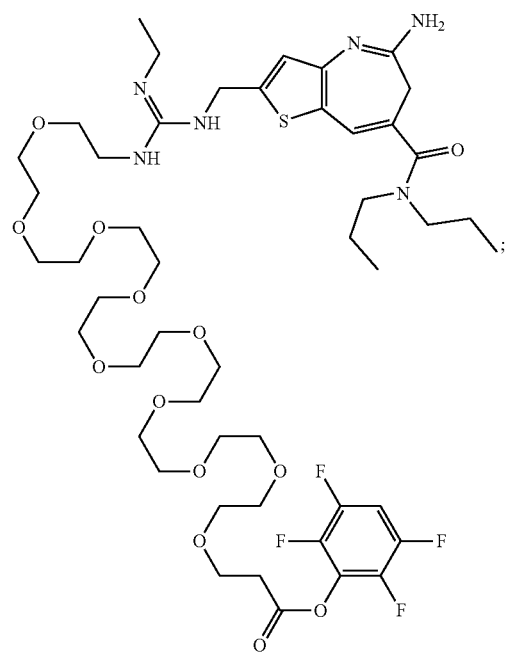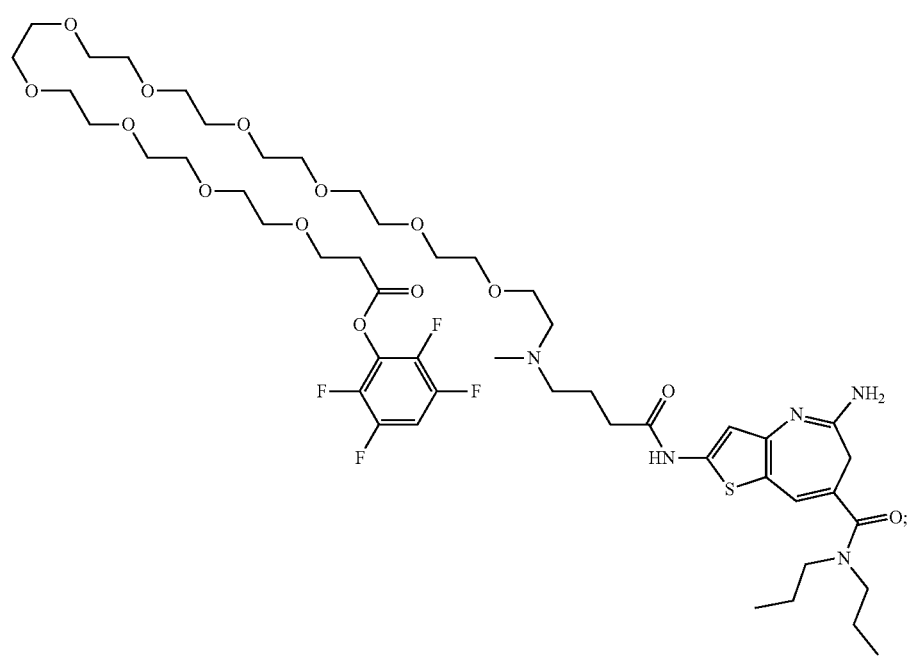

861
862
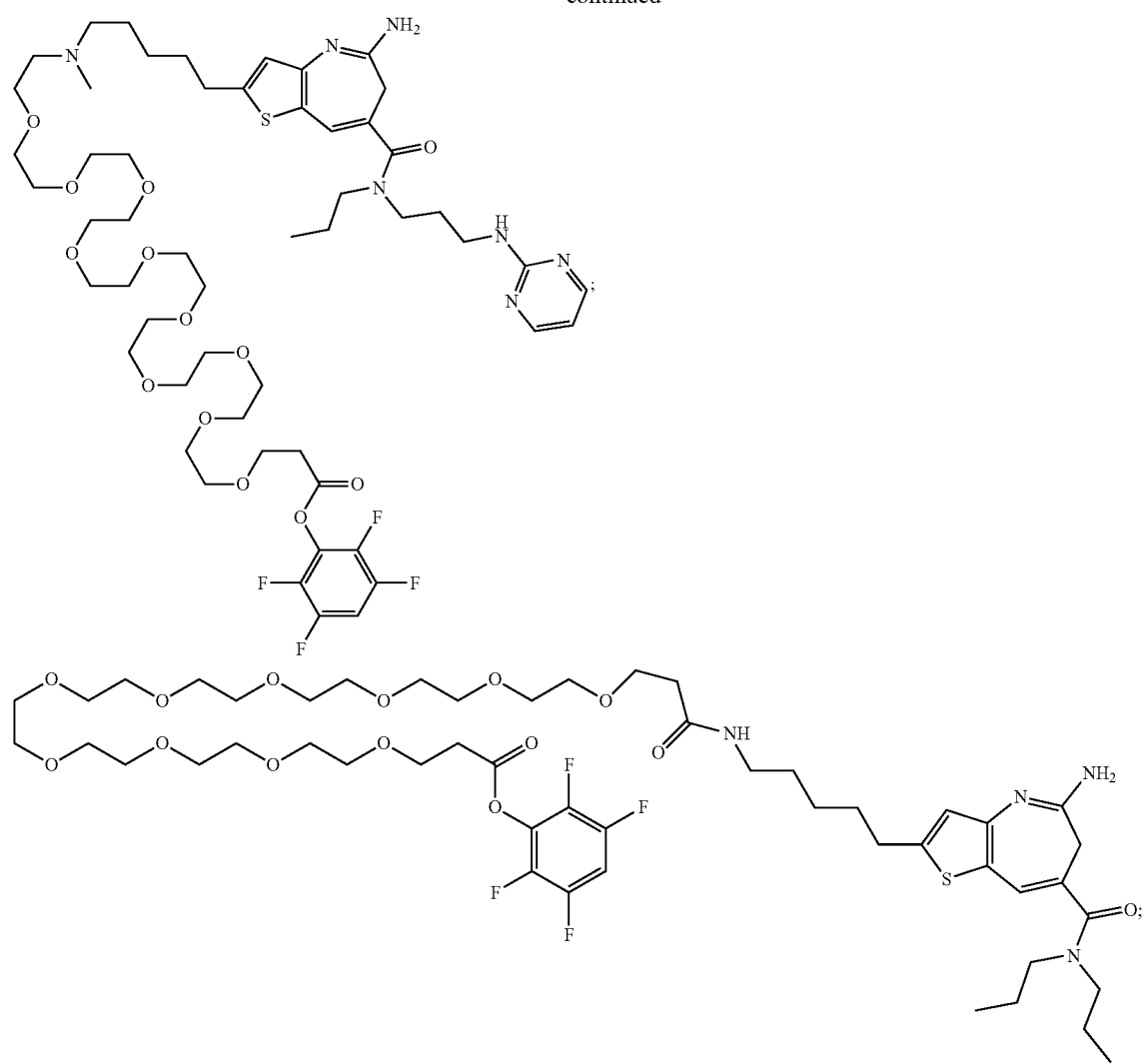
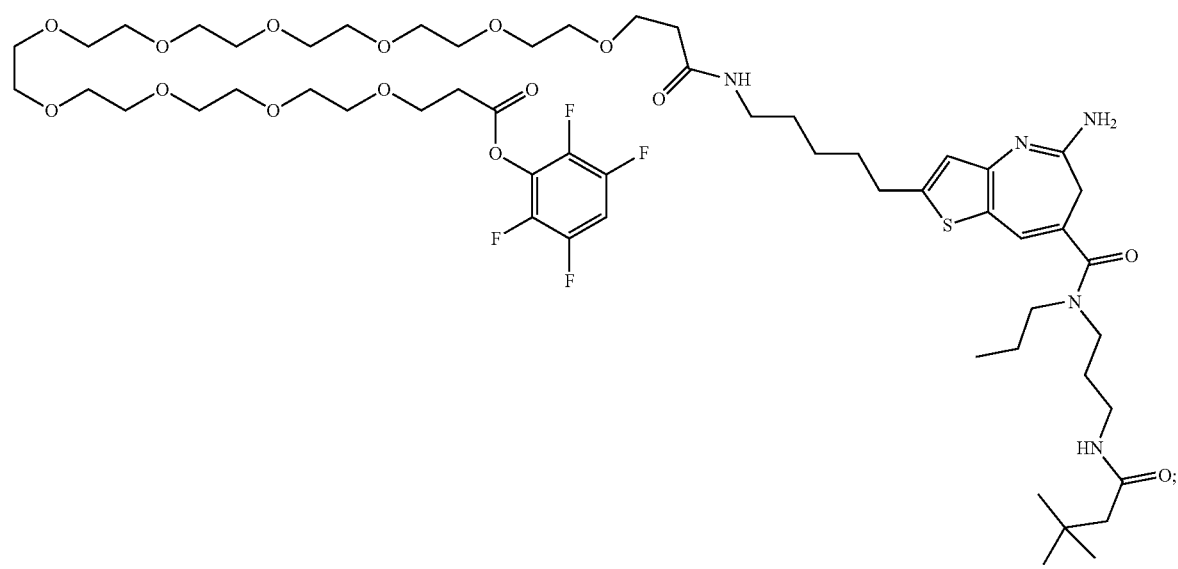

863
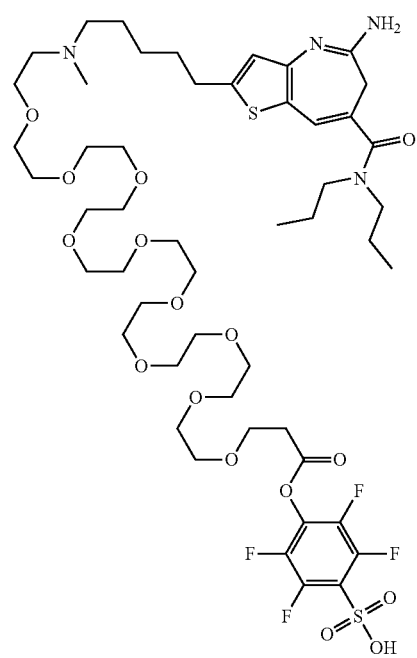
864
-continued
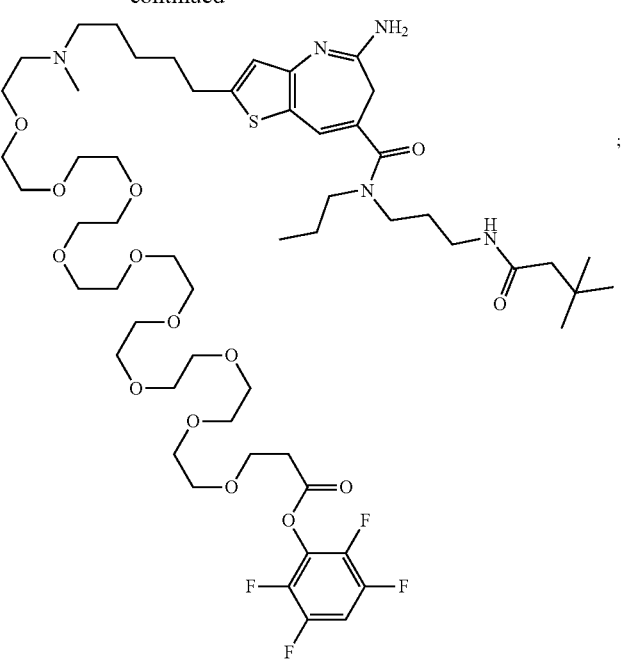
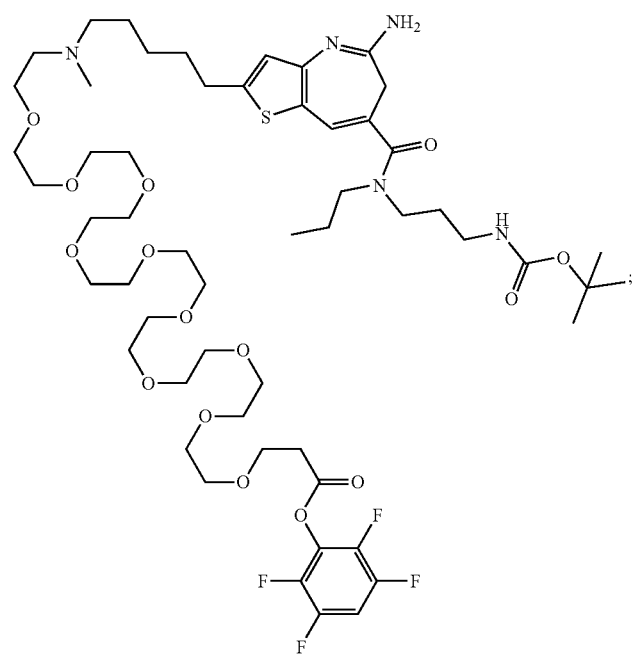

-continued
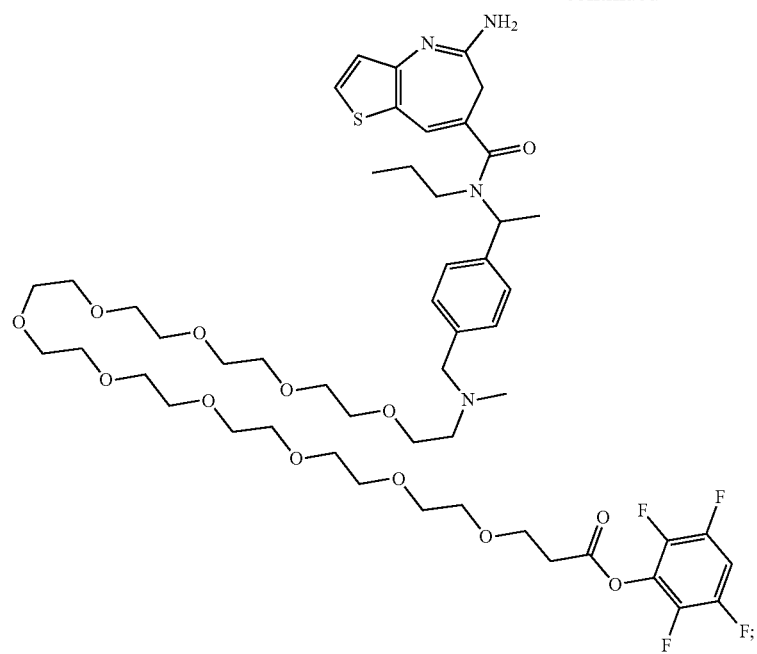
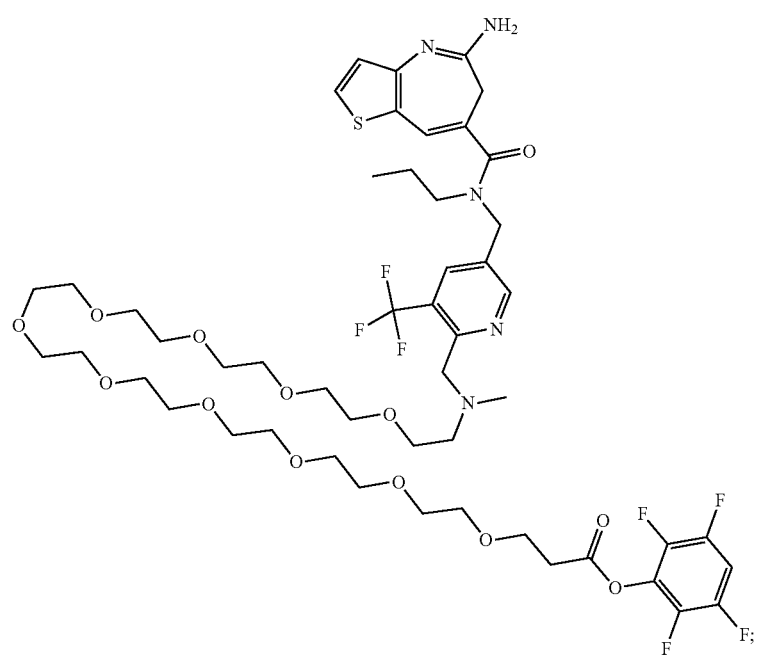

-continued
867
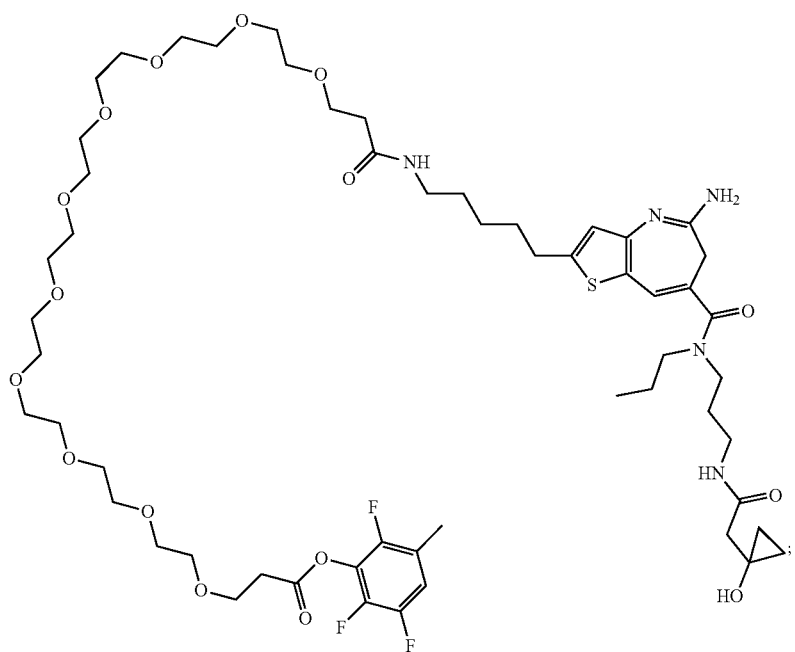
868
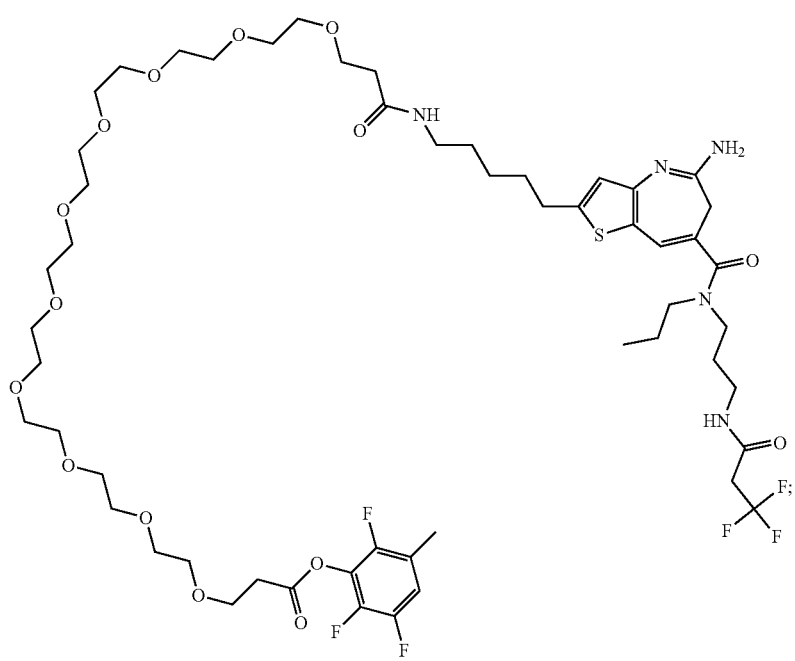

869
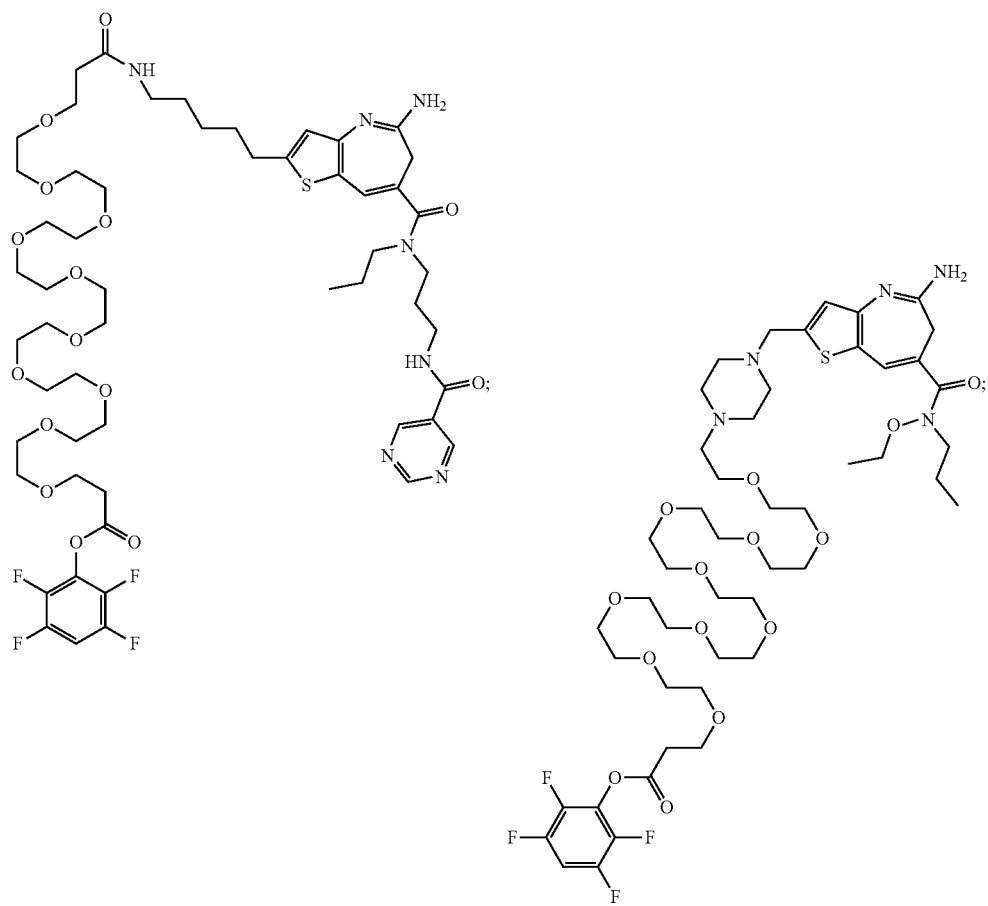
870
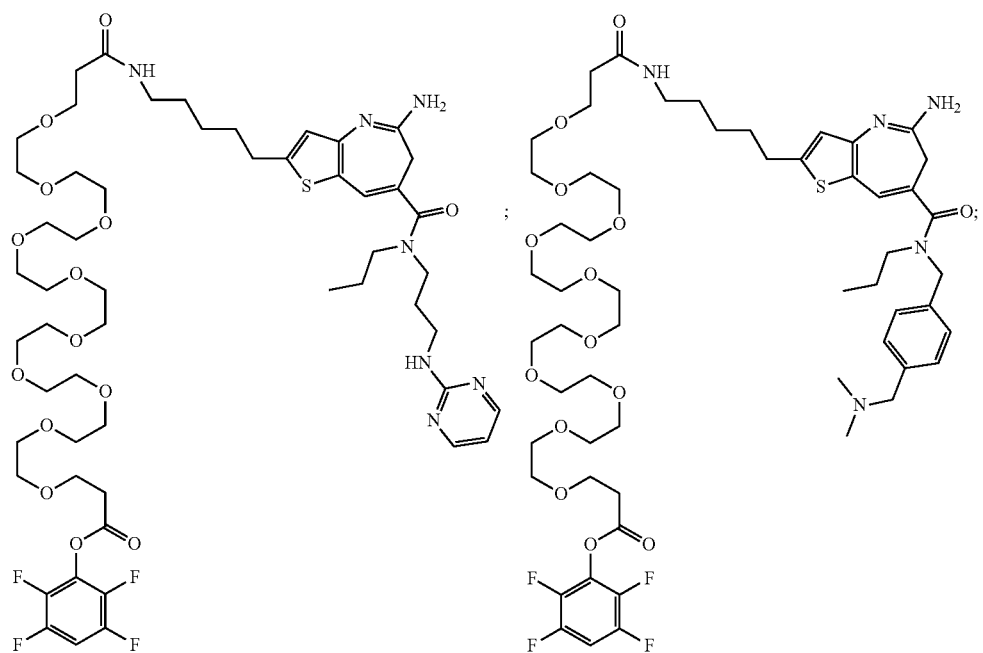

871
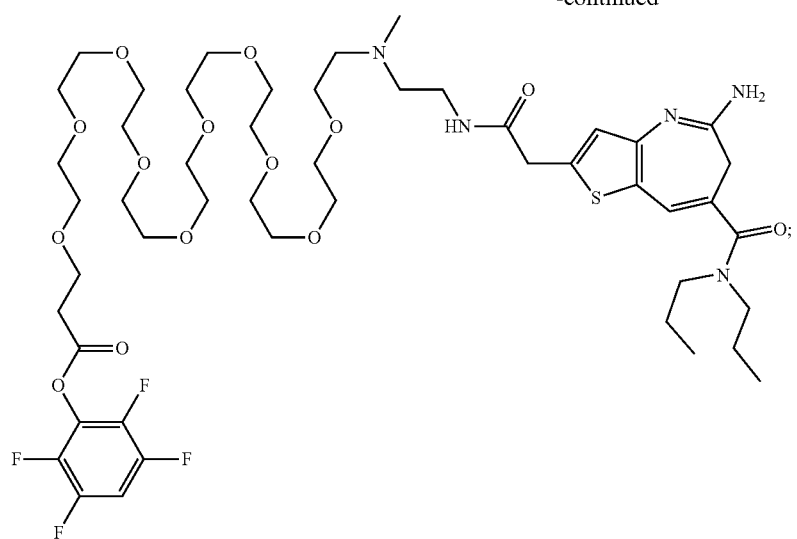
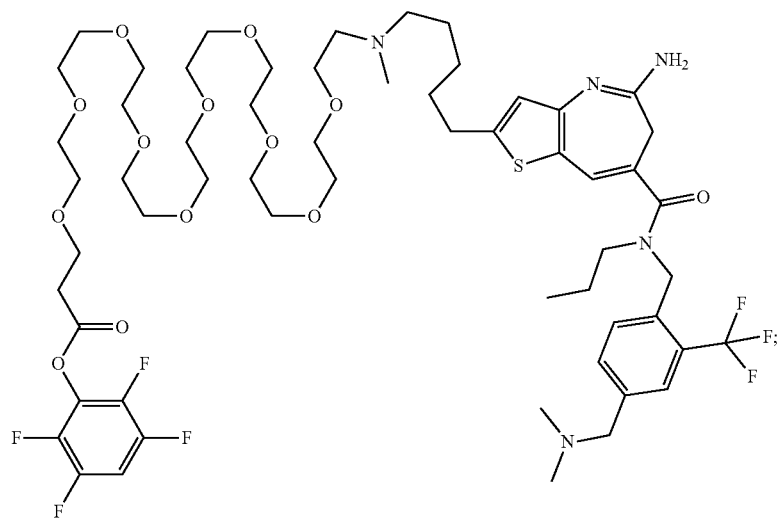
-continued
872
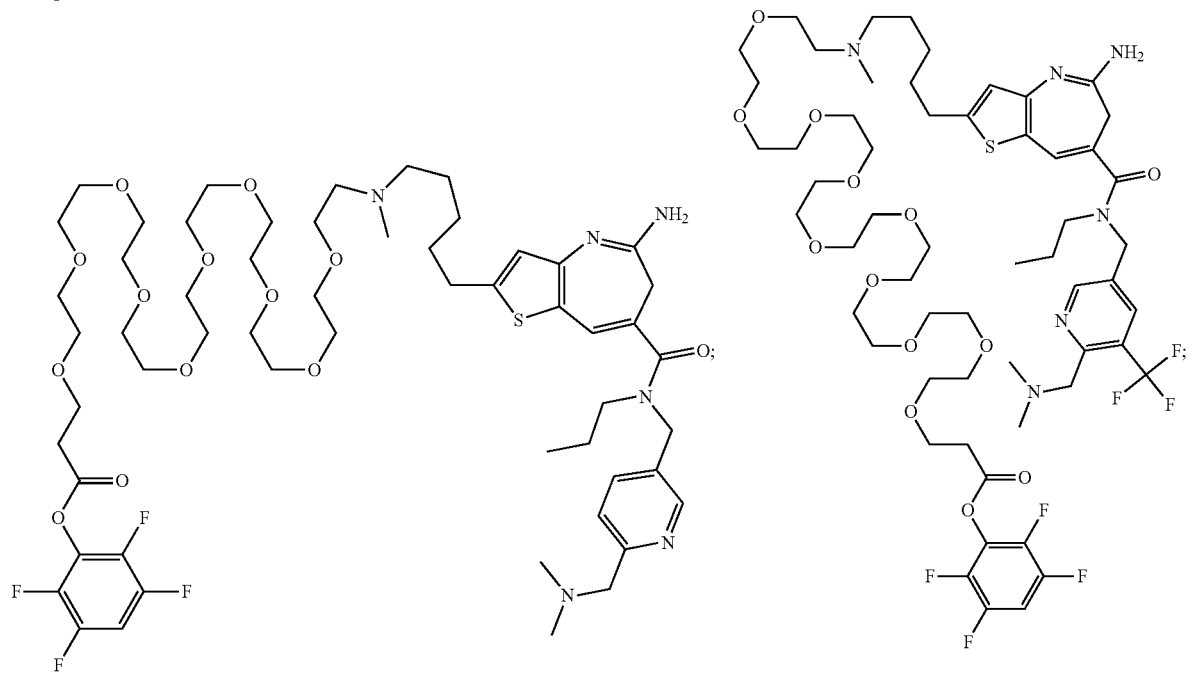

873 874
-continued
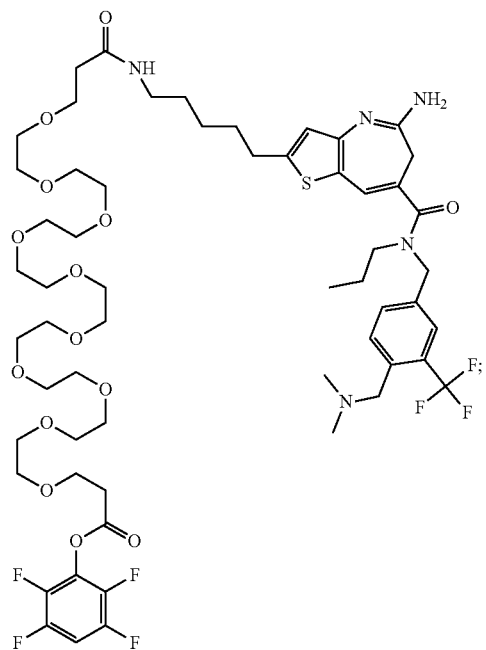
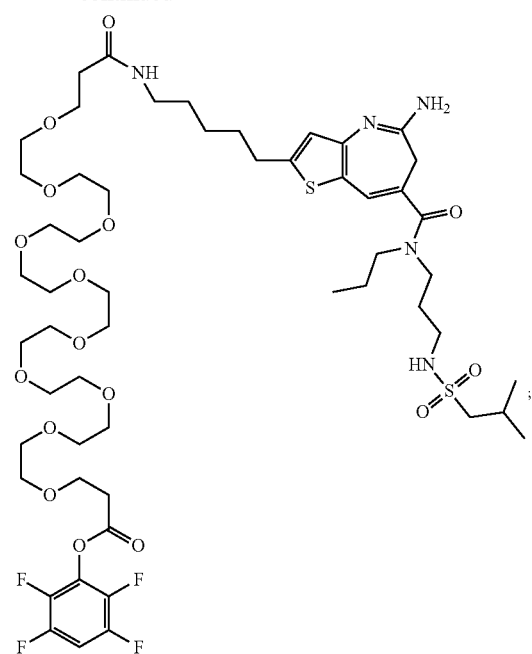
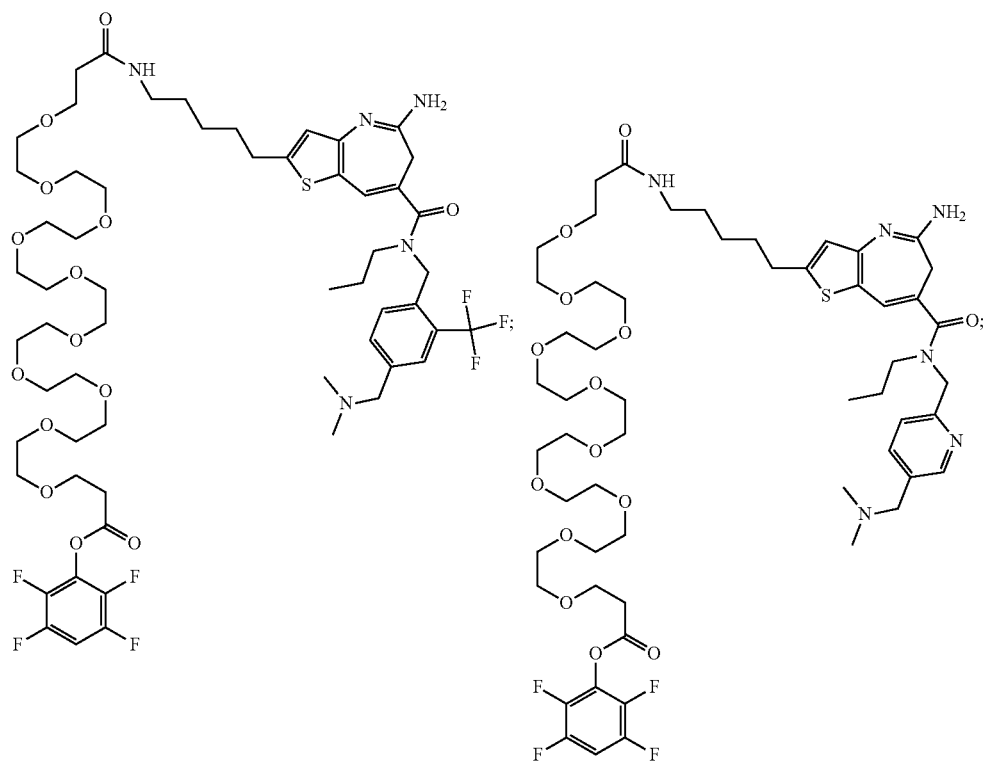

875 876
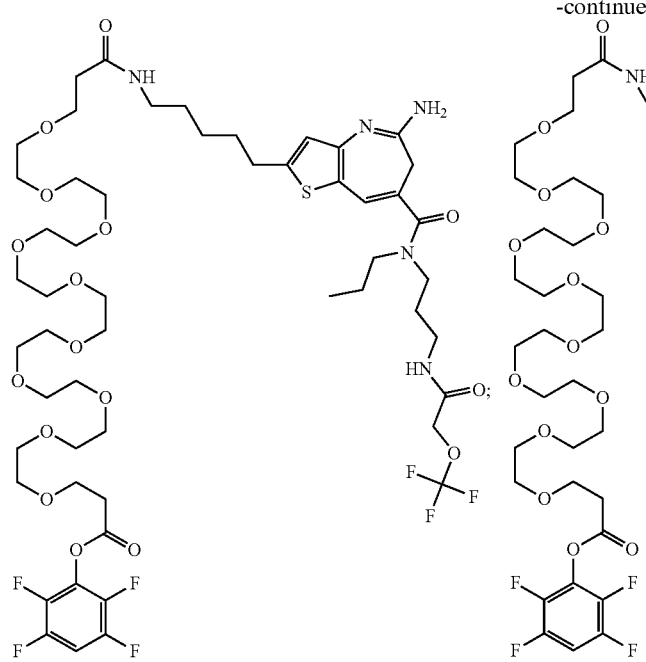
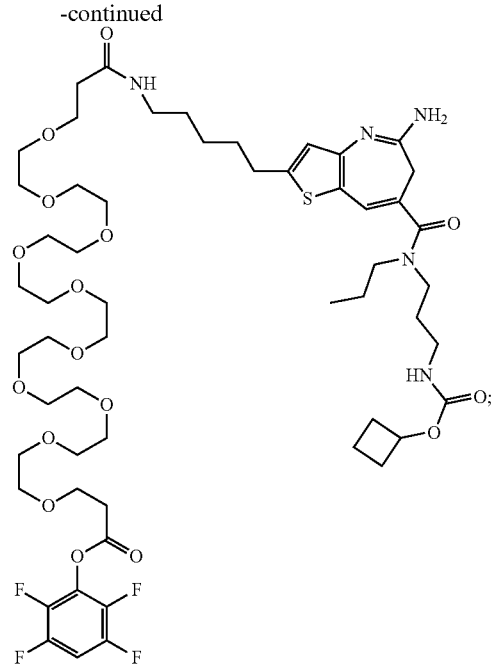
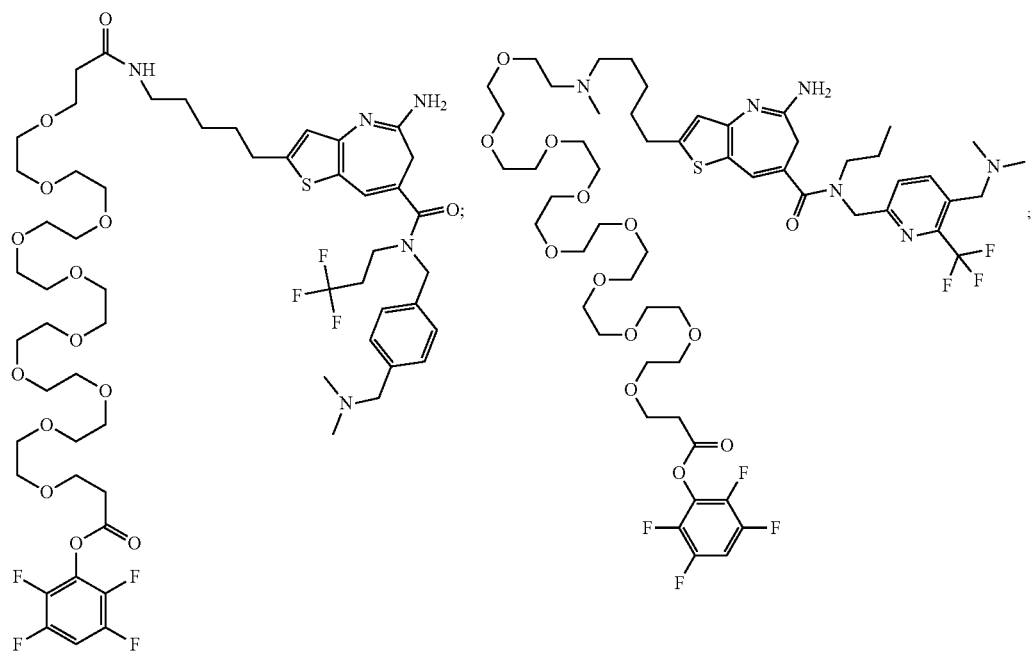

-continued
877
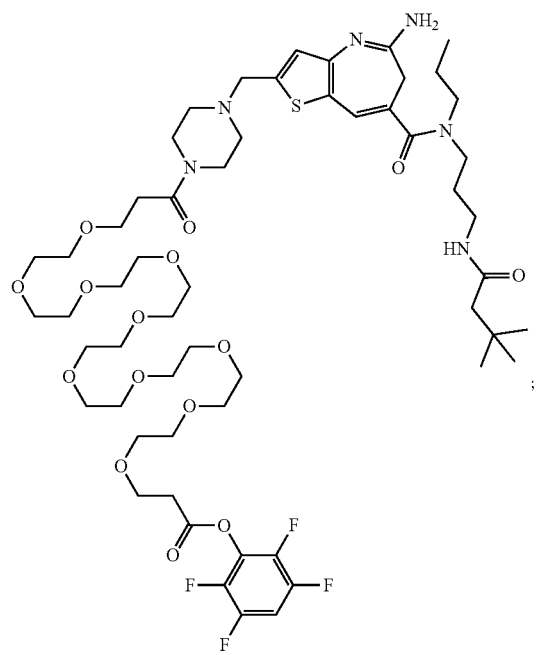
878
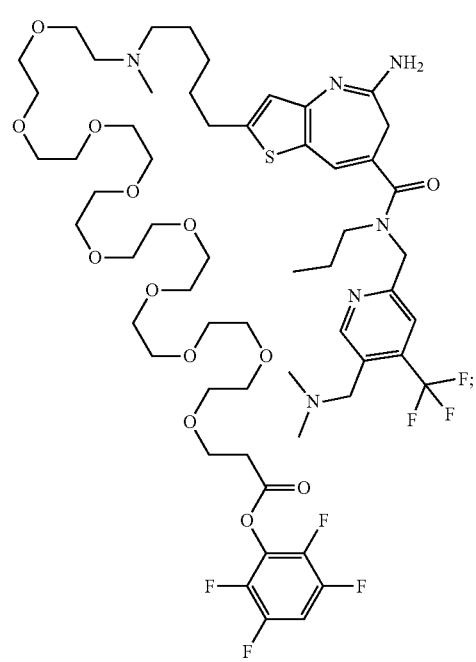
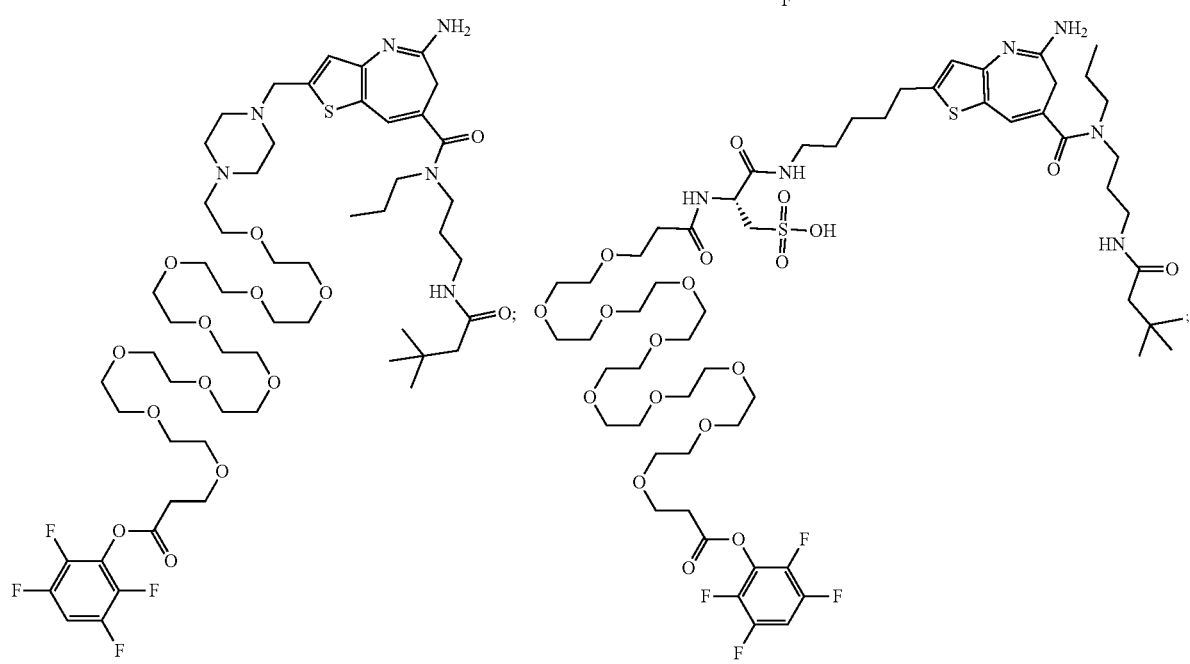
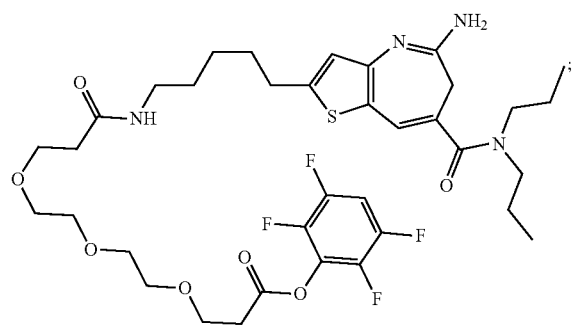

879 880
-continued
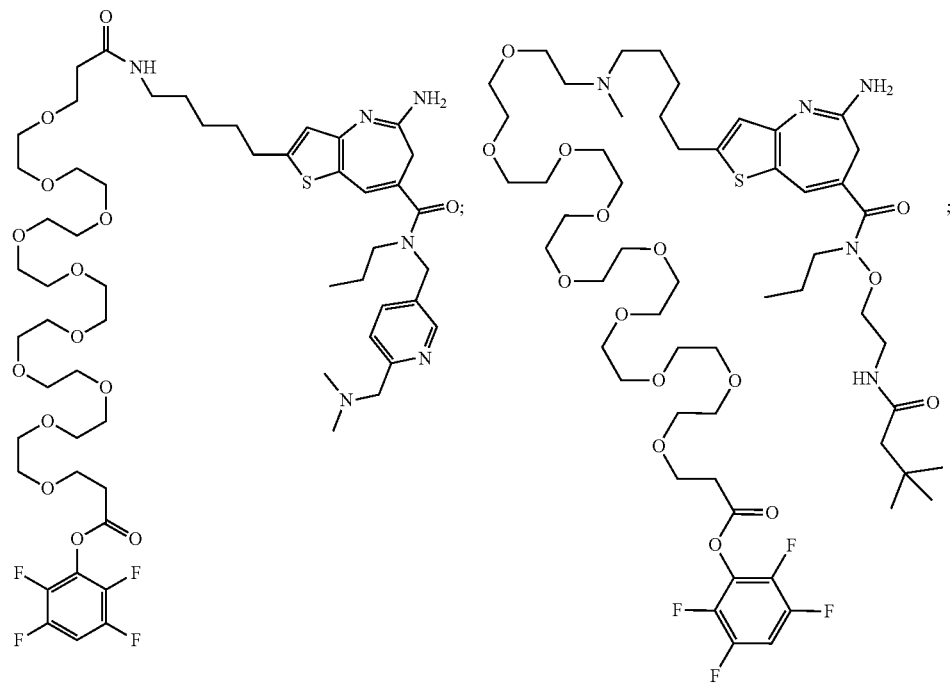
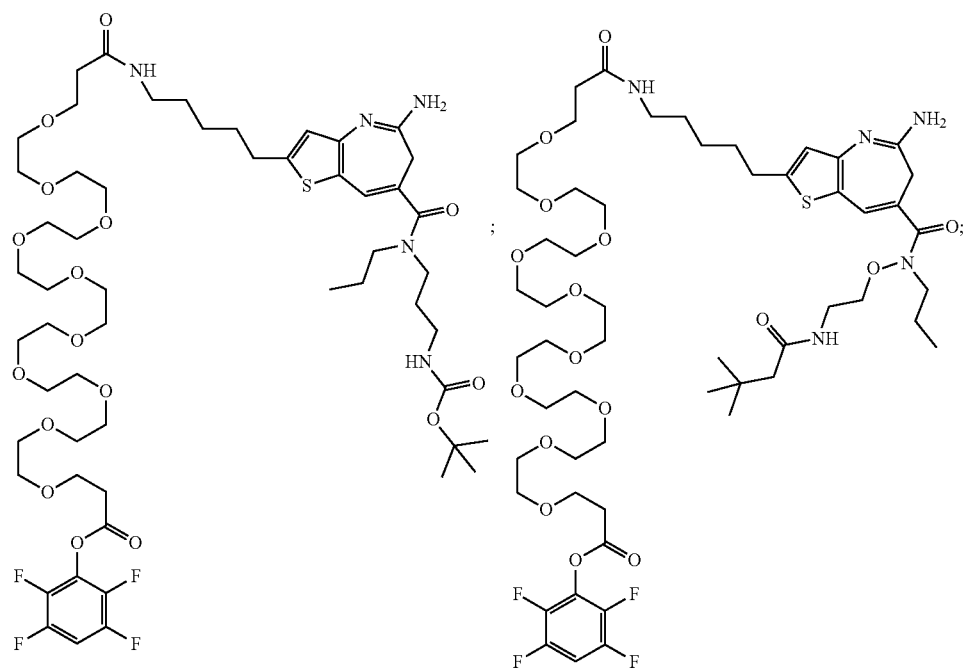

881
-continued
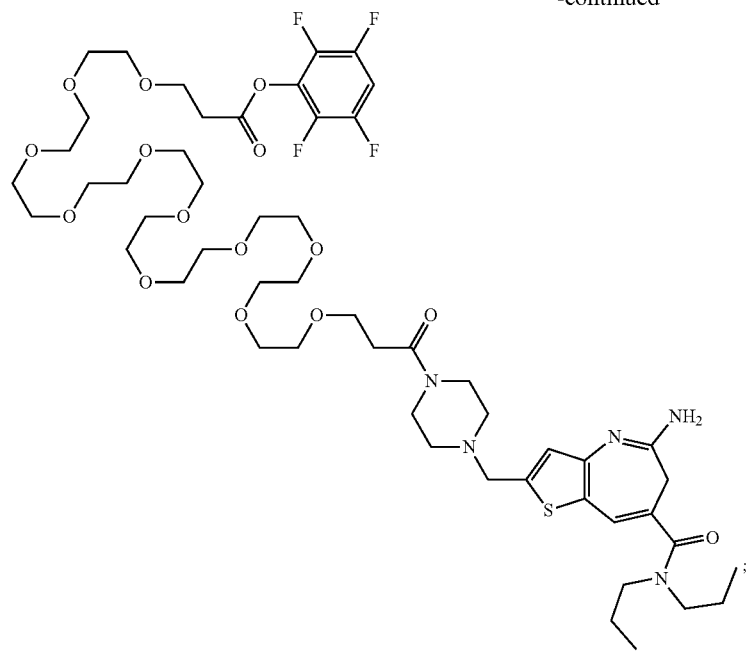
882
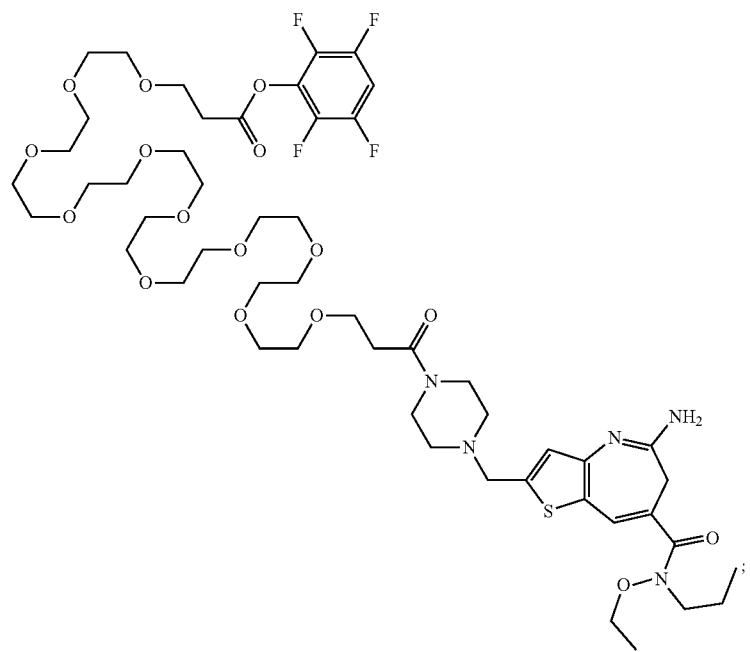

-continued
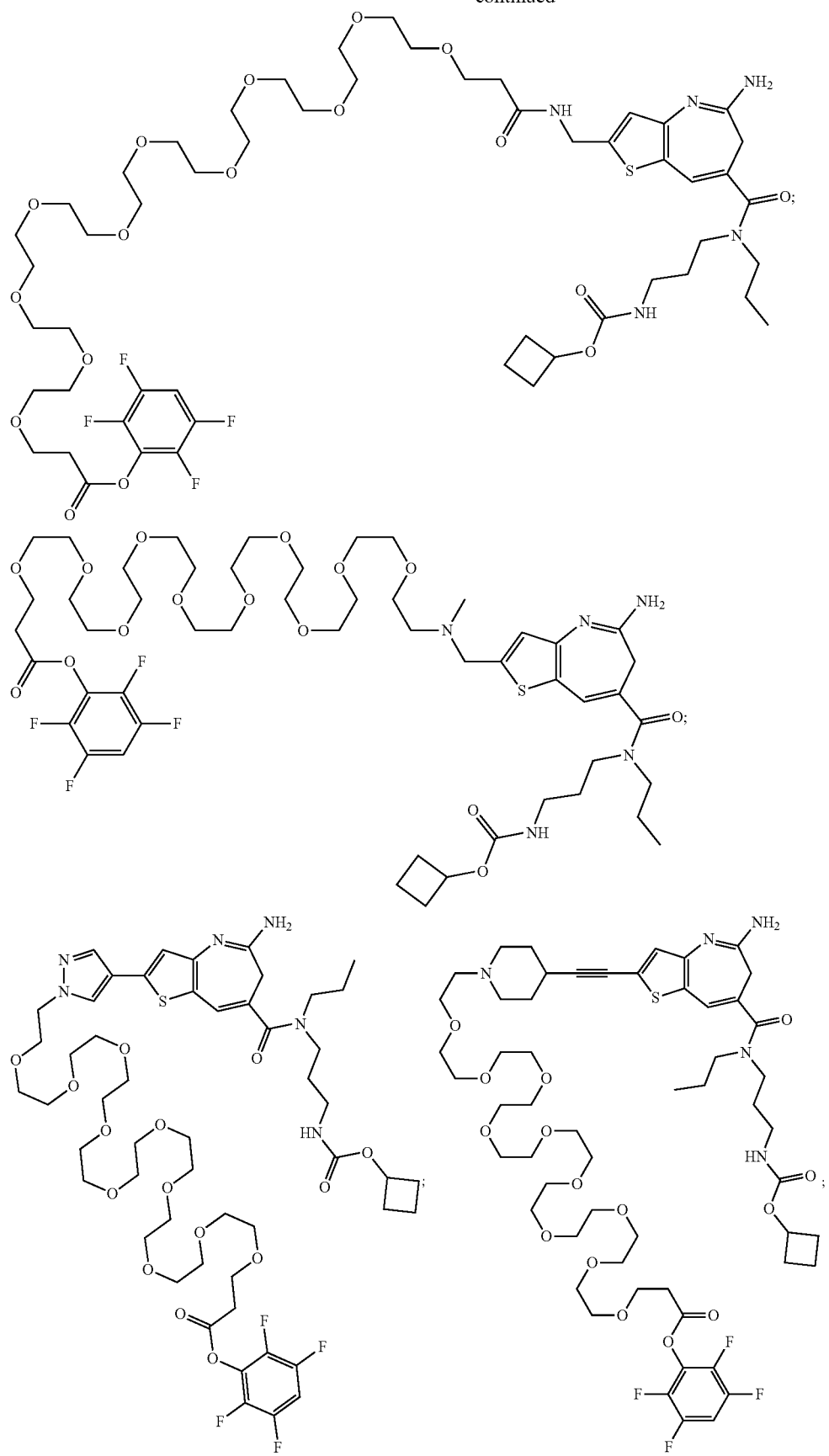

885 886
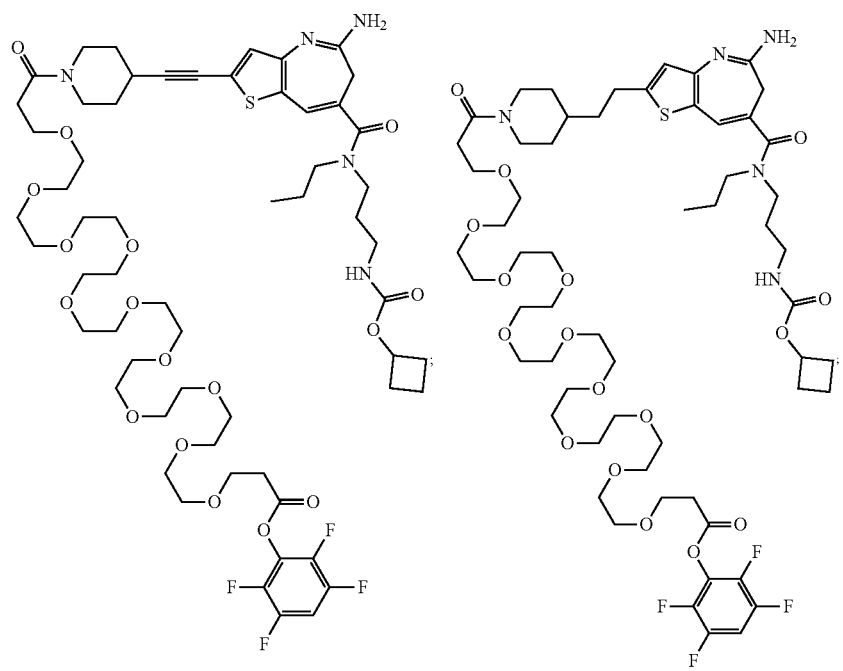
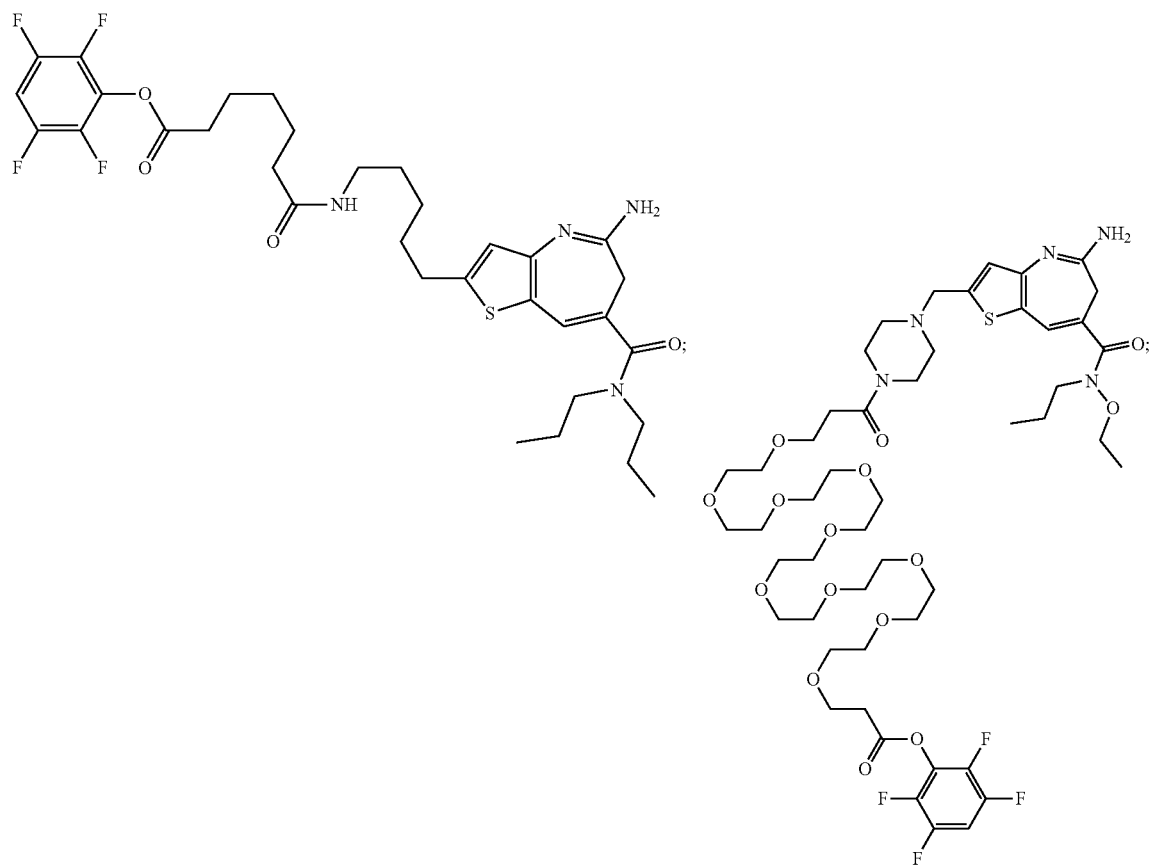

887 888
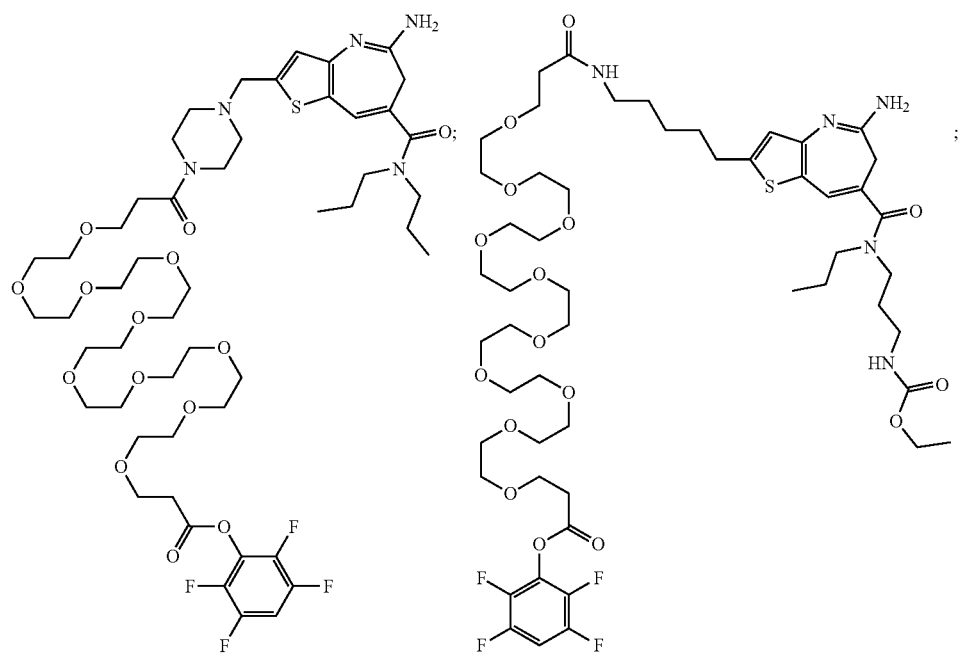
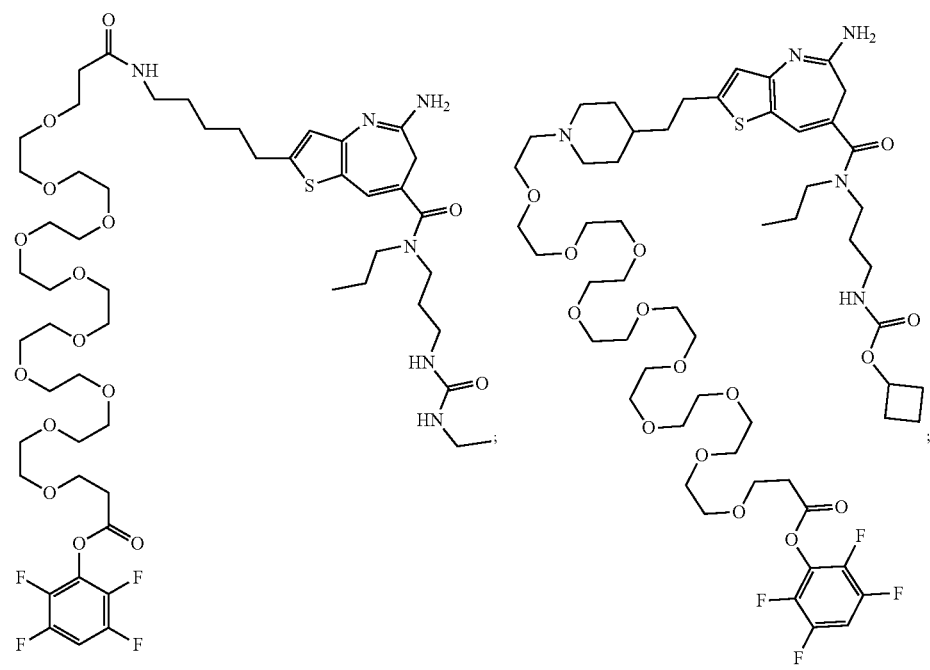

889 890
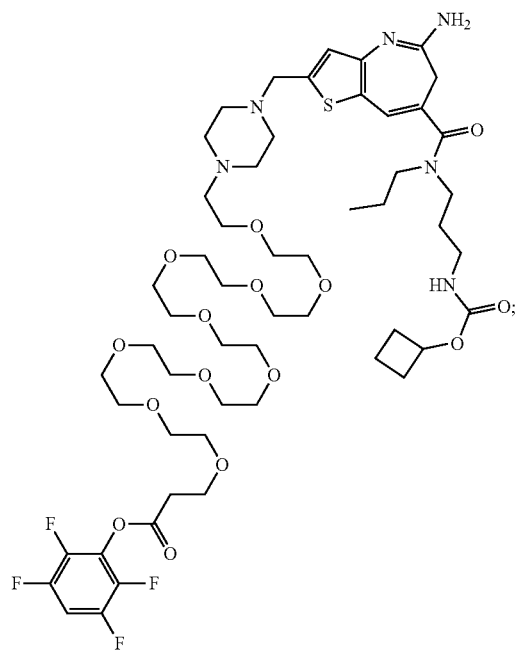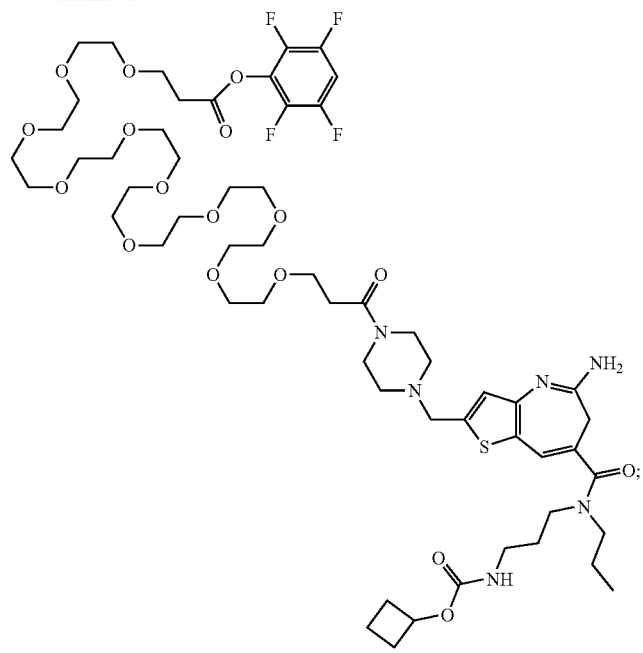
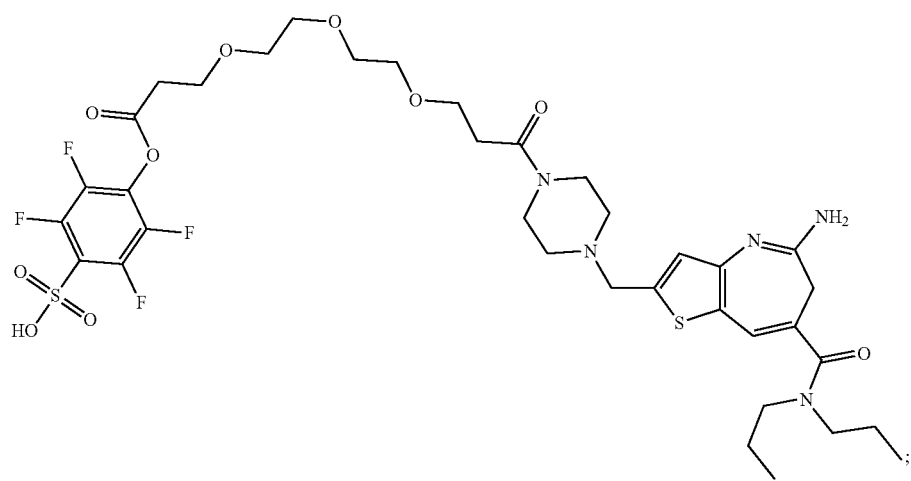

891
-continued
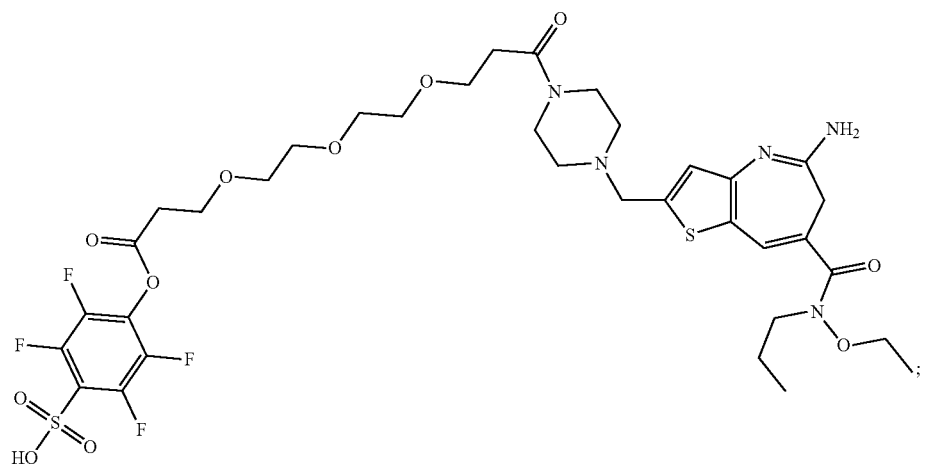
892
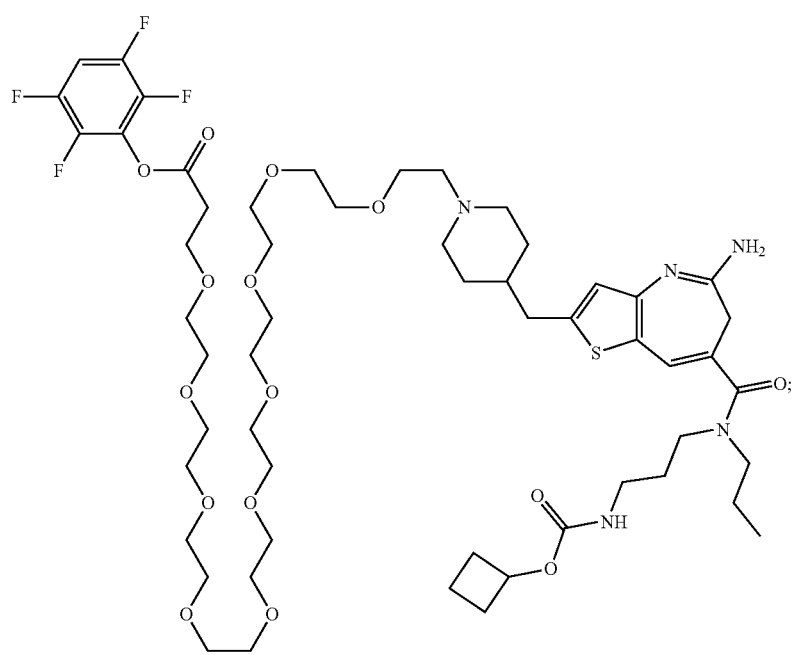

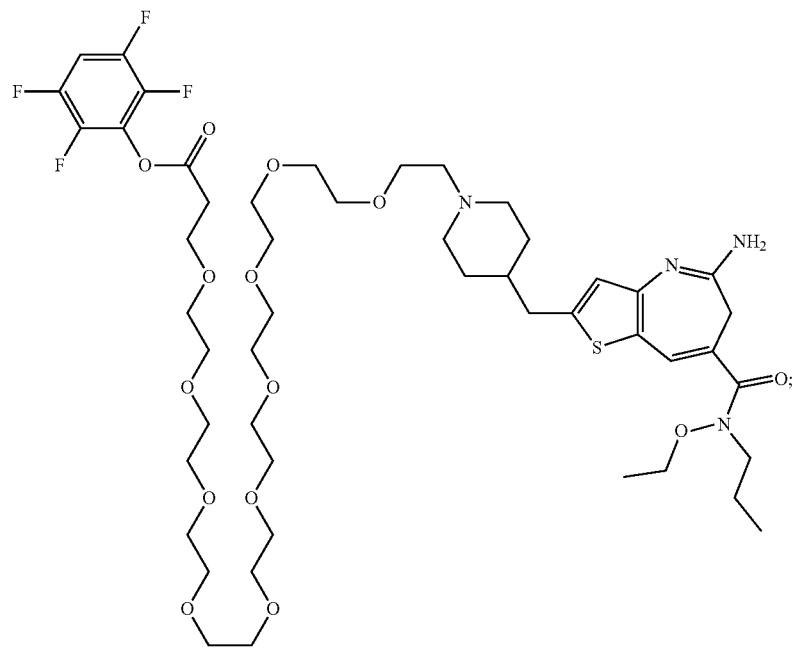
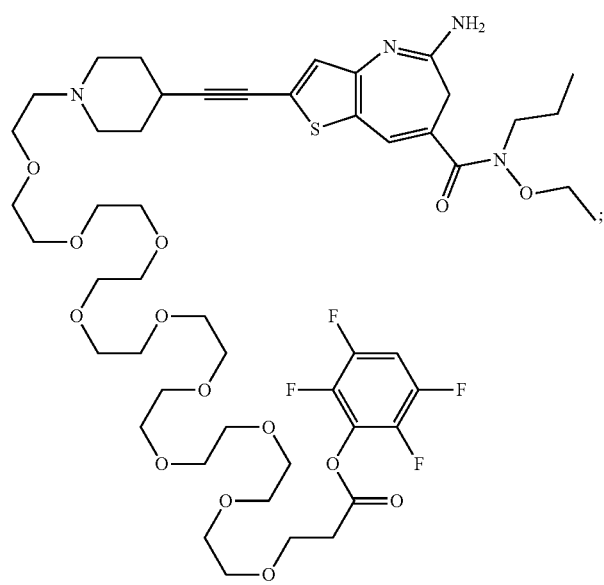

895
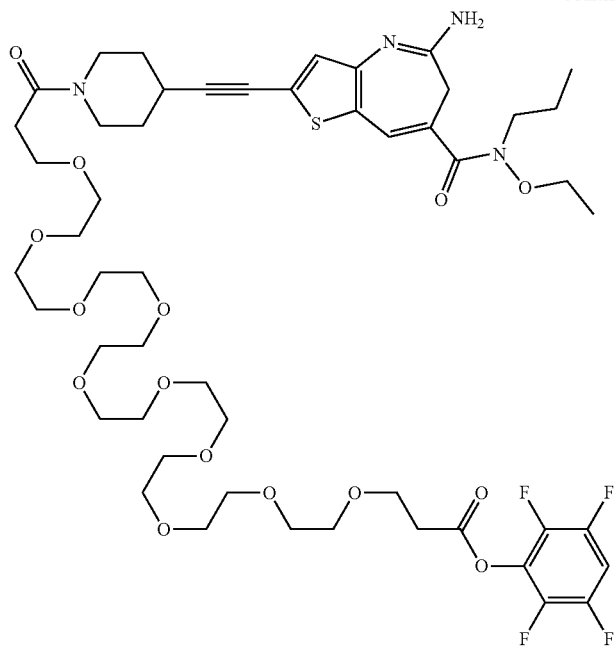
896
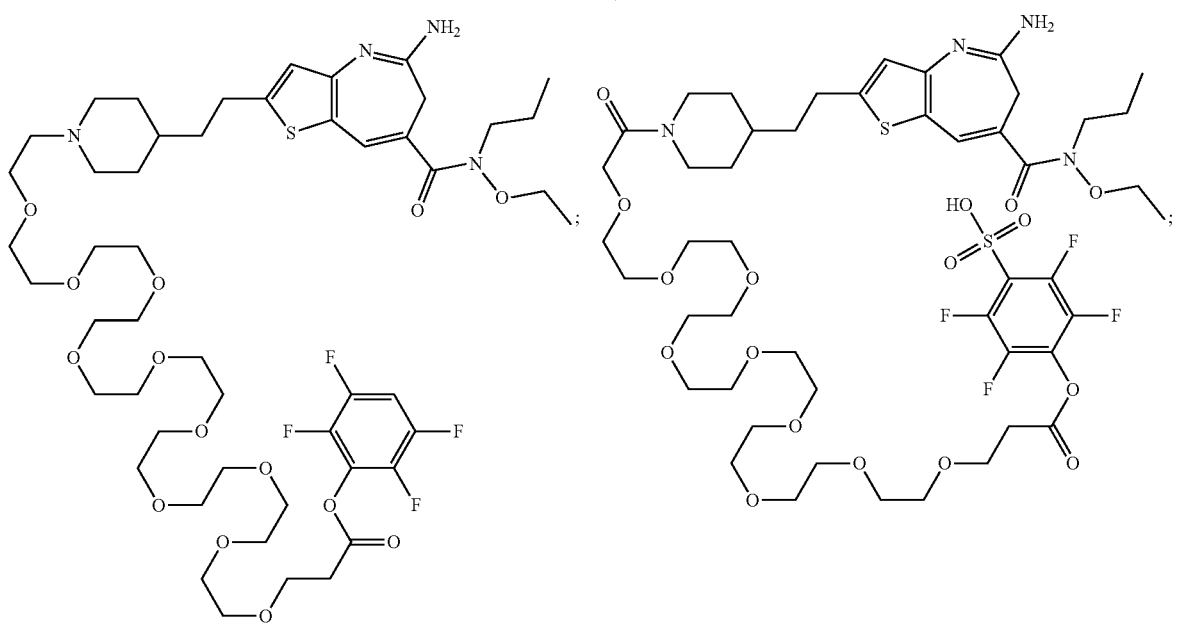
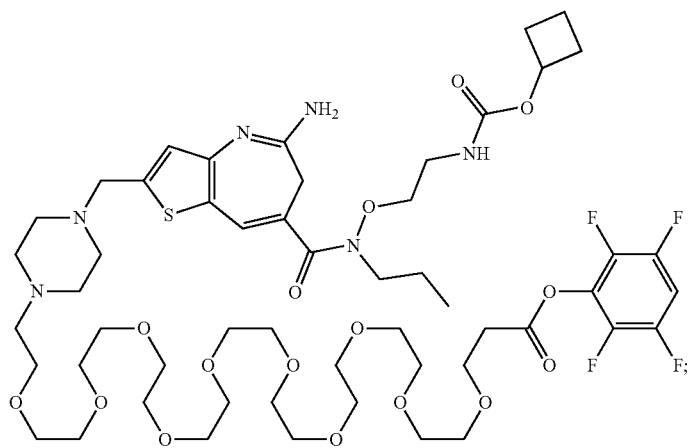

-continued
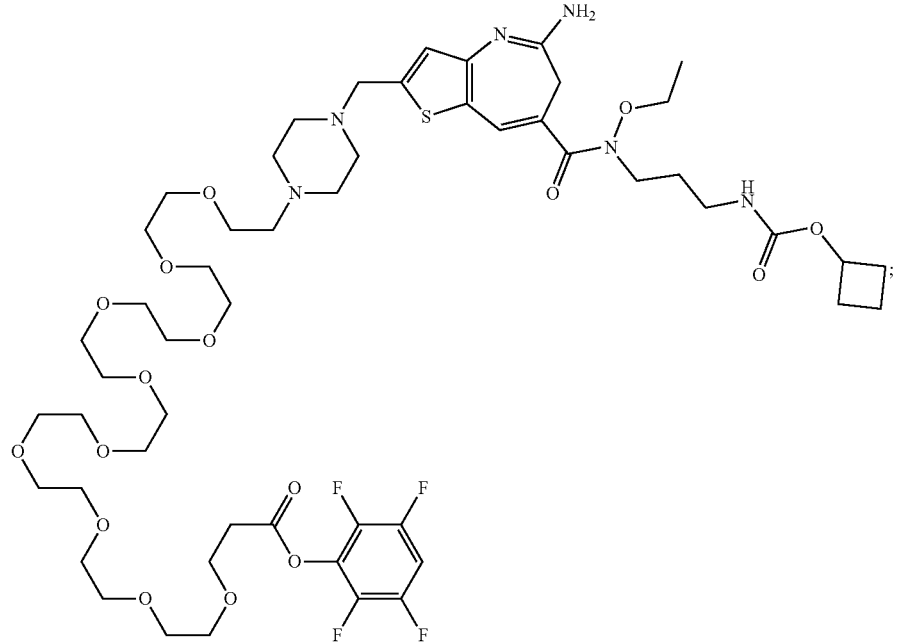
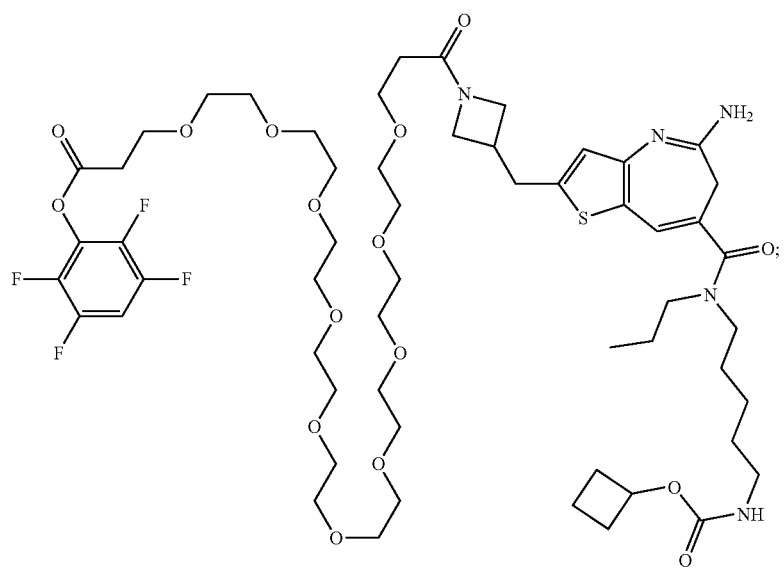

-continued
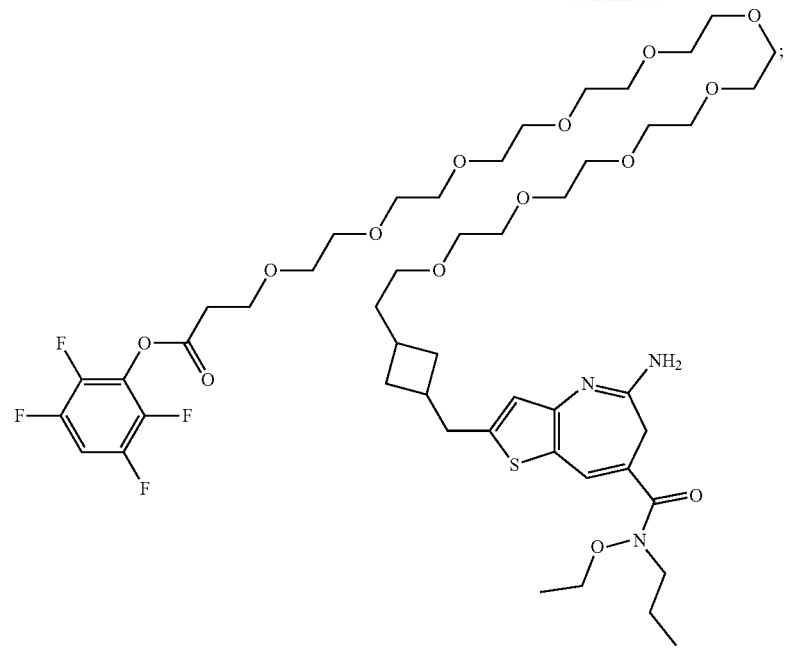
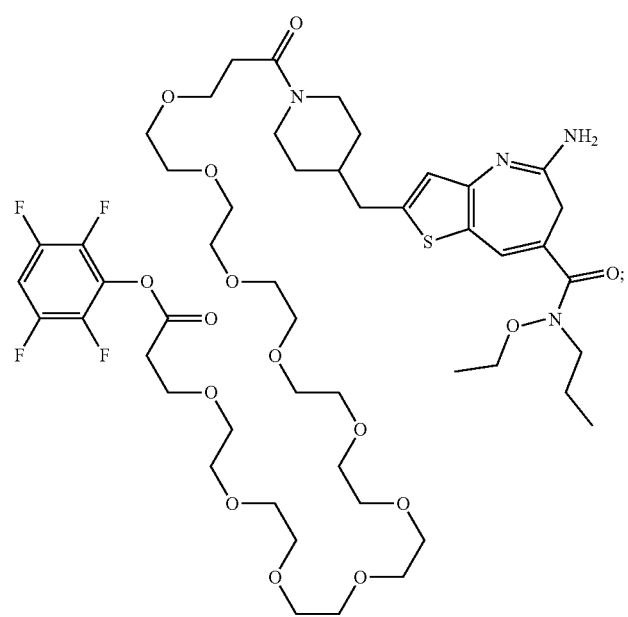

901
902
-continued
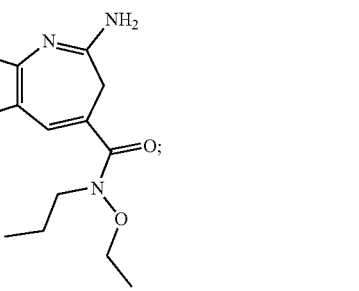
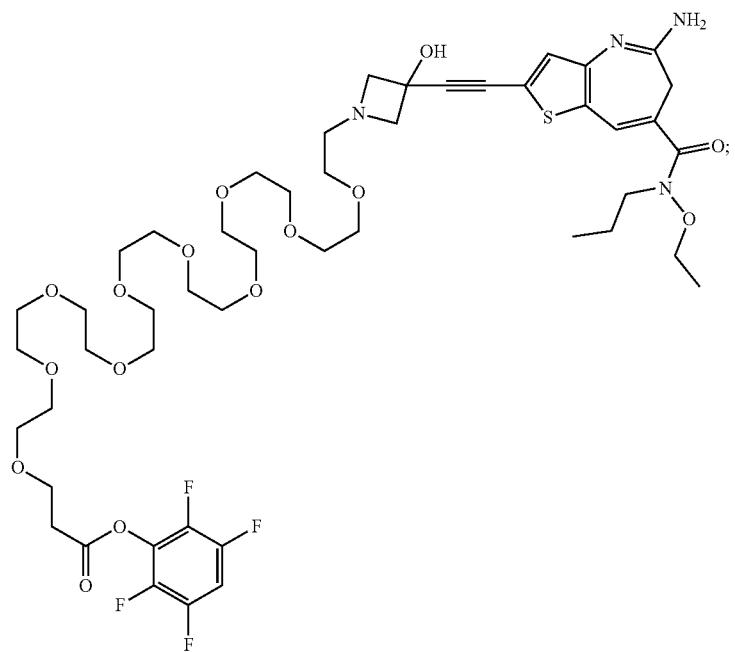
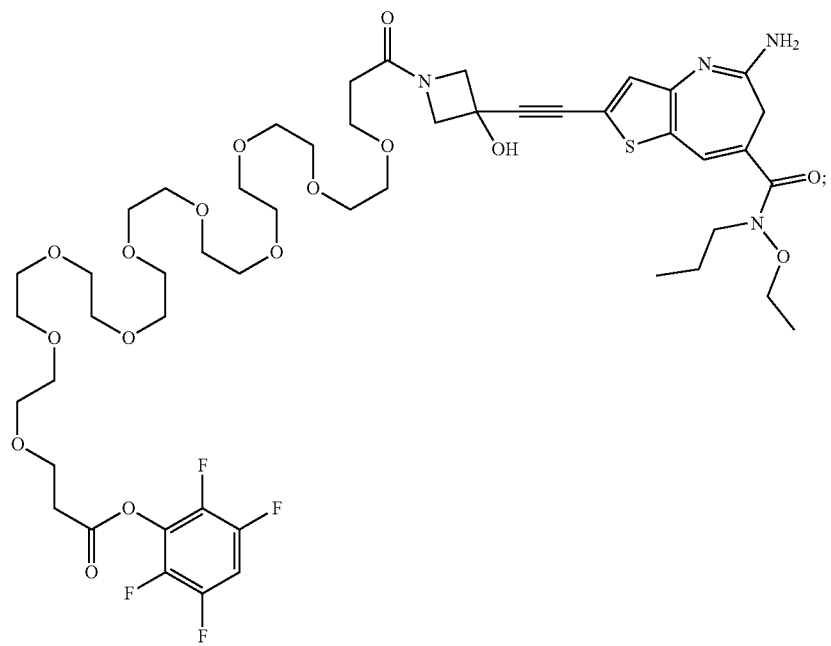

903
-continued
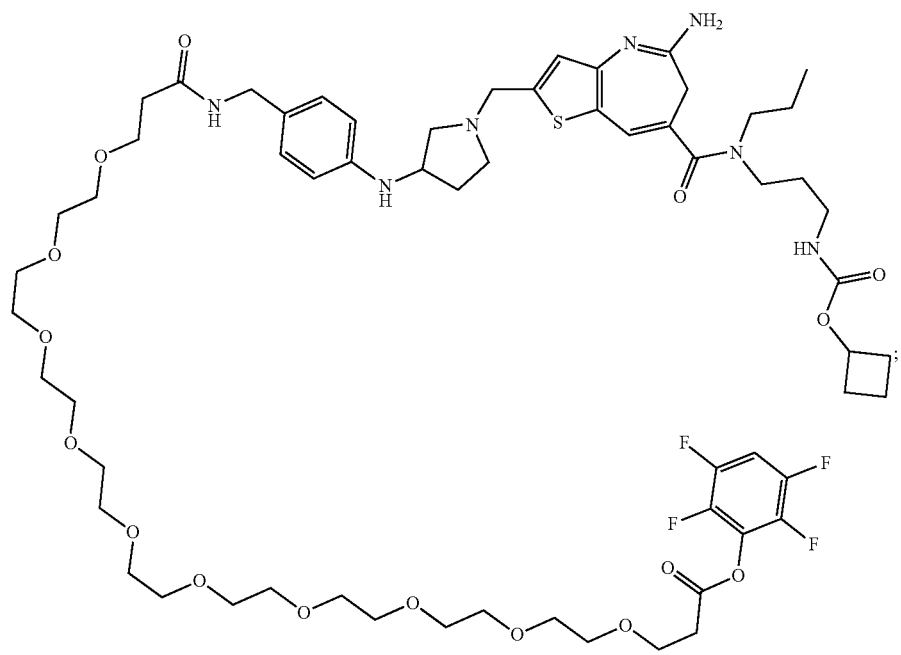
904
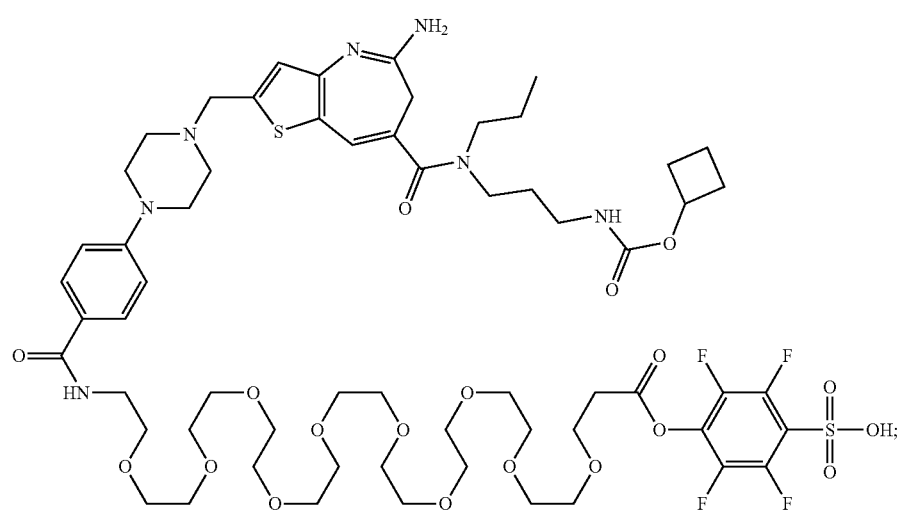

905 906
-continued
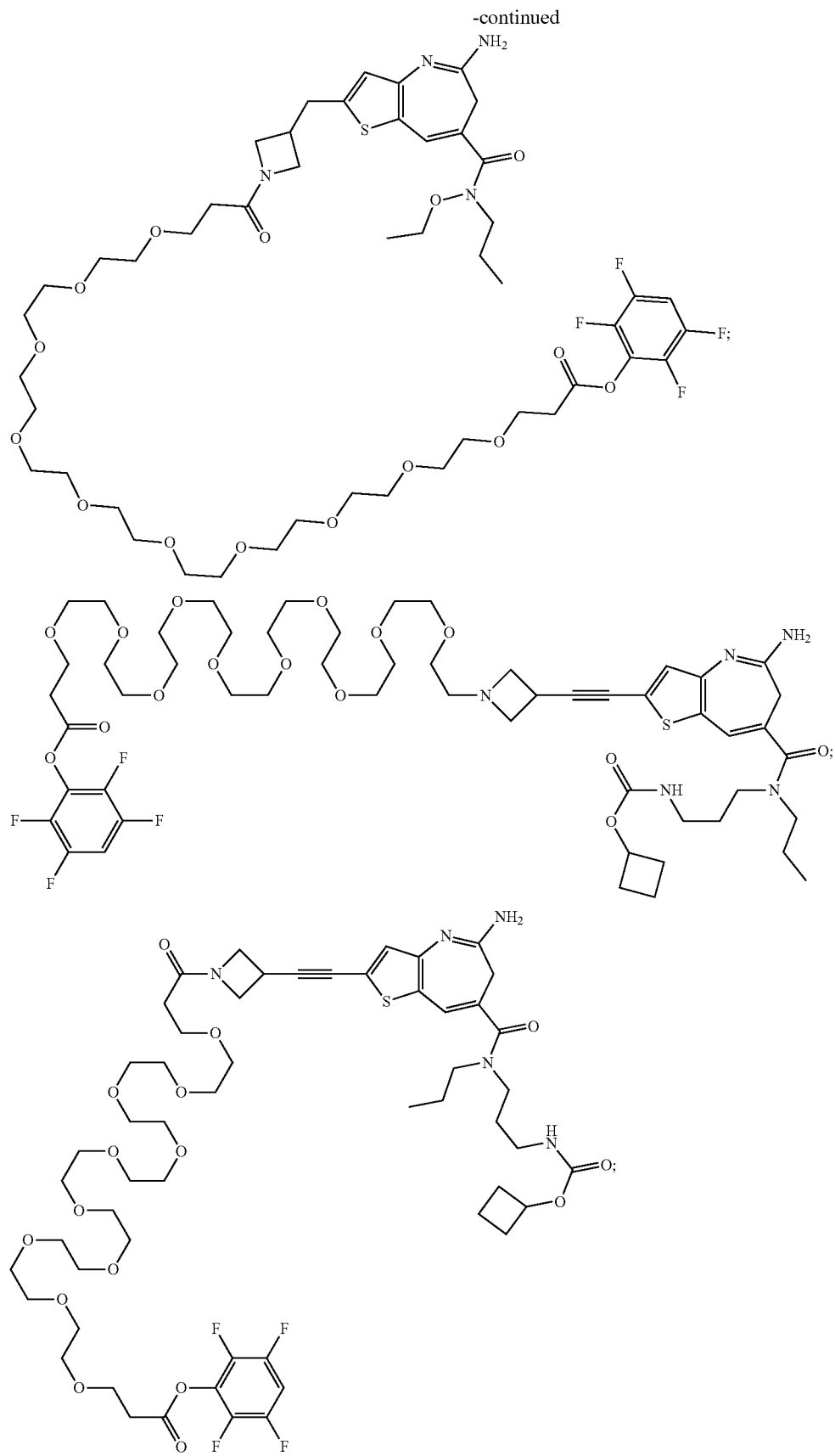

907                                    908
-continued
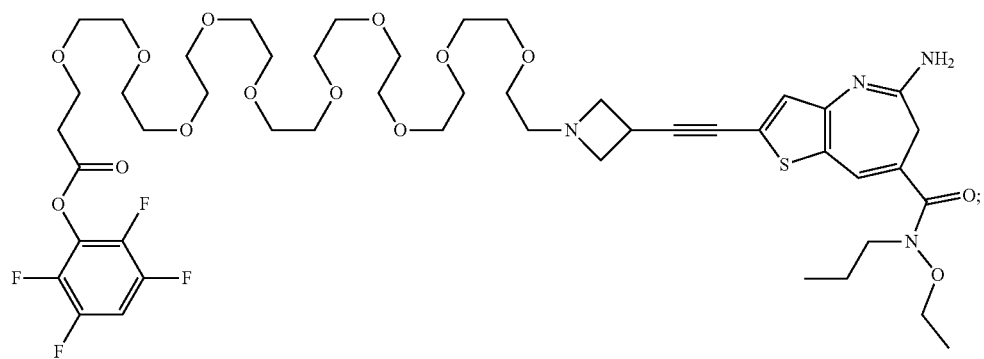
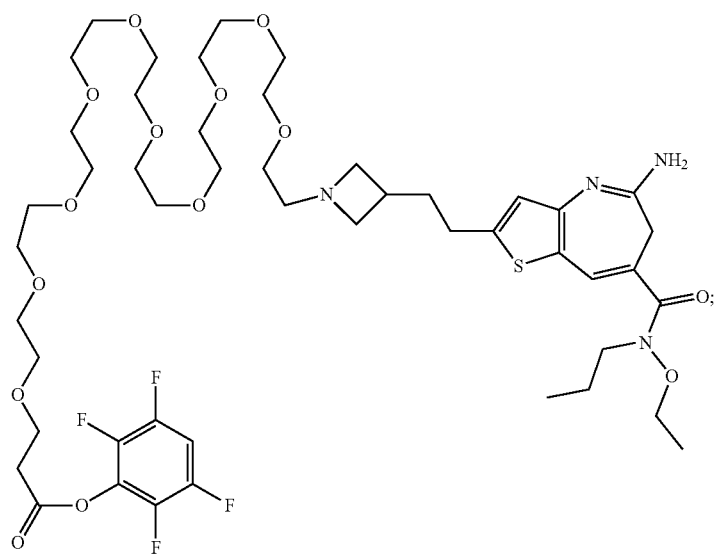
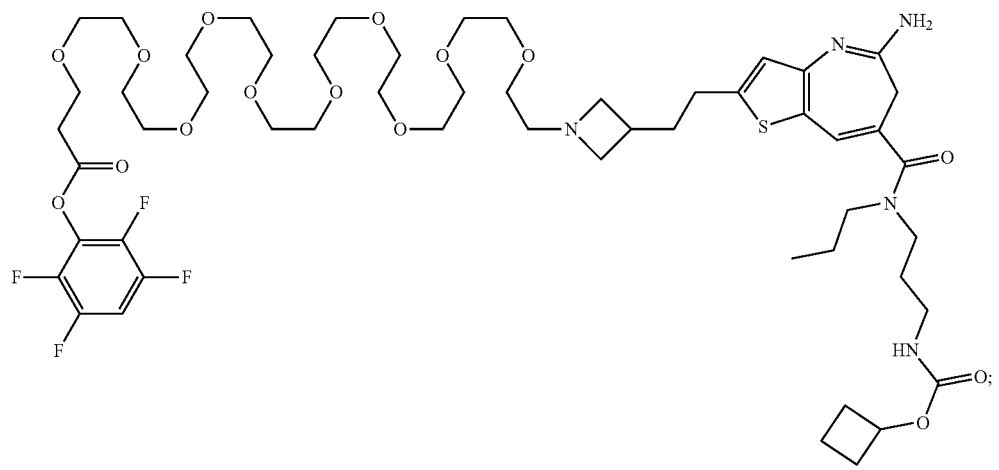

909
910
-continued
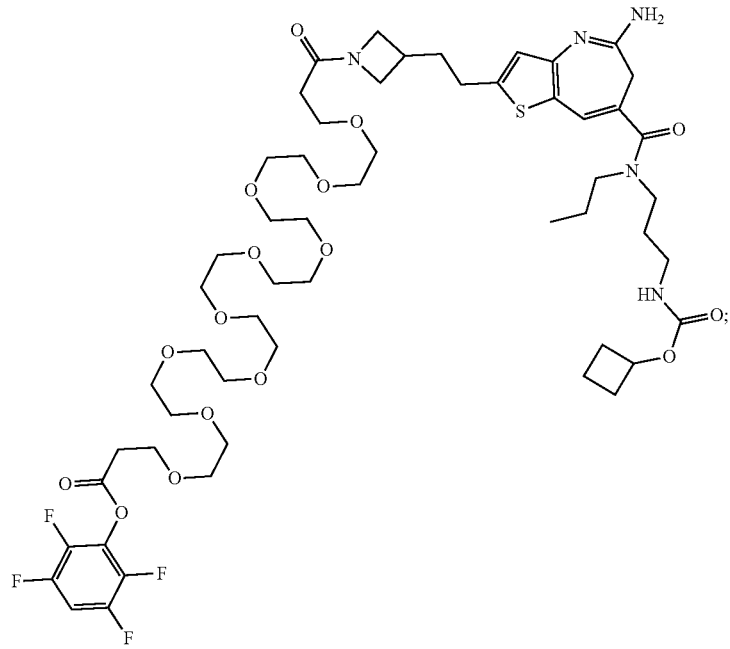
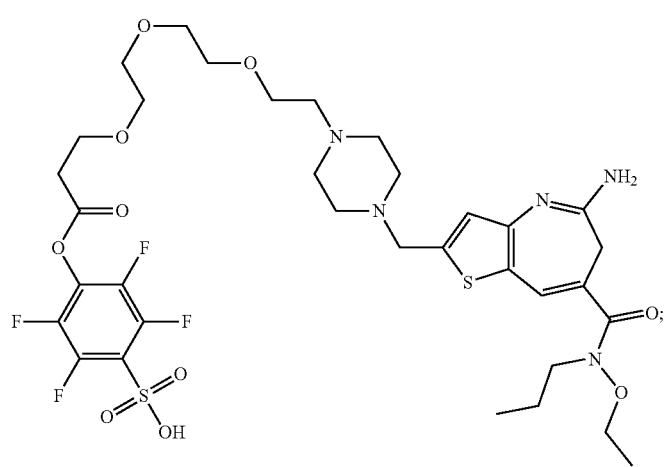

-continued
911
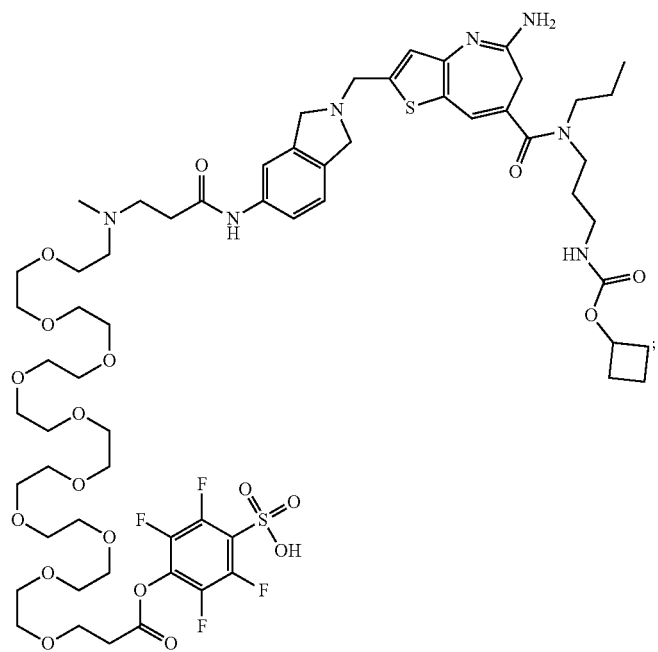
912
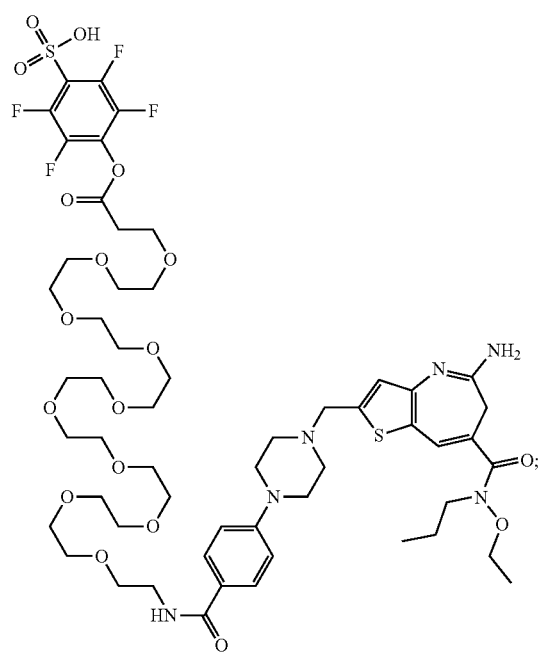

913
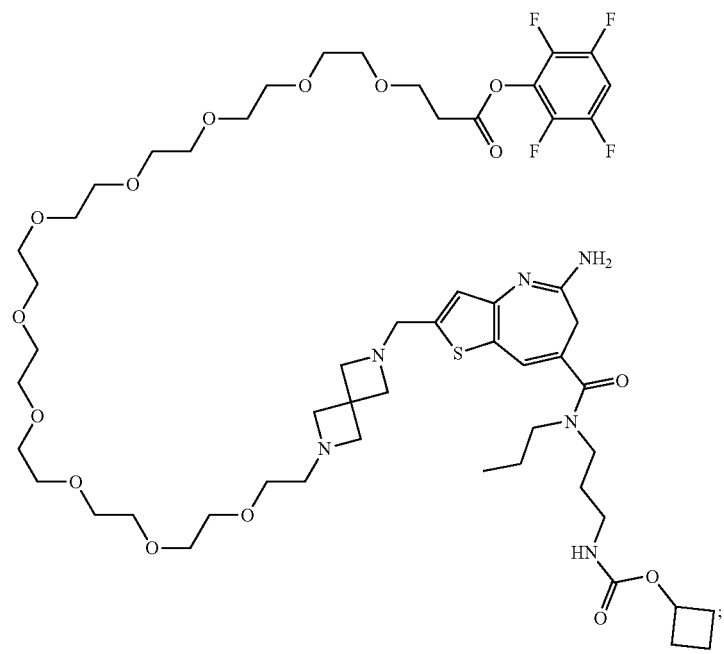
914
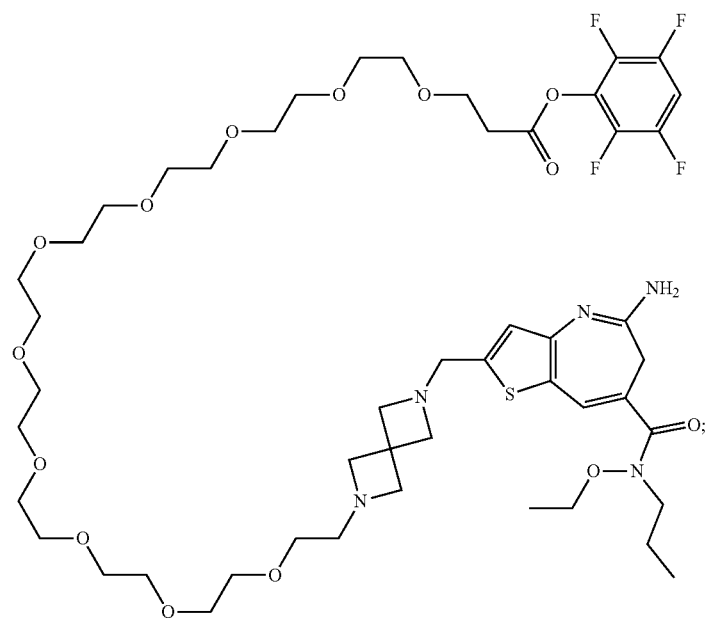

915
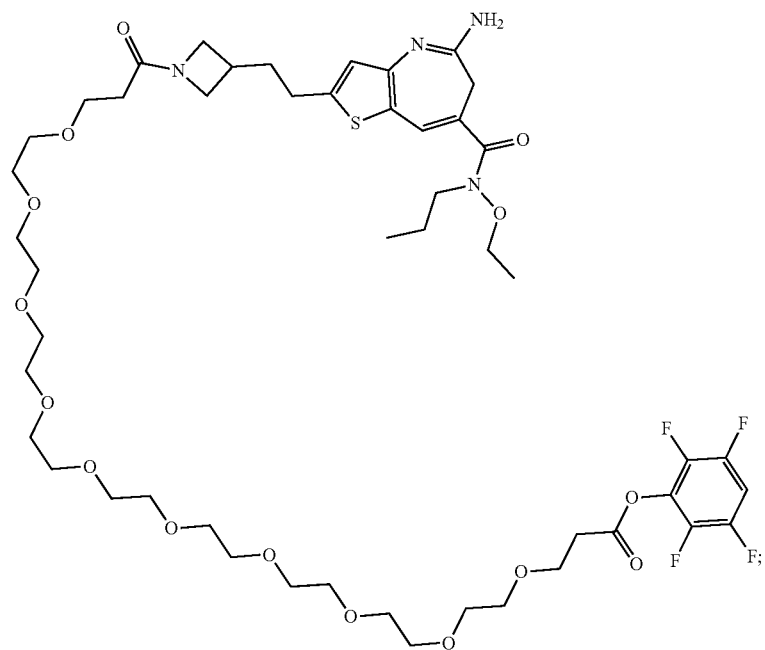
916
-continued
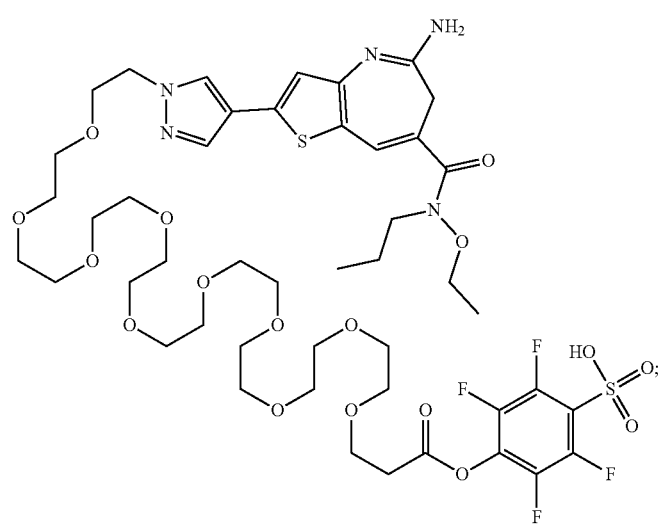

917
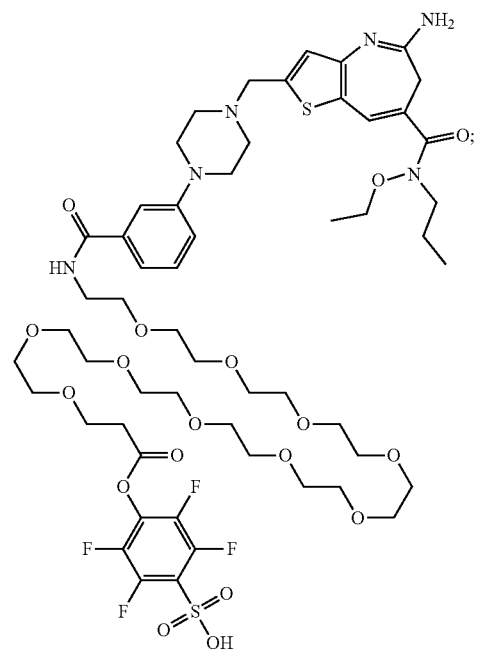
-continued
918
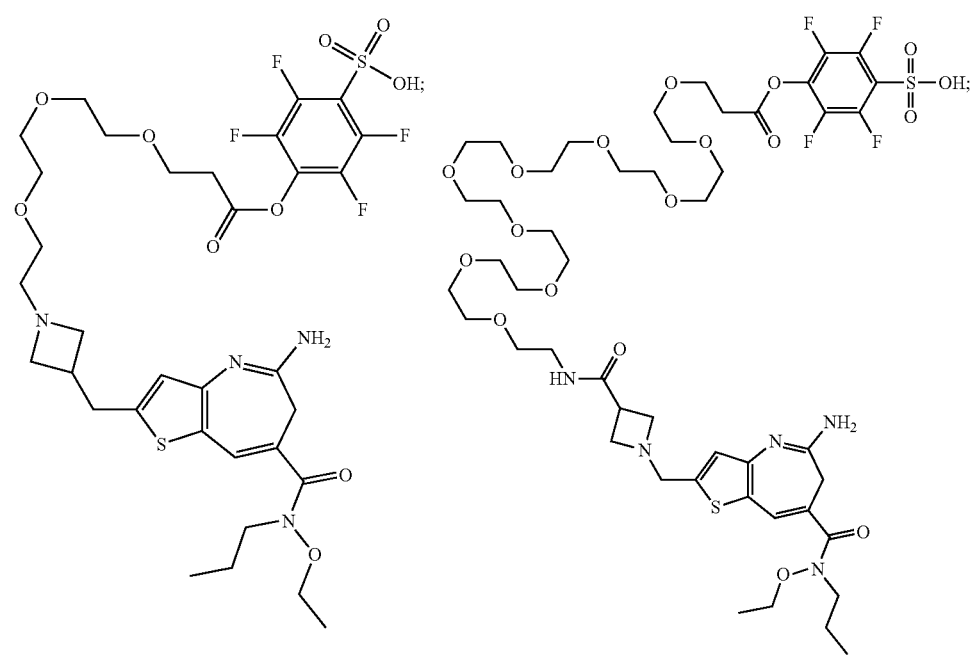

919 920
-continued
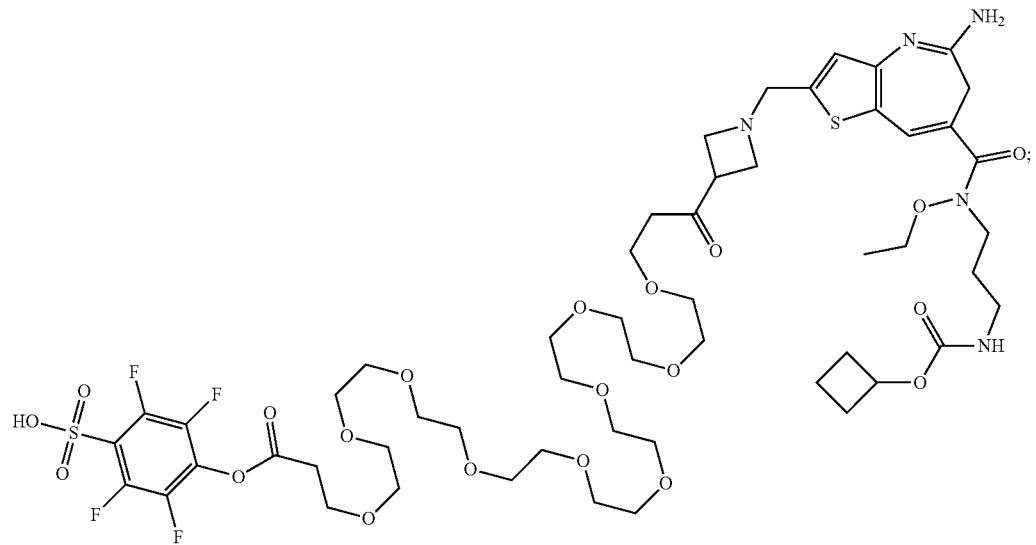
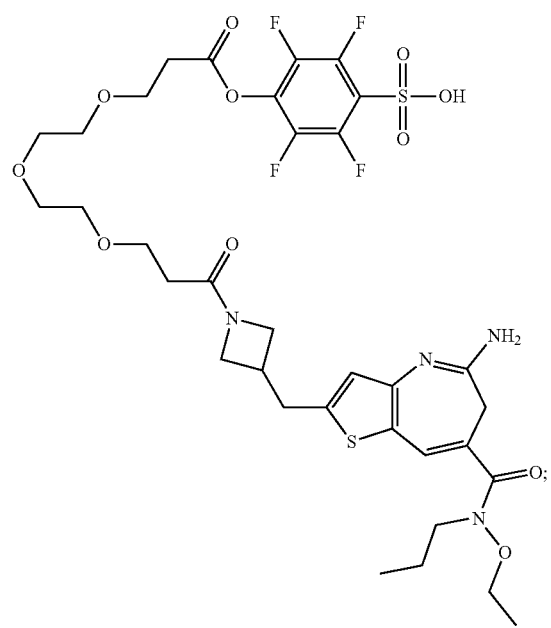

921
-continued
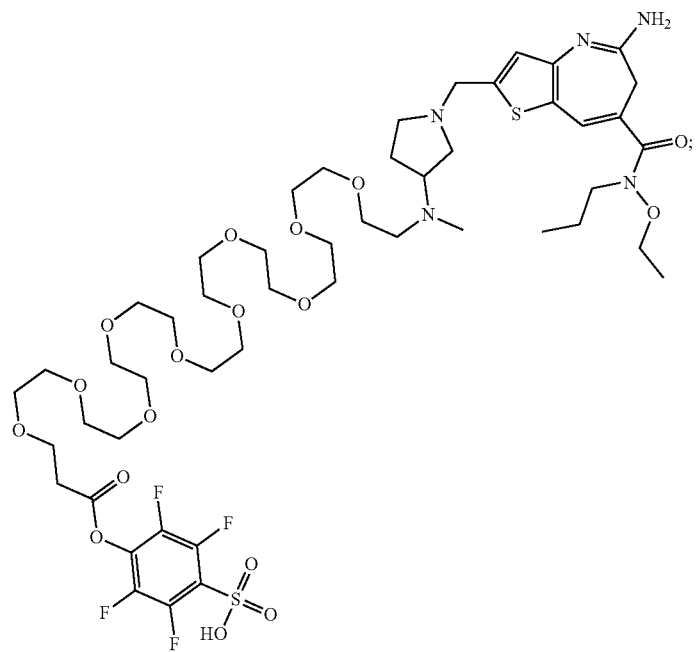
922
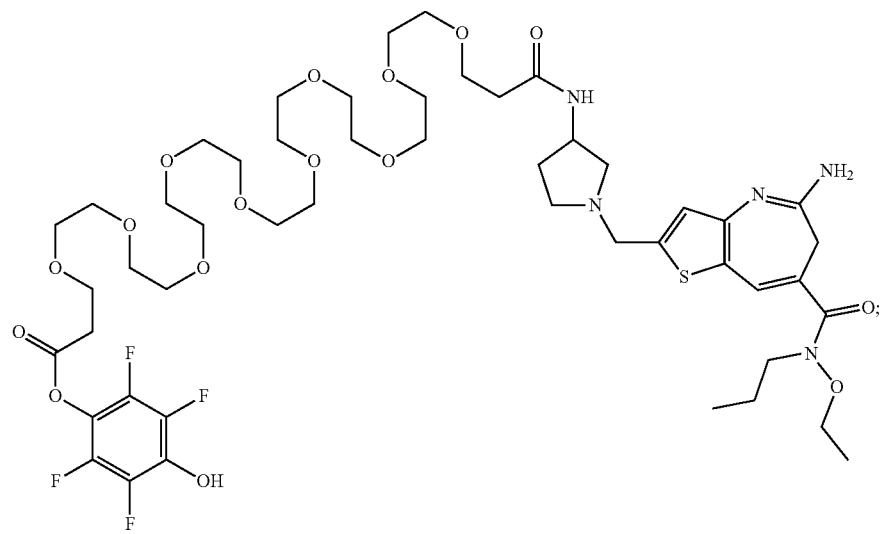

-continued
923
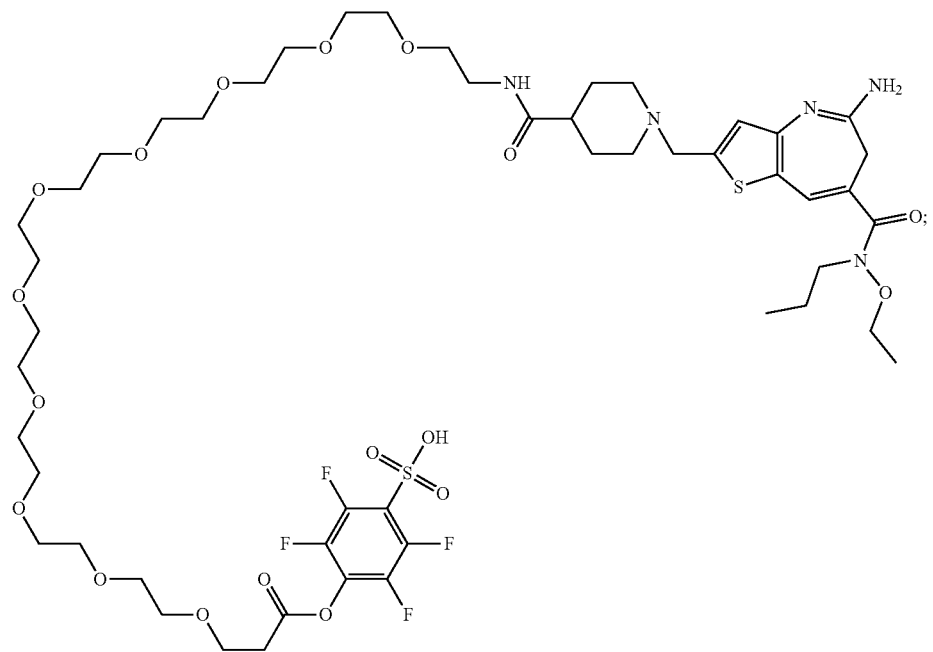
924
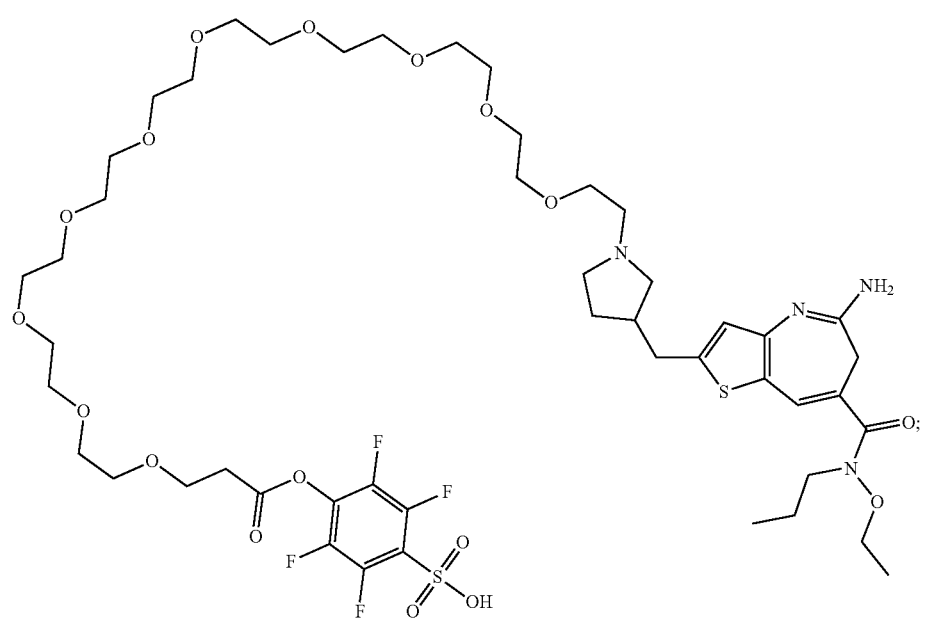

925
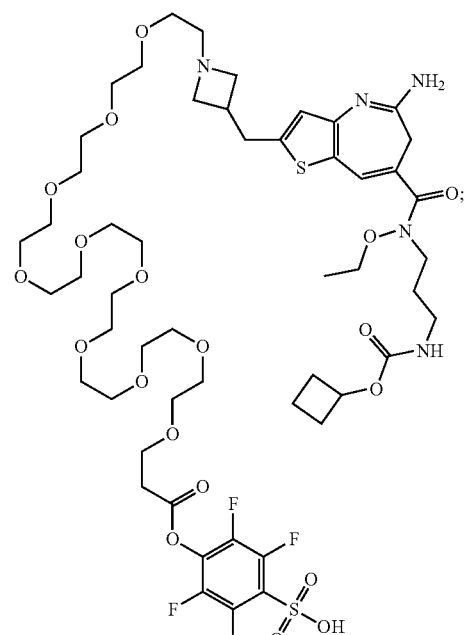
926
-continued
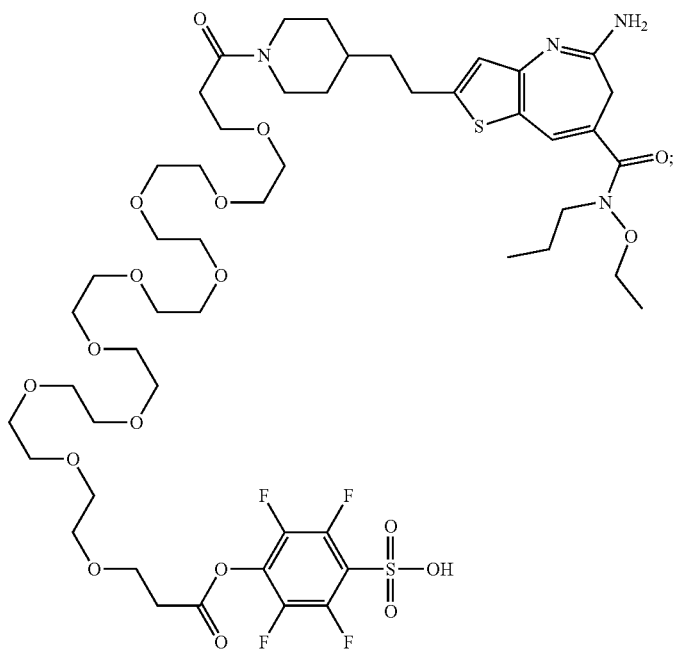
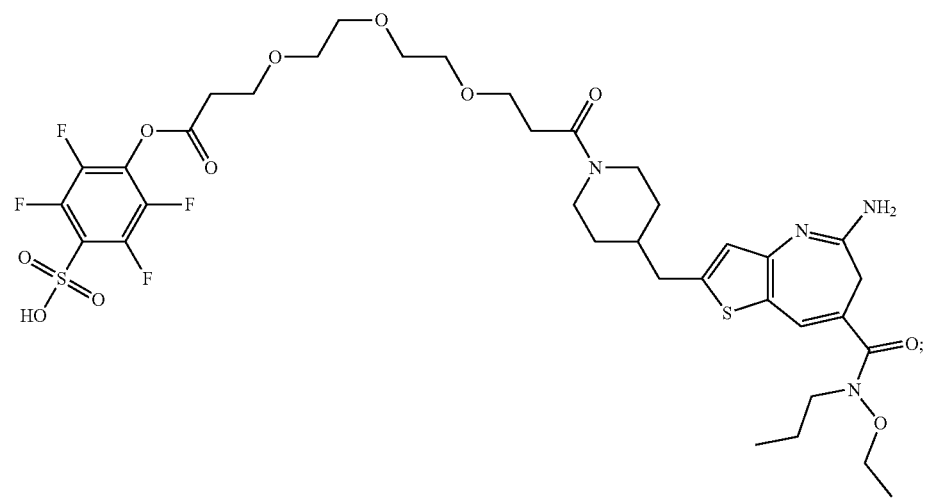

927
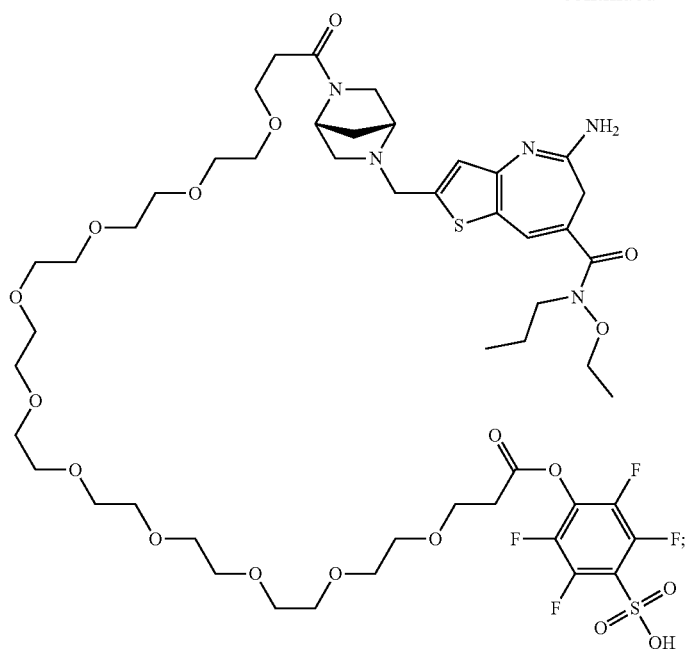
928
-continued
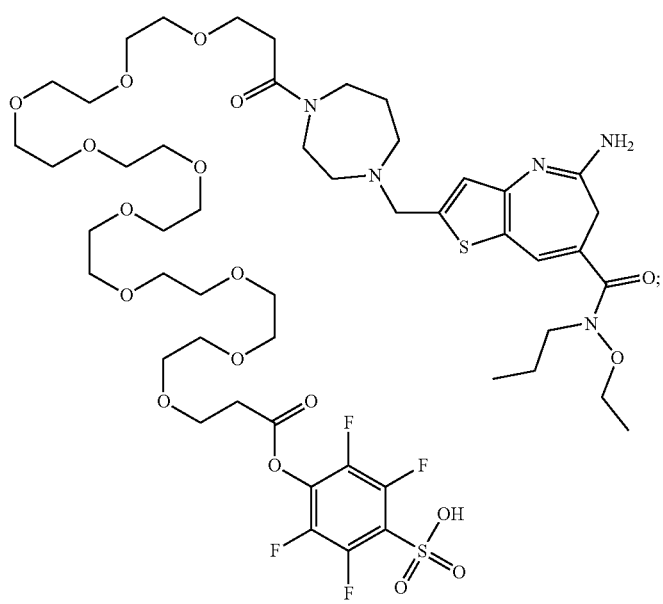

929
930
-continued
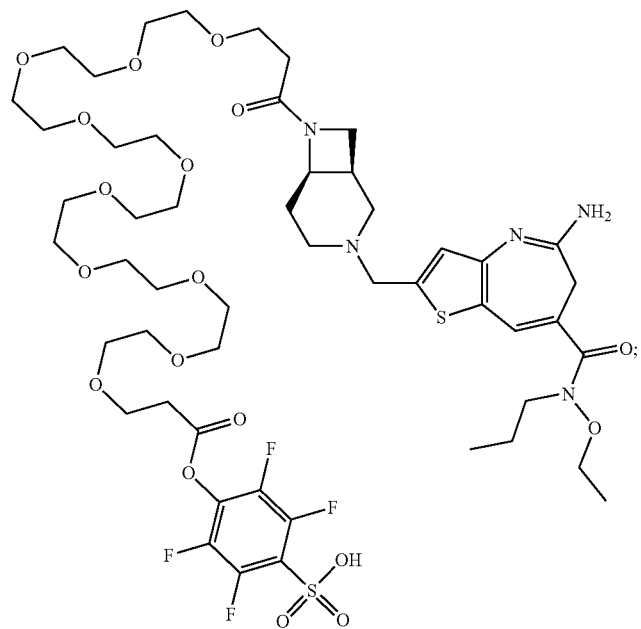
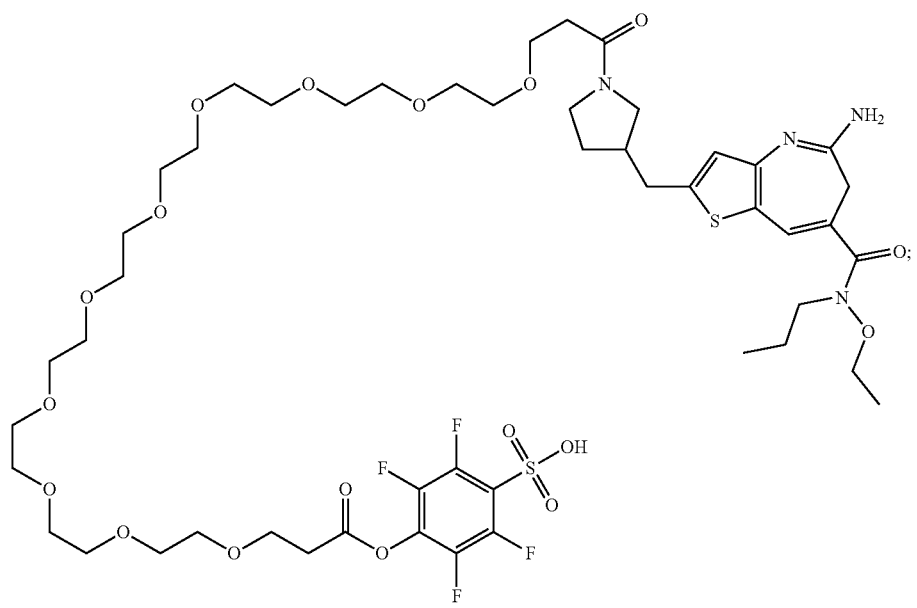

931
932
-continued
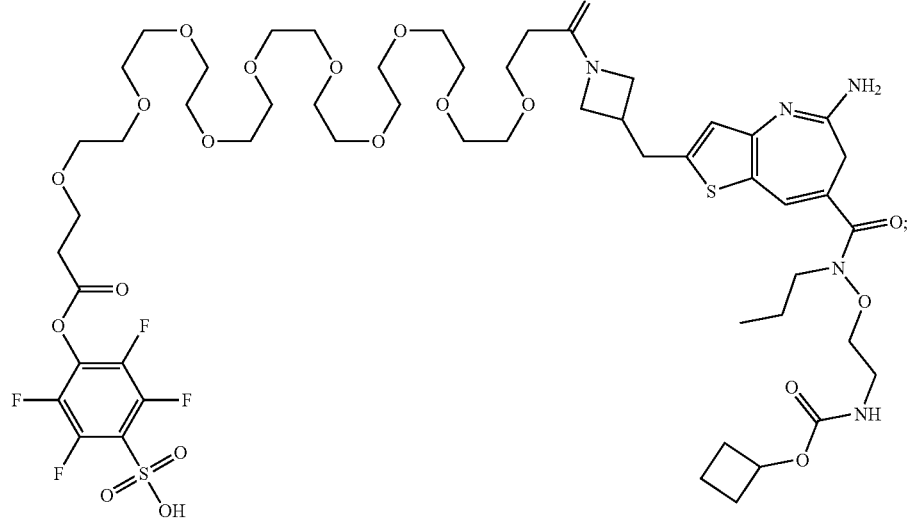
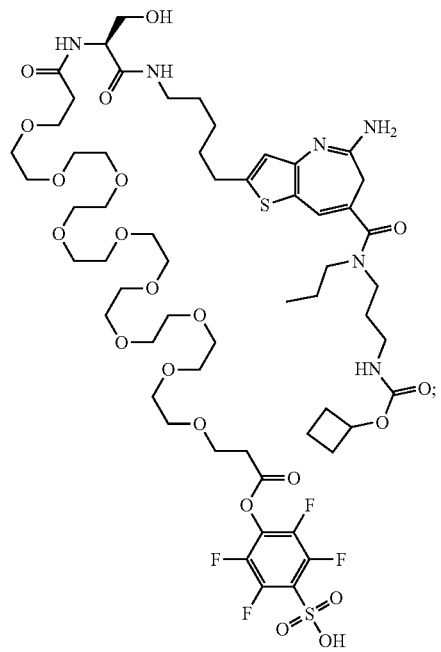
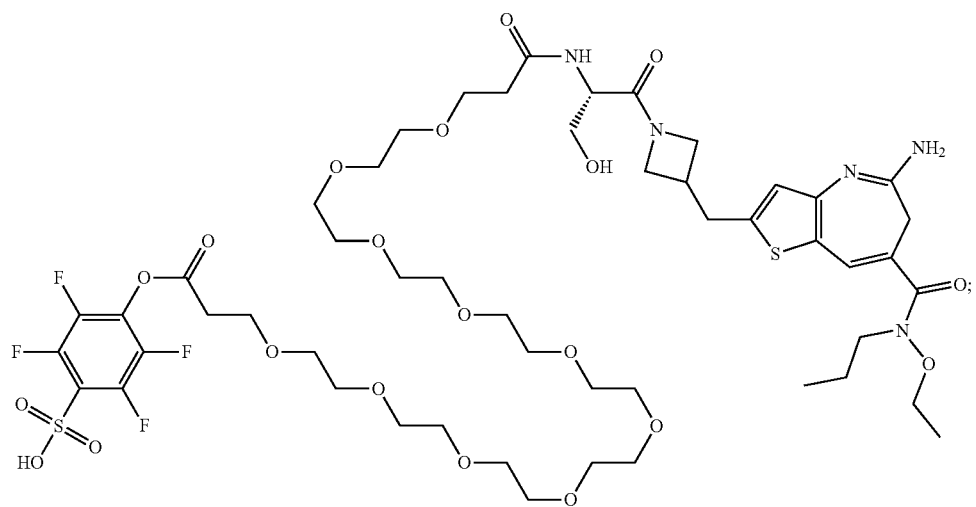

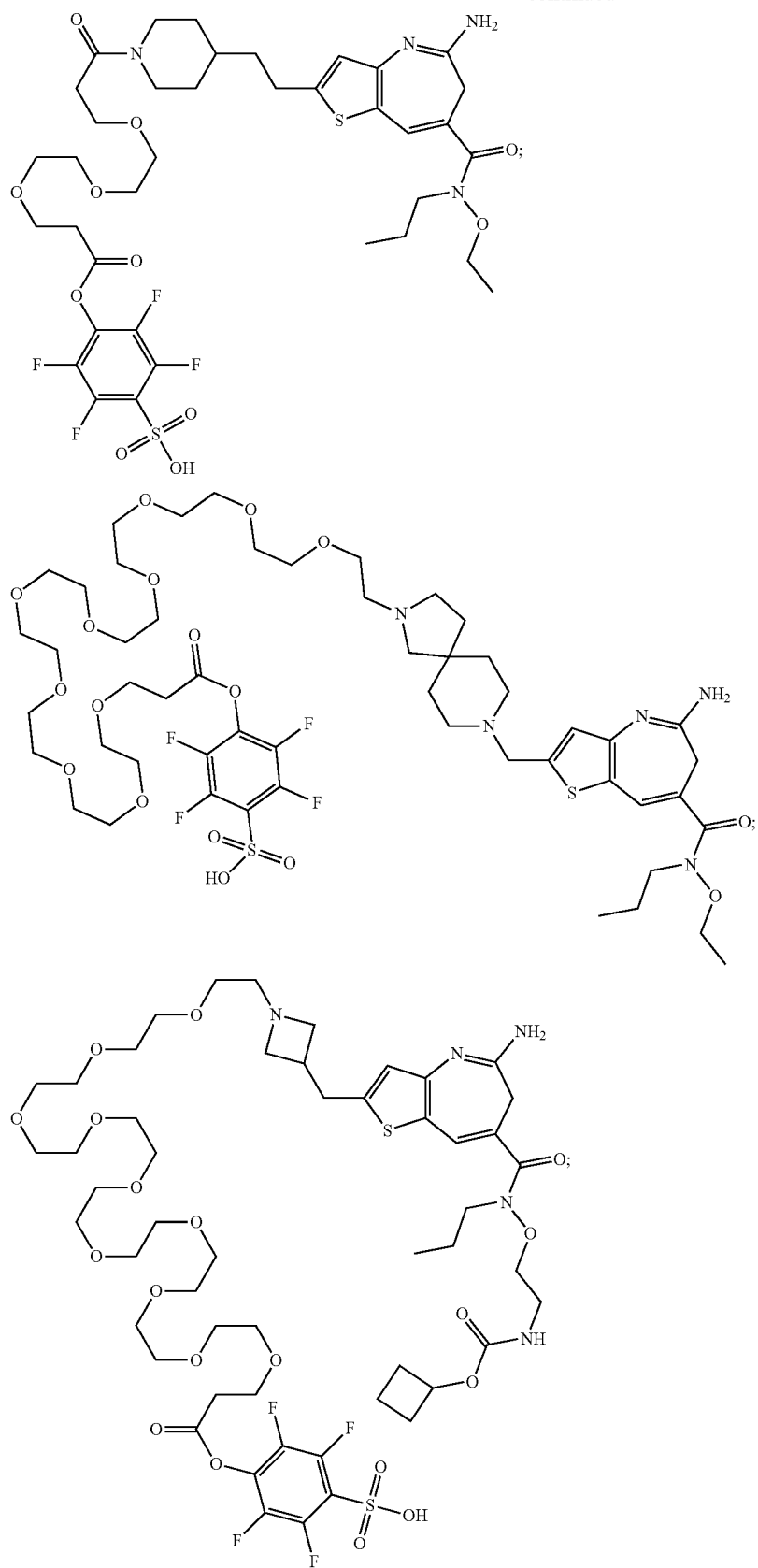

935 936
-continued
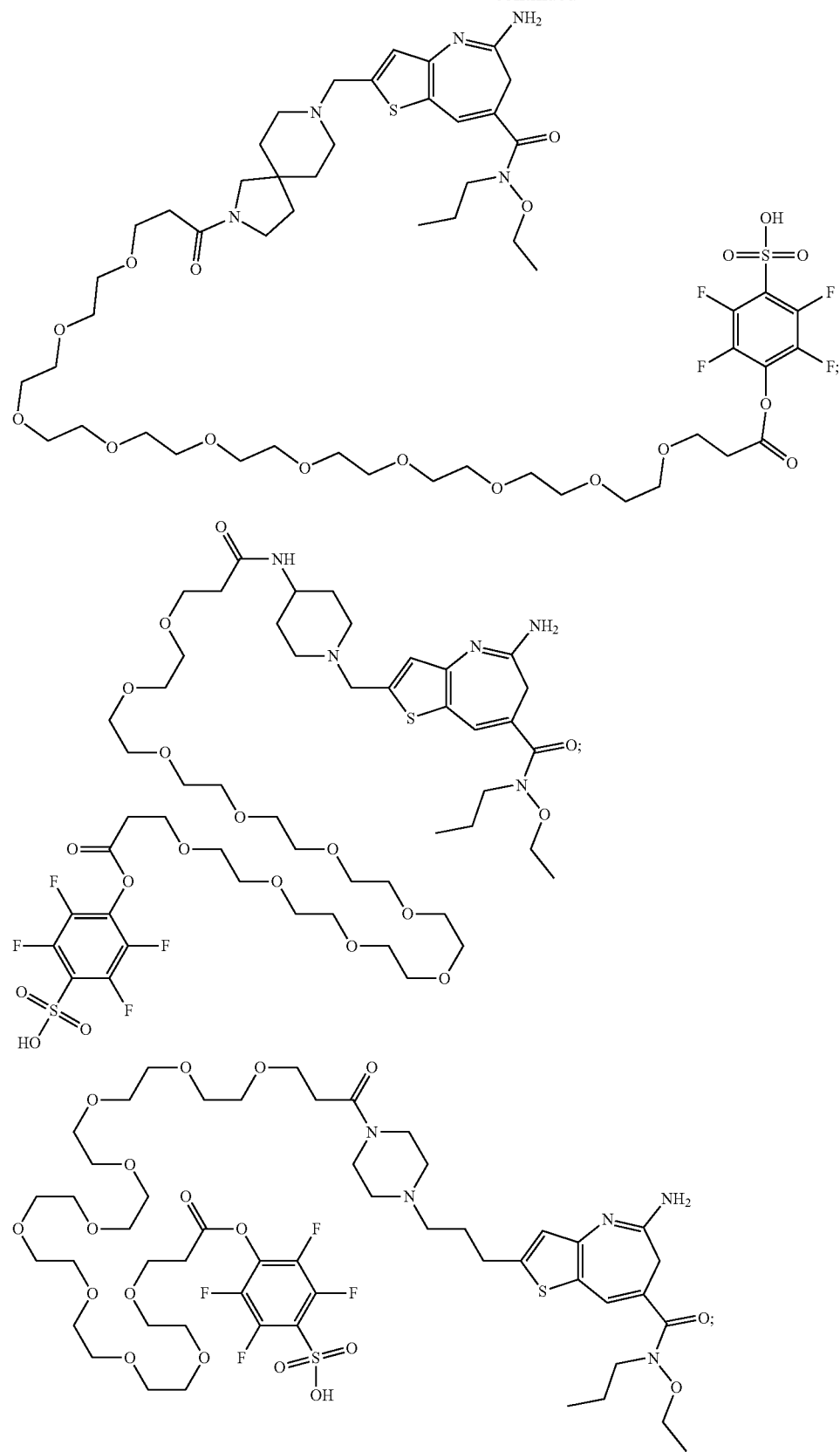

937 938
-continued
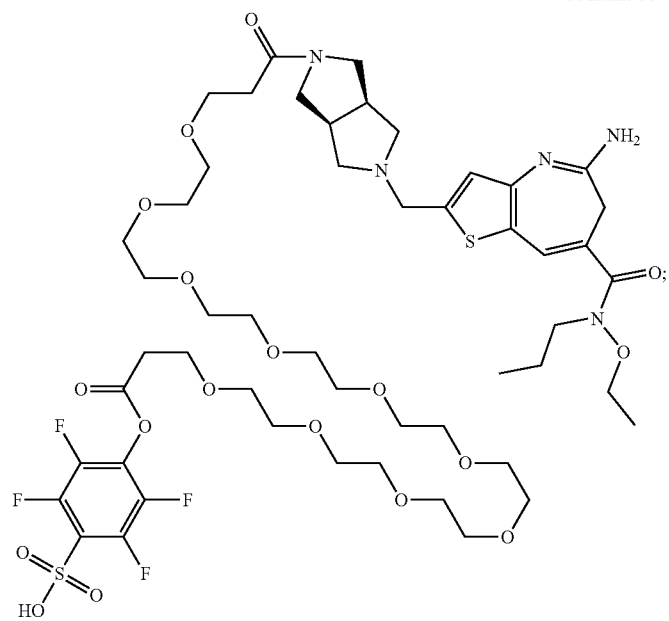
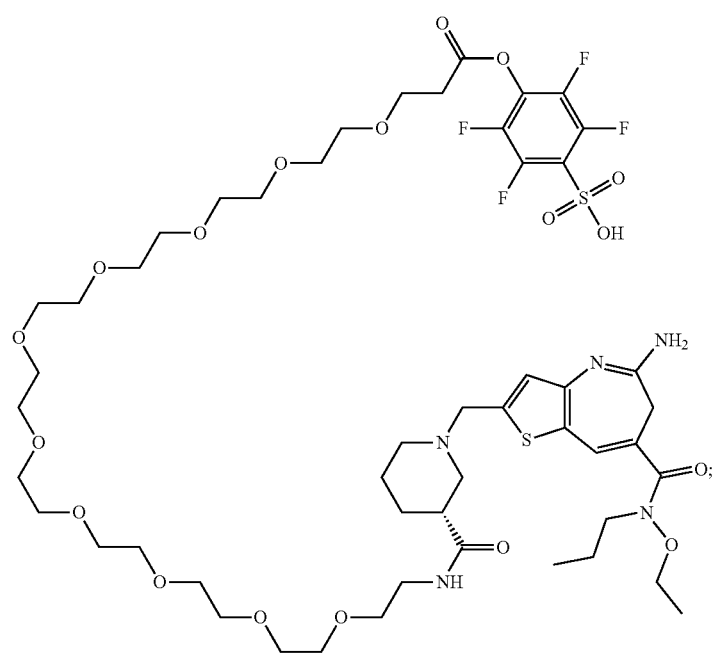

-continued
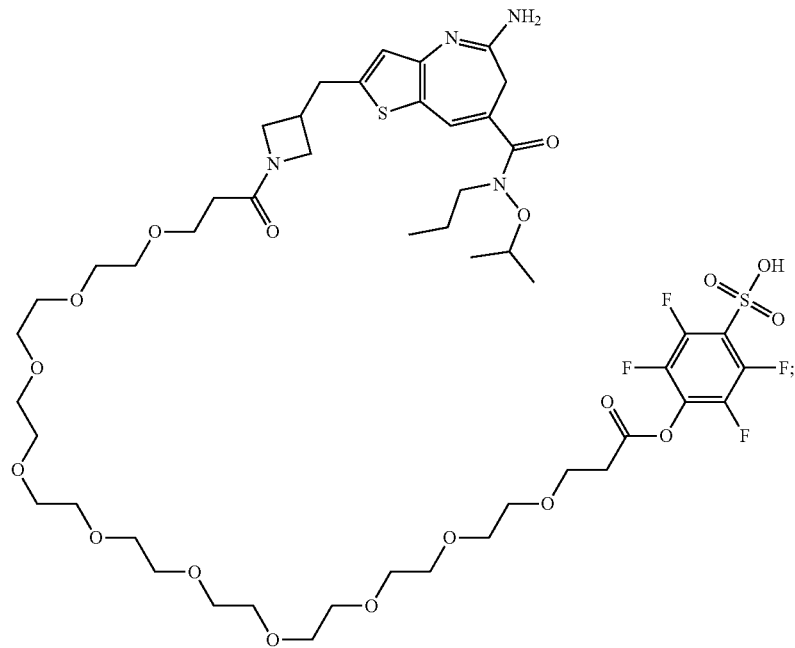
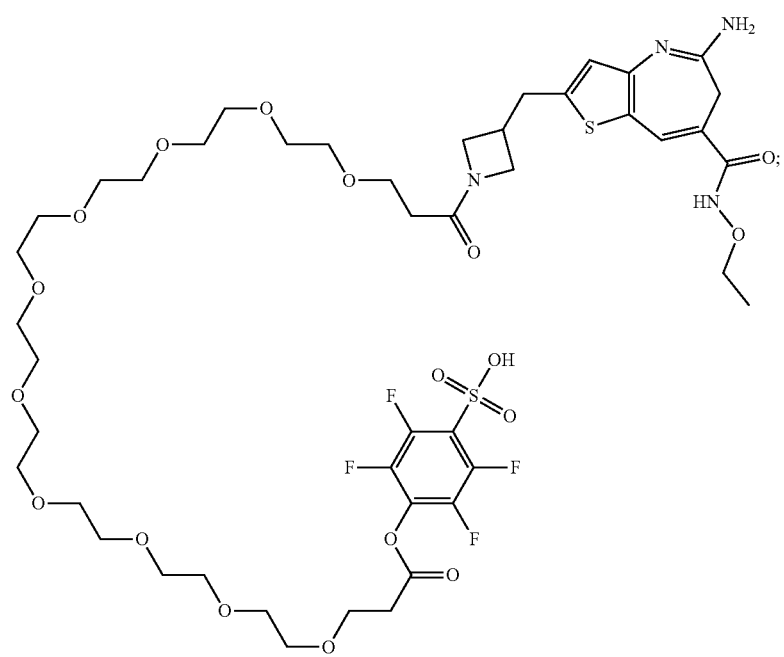

941
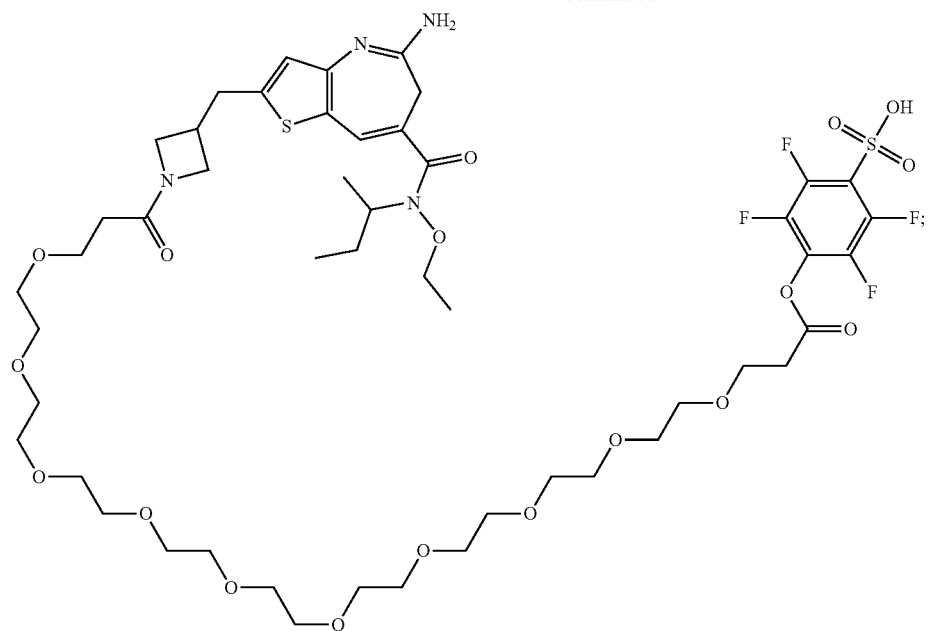
942
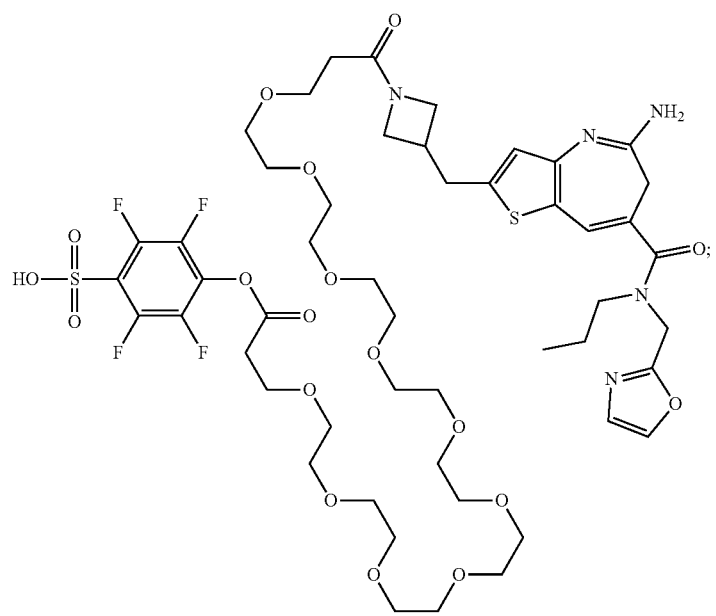

943
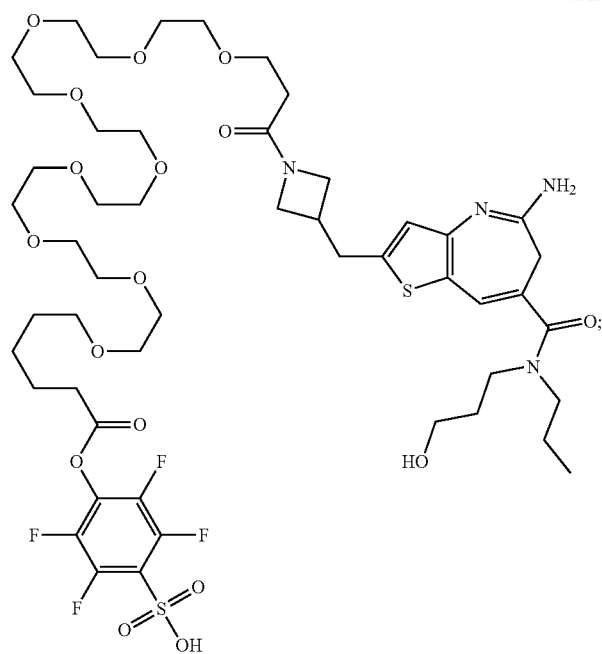
944
-continued
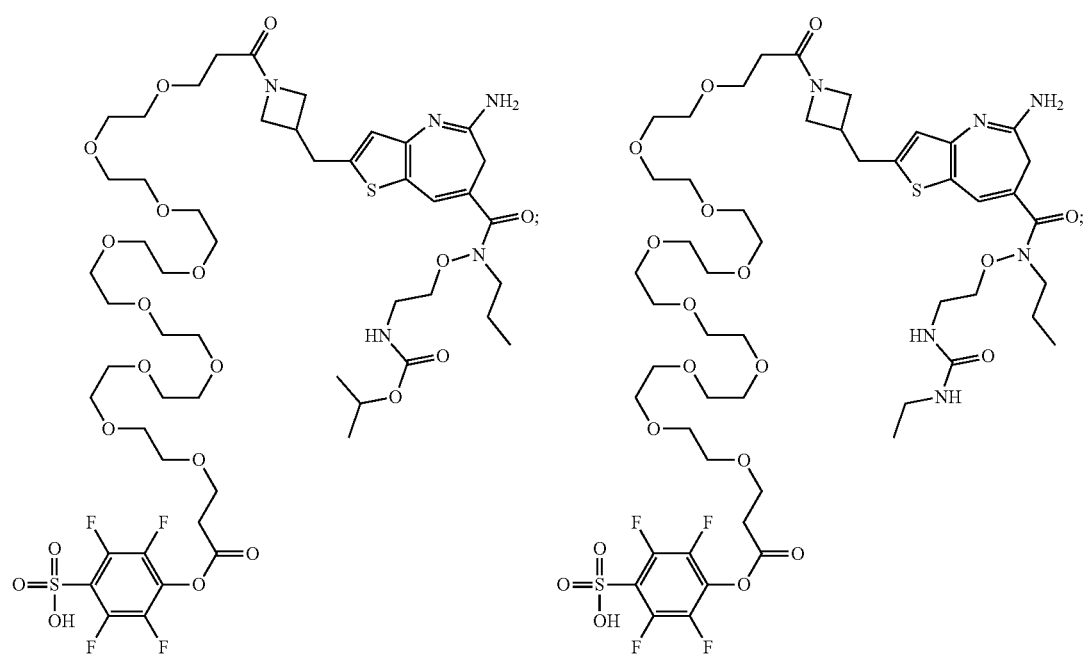

945
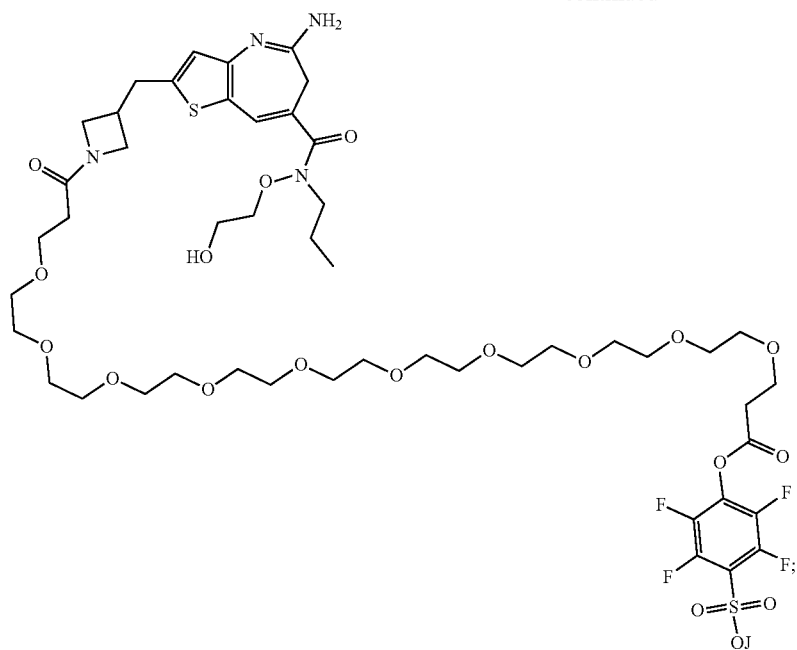
-continued
946
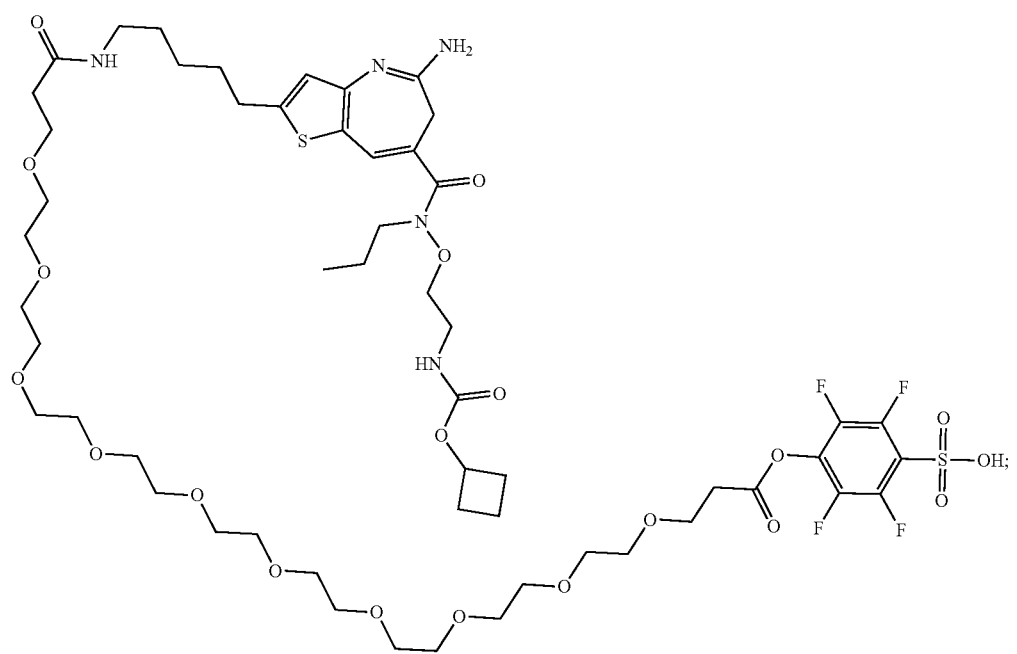

947
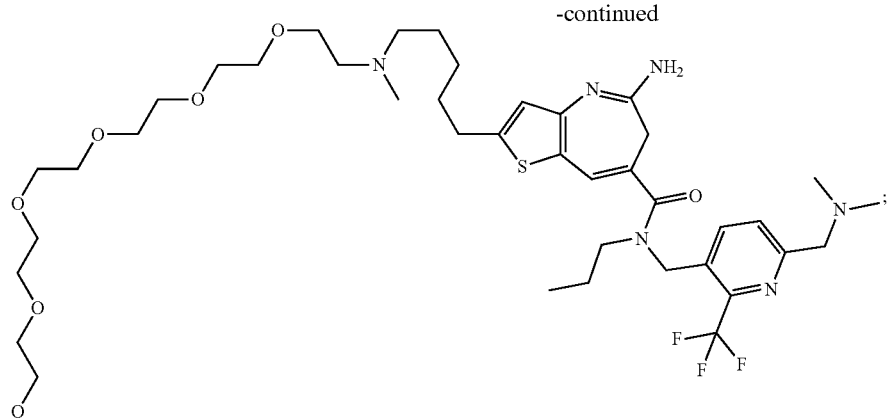
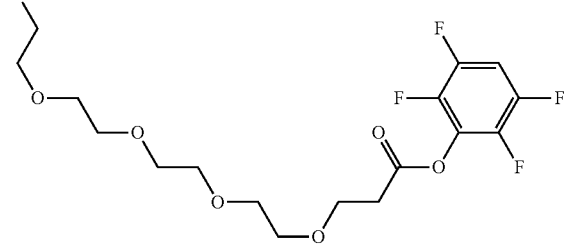
948
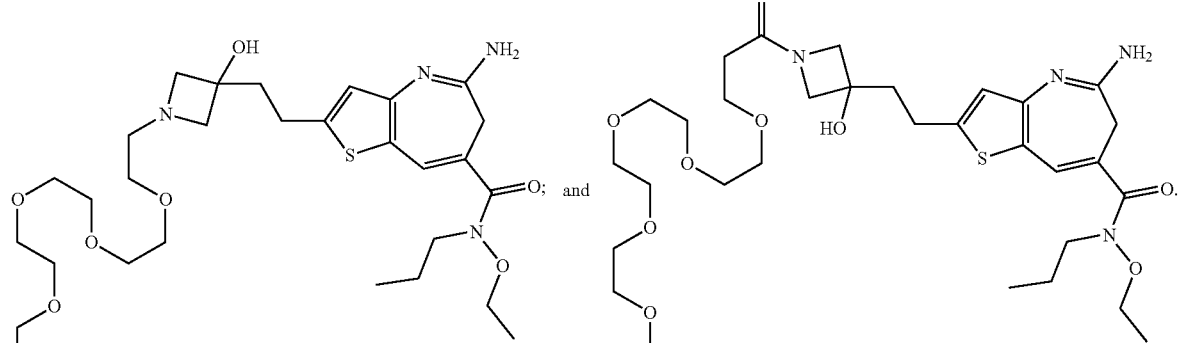
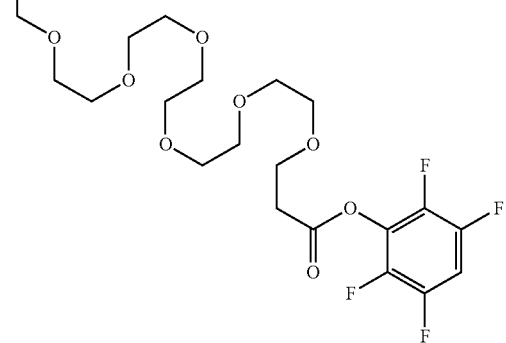
* * * * *

UNITED STATES PATENT AND TRADEMARK OFFICE
CERTIFICATE OF CORRECTION

PATENT NO. : 11,654,199 B2
APPLICATION NO. : 17/078467
DATED : May 23, 2023
INVENTOR(S) : Romas Kudirka and Brian Safina Page 1 of 7

It is certified that error appears in the above-identified patent and that said Letters Patent is hereby corrected as shown below:

In the Claims

Column 837, Claim 26, please delete

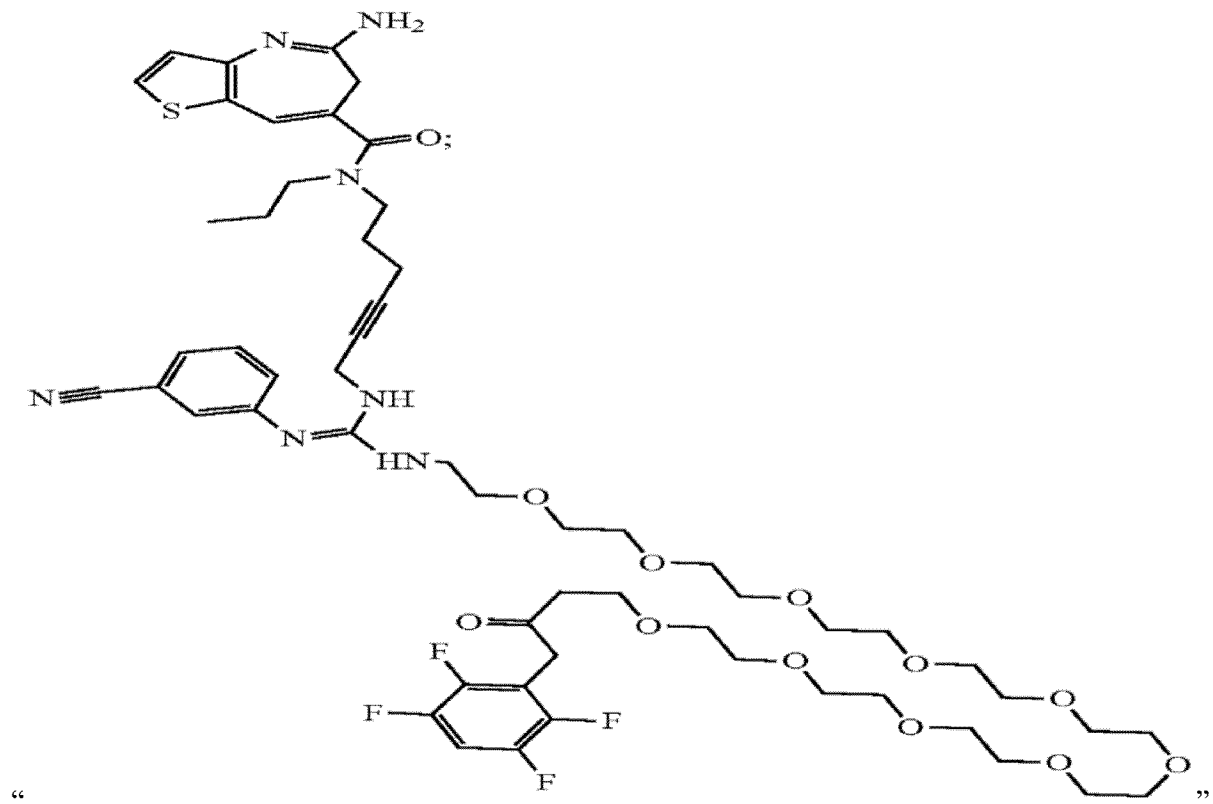

" "

Signed and Sealed this
Thirtieth Day of April, 2024

Katherine Kelly Vidal
*Director of the United States Patent and Trademark Office*

CERTIFICATE OF CORRECTION (continued)
U.S. Pat. No. 11,654,199 B2

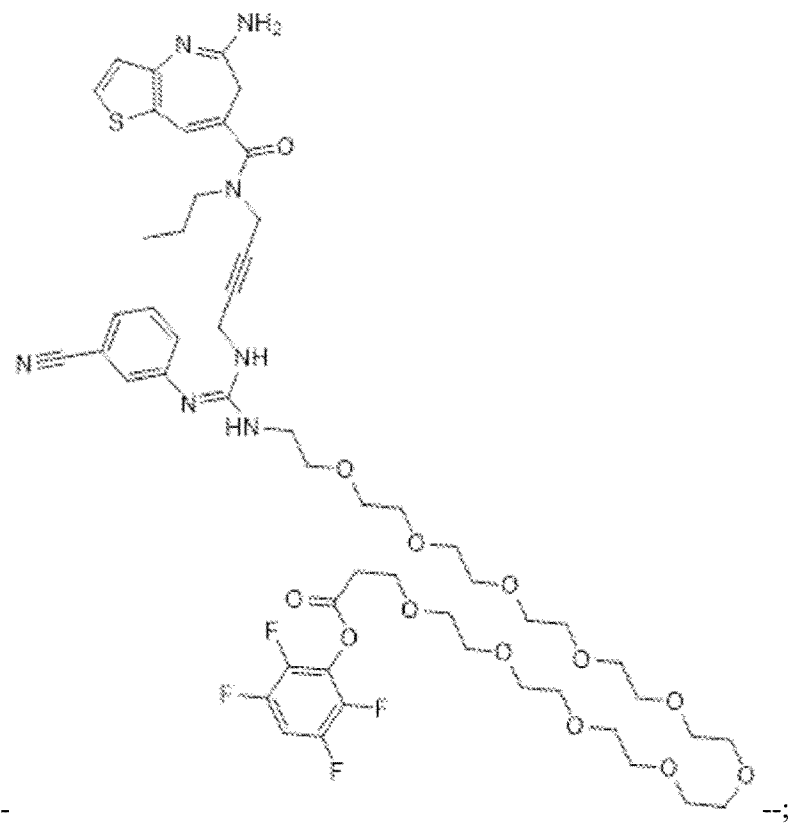

and insert --

Column 853, Bottom Structure, Claim 26, please delete

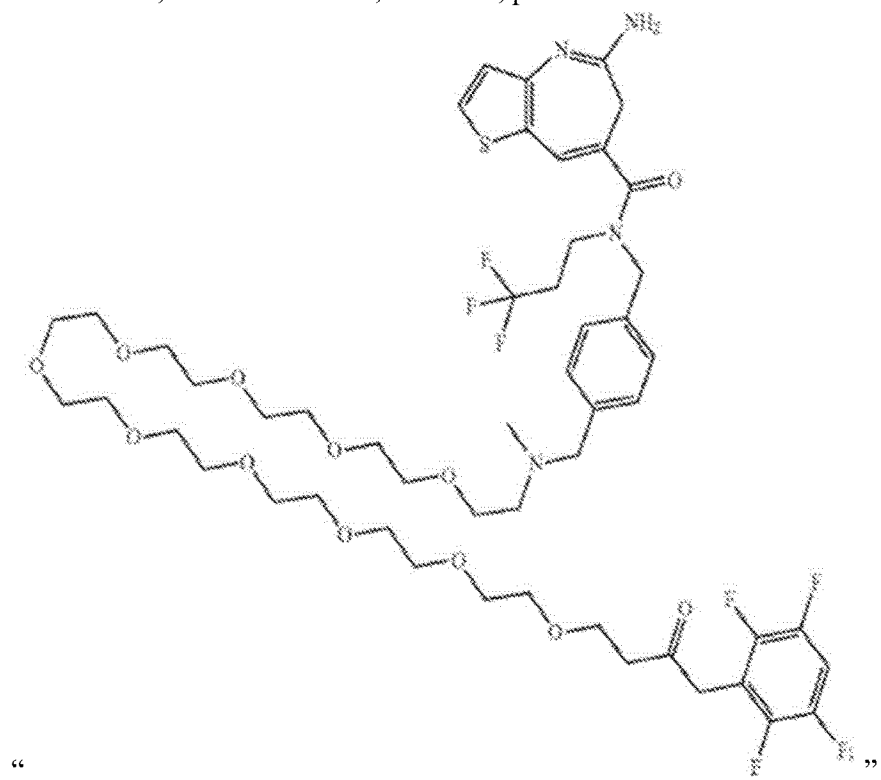

"

CERTIFICATE OF CORRECTION (continued)  Page 3 of 7
U.S. Pat. No. 11,654,199 B2

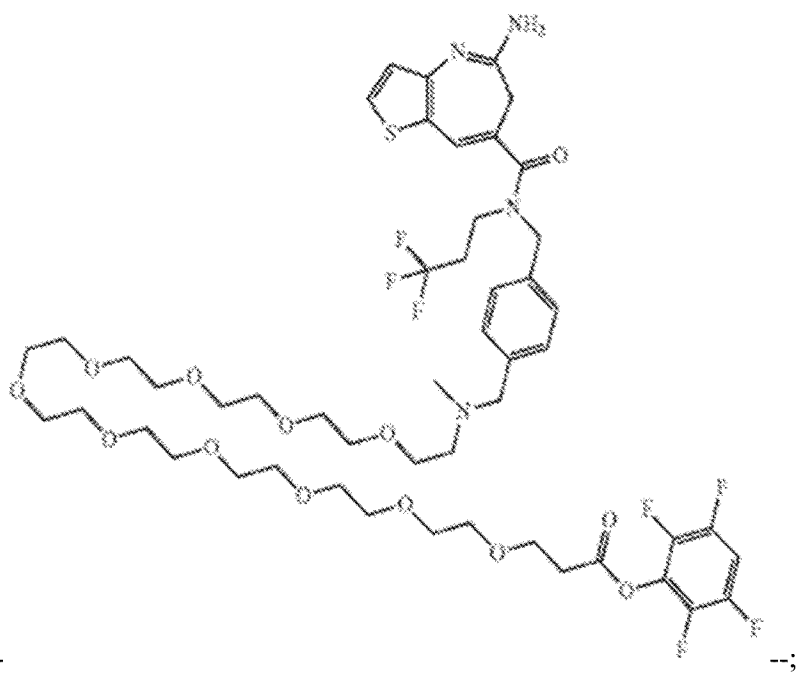

and insert -- --;

Column 867, Bottom Structure, Claim 26, please delete

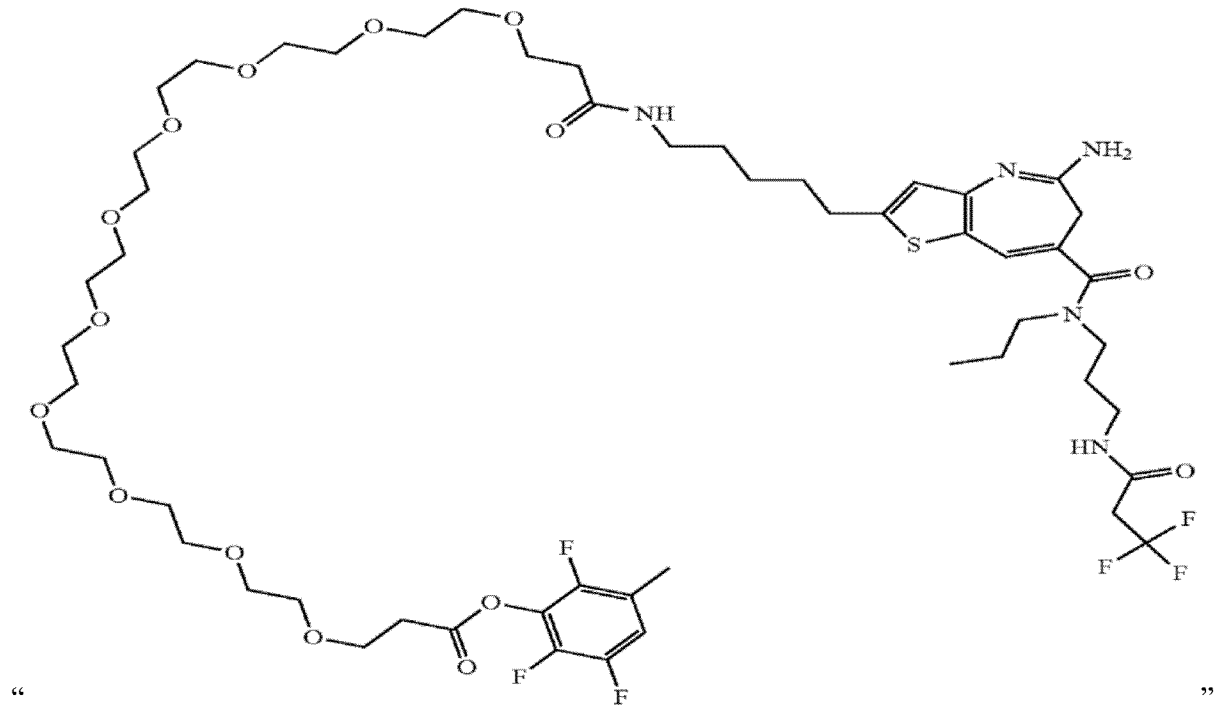

" "

CERTIFICATE OF CORRECTION (continued)
U.S. Pat. No. 11,654,199 B2

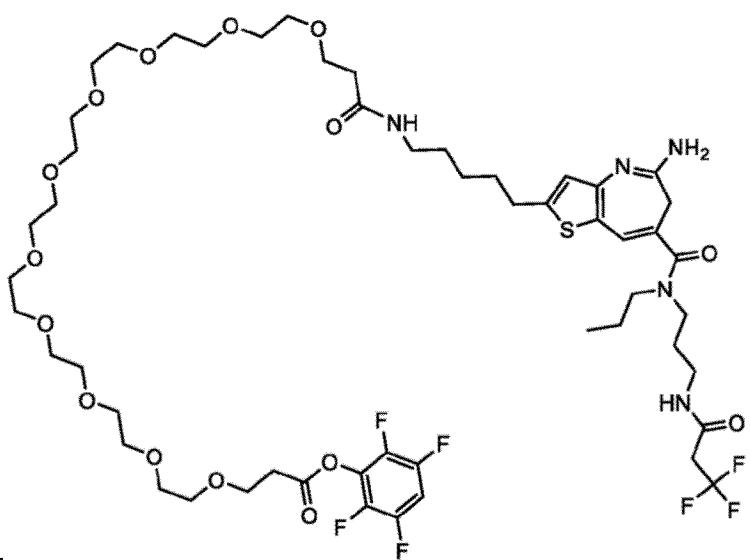

and insert -- -- ;

Column 897, Bottom Structure, Claim 26, please delete

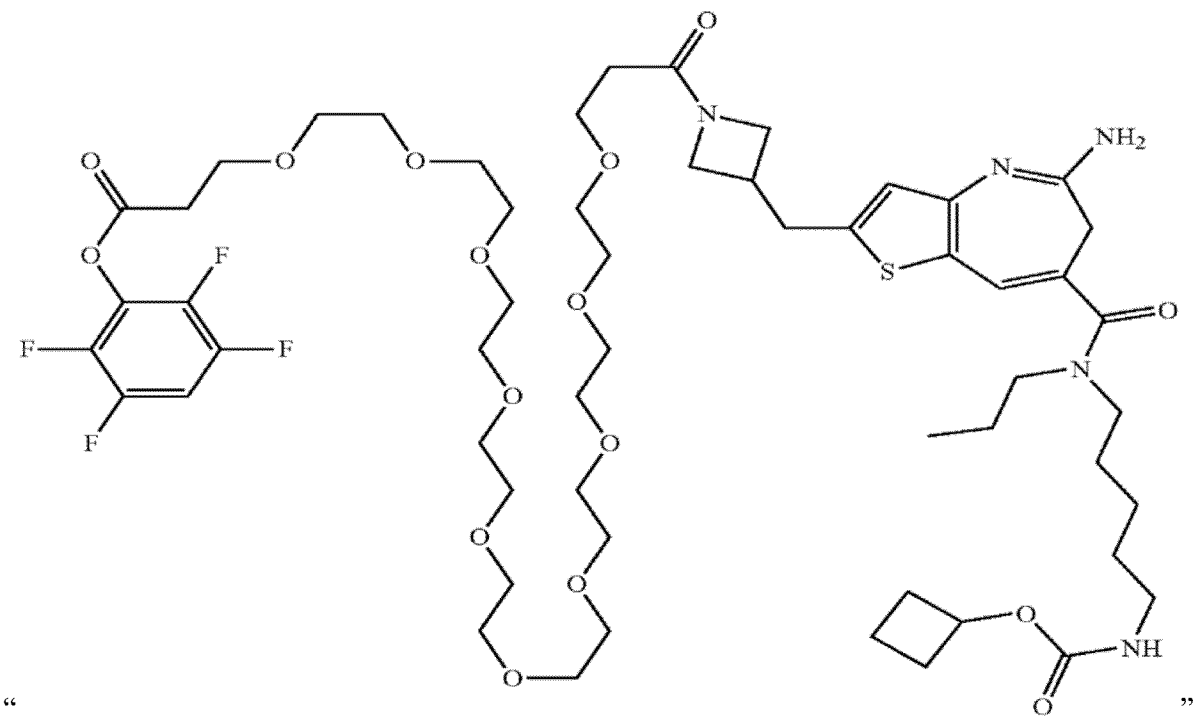

" "

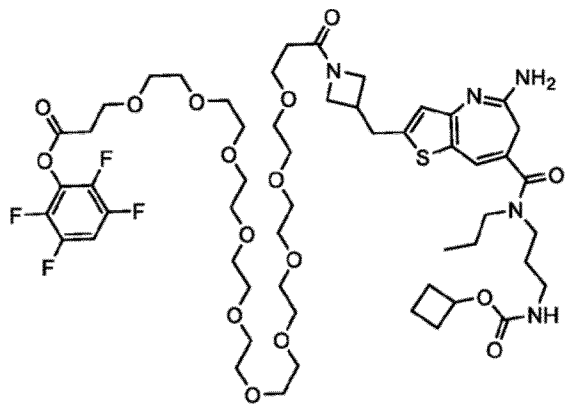
and insert -- 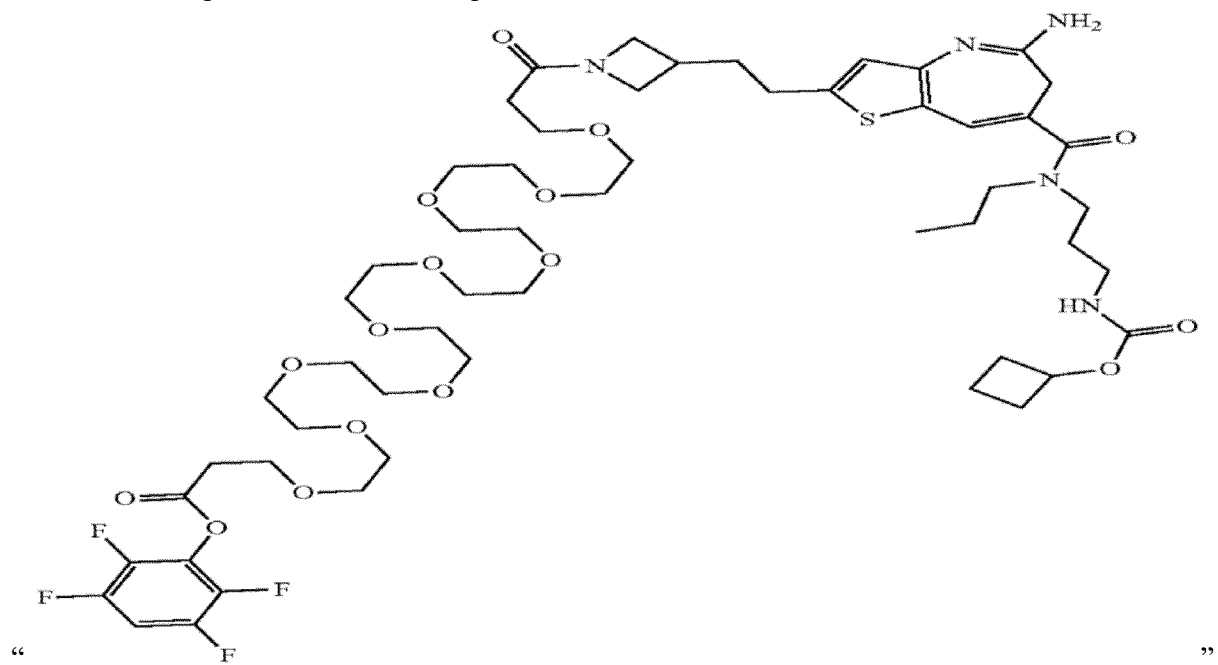 --;
Column 909, Top Structure, Claim 26, please delete
"  "

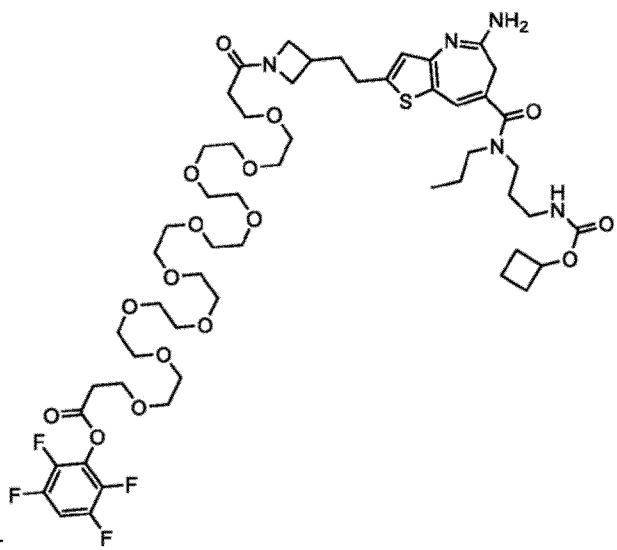
and insert -- --; and
Column 943, Top Structure, Claim 26, please delete "
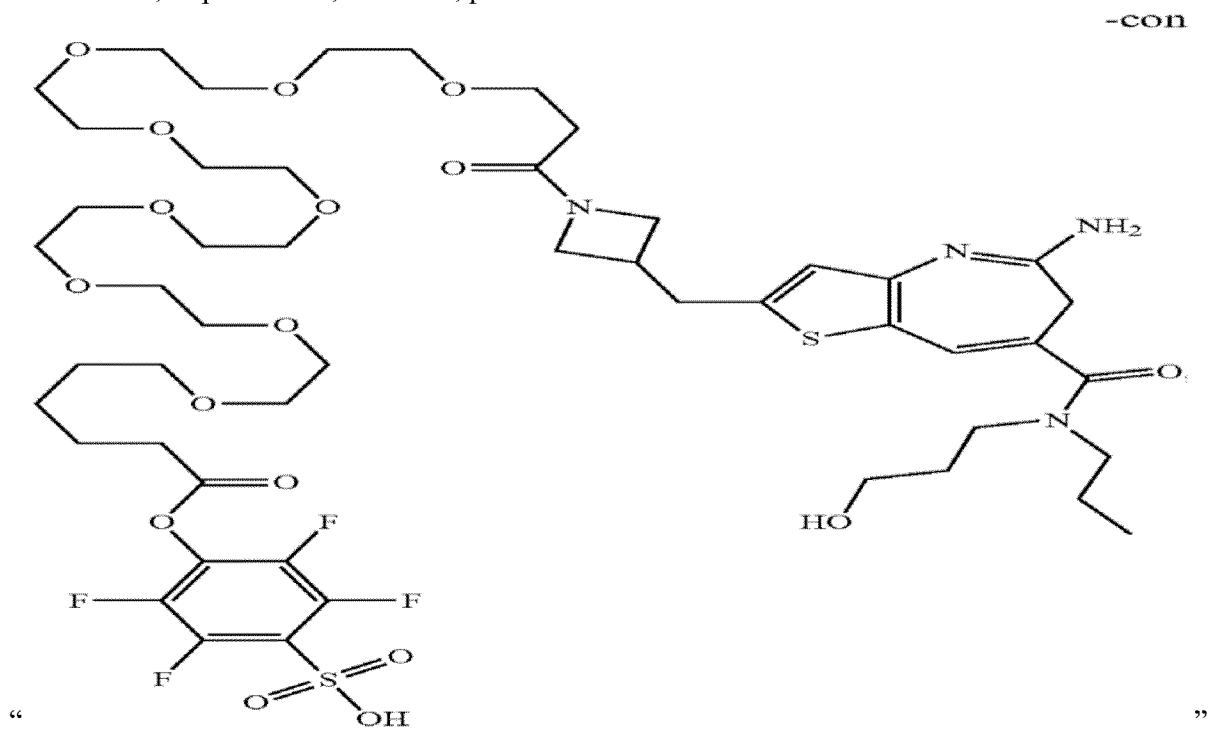
"

CERTIFICATE OF CORRECTION (continued)
U.S. Pat. No. 11,654,199 B2 and insert -- 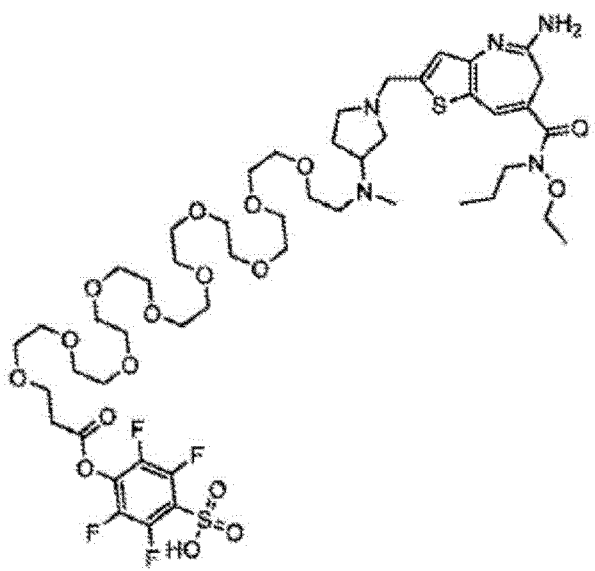 -- therefore.

```
                            SEQUENCE LISTING

<160> NUMBER OF SEQ ID NOS: 607

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Ala Ile Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Tyr Met His
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg His Leu Leu His
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser His His Met His
1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Phe Met His
1
```

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Tyr Tyr Ile His
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asn Tyr Tyr Ile His
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

His Tyr Tyr Met His
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Tyr Tyr Met His
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asn Tyr Met Tyr His
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 11

Thr Tyr Tyr Val His
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Tyr Ala Leu Ser
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg His Tyr Val His
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser His Tyr Met His
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Tyr Tyr Met His
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Tyr Thr Leu His
1               5

<210> SEQ ID NO 17
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 17

Asn His Tyr Met His
1               5

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asn Ser Tyr Met His
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Tyr Tyr Met His
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg His Phe Ile His
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Phe Gly Ile Ser
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Tyr Gly Ile Asn
1               5
```

```
<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Asn His Tyr Val His
1               5

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Val Ile Asn Pro Ser Ala Gly Ser Thr Asp Tyr Ala Gln Lys Phe Gln
1               5                   10                  15

Gly

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Trp Met Asn Pro Asn Ser Asp Ile Ala Gly Tyr Ala Gln Lys Phe Gln
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Trp Ile Ser Pro Gln His Gly Val Arg Asn Tyr Ala Gln Lys Phe Gln
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Val Ser Pro Ser His Gly Leu Thr Gly Tyr Ala Gln Lys Phe Gln
1               5                   10                  15

Gly
```

```
<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Met Ser Leu Asn Ser Gly Leu Thr Gly Tyr Ala Gln Lys Phe Gln
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Met Lys Pro Ser Ser Gly Thr Thr Gly Tyr Ala Gln Lys Phe Gln
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Met Asn Pro Asn Gly Asp Val Ala Gly Tyr Ala Gln Lys Phe Gln
1               5                   10                  15

Gly

<210> SEQ ID NO 31
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Ile Asp Pro Asn Ser Gly Gly Thr Asn Tyr Ala Gln Lys Phe Gln
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Met Asn Pro Asp Ser Gly Ser Thr Gly Tyr Ala Gln Lys Phe Gln
1               5                   10                  15

Gly
```

```
<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Met Ser Leu Asn Ser Gly Leu Thr Gly Tyr Ala Gln Lys Phe Gln
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Trp Met Asn Pro Asn Gly Asp Val Ala Gly Tyr Ala Asp Ser Phe Gln
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Ile Ser Thr Tyr His Gly Ser Thr Asn Tyr Ala Gln Lys Phe Gln
1               5                   10                  15

Gly

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Trp Met Asn Pro Asn Thr Val Tyr Thr Gly Ser Ala Gln Lys Phe Gln
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ile Ile Pro Ala Val Gly Ser Val Thr Tyr Ala Gln Lys Phe Gln
1               5                   10                  15
```

Gly

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ile Ile Pro Ile Phe Gly Thr Ala Asn Tyr Ala Gln Lys Phe Gln
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Met Ser Pro Ser Ser Gly Ile Thr Gly Tyr Ala Gln Lys Phe Gln
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Met Thr Pro Ser Thr Gly Asn Ala Gly Tyr Ala Gln Lys Phe Gln
1               5                   10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Met Asn Pro Asn Ser Gly Asn Thr Gly Tyr Ala Gln Lys Phe Gln
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Trp Met His Pro Asn Ser Gly His Thr Gly Tyr Ala Gln Lys Phe Gln
1               5                   10                  15

```
<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Met Asn Pro Asn Ser Gly His Thr Gly Asn Ala Gln Lys Phe Gln
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Ile Asp Pro Asn Ser Gly Val Thr Ser Ser Ala Gln Lys Phe Gln
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Ile Ser Pro Asn Ser Gly Val Thr Asp Phe Thr Gln Lys Phe Gln
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Met Asn Pro Asn Ser Gly His Thr Gly Tyr Ala Gln Arg Phe Gln
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Met Ser Pro Asn Gly Gly Asn Thr Gly Tyr Ala Gln Lys Phe Gln
```

```
<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Met Asp Pro Ser Ser Gly Tyr Thr Gly Ser Ala His Lys Phe Gln
1               5                   10                  15
Gly

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Met Asn Pro His Ser Ala Asp Thr Gly Tyr Ala Glu Lys Phe Gln
1               5                   10                  15
Gly

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Leu Thr Pro Ser Thr Gly His Ala Gly Tyr Ala Gln Lys Phe Gln
1               5                   10                  15
Gly

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Met Asn Pro Asn Ser Gly His Thr Gly Tyr Ala Gln Lys Phe Gln
1               5                   10                  15
Gly

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52
```

Trp Ile Ser Pro Gln His Gly Val Arg Asn Tyr Ala His Lys Phe Gln
1               5                   10                  15

Gly

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Met Ile Asn Pro Ser Gly Gly Ser Thr Ser Tyr Ala Gln Lys Phe Gln
1               5                   10                  15

Gly

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Trp Ile Ser Pro Arg Ser Gly Val Thr Ser Tyr Ala Gln Lys Phe Gln
1               5                   10                  15

Gly

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Trp Met Asp Pro Asn Ser Gly Asn Thr Gly Tyr Ala Gln Lys Phe Gln
1               5                   10                  15

Gly

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Met Asn Pro Thr Gly Gly Ile Thr Gly Tyr Ala Gln Lys Phe Gln
1               5                   10                  15

Gly

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Trp Val Ser Pro Ile His Gly Leu Thr Gly Tyr Ala Pro Arg Phe Gln
1               5                   10                  15

Gly

<210> SEQ ID NO 58
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asp Leu Tyr Pro Tyr Val Val Val Ala Ala Gly Ser Tyr Gly Met
1               5                   10                  15

Asp Val

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Ser Ile Val Gly Ala Tyr Asp Ala Phe Asp Ile
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Ser Val Glu Gly Tyr Phe Asp Leu
1               5

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Asp Asn Trp Asn Val His Asp Ala Phe Asp Ile
1               5                   10

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Thr Tyr Asn Asp Ala Phe Asp Ile
1               5
```

-continued

```
<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Glu Gln Trp Leu Val Asn Asp Ala Phe Asp Ile
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Ser Ser Gly Trp Met Arg Asn Asp Ala Phe Asp Ile
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ser Met Phe Pro Thr Ile Phe Gly Asp Asn Ala Phe Asp Ile
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ala Leu Phe Pro Tyr Pro Phe Tyr Tyr Tyr Tyr Met Asp Val
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asp Arg Gly Trp Phe Asp Pro
1               5

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68
```

```
Asp Ala Arg Gly Tyr Ser Gly Tyr Asp Leu
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Gly Arg His Gly Glu Tyr Leu Tyr
1               5

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Glu Gly Trp Gly Ser Ser Gly Tyr Phe Asp Tyr
1               5                   10

<210> SEQ ID NO 71
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

His Leu Phe Pro Thr Val Phe Asp Asp Tyr Tyr Gly Met Asp Val
1               5                   10                  15

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Gly Tyr Ser Tyr Gly Ser Phe Gln His
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Val Arg Trp Ser Ser Asp Ala Phe Asp Ile
1               5                   10

<210> SEQ ID NO 74
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 74

Glu Glu Trp Leu Gly His Phe Gln His
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Glu Arg Phe Leu Gly Gly Met Asp Val
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Asn Trp Val Asp Ala Phe Asp Ile
1               5

<210> SEQ ID NO 77
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Ser Glu Val Met Met Ala Tyr Phe Gln His
1               5                   10

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Ser Trp Ser Gly Glu Phe Asp Tyr
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Ala Val Ala Gly Pro Met Asp Val
1               5
```

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Ala Trp Glu Leu Leu Ala Phe Asp Ile
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Asp Arg Trp Asp Gly Asp Tyr Tyr Ser Ala
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Glu Ser Trp Glu Leu Thr Gly Phe Asp Tyr
1               5                   10

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Glu Arg Phe Ala Gly Gly Met Asp Ala
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asp Ser Gly Gly Ala Phe Asp Ile
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 85

Glu Val Phe Glu Gly Gly Met Asp Val
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Glu Gly Tyr Gly Gly Asn Tyr Gly Asn
1               5

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Asp Phe Tyr Gly Asp Phe Asp Tyr
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Leu Ser Arg Trp Gly Phe Asp Tyr
1               5

<210> SEQ ID NO 89
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Asp Ile Phe Pro Thr Met Ile Ala Gly Gly Gly Phe Asp Leu
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gly Tyr Ser Tyr Gly Ser Phe Asp Tyr
1               5                   10

<210> SEQ ID NO 91
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 91

Gly Ser Phe Pro Leu Val Phe Thr Ile Phe Gly Val Gly Asp Val
1               5                   10                  15

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asp Leu Asp Tyr Val Arg Ala Phe Asp Ile
1               5                   10

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Glu Ser Trp Gly Gly Tyr Phe Asp Leu
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Asp Arg Thr Thr Tyr Ala Phe Asp Ile
1               5

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Val His Gly Ser Gly Ser Asp Gly Met Asp Val
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ala Ser Gln Gly Ile Asp Ser Tyr Leu Ala
1               5                   10
```

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ala Ser Gln Ser Ile Ser Ser Trp Leu Ala
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Ala Ser Gln Ser Ile Ser Ser Tyr Leu Asn
1               5                   10

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Ser Gln Gly Ile Ser Ser Tyr Leu Ala
1               5                   10

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Ala Ser Gln Thr Ile Ser Asn Tyr Leu Asn
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Ala Ser Gln Ser Val Asp Arg Asn Tyr Val Thr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Ala Ser Gln Gly Ile Ser Gln Tyr Leu Ala
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Ala Ser Gln Asp Ile Gly Asn Tyr Leu Asn
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Ala Ser Gln Gly Ile Arg Asn Asp Leu Gly
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Ala Ser Gln Ile Ile Gly Asn Tyr Leu Ala
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Ala Ser Gln Ile Ile Ser Ser Tyr Leu Asn
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Ala Ser Gln Asp Ile Ser Asn Tyr Leu Asn
1               5                   10

<210> SEQ ID NO 108
<211> LENGTH: 11

```
-continued

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Ala Ser Gln Gly Ile Ser Asn Tyr Leu Ala
1               5                   10

<210> SEQ ID NO 109
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Ala Ser Gln Gly Ile Ser Asn Asn Leu Asn
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Ala Ser Gln Gly Ile Ser Asn Gly Leu Ser
1               5                   10

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ala Ser Gln Ser Ile Thr Gly Trp Leu Ala
1               5                   10

<210> SEQ ID NO 112
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Ala Ser Gln Gly Ile Arg Asn Asp Leu Ala
1               5                   10

<210> SEQ ID NO 113
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Ala Ser Gln Asp Ile Ser Ser Tyr Leu Asn
```

<210> SEQ ID NO 114
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Ala Ser Gln Ser Ile Thr Thr Tyr Leu Asn
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Arg Ala Ser Gln Ser Val Ser Thr Trp Leu Ala
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Arg Ala Ser Gln Ser Ile Ser Asn Trp Leu Ala
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Ala Ser Gln Gly Ile Ser Asn Tyr Leu Ala
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Arg Ala Ser Gln Ser Leu Ser Ser Ser Ser Leu Ala
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 119

Arg Ala Ser Glu His Ile Ala Asn Trp Leu Ala
1               5                   10

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Ala Ser Gln Ser Val Gly Ser Trp Val Ala
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Arg Ala Ser Gln Ser Ile Ser Pro Trp Leu Ala
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Arg Ala Ser Gln Gly Ile Ser Arg Tyr Leu Ala
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Arg Ala Ser Gln Thr Val Ser Ser Asn Tyr Leu Ala
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Arg Ser Ser Gln Gly Ile Arg Asn Asp Leu Ser
1               5                   10

<210> SEQ ID NO 125

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Arg Asp Ser His Ser Ile Thr Thr Trp Leu Ala
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Arg Ala Ser Gln Ser Ile Ser Arg Trp Leu Ala
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ala Ser Gln Val Ile Arg Asn Asp Leu Ala
1               5                   10

<210> SEQ ID NO 128

<400> SEQUENCE: 128

000

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ala Ala Ser Ser Leu Gln Ser
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Ala Ser Asn Leu Gln Ser
1               5

<210> SEQ ID NO 131
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 131

Gly Ala Ser Thr Arg Ala Thr
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Ala Ser Asn Leu His Ser
1               5

<210> SEQ ID NO 133
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ala Ser Ser Leu Glu Ser
1               5

<210> SEQ ID NO 134
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ser Ala Ser Asn Leu Gln Ser
1               5

<210> SEQ ID NO 135
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Ala Ser Thr Leu Glu Ser
1               5

<210> SEQ ID NO 136
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

His Ala Ser Ile Leu Glu Thr
1               5

```
<210> SEQ ID NO 137
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ala Ala Ser Thr Leu Gln Ser
1               5

<210> SEQ ID NO 138
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ala Ala Thr Thr Leu Gln Ser
1               5

<210> SEQ ID NO 139
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Asp Ala Thr His Leu Glu Thr
1               5

<210> SEQ ID NO 140
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ala Ala Ser Ser Leu Gln Thr
1               5

<210> SEQ ID NO 141
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Ala Ser Ser Leu Gln Gly
1               5

<210> SEQ ID NO 142
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 142

Ala Ala Ser Asn Leu Glu Ser
1               5

<210> SEQ ID NO 143
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Asp Val Ser His Leu Glu Ser
1               5

<210> SEQ ID NO 144
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asp Ala Ser Ser Leu Gln Ser
1               5

<210> SEQ ID NO 145
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Gly Val Ser Ser Leu Glu Ser
1               5

<210> SEQ ID NO 146
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Pro Ala Ser Thr Leu Gln Ser
1               5

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asp Ala Ser Asn Leu Glu Thr
1               5

<210> SEQ ID NO 148
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Ala Ser Thr Arg Ala Ser
1               5

<210> SEQ ID NO 149
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Asp Ser Ser Ser Leu Gln Thr
1               5

<210> SEQ ID NO 150
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ala Thr Ser Thr Leu Gln Ser
1               5

<210> SEQ ID NO 151
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Leu Ala Ser Asn Ser His Ser
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gln Gln Ser Tyr Ser Thr Pro Ile Thr
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Gln Gln Ser Tyr Thr Thr Pro Ile Thr
```

-continued 1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gln Gln Ile Phe Ser Thr Pro Leu Thr
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gln Gln Ser Tyr Ser Thr Pro Leu Thr
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Gln Ser Tyr Thr Thr Pro Tyr Thr
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Gln Gln Thr Phe Thr Thr Pro Leu Thr
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Gln Gln Ala Asn Ser Phe Pro Phe Thr
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 159

Gln Gln Ser Tyr Thr Thr Pro Tyr Ser
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Gln Gln Thr Phe Ile Thr Pro Leu Thr
1               5

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Gln Gln Ser Tyr Ser Thr Pro Thr
1               5

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gln Gln Gly Phe Ser Thr Pro Phe Thr
1               5

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gln Gln Ser Phe Thr Asn Pro Val Thr
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Ser Tyr Ser Ala Pro Tyr Thr
1               5

<210> SEQ ID NO 165

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gln Gln Ser Tyr Ser Thr Pro Tyr Thr
1               5

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gln Gln Ser His Ser Thr Pro Leu Thr
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gln Gln Ser Tyr Ser Thr Pro Phe Thr
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gln Gln Tyr Gly Ser Ser Pro Phe Thr
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Gln Thr Tyr Ser Thr Pro Ile Thr
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170
```

```
Gln Gln Tyr Tyr Thr Thr Pro Leu Thr
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gln Gln Ser Phe Ser Thr Pro Leu Thr
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gln Gln Ser Tyr Ser Thr Pro Pro Thr
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Leu Gln His Asn Ser Tyr Pro Leu Thr
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gln Gln Ser Tyr Ser Thr Pro Val Thr
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln His Phe Tyr Asn Thr Gln Tyr Thr
1               5

<210> SEQ ID NO 176
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 176

Gln Gln Ser Leu Gln Tyr Pro Ser His Phe
1               5                   10

<210> SEQ ID NO 177
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser
            20                  25                  30

<210> SEQ ID NO 178
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 179
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr
            20                  25                  30

<210> SEQ ID NO 181
<211> LENGTH: 30

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Gly His Ser Phe Thr
            20                  25                  30

<210> SEQ ID NO 182
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr
            20                  25                  30

<210> SEQ ID NO 183
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr
            20                  25                  30

<210> SEQ ID NO 184
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 184

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30

<210> SEQ ID NO 185
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gln Val Gln Leu Val Gln Ser Gly Ala Glu Val Lys Lys Pro Gly Ala
1               5                   10                  15
```

Ser Val Lys Val Ser Cys Lys Ala Ser Gly Asp Thr Phe Thr
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Gln Val Gln Leu Ala Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Ser
            20                  25                  30

<210> SEQ ID NO 189
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr
            20                  25                  30

<210> SEQ ID NO 190
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 190

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr
            20                  25                  30

<210> SEQ ID NO 192
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Trp Val Arg Gln Ala Pro Gly Gln Gly Leu Glu Trp Met Gly
1               5                   10

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Trp Val Arg Gln Ala Pro Gly Gln Gly Leu Glu Trp Leu Gly
1               5                   10

<210> SEQ ID NO 194
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Trp Val Arg Gln Ala Pro Gly Gln Gly Leu Glu Trp Ile Gly
1               5                   10

<210> SEQ ID NO 195
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

```
Trp Val Arg Gln Ala Pro Gly Gln Gly Leu Glu Trp Val Gly
1               5                   10
```

<210> SEQ ID NO 196
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

```
Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 197
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

```
Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Ile
            20                  25                  30
```

<210> SEQ ID NO 198
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

```
Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Thr Arg
            20                  25                  30
```

<210> SEQ ID NO 199
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

```
Arg Val Thr Ile Thr Ala Asp Glu Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30
```

<210> SEQ ID NO 200
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Arg Val Thr Met Thr Arg Asp Thr Ser Thr Ser Thr Val Asn Met Glu
1               5                   10                  15

Leu Ser Ser Leu Arg Ser Glu Asp Thr Ala Val Tyr Tyr Cys Ala Arg
            20                  25                  30

<210> SEQ ID NO 201
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Glu
            20                  25                  30

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Trp Gly Gln Gly Thr Leu Val Thr Val Ser Ser
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Trp Gly Gln Gly Thr Thr Val Thr Val Ser Ser
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Trp Gly Gln Gly Thr Met Val Thr Val Ser Ser
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

```
Trp Gly Pro Gly Thr Met Val Thr Val Ser Ser
1               5                   10
```

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

```
Trp Gly Arg Gly Thr Leu Val Thr Val Ser Ser
1               5                   10
```

<210> SEQ ID NO 207
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

```
Asp Ile Gln Met Thr Gln Ser Pro Ser Ser Leu Ser Ala Ser Val Gly
1               5                   10                  15
Asp Arg Val Thr Ile Thr Cys
            20
```

<210> SEQ ID NO 208
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

```
Glu Ile Val Met Thr Gln Ser Pro Ala Thr Leu Ser Val Ser Pro Gly
1               5                   10                  15
Glu Arg Ala Thr Leu Ser Cys
            20
```

<210> SEQ ID NO 209
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

```
Asp Ile Gln Ile Thr His Ser Pro Ser Ser Leu Ser Ala Ser Val Gly
1               5                   10                  15
Tyr Arg Leu Thr Ile Thr Cys
            20
```

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

```
Trp Tyr Gln Gln Lys Pro Gly Lys Ala Pro Lys Leu Leu Ile Tyr
1               5                   10                  15

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Trp Tyr Gln Gln Lys Pro Gly Gln Ala Pro Arg Leu Leu Ile Tyr
1               5                   10                  15

<210> SEQ ID NO 212
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Trp Tyr His Gln Lys Pro Trp Asn Ala Pro Lys Leu Met Ile Tyr
1               5                   10                  15

<210> SEQ ID NO 213
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 214
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 215
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Gly Val Pro Ser Arg Phe Ser Gly Ser Gly Ser Gly Thr Tyr Phe Thr
1               5                   10                  15
```

Leu Thr Ile Ser Ser Leu Gln Pro Glu Asp Phe Ala Thr Tyr Tyr Cys
            20                  25                  30

<210> SEQ ID NO 216
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Pro Tyr Tyr Cys
            20                  25                  30

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Phe Gly Gly Gly Thr Lys Val Glu Ile Lys
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Phe Gly Gln Gly Thr Lys Val Glu Ile Lys
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Phe Gly Gln Gly Thr Arg Leu Glu Ile Lys
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Phe Gly Gly Gly Thr Lys Leu Glu Ile Lys
1               5                   10

<210> SEQ ID NO 221
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Phe Gly Gln Gly Thr Lys Leu Glu Ile Lys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Phe Gly Pro Gly Thr Lys Val Asp Ile Lys
1               5                   10

<210> SEQ ID NO 223
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Val Ile Asn Pro Ser Ala Gly Ser Thr Asp Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Tyr Pro Tyr Val Val Val Ala Ala Gly Ser Tyr
            100                 105                 110

Gly Met Asp Val Trp Gly Gln Gly Thr Leu Val Thr Val Ser Ser
        115                 120                 125

<210> SEQ ID NO 224
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45
```

Gly Trp Met Asn Pro Asn Ser Asp Ile Ala Gly Tyr Ala Gln Lys Phe
            50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ile Pro Ser Ile Val Gly Ala Tyr Asp Ala Phe Asp Ile Trp Gly
            100                 105                 110

Gln Gly Thr Leu Val Thr Val Ser Ser
            115                 120

<210> SEQ ID NO 225
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg His
            20                  25                  30

Leu Leu His Trp Val Arg Gln Ala Pro Gly Gln Gly Leu Glu Trp Met
            35                  40                  45

Gly Trp Ile Ser Pro His Gly Val Arg Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Val Glu Gly Tyr Phe Asp Leu Trp Gly Gln Gly Thr
            100                 105                 110

Leu Val Thr Val Ser Ser
        115

<210> SEQ ID NO 226
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

His Met His Trp Val Arg Gln Ala Pro Gly Gln Gly Leu Glu Trp Met
            35                  40                  45

Gly Trp Val Ser Pro Ser His Gly Leu Thr Gly Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asn Trp Asn Val His Asp Ala Phe Asp Ile Trp Gly Gln
            100                 105                 110

Gly Thr Leu Val Thr Val Ser Ser
        115                 120

<210> SEQ ID NO 227
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Arg Phe
            20                  25                  30

Met His Trp Val Arg Gln Ala Pro Gly Gln Gly Leu Glu Trp Met Gly
        35                  40                  45

Trp Met Ser Leu Asn Ser Gly Leu Thr Gly Tyr Ala Gln Lys Phe Gln
    50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Thr
                85                  90                  95

Arg Gly Thr Tyr Asn Asp Ala Phe Asp Ile Trp Gly Gly Thr Leu
            100                 105                 110

Val Thr Val Ser Ser
        115

<210> SEQ ID NO 228
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Met Lys Pro Ser Ser Gly Thr Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gln Trp Leu Val Asn Asp Ala Phe Asp Ile Trp Gly Gln
            100                 105                 110

Gly Thr Leu Val Thr Val Ser Ser
        115                 120

<210> SEQ ID NO 229

<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 229

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Met
        35                  40                  45

Gly Trp Met Lys Pro Ser Ser Gly Thr Thr Gly Tyr Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gln Trp Leu Val Asn Asp Ala Phe Asp Ile Trp Gly Gln
            100                 105                 110

Gly Thr Leu Val Thr Val Ser Ser
        115                 120

<210> SEQ ID NO 230
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 230

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Ser Tyr
            20                  25                  30

Tyr Met His Trp Val Arg Gln Ala Pro Gly Gln Gly Leu Glu Trp Met
        35                  40                  45

Gly Gly Ile Asp Pro Asn Ser Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Met Phe Pro Thr Ile Phe Gly Asp Asn Ala Phe Asp Ile
            100                 105                 110

Trp Gly Gln Gly Thr Leu Val Thr Val Ser Ser
        115                 120

<210> SEQ ID NO 231
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 231

-continued

Gln Val Gln Leu Val Gln Ser Gly Ala Glu Val Lys Lys Pro Gly Ala
1               5                   10                  15

Ser Val Lys Val Ser Cys Lys Ala Ser Gly His Ser Phe Thr His Tyr
            20                  25                  30

Tyr Met His Trp Val Arg Gln Ala Pro Gly Gln Gly Leu Glu Trp Met
        35                  40                  45

Gly Trp Met Asn Pro Asp Ser Gly Ser Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ala Leu Phe Pro Tyr Pro Phe Tyr Tyr Tyr Met Asp Val
            100                 105                 110

Trp Gly Gln Gly Thr Leu Val Thr Val Ser Ser
        115                 120

<210> SEQ ID NO 232
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Ile
        35                  40                  45

Gly Trp Met Ser Leu Asn Ser Gly Leu Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Trp Phe Asp Pro Trp Gly Gln Gly Thr Leu Val
            100                 105                 110

Thr Val Ser Ser
        115

<210> SEQ ID NO 233
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Leu
        35                  40                  45

```
Gly Trp Met Asn Pro Asn Gly Asp Val Ala Gly Tyr Ala Asp Ser Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Ile Asp Ser Ser Gly Trp Met Arg Asn Asp Ala Phe Asp Ile Trp
            100                 105                 110

Gly Gln Gly Thr Leu Val Thr Val Ser Ser
        115                 120
```

<210> SEQ ID NO 234
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Asn Tyr
                20                  25                  30

Met Tyr His Trp Val Arg Gln Ala Pro Gly Gln Gly Leu Glu Trp Met
            35                  40                  45

Gly Trp Ile Ser Thr Tyr His Gly Ser Thr Asn Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Arg Gly Tyr Ser Gly Tyr Asp Leu Trp Gly Gln Gly
            100                 105                 110

Thr Leu Val Thr Val Ser Ser
        115
```

<210> SEQ ID NO 235
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Ser Tyr
                20                  25                  30

Tyr Met His Trp Val Arg Gln Ala Pro Gly Gln Gly Leu Glu Trp Met
            35                  40                  45

Gly Trp Met Asn Pro Asn Ser Asp Ile Ala Gly Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Glu Gly Arg His Gly Glu Tyr Leu Tyr Trp Gly Gln Gly Thr
            100                 105                 110

Leu Val Thr Val Ser Ser
        115

<210> SEQ ID NO 236
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Thr Tyr
            20                  25                  30

Tyr Val His Trp Val Arg Gln Ala Pro Gly Gln Gly Leu Glu Trp Met
        35                  40                  45

Gly Trp Met Asn Pro Asn Thr Val Tyr Thr Gly Ser Ala Gln Lys Phe
    50                  55                  60

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Trp Gly Ser Ser Gly Tyr Phe Asp Tyr Trp Gly Gln
            100                 105                 110

Gly Thr Leu Val Thr Val Ser Ser
        115                 120

<210> SEQ ID NO 237
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Leu Ser Trp Val Arg Gln Ala Pro Gly Gln Gly Leu Glu Trp Met
        35                  40                  45

Gly Arg Ile Ile Pro Ala Val Gly Ser Val Thr Tyr Ala Gln Lys Phe
    50                  55                  60

Gln Gly Arg Val Thr Ile Thr Ala Asp Glu Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg His Leu Phe Pro Thr Val Phe Asp Asp Tyr Tyr Gly Met Asp
            100                 105                 110

Val Trp Gly Gln Gly Thr Leu Val Thr Val Ser Ser
        115                 120

<210> SEQ ID NO 238
<211> LENGTH: 119

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Tyr Gly Ser Phe Gln His Trp Gly Gln Gly
            100                 105                 110

Thr Leu Val Thr Val Ser Ser
        115

<210> SEQ ID NO 239
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Arg His
            20                  25                  30

Tyr Val His Trp Val Arg Gln Ala Pro Gly Gln Gly Leu Glu Trp Met
        35                  40                  45

Gly Trp Met Ser Pro Ser Ser Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Arg Trp Ser Ser Asp Ala Phe Asp Ile Trp Gly Gln Gly
            100                 105                 110

Thr Leu Val Thr Val Ser Ser
        115

<210> SEQ ID NO 240
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gln Val Gln Leu Val Gln Ser Gly Ala Glu Val Lys Lys Pro Gly Ala
```

-continued

```
                1               5                  10                 15
            Ser Val Lys Val Ser Cys Lys Ala Ser Gly Tyr Thr Phe Thr Ser Tyr
                           20                  25                 30

Tyr Met His Trp Val Arg Gln Ala Pro Gly Gln Gly Leu Glu Trp Val
                           35                  40                 45

Gly Trp Met Thr Pro Ser Thr Gly Asn Ala Gly Tyr Ala Gln Lys Phe
                50                          55                 60

Gln Gly Arg Val Thr Met Thr Arg Asp Thr Ser Thr Ser Thr Val Tyr
             65                     70                  75                 80

Met Glu Leu Ser Ser Leu Arg Ser Glu Asp Thr Ala Val Tyr Tyr Cys
                               85                  90                 95

Ala Arg Glu Glu Trp Leu Gly His Phe Gln His Trp Gly Gln Gly Thr
                          100                 105                110

Leu Val Thr Val Ser Ser
                          115
```

<210> SEQ ID NO 241
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

```
            Gln Val Gln Leu Val Gln Ser Gly Ala Glu Val Lys Lys Pro Gly Ala
             1               5                  10                 15

Ser Val Lys Val Ser Cys Lys Ala Ser Gly Tyr Thr Phe Thr Ser His
                           20                  25                 30

Tyr Met His Trp Val Arg Gln Ala Pro Gly Gln Gly Leu Glu Trp Met
                           35                  40                 45

Gly Trp Met Asn Pro Asn Ser Gly Asn Thr Gly Tyr Ala Gln Lys Phe
                50                          55                 60

Gln Gly Arg Val Thr Met Thr Arg Asp Thr Ser Thr Ser Thr Val Tyr
             65                     70                  75                 80

Met Glu Leu Ser Ser Leu Arg Ser Glu Asp Thr Ala Val Tyr Tyr Cys
                               85                  90                 95

Ala Arg Glu Arg Phe Leu Gly Gly Met Asp Val Trp Gly Gln Gly Thr
                          100                 105                110

Thr Val Thr Val Ser Ser
                          115
```

<210> SEQ ID NO 242
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

```
            Gln Val Gln Leu Val Gln Ser Gly Ala Glu Val Lys Lys Pro Gly Ala
             1               5                  10                 15

Ser Val Lys Val Ser Cys Lys Ala Ser Gly Tyr Thr Phe Thr Asp Tyr
                           20                  25                 30

Tyr Met His Trp Val Arg Gln Ala Pro Gly Gln Gly Leu Glu Trp Met
                           35                  40                 45

Gly Trp Met His Pro Asn Ser Gly His Thr Gly Tyr Ala Gln Lys Phe
```

```
                50                  55                  60
Gln Gly Arg Val Thr Met Thr Arg Asp Thr Ser Thr Ser Thr Val Asn
 65                  70                  75                  80

Met Glu Leu Ser Ser Leu Arg Ser Glu Asp Thr Ala Val Tyr Tyr Cys
                 85                  90                  95

Ala Arg Glu Glu Trp Leu Gly His Phe Gln His Trp Gly Gln Gly Thr
            100                 105                 110

Leu Val Thr Val Ser Ser
        115

<210> SEQ ID NO 243
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser His
                20                  25                  30

Tyr Met His Trp Val Arg Gln Ala Pro Gly Gln Gly Leu Glu Trp Met
            35                  40                  45

Gly Trp Met Asn Pro Asn Ser Gly His Thr Gly Asn Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Gly Asn Trp Val Asp Ala Phe Asp Ile Trp Gly Gln Gly Thr
            100                 105                 110

Met Val Thr Val Ser Ser
        115

<210> SEQ ID NO 244
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Thr Leu His Trp Val Arg Gln Ala Pro Gly Gln Gly Leu Glu Trp Met
            35                  40                  45

Gly Trp Ile Asp Pro Asn Ser Gly Val Thr Ser Ser Ala Gln Lys Phe
        50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ser Glu Val Met Met Ala Tyr Phe Gln His Trp Gly Gln
```

```
                    100                 105                 110

Gly Thr Leu Val Thr Val Ser Ser
            115                 120

<210> SEQ ID NO 245
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Ser Pro Asn Ser Gly Val Thr Asp Phe Thr Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Ser Gly Glu Phe Asp Tyr Trp Gly Gln Gly Thr
            100                 105                 110

Leu Val Thr Val Ser Ser
        115

<210> SEQ ID NO 246
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gln Val Gln Leu Val Gln Ser Gly Ala Glu Val Lys Lys Pro Gly Ala
1               5                   10                  15

Ser Val Lys Val Ser Cys Lys Ala Ser Gly Asp Thr Phe Thr Asn His
            20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Tyr Ala Gln Arg Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Val Ala Gly Pro Met Asp Val Trp Gly Gln Gly Thr
            100                 105                 110

Thr Val Thr Val Ser Ser
        115

<210> SEQ ID NO 247
<211> LENGTH: 119
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 247

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Met Asn Pro Asn Ser Asp Ile Ala Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ala Trp Glu Leu Leu Ala Phe Asp Ile Trp Gly Gln Gly
            100                 105                 110

Thr Leu Val Thr Val Ser Ser
        115

<210> SEQ ID NO 248
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 248

Gln Val Gln Leu Ala Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Trp Asp Gly Asp Tyr Tyr Ser Ala Trp Gly Gln Gly
            100                 105                 110

Thr Leu Val Thr Val Ser Ser
        115

<210> SEQ ID NO 249
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Gln Val Gln Leu Val Gln Ser Gly Ala Glu Val Lys Lys Pro Gly Ala
1               5                   10                  15

-continued

```
Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Met
        35                  40                  45

Gly Trp Met Ser Pro Asn Gly Gly Asn Thr Gly Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Glu Ser Trp Glu Leu Thr Gly Phe Asp Tyr Trp Gly Gln Gly
            100                 105                 110

Thr Leu Val Thr Val Ser Ser
        115

<210> SEQ ID NO 250
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                85                  90                  95

Ala Arg Glu Arg Phe Ala Gly Gly Met Asp Ala Trp Gly Gln Gly Thr
            100                 105                 110

Thr Val Thr Val Ser Ser
        115

<210> SEQ ID NO 251
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Ser Asn Ser
            20                  25                  30

Tyr Met His Trp Val Arg Gln Ala Pro Gly Gln Gly Leu Glu Trp Met
        35                  40                  45

Gly Trp Met Asp Pro Ser Ser Gly Tyr Thr Gly Ser Ala His Lys Phe
 50                  55                  60
```

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Glu Asp Ser Gly Gly Ala Phe Asp Ile Trp Gly Gln Gly Thr Met
            100                 105                 110

Val Thr Val Ser Ser
        115

<210> SEQ ID NO 252
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Ser Thr Tyr
            20                  25                  30

Tyr Met His Trp Val Arg Gln Ala Pro Gly Gln Gly Leu Glu Trp Met
        35                  40                  45

Gly Trp Met Asn Pro His Ser Ala Asp Thr Gly Tyr Ala Glu Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Val Phe Glu Gly Gly Met Asp Val Trp Gly Gln Gly Thr
            100                 105                 110

Thr Val Thr Val Ser Ser
        115

<210> SEQ ID NO 253
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Leu Thr Pro Ser Thr Gly His Ala Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Gly Gly Asn Tyr Gly Asn Trp Gly Gln Gly Thr
            100                 105                 110

```
Leu Val Thr Val Ser Ser
        115

<210> SEQ ID NO 254
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Asp Phe Tyr Gly Asp Phe Asp Tyr Trp Gly Gln Gly Thr
            100                 105                 110

Leu Val Thr Val Ser Ser
        115

<210> SEQ ID NO 255
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg His
            20                  25                  30

Phe Ile His Trp Val Arg Gln Ala Pro Gly Gln Gly Leu Glu Trp Met
        35                  40                  45

Gly Trp Ile Asp Pro Asn Ser Gly Val Thr Ser Ser Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Leu Ser Arg Trp Gly Phe Asp Tyr Trp Gly Pro Gly Thr
            100                 105                 110

Met Val Thr Val Ser Ser
        115

<210> SEQ ID NO 256
<211> LENGTH: 118
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 256

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg His
                20                  25                  30

Leu Leu His Trp Val Arg Gln Ala Pro Gly Gln Gly Leu Glu Trp Met
            35                  40                  45

Gly Trp Ile Ser Pro Gln His Gly Val Arg Asn Tyr Ala His Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Val Glu Gly Tyr Phe Asp Leu Trp Gly Arg Gly Thr
                100                 105                 110

Leu Val Thr Val Ser Ser
            115

<210> SEQ ID NO 257
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Ser Ser Tyr
                20                  25                  30

Tyr Met His Trp Val Arg Gln Ala Pro Gly Gln Gly Leu Glu Trp Met
            35                  40                  45

Gly Met Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Ile Phe Pro Thr Met Ile Ala Gly Gly Phe Asp Leu
                100                 105                 110

Trp Gly Arg Gly Thr Leu Val Thr Val Ser Ser
            115                 120

<210> SEQ ID NO 258
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 258

Gln Val Gln Leu Val Gln Ser Gly Ala Glu Val Lys Lys Pro Gly Ser
1               5                   10                  15
```

-continued

Ser Val Lys Val Ser Cys Lys Ala Ser Gly Thr Phe Thr Phe
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Ser Tyr Gly Ser Phe Asp Tyr Trp Gly Gln Gly
            100                 105                 110

Thr Leu Val Thr Val Ser Ser
            115

<210> SEQ ID NO 259
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ser Phe Pro Leu Val Phe Thr Ile Phe Gly Val Gly Asp
            100                 105                 110

Val Trp Gly Gln Gly Thr Met Val Thr Val Ser Ser
        115                 120

<210> SEQ ID NO 260
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Ser Pro Arg Ser Gly Val Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Asp Tyr Val Arg Ala Phe Asp Ile Trp Gly Gln Gly
            100                 105                 110

Thr Thr Val Thr Val Ser Ser
        115

<210> SEQ ID NO 261
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Met His Trp Val Arg Gln Ala Pro Gly Gln Gly Leu Glu Trp Met
        35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Gly Gly Tyr Phe Asp Leu Trp Gly Arg Gly Thr
            100                 105                 110

Leu Val Thr Val Ser Ser
        115

<210> SEQ ID NO 262
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asn His
            20                  25                  30

Tyr Val His Trp Val Arg Gln Ala Pro Gly Gln Gly Leu Glu Trp Met
        35                  40                  45

Gly Trp Met Asn Pro Thr Gly Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Thr Thr Tyr Ala Phe Asp Ile Trp Gly Gln Gly Thr
            100                 105                 110

Met Val Thr Val Ser Ser
        115

<210> SEQ ID NO 263
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 263

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Asn Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asn Trp Val Asp Ala Phe Asp Ile Trp Gly Gln Gly Thr
            100                 105                 110

Met Val Thr Val Ser Ser
        115

<210> SEQ ID NO 264
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg His
            20                  25                  30

Leu Leu His Trp Val Arg Gln Ala Pro Gly Gln Gly Leu Glu Trp Met
        35                  40                  45

Gly Trp Val Ser Pro Ile His Gly Leu Thr Gly Tyr Ala Pro Arg Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val His Gly Ser Gly Ser Asp Gly Met Asp Val Trp Gly Gln
            100                 105                 110

Gly Thr Thr Val Thr Val Ser Ser
        115                 120

<210> SEQ ID NO 265
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 265

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asp Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gly Gly Thr Lys Val Glu Ile Lys
            100                 105

<210> SEQ ID NO 266
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Ile
                85                  90                  95

Thr Phe Gly Gly Gly Thr Lys Val Glu Ile Lys
            100                 105

<210> SEQ ID NO 267
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly

-continued

```
                 50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ile Phe Ser Thr Pro Leu
                 85                  90                  95

Thr Phe Gly Gly Gly Thr Lys Val Glu Ile Lys
            100                 105

<210> SEQ ID NO 268
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Gly Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
            100                 105

<210> SEQ ID NO 269
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Thr Ile Ser Asn Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Ile
                 85                  90                  95

Thr Phe Gly Gly Gly Thr Lys Val Glu Ile Lys
            100                 105

<210> SEQ ID NO 270
<211> LENGTH: 108
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 270

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Arg Asn
            20                  25                  30

Tyr Val Thr Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Ser Tyr Thr Thr Pro
                85                  90                  95

Tyr Thr Phe Gly Gln Gly Thr Lys Val Glu Ile Lys
            100                 105

<210> SEQ ID NO 271
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Gln Tyr
            20                  25                  30

Leu Ala Trp Tyr Gln Gln Lys Pro Gly Lys Ala Pro Lys Leu Leu Ile
        35                  40                  45

Tyr Gly Ala Ser Asn Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Thr Thr Pro Leu
                85                  90                  95

Thr Phe Gly Gly Gly Thr Lys Val Glu Ile Lys
            100                 105

<210> SEQ ID NO 272
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Gly Asn Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
                100                 105

<210> SEQ ID NO 273
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Leu Leu Ile
        35                  40                  45

Tyr Ser Ala Ser Asn Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gln Ala Asn Ser Phe Pro Phe
                 85                  90                  95

Thr Phe Gly Gly Gly Thr Lys Val Glu Ile Lys
                100                 105

<210> SEQ ID NO 274
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 274

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
        35                  40                  45

Tyr Ala Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
 65              70                  75                      80

Glu Asp Phe Ala Thr Tyr Tyr Cys Gln Gln Ser Tyr Thr Thr Pro Tyr
                 85                  90                  95

Ser Phe Gly Gly Gly Thr Lys Val Glu Ile Lys
                100                 105

<210> SEQ ID NO 275
```

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 275

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Gln Tyr
            20                  25                  30

Leu Ala Trp Tyr Gln Gln Lys Pro Gly Lys Ala Pro Lys Leu Leu Ile
        35                  40                  45

Tyr Gly Ala Ser Asn Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Phe Ile Thr Pro Leu
                85                  90                  95

Thr Phe Gly Gly Gly Thr Lys Val Glu Ile Lys
            100                 105

<210> SEQ ID NO 276
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 276

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Gly Asn Tyr
            20                  25                  30

Leu Ala Trp Tyr Gln Gln Lys Pro Gly Lys Ala Pro Lys Leu Leu Ile
        35                  40                  45

Tyr His Ala Ser Ile Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Thr
                85                  90                  95

Phe Gly Gly Gly Thr Lys Val Glu Ile Lys
            100                 105

<210> SEQ ID NO 277
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 277

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Ser Ser Tyr
            20                  25                  30
```

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Phe Ser Thr Pro Phe
                 85                  90                  95

Thr Phe Gly Gly Gly Thr Lys Val Glu Ile Lys
            100                 105
```

<210> SEQ ID NO 278
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 278

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
                 20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Phe Thr Asn Pro Val
                 85                  90                  95

Thr Phe Gly Gly Gly Thr Lys Val Glu Ile Lys
            100                 105
```

<210> SEQ ID NO 279
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 279

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Asn Tyr
                 20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ala Pro Tyr
                 85                  90                  95

Thr Phe Gly Gly Gly Thr Lys Val Glu Ile Lys
            100                 105
```

<210> SEQ ID NO 280
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 280

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asn
            20                  25                  30

Leu Asn Trp Tyr Gln Gln Lys Pro Gly Lys Ala Pro Lys Leu Leu Ile
        35                  40                  45

Tyr Ala Ala Thr Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gly Gly Thr Lys Val Glu Ile Lys
            100                 105

<210> SEQ ID NO 281
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 281

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 282
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 282

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Gly

```
                20                  25                  30

Leu Ser Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser His Ser Thr Pro Leu
                85                  90                  95

Thr Phe Gly Gly Gly Thr Lys Val Glu Ile Lys
            100                 105

<210> SEQ ID NO 283
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 283

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Gly Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 284
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 284

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Thr His Leu Glu Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
```

<210> SEQ ID NO 285
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 285

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 286
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 286

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 287
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 287

```
Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Ser Ile Thr Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 288
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Leu Glu Ile Lys
            100                 105

<210> SEQ ID NO 289
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 289

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 290
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 290

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Trp
            20                  25                  30

Leu Ala Trp Tyr Gln Gln Lys Pro Gly Lys Ala Pro Lys Leu Leu Ile
        35                  40                  45

Tyr Asp Val Ser His Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Pro Gly Thr Lys Val Asp Ile Lys
            100                 105

<210> SEQ ID NO 291
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 291

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Asp Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 292
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 292

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Leu Ser Ser Ser
            20                  25                  30

Ser Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105
```

<210> SEQ ID NO 293
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 293

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu His Ile Ala Asn Trp
            20                  25                  30

Leu Ala Trp Tyr Gln Gln Lys Pro Gly Lys Ala Pro Lys Leu Leu Ile
        35                  40                  45

Tyr Gly Val Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 294
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 294

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Ser Trp
            20                  25                  30

Val Ala Trp Tyr Gln Gln Lys Pro Gly Lys Ala Pro Lys Leu Leu Ile
        35                  40                  45

Tyr Pro Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 295
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 295

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Pro Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ser Thr Pro Ile
                85                  90                  95

Thr Phe Gly Gln Gly Thr Arg Leu Glu Ile Lys
            100                 105

<210> SEQ ID NO 296
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 296

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 297
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 297

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Thr Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Thr Arg Ala Ser Gly Ile Pro Ala Arg Phe Ser
50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln Gln Tyr Tyr Thr Thr Pro
                85                  90                  95

Leu Thr Phe Gly Gly Gly Thr Lys Val Glu Ile Lys
            100                 105

<210> SEQ ID NO 298
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Leu
                85                  90                  95

Thr Phe Gly Gln Gly Thr Arg Leu Glu Ile Lys
            100                 105

<210> SEQ ID NO 299
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 299

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Leu Thr Ile Ser Ser Leu Gln Pro

```
                65                  70                  75                  80
Glu Asp Phe Ala Thr Tyr Tyr Cys Gln Gln Ser Tyr Ser Thr Pro Pro
                    85                  90                  95

Thr Phe Gly Gln Gly Thr Lys Val Glu Ile Lys
            100                 105
```

<210> SEQ ID NO 300
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 300

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Asn
            20                  25                  30

Leu Asn Trp Tyr Gln Gln Lys Pro Gly Lys Ala Pro Lys Leu Leu Ile
        35                  40                  45

Tyr Ala Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105
```

<210> SEQ ID NO 301
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Gly Ile Arg Asn Asp
            20                  25                  30

Leu Ser Trp Tyr Gln Gln Lys Pro Gly Lys Ala Pro Lys Leu Leu Ile
        35                  40                  45

Tyr Leu Ala Ser Asn Ser His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
            100                 105
```

<210> SEQ ID NO 302
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 302

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 303
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ser Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Val
                85                  90                  95

Thr Phe Gly Gln Gly Thr Lys Val Glu Ile Lys
            100                 105

<210> SEQ ID NO 304
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Asp Ile Gln Ile Thr His Ser Pro Ser Ser Leu Ser Ala Ser Val Gly
1               5                   10                  15

Tyr Arg Leu Thr Ile Thr Cys Asp Ser His Ser Ile Thr Thr Trp
            20                  25                  30

Leu Ala Trp Tyr His Gln Lys Pro Trp Asn Ala Pro Lys Leu Met Ile
        35                  40                  45

Tyr Ala Ala Ser Asn Leu Glu Ser Gly Val Pro Ser Arg Phe Ser Gly
    50                  55                  60

Ser Gly Ser Gly Thr Tyr Phe Thr Leu Thr Ile Ser Ser Leu Gln Pro
65                  70                  75                  80

Glu Asp Phe Ala Thr Tyr Tyr Cys Gln His Phe Tyr Asn Thr Gln Tyr
                85                  90                  95

Thr Phe Gly Gln Gly Thr Lys Val Glu Ile Lys
            100                 105

<210> SEQ ID NO 305
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Arg Asn Asp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Leu Gln Tyr Pro Ser
                85                  90                  95

His Phe Phe Gly Gln Gly Thr Lys Val Glu Ile Lys
            100                 105

<210> SEQ ID NO 306
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Pro Tyr Tyr Cys Gln Gln Ser Tyr Ser Thr Pro Leu
                85                  90                  95

Thr Phe Gly Pro Gly Thr Lys Val Asp Ile Lys
            100                 105

<210> SEQ ID NO 307
<211> LENGTH: 290
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 307

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 308
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Asp Tyr Met His
1               5

<210> SEQ ID NO 309
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Gly Tyr Tyr Met His
1               5

<210> SEQ ID NO 310
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ser Tyr Tyr Met His
1               5

<210> SEQ ID NO 311
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Gly Tyr Tyr Ile His
1               5

<210> SEQ ID NO 312
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Thr His Tyr Met His
1               5

<210> SEQ ID NO 313
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ser His Asp Ile Asn
1               5

<210> SEQ ID NO 314
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314
```

-continued

Asp His Tyr Leu His
1               5

<210> SEQ ID NO 315
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Asn Tyr Tyr Met His
1               5

<210> SEQ ID NO 316
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ala Tyr Tyr Val His
1               5

<210> SEQ ID NO 317
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Arg His Tyr Val His
1               5

<210> SEQ ID NO 318
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

Asn Tyr Ile His
1

<210> SEQ ID NO 319
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Asn His Tyr Val His
1               5

<210> SEQ ID NO 320
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 320

Ser His Tyr Met His
1               5

<210> SEQ ID NO 321
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Arg His Leu Leu His
1               5

<210> SEQ ID NO 322
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Trp Met Ser Pro Tyr Asn Gly Ile Thr Gly Tyr Ala Gln Lys Phe Gln
1               5                   10                  15

Gly

<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Trp Met Ser Pro Ser Ser Gly Ile Thr Gly Tyr Ala Gln Lys Phe Gln
1               5                   10                  15

Gly

<210> SEQ ID NO 324
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Trp Met Thr Thr Asn Ser Gly Ile Thr Gly Tyr Ala Gln Lys Phe Gln
1               5                   10                  15

Gly

<210> SEQ ID NO 325
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 325

Gly Ile Ile Pro Ile Phe Gly Thr Ala Ser Tyr Ala Gln Lys Phe Gln
1               5                   10                  15
Gly

<210> SEQ ID NO 326
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Trp Met Asn Pro Asn Ser Gly His Ala Gly Ser Ala Gln Lys Phe Gln
1               5                   10                  15
Gly

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Trp Met Asn Pro Asn Ser Gly Asn Thr Gly Tyr Ala Gln Lys Phe Gln
1               5                   10                  15
Gly

<210> SEQ ID NO 328
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Trp Met Asn Pro Asn Ser Gly Asn Thr Gly Tyr Ser Gln Lys Phe Gln
1               5                   10                  15
Gly

<210> SEQ ID NO 329
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Trp Met Asn Pro Asn Ile Gly Asn Thr Gly Tyr Ala Gln Lys Phe Gln
1               5                   10                  15
Gly

<210> SEQ ID NO 330
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 330

Trp Met Asn Pro Asn Gly Gly Thr Thr Gly Tyr Ala Gln Asn Phe Gln
1               5                   10                  15

Gly

<210> SEQ ID NO 331
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Trp Met Asn Pro Asn Arg Gly Ile Thr Asp Ser Ala Gln Lys Phe Gln
1               5                   10                  15

Gly

<210> SEQ ID NO 332
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Trp Met Asn Pro Asn Ser Gly Ser Ala Gly Tyr Ala Gln Lys Phe Gln
1               5                   10                  15

Gly

<210> SEQ ID NO 333
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Trp Ile His Pro Arg Ser Gly Ala Thr Gly Tyr Ala Pro Lys Phe Gln
1               5                   10                  15

Gly

<210> SEQ ID NO 334
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Trp Ile Ser Pro Arg Ser Gly Val Thr Ser Tyr Ala Gln Lys Phe Gln
1               5                   10                  15

Gly

<210> SEQ ID NO 335
<211> LENGTH: 17
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 335

Trp Met Asp Pro Asn Ser Gly Asn Thr Gly Tyr Ala Gln Lys Phe Gln
1               5                   10                  15

Gly

<210> SEQ ID NO 336
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Trp Met Asn Pro Thr Gly Gly Ile Thr Gly Tyr Ala Gln Lys Phe Gln
1               5                   10                  15

Gly

<210> SEQ ID NO 337
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Trp Met Asn Pro Asn Ser Gly His Thr Gly Asn Ala Gln Lys Phe Gln
1               5                   10                  15

Gly

<210> SEQ ID NO 338
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Trp Val Ser Pro Ile His Gly Leu Thr Gly Tyr Ala Pro Arg Phe Gln
1               5                   10                  15

Gly

<210> SEQ ID NO 339
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

Asp Arg Phe Ser Gly Ser Tyr Asp Tyr
1               5

<210> SEQ ID NO 340
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 340

Asp Arg Gly Trp Phe Asp Pro
1               5

<210> SEQ ID NO 341
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Glu Gly Tyr Ser Ser Gly Leu Asp Tyr
1               5

<210> SEQ ID NO 342
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Asp Gly Arg Phe Trp Ser Gly Tyr Pro Asp Tyr
1               5                   10

<210> SEQ ID NO 343
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Glu Ser Ile Ala Val Ala Gly Tyr Asp Tyr
1               5                   10

<210> SEQ ID NO 344
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Asp Arg Trp Tyr Met Gly Ser Ala Asp Tyr
1               5                   10

<210> SEQ ID NO 345
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Asp Asp Trp Gly Gly Asp Trp Phe Asp Pro
1               5                   10

<210> SEQ ID NO 346
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Glu Arg Leu Ser Val Ala Gly Phe Asp Tyr
1               5                   10

<210> SEQ ID NO 347
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Glu Pro Leu Gln Leu Gly Gly Phe Asp Tyr
1               5                   10

<210> SEQ ID NO 348
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Glu Gly Phe Gly Pro Asn Ala Phe Asp Ile
1               5                   10

<210> SEQ ID NO 349
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Asp Ser Trp Tyr Gly Asp Trp Phe Asp Pro
1               5                   10

<210> SEQ ID NO 350
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Glu Val Ile Glu Val Gly Met Asp Val
1               5

<210> SEQ ID NO 351
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Glu Ala Trp Phe Gly Glu Leu Ser Thr
```

```
<210> SEQ ID NO 352
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Glu Ala Tyr Val Ala Ala Phe Asp Ile
1               5

<210> SEQ ID NO 353
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Glu Arg Gly Tyr Asn Ala Phe Asp Tyr
1               5

<210> SEQ ID NO 354
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Asp Ser Val Phe Gly Leu Asp Tyr
1               5

<210> SEQ ID NO 355
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Asp Leu Asp Tyr Val Arg Ala Phe Asp Ile
1               5                   10

<210> SEQ ID NO 356
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Glu Ser Trp Gly Gly Tyr Phe Asp Leu
1               5

<210> SEQ ID NO 357
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 357

Asp Arg Thr Thr Tyr Ala Phe Asp Ile
1               5

<210> SEQ ID NO 358
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Gly Asn Trp Val Asp Ala Phe Asp Ile
1               5

<210> SEQ ID NO 359
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Val His Gly Ser Gly Ser Asp Gly Met Asp Val
1               5                   10

<210> SEQ ID NO 360
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Arg Ala Ser Gln Ser Ile Ser Ser Trp Leu Ala
1               5                   10

<210> SEQ ID NO 361
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Arg Ala Ser Gln Ser Val Gly Thr Trp Leu Ala
1               5                   10

<210> SEQ ID NO 362
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Arg Ala Ser Gln Gly Ile Ser Asn Tyr Leu Ala
1               5                   10

<210> SEQ ID NO 363

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Arg Ala Ser Gln Ser Ile Ser Thr Trp Leu Ala
1               5                   10

<210> SEQ ID NO 364
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Gln Ala Ser Gln Asp Ile Ser Asn His Leu Asn
1               5                   10

<210> SEQ ID NO 365
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Arg Ala Ser Gln Gly Ile Ser Ser Trp Leu Ala
1               5                   10

<210> SEQ ID NO 366
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Arg Ala Ser Glu Ser Ile Ser Ser Trp Leu Ala
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Arg Ala Ser Gln Ser Val Gly Ser Trp Leu Ala
1               5                   10

<210> SEQ ID NO 368
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368
```

```
Arg Ala Ser Gln Asn Ile Ser Asn Phe Leu Asn
1               5                   10

<210> SEQ ID NO 369
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Arg Ala Ser Gln Ser Leu Ser Ser Ser Tyr Leu Ala
1               5                   10

<210> SEQ ID NO 370
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Arg Ala Ser Gln Ser Ile Ser Ser Tyr Leu Asn
1               5                   10

<210> SEQ ID NO 371
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Arg Ala Ser Gln Ser Ile Ser Arg Trp Leu Ala
1               5                   10

<210> SEQ ID NO 372
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Arg Asp Ser His Ser Ile Thr Thr Trp Leu Ala
1               5                   10

<210> SEQ ID NO 373
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Arg Ala Ser Gln Val Ile Arg Asn Asp Leu Ala
1               5                   10

<210> SEQ ID NO 374
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 374

Arg Ala Ser Gln Ser Ile Ser Arg Tyr Leu Asn
1               5                   10

<210> SEQ ID NO 375
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Ala Ala Ser Ser Leu Gln Ser
1               5

<210> SEQ ID NO 376
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 376

Ala Ala Ser Thr Leu Glu Asn
1               5

<210> SEQ ID NO 377
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Arg Ala Ser Asn Leu Glu Ser
1               5

<210> SEQ ID NO 378
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Ala Ala Ser Thr Leu Gln Arg
1               5

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Ala Ala Ser Thr Leu Gln Ser
1               5

```
<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Gly Ala Ser Asn Leu Gln Arg
1               5

<210> SEQ ID NO 381
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 381

Ala Ala Ser Asn Leu Gln Ser
1               5

<210> SEQ ID NO 382
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 382

Gly Ala Ser Ser Leu Gln Ser
1               5

<210> SEQ ID NO 383
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 383

Ala Ala Ser His Leu Gln Ser
1               5

<210> SEQ ID NO 384

<400> SEQUENCE: 384

000

<210> SEQ ID NO 385
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 385

Asp Ser Ser Ser Leu Gln Thr
1               5

<210> SEQ ID NO 386
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 386

Ala Ala Ser Asn Leu Glu Ser
1               5

<210> SEQ ID NO 387
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 387

Gln Gln Ser Tyr Ser Thr Pro Tyr Thr
1               5

<210> SEQ ID NO 388
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 388

Gln Gln Ser Phe Ser Thr Pro Tyr Thr
1               5

<210> SEQ ID NO 389
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 389

Gln Gln Ser Tyr Ser Thr Pro Leu Thr
1               5

<210> SEQ ID NO 390
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 390

Gln Gln Ser Tyr Ser Thr Pro Phe Thr
1               5

<210> SEQ ID NO 391
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 391

Gln Gln Ser Tyr Ser Thr Pro Ile Thr
```

```
<210> SEQ ID NO 392
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gln Gln Tyr Tyr Ser Thr Pro Tyr Thr
1               5

<210> SEQ ID NO 393
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Gln Gln Ser Tyr Ser Leu Pro Tyr Thr
1               5

<210> SEQ ID NO 394
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

His Gln Tyr Phe Thr Thr Pro Leu Thr
1               5

<210> SEQ ID NO 395
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Gln Gln Ser Tyr Ser Met Pro Tyr Thr
1               5

<210> SEQ ID NO 396
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Gln Gln Ser Tyr Ser Thr Pro Val Thr
1               5

<210> SEQ ID NO 397
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 397

Gln His Phe Tyr Asn Thr Gln Tyr Thr
1               5

<210> SEQ ID NO 398
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Gln Gln Ser Leu Gln Tyr Pro Ser His Phe
1               5                   10

<210> SEQ ID NO 399
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser
            20                  25                  30

<210> SEQ ID NO 400
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 401
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr
            20                  25                  30

<210> SEQ ID NO 402
<211> LENGTH: 30
<212> TYPE: PRT
<213> ORGANISM: Artificial Sequence
<220> FEATURE:
<223> OTHER INFORMATION: Description of Artificial Sequence: Synthetic -continued

```
      polypeptide

<400> SEQUENCE: 402

Gln Val Gln Leu Val Gln Ser Gly Ala Glu Val Lys Glu Pro Gly Ala
1               5                   10                  15

Ser Val Lys Val Ser Cys Lys Ala Ser Gly Tyr Thr Phe Thr
            20                  25                  30

<210> SEQ ID NO 403
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ser
            20                  25                  30

<210> SEQ ID NO 404

<400> SEQUENCE: 404

000

<210> SEQ ID NO 405
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr
            20                  25                  30

<210> SEQ ID NO 406
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile
            20                  25                  30

<210> SEQ ID NO 407
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407
```

```
Trp Val Arg Gln Ala Pro Gly Gln Gly Leu Glu Trp Met Gly
1               5                  10
```

<210> SEQ ID NO 408
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

```
Trp Met Arg Gln Ala Pro Gly Gln Gly Leu Glu Trp Ile Gly
1               5                  10
```

<210> SEQ ID NO 409
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

```
Arg Val Thr Met Thr Arg Asp Thr Ser Thr Ser Thr Val Tyr Met Glu
1               5                  10                  15

Leu Ser Ser Leu Arg Ser Glu Asp Thr Ala Val Tyr Tyr Cys Ala Arg
            20                  25                  30
```

<210> SEQ ID NO 410
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

```
Arg Val Thr Ile Thr Ala Asp Glu Ser Thr Ser Thr Ala Tyr Met Glu
1               5                  10                  15

Leu Ser Ser Leu Arg Ser Glu Asp Thr Ala Val Tyr Tyr Cys Ala Arg
            20                  25                  30
```

<210> SEQ ID NO 411
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 411

```
Trp Gly Gln Gly Thr Leu Val Thr Val Ser Ser
1               5                  10
```

<210> SEQ ID NO 412
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 412

```
Trp Gly Gln Gly Thr Thr Val Thr Val Ser Ser
1               5                  10
```

```
<210> SEQ ID NO 413
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 413

Trp Gly Arg Gly Thr Leu Val Thr Val Ser Ser
1               5                   10

<210> SEQ ID NO 414
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 414

Trp Gly Gln Gly Thr Met Val Thr Val Ser Ser
1               5                   10

<210> SEQ ID NO 415
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 415

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 416
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 416

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 417
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 417

Asp Ile Gln Ile Thr His Ser Pro Ser Ser Leu Ser Ala Ser Val Gly
1               5                   10                  15

Tyr Arg Leu Thr Ile Thr Cys
            20
```

<210> SEQ ID NO 418
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 418

Trp Tyr Gln Gln Lys Pro Gly Lys Ala Pro Lys Leu Leu Ile Tyr
1               5                   10                  15

<210> SEQ ID NO 419
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 419

Trp Tyr Gln Gln Lys Pro Gly Gln Ala Pro Arg Leu Leu Ile Tyr
1               5                   10                  15

<210> SEQ ID NO 420
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 420

Trp Tyr His Gln Lys Pro Trp Asn Ala Pro Lys Leu Met Ile Tyr
1               5                   10                  15

<210> SEQ ID NO 421
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 422
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 423
<211> LENGTH: 32

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Gly Val Pro Ser Arg Phe Ser Gly Ser Gly Ser Gly Thr Tyr Phe Thr
1               5                   10                  15
Leu Thr Ile Ser Ser Leu Gln Pro Glu Asp Phe Ala Thr Tyr Tyr Cys
            20                  25                  30

<210> SEQ ID NO 424
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Pro Tyr Tyr Cys
            20                  25                  30

<210> SEQ ID NO 425
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Phe Gly Gly Gly Thr Lys Val Glu Ile Lys
1               5                   10

<210> SEQ ID NO 426
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Phe Gly Gln Gly Thr Lys Leu Glu Ile Lys
1               5                   10

<210> SEQ ID NO 427
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Phe Gly Gln Gly Thr Lys Val Glu Ile Lys
1               5                   10

<210> SEQ ID NO 428
<211> LENGTH: 10
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 428

Phe Gly Gln Gly Thr Arg Leu Glu Ile Lys
1               5                   10

<210> SEQ ID NO 429
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 429

Phe Gly Pro Gly Thr Lys Val Asp Ile Lys
1               5                   10

<210> SEQ ID NO 430
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Asp
            20                  25                  30

Tyr Met His Trp Val Arg Gln Ala Pro Gly Gln Gly Leu Glu Trp Met
        35                  40                  45

Gly Trp Met Ser Pro Tyr Asn Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Phe Ser Gly Ser Tyr Asp Tyr Trp Gly Gln Gly Thr
            100                 105                 110

Leu Val Thr Val Ser Ser
        115

<210> SEQ ID NO 431
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Met Ser Pro Ser Ser Gly Ile Thr Gly Tyr Ala Gln Lys Phe
    50                  55                  60

```
Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Gly Trp Phe Asp Pro Trp Gly Gln Gly Thr Leu Val
            100                 105                 110

Thr Val Ser Ser
        115

<210> SEQ ID NO 432
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Tyr
            20                  25                  30

Tyr Met His Trp Val Arg Gln Ala Pro Gly Gln Gly Leu Glu Trp Met
        35                  40                  45

Gly Trp Met Thr Thr Asn Ser Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Tyr Ser Ser Gly Leu Asp Tyr Trp Gly Gln Gly Thr
            100                 105                 110

Leu Val Thr Val Ser Ser
        115

<210> SEQ ID NO 433
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Gly Tyr
            20                  25                  30

Tyr Ile His Trp Val Arg Gln Ala Pro Gly Gln Gly Leu Glu Trp Met
        35                  40                  45

Gly Gly Ile Ile Pro Ile Phe Gly Thr Ala Ser Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Arg Phe Trp Ser Gly Tyr Pro Asp Tyr Trp Gly Gln
            100                 105                 110
```

Gly Thr Leu Val Thr Val Ser Ser
        115                 120

<210> SEQ ID NO 434
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr His
            20                  25                  30

Tyr Met His Trp Val Arg Gln Ala Pro Gly Gln Gly Leu Glu Trp Met
        35                  40                  45

Gly Trp Met Asn Pro Asn Ser Gly His Ala Gly Ser Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Ile Ala Val Ala Gly Tyr Asp Tyr Trp Gly Gln Gly
            100                 105                 110

Thr Leu Val Thr Val Ser Ser
        115

<210> SEQ ID NO 435
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Asp Ile Asn Trp Val Arg Gln Ala Pro Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Trp Tyr Met Gly Ser Ala Asp Tyr Trp Gly Gln Gly
            100                 105                 110

Thr Leu Val Thr Val Ser Ser
        115

<210> SEQ ID NO 436
<211> LENGTH: 119
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 436

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Asp Trp Gly Gly Asp Trp Phe Asp Pro Trp Gly Gln Gly
            100                 105                 110

Thr Leu Val Thr Val Ser Ser
        115

<210> SEQ ID NO 437
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr His
                20                  25                  30

Tyr Met His Trp Val Arg Gln Ala Pro Gly Gln Gly Leu Glu Trp Met
            35                  40                  45

Gly Trp Met Asn Pro Asn Ser Gly Asn Thr Gly Tyr Ser Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Leu Ser Val Ala Gly Phe Asp Tyr Trp Gly Gln Gly
            100                 105                 110

Thr Leu Val Thr Val Ser Ser
        115

<210> SEQ ID NO 438
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Gln Val Gln Leu Val Gln Ser Gly Ala Glu Val Lys Glu Pro Gly Ala
1               5                   10                  15
```

Ser Val Lys Val Ser Cys Lys Ala Ser Gly Tyr Thr Phe Thr Asp His
              20                  25                  30

Tyr Leu His Trp Val Arg Gln Ala Pro Gly Gln Gly Leu Glu Trp Met
          35                  40                  45

Gly Trp Met Asn Pro Asn Ile Gly Asn Thr Gly Tyr Ala Gln Lys Phe
     50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
             85                   90                  95

Ala Arg Glu Pro Leu Gln Leu Gly Gly Phe Asp Tyr Trp Gly Gln Gly
            100                 105                 110

Thr Leu Val Thr Val Ser Ser
            115

<210> SEQ ID NO 439
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Met Asn Pro Asn Gly Gly Thr Thr Gly Tyr Ala Gln Asn Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
             85                  90                  95

Ala Arg Glu Gly Phe Gly Pro Asn Ala Phe Asp Ile Trp Gly Gln Gly
            100                 105                 110

Thr Thr Val Thr Val Ser Ser
            115

<210> SEQ ID NO 440
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

Gly Trp Met Asn Pro Asn Ser Gly Asn Thr Gly Tyr Ala Gln Lys Phe
    50                  55                  60

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Ser Trp Tyr Gly Asp Trp Phe Asp Pro Trp Gly Gln Gly
            100                 105                 110

Thr Leu Val Thr Val Ser Ser
        115
```

<210> SEQ ID NO 441
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                 20                  25                  30

Tyr Met His Trp Met Arg Gln Ala Pro Gly Gln Gly Leu Glu Trp Ile
            35                  40                  45

Gly Trp Met Ser Pro Tyr Asn Gly Ile Thr Gly Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Val Ile Glu Val Gly Met Asp Val Trp Gly Gln Gly Thr
            100                 105                 110

Thr Val Thr Val Ser Ser
        115
```

<210> SEQ ID NO 442
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
                 20                  25                  30

Tyr Met His Trp Val Arg Gln Ala Pro Gly Gln Gly Leu Glu Trp Met
            35                  40                  45

Gly Trp Met Ser Pro Ser Ser Gly Ile Thr Gly Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Ala Trp Phe Gly Glu Leu Ser Thr Trp Gly Gln Gly Thr
            100                 105                 110
```

Leu Val Thr Val Ser Ser
        115

<210> SEQ ID NO 443
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Phe Ser Ala Tyr
            20                  25                  30

Tyr Val His Trp Val Arg Gln Ala Pro Gly Gln Gly Leu Glu Trp Met
        35                  40                  45

Gly Trp Met Asn Pro Asn Arg Gly Ile Thr Asp Ser Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ala Tyr Val Ala Ala Phe Asp Ile Trp Gly Gln Gly Thr
            100                 105                 110

Thr Val Thr Val Ser Ser
        115

<210> SEQ ID NO 444
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg His
            20                  25                  30

Tyr Val His Trp Val Arg Gln Ala Pro Gly Gln Gly Leu Glu Trp Met
        35                  40                  45

Gly Trp Met Asn Pro Asn Ser Gly Ser Ala Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Gly Tyr Asn Ala Phe Asp Tyr Trp Gly Gln Gly Thr
            100                 105                 110

Leu Val Thr Val Ser Ser
        115

<210> SEQ ID NO 445
<211> LENGTH: 116
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 445

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Pro Asn Tyr
            20                  25                  30

Ile His Trp Val Arg Gln Ala Pro Gly Gln Gly Leu Glu Trp Met Gly
        35                  40                  45

Trp Ile His Pro Arg Ser Gly Ala Thr Gly Tyr Ala Pro Lys Phe Gln
    50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Asp Ser Val Phe Gly Leu Asp Tyr Trp Gly Gln Gly Thr Leu Val
            100                 105                 110

Thr Val Ser Ser
        115

<210> SEQ ID NO 446
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Trp Ile Ser Pro Arg Ser Gly Val Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Leu Asp Tyr Val Arg Ala Phe Asp Ile Trp Gly Gln Gly
            100                 105                 110

Thr Thr Val Thr Val Ser Ser
        115

<210> SEQ ID NO 447
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr 20                  25                  30

Tyr Met His Trp Val Arg Gln Ala Pro Gly Gln Gly Leu Glu Trp Met
            35                  40                  45

Gly Trp Met Asp Pro Asn Ser Gly Asn Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Gly Gly Tyr Phe Asp Leu Trp Gly Arg Gly Thr
            100                 105                 110

Leu Val Thr Val Ser Ser
        115

<210> SEQ ID NO 448
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Asn His
            20                  25                  30

Tyr Val His Trp Val Arg Gln Ala Pro Gly Gln Gly Leu Glu Trp Met
        35                  40                  45

Gly Trp Met Asn Pro Thr Gly Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Thr Thr Tyr Ala Phe Asp Ile Trp Gly Gln Gly Thr
            100                 105                 110

Met Val Thr Val Ser Ser
        115

<210> SEQ ID NO 449
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Tyr Met His Trp Val Arg Gln Ala Pro Gly Gln Gly Leu Glu Trp Met
        35                  40                  45

Gly Trp Met Asn Pro Asn Ser Gly His Thr Gly Asn Ala Gln Lys Phe
    50                  55                  60

Gln Gly Arg Val Thr Met Thr Arg Asp Thr Ser Thr Ser Thr Val Tyr

```
               65                  70                  75                  80
Met Glu Leu Ser Ser Leu Arg Ser Glu Asp Thr Ala Val Tyr Tyr Cys
                    85                  90                  95

Ala Arg Gly Asn Trp Val Asp Ala Phe Asp Ile Trp Gly Gln Gly Thr
                100                 105                 110

Met Val Thr Val Ser Ser
        115

<210> SEQ ID NO 450
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Arg His
                20                  25                  30

Leu Leu His Trp Val Arg Gln Ala Pro Gly Gln Gly Leu Glu Trp Met
            35                  40                  45

Gly Trp Val Ser Pro Ile His Gly Leu Thr Gly Tyr Ala Pro Arg Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Val His Gly Ser Gly Ser Asp Gly Met Asp Val Trp Gly Gln
                100                 105                 110

Gly Thr Thr Val Thr Val Ser Ser
        115                 120

<210> SEQ ID NO 451
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                    85                  90                  95

Thr Phe Gly Gly Gly Thr Lys Val Glu Ile Lys
                100                 105
```

-continued

```
<210> SEQ ID NO 452
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Thr Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Glu Asn Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Pro Tyr
                85                  90                  95

Thr Phe Gly Gly Gly Thr Lys Val Glu Ile Lys
            100                 105

<210> SEQ ID NO 453
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gly Gly Thr Lys Val Glu Ile Lys
            100                 105

<210> SEQ ID NO 454
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30
```

Leu Ala Trp Tyr Gln Gln Lys Pro Gly Lys Ala Pro Lys Leu Leu Ile
            35                  40                  45

Tyr Arg Ala Ser Asn Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 455
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Arg Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105

<210> SEQ ID NO 456
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Trp
            20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Thr Phe Gly Gln Gly Thr Lys Val Glu Ile Lys
            100                 105

<210> SEQ ID NO 457
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn His
            20                  25                  30

Leu Asn Trp Tyr Gln Gln Lys Pro Gly Lys Ala Pro Lys Leu Leu Ile
        35                  40                  45

Tyr Gly Ala Ser Asn Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 458
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Val Glu Ile Lys
            100                 105

<210> SEQ ID NO 459
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Leu Glu Ile Lys
            100                 105

<210> SEQ ID NO 460
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Tyr
                85                  90                  95

Thr Phe Gly Gln Gly Thr Lys Val Glu Ile Lys
            100                 105

<210> SEQ ID NO 461
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

```
Thr Phe Gly Gly Gly Thr Lys Val Glu Ile Lys
            100                 105
```

<210> SEQ ID NO 462
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser His Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Arg Leu Glu Ile Lys
            100                 105
```

<210> SEQ ID NO 463
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Asn Phe
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Leu Pro Tyr
                85                  90                  95

Thr Phe Gly Gln Gly Thr Lys Val Glu Ile Lys
            100                 105
```

<210> SEQ ID NO 464
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

```
Asp Ile Gln Met Thr Gln Ser Pro Ser Ser Leu Ser Ala Ser Val Gly
```

```
                1               5                  10                 15
Asp Arg Val Thr Ile Thr Cys Arg Ala Ser Gln Gly Ile Ser Ser Trp
                20                 25                 30

Leu Ala Trp Tyr Gln Gln Lys Pro Gly Lys Ala Pro Lys Leu Leu Ile
           35                 40                 45

Tyr Ala Ala Ser Ser Leu Gln Ser Gly Val Pro Ser Arg Phe Ser Gly
           50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ser Tyr Ser Thr Pro Leu
               85                  90                 95

Thr Phe Gly Gly Gly Thr Lys Val Glu Ile Lys
               100                105
```

<210> SEQ ID NO 465
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465

```
Glu Ile Val Met Thr Gln Ser Pro Ala Thr Leu Ser Val Ser Pro Gly
1               5                  10                 15

Glu Arg Ala Thr Leu Ser Cys Arg Ala Ser Gln Ser Leu Ser Ser Ser
                20                 25                 30

Tyr Leu Ala Trp Tyr Gln Gln Lys Pro Gly Gln Ala Pro Arg Leu Leu
           35                 40                 45

Ile Tyr Gly Ala Ser Thr Arg Ala Thr Gly Ile Pro Ala Arg Phe Ser
       50                 55                 60

Gly Ser Gly Ser Gly Thr Glu Phe Thr Leu Thr Ile Ser Ser Leu Gln
65                 70                 75                 80

Ser Glu Asp Phe Ala Val Tyr Tyr Cys His Gln Tyr Phe Thr Thr Pro
               85                 90                  95

Leu Thr Phe Gly Gln Gly Thr Arg Leu Glu Ile Lys
               100                105
```

<210> SEQ ID NO 466
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

```
Asp Ile Gln Met Thr Gln Ser Pro Ser Ser Leu Ser Ala Ser Val Gly
1               5                  10                 15

Asp Arg Val Thr Ile Thr Cys Arg Ala Ser Gln Ser Ile Ser Ser Tyr
                20                 25                 30

Leu Asn Trp Tyr Gln Gln Lys Pro Gly Lys Ala Pro Lys Leu Leu Ile
           35                 40                 45

Tyr Ala Ala Ser Thr Leu Gln Ser Gly Val Pro Ser Arg Phe Ser Gly
           50                 55                 60

Ser Gly Ser Gly Thr Asp Phe Thr Leu Thr Ile Ser Ser Leu Gln Pro
65                 70                 75                 80

Glu Asp Phe Ala Thr Tyr Tyr Cys Gln Gln Ser Tyr Ser Met Pro Tyr
```

```
                       85                  90                  95

Thr Phe Gly Gln Gly Thr Lys Leu Glu Ile Lys
                100                 105

<210> SEQ ID NO 467
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
                100                 105

<210> SEQ ID NO 468
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 468

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ser Ser Ser Leu Gln Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Val
                85                  90                  95

Thr Phe Gly Gln Gly Thr Lys Val Glu Ile Lys
                100                 105

<210> SEQ ID NO 469
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 469
```

```
Asp Ile Gln Ile Thr His Ser Pro Ser Ser Leu Ser Ala Ser Val Gly
1               5                   10                  15

Tyr Arg Leu Thr Ile Thr Cys Arg Asp Ser His Ser Ile Thr Thr Trp
            20                  25                  30

Leu Ala Trp Tyr His Gln Lys Pro Trp Asn Ala Pro Lys Leu Met Ile
        35                  40                  45

Tyr Ala Ala Ser Asn Leu Glu Ser Gly Val Pro Ser Arg Phe Ser Gly
    50                  55                  60

Ser Gly Ser Gly Thr Tyr Phe Thr Leu Thr Ile Ser Ser Leu Gln Pro
65              70                  75                  80

Glu Asp Phe Ala Thr Tyr Tyr Cys Gln His Tyr Asn Thr Gln Tyr
                85                  90                  95

Thr Phe Gly Gln Gly Thr Lys Val Glu Ile Lys
            100                 105
```

<210> SEQ ID NO 470
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 470

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Arg Asn Asp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Ser Leu Gln Tyr Pro Ser
                85                  90                  95

His Phe Phe Gly Gln Gly Thr Lys Val Glu Ile Lys
            100                 105
```

<210> SEQ ID NO 471
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 471

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Arg Tyr
            20                  25                  30

Leu Asn Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80
```

Glu Asp Phe Ala Pro Tyr Tyr Cys Gln Gln Ser Tyr Ser Thr Pro Leu
                85                  90                  95

Thr Phe Gly Pro Gly Thr Lys Val Asp Ile Lys
            100                 105

<210> SEQ ID NO 472
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 472

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ser
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Ser Leu Tyr Arg Ser
                85                  90                  95

Phe Gly Gln Gly Thr Lys Val Glu Ile Lys
            100                 105

<210> SEQ ID NO 473
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 473

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 474
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 474

Lys Ala Ser Gln Asp Val Gly Thr Ser Val Ala
1               5                   10

<210> SEQ ID NO 475
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 475

Trp Tyr Gln Gln Lys Pro Gly Lys Ala Pro Lys Leu Leu Ile Tyr
1               5                   10                  15

<210> SEQ ID NO 476
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 476

Trp Thr Ser Thr Arg His Thr
1               5

<210> SEQ ID NO 477
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 477

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 478
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 478

Gln Gln Tyr Ser Leu Tyr Arg Ser
1               5

<210> SEQ ID NO 479
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 479

Phe Gly Gln Gly Thr Lys Val Glu Ile Lys
1               5                   10

<210> SEQ ID NO 480
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 480

Glu Val Gln Leu Val Glu Ser Gly Gly Gly Val Val Gln Pro Gly Arg
1               5                   10                  15

Ser Leu Arg Leu Ser Cys Ser Ser Ser Gly Phe Asp Phe Thr Thr Tyr
```

```
                20                  25                  30
Trp Met Ser Trp Val Arg Gln Ala Pro Gly Lys Gly Leu Glu Trp Val
             35                  40                  45

Ala Glu Ile His Pro Asp Ser Ser Thr Ile Asn Tyr Ala Pro Ser Leu
 50                  55                  60

Lys Asp Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                 85                  90                  95

Ala Ser Leu Tyr Phe Gly Phe Pro Trp Phe Ala Tyr Trp Gly Gln Gly
                100                 105                 110

Thr Pro Val Thr Val Ser Ser
        115
```

<210> SEQ ID NO 481
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 481

```
Glu Val Gln Leu Val Glu Ser Gly Gly Val Val Gln Pro Gly Arg
1               5                  10                  15

Ser Leu Arg Leu Ser Cys Ser Ser Ser Gly Phe Asp Phe Thr
                 20                  25                  30
```

<210> SEQ ID NO 482
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 482

```
Thr Tyr Trp Met Ser
1               5
```

<210> SEQ ID NO 483
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 483

```
Trp Val Arg Gln Ala Pro Gly Lys Gly Leu Glu Trp Val Ala
1               5                  10
```

<210> SEQ ID NO 484
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 484

```
Glu Ile His Pro Asp Ser Ser Thr Ile Asn Tyr Ala Pro Ser Leu Lys
1               5                  10                  15
```

Asp

<210> SEQ ID NO 485
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 485

```
Arg Phe Thr Ile Ser Arg Asp Asn Ser Lys Asn Thr Leu Phe Leu Gln
1               5                   10                  15

Met Asp Ser Leu Arg Pro Glu Asp Thr Gly Val Tyr Phe Cys Ala Ser
            20                  25                  30
```

<210> SEQ ID NO 486
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 486

```
Leu Tyr Phe Gly Phe Pro Trp Phe Ala Tyr
1               5                   10
```

<210> SEQ ID NO 487
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 487

```
Trp Gly Gln Gly Thr Pro Val Thr Val Ser Ser
1               5                   10
```

<210> SEQ ID NO 488
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 488

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Ala Ala Val Gly Thr Tyr
            20                  25                  30

Val Ala Trp Tyr Gln Gln Lys Pro Gly Lys Ala Pro Lys Leu Leu Ile
        35                  40                  45

Tyr Ser Ala Ser Tyr Arg Lys Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Gln Tyr Tyr Thr Tyr Pro Leu
                85                  90                  95

Phe Thr Phe Gly Gln Gly Thr Lys Leu Glu Ile Lys
            100                 105
```

<210> SEQ ID NO 489
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 490
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

Lys Ala Ser Ala Ala Val Gly Thr Tyr Val Ala
1               5                   10

<210> SEQ ID NO 491
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 491

Trp Tyr Gln Gln Lys Pro Gly Lys Ala Pro Lys Leu Leu Ile Tyr
1               5                   10                  15

<210> SEQ ID NO 492
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 492

Ser Ala Ser Tyr Arg Lys Arg
1               5

<210> SEQ ID NO 493
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 493

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 494
<211> LENGTH: 10

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 494

His Gln Tyr Tyr Thr Tyr Pro Leu Phe Thr
1               5                   10

<210> SEQ ID NO 495
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 495

Phe Gly Gln Gly Thr Lys Leu Glu Ile Lys
1               5                   10

<210> SEQ ID NO 496
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 497
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 497

Glu Phe Gly Met Asn
1               5

<210> SEQ ID NO 498
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 498

Trp Val Arg Gln Ala Pro Gly Gln Gly Leu Glu Trp Met Gly
1               5                   10

<210> SEQ ID NO 499
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 499

Trp Ile Asn Thr Lys Thr Gly Glu Ala Thr Tyr Val Glu Glu Phe Lys
1               5                   10                  15

Gly

<210> SEQ ID NO 500
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Arg Val Thr Phe Thr Thr Asp Thr Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 501
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 501

Trp Asp Phe Ala Tyr Tyr Val Glu Ala Met Asp Tyr
1               5                   10

<210> SEQ ID NO 502
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 502

Trp Gly Gln Gly Thr Thr Val Thr Val Ser Ser
1               5                   10

<210> SEQ ID NO 503
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 503

Glu Asn Val Leu Thr Gln Ser Pro Ser Ser Met Ser Ala Ser Val Gly
1               5                   10                  15

Asp Arg Val Asn Ile Ala Cys Ser Ala Ser Ser Val Ser Tyr Met
            20                  25                  30

His Trp Phe Gln Gln Lys Pro Gly Lys Ser Pro Lys Leu Trp Ile Tyr
        35                  40                  45

Ser Thr Ser Asn Leu Ala Ser Gly Val Pro Ser Arg Phe Ser Gly Ser
    50                  55                  60

Gly Ser Gly Thr Asp Tyr Ser Leu Thr Ile Ser Ser Met Gln Pro Glu
65                  70                  75                  80

Asp Ala Ala Thr Tyr Tyr Cys Gln Gln Arg Ser Ser Tyr Pro Leu Thr

```
                    85                  90                  95
Phe Gly Gly Gly Thr Lys Leu Glu Ile Lys
            100                 105

<210> SEQ ID NO 504
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 504

Glu Asn Val Leu Thr Gln Ser Pro Ser Ser Met Ser Ala Ser Val Gly
1               5                   10                  15

Asp Arg Val Asn Ile Ala Cys
            20

<210> SEQ ID NO 505
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Ser Ala Ser Ser Ser Val Ser Tyr Met His
1               5                   10

<210> SEQ ID NO 506
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Trp Phe Gln Gln Lys Pro Gly Lys Ser Pro Lys Leu Trp Ile Tyr
1               5                   10                  15

<210> SEQ ID NO 507
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Ser Thr Ser Asn Leu Ala Ser
1               5

<210> SEQ ID NO 508
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 508

Gly Val Pro Ser Arg Phe Ser Gly Ser Gly Ser Gly Thr Asp Tyr Ser
1               5                   10                  15

Leu Thr Ile Ser Ser Met Gln Pro Glu Asp Ala Ala Thr Tyr Tyr Cys
```

-continued

```
                20                  25                  30
```

<210> SEQ ID NO 509
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 509

```
Gln Gln Arg Ser Ser Tyr Pro Leu Thr
1               5
```

<210> SEQ ID NO 510
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

```
Phe Gly Gly Gly Thr Lys Leu Glu Ile Lys
1               5                   10
```

<210> SEQ ID NO 511
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 511

```
Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Arg Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Leu Val Thr Val Ser Ser
        115                 120
```

<210> SEQ ID NO 512
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 512

```
Gln Val Lys Leu Glu Gln Ser Gly Ala Glu Val Val Lys Pro Gly Ala
1               5                   10                  15
```

```
Ser Val Lys Leu Ser Cys Lys Ala Ser Gly Phe Asn Ile Lys
            20                  25                  30
```

<210> SEQ ID NO 513
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

```
Asp Ser Tyr Met His
1               5
```

<210> SEQ ID NO 514
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

```
Trp Leu Arg Gln Gly Pro Gly Gln Arg Leu Glu Trp Ile Gly
1               5                   10
```

<210> SEQ ID NO 515
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

```
Trp Ile Asp Pro Glu Asn Gly Asp Thr Glu Tyr Ala Pro Lys Phe Gln
1               5                   10                  15

Gly
```

<210> SEQ ID NO 516
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 516

```
Lys Ala Thr Phe Thr Thr Asp Thr Ser Ala Asn Thr Ala Tyr Leu Gly
1               5                   10                  15

Leu Ser Ser Leu Arg Pro Glu Asp Thr Ala Val Tyr Tyr Cys Asn Glu
            20                  25                  30
```

<210> SEQ ID NO 517
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

```
Gly Thr Pro Thr Gly Pro Tyr Tyr Phe Asp Tyr
1               5                   10
```

```
<210> SEQ ID NO 518
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Trp Gly Gln Gly Thr Leu Val Thr Val Ser Ser
1               5                   10

<210> SEQ ID NO 519
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 519

Glu Asn Val Leu Thr Gln Ser Pro Ser Ser Met Ser Val Ser Val Gly
1               5                   10                  15

Asp Arg Val Thr Ile Ala Cys Ser Ala Ser Ser Ser Val Pro Tyr Met
            20                  25                  30

His Trp Leu Gln Gln Lys Pro Gly Lys Ser Pro Lys Leu Leu Ile Tyr
        35                  40                  45

Leu Thr Ser Asn Leu Ala Ser Gly Val Pro Ser Arg Phe Ser Gly Ser
    50                  55                  60

Gly Ser Gly Thr Asp Tyr Ser Leu Thr Ile Ser Ser Val Gln Pro Glu
65                  70                  75                  80

Asp Ala Ala Thr Tyr Tyr Cys Gln Gln Arg Ser Ser Tyr Pro Leu Thr
                85                  90                  95

Phe Gly Gly Gly Thr Lys Leu Glu Ile Lys
            100                 105

<210> SEQ ID NO 520
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Glu Asn Val Leu Thr Gln Ser Pro Ser Ser Met Ser Val Ser Val Gly
1               5                   10                  15

Asp Arg Val Thr Ile Ala Cys
            20

<210> SEQ ID NO 521
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Ser Ala Ser Ser Ser Val Pro Tyr Met His
1               5                   10

<210> SEQ ID NO 522
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Trp Leu Gln Gln Lys Pro Gly Lys Ser Pro Lys Leu Leu Ile Tyr
1               5                   10                  15

<210> SEQ ID NO 523
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Leu Thr Ser Asn Leu Ala Ser
1               5

<210> SEQ ID NO 524
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 524

Gly Val Pro Ser Arg Phe Ser Gly Ser Gly Ser Gly Thr Asp Tyr Ser
1               5                   10                  15

Leu Thr Ile Ser Ser Val Gln Pro Glu Asp Ala Ala Thr Tyr Tyr Cys
            20                  25                  30

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Gln Gln Arg Ser Ser Tyr Pro Leu Thr
1               5

<210> SEQ ID NO 526
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Phe Gly Gly Gly Thr Lys Leu Glu Ile Lys
1               5                   10

<210> SEQ ID NO 527
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 527

Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys Asp Ser
            20                  25                  30

Tyr Met His Trp Leu Arg Gln Gly Pro Gly Gln Arg Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ala Asn Thr Ala Tyr
65                  70                  75                  80

Leu Gly Leu Ser Ser Leu Arg Pro Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Leu Val Thr Val Ser Ser
        115                 120

<210> SEQ ID NO 528
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 528

Gln Val Lys Leu Glu Gln Ser Gly Ala Glu Val Val Lys Pro Gly Ala
1               5                   10                  15

Ser Val Lys Leu Ser Cys Lys Ala Ser Gly Phe Asn Ile Lys
            20                  25                  30

<210> SEQ ID NO 529
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Asp Ser Tyr Met His
1               5

<210> SEQ ID NO 530
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Trp Leu Arg Gln Gly Pro Gly Gln Arg Leu Glu Trp Ile Gly
1               5                   10

<210> SEQ ID NO 531
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 531

Trp Ile Asp Pro Glu Asn Gly Asp Thr Glu Tyr Ala Pro Lys Phe Gln
1               5                   10                  15

Gly

<210> SEQ ID NO 532
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 532

Lys Ala Thr Phe Thr Thr Asp Thr Ser Ala Asn Thr Ala Tyr Leu Gly
1               5                   10                  15

Leu Ser Ser Leu Arg Pro Glu Asp Thr Ala Val Tyr Tyr Cys Asn Glu
            20                  25                  30

<210> SEQ ID NO 533
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 533

Gly Thr Pro Thr Gly Pro Tyr Tyr Phe Asp Tyr
1               5                   10

<210> SEQ ID NO 534
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 534

Trp Gly Gln Gly Thr Leu Val Thr Val Ser Ser
1               5                   10

<210> SEQ ID NO 535
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 535

Gln Thr Val Leu Ser Gln Ser Pro Ala Ile Leu Ser Ala Ser Pro Gly
1               5                   10                  15

Glu Lys Val Thr Met Thr Cys
            20

<210> SEQ ID NO 536
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 536

Arg Ala Ser Ser Ser Val Thr Tyr Ile His
1               5                   10

<210> SEQ ID NO 537
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Trp Tyr Gln Gln Lys Pro Gly Ser Ser Pro Lys Ser Trp Ile Tyr
1               5                   10                  15

<210> SEQ ID NO 538
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Ala Thr Ser Asn Leu Ala Ser
1               5

<210> SEQ ID NO 539
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 539

Gly Val Pro Ala Arg Phe Ser Gly Ser Gly Ser Gly Thr Ser Tyr Ser
1               5                   10                  15

Leu Thr Ile Ser Arg Val Glu Ala Glu Asp Ala Ala Thr Tyr Tyr Cys
            20                  25                  30

<210> SEQ ID NO 540
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Gln His Trp Ser Ser Lys Pro Pro Thr
1               5

<210> SEQ ID NO 541
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Phe Gly Gly Gly Thr Lys Leu Glu Ile Lys
1               5                   10
```

```
<210> SEQ ID NO 542
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 542
```

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Leu Thr Val Ser Ser
        115                 120

```
<210> SEQ ID NO 543
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 543
```

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr
            20                  25                  30

```
<210> SEQ ID NO 544
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 544
```

Asp Tyr Tyr Met Asn
1               5

```
<210> SEQ ID NO 545
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 545
```

Trp Val Arg Gln Pro Pro Gly Lys Ala Leu Glu Trp Leu Gly
1               5                   10

<210> SEQ ID NO 546
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 546

Phe Ile Gly Asn Lys Ala Asn Gly Tyr Thr Thr Glu Tyr Ser Ala Ser
1               5                   10                  15

Val Lys Gly

<210> SEQ ID NO 547
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 547

Arg Phe Thr Ile Ser Arg Asp Lys Ser Gln Ser Ile Leu Tyr Leu Gln
1               5                   10                  15

Met Asn Thr Leu Arg Ala Glu Asp Ser Ala Thr Tyr Tyr Cys Thr Arg
            20                  25                  30

<210> SEQ ID NO 548
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 548

Asp Arg Gly Leu Arg Phe Tyr Phe Asp Tyr
1               5                   10

<210> SEQ ID NO 549
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 549

Trp Gly Gln Gly Thr Thr Leu Thr Val Ser Ser
1               5                   10

<210> SEQ ID NO 550
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 550

Asp Ile Gln Leu Thr Gln Ser Pro Ser Ser Leu Ser Ala Ser Val Gly
1               5                   10                  15

Asp Arg Val Thr Ile Thr Cys Arg Ala Gly Glu Ser Val Asp Ile Phe
            20                  25                  30

Gly Val Gly Phe Leu His Trp Tyr Gln Gln Lys Pro Gly Lys Ala Pro

```
                35                  40                  45
Lys Leu Leu Ile Tyr Arg Ala Ser Asn Leu Glu Ser Gly Val Pro Ser
             50                  55                  60

Arg Phe Ser Gly Ser Gly Ser Arg Thr Asp Phe Thr Leu Thr Ile Ser
 65                  70                  75                  80

Ser Leu Gln Pro Glu Asp Phe Ala Thr Tyr Tyr Cys Gln Gln Thr Asn
                 85                  90                  95

Glu Asp Pro Tyr Thr Phe Gly Gln Gly Thr Lys Val Glu Ile Lys
            100                 105                 110

<210> SEQ ID NO 551
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 551

Asp Ile Gln Leu Thr Gln Ser Pro Ser Ser Leu Ser Ala Ser Val Gly
 1               5                  10                  15

Asp Arg Val Thr Ile Thr Cys
             20

<210> SEQ ID NO 552
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 552

Arg Ala Gly Glu Ser Val Asp Ile Phe Gly Val Gly Phe Leu His
 1               5                  10                  15

<210> SEQ ID NO 553
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 553

Trp Tyr Gln Gln Lys Pro Gly Lys Ala Pro Lys Leu Leu Ile Tyr
 1               5                  10                  15

<210> SEQ ID NO 554
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 554

Arg Ala Ser Asn Leu Glu Ser
 1               5

<210> SEQ ID NO 555
<211> LENGTH: 32
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 555

Gly Val Pro Ser Arg Phe Ser Gly Ser Gly Ser Arg Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 556
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 556

Gln Gln Thr Asn Glu Asp Pro Tyr Thr
1               5

<210> SEQ ID NO 557
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 557

Phe Gly Gln Gly Thr Lys Val Glu Ile Lys
1               5                   10

<210> SEQ ID NO 558
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 558

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Met His Trp Val Arg Gln Ala Pro Gly Lys Gly Leu Glu Trp Val
        35                  40                  45

Ala Arg Ile Asp Pro Ala Asn Gly Asn Ser Lys Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Leu Val Thr Val Ser Ser
        115                 120

<210> SEQ ID NO 559
<211> LENGTH: 30
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 559

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 560
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 560

Asp Thr Tyr Met His
1               5

<210> SEQ ID NO 561
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 561

Trp Val Arg Gln Ala Pro Gly Lys Gly Leu Glu Trp Val Ala
1               5                   10

<210> SEQ ID NO 562
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 562

Arg Ile Asp Pro Ala Asn Gly Asn Ser Lys Tyr Ala Asp Ser Val Lys
1               5                   10                  15

Gly

<210> SEQ ID NO 563
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 563

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Pro
            20                  25                  30

<210> SEQ ID NO 564
<211> LENGTH: 12
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 564

Phe Gly Tyr Tyr Val Ser Asp Tyr Ala Met Ala Tyr
1               5                   10

<210> SEQ ID NO 565
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 565

Trp Gly Gln Gly Thr Leu Val Thr Val Ser Ser
1               5                   10

<210> SEQ ID NO 566
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 566

Asp Ile Gln Met Thr Gln Ser Pro Ala Ser Leu Ser Ala Ser Val Gly
1               5                   10                  15

Asp Arg Val Thr Ile Thr Cys Arg Ala Ser Glu Asn Ile Phe Ser Tyr
            20                  25                  30

Leu Ala Trp Tyr Gln Gln Lys Pro Gly Lys Ser Pro Lys Leu Leu Val
        35                  40                  45

Tyr Asn Thr Arg Thr Leu Ala Glu Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Phe Ala Thr Tyr Tyr Cys Gln His His Tyr Gly Thr Pro Phe
                85                  90                  95

Thr Phe Gly Ser Gly Thr Lys Leu Glu Ile Lys
            100                 105

<210> SEQ ID NO 567
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 567

Asp Ile Gln Met Thr Gln Ser Pro Ala Ser Leu Ser Ala Ser Val Gly
1               5                   10                  15

Asp Arg Val Thr Ile Thr Cys
            20

<210> SEQ ID NO 568
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 568

Arg Ala Ser Glu Asn Ile Phe Ser Tyr Leu Ala
1               5                   10

<210> SEQ ID NO 569
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 569

Trp Tyr Gln Gln Lys Pro Gly Lys Ser Pro Lys Leu Leu Val Tyr
1               5                   10                  15

<210> SEQ ID NO 570
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 570

Asn Thr Arg Thr Leu Ala Glu
1               5

<210> SEQ ID NO 571
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 571

Gly Val Pro Ser Arg Phe Ser Gly Ser Gly Ser Gly Thr Asp Phe Ser
1               5                   10                  15

Leu Thr Ile Ser Ser Leu Gln Pro Glu Asp Phe Ala Thr Tyr Tyr Cys
            20                  25                  30

<210> SEQ ID NO 572
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 572

Gln His His Tyr Gly Thr Pro Phe Thr
1               5

<210> SEQ ID NO 573
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 573

Phe Gly Ser Gly Thr Lys Leu Glu Ile Lys
1               5                   10
```

<210> SEQ ID NO 574
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 574

Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser Ser Tyr
            20                  25                  30

Asp Met Ser Trp Val Arg Gln Thr Pro Glu Arg Gly Leu Glu Trp Val
        35                  40                  45

Ala Tyr Ile Ser Ser Gly Gly Ile Thr Tyr Ala Pro Ser Thr Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Thr Ser Glu Asp Thr Ala Val Tyr Tyr Cys
                85                  90                  95

Ala Ala His Tyr Phe Gly Ser Ser Gly Pro Phe Ala Tyr Trp Gly Gln
            100                 105                 110

Gly Thr Leu Val Thr Val Ser Ser
        115                 120

<210> SEQ ID NO 575
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 575

Glu Val Gln Leu Gln Glu Ser Gly Pro Gly Leu Val Lys Pro Gly Gly
1               5                   10                  15

Ser Leu Ser Leu Ser Cys Ala Ala Ser Gly Phe Val Phe Ser
            20                  25                  30

<210> SEQ ID NO 576
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 576

Ser Tyr Asp Met Ser
1               5

<210> SEQ ID NO 577
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 577

Trp Val Arg Gln Thr Pro Glu Arg Gly Leu Glu Trp Val Ala
1               5                   10

<210> SEQ ID NO 578
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 578

Tyr Ile Ser Ser Gly Gly Gly Ile Thr Tyr Ala Pro Ser Thr Val Lys
1               5                   10                  15

Gly

<210> SEQ ID NO 579
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 579

Arg Phe Thr Val Ser Arg Asp Asn Ala Lys Asn Thr Leu Tyr Leu Gln
1               5                   10                  15

Met Asn Ser Leu Thr Ser Glu Asp Thr Ala Val Tyr Tyr Cys Ala Ala
            20                  25                  30

<210> SEQ ID NO 580
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 580

His Tyr Phe Gly Ser Ser Gly Pro Phe Ala Tyr
1               5                   10

<210> SEQ ID NO 581
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 581

Trp Gly Gln Gly Thr Leu Val Thr Val Ser Ser
1               5                   10

<210> SEQ ID NO 582
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 582

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
             35                  40                  45

Leu Leu Arg Tyr Lys Ser Asp Ser Asp Lys Gln Gln Gly Ser Gly Val
 50                  55                  60

Ser Ser Arg Phe Ser Ala Ser Lys Asp Ala Ser Ala Asn Ala Gly Ile
 65                  70                  75                  80

Leu Leu Ile Ser Gly Leu Gln Ser Glu Asp Glu Ala Asp Tyr Tyr Cys
                 85                  90                  95

Met Ile Trp His Ser Gly Ala Ser Ala Val Phe Gly Gly Gly Thr Lys
                100                 105                 110

Leu Thr Val Leu
        115

<210> SEQ ID NO 583
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 583

Gln Ala Val Leu Thr Gln Pro Ala Ser Leu Ser Ala Ser Pro Gly Ala
 1               5                  10                  15

Ser Ala Ser Leu Thr Cys
             20

<210> SEQ ID NO 584
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Thr Leu Arg Arg Gly Ile Asn Val Gly Ala Tyr Ser Ile Tyr
 1               5                  10

<210> SEQ ID NO 585
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 585

Trp Tyr Gln Gln Lys Pro Gly Ser Pro Pro Gln Tyr Leu Leu Arg
 1               5                  10                  15

<210> SEQ ID NO 586
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 586

Tyr Lys Ser Asp Ser Asp Lys Gln Gln Gly Ser
 1               5                  10

<210> SEQ ID NO 587

```
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 587
```

Gly Val Ser Ser Arg Phe Ser Ala Ser Lys Asp Ala Ser Ala Asn Ala
1               5                   10                  15

Gly Ile Leu Leu Ile Ser Gly Leu Gln Ser Glu Asp Glu Ala Asp Tyr
            20                  25                  30

Tyr Cys

```
<210> SEQ ID NO 588
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 588
```

Met Ile Trp His Ser Gly Ala Ser Ala Val
1               5                   10

```
<210> SEQ ID NO 589
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 589
```

Phe Gly Gly Gly Thr Lys Leu Thr Val Leu
1               5                   10

```
<210> SEQ ID NO 590
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 590
```

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser
        115                 120

<210> SEQ ID NO 591
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 591

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser
            20                  25                  30

<210> SEQ ID NO 592
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 592

Ser Tyr Trp Met His
1               5

<210> SEQ ID NO 593
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 593

Trp Val Arg Gln Ala Pro Gly Lys Gly Leu Glu Trp Val Gly
1               5                   10

<210> SEQ ID NO 594
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 594

Phe Ile Arg Asn Lys Ala Asn Gly Gly Thr Thr Glu Tyr Ala Ala Ser
1               5                   10                  15

Val Lys Gly

<210> SEQ ID NO 595
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 595

Phe Ile Arg Asn Lys Ala Asn Ser Gly Thr Thr Glu Tyr Ala Ala Ser
1               5                   10                  15

Val Lys Gly

```
<210> SEQ ID NO 596
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 596

Arg Phe Thr Ile Ser Arg Asp Asp Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 597
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 597

Asp Arg Gly Leu Arg Phe Tyr Phe Asp Tyr
1               5                   10

<210> SEQ ID NO 598
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 598

Trp Gly Gln Gly Thr Thr Val Thr Val Ser Ser
1               5                   10

<210> SEQ ID NO 599
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 599

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Leu Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser
        115                 120
```

<210> SEQ ID NO 600
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 600

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser
            20                  25                  30

<210> SEQ ID NO 601
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 601

Ser Tyr Trp Met His
1               5

<210> SEQ ID NO 602
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 602

Trp Val Arg Gln Ala Pro Gly Lys Gly Leu Glu Trp Val Gly
1               5                   10

<210> SEQ ID NO 603
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 603

Phe Ile Leu Asn Lys Ala Asn Gly Gly Thr Thr Glu Tyr Ala Ala Ser
1               5                   10                  15

Val Lys Gly

<210> SEQ ID NO 604
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 604

Arg Phe Thr Ile Ser Arg Asp Asp Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

```
<210> SEQ ID NO 605
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 605

Asp Arg Gly Leu Arg Phe Tyr Phe Asp Tyr
1               5                   10

<210> SEQ ID NO 606
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 606

Trp Gly Gln Gly Thr Thr Val Thr Val Ser Ser
1               5                   10

<210> SEQ ID NO 607
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 607

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Pro
            20                  25                  30
```